US010393752B2

(12) United States Patent
Rychnovsky et al.

(10) Patent No.: US 10,393,752 B2
(45) Date of Patent: *Aug. 27, 2019

(54) MASS SPECTROMETRY-CLEAVABLE CROSS-LINKING AGENTS

(71) Applicant: The Regents of The University of California, Oakland, CA (US)

(72) Inventors: Scott D. Rychnovsky, Irvine, CA (US); Lan Huang, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/275,001

(22) Filed: Sep. 23, 2016

(65) Prior Publication Data

US 2017/0082635 A1 Mar. 23, 2017

Related U.S. Application Data

(63) Continuation-in-part of application No. 14/927,332, filed on Oct. 29, 2015, which is a continuation of application No. 13/471,365, filed on May 14, 2012, now Pat. No. 9,222,943.

(60) Provisional application No. 62/222,690, filed on Sep. 23, 2015, provisional application No. 61/486,260, filed on May 14, 2011.

(51) Int. Cl.
| | |
|---|---|
| *G01N 33/68* | (2006.01) |
| *G16C 20/40* | (2019.01) |
| *G16C 20/50* | (2019.01) |
| *C07D 207/46* | (2006.01) |
| *C07D 405/14* | (2006.01) |

(52) U.S. Cl.
CPC ....... *G01N 33/6848* (2013.01); *C07D 207/46* (2013.01); *C07D 405/14* (2013.01); *G16C 20/40* (2019.02); *G16C 20/50* (2019.02)

(58) Field of Classification Search
CPC combination set(s) only.
See application file for complete search history.

(56) References Cited

U.S. PATENT DOCUMENTS 9,222,943 B2 * 12/2015 Rychnovsky ...... G01N 33/6848

OTHER PUBLICATIONS

U.S. Appl. No. 14/927,332, filed Oct. 2015, Rychnovsky; Scott.*
Chemical Abstract Service STN [Database online] Registry No. 1202638-85-4 [entered STN: Jan. 20, 2010]. (Year: 2010).*
Chemical Abstract Service STN [Database online] Registry No. 1189498-30-3 [entered STN: Oct. 22, 2009]. (Year: 2009).*
Chemical Abstract Service STN [Database online] Registry No. 1094107-58-0 [entered STN: Jan. 16, 2009]. (Year: 2009).*
Chemical Abstract Service STN [Database online] Registry No. 72767-34-1 [entered STN: Nov. 16, 1984]. (Year: 1984).*
Kao et al. "Development of a Novel Cross-linking Strategy for Fast and Accurate Identification of Cross-linked Peptides of Protein Complexes" Mol. Cell. Proteomics 2011, 10:M110.002212 (pub. Aug. 24, 2010). (Year: 2010).*
Kaake et al. "A New in Vivo Cross-linking Mass Spectrometry Platform to Define Protein-Protein Interactions in Living Cells" Mol. Cell. Proteomics 2014, 13:M114.042630, 3533-3543 (Year: 2014).*
Yu et al. "Developing New Isotope-Coded Mass Spectrometry-Cleavable Cross-Linkers for Elucidating Protein Structures" Anal. Chem. 2014, 86, 2099-2106 (Year: 2014).*
Burke et al. "Synthesis of two new enrichable and MS-cleavable cross-linkers to define protein-protein interactions by mass spectrometry" Org. Biomol. Chem. 2015, 13, 5030-503 (Year: 2015).*
Back, J.W., et al., A new crosslinker for mass spectrometric analysis of the quaternary structure of protein complexes, Journal of the American Society for Mass Spectrometry, vol. 12, No. 2, pp. 222-227, Feb. 2001.
Back, J.W., et al., Chemical cross-linking and mass spectrometry for protein structural modeling, Journal of Molecular Biology, vol. 331, No. 2, pp. 303-313, Aug. 8, 2003.
Beck, F., et al., Near-atomic resolution structural model of the yeast 26S proteasome, Proceedings of the National Academy of Sciences, vol. 109, No. 37, pp. 14870-14875, Sep. 11, 2012.
Burke, A.M., Reagents for in vivo protein cross-Linking and automated analysis of protein-protein interactions with tandem mass spectrometry, Ph.D. thesis, University of California, Irvine, 2011.
Burke, A.M. et al., Synthesis of two new enrichable and MS-cleavable cross-linkers to define protein-protein interactions by mass spectrometry. Organic & biomolecular Chemisty, vol. 13, pp. 5030-5037, 2015.
Chavez, J.D., et al., Protein interactions, post-translational modifications and topologies in human cells, Molecular & Cellular Proteomics, vol. 12, No. 5, pp. 1451-1467, May 2013.
Chen, Z.A., et al., Architecture of the RNA polymerase II-TFIIF complex revealed by cross-linking and mass spectrometry, The EMBO Journal, vol. 29, No. 4, pp. 717-726, Feb. 17, 2010.
Chowdhury, S.M., et al., Identification of cross-linked peptides after click-based enrichment using sequential collision-induced dissociation and electron transfer dissociation tandem mass spectrometry, Analytical Chemistry, vol. 81, No. 13, pp. 5524-5532, Jul. 1, 2009.
Chu, F., et al., Isotope-coded and affinity-tagged cross-linking (ICATXL): an efficient strategy to probe protein interaction surfaces, Journal of the American Chemical Society, vol. 128, No. 32, pp. 10362-10363, Aug. 16, 2006.

(Continued)

Primary Examiner — Amanda L Aguirre
(74) *Attorney, Agent, or Firm* — Knobbe, Martens, Olson & Bear, LLP

(57) ABSTRACT

Provided herein is synthesis of novel mass spectrometry-cleavable cross-linking agents. The novel mass spectrometry-cleavable cross-linking agents can be used in mass spectrometry, tandem mass spectrometry, and multi-stage tandem mass spectrometry to facilitate structural analysis of intra-protein interactions in proteins and inter-protein interactions in protein complexes. Also provided are methods of mapping intra-protein interactions in proteins and inter-protein interactions in protein complexes.

26 Claims, 39 Drawing Sheets
Specification includes a Sequence Listing.

(56) References Cited

OTHER PUBLICATIONS

Chu, F., et al., Finding chimeras: a bioinformatics strategy for identification of cross-linked peptides, Molecular & Cellular Proteomics, vol. 9, No. 1, pp. 25-31, Jan. 2010.

Collins, B.C., et al., Quantifying protein interaction dynamics by SWATH mass spectrometry: application to the 14-3-3 system, Nature Methods, vol. 10, No. 12, pp. 1246-1253, Dec. 2013.

Collins, C.J., et al., Isotopically labeled crosslinking reagents: resolution of mass degeneracy in the identification of crosslinked peptides, Bioorganic and Medicinal Chemistry, vol. 13, No. 22, pp. 4023-4026, Nov. 17, 2003.

Denison, C., et al., Toward a general chemical method for rapidly mapping multi-protein complexes, Journal of Proteome Research, vol. 3, No. 3, pp. 417-425, May-Jun. 2004.

Dihazi, G.H., et al., Mapping low-resolution three-dimensional protein structures using chemical cross-linking and Fourier transform ion-cyclotron resonance mass spectrometry, Rapid Communications in Mass Spectrometry, vol. 17, No. 17, pp. 2005-0214, Sep. 15, 2003.

Dreiocker, F., et al., Collision-induced dissociative chemical cross-linking reagent for protein structure characterization: applied Edman chemistry in the gas phase, Journal of Mass Spectrometry, vol. 45, No. 2, pp. 178-189, Feb. 2010.

Erzberger, J.P., et al., Molecular architecture of the 40S•elF1.elF3 translation initiation complex, Cell, vol. 158, No. 5, pp. 1123-1135, Aug. 28, 2014.

Fang, L., et al., Mapping the protein interaction network of the human COP9 signalosome complex using a label-free QTAX strategy, Molecular & Cellular Proteomics, vol. 11, No. 5, pp. 138-147, May 2012.

Finn, M.G., et al., Click chemistry: function follows form, Chemical Society Reviews, vol. 39, No. 4, pp. 1231-1232, Apr. 2010.

Fulmer, G.R., et al., NMR chemical shifts of trace impurities: Common laboratory solvents, organics, and gases in deuterated solvents relevant to the organometallic chemist, Organometallics, vol. 29, No. 9, pp. 2176-2179, Apr. 16, 2010.

Gao, Q., et al., Minimize the detection of false positives by the software program DetectShift for O-labeled cross-linked peptide analysis, European Journal of Mass Spectrometry, vol. 14, No. 5, pp. 275-280, 2008.

Gardner, M.W., et al., Chromogenic cross-linker for the characterization of protein structure by infrared multiphoton dissociation mass spectrometry, Analytical Chemistry, vol. 80, No. 13, pp. 4807-4819, Jul. 1, 2008.

Gavin, A.C., et al., Recent advances in charting protein-protein interaction: mass spectrometry-based approaches, Current Opinion in Biotechnology, vol. 22, No. 1, pp. 42-49, Feb. 2011.

Gordon, C.G., et al., Reactivity of biarylazacyclooctynones in copper-free click chemistry, Journal of the American Chemical Society, vol. 134, No. 22, pp. 9199-9208, May 2012.

Greber, B.J., et al., Architecture of the large subunit of the mammalian mitochondrial ribosome, Nature, vol. 505, No. 7484, pp. 515-519, Jan. 23, 2014.

Gringas, A.C., et al., Analysis of protein complexes using mass spectrometry, Nature Reviews Molecular and Cell Biology, vol. 8, No. 8, pp. 645-654, Aug. 2007.

Guan, H., et al., Advanced technologies for studies on protein interactomes, Advances in Biochemical Engineering/Biotechnology, vol. 110, pp. 1-24, Jan. 25, 2008.

Guerrero, C., et al., An integrated mass spectrometry-based proteomic approach: quantitative analysis of tandem affinity-purified in vivo cross-linked protein complexes (QTAX) to decipher the 26 S proteasome-interacting network, Molecular & Cellular Proteomics, vol. 5, No. 2, pp. 366-378, Nov. 11, 2005.

Guerrero, C., et al., Characterization of the proteasome interaction network using a QTAX-based tag-team strategy and protein interaction network analysis, Proceedings of the National Academy of Sciences, vol. 105, No. 36, pp. 13333-13338, Sep. 9, 2008.

Guo, X., et al., Partial acetylation of lysine residues improves intraprotein cross-linking, Analytical Chemistry, vol. 80, No. 4, pp. 951-960, Feb. 15, 2008.

Herzog, F., et al., Structural probing of a protein phosphatase 2A network by chemical cross-linking and mass spectrometry, Science, vol. 337, No. 6100, pp. 1348-1352, Sep. 14, 2012.

Huang da, W., et al., Systematic and integrative analysis of large gene lists using DAVID bioinformatics resources, Nature Protocols, vol. 4, No. 1, pp. 44-57, 2009.

Jewett, J.C., et al., Rapid cu-free click chemistry with readily synthesized biarylazacyclooctynones, Journal of the American Chemical Society, vol. 132, No. 11, pp. 3688-3690, Feb. 26, 2010.

Kaake, R.M., et al., A new in vivo cross-linking mass spectrometry platform to define protein-protein interactions in living cells, Molecular & Cellular Proteomics, vol. 13, No. 12, pp. 3533-3543, Dec. 2014.

Kaake, R.M., et al., Characterization of cell cycle specific protein interaction networks of the yeast 26S proteasome complex by the QTAX strategy, Journal of Proteome Research, vol. 9, No. 4, pp. 2016-2029, Apr. 5, 2010.

Kao, A., et al., Development of a novel cross-linking strategy for fast and accurate identification of cross-linked peptides of protein complexes, Molecular & Cellular Proteomics, vol. 10, No. 1, DOI: 10.1074/mcp.M110.002212, Aug. 24, 2010.

Kao, A., et al., Mapping the structural topology of the yeast 19S proteasomal regulatory particle using chemical cross-linking and probabilistic modeling, Molecular & Cellular Proteomics, vol. 11, No. 12, pp. 1566-1577, Dec. 2012.

Kasper, P.T., et al., An aptly positioned azido group in the spacer of a protein cross-linker for facile mapping of lysines in close proximity, ChemBioChem, vol. 8, No. 11, pp. 1281-1292, Jul. 23, 2007.

Kocher, T., et al., Mass spectrometry-based functional proteomics: from molecular machines to protein networks, Nature Methods, vol. 4, No. 10, pp. 807-815, Oct. 2007.

Kruppa, G.H., et al., A topdown approach to protein structural studies using chemical cross-linking and Fourier transform mass spectrometry, Rapid Communications in Mass Spectrometry, vol. 17, No. 2, pp. 155-162, 2003.

Lai, C. F., et al., Alphavbeta integrins play an essential role in BMP-2 induction of osteoblast differentiation, Journal of Bone Mineral Research, vol. 20, No. 2, pp. 330-340, Feb. 2005.

Lambert, J.P., et al., Mapping differential interactomes by affinity purification coupled with data-independent mass spectrometry acquisition, Nature Methods, vol. 10, No. 12, pp. 1239-1245, Dec. 2013.

Lander, G.C., et al., Complete subunit architecture of the proteasome regulatory particle, Nature, vol. 482, No. 7384, pp. 186-191, Feb. 9, 2012.

Lasker, K., et al., Molecular architecture of the 26S proteasome holocomplex determined by an integrative approach, Proceedings of the National Academy of Sciences, vol. 109, No. 5, pp. 1380-1387, Jan. 31, 2012.

Lee, Y.J., et al., Shotgun cross-linking analysis for studying quaternary and tertiary protein structures, Journal of Proteome Research, vol. 6, No. 10, pp. 3908-3917, Oct. 2007.

Leggett, D.S., et al., Multiple associated proteins regulate proteasome structure and function, Molecular Cell, vol. 10, No. 3, pp. 495-507, Sep. 2002.

Leitner, A., et al., Chemical cross-linking/mass spectrometry targeting acidic residues in proteins and protein complexes, Proceedings of the National Academy of Sciences, vol. 111, No. 26, pp. 9455-9460, Jul. 1, 2014.

Leitner, A., et al., Probing native protein structures by chemical cross-linking, mass spectrometry, and bioinformatics, Molecular & Cellular Proteomics, vol. 9, No. 8, pp. 1634-1649, Aug. 1, 2010.

Leitner, A., et al., The molecular architecture of the eukaryotic chaperonin TRiC/CCT, Structure, vol. 20, No. 5, pp. 814-825, May 9, 2012.

Leonard, N.M., et al., In situ formation of N-trifluoroacetoxy succinimide (TFA-NHS): one-pot formation of succinimidyl esters, N-trifluoroacetyl amino acid succinimidyl esters, and N-maleoyl amino acid succinimidyl esters, Journal of Organic Chemistry, vol. 76, No. 21, pp. 9169-9174, Nov. 4, 2011.

(56) References Cited

OTHER PUBLICATIONS

Lu, Y., et al., Ionic reagent for controlling the gas-phase fragmentation reactions of cross-linked peptides, Analytical Chemistry, vol. 80, No. 23, pp. 9270-9287, Oct. 31, 2008.

Luo, J., et al., An integrated chemical cross-linking and mass spectrometry approach to study protein complex architecture and function, Molecular & Cellular Proteomics, vol. 11, No. 2, DOI: 10.1074/mcp.M111.008318, Feb. 2012.

Ma, Y., A tandem reaction of 4-bromoalkyl aldehydes with sodium azide: Synthesis of 5,6,7,7a-tetrahydro-pyrrolo[1,2-d]-[1.2.3.4]oxatriazole, Heteroatom Chemistry, vol. 13, No. 4, pp. 307-309, May 16, 2002.

Maiolica, A., et al., Structural analysis of multiprotein complexes by cross-linking, mass spectrometry, and database searching, Molecular & Cellular Proteomics, vol. 6, No. 12, pp. 2200-2211, Oct. 5, 2007.

Mirkin, N., et al., High resolution X-ray crystallographic structure of bovine heart cytochrome c and its application to the design of an electron transfer biosensor, Proteins, vol. 70, No. 1, pp. 83-92, Jan. 1, 2008.

Muller, M.Q., et al., Cleavable cross-linker for protein structure analysis: reliable identification of cross-linking products by tandem MS, Analytical Chemistry, vol. 82, No. 16, pp. 6958-6968, Jul. 2010.

Muller, M.Q., Fragmentation behavior of a thiourea-based reagent for protein structure analysis by collision-induced dissociative chemical cross-linking, Journal of Mass Spectrometry, vol. 45, No. 8, pp. 880-891, Aug. 2010.

Murguía, M.C., et al., a facile, selective preparation of monoketals from pentaerythritol and ketones, Synthesis, vol. 7, pp. 1093-1097, Jun. 2001.

Nadeau, O.W., et al., CrossSearch, a user-friendly search engine for detecting chemically cross-linked peptides in conjugated proteins, Molecular & Cellular Proteomics, vol. 7, No. 4, pp. 739-749, Feb. 16, 2008.

Nessen, M.A., et al., Selective enrichment of azide-containing peptides from complex mixtures, Journal of Proteome Research, vol. 8, No. 7, pp. 3702-3711, Jul. 2009.

Panchaud, A., et al., xComb: a cross-linked peptide database approach to protein-protein interaction analysis, Journal of Proteome Research, vol. 9, No. 5, pp. 2508-2515, May 7, 2010.

Pangborn, A.B., et al., Safe and convenient procedure for solvent purification, Organometallics, vol. 15, No. 5, pp. 1518-1520, Mar. 5, 1996.

Paramelle, D., et al., Chemical cross-linkers for protein structure studies by mass spectrometry, Proteomics, vol. 13, No. 3-4, pp. 438-456, Feb. 2013.

Pearson, K.M., et al., Intramolecular cross-linking experiments on cytochrome c and ribonuclease A using an isotope multiplet method, Rapid Communications in Mass Spectrometry, vol. 16, No. 3, pp. 149-159, 2002.

Petrotchenko, E.V., et al., An isotopically coded CID-cleavable biotinylated cross-linker for structural proteomics, Molecular & Cellular Proteomics, vol. 10, No. 2, DOI: 10.1074/mcp.M110.001420, 2011.

Petrotchenko, E.V., et al., BiPS, a photocleavable, isotopically coded, fluorescent cross-linker for structural proteomics, Molecular & Cellular Proteomics, vol. 8, No. 2, pp. 273-286, Feb. 2009.

Petrotchenko, E.V., et al., ICC-CLASS: isotopically-coded cleavable crosslinking analysis software suite, BMC Bioinformatics, vol. 11, No. 1, pp. 64, Jan. 2010.

Petrotchenko, E.V., et al., Isotopically coded cleavable cross-linker for studying protein-protein interaction and protein complexes, Molecular & Cellular Proteomics, vol. 4, pp. 1167-1179, Aug. 1, 2005.

Pettersen, E.F., et al., UCSF Chimera—A visualization system for exploratory research and analysis, Journal of Computational Chemistry, vol. 25, No. 13, pp. 1605-1612, Oct. 2004.

Pickart, C.M., et al., Proteasomes and their kin: proteases in the machine age, Nature Reviews Molecular Cell Biology, vol. 5, No. 3, pp. 177-187, Mar. 2004.

Politis, A., et al., A mass spectrometry-based hybrid method for structural modeling of protein complexes, vol. 11, No. 4, pp. 403-406, Apr. 2014.

Rappsilber, J., et al., A generic strategy to analyze the spatial organization of multi-protein complexes by cross-linking and mass spectrometry, Analytical Chemistry, vol. 72, No. 2, pp. 267-275, Jan. 15, 2000.

Reid, G.E., et al., Statistical and mechanistic approaches to understanding the gas-phase fragmentation behavior of methionine sulfoxide containing peptides, Journal of Proteome Research, vol. 3, No. 4, pp. 751-759, Aug. 2004.

Rinner, O., et al., Identification of cross-linked peptides from large sequence databases, Nature Methods, vol. 5, No. 4, pp. 315-318, Apr. 2008.

Robinson, C.V., et al., The molecular sociology of the cell, Nature, vol. 450, No. 7172, pp. 973-983, Dec. 13, 2007.

Ryan, C.J., et al., High-resolution network biology: connecting sequence with function, Nature Reviews Genetics, vol. 14, No. 12, pp. 865-879, Dec. 2013.

Ryan, D.P., et al., Protein-protein interactions in human disease, Current Opinion in Structural Biology, vol. 15, No. 4, pp. 441-446, Aug. 2005.

Schilling, B., et al., MS2Assign, automated assignment and nomenclature of tandem mass spectra of chemically crosslinked peptides, Journal of the American Society of Mass Spectrometry, vol. 14, No. 8, pp. 834-850, Aug. 2003.

Schmitt-Ulms, G., et al., Time-controlled transcardiac perfusion cross-linking for the study of protein interactions in complex tissue, Nature Biotechnology, vol. 22, No. 6, pp. 724-731, Jun. 2004.

Singh, P., et al., Characterization of protein cross-links via mass spectrometry and an open-modification search strategy, Analytical Chemistry, vol. 80, No. 22, pp. Nov. 15, 2008.

Sinz, A., Chemical cross-linking and mass spectrometry for mapping three-dimensional structures of proteins and protein complexes, Journal of Mass Spectrometry, vol. 38, No. 12, pp. 1225-1237, Dec. 11, 2003.

Sinz, A., Chemical cross-linking and mass spectrometry to map three-dimensional protein structures and protein-protein interactions, Mass Spectrometry Reviews, vol. 25, No. 4, pp. 663-682, Jul.-Aug. 2006.

Sinz, A., Investigation of protein-protein interactions in living cells by chemical cross-linking and mass spectrometry, Analytical and Bioanalytical Chemistry, vol. 397, No. 8, pp. 3433-3440, Aug. 2010.

Sinz, A., et al., Mapping spatial proximities of sulfhydryl groups in proteins using a fluorogenic cross-linker and mass spectrometry, Analytical Biochemistry, vol. 331, No. 1, pp. 27-32, Sep. 2004.

Soderblom, E.J., et al., Collision-induced dissociative chemical cross-linking reagents and methodology, Applications to protein structural characterization using tandem mass spectrometry analysis, Analytical Chemistry, vol. 78, No. 23, pp. 8059-8068, Oct. 28, 2006.

Soderblom, E.J., et al., Tandem mass spectrometry acquisition approaches to enhance identification of protein-protein interactions using low-energy collision-induced dissociative chemical crosslinking reagents, Rapid Communications in Mass Spectrometry, vol. 21, No. 21, pp. 3395-3408, Nov. 15, 2007.

Sowa, M.E., et al., Defining the human deubiquitinating enzyme interaction landscape, Cell, vol. 138, No. 2, pp. 389-403, Jul. 23, 2009.

Still, W.C., et al., Rapid chromatographic technique for preparative separations with moderate resolution, Journal of Organic Chemistry, vol. 43, No. 14, pp. 2923-2925, 1978.

Sutherland, B.W., Utility of formaldehyde cross-linking and mass spectrometry in the study of protein-protein interactions, Journal of Mass Spectrometry, vol. 43, No. 6, pp. 699-715, Jun. 2008.

Szychowski, J., et al., Cleavable biotin probes for labeling of biomolecules via azide-alkyne cycloaddition, vol. 132, No. 51, pp. 18351-18360, Dec. 8, 2010.

(56) References Cited

OTHER PUBLICATIONS

Tagwerker, C., et al., A tandem affinity tag for two-step purification under fully denaturing conditions, Molecular & Cellular Proteomics, vol. 5, No. 4, pp. 737-748, Jan. 23, 2006.

Tang, X., et al., Mass spectrometry identifiable cross-linking strategy for studying protein-protein interactions, Analytical Chemistry, vol. 77, No. 1, pp. 311-318, Jan. 1, 2005.

Tardiff, D.F., et al., Protein characterization of *Saccharomyces cerevisiae* RNA polymerase II after in vivo cross-linking, Proceedings of the National Academy of Sciences, vol. 104, No. 50, pp. 19948-19953, Dec. 11, 2007.

Trester-Zedlitz, M., et al., A modular cross-linking approach for exploring protein interactions, Journal of the American Chemical Society, vol. 125, No. 9, pp. 2416-2425, Mar. 5, 2003.

Trnka, M.J., et al., Matching cross-linked peptide spectra: only as good as the worse identification, Molecular & Cellular Proteomics, vol. 13, No. 2, pp. 420-434, Feb. 2014.

Tsunoda, T., et al., A facile procedure for acetalization under aprotic conditions, Tetrahedron Letters, vol. 21, No. 14, pp. 1357-1358, 1980.

Vasilescu, J. et al., Identification of protein-protein interactions using in vivo cross-linking and mass spectrometry, Proteomics, vol. 4, No. 12, pp. 3845-3854, Dec. 12, 2004.

Vellucci, D., et al., Selective enrichment and identification of azide-tagged cross-linked peptides using chemical ligation and mass spectrometry, Journal of the American Society for Mass Spectrometry, vol. 21, No. 8, pp. 1432-1445, Aug. 2010.

Walzthoeni, T., et al., False discovery rate estimation for cross-linked peptides identified by mass spectrometry, Nature Methods, vol. 9, No. 9, pp. 901-903, Sep. 2012.

Yabe, J T. et al. Regulation of the transition from vimentin to neurofilaments during neuronal differentiation, Cell Motility and the Cytoskeleton, vol. 56, No. 3, pp. 193-205, Nov. 2003.

Yang, B., et al., Identification of cross-linked peptides from complex samples, Nature Methods, vol. 9, No. 9, pp. 904-906, Sep. 2012.

Yang, L., et al., A photocleavable and mass spectrometry identifiable cross-linker for protein interaction studies, Analytical Chemistry, vol. 82, No. 9, pp. 3556-3566, May 1, 2010.

Yu, C. et al. Developing new isotope-coded mass spectrometry-cleavable cross-linkers for elucidating protein structures, Analytical Chemistry, vol. 86, No. 4, pp. 2099-2106, Feb. 18, 2014.

Zhang, H., et al., Identification of protein-protein interactions and topologies in living cells with chemical cross-linking and mass spectrometry, Molecular & Cellular Proteomics, vol. 8, No. 3, pp. 409-420, Nov. 2009.

Zhang, H., et al., In vivo identification of the outer membrane protein OmcA-MtrC interaction network in Shewanella oneidensis MR-1 cells using novel hydrophobic chemical cross-linkers, Journal of Proteome Research, vol. 7, No. 4, pp. 1712-1720, Apr. 2008.

Zheng, Y., et al., Temporal regulation of EGF signaling networks by the scaffold protein Shc1, Nature, vol. 499, pp. 166-177, Jul. 11, 2013.

\* cited by examiner

Compound 1 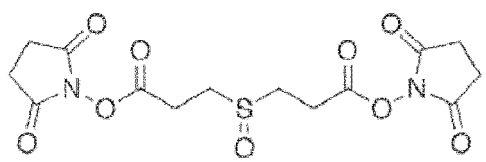
General Structure 2 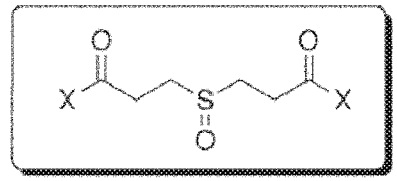
Compound 3    X = 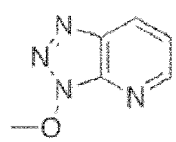
Compound 4    X = 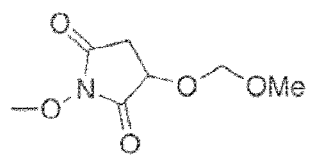
Compound 5    X = 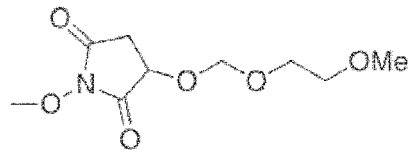
Compound 6    X = 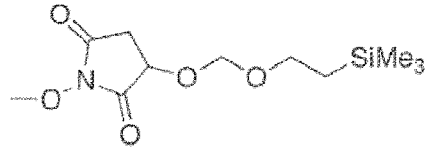
Compound 7    X = 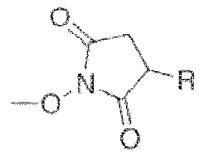    Where R is any organic group
Compound 8    X = 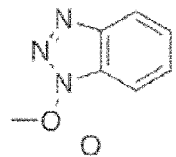
Compound 9    X = 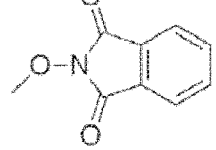
FIG. 1

FIG. 14
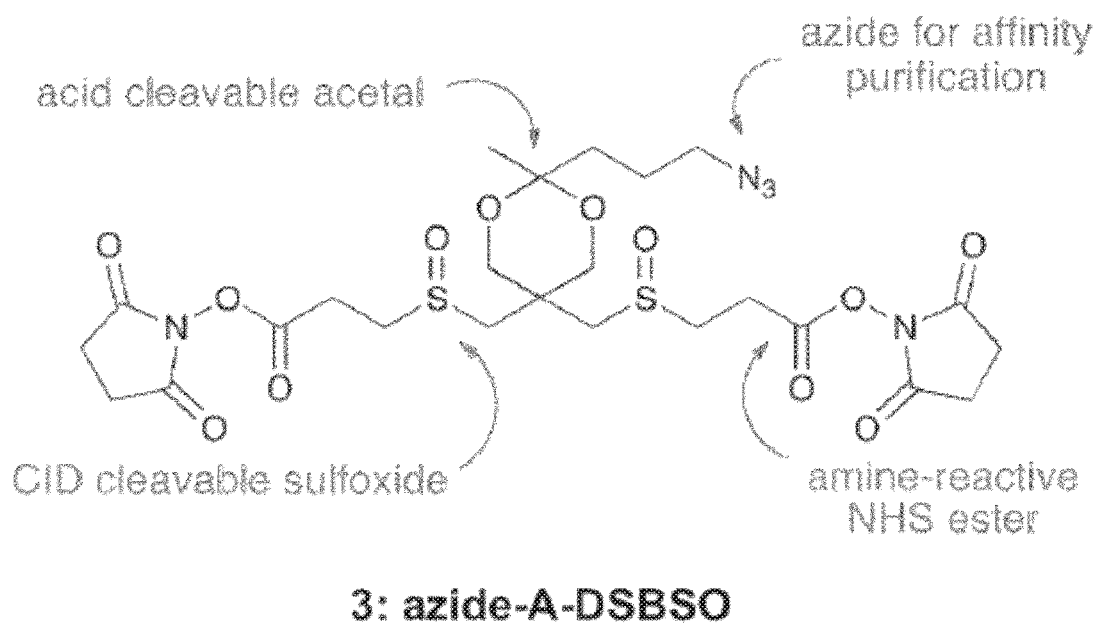
3: azide-A-DSBSO
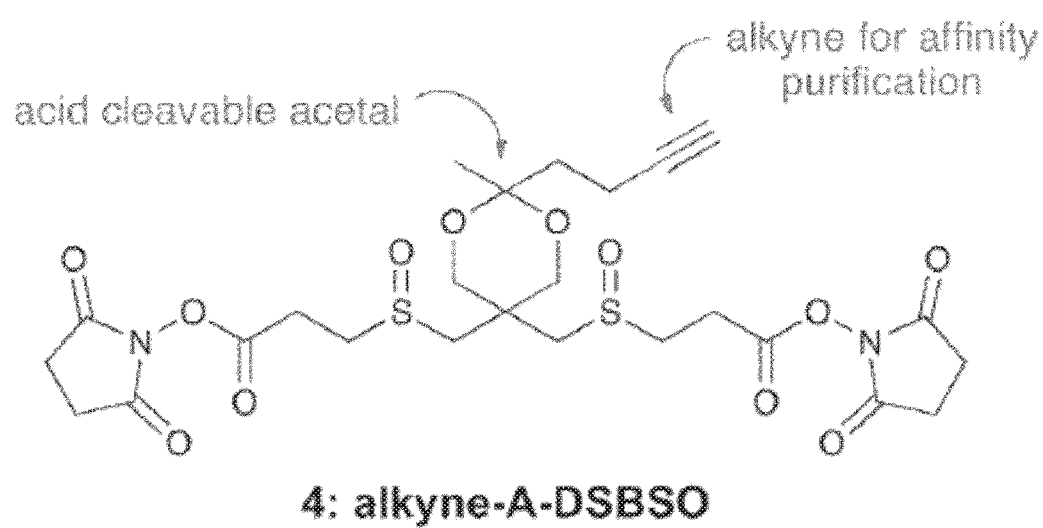
4: alkyne-A-DSBSO

FIG. 28A
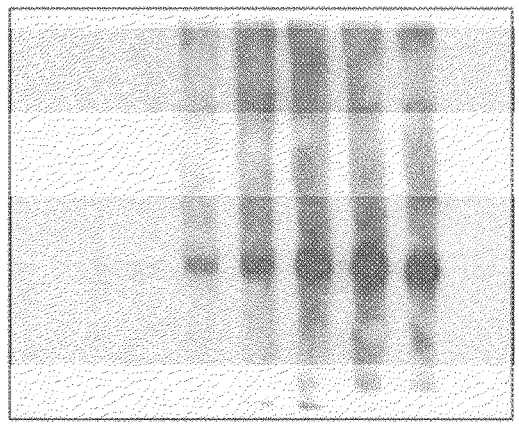
FIG. 28C
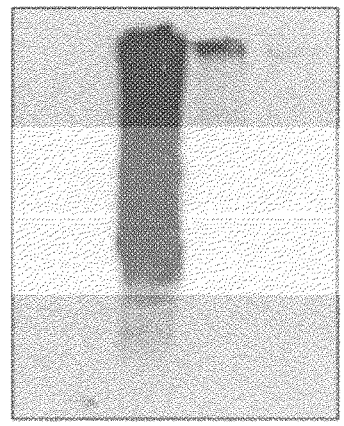
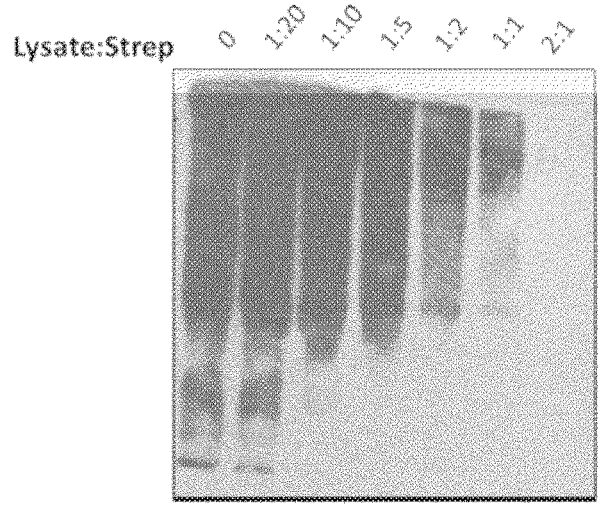
FIG. 28B

FIG. 29A
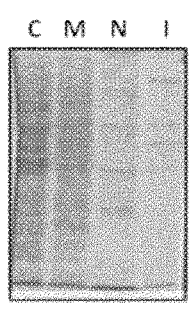
FIG. 29B
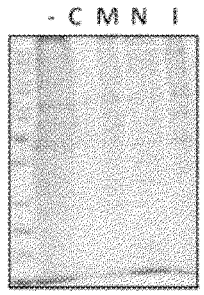
FIG. 29C
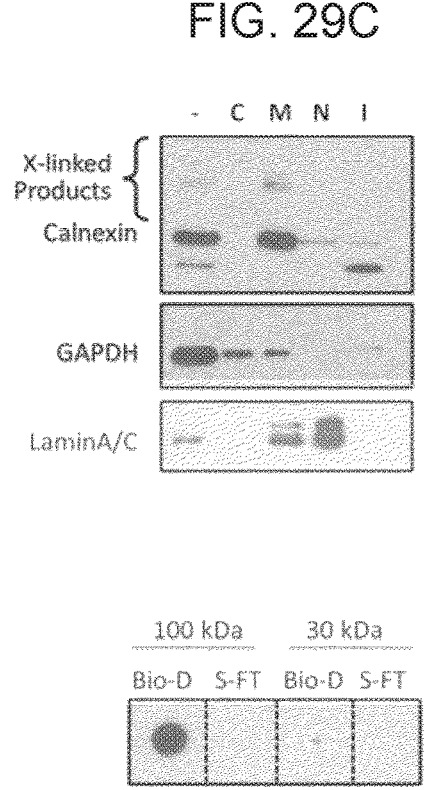
FIG. 29D
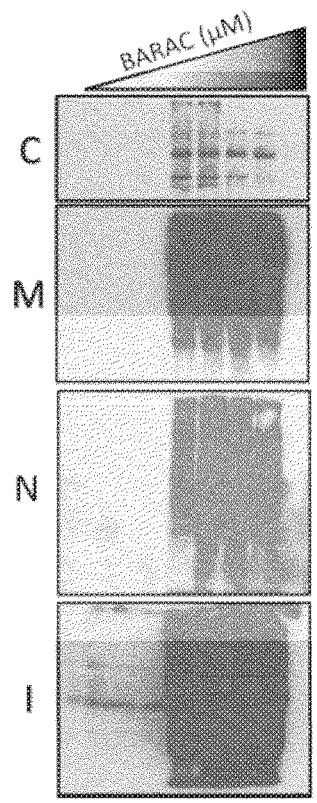
FIG. 29E FIG. 31A
FIG. 31B
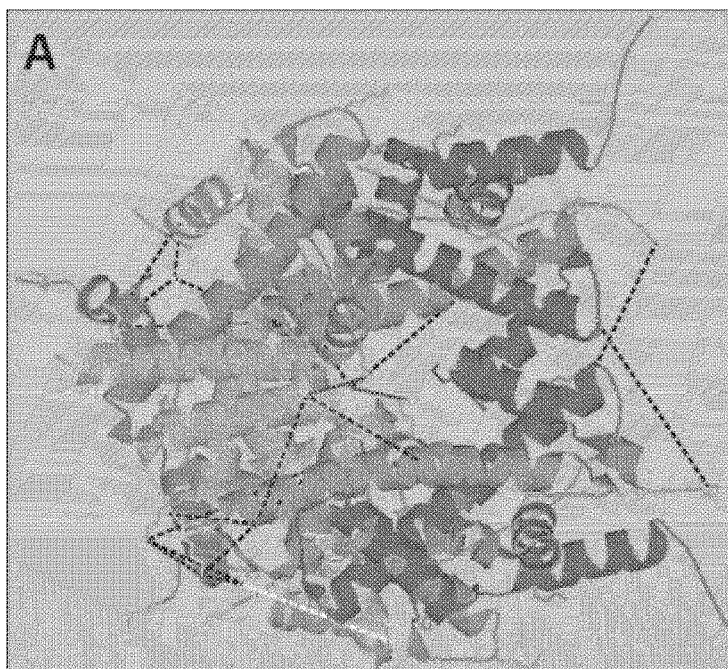
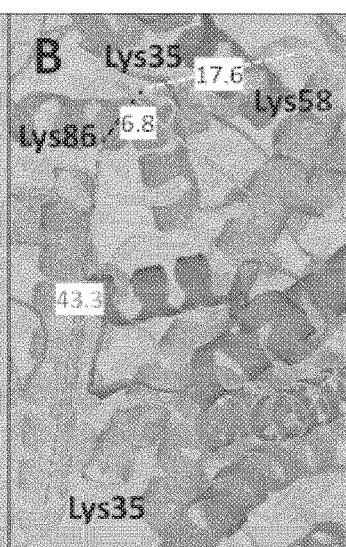
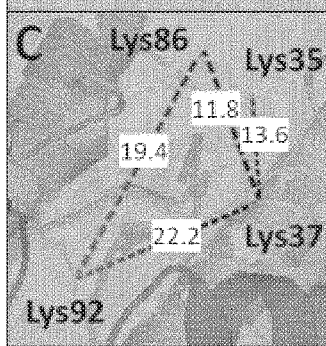
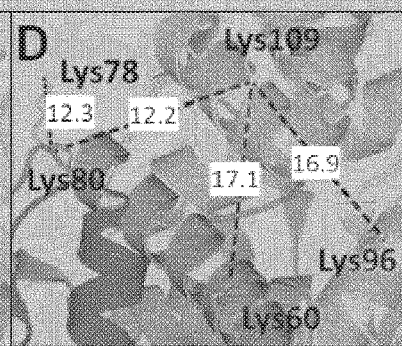
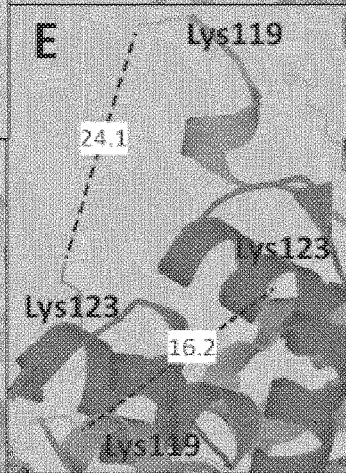
FIG. 31C
FIG. 31D
FIG. 31E

```
                     SEQUENCE LISTING

<160> NUMBER OF SEQ ID NOS: 445

<210> SEQ ID NO 1
<211> LENGTH: 7
<212> TYPE: PRT
<213> ORGANISM: Artificial
<220> FEATURE:
<223> OTHER INFORMATION: Synthetic

<400> SEQUENCE: 1

Ile Glu Ala Glu Lys Gly Arg
1               5

<210> SEQ ID NO 2
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: N terminal acetyl

<400> SEQUENCE: 2

Ile Glu Ala Glu Lys Gly Arg
1               5

<210> SEQ ID NO 3
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: N terminal acetyl
<220> FEATURE:
<221> NAME/KEY: MISC_FEATURE
<222> LOCATION: (5)..(5)
<223> OTHER INFORMATION: Alkene modification of Lysine 5

<400> SEQUENCE: 3

Ile Glu Ala Glu Lys Gly Arg
1               5

<210> SEQ ID NO 4
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: N terminal acetyl
<220> FEATURE:
<221> NAME/KEY: MISC_FEATURE
<222> LOCATION: (5)..(5)
<223> OTHER INFORMATION: Sulfenic acid modification of Lysine 5

<400> SEQUENCE: 4

Ile Glu Ala Glu Lys Gly Arg
```

```
1               5

<210> SEQ ID NO 5
<211> LENGTH: 11
<212> TYPE: PRT
<213> ORGANISM: Artificial
<220> FEATURE:
<223> OTHER INFORMATION: Synthetic

<400> SEQUENCE: 5

Ala Ser Gln Lys Arg Pro Ser Gln Arg His Gly
1               5                   10

<210> SEQ ID NO 6
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: N terminal acetyl

<400> SEQUENCE: 6

Ala Ser Gln Lys Arg Pro Ser Gln Arg His Gly
1               5                   10

<210> SEQ ID NO 7
<211> LENGTH: 7
<212> TYPE: PRT
<213> ORGANISM: Artificial
<220> FEATURE:
<223> OTHER INFORMATION: Synthetic

<400> SEQUENCE: 7

Arg Pro Lys Pro Gln Gln Phe
1               5

<210> SEQ ID NO 8
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification of Lysine 3

<400> SEQUENCE: 8

Arg Pro Lys Pro Gln Gln Phe
1               5

<210> SEQ ID NO 9
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Dead-end modification of Lysine 3

<400> SEQUENCE: 9

Arg Pro Lys Pro Gln Gln Phe
1               5
```

```
-continued

<210> SEQ ID NO 10
<211> LENGTH: 8
<212> TYPE: PRT
<213> ORGANISM: Artificial
<220> FEATURE:
<223> OTHER INFORMATION: Synthetic

<400> SEQUENCE: 10

Gly Asp Val Glu Lys Gly Lys Lys
1               5

<210> SEQ ID NO 11
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: N terminal acetyl

<400> SEQUENCE: 11

Gly Asp Val Glu Lys Gly Lys Lys
1               5

<210> SEQ ID NO 12
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: N terminal acetyl
<220> FEATURE:
<221> NAME/KEY: MISC_FEATURE
<222> LOCATION: (5)..(5)
<223> OTHER INFORMATION: Alkene modification of Lysine 5

<400> SEQUENCE: 12

Gly Asp Val Glu Lys Gly Lys Lys
1               5

<210> SEQ ID NO 13
<211> LENGTH: 5
<212> TYPE: PRT
<213> ORGANISM: Artificial
<220> FEATURE:
<223> OTHER INFORMATION: Synthetic

<400> SEQUENCE: 13

Lys Lys Gly Glu Arg
1               5

<210> SEQ ID NO 14
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification of Lysine 1

<400> SEQUENCE: 14

Lys Lys Gly Glu Arg
1               5
```

```
<210> SEQ ID NO 15
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification of Lysine 1

<400> SEQUENCE: 15

Lys Lys Gly Glu Arg
1               5

<210> SEQ ID NO 16
<211> LENGTH: 13
<212> TYPE: PRT
<213> ORGANISM: Artificial
<220> FEATURE:
<223> OTHER INFORMATION: Synthetic

<400> SEQUENCE: 16

His Lys Thr Gly Pro Asn Leu His Gly Leu Phe Gly Arg
1               5                   10

<210> SEQ ID NO 17
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification of Lysine 2

<400> SEQUENCE: 17

His Lys Thr Gly Pro Asn Leu His Gly Leu Phe Gly Arg
1               5                   10

<210> SEQ ID NO 18
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification of Lysine 2

<400> SEQUENCE: 18

His Lys Thr Gly Pro Asn Leu His Gly Leu Phe Gly Arg
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic

<400> SEQUENCE: 19

Lys Thr Gly Gln Ala Pro Gly Phe Ser Tyr Thr Asp Ala Asn Lys
1               5                   10                  15

<210> SEQ ID NO 20
<211> LENGTH: 15
```

```
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Dead-end modification of Lysine 1

<400> SEQUENCE: 20

Lys Thr Gly Gln Ala Pro Gly Phe Ser Tyr Thr Asp Ala Asn Lys
 1               5                  10                  15

<210> SEQ ID NO 21
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification of Lysine 1

<400> SEQUENCE: 21

Lys Thr Gly Gln Ala Pro Gly Phe Ser Tyr Thr Asp Ala Asn Lys
 1               5                  10                  15

<210> SEQ ID NO 22
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification of Lysine 1

<400> SEQUENCE: 22

Lys Thr Gly Gln Ala Pro Gly Phe Ser Tyr Thr Asp Ala Asn Lys
 1               5                  10                  15

<210> SEQ ID NO 23
<211> LENGTH: 16
<212> TYPE: PRT
<213> ORGANISM: Artificial
<220> FEATURE:
<223> OTHER INFORMATION: Synthetic

<400> SEQUENCE: 23

Gly Gly Lys His Lys Thr Gly Pro Asn Leu His Gly Leu Phe Gly Arg
 1               5                  10                  15

<210> SEQ ID NO 24
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(5)
<223> OTHER INFORMATION: Lysine 3 and Lysine 5 intra-peptide linkage

<400> SEQUENCE: 24

Gly Gly Lys His Lys Thr Gly Pro Asn Leu His Gly Leu Phe Gly Arg
 1               5                  10                  15
```

```
<210> SEQ ID NO 25
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification of Lysine 3
<220> FEATURE:
<221> NAME/KEY: MISC_FEATURE
<222> LOCATION: (5)..(5)
<223> OTHER INFORMATION: Thiol modification of Lysine 5

<400> SEQUENCE: 25

Gly Gly Lys His Lys Thr Gly Pro Asn Leu His Gly Leu Phe Gly Arg
1               5                   10                  15

<210> SEQ ID NO 26
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification of Lysine 3
<220> FEATURE:
<221> NAME/KEY: MISC_FEATURE
<222> LOCATION: (5)..(5)
<223> OTHER INFORMATION: Alkene modification of Lysine 5

<400> SEQUENCE: 26

Gly Gly Lys His Lys Thr Gly Pro Asn Leu His Gly Leu Phe Gly Arg
1               5                   10                  15

<210> SEQ ID NO 27
<211> LENGTH: 14
<212> TYPE: PRT
<213> ORGANISM: Artificial
<220> FEATURE:
<223> OTHER INFORMATION: Synthetic

<400> SEQUENCE: 27

Asn Lys Pro Glu Leu Tyr Gln Ile Asp Tyr Leu Gly Thr Lys
1               5                   10

<210> SEQ ID NO 28
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification of Lysine 2

<400> SEQUENCE: 28

Asn Lys Pro Glu Leu Tyr Gln Ile Asp Tyr Leu Gly Thr Lys
1               5                   10

<210> SEQ ID NO 29
<211> LENGTH: 14
<212> TYPE: PRT
<213> ORGANISM: Artificial
<220> FEATURE:
<223> OTHER INFORMATION: Synthetic
```

```
<400> SEQUENCE: 29

Leu Gly Ser Gln Ser Leu Gly Val Ser Asn Lys Phe Glu Lys
1               5                   10

<210> SEQ ID NO 30
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Thiol modification of Lysine 11

<400> SEQUENCE: 30

Leu Gly Ser Gln Ser Leu Gly Val Ser Asn Lys Phe Glu Lys
1               5                   10

<210> SEQ ID NO 31
<211> LENGTH: 7
<212> TYPE: PRT
<213> ORGANISM: Artificial
<220> FEATURE:
<223> OTHER INFORMATION: Synthetic

<400> SEQUENCE: 31

Gly Asp Val Glu Lys Gly Lys
1               5

<210> SEQ ID NO 32
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: N terminal acetyl

<400> SEQUENCE: 32

Gly Asp Val Glu Lys Gly Lys
1               5

<210> SEQ ID NO 33
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: N terminal acetyl
<220> FEATURE:
<221> NAME/KEY: MISC_FEATURE
<222> LOCATION: (5)..(5)
<223> OTHER INFORMATION: Thiol modification of Lysine 5

<400> SEQUENCE: 33

Gly Asp Val Glu Lys Gly Lys
1               5

<210> SEQ ID NO 34
<211> LENGTH: 7
<212> TYPE: PRT
<213> ORGANISM: Artificial
<220> FEATURE:
<223> OTHER INFORMATION: Synthetic
<220> FEATURE:
```

```
<221> NAME/KEY: MISC_FEATURE
<223> OTHER INFORMATION: N terminal acetyl
<220> FEATURE:
<221> NAME/KEY: MISC_FEATURE
<222> LOCATION: (5)..(5)
<223> OTHER INFORMATION: Alkene modification of Lysine 5

<400> SEQUENCE: 34

Gly Asp Val Glu Lys Gly Lys
1               5

<210> SEQ ID NO 35
<211> LENGTH: 6
<212> TYPE: PRT
<213> ORGANISM: Artificial
<220> FEATURE:
<223> OTHER INFORMATION: Synthetic

<400> SEQUENCE: 35

Lys Ile Phe Val Gln Lys
1               5

<210> SEQ ID NO 36
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification of Lysine 1

<400> SEQUENCE: 36

Lys Ile Phe Val Gln Lys
1               5

<210> SEQ ID NO 37
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification of Lysine 1

<400> SEQUENCE: 37

Lys Ile Phe Val Gln Lys
1               5

<210> SEQ ID NO 38
<211> LENGTH: 4
<212> TYPE: PRT
<213> ORGANISM: Artificial
<220> FEATURE:
<223> OTHER INFORMATION: Synthetic

<400> SEQUENCE: 38

Lys Gly Glu Arg
1

<210> SEQ ID NO 39
<211> LENGTH: 9
<212> TYPE: PRT
<213> ORGANISM: Artificial
<220> FEATURE:
<223> OTHER INFORMATION: Synthetic
```

-continued

```
<400> SEQUENCE: 39

Glu Asp Leu Ile Ala Tyr Leu Lys Lys
1               5

<210> SEQ ID NO 40
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: Alkene modification of Lysine 8
<220> FEATURE:
<221> NAME/KEY: MISC_FEATURE
<222> LOCATION: (8)..(8)
<223> OTHER INFORMATION: Alkene modification of Lysine 8

<400> SEQUENCE: 40

Glu Asp Leu Ile Ala Tyr Leu Lys Lys
1               5

<210> SEQ ID NO 41
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Thiol modification of Lysine 8

<400> SEQUENCE: 41

Glu Asp Leu Ile Ala Tyr Leu Lys Lys
1               5

<210> SEQ ID NO 42
<211> LENGTH: 5
<212> TYPE: PRT
<213> ORGANISM: Artificial
<220> FEATURE:
<223> OTHER INFORMATION: Synthetic

<400> SEQUENCE: 42

Lys Ala Thr Asn Glu
1               5

<210> SEQ ID NO 43
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification of Lysine 1

<400> SEQUENCE: 43

Lys Ala Thr Asn Glu
1               5

<210> SEQ ID NO 44
<211> LENGTH: 5
<212> TYPE: PRT
<213> ORGANISM: Artificial
<220> FEATURE:
```

```
<223> OTHER INFORMATION: Synthetic

<400> SEQUENCE: 44

Gly Gly Lys His Lys
1               5

<210> SEQ ID NO 45
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification of Lysine 3

<400> SEQUENCE: 45

Gly Gly Lys His Lys
1               5

<210> SEQ ID NO 46
<211> LENGTH: 16
<212> TYPE: PRT
<213> ORGANISM: Artificial
<220> FEATURE:
<223> OTHER INFORMATION: Synthetic

<400> SEQUENCE: 46

Thr Gly Gln Ala Pro Gly Phe Ser Tyr Thr Asp Ala Asn Lys Asn Lys
1               5                   10                  15

<210> SEQ ID NO 47
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Thiol modification of Lysine 14

<400> SEQUENCE: 47

Thr Gly Gln Ala Pro Gly Phe Ser Tyr Thr Asp Ala Asn Lys Asn Lys
1               5                   10                  15

<210> SEQ ID NO 48
<211> LENGTH: 13
<212> TYPE: PRT
<213> ORGANISM: Artificial
<220> FEATURE:
<223> OTHER INFORMATION: Synthetic

<400> SEQUENCE: 48

Tyr Ile Pro Gly Thr Lys Met Ile Phe Ala Gly Ile Lys
1               5                   10

<210> SEQ ID NO 49
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Oxidation of Methionine 7
```

```
<400> SEQUENCE: 49

Tyr Ile Pro Gly Thr Lys Met Ile Phe Ala Gly Ile Lys
1               5                   10

<210> SEQ ID NO 50
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification of Lysine 6
<220> FEATURE:
<221> NAME/KEY: MISC_FEATURE
<222> LOCATION: (7)..(7)
<223> OTHER INFORMATION: Oxdation of Methionine 7

<400> SEQUENCE: 50

Tyr Ile Pro Gly Thr Lys Met Ile Phe Ala Gly Ile Lys
1               5                   10

<210> SEQ ID NO 51
<211> LENGTH: 7
<212> TYPE: PRT
<213> ORGANISM: Artificial
<220> FEATURE:
<223> OTHER INFORMATION: Synthetic

<400> SEQUENCE: 51

Lys Tyr Ile Pro Gly Thr Lys
1               5

<210> SEQ ID NO 52
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification of Lysine 1

<400> SEQUENCE: 52

Lys Tyr Ile Pro Gly Thr Lys
1               5

<210> SEQ ID NO 53
<211> LENGTH: 8
<212> TYPE: PRT
<213> ORGANISM: Artificial
<220> FEATURE:
<223> OTHER INFORMATION: Synthetic

<400> SEQUENCE: 53

Met Ile Phe Ala Gly Ile Lys Lys
1               5

<210> SEQ ID NO 54
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: Oxidation of Methionine 1

<400> SEQUENCE: 54

Met Ile Phe Ala Gly Ile Lys Lys
1               5

<210> SEQ ID NO 55
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Oxidation of Methionine 1
<220> FEATURE:
<221> NAME/KEY: MISC_FEATURE
<222> LOCATION: (7)..(7)
<223> OTHER INFORMATION: Thiol modification of Lysine 7

<400> SEQUENCE: 55

Met Ile Phe Ala Gly Ile Lys Lys
1               5

<210> SEQ ID NO 56
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Thiol modification of Lysine 7

<400> SEQUENCE: 56

Met Ile Phe Ala Gly Ile Lys Lys
1               5

<210> SEQ ID NO 57
<211> LENGTH: 21
<212> TYPE: PRT
<213> ORGANISM: Artificial
<220> FEATURE:
<223> OTHER INFORMATION: Synthetic

<400> SEQUENCE: 57

Thr Leu Thr Gly Lys Thr Ile Thr Leu Glu Val Glu Pro Ser Asp Thr
1               5                   10                  15

Ile Glu Asn Val Lys
            20

<210> SEQ ID NO 58
<211> LENGTH: 13
<212> TYPE: PRT
<213> ORGANISM: Artificial
<220> FEATURE:
<223> OTHER INFORMATION: Synthetic

<400> SEQUENCE: 58

Ile Gln Asp Lys Glu Gly Ile Pro Pro Asp Gln Gln Arg
1               5                   10

<210> SEQ ID NO 59
<211> LENGTH: 13
<212> TYPE: PRT
<213> ORGANISM: Artificial
```

```
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification of Lysine 4

<400> SEQUENCE: 59

Ile Gln Asp Lys Glu Gly Ile Pro Pro Asp Gln Gln Arg
1               5                   10

<210> SEQ ID NO 60
<211> LENGTH: 12
<212> TYPE: PRT
<213> ORGANISM: Artificial
<220> FEATURE:
<223> OTHER INFORMATION: Synthetic

<400> SEQUENCE: 60

Leu Ile Phe Ala Gly Lys Gln Leu Glu Asp Gly Arg
1               5                   10

<210> SEQ ID NO 61
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification of Lysine 6

<400> SEQUENCE: 61

Leu Ile Phe Ala Gly Lys Gln Leu Glu Asp Gly Arg
1               5                   10

<210> SEQ ID NO 62
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Thiol modification of Lysine 6

<400> SEQUENCE: 62

Leu Ile Phe Ala Gly Lys Gln Leu Glu Asp Gly Arg
1               5                   10

<210> SEQ ID NO 63
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Inter-peptide linkage at Lysine 6

<400> SEQUENCE: 63

Leu Ile Phe Ala Gly Lys Gln Leu Glu Asp Gly Arg
1               5                   10

<210> SEQ ID NO 64
<211> LENGTH: 18
```

```
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification of Lysine 9

<400> SEQUENCE: 64

Thr Leu Ser Asp Tyr Asn Ile Gln Lys Glu Ser Thr Leu His Leu Val
1               5                   10                  15

Leu Arg

<210> SEQ ID NO 65
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Thiol modification of Lysine 9

<400> SEQUENCE: 65

Thr Leu Ser Asp Tyr Asn Ile Gln Lys Glu Ser Thr Leu His Leu Val
1               5                   10                  15

Leu Arg

<210> SEQ ID NO 66
<211> LENGTH: 20
<212> TYPE: PRT
<213> ORGANISM: Artificial
<220> FEATURE:
<223> OTHER INFORMATION: Synthetic

<400> SEQUENCE: 66

Ala Thr Ala Thr Gly Pro Lys Gln Gln Glu Ile Thr Thr Asn Leu Glu
1               5                   10                  15

Asn His Phe Lys
            20

<210> SEQ ID NO 67
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene modification of Lysine 7

<400> SEQUENCE: 67

Ala Thr Ala Thr Gly Pro Lys Gln Gln Glu Ile Thr Thr Asn Leu Glu
1               5                   10                  15

Asn His Phe Lys
            20

<210> SEQ ID NO 68
<211> LENGTH: 5
<212> TYPE: PRT
<213> ORGANISM: Artificial
<220> FEATURE:
<223> OTHER INFORMATION: Synthetic
```

```
<400> SEQUENCE: 68

Lys Val Pro Asp Lys
1               5

<210> SEQ ID NO 69
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification of Lysine 1

<400> SEQUENCE: 69

Lys Val Pro Asp Lys
1               5

<210> SEQ ID NO 70
<211> LENGTH: 8
<212> TYPE: PRT
<213> ORGANISM: Artificial
<220> FEATURE:
<223> OTHER INFORMATION: Synthetic

<400> SEQUENCE: 70

Lys Val Ala His Thr Ser Tyr Lys
1               5

<210> SEQ ID NO 71
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification of Lysine 1

<400> SEQUENCE: 71

Lys Val Ala His Thr Ser Tyr Lys
1               5

<210> SEQ ID NO 72
<211> LENGTH: 7
<212> TYPE: PRT
<213> ORGANISM: Artificial
<220> FEATURE:
<223> OTHER INFORMATION: Synthetic

<400> SEQUENCE: 72

Val Leu Val Asp Lys Ser Arg
1               5

<210> SEQ ID NO 73
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification of Lysine 5

<400> SEQUENCE: 73
```

-continued

Val Leu Val Asp Lys Ser Arg
1               5

<210> SEQ ID NO 74
<211> LENGTH: 8
<212> TYPE: PRT
<213> ORGANISM: Artificial
<220> FEATURE:
<223> OTHER INFORMATION: Synthetic

<400> SEQUENCE: 74

Ile Phe Lys Pro Gln Glu Ile Lys
1               5

<210> SEQ ID NO 75
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification of Lysine 3

<400> SEQUENCE: 75

Ile Phe Lys Pro Gln Glu Ile Lys
1               5

<210> SEQ ID NO 76
<211> LENGTH: 7
<212> TYPE: PRT
<213> ORGANISM: Artificial
<220> FEATURE:
<223> OTHER INFORMATION: Synthetic

<400> SEQUENCE: 76

Leu Tyr Lys Leu Asn Asp Lys
1               5

<210> SEQ ID NO 77
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification of Lysine 3

<400> SEQUENCE: 77

Leu Tyr Lys Leu Asn Asp Lys
1               5

<210> SEQ ID NO 78
<211> LENGTH: 21
<212> TYPE: PRT
<213> ORGANISM: Artificial
<220> FEATURE:
<223> OTHER INFORMATION: Synthetic

<400> SEQUENCE: 78

Ile His Ala Gln Asn Tyr Leu Lys Thr Tyr Asn Glu Asp Ile Pro Val
1               5                   10                  15

Glu Ile Leu Val Arg
            20

```
<210> SEQ ID NO 79
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Thiol modification of Lysine 8

<400> SEQUENCE: 79

Ile His Ala Gln Asn Tyr Leu Lys Thr Tyr Asn Glu Asp Ile Pro Val
1               5                   10                  15

Glu Ile Leu Val Arg
            20

<210> SEQ ID NO 80
<211> LENGTH: 7
<212> TYPE: PRT
<213> ORGANISM: Artificial
<220> FEATURE:
<223> OTHER INFORMATION: Synthetic

<400> SEQUENCE: 80

Tyr Lys Thr Asn Leu Tyr Lys
1               5

<210> SEQ ID NO 81
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification of Lysine 2

<400> SEQUENCE: 81

Tyr Lys Thr Asn Leu Tyr Lys
1               5

<210> SEQ ID NO 82
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification of Lysine 2

<400> SEQUENCE: 82

Tyr Lys Thr Asn Leu Tyr Lys
1               5

<210> SEQ ID NO 83
<211> LENGTH: 9
<212> TYPE: PRT
<213> ORGANISM: Artificial
<220> FEATURE:
<223> OTHER INFORMATION: Synthetic

<400> SEQUENCE: 83

Glu Phe Leu Glu Lys Asn Tyr Asp Arg
1               5
```

```
<210> SEQ ID NO 84
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification of Lysine 5

<400> SEQUENCE: 84

Glu Phe Leu Glu Lys Asn Tyr Asp Arg
1               5

<210> SEQ ID NO 85
<211> LENGTH: 6
<212> TYPE: PRT
<213> ORGANISM: Artificial
<220> FEATURE:
<223> OTHER INFORMATION: Synthetic

<400> SEQUENCE: 85

Asn Ser Lys Thr Val Arg
1               5

<210> SEQ ID NO 86
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkane modification of Lysine 3

<400> SEQUENCE: 86

Asn Ser Lys Thr Val Arg
1               5

<210> SEQ ID NO 87
<211> LENGTH: 9
<212> TYPE: PRT
<213> ORGANISM: Artificial
<220> FEATURE:
<223> OTHER INFORMATION: Synthetic

<400> SEQUENCE: 87

Ile Leu Lys Gln Val Met Glu Glu Lys
1               5

<210> SEQ ID NO 88
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification of Lysine 3

<400> SEQUENCE: 88

Ile Leu Lys Gln Val Met Glu Glu Lys
1               5
```

```
<210> SEQ ID NO 89
<211> LENGTH: 5
<212> TYPE: PRT
<213> ORGANISM: Artificial
<220> FEATURE:
<223> OTHER INFORMATION: Synthetic

<400> SEQUENCE: 89

Glu Leu Lys Glu Lys
1               5

<210> SEQ ID NO 90
<211> LENGTH: 6
<212> TYPE: PRT
<213> ORGANISM: Artificial
<220> FEATURE:
<223> OTHER INFORMATION: Synthetic

<400> SEQUENCE: 90

Ser Tyr Lys Phe Pro Arg
1               5

<210> SEQ ID NO 91
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification of Lysine 3

<400> SEQUENCE: 91

Ser Tyr Lys Phe Pro Arg
1               5

<210> SEQ ID NO 92
<211> LENGTH: 5
<212> TYPE: PRT
<213> ORGANISM: Artificial
<220> FEATURE:
<223> OTHER INFORMATION: Synthetic

<400> SEQUENCE: 92

Glu Glu Lys Gln Lys
1               5

<210> SEQ ID NO 93
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification of Lysine 3

<400> SEQUENCE: 93

Glu Glu Lys Gln Lys
1               5

<210> SEQ ID NO 94
<211> LENGTH: 5
<212> TYPE: PRT
<213> ORGANISM: Artificial
<220> FEATURE:
<223> OTHER INFORMATION: Synthetic
```

```
<400> SEQUENCE: 94

Leu Lys Glu Glu Arg
1               5

<210> SEQ ID NO 95
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification of Lysine 2

<400> SEQUENCE: 95

Leu Lys Glu Glu Arg
1               5

<210> SEQ ID NO 96
<211> LENGTH: 5
<212> TYPE: PRT
<213> ORGANISM: Artificial
<220> FEATURE:
<223> OTHER INFORMATION: Synthetic

<400> SEQUENCE: 96

Tyr Leu Lys Met Arg
1               5

<210> SEQ ID NO 97
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Oxidation of Methionine 4

<400> SEQUENCE: 97

Tyr Leu Lys Met Arg
1               5

<210> SEQ ID NO 98
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification of Lysine 3
<220> FEATURE:
<221> NAME/KEY: MISC_FEATURE
<222> LOCATION: (4)..(4)
<223> OTHER INFORMATION: Oxidation of Methionine 4

<400> SEQUENCE: 98

Tyr Leu Lys Met Arg
1               5

<210> SEQ ID NO 99
<211> LENGTH: 15
<212> TYPE: PRT
<213> ORGANISM: Artificial
```

```
<220> FEATURE:
<223> OTHER INFORMATION: Synthetic

<400> SEQUENCE: 99

Val Gln Asp Ser Val Ile Leu Ala Ser Ser Lys Ala Val Thr Arg
1               5                   10                  15

<210> SEQ ID NO 100
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Alkane modification of Lysine 11

<400> SEQUENCE: 100

Val Gln Asp Ser Val Ile Leu Ala Ser Ser Lys Ala Val Thr Arg
1               5                   10                  15

<210> SEQ ID NO 101
<211> LENGTH: 13
<212> TYPE: PRT
<213> ORGANISM: Artificial
<220> FEATURE:
<223> OTHER INFORMATION: Synthetic

<400> SEQUENCE: 101

Gly Ile Ser Val Leu Lys Asp Ser Asp Asp Lys Thr Arg
1               5                   10

<210> SEQ ID NO 102
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Thiol modification of Lysine 6

<400> SEQUENCE: 102

Gly Ile Ser Val Leu Lys Asp Ser Asp Asp Lys Thr Arg
1               5                   10

<210> SEQ ID NO 103
<211> LENGTH: 6
<212> TYPE: PRT
<213> ORGANISM: Artificial
<220> FEATURE:
<223> OTHER INFORMATION: Synthetic

<400> SEQUENCE: 103

Phe Lys Asn Ser Val Lys
1               5

<210> SEQ ID NO 104
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification of Lysine 2
```

<400> SEQUENCE: 104

Phe Lys Asn Ser Val Lys
1               5

<210> SEQ ID NO 105
<211> LENGTH: 6
<212> TYPE: PRT
<213> ORGANISM: Artificial
<220> FEATURE:
<223> OTHER INFORMATION: Synthetic

<400> SEQUENCE: 105

Lys Leu Ala Val Glu Arg
1               5

<210> SEQ ID NO 106
<211> LENGTH: 12
<212> TYPE: PRT
<213> ORGANISM: Artificial
<220> FEATURE:
<223> OTHER INFORMATION: Synthetic

<400> SEQUENCE: 106

Asn Gln Tyr Glu Pro Gly Thr Asn Gly Lys Val Lys
1               5                   10

<210> SEQ ID NO 107
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Alkene modification of Lysine 10

<400> SEQUENCE: 107

Asn Gln Tyr Glu Pro Gly Thr Asn Gly Lys Val Lys
1               5                   10

<210> SEQ ID NO 108
<211> LENGTH: 4
<212> TYPE: PRT
<213> ORGANISM: Artificial
<220> FEATURE:
<223> OTHER INFORMATION: Synthetic

<400> SEQUENCE: 108

Lys Pro Leu Lys
1

<210> SEQ ID NO 109
<211> LENGTH: 17
<212> TYPE: PRT
<213> ORGANISM: Artificial
<220> FEATURE:
<223> OTHER INFORMATION: Synthetic

<400> SEQUENCE: 109

Ala Glu Leu Glu Lys Leu Val Asp His His Pro Glu Gly Leu Ser Ala
1               5                   10                  15

Arg

<210> SEQ ID NO 110

```
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: Dead-end modification of Lysine 5

<400> SEQUENCE: 110

Ala Glu Leu Glu Lys Leu Val Asp His His Pro Glu Gly Leu Ser Ala
1               5                   10                  15

Arg

<210> SEQ ID NO 111
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification of Lysine 5

<400> SEQUENCE: 111

Ala Glu Leu Glu Lys Leu Val Asp His His Pro Glu Gly Leu Ser Ala
1               5                   10                  15

Arg

<210> SEQ ID NO 112
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Thiol modification of Lysine 5

<400> SEQUENCE: 112

Ala Glu Leu Glu Lys Leu Val Asp His His Pro Glu Gly Leu Ser Ala
1               5                   10                  15

Arg

<210> SEQ ID NO 113
<211> LENGTH: 14
<212> TYPE: PRT
<213> ORGANISM: Artificial
<220> FEATURE:
<223> OTHER INFORMATION: Synthetic

<400> SEQUENCE: 113

Lys Tyr Ile Pro Gly Thr Lys Met Ile Phe Ala Gly Ile Lys
1               5                   10

<210> SEQ ID NO 114
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Oxidation of Methionine 8
```

```
<400> SEQUENCE: 114

Lys Tyr Ile Pro Gly Thr Lys Met Ile Phe Ala Gly Ile Lys
1               5                   10

<210> SEQ ID NO 115
<211> LENGTH: 15
<212> TYPE: PRT
<213> ORGANISM: Artificial
<220> FEATURE:
<223> OTHER INFORMATION: Synthetic

<400> SEQUENCE: 115

Lys Tyr Ile Pro Gly Thr Lys Met Ile Phe Ala Gly Ile Lys Lys
1               5                   10                  15

<210> SEQ ID NO 116
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Oxidation of Methionine 8

<400> SEQUENCE: 116

Lys Tyr Ile Pro Gly Thr Lys Met Ile Phe Ala Gly Ile Lys Lys
1               5                   10                  15

<210> SEQ ID NO 117
<211> LENGTH: 9
<212> TYPE: PRT
<213> ORGANISM: Artificial
<220> FEATURE:
<223> OTHER INFORMATION: Synthetic

<400> SEQUENCE: 117

Met Ile Phe Ala Gly Ile Lys Lys Lys
1               5

<210> SEQ ID NO 118
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Oxidation of Methionine 1

<400> SEQUENCE: 118

Met Ile Phe Ala Gly Ile Lys Lys Lys
1               5

<210> SEQ ID NO 119
<211> LENGTH: 13
<212> TYPE: PRT
<213> ORGANISM: Artificial
<220> FEATURE:
<223> OTHER INFORMATION: Synthetic

<400> SEQUENCE: 119

Glu Asp Leu Ile Ala Tyr Leu Lys Lys Ala Thr Asn Glu
1               5                   10
```

```
<210> SEQ ID NO 120
<211> LENGTH: 15
<212> TYPE: PRT
<213> ORGANISM: Artificial
<220> FEATURE:
<223> OTHER INFORMATION: Synthetic

<400> SEQUENCE: 120

Tyr Ile Pro Gly Thr Lys Met Ile Phe Ala Gly Ile Lys Lys Lys
1               5                   10                  15

<210> SEQ ID NO 121
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Oxidation of Methionine 7

<400> SEQUENCE: 121

Tyr Ile Pro Gly Thr Lys Met Ile Phe Ala Gly Ile Lys Lys Lys
1               5                   10                  15

<210> SEQ ID NO 122
<211> LENGTH: 12
<212> TYPE: PRT
<213> ORGANISM: Artificial
<220> FEATURE:
<223> OTHER INFORMATION: Synthetic

<400> SEQUENCE: 122

Met Ile Phe Ala Gly Ile Lys Lys Lys Gly Glu Arg
1               5                   10

<210> SEQ ID NO 123
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Oxidation of Methionine 1

<400> SEQUENCE: 123

Met Ile Phe Ala Gly Ile Lys Lys Lys Gly Glu Arg
1               5                   10

<210> SEQ ID NO 124
<211> LENGTH: 8
<212> TYPE: PRT
<213> ORGANISM: Artificial
<220> FEATURE:
<223> OTHER INFORMATION: Synthetic

<400> SEQUENCE: 124

Gly Lys Lys Ile Phe Val Gln Lys
1               5

<210> SEQ ID NO 125
<211> LENGTH: 13
<212> TYPE: PRT
<213> ORGANISM: Artificial
<220> FEATURE:
<223> OTHER INFORMATION: Synthetic
```

<400> SEQUENCE: 125

Gly Asp Val Glu Lys Gly Lys Lys Ile Phe Val Gln Lys
1               5                   10

<210> SEQ ID NO 126
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: N terminal acetyl

<400> SEQUENCE: 126

Gly Asp Val Glu Lys Gly Lys Lys Ile Phe Val Gln Lys
1               5                   10

<210> SEQ ID NO 127
<211> LENGTH: 11
<212> TYPE: PRT
<213> ORGANISM: Artificial
<220> FEATURE:
<223> OTHER INFORMATION: Synthetic

<400> SEQUENCE: 127

Met Gln Ile Phe Val Lys Thr Leu Thr Gly Lys
1               5                   10

<210> SEQ ID NO 128
<211> LENGTH: 6
<212> TYPE: PRT
<213> ORGANISM: Artificial
<220> FEATURE:
<223> OTHER INFORMATION: Synthetic

<400> SEQUENCE: 128

Ala Lys Ile Gln Asp Lys
1               5

<210> SEQ ID NO 129
<211> LENGTH: 21
<212> TYPE: PRT
<213> ORGANISM: Artificial
<220> FEATURE:
<223> OTHER INFORMATION: Synthetic

<400> SEQUENCE: 129

Leu Ile Phe Ala Gly Lys Gln Leu Glu Asp Gly Arg Thr Leu Ser Asp
1               5                   10                  15

Tyr Asn Ile Gln Lys
            20

<210> SEQ ID NO 130
<211> LENGTH: 15
<212> TYPE: PRT
<213> ORGANISM: Artificial
<220> FEATURE:
<223> OTHER INFORMATION: Synthetic

<400> SEQUENCE: 130

Ala Lys Ile Gln Asp Lys Glu Gly Ile Pro Pro Asp Gln Gln Arg
1               5                   10                  15

<210> SEQ ID NO 131

```
<211> LENGTH: 9
<212> TYPE: PRT
<213> ORGANISM: Artificial
<220> FEATURE:
<223> OTHER INFORMATION: Synthetic

<400> SEQUENCE: 131

Ala Lys Ala Glu Ala Ala Glu Phe Arg
1               5

<210> SEQ ID NO 132
<211> LENGTH: 6
<212> TYPE: PRT
<213> ORGANISM: Artificial
<220> FEATURE:
<223> OTHER INFORMATION: Synthetic

<400> SEQUENCE: 132

Thr Phe Leu Glu Lys Arg
1               5

<210> SEQ ID NO 133
<211> LENGTH: 15
<212> TYPE: PRT
<213> ORGANISM: Artificial
<220> FEATURE:
<223> OTHER INFORMATION: Synthetic

<400> SEQUENCE: 133

Lys Val Thr Ser Thr Leu Leu Glu Gln Asp Thr Ser Thr Glu Lys
1               5                   10                  15

<210> SEQ ID NO 134
<211> LENGTH: 9
<212> TYPE: PRT
<213> ORGANISM: Artificial
<220> FEATURE:
<223> OTHER INFORMATION: Synthetic

<400> SEQUENCE: 134

Ser Thr Leu Lys Leu Gln Asp Thr Arg
1               5

<210> SEQ ID NO 135
<211> LENGTH: 8
<212> TYPE: PRT
<213> ORGANISM: Artificial
<220> FEATURE:
<223> OTHER INFORMATION: Synthetic

<400> SEQUENCE: 135

Ile Thr Pro Ser Lys Val Ser Lys
1               5

<210> SEQ ID NO 136
<211> LENGTH: 7
<212> TYPE: PRT
<213> ORGANISM: Artificial
<220> FEATURE:
<223> OTHER INFORMATION: Synthetic

<400> SEQUENCE: 136

Ile Leu Ile Glu Lys Ala Arg
1               5

<210> SEQ ID NO 137
<211> LENGTH: 9
```

```
<212> TYPE: PRT
<213> ORGANISM: Artificial
<220> FEATURE:
<223> OTHER INFORMATION: Synthetic

<400> SEQUENCE: 137

Thr Ala Glu Leu Ile Lys Glu Leu Lys
1               5

<210> SEQ ID NO 138
<211> LENGTH: 9
<212> TYPE: PRT
<213> ORGANISM: Artificial
<220> FEATURE:
<223> OTHER INFORMATION: Synthetic

<400> SEQUENCE: 138

Leu Leu Val Pro Gln Lys Asn Val Lys
1               5

<210> SEQ ID NO 139
<211> LENGTH: 8
<212> TYPE: PRT
<213> ORGANISM: Artificial
<220> FEATURE:
<223> OTHER INFORMATION: Synthetic

<400> SEQUENCE: 139

Glu Ala Val Lys Gln Ala Ala Lys
1               5

<210> SEQ ID NO 140
<211> LENGTH: 7
<212> TYPE: PRT
<213> ORGANISM: Artificial
<220> FEATURE:
<223> OTHER INFORMATION: Synthetic

<400> SEQUENCE: 140

Thr Asn Leu Tyr Lys Leu Lys
1               5

<210> SEQ ID NO 141
<211> LENGTH: 8
<212> TYPE: PRT
<213> ORGANISM: Artificial
<220> FEATURE:
<223> OTHER INFORMATION: Synthetic

<400> SEQUENCE: 141

Gln Glu Leu Ala Lys Ser Ile Arg
1               5

<210> SEQ ID NO 142
<211> LENGTH: 8
<212> TYPE: PRT
<213> ORGANISM: Artificial
<220> FEATURE:
<223> OTHER INFORMATION: Synthetic

<400> SEQUENCE: 142

Ile Val Asp Lys Asp Gly Ile Arg
1               5

<210> SEQ ID NO 143
<211> LENGTH: 9
<212> TYPE: PRT
```

```
<213> ORGANISM: Artificial
<220> FEATURE:
<223> OTHER INFORMATION: Synthetic

<400> SEQUENCE: 143

Lys Leu Ser Ile Asn Ser Ala Ala Arg
1               5

<210> SEQ ID NO 144
<211> LENGTH: 7
<212> TYPE: PRT
<213> ORGANISM: Artificial
<220> FEATURE:
<223> OTHER INFORMATION: Synthetic

<400> SEQUENCE: 144

Lys Glu Phe Tyr Glu Leu Lys
1               5

<210> SEQ ID NO 145
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Loss of Methionine sulfoxide at Methionine 1
<220> FEATURE:
<221> NAME/KEY: MISC_FEATURE
<222> LOCATION: (1)..(1)
<223> OTHER INFORMATION: Acetyl at Methionine 1
<220> FEATURE:
<221> NAME/KEY: MISC_FEATURE
<222> LOCATION: (6)..(6)
<223> OTHER INFORMATION: Alkene modification of Lysine 6

<400> SEQUENCE: 145

Met Gly Asp Val Glu Lys Gly Lys
1               5

<210> SEQ ID NO 146
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Loss of Methionine sulfoxide at Methionine 1
<220> FEATURE:
<221> NAME/KEY: MISC_FEATURE
<222> LOCATION: (1)..(1)
<223> OTHER INFORMATION: Acetyle at Methionine 1
<220> FEATURE:
<221> NAME/KEY: MISC_FEATURE
<222> LOCATION: (6)..(6)
<223> OTHER INFORMATION: Alkene modification of Lysine 6

<400> SEQUENCE: 146

Met Gly Asp Val Glu Lys Gly Lys Lys
1               5

<210> SEQ ID NO 147
<211> LENGTH: 13
<212> TYPE: PRT
<213> ORGANISM: Artificial
<220> FEATURE:
<223> OTHER INFORMATION: Synthetic
```

```
<220> FEATURE:
<221> NAME/KEY: MISC_FEATURE
<222> LOCATION: (2)..(2)
<223> OTHER INFORMATION: Alkene modification of Lysine 2

<400> SEQUENCE: 147

Lys Lys Gly Glu Arg Glu Asp Leu Ile Ala Tyr Leu Lys
1               5                   10

<210> SEQ ID NO 148
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification of Lysine 2
<220> FEATURE:
<221> NAME/KEY: MISC_FEATURE
<222> LOCATION: (3)..(3)
<223> OTHER INFORMATION: Alkene modification of Lysine 3

<400> SEQUENCE: 148

Gly Lys Lys Ile Phe Val Gln Lys
1               5

<210> SEQ ID NO 149
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification of Lysine 1

<400> SEQUENCE: 149

Lys Lys Gly Glu Arg Glu Asp Leu Ile Ala Tyr Leu Lys
1               5                   10

<210> SEQ ID NO 150
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification of Lysine 2

<400> SEQUENCE: 150

Lys Lys Gly Glu Arg Glu Asp Leu Ile Ala Tyr Leu Lys
1               5                   10

<210> SEQ ID NO 151
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Alkene modification of Lysine 7

<400> SEQUENCE: 151
```

```
Met Ile Phe Ala Gly Ile Lys Lys
1               5
```

<210> SEQ ID NO 152
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (1)..(1)
<223> OTHER INFORMATION: Alkene modification of Lysine 1

<400> SEQUENCE: 152

```
Lys Gly Glu Arg Glu Asp Leu Ile Ala Tyr Leu Lys
1               5                   10
```

<210> SEQ ID NO 153
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (4)..(4)
<223> OTHER INFORMATION: Alkene modification at Lysine 4

<400> SEQUENCE: 153

```
Ala Val Thr Lys Tyr Thr Ser Ala Lys
1               5
```

<210> SEQ ID NO 154
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (1)..(1)
<223> OTHER INFORMATION: Alkene modification at Lysine 1

<400> SEQUENCE: 154

```
Lys Glu Ser Tyr Ser Val Tyr Val Tyr Lys
1               5                   10
```

<210> SEQ ID NO 155
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (1)..(1)
<223> OTHER INFORMATION: Alkene modification at Lysine 1

<400> SEQUENCE: 155

```
Lys Gly Asn Tyr Ala Glu Arg
1               5
```

<210> SEQ ID NO 156
<211> LENGTH: 17
<212> TYPE: PRT
<213> ORGANISM: Artificial
<220> FEATURE:
<223> OTHER INFORMATION: Synthetic
<220> FEATURE:

```
<221> NAME/KEY: MISC_Feature
<222> LOCATION: (9)..(9)
<223> OTHER INFORMATION: Alkene modification at Lysine 9

<400> SEQUENCE: 156

Leu Leu Leu Pro Gly Glu Leu Ala Lys His Ala Val Ser Glu Gly Thr
1               5                   10                  15

Lys

<210> SEQ ID NO 157
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (2)..(2)
<223> OTHER INFORMATION: Alkene modification at Lysine 2

<400> SEQUENCE: 157

Gly Lys Gln Gly Gly Lys
1               5

<210> SEQ ID NO 158
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (1)..(1)
<223> OTHER INFORMATION: Alkene modification at Lysine 1

<400> SEQUENCE: 158

Lys Gly Asn Tyr Ser Glu Arg
1               5

<210> SEQ ID NO 159
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (3)..(3)
<223> OTHER INFORMATION: Alkene modification at Lysine 3

<400> SEQUENCE: 159

Gly Gly Lys Gly Leu Gly Lys
1               5

<210> SEQ ID NO 160
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (3)..(3)
<223> OTHER INFORMATION: Alkene modification at Lysine 3
<220> FEATURE:
<221> NAME/KEY: MISC_Feature
<222> LOCATION: (7)..(7)
<223> OTHER INFORMATION: Acetyl at Lysine 7
<220> FEATURE:
<221> NAME/KEY: MISC_Feature
```

```
<222> LOCATION: (11)..(11)
<223> OTHER INFORMATION: Acetyl at Lysine 11

<400> SEQUENCE: 160

Gly Gly Lys Gly Leu Gly Lys Gly Gly Ala Lys Arg
1               5                   10

<210> SEQ ID NO 161
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (2)..(2)
<223> OTHER INFORMATION: Acetyl at Lysine 2
<220> FEATURE:
<221> NAME/KEY: MISC_Feature
<222> LOCATION: (5)..(5)
<223> OTHER INFORMATION: Alkene modification at Lysine 5
<220> FEATURE:
<221> NAME/KEY: MISC_Feature
<222> LOCATION: (9)..(9)
<223> OTHER INFORMATION: Acetyl at Lysine 9
<220> FEATURE:
<221> NAME/KEY: MISC_Feature
<222> LOCATION: (13)..(13)
<223> OTHER INFORMATION: Acetyl at Lysine 13

<400> SEQUENCE: 161

Gly Lys Gly Gly Lys Gly Leu Gly Lys Gly Gly Ala Lys Arg
1               5                   10

<210> SEQ ID NO 162
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (4)..(4)
<223> OTHER INFORMATION: Alkene modification at Lysine 4

<400> SEQUENCE: 162

Gly Leu Gly Lys Gly Gly Ala Lys
1               5

<210> SEQ ID NO 163
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Acetyl at Lysine 4
<220> FEATURE:
<221> NAME/KEY: MISC_FEATURE
<222> LOCATION: (8)..(8)
<223> OTHER INFORMATION: Alkene at Lysine 8

<400> SEQUENCE: 163

Gly Leu Gly Lys Gly Gly Ala Lys Arg
1               5

<210> SEQ ID NO 164
<211> LENGTH: 11
<212> TYPE: PRT
```

```
<213> ORGANISM: Artificial
<220> FEATURE:
<223> OTHER INFORMATION: Synthetic
<220> FEATURE:
<221> NAME/KEY: MISC_Feature
<222> LOCATION: (7)..(7)
<223> OTHER INFORMATION: Alkene modification at Lysine 7

<400> SEQUENCE: 164

Glu Ile Ala Gln Asp Phe Lys Thr Asp Leu Arg
1               5                   10

<210> SEQ ID NO 165
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (1)..(1)
<223> OTHER INFORMATION: Alkene modification at Lysine 1

<400> SEQUENCE: 165

Lys Gln Leu Ala Thr Lys
1               5

<210> SEQ ID NO 166
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (7)..(7)
<223> OTHER INFORMATION: Alkene modification at Lysine 7

<400> SEQUENCE: 166

Phe Ala Asn Tyr Ile Asp Lys Val Arg
1               5

<210> SEQ ID NO 167
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (4)..(4)
<223> OTHER INFORMATION: Thiol modification at Lysine 4

<400> SEQUENCE: 167

Gly Gln Gly Lys Ser Arg
1               5

<210> SEQ ID NO 168
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (1)..(1)
<223> OTHER INFORMATION: Alkene modification at Lysine 1

<400> SEQUENCE: 168

Lys Leu Leu Glu Gly Glu Glu Thr Arg
```

```
1               5

<210> SEQ ID NO 169
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (1)..(1)
<223> OTHER INFORMATION: Conversion of Glutamine 1 to Pyroglutamic acid
<220> FEATURE:
<221> NAME/KEY: MISC_Feature
<222> LOCATION: (2)..(2)
<223> OTHER INFORMATION: Alkene modification at Lysine 2

<400> SEQUENCE: 169

Gln Lys Gln Ala Ser His Ala Gln Leu Gly Asp Ala Tyr Asp Gln Glu
1               5                   10                  15

Ile Arg

<210> SEQ ID NO 170
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (8)..(8)
<223> OTHER INFORMATION: Alkene modification at Lysine 8

<400> SEQUENCE: 170

Thr Asp Ile Ser Thr Ala Leu Lys Glu Ile Arg
1               5                   10

<210> SEQ ID NO 171
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (5)..(5)
<223> OTHER INFORMATION: Alkene modification at Lysine 5

<400> SEQUENCE: 171

Thr Leu Leu Ile Lys Thr Val Glu Thr Arg
1               5                   10

<210> SEQ ID NO 172
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (12)..(12)
<223> OTHER INFORMATION: Thiol modification at Lysine 12

<400> SEQUENCE: 172

Ala Asp Leu Ile Asn Asn Leu Gly Thr Ile Ala Lys Ser Gly Thr Lys
1               5                   10                  15

<210> SEQ ID NO 173
<211> LENGTH: 12
```

```
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (10)..(10)
<223> OTHER INFORMATION: Alkene modification of Lysine 10

<400> SEQUENCE: 173

Asn Leu Gln Glu Ala Glu Glu Trp Tyr Lys Ser Lys
1               5                   10

<210> SEQ ID NO 174
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (14)..(14)
<223> OTHER INFORMATION: Alkene modification at Lysine 14

<400> SEQUENCE: 174

Ala Thr Ile Ala Gly Gly Gly Val Ile Pro His Ile His Lys Ser Leu
1               5                   10                  15

Ile Gly Lys

<210> SEQ ID NO 175
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (1)..(1)
<223> OTHER INFORMATION: Alkene modification at Lysine 1

<400> SEQUENCE: 175

Lys Glu Ser Tyr Ser Ile Tyr Val Tyr Lys
1               5                   10

<210> SEQ ID NO 176
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (14)..(14)
<223> OTHER INFORMATION: Alkene modification at Lysine 14

<400> SEQUENCE: 176

His Leu Gln Leu Ala Ile Arg Asn Asp Glu Glu Leu Asn Lys Leu Leu
1               5                   10                  15

Gly Lys

<210> SEQ ID NO 177
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (1)..(1)
```

```
<223> OTHER INFORMATION: Alkene modification at Lysine 1

<400> SEQUENCE: 177

Lys Thr Glu Ser His His Lys
1               5

<210> SEQ ID NO 178
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (7)..(7)
<223> OTHER INFORMATION: Alkene modification at Lysine 7

<400> SEQUENCE: 178

Arg Val Thr Ile Met Pro Lys Asp Ile Gln Leu Ala Arg
1               5                   10

<210> SEQ ID NO 179
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (19)..(19)
<223> OTHER INFORMATION: Alkene modification at Lysine 19

<400> SEQUENCE: 179

Val Thr Ile Ala Gln Gly Gly Val Leu Pro Asn Ile Gln Ala Val Leu
1               5                   10                  15

Leu Pro Lys Lys
            20

<210> SEQ ID NO 180
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (4)..(4)
<223> OTHER INFORMATION: Thiol modification at Lysine 4

<400> SEQUENCE: 180

Gly Gly Val Lys Arg
1               5

<210> SEQ ID NO 181
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (6)..(6)
<223> OTHER INFORMATION: Alkene modification at Lysine 6

<400> SEQUENCE: 181

Leu Ala His Tyr Asn Lys Arg
1               5
```

```
<210> SEQ ID NO 182
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_Feature
<222> LOCATION: (10)..(10)
<223> OTHER INFORMATION: Alkene modification at Lysine 10

<400> SEQUENCE: 182

Asp Ala Val Thr Tyr Thr Glu His Ala Lys Arg
1               5                   10

<210> SEQ ID NO 183
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Alkene modification at Lysine 10

<400> SEQUENCE: 183

Asp Ala Val Thr Tyr Thr Glu His Ala Lys Arg Lys
1               5                   10

<210> SEQ ID NO 184
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 184

Gly Val Leu Lys Val Phe Leu Glu Asn Val Ile Arg
1               5                   10

<210> SEQ ID NO 185
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 185

Ala Lys Ala Val Arg Ala Leu Lys
1               5

<210> SEQ ID NO 186
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4
```

```
<400> SEQUENCE: 186

Ala Val Thr Lys Ala Gln Lys
1               5

<210> SEQ ID NO 187
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 187

Lys Ala Val Thr Lys
1               5

<210> SEQ ID NO 188
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene modification at Lysine 8

<400> SEQUENCE: 188

Ile Glu Glu Glu Leu Gly Ser Lys Ala Lys
1               5                   10

<210> SEQ ID NO 189
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene modification at Lysine 8

<400> SEQUENCE: 189

Leu Asn Val Thr Glu Gln Glu Lys Ile Asp Lys
1               5                   10

<210> SEQ ID NO 190
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Thiol modification at Lysine 4

<400> SEQUENCE: 190

Asn Val Ile Lys Glu Lys
1               5

<210> SEQ ID NO 191
<211> LENGTH: 9
<212> TYPE: PRT
<213> ORGANISM: Artificial
<220> FEATURE:
```

```
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 191

Ala Lys Met Gln Ala Ser Ile Glu Lys
1               5

<210> SEQ ID NO 192
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 192

Asp Ser Lys Pro Ser Ser Thr Pro Arg
1               5

<210> SEQ ID NO 193
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene modification at Lysine 7

<400> SEQUENCE: 193

Leu Leu Ser Ile Ser Gly Lys Arg
1               5

<210> SEQ ID NO 194
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Conversion of Glutamine 1 to Pyroglutamic acid
<220> FEATURE:
<221> NAME/KEY: MISC_FEATURE
<222> LOCATION: (3)..(3)
<223> OTHER INFORMATION: Alkene modification at Lysine 3

<400> SEQUENCE: 194

Gln Glu Lys Thr Pro Lys
1               5

<210> SEQ ID NO 195
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 195
```

```
Ser Lys Gly Gln Glu Ser Phe Lys
1               5

<210> SEQ ID NO 196
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Acetyl at Lysine 4
<220> FEATURE:
<221> NAME/KEY: MISC_FEATURE
<222> LOCATION: (8)..(8)
<223> OTHER INFORMATION: Alkene at Lysine 8

<400> SEQUENCE: 196

Gly Leu Gly Lys Gly Gly Ala Lys Arg
1               5

<210> SEQ ID NO 197
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Thiol modification at Lysine 14

<400> SEQUENCE: 197

Ala Thr Ile Ala Gly Gly Gly Val Ile Pro His Ile His Lys Ser Leu
1               5                   10                  15

Ile Gly Lys

<210> SEQ ID NO 198
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification at Lysine 1

<400> SEQUENCE: 198

Lys Thr Glu Ser His His Lys
1               5

<210> SEQ ID NO 199
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification at Lysine 1

<400> SEQUENCE: 199

Lys Gly Asn Tyr Ala Glu Arg
1               5
```

```
<210> SEQ ID NO 200
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Oxidation at Methionine 5
<220> FEATURE:
<221> NAME/KEY: MISC_FEATURE
<222> LOCATION: (7)..(7)
<223> OTHER INFORMATION: Alkene modification at Lysine 7

<400> SEQUENCE: 200

Arg Val Thr Ile Met Pro Lys Asp Ile Gln Leu Ala Arg
1               5                   10

<210> SEQ ID NO 201
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification at Lysine 1

<400> SEQUENCE: 201

Lys Ala Val Thr Lys
1               5

<210> SEQ ID NO 202
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 202

Gln Glu Lys Thr Pro Lys
1               5

<210> SEQ ID NO 203
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification at Lysine 2

<400> SEQUENCE: 203

Ser Lys Gly Gln Glu Ser Phe Lys
1               5

<210> SEQ ID NO 204
<211> LENGTH: 9
<212> TYPE: PRT
<213> ORGANISM: Artificial
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Thiol modification at Lysine 1

<400> SEQUENCE: 204

Lys Leu Leu Glu Gly Glu Glu Thr Arg
1               5

<210> SEQ ID NO 205
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Alkene modification of Lysine 12

<400> SEQUENCE: 205

Ala Asp Leu Ile Asn Asn Leu Gly Thr Ile Ala Lys Ser Gly Thr Lys
1               5                   10                  15

<210> SEQ ID NO 206
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene at Lysine 4
<220> FEATURE:
<221> NAME/KEY: MISC_FEATURE
<222> LOCATION: (8)..(8)
<223> OTHER INFORMATION: Acetyl at Lysine 8

<400> SEQUENCE: 206

Gly Leu Gly Lys Gly Gly Ala Lys Arg
1               5

<210> SEQ ID NO 207
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4
<220> FEATURE:
<221> NAME/KEY: MISC_FEATURE
<222> LOCATION: (8)..(8)
<223> OTHER INFORMATION: Acetyl at Lysine 8

<400> SEQUENCE: 207

Gly Leu Gly Lys Gly Gly Ala Lys Arg
1               5

<210> SEQ ID NO 208
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5
```

```
<400> SEQUENCE: 208

Ala Glu Val Gly Lys Gly Glu Gln Lys
1               5

<210> SEQ ID NO 209
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 209

Ala Lys Ser Pro Val Pro Lys
1               5

<210> SEQ ID NO 210
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 210

Asp Val Pro Glu Lys Lys
1               5

<210> SEQ ID NO 211
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Thiol modification at Lysine 14

<400> SEQUENCE: 211

Glu Glu Glu Pro Glu Ala Glu Glu Glu Val Ala Ala Lys Lys
1               5                   10                  15

<210> SEQ ID NO 212
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 212

Glu Glu Gly Lys Pro Leu Gln Gln Glu Lys
1               5                   10

<210> SEQ ID NO 213
<211> LENGTH: 6
<212> TYPE: PRT
<213> ORGANISM: Artificial
```

```
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 213

Gly Ala Lys Gly Ser Arg
1               5

<210> SEQ ID NO 214
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Thiol modification at Lysine 4

<400> SEQUENCE: 214

Gly Glu Gln Lys Glu Glu Glu Glu Lys
1               5

<210> SEQ ID NO 215
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 215

Gly Gly Asp Lys Ser Glu Glu Lys
1               5

<210> SEQ ID NO 216
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 216

Gly Lys Ser Pro Val Pro Lys
1               5

<210> SEQ ID NO 217
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 217

Gly Lys Ser Pro Val Ser Lys
1               5
```

```
<210> SEQ ID NO 218
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Alkene modification at Lysine 11

<400> SEQUENCE: 218

Gly Ser Pro Ser Thr Val Ser Ser Ser Tyr Lys Arg
1               5                   10

<210> SEQ ID NO 219
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Deamidation at Asparagine 5
<220> FEATURE:
<221> NAME/KEY: MISC_FEATURE
<222> LOCATION: (15)..(15)
<223> OTHER INFORMATION: Thiol modification at Lysine 15

<400> SEQUENCE: 219

Gly Val Val Thr Asn Gly Leu Asp Leu Ser Pro Ala Asp Glu Lys Lys
1               5                   10                  15

<210> SEQ ID NO 220
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 220

Lys Asp Tyr Leu Lys
1               5

<210> SEQ ID NO 221
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9

<400> SEQUENCE: 221

Leu Thr Glu Ala Ala Glu Gln Asn Lys Glu Ala Ile Arg
1               5                   10

<210> SEQ ID NO 222
<211> LENGTH: 13
<212> TYPE: PRT
<213> ORGANISM: Artificial
<220> FEATURE:
```

```
<223> OTHER INFORMATION: Synthetic
<220> FEATURE:
<221> NAME/KEY: MISC_FEATURE
<222> LOCATION: (9)..(9)
<223> OTHER INFORMATION: Thiol modification at Lysine 9

<400> SEQUENCE: 222

Leu Thr Glu Ala Ala Glu Gln Asn Lys Glu Ala Ile Arg
1               5                   10

<210> SEQ ID NO 223
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Thiol modification at Lysine 5

<400> SEQUENCE: 223

Leu Val Ser Thr Lys Lys
1               5

<210> SEQ ID NO 224
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 224

Ser Glu Glu Lys Val Val Val Thr Lys
1               5

<210> SEQ ID NO 225
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Thiol modification at Lysine 7

<400> SEQUENCE: 225

Ser Glu Glu Val Ala Thr Lys Glu Glu Leu Val Ala Asp Ala Lys
1               5                   10                  15

<210> SEQ ID NO 226
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 226

Ser Lys Ala Glu Val Gly Lys
1               5
```

```
<210> SEQ ID NO 227
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 227

Ser Pro Val Glu Glu Lys Ala Lys
1               5

<210> SEQ ID NO 228
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 228

Ser Pro Val Glu Glu Lys Gly Lys
1               5

<210> SEQ ID NO 229
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Thiol modification at Lysine 6

<400> SEQUENCE: 229

Ser Pro Val Glu Glu Lys Gly Lys
1               5

<210> SEQ ID NO 230
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 230

Ser Pro Val Pro Lys Ser Pro Val Glu Glu Lys
1               5                   10

<210> SEQ ID NO 231
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Thiol modification at Lysine 5
```

<400> SEQUENCE: 231

Ser Pro Val Pro Lys Ser Pro Val Glu Glu Lys
1               5                   10

<210> SEQ ID NO 232
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Thiol modification at Lysine 4

<400> SEQUENCE: 232

Thr Val Glu Lys Ile Thr Ser Glu Gly Gly Asp Gly Ala Thr Lys
1               5                   10                  15

<210> SEQ ID NO 233
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 233

Val Glu Ala Pro Lys Leu Lys
1               5

<210> SEQ ID NO 234
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 234

Val Val Val Thr Lys Thr Val Glu Lys
1               5

<210> SEQ ID NO 235
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Thiol modification at Lysine 5

<400> SEQUENCE: 235

Val Val Val Thr Lys Thr Val Glu Lys
1               5

<210> SEQ ID NO 236
<211> LENGTH: 7
<212> TYPE: PRT
<213> ORGANISM: Artificial

```
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 236

Gly Ser Ser Lys Ser Gly Lys
1               5

<210> SEQ ID NO 237
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 237

Lys Glu Leu Thr Gln Ile Lys
1               5

<210> SEQ ID NO 238
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 238

Asp Ala Lys Leu Asp Lys
1               5

<210> SEQ ID NO 239
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene modification at Lysine 7

<400> SEQUENCE: 239

Ile Thr Ile Thr Asn Asp Lys Gly Arg
1               5

<210> SEQ ID NO 240
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 240

Leu Ser Lys Glu Glu Ile Glu Arg
1               5
```

<210> SEQ ID NO 241
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 241

Lys Leu Leu Glu Gly Glu Glu Ser Arg
1               5

<210> SEQ ID NO 242
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 242

Lys Val Glu Ser Leu Gln Glu Glu Ile Ala Phe Leu Lys
1               5                   10

<210> SEQ ID NO 243
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: Alkene modification at Lysine 19

<400> SEQUENCE: 243

Leu Leu Gln Asp Ser Val Asp Phe Ser Leu Ala Asp Ala Ile Asn Thr
1               5                   10                  15

Glu Phe Lys Asn Thr Arg
            20

<210> SEQ ID NO 244
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene modification at Lysine 7

<400> SEQUENCE: 244

Ala Ala Ser Gly Glu Ala Lys Pro Lys
1               5

<210> SEQ ID NO 245
<211> LENGTH: 7
<212> TYPE: PRT
<213> ORGANISM: Artificial
<220> FEATURE:
<223> OTHER INFORMATION: Synthetic

```
<220> FEATURE:
<221> NAME/KEY: MISC_FEATURE
<222> LOCATION: (5)..(5)
<223> OTHER INFORMATION: Alkene modification at Lysine 5

<400> SEQUENCE: 245

Ala Gly Ala Ala Lys Ala Lys
1               5

<210> SEQ ID NO 246
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Alkene modification at Lysine 11

<400> SEQUENCE: 246

Glu Arg Ser Gly Val Ser Leu Ala Ala Leu Lys Lys
1               5                   10

<210> SEQ ID NO 247
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene modification at Lysine 7

<400> SEQUENCE: 247

Gly Thr Leu Val Gln Thr Lys Gly Thr Gly Ala Ser Gly Ser Phe Lys
1               5                   10                  15

<210> SEQ ID NO 248
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 248

Lys Ala Ser Gly Pro Pro Val Ser Glu Leu Ile Thr Lys
1               5                   10

<210> SEQ ID NO 249
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 249

Lys Ser Ala Gly Ala Ala Lys
1               5
```

```
<210> SEQ ID NO 250
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 250

Lys Gly Val Ile Thr Val Lys
1               5

<210> SEQ ID NO 251
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 251

Ser Ile Asp Leu Lys Asp Lys
1               5

<210> SEQ ID NO 252
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Thiol modification at Lysine 6

<400> SEQUENCE: 252

Phe Ser Glu Val Leu Lys Arg
1               5

<210> SEQ ID NO 253
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 253

Phe Ala Ala Lys Gly Glu Gly Gln Leu Gly Pro Ala Glu Arg
1               5                   10

<210> SEQ ID NO 254
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5
```

```
<400> SEQUENCE: 254

Ala Arg Glu Glu Lys Gln Lys
1               5

<210> SEQ ID NO 255
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene modification at Lysine 8

<400> SEQUENCE: 255

Ala Leu Glu Leu Thr Gly Leu Lys Val Phe Gly Asn Glu Ile Lys
1               5                   10                  15

<210> SEQ ID NO 256
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 256

Gly Gly Lys Asn Ser Thr Trp Ser Gly Glu Ser Lys
1               5                   10

<210> SEQ ID NO 257
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification at Lysine 1

<400> SEQUENCE: 257

Lys Ala Ala Val Thr Pro Gly Lys
1               5

<210> SEQ ID NO 258
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 258

Ser Lys Gly Ile Ala Tyr Ile Glu Phe Lys
1               5                   10

<210> SEQ ID NO 259
<211> LENGTH: 9
<212> TYPE: PRT
<213> ORGANISM: Artificial
<220> FEATURE:
```

```
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 259

Ala Lys Leu Gln Ile Glu Leu Gly Lys
1               5

<210> SEQ ID NO 260
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 260

Glu Lys Asp Asn Ser Arg
1               5

<210> SEQ ID NO 261
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 261

Lys Ile Gly Asp Thr Ser Val Ser Tyr Lys
1               5                   10

<210> SEQ ID NO 262
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 262

Lys Pro Ala Leu Val Ala Lys
1               5

<210> SEQ ID NO 263
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 263

His Lys Asn Pro Lys
1               5
```

```
<210> SEQ ID NO 264
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 264

Lys Phe Ile Ser Asp Lys
1               5

<210> SEQ ID NO 265
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 265

Lys Gln Ser Glu Gly Leu Thr Lys
1               5

<210> SEQ ID NO 266
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Thiol modification at Lysine 6

<400> SEQUENCE: 266

Gly Glu Ile Ile Ala Lys Gln Gly Gly Gly Gly Gly Gly Gly Ser Val
1               5                   10                  15

Pro Gly Ile Glu Arg
            20

<210> SEQ ID NO 267
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification Lysine 3

<400> SEQUENCE: 267

Phe Met Lys Pro Gly Lys
1               5

<210> SEQ ID NO 268
<211> LENGTH: 6
<212> TYPE: PRT
<213> ORGANISM: Artificial
<220> FEATURE:
<223> OTHER INFORMATION: Synthetic
<220> FEATURE:
```

```
<221> NAME/KEY: MISC_FEATURE
<222> LOCATION: (2)..(2)
<223> OTHER INFORMATION: Oxidation at Methionine 2
<220> FEATURE:
<221> NAME/KEY: MISC_FEATURE
<222> LOCATION: (3)..(3)
<223> OTHER INFORMATION: Alkene modification at Lysine 3

<400> SEQUENCE: 268

Phe Met Lys Pro Gly Lys
1               5

<210> SEQ ID NO 269
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification at Lysine 2

<400> SEQUENCE: 269

Gly Lys Gly Gly Glu Ile Gln Pro Val Ser Val Lys
1               5                   10

<210> SEQ ID NO 270
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 270

Gly Lys Gly Gly Glu Ile Gln Pro Val Ser Val Lys
1               5                   10

<210> SEQ ID NO 271
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9

<400> SEQUENCE: 271

Asp Leu Ala Gly Ser Ile Ile Gly Lys Gly Gly Gln Arg
1               5                   10

<210> SEQ ID NO 272
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene modification at Lysine 8

<400> SEQUENCE: 272

His Glu Ser Gly Ala Ser Ile Lys Ile Asp Glu Pro Leu Glu Gly Ser
```

```
1               5                   10                  15
Glu Asp Arg

<210> SEQ ID NO 273
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Thiol modification at Lysine 4

<400> SEQUENCE: 273

Gly Gly Ala Lys Arg
1               5

<210> SEQ ID NO 274
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification at Lysine 2

<400> SEQUENCE: 274

Gly Lys Gly Gly Lys
1               5

<210> SEQ ID NO 275
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 275

Gly Pro Ile Lys Phe Asn Val Trp Asp Thr Ala Gly Gln Glu Lys
1               5                   10                  15

<210> SEQ ID NO 276
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 276

Lys Glu Ala Pro Pro Met Glu Lys Pro Glu Val Val Lys
1               5                   10

<210> SEQ ID NO 277
<211> LENGTH: 13
<212> TYPE: PRT
<213> ORGANISM: Artificial
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: Alkene modification at Lysine 1

<400> SEQUENCE: 277

Lys Glu Ala Pro Pro Met Glu Lys Pro Glu Val Val Lys
1               5                   10

<210> SEQ ID NO 278
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Thiol modification at Lysine 7

<400> SEQUENCE: 278

Ala Leu Ser Thr Gly Glu Lys Gly Phe Gly Tyr Lys
1               5                   10

<210> SEQ ID NO 279
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 279

Leu Ser Asp Lys Gly Leu Lys
1               5

<210> SEQ ID NO 280
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Conversion of Glutamine 1 to Pyroglutamic acid
<220> FEATURE:
<221> NAME/KEY: MISC_FEATURE
<222> LOCATION: (5)..(5)
<223> OTHER INFORMATION: Alkene modification at Lysine 5

<400> SEQUENCE: 280

Gln Arg Thr Gln Lys Lys
1               5

<210> SEQ ID NO 281
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 281
```

Ile Asp Gln Lys Ala Val Asp Ser Gln Ile Leu Pro Lys
1               5                   10

<210> SEQ ID NO 282
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Alkene modification at Lysine 14

<400> SEQUENCE: 282

Ile Phe Val Gly Gly Leu Ser Pro Asp Thr Pro Glu Glu Lys Ile Arg
1               5                   10                  15

<210> SEQ ID NO 283
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene modification at Lysine 7

<400> SEQUENCE: 283

Ala Gln Phe Glu Gln Leu Lys Asp Gly Lys
1               5                   10

<210> SEQ ID NO 284
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 284

Ala Ser Phe Ala Glu Lys Thr Ala Gln Leu Glu Arg
1               5                   10

<210> SEQ ID NO 285
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 285

Glu Ala Lys Glu Leu Gln Gln Arg
1               5

<210> SEQ ID NO 286
<211> LENGTH: 9
<212> TYPE: PRT
<213> ORGANISM: Artificial
<220> FEATURE:
<223> OTHER INFORMATION: Synthetic
<220> FEATURE:

```
<221> NAME/KEY: MISC_FEATURE
<222> LOCATION: (1)..(1)
<223> OTHER INFORMATION: Alkene modification at Lysine 1

<400> SEQUENCE: 286

Lys Ala Ala Leu Glu Glu Val Glu Arg
1               5

<210> SEQ ID NO 287
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification at Lysine 2

<400> SEQUENCE: 287

Asp Lys Gly Phe Gly Phe Ile Arg
1               5

<210> SEQ ID NO 288
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 288

Ala Arg Ala Lys Ala Lys
1               5

<210> SEQ ID NO 289
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1
<220> FEATURE:
<221> NAME/KEY: MISC_FEATURE
<222> LOCATION: (6)..(6)
<223> OTHER INFORMATION: Acetyl at Lysine 6

<400> SEQUENCE: 289

Lys Gln Leu Ala Thr Lys Ala Ala Arg
1               5

<210> SEQ ID NO 290
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1
<220> FEATURE:
<221> NAME/KEY: MISC_FEATURE
<222> LOCATION: (6)..(6)
<223> OTHER INFORMATION: Acetyl at Lysine 6
```

<400> SEQUENCE: 290

Lys Gln Leu Ala Thr Lys Ala Ala Arg
1               5

<210> SEQ ID NO 291
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1
<220> FEATURE:
<221> NAME/KEY: MISC_FEATURE
<222> LOCATION: (6)..(6)
<223> OTHER INFORMATION: Acetyl at Lysine 6

<400> SEQUENCE: 291

Lys Gln Leu Ala Thr Lys Ala Ala Arg
1               5

<210> SEQ ID NO 292
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 292

Lys Ser Ala Pro Ala Thr Gly Gly Val Lys
1               5                   10

<210> SEQ ID NO 293
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 293

Lys Ser Thr Gly Gly Lys
1               5

<210> SEQ ID NO 294
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 294

Thr Lys Gln Thr Ala Arg
1               5

```
<210> SEQ ID NO 295
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification at Lysine 2

<400> SEQUENCE: 295

Thr Lys Gln Thr Ala Arg
1               5

<210> SEQ ID NO 296
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 296

Thr Lys Ala Val Ser Arg
1               5

<210> SEQ ID NO 297
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 297

Ser Arg Lys Glu Ser Tyr Ser Val Tyr Val Tyr Lys
1               5                   10

<210> SEQ ID NO 298
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification at Lysine 1

<400> SEQUENCE: 298

Lys Gly Ser Lys
1

<210> SEQ ID NO 299
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Thiol modification at Lysine 9
```

```
<400> SEQUENCE: 299

Leu Leu Leu Pro Gly Glu Leu Ala Lys His Ala Val Ser Glu Gly Thr
1               5                   10                  15

Lys

<210> SEQ ID NO 300
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Loss of Methionine sulfoxide at Methionine 1
<220> FEATURE:
<221> NAME/KEY: MISC_FEATURE
<222> LOCATION: (6)..(6)
<223> OTHER INFORMATION: Thiol at Lysine 6

<400> SEQUENCE: 300

Met Pro Glu Pro Ala Lys Ser Ala Pro Ala Pro Lys
1               5                   10

<210> SEQ ID NO 301
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Loss of Methionine sulfoxide at Methionine 1
<220> FEATURE:
<221> NAME/KEY: MISC_FEATURE
<222> LOCATION: (6)..(6)
<223> OTHER INFORMATION: Alkene at Lysine 6

<400> SEQUENCE: 301

Met Pro Glu Pro Ala Lys Ser Ala Pro Ala Pro Lys
1               5                   10

<210> SEQ ID NO 302
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene modification at Lysine 7

<400> SEQUENCE: 302

Asn Asp Glu Glu Leu Asn Lys Leu Leu Gly Lys
1               5                   10

<210> SEQ ID NO 303
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 303
```

Thr Asn Glu Lys Val Glu Leu Gln Glu Leu Asn Asp Arg
1               5                   10

<210> SEQ ID NO 304
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification at Lysine 3

<400> SEQUENCE: 304

Tyr Ala Lys Leu Thr Glu Ala Ala Glu Gln Asn Lys
1               5                   10

<210> SEQ ID NO 305
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 305

Tyr Ala Lys Leu Thr Glu Ala Ala Glu Gln Asn Lys
1               5                   10

<210> SEQ ID NO 306
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Alkene modification at Lysine 12

<400> SEQUENCE: 306

Glu Leu Ile Ser Asn Ala Ser Asp Ala Leu Asp Lys Ile Arg
1               5                   10

<210> SEQ ID NO 307
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Alkene modification at Lysine 12

<400> SEQUENCE: 307

Glu Leu Ile Ser Asn Ala Ser Asp Ala Leu Asp Lys Ile Arg
1               5                   10

<210> SEQ ID NO 308
<211> LENGTH: 12
<212> TYPE: PRT
<213> ORGANISM: Artificial
<220> FEATURE:
<223> OTHER INFORMATION: Synthetic

```
<220> FEATURE:
<221> NAME/KEY: MISC_FEATURE
<222> LOCATION: (2)..(2)
<223> OTHER INFORMATION: Alkene modification at Lysine 2

<400> SEQUENCE: 308

Ser Lys Phe Ala Asp Leu Ser Glu Ala Ala Asn Arg
1               5                   10

<210> SEQ ID NO 309
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 309

Arg Tyr Gln Lys Ser Thr Glu Leu Leu Ile Arg
1               5                   10

<210> SEQ ID NO 310
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 310

Tyr Gln Lys Ser Thr Glu Leu Leu Ile Arg
1               5                   10

<210> SEQ ID NO 311
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification at Lysine 3

<400> SEQUENCE: 311

Tyr Gln Lys Ser Thr Glu Leu Leu Ile Arg
1               5                   10

<210> SEQ ID NO 312
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 312

Val Thr Ile Met Pro Lys Asp Ile Gln Leu Ala Arg
1               5                   10
```

```
<210> SEQ ID NO 313
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Oxidation at Methionine 4
<220> FEATURE:
<221> NAME/KEY: MISC_FEATURE
<222> LOCATION: (6)..(6)
<223> OTHER INFORMATION: Alkene modification at Lysine 6

<400> SEQUENCE: 313

Val Thr Ile Met Pro Lys Asp Ile Gln Leu Ala Arg
1               5                   10

<210> SEQ ID NO 314
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 314

Met Gln Ile Phe Val Lys Thr Leu Thr Gly Lys
1               5                   10

<210> SEQ ID NO 315
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 315

Met Gln Ile Phe Val Lys Thr Leu Thr Gly Lys
1               5                   10

<210> SEQ ID NO 316
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Oxidation at Methionine 1
<220> FEATURE:
<221> NAME/KEY: MISC_FEATURE
<222> LOCATION: (6)..(6)
<223> OTHER INFORMATION: Thiol modification at Lysine 6

<400> SEQUENCE: 316

Met Gln Ile Phe Val Lys Thr Leu Thr Gly Lys
1               5                   10

<210> SEQ ID NO 317
<211> LENGTH: 11
<212> TYPE: PRT
```

```
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 317

Met Gln Ile Phe Val Lys Thr Leu Thr Gly Lys
1               5                   10

<210> SEQ ID NO 318
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Thiol modification at Lysine 6

<400> SEQUENCE: 318

Met Gln Ile Phe Val Lys Thr Leu Thr Gly Lys
1               5                   10

<210> SEQ ID NO 319
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 319

Leu Ile Phe Ala Gly Lys Gln Leu Glu Asp Gly Arg
1               5                   10

<210> SEQ ID NO 320
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Alkene modification at Lysine 12

<400> SEQUENCE: 320

Thr Val Thr Ala Met Asp Val Val Tyr Ala Leu Lys Arg
1               5                   10

<210> SEQ ID NO 321
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Oxidation at Methionine 5
<220> FEATURE:
<221> NAME/KEY: MISC_FEATURE
<222> LOCATION: (12)..(12)
<223> OTHER INFORMATION: Alkene modification at Lysine 12
```

<400> SEQUENCE: 321

Thr Val Thr Ala Met Asp Val Val Tyr Ala Leu Lys Arg
1               5                   10

<210> SEQ ID NO 322
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Acetyl at Lysine 2
<220> FEATURE:
<221> NAME/KEY: MISC_FEATURE
<222> LOCATION: (5)..(5)
<223> OTHER INFORMATION: Alkene at Lysine 5
<220> FEATURE:
<221> NAME/KEY: MISC_FEATURE
<222> LOCATION: (9)..(9)
<223> OTHER INFORMATION: Acetyl at Lysine 9
<220> FEATURE:
<221> NAME/KEY: MISC_FEATURE
<222> LOCATION: (13)..(13)
<223> OTHER INFORMATION: Acetyl at Lysine 13

<400> SEQUENCE: 322

Gly Lys Gly Gly Lys Gly Leu Gly Lys Gly Gly Ala Lys Arg
1               5                   10

<210> SEQ ID NO 323
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene modification at Lysine 8

<400> SEQUENCE: 323

Gly His Leu Ser Gly Leu Ala Lys Arg
1               5

<210> SEQ ID NO 324
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: Thiol modification at Lysine 19

<400> SEQUENCE: 324

Val Thr Ile Ala Gln Gly Gly Val Leu Pro Asn Ile Gln Ala Val Leu
1               5                   10                  15

Leu Pro Lys Lys
            20

<210> SEQ ID NO 325
<211> LENGTH: 7
<212> TYPE: PRT
<213> ORGANISM: Artificial
<220> FEATURE:
<223> OTHER INFORMATION: Synthetic

```
<220> FEATURE:
<221> NAME/KEY: MISC_FEATURE
<222> LOCATION: (6)..(6)
<223> OTHER INFORMATION: Thiol modification at Lysine 6

<400> SEQUENCE: 325

Ser Ala Pro Ala Pro Lys Lys
1               5

<210> SEQ ID NO 326
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Loss of Methionine sulfoxide at Methionine 1
<220> FEATURE:
<221> NAME/KEY: MISC_FEATURE
<222> LOCATION: (1)..(1)
<223> OTHER INFORMATION: Acetyl at Methionine 1
<220> FEATURE:
<221> NAME/KEY: MISC_FEATURE
<222> LOCATION: (5)..(5)
<223> OTHER INFORMATION: Alkene modification at Lysine 5

<400> SEQUENCE: 326

Met Ser Ile Leu Lys Ile His Ala Arg
1               5

<210> SEQ ID NO 327
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Thiol modification at Lysine 9

<400> SEQUENCE: 327

Thr Ile Ala Pro Ala Leu Val Ser Lys Lys
1               5                   10

<210> SEQ ID NO 328
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 328

Thr Ala Ile Gly Lys Ala Gly Tyr Thr Asp Lys
1               5                   10

<210> SEQ ID NO 329
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
```

```
<223> OTHER INFORMATION: Alkene modification at Lysine 3

<400> SEQUENCE: 329

Thr Pro Lys Gly Pro Ser Ser Val Glu Asp Ile Lys
1               5                   10

<210> SEQ ID NO 330
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification at Lysine 3

<400> SEQUENCE: 330

Thr Pro Lys Gly Pro Ser Ser Val Glu Asp Ile Lys
1               5                   10

<210> SEQ ID NO 331
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 331

Thr Pro Lys Thr Pro Lys
1               5

<210> SEQ ID NO 332
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene modification at Lysine 7

<400> SEQUENCE: 332

Ser Pro Val Glu Glu Ala Lys Ser Lys
1               5

<210> SEQ ID NO 333
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 333

Ser Pro Val Ser Lys Ser Pro Val Glu Glu Lys
1               5                   10

<210> SEQ ID NO 334
<211> LENGTH: 6
<212> TYPE: PRT
```

```
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 334

Val Glu Lys Pro Glu Lys
1               5

<210> SEQ ID NO 335
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification at Lysine 3

<400> SEQUENCE: 335

Val Glu Lys Pro Glu Lys
1               5

<210> SEQ ID NO 336
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 336

Lys Ala Glu Ser Pro Val Lys
1               5

<210> SEQ ID NO 337
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 337

Ser Pro Val Lys Ala Thr Ala Pro Glu Val Lys
1               5                   10

<210> SEQ ID NO 338
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification at Lysine 2

<400> SEQUENCE: 338

Glu Lys Ala Gly Gly Glu Gly Gly Ser Glu Glu Glu Gly Ser Asp Lys
```

<210> SEQ ID NO 339
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 339

Lys Glu Asp Ile Ala Val Asn Gly Glu Val Glu Gly Lys
1               5                   10

<210> SEQ ID NO 340
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1
<220> FEATURE:
<221> NAME/KEY: MISC_FEATURE
<222> LOCATION: (7)..(7)
<223> OTHER INFORMATION: Deamidation at Asparagine 7

<400> SEQUENCE: 340

Lys Glu Asp Ile Ala Val Asn Gly Glu Val Glu Gly Lys
1               5                   10

<210> SEQ ID NO 341
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification at Lysine 1

<400> SEQUENCE: 341

Lys Val Gln Ser Leu Gln Asp Glu Val Ala Phe Leu Arg
1               5                   10

<210> SEQ ID NO 342
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 342

Ser Ala Lys Glu Glu Ile Ala Glu Tyr Arg
1               5                   10

<210> SEQ ID NO 343
<211> LENGTH: 11
<212> TYPE: PRT
<213> ORGANISM: Artificial

```
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 343

Ser Ala Lys Glu Glu Ile Ala Glu Tyr Arg Arg
1               5                   10

<210> SEQ ID NO 344
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 344

Val Glu Lys Val Thr Ser His Ala Ile Val Lys
1               5                   10

<210> SEQ ID NO 345
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 345

Ser Pro Val Pro Lys Ser Pro Val Glu Glu Ala Lys
1               5                   10

<210> SEQ ID NO 346
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 346

Tyr Ile Thr Lys Ser Val Thr Val Thr Gln Lys
1               5                   10

<210> SEQ ID NO 347
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Thiol modification at Lysine 4

<400> SEQUENCE: 347

Tyr Ile Thr Lys Ser Val Thr Val Thr Gln Lys
1               5                   10
```

```
<210> SEQ ID NO 348
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 348

Val Gln His Lys Phe Val Glu Glu Ile Ile Glu Glu Thr Lys
1               5                   10

<210> SEQ ID NO 349
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Alkene modification at Lysine 12

<400> SEQUENCE: 349

Glu Leu Ile Ser Asn Ser Ser Asp Ala Leu Asp Lys Ile Arg
1               5                   10

<210> SEQ ID NO 350
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Thiol modification at Lysine 2

<400> SEQUENCE: 350

Leu Lys Gly Asp Asp Leu Gln Ala Ile Lys
1               5                   10

<210> SEQ ID NO 351
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Conversion of Glutamine 1 to Pyroglutamic acid
<220> FEATURE:
<221> NAME/KEY: MISC_FEATURE
<222> LOCATION: (2)..(2)
<223> OTHER INFORMATION: Alkene modification at Lysine 2

<400> SEQUENCE: 351

Gln Lys Val Asp Ser Leu Leu Glu Asn Leu Glu Lys
1               5                   10

<210> SEQ ID NO 352
<211> LENGTH: 12
<212> TYPE: PRT
<213> ORGANISM: Artificial
<220> FEATURE:
```

```
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 352

Gln Lys Val Asp Ser Leu Leu Glu Asn Leu Glu Lys
1               5                   10

<210> SEQ ID NO 353
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Thiol modification at Lysine 6

<400> SEQUENCE: 353

Ser Gly Phe Asn Ser Lys Ser Gly Gln Arg
1               5                   10

<210> SEQ ID NO 354
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene modification at Lysine 8

<400> SEQUENCE: 354

Ser Thr Leu Glu Pro Val Glu Lys Ala Leu Arg
1               5                   10

<210> SEQ ID NO 355
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 355

Thr Gly Lys Gly Glu Arg
1               5

<210> SEQ ID NO 356
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Thiol modification at Lysine 7

<400> SEQUENCE: 356

Phe Leu Glu Gln Gln Asn Lys Ile Leu Leu Ala Glu Leu Glu Gln Leu
1               5                   10                  15
```

Lys

<210> SEQ ID NO 357
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 357

Arg Thr Leu Leu Ile Lys Thr Val Glu Thr Arg
1               5                   10

<210> SEQ ID NO 358
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Thiol modification at Lysine 12

<400> SEQUENCE: 358

Val Glu Ser Leu Gln Glu Glu Ile Ala Phe Leu Lys Lys
1               5                   10

<210> SEQ ID NO 359
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 359

Gly Gln Gln Lys Thr Val
1               5

<210> SEQ ID NO 360
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 360

Lys Gly Gln Gln Lys
1               5

<210> SEQ ID NO 361
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 361

Ser Leu Val Ser Lys Gly Thr Leu Val Gln Thr Lys
1               5                   10

<210> SEQ ID NO 362
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 362

Lys Pro Ala Gly Ala Ala Lys
1               5

<210> SEQ ID NO 363
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 363

Ile Lys Leu Gly Leu Lys
1               5

<210> SEQ ID NO 364
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 364

Leu Gly Leu Lys Ser Leu Val Ser Lys
1               5

<210> SEQ ID NO 365
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Thiol modification at Lysine 4

<400> SEQUENCE: 365

Thr Pro Val Lys Lys
1               5

<210> SEQ ID NO 366
<211> LENGTH: 16

```
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: Alkene modification at Lysine 15

<400> SEQUENCE: 366

Arg Gly Val Met Leu Ala Val Asp Ala Val Ile Ala Glu Leu Lys Lys
1               5                   10                  15

<210> SEQ ID NO 367
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 367

Tyr Lys Asn Ile Gly Ala Lys
1               5

<210> SEQ ID NO 368
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification at Lysine 3

<400> SEQUENCE: 368

Leu Gln Lys Arg
1

<210> SEQ ID NO 369
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 369

Leu Ile Glu Lys Leu Asp Ile Lys
1               5

<210> SEQ ID NO 370
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 370
```

Lys Leu Ile Glu Leu Gln Ala Gly Lys
1               5

<210> SEQ ID NO 371
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9

<400> SEQUENCE: 371

Thr Gly Ile Ser Asp Val Phe Ala Lys Asn Asp Leu Ala Val Val Asp
1               5                   10                  15

Val Arg

<210> SEQ ID NO 372
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 372

Thr Leu Leu Ala Lys Asn Leu Pro Tyr Lys
1               5                   10

<210> SEQ ID NO 373
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 373

Lys Val Ala Val Ala Thr Pro Ala Lys
1               5

<210> SEQ ID NO 374
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 374

Lys Gln Leu Ala Asp Glu Thr Leu Leu Lys
1               5                   10

<210> SEQ ID NO 375
<211> LENGTH: 12
<212> TYPE: PRT
<213> ORGANISM: Artificial
<220> FEATURE:

```
<223> OTHER INFORMATION: Synthetic
<220> FEATURE:
<221> NAME/KEY: MISC_FEATURE
<222> LOCATION: (10)..(10)
<223> OTHER INFORMATION: Thiol modification at Lysine 10

<400> SEQUENCE: 375

Ile Gln Glu Leu Glu Asp Leu Leu Ala Lys Glu Lys
1               5                   10

<210> SEQ ID NO 376
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 376

Val Ile Leu Lys Asn Ser Gln Gly Glu Glu Val Ala Gln Arg
1               5                   10

<210> SEQ ID NO 377
<211> LENGTH: 26
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Conversion of Glutamine 1 to Pyroglutamic acid
<220> FEATURE:
<221> NAME/KEY: MISC_FEATURE
<222> LOCATION: (11)..(11)
<223> OTHER INFORMATION: Alkene modification at Lysine 11

<400> SEQUENCE: 377

Gln Val His Pro Asp Thr Gly Ile Ser Ser Lys Ala Met Gly Ile Met
1               5                   10                  15

Asn Ser Phe Val Asn Asp Ile Phe Glu Arg
            20                  25

<210> SEQ ID NO 378
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene modification at Lysine 7

<400> SEQUENCE: 378

Leu Ala Gln Tyr Glu Ser Lys Lys
1               5

<210> SEQ ID NO 379
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
```

<223> OTHER INFORMATION: Alkene modification at Lysine 4

<400> SEQUENCE: 379

Leu Leu Ser Lys Thr Pro Glu Leu Asn Leu Asp Gln Phe His Asp Lys
1               5                   10                  15

<210> SEQ ID NO 380
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Alkene modification at Lysine 10

<400> SEQUENCE: 380

Thr Ala Asp Gly Ile Val Ser His Leu Lys Lys
1               5                   10

<210> SEQ ID NO 381
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 381

Leu Glu Lys Ala Glu Asn Gln Val Leu Ala Met Arg
1               5                   10

<210> SEQ ID NO 382
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Alkene modification at Lysine 10

<400> SEQUENCE: 382

Ile Asn Glu Ile Leu Ser Asn Ala Leu Lys Arg
1               5                   10

<210> SEQ ID NO 383
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Thiol modification at Lysine 9

<400> SEQUENCE: 383

Tyr Ser Val Asp Ile Pro Leu Asp Lys Thr Val Val Asn Lys
1               5                   10

<210> SEQ ID NO 384
<211> LENGTH: 14
<212> TYPE: PRT

```
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9

<400> SEQUENCE: 384

Tyr Ser Val Asp Ile Pro Leu Asp Lys Thr Val Val Asn Lys
1               5                   10

<210> SEQ ID NO 385
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 385

Ile Lys Gln Ile Arg
1               5

<210> SEQ ID NO 386
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Thiol modification at Lysine 4

<400> SEQUENCE: 386

Gly Val Leu Lys Val Phe Leu Glu Asn Val Ile Arg
1               5                   10

<210> SEQ ID NO 387
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 387

Lys Tyr Val Ala Thr Leu Gly Val Glu Val His Pro Leu Val Phe His
1               5                   10                  15

Thr Asn Arg

<210> SEQ ID NO 388
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Conversion of Glutamine 1 to Pyroglutamic acid
<220> FEATURE:
<221> NAME/KEY: MISC_FEATURE
```

```
<222> LOCATION: (6)..(6)
<223> OTHER INFORMATION: Thiol modification at Lysine 6

<400> SEQUENCE: 388

Gln His Ser Leu Leu Lys Arg
1               5

<210> SEQ ID NO 389
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Conversion of Glutamine 1 to Pyroglutamic acid
<220> FEATURE:
<221> NAME/KEY: MISC_FEATURE
<222> LOCATION: (6)..(6)
<223> OTHER INFORMATION: Alkene modification at Lysine 6

<400> SEQUENCE: 389

Gln His Ser Leu Leu Lys Arg
1               5

<210> SEQ ID NO 390
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene modification at Lysine 3

<400> SEQUENCE: 390

Val Pro Lys Thr Ala Glu Asn Phe Arg
1               5

<210> SEQ ID NO 391
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 391

Val Ser Glu Leu Lys Glu Glu Leu Lys
1               5

<210> SEQ ID NO 392
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 392

Thr Thr Trp Val Thr Lys His Ala Ala Glu Asn Pro Gly Lys
1               5                   10
```

```
<210> SEQ ID NO 393
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 393

Ile Lys Ala Ile Pro Gln Leu Gln Gly Tyr Leu Arg
1               5                   10

<210> SEQ ID NO 394
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Thiol modification at Lysine 4

<400> SEQUENCE: 394

Ile Met Glu Lys Lys
1               5

<210> SEQ ID NO 395
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Alkene modification at Lysine 11

<400> SEQUENCE: 395

Thr Pro Val Glu Val Pro Val Gly Gly Phe Lys Gly Arg
1               5                   10

<210> SEQ ID NO 396
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9

<400> SEQUENCE: 396

Ser Ala Glu Ala Glu Leu Gln Ser Lys Arg
1               5                   10

<210> SEQ ID NO 397
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: Conversion of Glutamine 1 to Pyroglutamic acid
<220> FEATURE:
<221> NAME/KEY: MISC_FEATURE
<222> LOCATION: (10)..(10)
<223> OTHER INFORMATION: Thiol modification at Lysine 10

<400> SEQUENCE: 397

Gln Leu Ala Glu Ala His Ala Gln Ala Lys Ala Gln Ala Glu Arg
1               5                   10                  15

<210> SEQ ID NO 398
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Thiol modification at Lysine 3

<400> SEQUENCE: 398

Val Gln Lys Ser Leu Ala Ala Glu Glu Glu Ala Ala Arg
1               5                   10

<210> SEQ ID NO 399
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 399

Gly Lys Gln Leu Arg
1               5

<210> SEQ ID NO 400
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Thiol modification at Lysine 6

<400> SEQUENCE: 400

Leu Ala His Tyr Asn Lys Arg
1               5

<210> SEQ ID NO 401
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Loss of Methionine sulfoxide at Methionine 1
<220> FEATURE:
<221> NAME/KEY: MISC_FEATURE
<222> LOCATION: (1)..(1)
<223> OTHER INFORMATION: Acetyl at Methionine 1
<220> FEATURE:
<221> NAME/KEY: MISC_FEATURE
```

```
<222> LOCATION: (6)..(6)
<223> OTHER INFORMATION: Alkene modification at Lysine 6

<400> SEQUENCE: 401

Met Ser Gly Arg Gly Lys Gln Gly Gly Lys
1               5                   10

<210> SEQ ID NO 402
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: TriMethyl at Lysine 1
<220> FEATURE:
<221> NAME/KEY: MISC_FEATURE
<222> LOCATION: (6)..(6)
<223> OTHER INFORMATION: Alkene modification at Lysine 6

<400> SEQUENCE: 402

Lys Ser Thr Gly Gly Lys Ala Pro Arg
1               5

<210> SEQ ID NO 403
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Dimethyl at Lysine 1
<220> FEATURE:
<221> NAME/KEY: MISC_FEATURE
<222> LOCATION: (6)..(6)
<223> OTHER INFORMATION: Alkene modification at Lysine 6

<400> SEQUENCE: 403

Lys Ser Thr Gly Gly Lys Ala Pro Arg
1               5

<210> SEQ ID NO 404
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Dimethyl at Lysine 1
<220> FEATURE:
<221> NAME/KEY: MISC_FEATURE
<222> LOCATION: (6)..(6)
<223> OTHER INFORMATION: Alkene modification at Lysine 6

<400> SEQUENCE: 404

Lys Ser Thr Gly Gly Lys Ala Pro Arg
1               5

<210> SEQ ID NO 405
<211> LENGTH: 9
<212> TYPE: PRT
<213> ORGANISM: Artificial
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Alkene modification at Lysine 1
<220> FEATURE:
<221> NAME/KEY: MISC_FEATURE
<222> LOCATION: (6)..(6)
<223> OTHER INFORMATION: Acetyl at Lysine 6

<400> SEQUENCE: 405

Lys Ser Thr Gly Gly Lys Ala Pro Arg
1               5

<210> SEQ ID NO 406
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Gln->pyro-Glu at Glutamine 1
<220> FEATURE:
<221> NAME/KEY: MISC_FEATURE
<222> LOCATION: (5)..(5)
<223> OTHER INFORMATION: Alkene modification at Lysine 5

<400> SEQUENCE: 406

Gln Leu Ala Thr Lys Ala Ala Arg
1               5

<210> SEQ ID NO 407
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Thiol modification at Lysine 6

<400> SEQUENCE: 407

Thr His Gln Glu Glu Lys Lys
1               5

<210> SEQ ID NO 408
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 408

Val Ile Asn Asp Lys His Asp Asp Val Met Ala Lys
1               5                   10

<210> SEQ ID NO 409
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6
```

<400> SEQUENCE: 409

Thr Gln Ile Ile Ser Lys Lys
1               5

<210> SEQ ID NO 410
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 410

Ile Met Ala Lys Tyr Tyr Thr Arg
1               5

<210> SEQ ID NO 411
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 411

Asn Val Gly Lys Gln Asp Pro Lys
1               5

<210> SEQ ID NO 412
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9

<400> SEQUENCE: 412

Val Val Gly Ser Glu Leu Ile Gln Lys Tyr Leu Gly Asp Gly Pro Lys
1               5                   10                  15

<210> SEQ ID NO 413
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Alkene modification at Lysine 10

<400> SEQUENCE: 413

Glu Phe Leu His Ala Gln Glu Glu Val Lys Arg
1               5                   10

<210> SEQ ID NO 414
<211> LENGTH: 16
<212> TYPE: PRT
<213> ORGANISM: Artificial

```
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9

<400> SEQUENCE: 414

Val Val Gly Ser Glu Phe Val Gln Lys Tyr Leu Gly Glu Gly Pro Arg
1               5                   10                  15

<210> SEQ ID NO 415
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 415

Phe Ile Val Lys Ala Thr Asn Gly Pro Arg
1               5                   10

<210> SEQ ID NO 416
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 416

Leu Asp Ile Leu Lys Ile His Ser Arg
1               5

<210> SEQ ID NO 417
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 417

Val Met Gln Lys Asp Ser Glu Lys
1               5

<210> SEQ ID NO 418
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Thiol modification at Lysine 5

<400> SEQUENCE: 418

Asn Met Ser Ile Lys Lys
1               5
```

```
<210> SEQ ID NO 419
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 419

Asn Met Ser Ile Lys Lys
1               5

<210> SEQ ID NO 420
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 420

Leu Ser Lys Glu Glu Ile Glu Arg
1               5

<210> SEQ ID NO 421
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9

<400> SEQUENCE: 421

Val Thr His Glu Leu Gln Ala Met Lys Asp Lys
1               5                   10

<210> SEQ ID NO 422
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 422

Asn Glu Leu Asn Ala Lys Val Arg
1               5

<210> SEQ ID NO 423
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
```

<223> OTHER INFORMATION: Thiol modification at Lysine 4

<400> SEQUENCE: 423

Ala Met Asp Lys Lys
1               5

<210> SEQ ID NO 424
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 424

Ala Met Asp Lys Lys
1               5

<210> SEQ ID NO 425
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 425

Lys Val Leu Val Lys
1               5

<210> SEQ ID NO 426
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene modification at Lysine 4

<400> SEQUENCE: 426

Lys Val Leu Val Lys
1               5

<210> SEQ ID NO 427
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 427

Val His Pro Glu Gly Lys Phe Val Val Asp Val Asp Lys
1               5                   10

<210> SEQ ID NO 428
<211> LENGTH: 8
<212> TYPE: PRT

```
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 428

Lys His Glu Glu Glu Glu Ala Lys
1               5

<210> SEQ ID NO 429
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Thiol modification at Lysine 1

<400> SEQUENCE: 429

Lys Val Glu Asp Met Met Lys
1               5

<210> SEQ ID NO 430
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Carbamidomethyl at Cysteine 1
<220> FEATURE:
<221> NAME/KEY: MISC_FEATURE
<222> LOCATION: (7)..(7)
<223> OTHER INFORMATION: Alkene modification at Lysine 7

<400> SEQUENCE: 430

Cys Val Ala Gln Ala Ser Lys Asn Arg
1               5

<210> SEQ ID NO 431
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene modification at Lysine 8

<400> SEQUENCE: 431

Ala Leu Ser Val Gly Leu Val Lys Gly Ser Ile Asp Glu Val Asp Lys
1               5                   10                  15

<210> SEQ ID NO 432
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9
```

```
<400> SEQUENCE: 432

Val Ser Gly Ser Glu Leu Val Gln Lys Phe Ile Gly Glu Gly Ala Arg
1               5                   10                  15

<210> SEQ ID NO 433
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Thiol modification at Lysine 9

<400> SEQUENCE: 433

Val Ser Gly Ser Glu Leu Val Gln Lys Phe Ile Gly Glu Gly Ala Arg
1               5                   10                  15

<210> SEQ ID NO 434
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene modification at Lysine 6

<400> SEQUENCE: 434

Thr Met Asp Val Ser Lys Leu Ser Ala Glu Lys
1               5                   10

<210> SEQ ID NO 435
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5

<400> SEQUENCE: 435

Leu Ser Ala Glu Lys Val Glu Ile Ala Thr Leu Thr Arg
1               5                   10

<210> SEQ ID NO 436
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene modification at Lysine 9

<400> SEQUENCE: 436

Met Thr Pro Glu Gln Leu Ala Ile Lys Asn Val Gly Lys
1               5                   10

<210> SEQ ID NO 437
<211> LENGTH: 7
<212> TYPE: PRT
<213> ORGANISM: Artificial
```

```
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene modification at Lysine 2

<400> SEQUENCE: 437

Ile Lys Glu Asn Ser Glu Lys
1               5

<210> SEQ ID NO 438
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 438

Lys Met Asn Leu Thr Arg
1               5

<210> SEQ ID NO 439
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Conversion of Glutamine 1 to Pyroglutamic acid
<220> FEATURE:
<221> NAME/KEY: MISC_FEATURE
<222> LOCATION: (2)..(2)
<223> OTHER INFORMATION: Alkene modification at Lysine 2

<400> SEQUENCE: 439

Gln Lys Glu Val Glu Gln Leu Ile Lys
1               5

<210> SEQ ID NO 440
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene modification at Lysine 1

<400> SEQUENCE: 440

Lys Leu Trp Gly Asp Arg
1               5

<210> SEQ ID NO 441
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene modification at Lysine 5
```

```
<400> SEQUENCE: 441

Phe Asp Leu Leu Lys Arg
1               5

<210> SEQ ID NO 442
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene modification at Lysine 8

<400> SEQUENCE: 442

Ser Ala Pro Gly Gly Gly Ser Lys Val Pro Gln Lys
1               5                   10

<210> SEQ ID NO 443
<211> LENGTH: 18
<212> TYPE: PRT
<213> ORGANISM: Artificial
<220> FEATURE:
<223> OTHER INFORMATION: Synthetic

<400> SEQUENCE: 443

Thr Leu Ser Asp Tyr Asn Ile Gln Lys Glu Ser Thr Leu His Leu Val
1               5                   10                  15

Leu Arg

<210> SEQ ID NO 444
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene at Lysine 4
<220> FEATURE:
<221> NAME/KEY: MISC_FEATURE
<222> LOCATION: (8)..(8)
<223> OTHER INFORMATION: Acetyl at Lysine 8

<400> SEQUENCE: 444

Gly Leu Gly Lys Gly Gly Ala Lys Arg
1               5

<210> SEQ ID NO 445
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene at Lysine 2
<220> FEATURE:
<221> NAME/KEY: MISC_FEATURE
<222> LOCATION: (5)..(5)
<223> OTHER INFORMATION: Acetyl at Lysine 5
<220> FEATURE:
<221> NAME/KEY: MISC_FEATURE
<222> LOCATION: (9)..(9)
<223> OTHER INFORMATION: Acetyl at Lysine 9
<220> FEATURE:
<221> NAME/KEY: MISC_FEATURE
```

```
<222> LOCATION: (13)..(13)
<223> OTHER INFORMATION: Acetyl at Lysine 13

<400> SEQUENCE: 445

Gly Lys Gly Gly Lys Gly Leu Gly Lys Gly Gly Ala Lys Arg
1               5                   10
```

MASS SPECTROMETRY-CLEAVABLE CROSS-LINKING AGENTS

CROSS-REFERENCE TO RELATED APPLICATIONS

This application is a Continuation-in-Part Application of U.S. application Ser. No. 14/927,332, filed Oct. 29, 2015, which is Continuation Application of U.S. application Ser. No. 13/471,365, filed May 14, 2012, and issued as U.S. Pat. No. 9,222,943 on Dec. 29, 2015, which claims the benefit of U.S. Provisional Application No. 61/486,260, filed May 14, 2011, which are hereby incorporated by reference in their entirety. This Continuation-in-Part Application claims the benefit of U.S. Provisional Application No. 62/222,690, filed Sep. 23, 2015, which is hereby incorporated by reference in its entirety.

STATEMENT REGARDING FEDERALLY SPONSORED RESEARCH OR DEVELOPMENT

This invention was made with Government support under Grant No. R01GM074830 awarded by the National Institutes of Health, Grant No. R21CA161807 awarded by the National Institutes of Health, and Grant No. R01GM106003 awarded by the National Institutes of Health. The Government has certain rights in this invention.

SEQUENCE LISTING IN ELECTRONIC FORMAT

The present application is being filed along with a Sequence Listing as an ASCII text file via EFS-Web. The Sequence Listing is provided as a file entitled UCI012001P1SEQLIST.txt, created and last saved on Dec. 5, 2016, which is 88,797 bytes in size, and updated by a file entitled UCI012001P1SEQLISTREPLACEMENT.txt, created and last saved on Oct. 1, 2017, which is 121,214 bytes in size. The information in the electronic format of the Sequence Listing is incorporated herein by reference in its entirety in accordance with 35 U.S.C. § 1.52(e).

FIELD

The disclosure relates generally to cross-linking agents and methods of using cross-linking agents to facilitate structural analysis of proteins and protein complexes. In some embodiments, the disclosure relates to MS-cleavable cross-linking agents that are diester derivatives of 3,3'-sulfinylbispropanoic acid and methods of using MS-cleavable cross-linking agents that are diester derivatives of 3,3'-sulfinylbispropanoic acid to facilitate structural analysis of proteins and protein complexes.

In some embodiments, the disclosure relates to azide-tagged, acid-cleavable disuccinimidyl-bisulfoxide (azide-A-DSBSO) cross-linking agent and methods of using azide-A-DSBSO to facilitate structural analysis of proteins and protein complexes.

In some embodiments, the disclosure relates to alkyne-tagged, acid-cleavable disuccinimidyl-bisulfoxide (alkyne-A-DSBSO) cross-linking agent and methods of using alkyne-A-DSBSO to facilitate structural analysis of proteins and protein complexes.

BACKGROUND

Knowledge of elaborate structures of protein complexes is fundamental for understanding their functions and regulations. Although cross-linking coupled with mass spectrometry (MS) has been presented as a feasible strategy for structural elucidation of large multi-subunit protein complexes, this method has proven challenging due to technical difficulties in unambiguous identification of cross-linked peptides and determination of cross-linked sites by MS analysis.

Despite the availability of multiple types of MS-cleavable cross-linkers, most of the applications have been limited to the study of model peptides and single proteins. Additionally, complicated synthesis and fragmentation patterns have impeded most of the known MS-cleavable cross-linkers from wide adaptation by the community.

SUMMARY

In some embodiments, an MS-cleavable cross-linker for mapping intra-protein interactions in a protein, inter-protein interactions in a protein complex or a combination thereof is provided. In some embodiments, the MS-cleavable cross-linker comprises at least one amine-reactive N-hydroxysuccinimdyl (NHS) ester group and at least one collision-induced dissociation (CID) cleavable bond.

In some embodiments of the MS-cleavable cross-linker, the amine-reactive NHS ester group is designed to react with a lysine side chain in a peptide or a protein. In some embodiments of the MS-cleavable cross-linker, the at least one CID cleavable bond is a sulfoxide bond. In some embodiments of the MS-cleavable cross-linker, the MS-cleavable cross-linker is DSSO, comprising the structure:

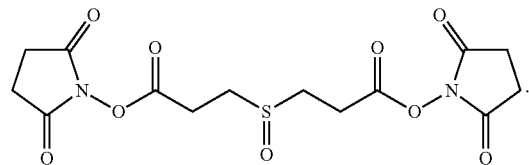 [SMILES: O=C(CCS(=O)CCC(=O)ON1C(=O)CCC1=O)ON1C(=O)CCC1=O]

In some embodiments, the MS-cleavable cross-linker additionally comprises at least one enrichment handle and at least one acid cleavage site, wherein the MS-cleavable cross-linker is membrane permeable.

In some embodiments of the MS-cleavable cross-linker, the at least one enrichment handle comprises a functional group, wherein the functional group is an azide functional group or an alkyne functional group, and wherein the functional group is designed for a click reaction with strained alkynes or a CuAAC reaction.

In some embodiments of the MS-cleavable cross-linker, the acid cleavable site is an acid labile acetal bond, wherein the acid labile acetal bond is designed to be cleaved under aqueous acidic conditions.

In some embodiments, wherein the MS-cleavable cross-linker is azide-A-DSBSO, comprising the structure:

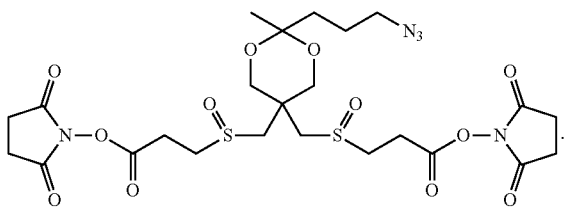 [SMILES: CC1(CCCN=[N+]=[N-])OCC(CS(=O)CCC(=O)ON2C(=O)CCC2=O)(CS(=O)CCC(=O)ON2C(=O)CCC2=O)CO1]

In some embodiments, the MS-cleavable cross-linker is alkyne-A DSBSO, comprising the structure:

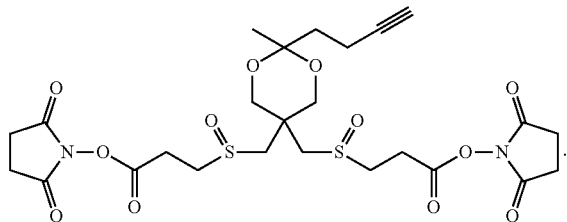 [SMILES: C#CCCC1(C)OCC(CS(=O)CCC(=O)ON2C(=O)CCC2=O)(CS(=O)CCC(=O)ON2C(=O)CCC2=O)CO1]

In some embodiments, a method for synthesis of an MS-cleavable cross-linker for mapping intra-protein interactions in a protein, inter-protein interactions in a protein complex or a combination thereof is provided.

In some embodiments, the method comprises the steps of:
 (i) providing 3,3'-thiodipropionic acid;
 (ii) deriving bis(2,5-dioxopyrrolidin-1-yl) 3,3'-thiodipropionate from the compound of step (i); and
 (iii) deriving DSSO from the compound of step (ii).

In some embodiments, a method for synthesis of an MS-cleavable cross-linker for mapping intra-protein interactions in a protein, inter-protein interactions in a protein complex or a combination thereof is provided.

In some embodiment, the method comprises the steps of:
 (i) providing 2,2-bis(hydroxymethyl)propane-1,3-diol;
 (ii) deriving (1,5-dioxaspiro[5.5]undecane-3,3-diyl)dimethanol from the compound of step (i);
 (iii) deriving (1,5-dioxaspiro[5.5]undecane-3,3-diyl)bis(methylene) dimethanesulfonate from the compound of step (ii);
 (iv) deriving S,S'-((1,5-dioxaspiro[5.5]undecane-3,3-diyl)bis(methylene)) diethanethioate from the compound of step (iii);
 (v) deriving dimethyl 3,3'-(((1,5-dioxaspiro[5.5]undecane-3,3-diyl)bis(methylene))bis(sulfanediyl))dipropionate from the compound of step (iv);
 (vi) deriving dimethyl 3,3'-((2,2-bis(hydroxymethyl)propane-1,3-diyl)bis(sulfanediyl))dipropionate from the compound of step (v);
 (vii) deriving dimethyl 3,3'-(((2-(3-azidopropyl)-2-methyl-1,3-dioxane-5,5-diyl)bis(methylene))bis(sulfanediyl))dipropionate from the compound of step (vi);
 (viii) deriving 3,3'-(((2-(3-azidopropyl)-2-methyl-1,3-dioxane-5,5-diyl)bis(methylene))bis(sulfanediyl))dipropionic acid from the compound of step (vii);
 (ix) deriving bis(2,5-dioxopyrrolidin-1-yl) 3,3'-(((2-(3-azidopropyl)-2-methyl-1,3-dioxane-5,5-diyl)bis(methylene))bis(sulfanediyl))dipropionate from the compound of step (viii);
 (x) deriving azide-A-DSBSO from the compound of step (ix).

In some embodiments, a method for synthesis of an MS-cleavable cross-linker for mapping intra-protein interactions in a protein, inter-protein interactions in a protein complex or a combination thereof is provided.

In some embodiments, the method comprises the steps of:
 (i) providing 2,2-bis(bromomethyl)propane-1,3-diol and methyl 3-mercaptopropanoate;
 (ii) deriving dimethyl 3,3'-((2,2-bis(hydroxymethyl)propane-1,3-diyl)bis(sulfanediyl))dipropionate from the compounds of step (i);
 (iii) deriving dimethyl 3,3'-(((2-(3-azidopropyl)-2-methyl-1,3-dioxane-5,5-diyl)bis(methylene))bis(sulfanediyl))dipropionate from the compound of step (ii);
 (iv) deriving bis(2,5-dioxopyrrolidin-1-yl) 3,3'-(((2-(3-azidopropyl)-2-methyl-1,3-dioxane-5,5-diyl)bis(methylene))bis(sulfanediyl))dipropionate from the compound of step (iii); and
 (v) deriving azide-A-DSBSO from the compound of step (iv).

In some embodiments, a method for synthesis of an MS-cleavable cross-linker for mapping intra-protein interactions in a protein, inter-protein interactions in a protein complex or a combination thereof is provided.

In some embodiment, the method comprises the steps of:
 (i) providing dimethyl 3,3'-((2,2-bis(hydroxymethyl)propane-1,3-diyl)bis(sulfanediyl))dipropionate;
 (ii) deriving dimethyl 3,3'-(((2-(but-3-yn-1-yl)-2-methyl-1,3-dioxane-5,5-diyl)bis(methylene))bis(sulfanediyl))dipropionate from the compound of step (i);
 (iii) deriving bis(2,5-dioxopyrrolidin-1-yl) 3,3'-(((2-(but-3-yn-1-yl)-2-methyl-1,3-dioxane-5,5-diyl)bis(methylene))bis(sulfanediyl))dipropionate from the compound of step (ii); and
 (iv) deriving alkyne-A-DSBSO from the compound of step (iii).

In some embodiments, a method for mapping intra-protein interactions in a protein, inter-protein interactions in a protein complex or a combination thereof is provided. In some embodiment, the method comprises the steps of providing an MS-cleavable cross-linker, wherein the MS-cleavable cross-linker comprises at least one amine-reactive N-hydroxysuccinimdyl (NHS) ester group and at least one collision-induced dissociation (CID) cleavable bond, forming a cross-linked protein or protein complex by cross-linking the protein or the protein complex with the MS-cleavable cross-linker, forming one or more peptide fragments that are chemically bound to the MS-cleavable cross-linker by digesting the cross-linked protein or protein complex with an enzyme, and identifying the one or more peptide fragments using tandem mass spectrometry (MS"), thereby mapping intra-protein interactions in a protein and inter-protein interactions in a protein complex.

In some embodiments of the method, the MS-cleavable cross-linking agent is a derivative of a compound of structure:

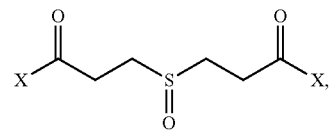

wherein X is selected from the group consisting of:

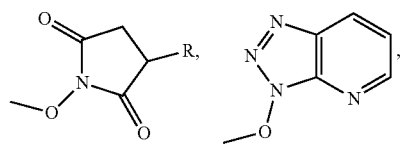

-continued

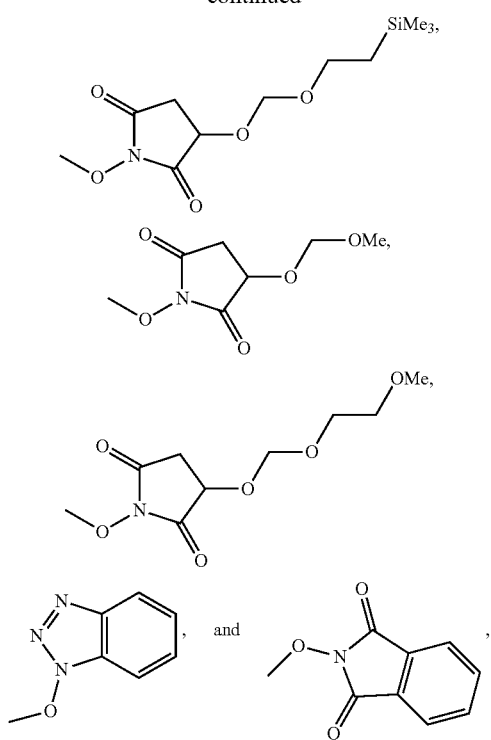

wherein R is H, methyl or ethyl.

In some embodiments of the method, the MS-cleavable cross-linking agent is DSSO, comprising the structure:

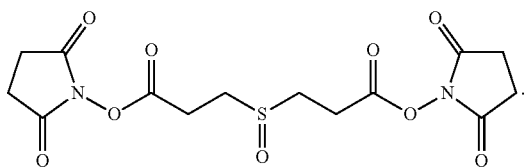 [SMILES: O=C(CCS(=O)CCC(=O)ON1C(=O)CCC1=O)ON1C(=O)CCC1=O]

In some embodiments of the method, the MS-cleavable cross-linking agent additionally comprises at least one enrichment handle, and at least one acid cleavage site, wherein the MS-cleavable cross-linker is membrane permeable.

In some embodiments of the method, the MS-cleavable cross-linking agent is azide-A-DSBSO, comprising the structure:

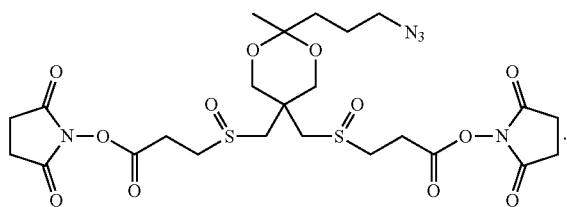 [SMILES: CC1(CCCN=[N+]=[N-])OCC(CS(=O)CCC(=O)ON2C(=O)CCC2=O)(CS(=O)CCC(=O)ON2C(=O)CCC2=O)CO1]

In some embodiments of the method, the MS-cleavable cross-linking agent is alkyne-A-DSBSO, comprising the structure:

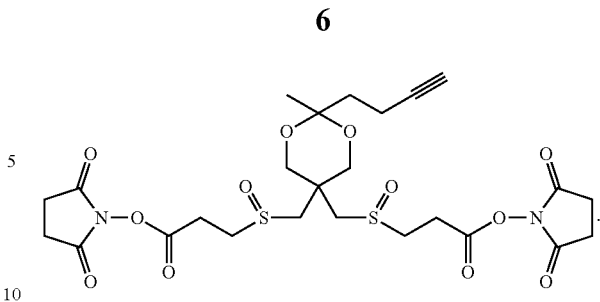

In some embodiments of the method, the at least one enrichment handle comprises a functional group for an enrichment strategy, wherein the functional group is an azide functional group or an alkyne functional group, and wherein the functional group is designed for a click reaction with strained alkynes or a CuAAC reaction.

In some embodiments of the method, the enrichment strategy is an affinity purification wherein the affinity purification comprises direct coupling with alkyne or azide functionalized beads or linking with one or more common affinity ligands such as biotin.

In some embodiments of the method, the acid cleavable site is an acid labile acetal bond, wherein the acid labile acetal bond is designed to be cleaved under aqueous acidic conditions for selective elution from an affinity column.

In some embodiments, a method for cross-linking mass spectrometry (XL-MS) for identifying one or more cross-linked peptides is provided. In some embodiments, the method comprises performing cross-linking with an MS-cleavable cross-linker to obtain one or more cross-linked proteins, wherein the MS-cleavable cross-linker comprises at least one amine-reactive N-hydroxysuccinimdyl (NHS) ester group, and at least one collision-induced dissociation (CID) cleavable bond, digesting the one or more cross-linked proteins with trypsin to obtain one or more cross-linked peptides, performing a liquid chromatography-tandem mass spectrometry (LC-MS$^n$) analysis on the one or more cross-linked peptides, wherein the LC-MSn analysis comprises detecting the one or more cross-linked peptides by MS1 analysis, selecting the one or more cross-linked peptides detected by MS1 for MS2 analysis, selectively fragmenting the at least one CID cleavable bond and separating the one or more cross-linked peptides during MS2 analysis, sequencing the one or more cross-linked peptides separated during MS2 analysis by MS3 analysis, and integrating data obtained during MS1, MS2 and MS3 analyses to identify the one or more cross-linked peptides.

In some embodiments of the method, the MS-cleavable cross-linking agent is DSSO, comprising the structure:

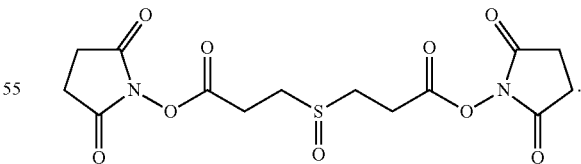

In some embodiments of the method, the MS-cleavable cross-linking agent additionally comprises at least one enrichment handle and at least one acid cleavage site, wherein the MS-cleavable cross-linker is membrane permeable.

In some embodiments of the method, the MS-cleavable cross-linking agent is azide-A-DSBSO, comprising the structure:

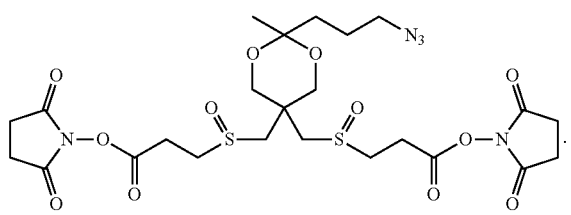 [SMILES: CC1(CCCN=[N+]=[N-])OCC(CS(=O)CCC(=O)ON2C(=O)CCC2=O)(CS(=O)CCC(=O)ON2C(=O)CCC2=O)CO1]

In some embodiments of the method, MS-cleavable cross-linking agent is alkyne-A-DSBSO, comprising the structure:

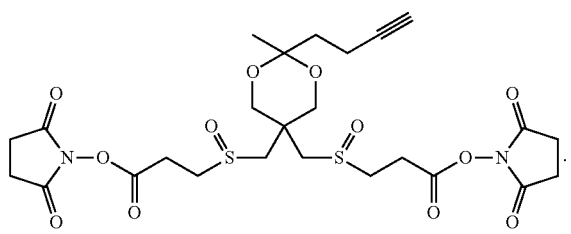 [SMILES: C#CCCC1(C)OCC(CS(=O)CCC(=O)ON2C(=O)CCC2=O)(CS(=O)CCC(=O)ON2C(=O)CCC2=O)CO1]

BRIEF DESCRIPTION OF THE DRAWINGS

FIG. 1 shows exemplary Compounds 1 and 3-9 and General Structure 2 according to the invention.

FIG. 14 shows protein cross-linkers designed with CID cleavable sulfoxide groups. azide (3) or alkyne (4) groups for click chemistry enrichment strategies, and an acid labile acetal to facilitate affinity purification.

FIG. 19A shows schematic illustration of MS$^2$ analysis of a azide-A•DSBSO interlinked homodimeric peptide (α-α). During collision-induced dissociation in MS$^2$, cleavage of either of the two symmetric MS-cleavable C—S bonds leads to physical separation of the two inter-linked peptides, thus generating pairs of peptide fragments: i.e. $\alpha_A$, and $\alpha_T$.

FIG. 19B shows the interlinked Ac-myelin was detected as multiple charged ions (m/z 1001.82$^{3+}$, m/z 751.62$^{4+}$, m/z 601.45$^{5+}$, m/z 501.41$^{6+}$.

FIG. 19C shows one of the two predicted peptide fragment pairs observed as $\alpha_T^{2+}/\beta_A^{2+}$ (m/z 675.35$^{2+}$/819.89$^{2+}$).

FIG. 19D shows the second of the two predicted peptide fragment pairs observed as $\alpha_T^{3+}/\beta_A^{3+}$ (449.90$^{3+}$/546.93$^{3+}$).

FIG. 21A shows MS$^1$ spectrum of the selected peptide.

FIG. 21B shows MS$^2$ spectrum of the selected peptide. In MS$^2$ spectrum, two pairs of peptide fragments: i.e. $\alpha_A/\beta_T$ (m/z 430.75$^{2+}$/580.28$^{2+}$) and $\alpha_T/\beta_A$ (m/z 521.752+/1489.282+) were detected. Note: $\alpha_A$, $\beta_A$, and K$_A$ are alkene modified species (+54 Da); $\alpha_T$ and $\beta_T$ are unsaturated thiol modified species (+236 Da).

FIG. 21C shows MS$^3$ spectra of $\alpha_A$ (m/z 430.75$^{2+}$) fragments detected in MS$^2$. The detection of a series of y and b ions has unambiguously identified its sequences as KAY-IPGTK.

FIG. 21D shows MS$^3$ spectra of $\beta_A$ (489.28$^{2+}$) fragment detected in MS$^2$. The detection of a series of y and b ions has unambiguously identified its sequences as Mox1FAGIKAK. Mox: oxidized methionine.

FIG. 24A shows graphic illustration of characteristic fragmentation of a DSBSO interlinked peptide (α-β) during collision-induced dissociation (CID) in MS2 at the top. At the bottom are shown MS1 and MS2 spectra of the representative cross-linked peptide (m/z 869.15524+). In the MS2 spectrum, two pairs of peptide fragments (i.e. αA/βT (m/z 590.312+/1139.502+) and αT/βA (681.312+/1048.002+)) were detected. αA, βA, and KA are alkene modified species (+54 Da); αT and βT are unsaturated thiol modified species (+236 Da).

FIG. 24B shows respective MS3 spectra of αA (m/z 590.312+) and PA (1048.002+) fragments detected in MS2. The detection of a series of y and b ions unambiguously identified their sequences as FANYIDKAVR and QKAQASHAQLGDAYDQEIR, respectively.

FIG. 24C shows integration of MS$^n$ data identified this peptide as a DSBSO interlinked peptide (i.e. [FANYIDK120VR] cross-linked to [QK139QASHAQLGDAYDQEIR]).

FIG. 26A shows MS$^1$ spectrum of a representative DSBSO interlinked peptide [α-β] (m/z 659.82594+).

FIG. 26B shows MS$^2$ spectrum of [α-β] (m/z 659.82594+) in which interlinked peptide [α-β] was separated into fragment ions $\alpha_A$ (m/z 499.272+), $\beta_A$ (m/z 720.372+), and $\beta_T$ (m/z 811.372+).

FIG. 26C shows MS³ spectra of αA fragment ion which identified it as peptide NELNAKAVR of proteasome subunit Rpt6.

FIG. 26D shows MS³ spectra of βT fragment ion which identified it as peptide EFLHAQEEVKTR of proteasome subunit Rpt3.

FIG. 27A shows Western blot analysis of biotin-conjugated products of Azide-A-DSBSO cross-linked cytochrome C after reacting with increasing amounts of BARAC. The effectiveness of biotin conjugation of Azide-A-DSBSO cross-linked cytochrome C and subsequent purification by binding to streptavidin resins was monitored by SDS-PAGE and immunoblotting. Top: reaction in phosphate buffer conditions; Bottom: reaction in 8M urea lysis buffer conditions. Western blots are probed with streptavidin-conjugated to HRP.

FIG. 27B shows Assessment of CytC cross-linking, biotin-conjugation, and streptavidin enrichment under optimal conditions by SDS-PAGE analysis and Coomassie blue staining. Different membranes were tested for their capabilities of handling cross-linked samples, the boxed region shows the same sample that was filtered with 3 different filter membranes; last two lanes were loaded at a 1:10 dilution in order to compare equivalent amounts of biotin-conjugated CytC before (original load) and after (flow thru) binding to streptavidin beads.

FIG. 28A-FIG. 28C show optimization of BARAC conjugation and affinity purification on lysates of in vivo azide-A-DSBSO cross-linked human 293 cells.

FIG. 28A shows Western blot analysis of click chemistry reaction with Azide-A-DSBSO cross-linked 293 cell lysate and increasing amounts of BARAC (1-1000 µM).

FIG. 28B shows Western blot analysis of streptavidin binding efficiency using increasing ratios of lysate to streptavidin beads.

FIG. 28C shows Evaluation of biotin-conjugation and streptavidin binding efficiency of cross-linked lysate by immunoblotting. Samples were loaded in the following order: cross-linked lysate, biotin-conjugated crosslinked lysate, flow thru of biotin-conjugated cross-linked lysate after binding to streptavidin, and washes of streptavidin beads. XL=Cross-linked; FT=Flow Thru.

FIG. 29A-FIG. 29E show optimization of biotin-conjugation and affinity purification on cell fractionated and size fractionated in vivo azide-A-DSBSO cross-linked 293 cell lysates.

FIG. 29A shows SDS-PAGE analysis of non-crosslinked 293 cell fractions [C=Cytosolic; M=Membrane; N=Nuclear; I=Insoluble].

FIG. 29B shows SDS-PAGE analysis of Azide-ADSBSO cross-linked 293 cell lysate and cell fractions. ["-"=No fractionation].

FIG. 29C shows Western blot analysis of 293 cell lysate and cell fractions. Top: probed with calnexin antibody (membrane protein); Middle: probed with GAPDH antibody (cytosolic protein); Bottom: probed with Lamin A/C antibody (nuclear protein).

FIG. 29D shows 293 cell lysates reacted with increasing amounts of BARAC (0, 1, 10, 50, 100, 250. 500, 1000 µM), separated by SDS-PAGE and analyzed by Western blot probing for Streptavidin-HRP.

FIG. 29E shows dot blot of 100 and 30 kDa filtered lysates; [Bio-D=biotin-conjugated digest; S-FT=streptavidin flow thru].

FIG. 31A-FIG. 31E show identified Intra- and Inter-Subunit Inter-Linked Peptides, Mapped onto 2.5 Å Nucleosome Crystal Structure Containing Histone H2A, H2B, H3.2, and H4. Visualization and distance measurements (in A) were done with Pymol.

FIG. 31A shows nucleosome crystal structure downloaded from the Protein Data Bank (PDB); PDB ID=3AV1. Nucleosome complex consists of two copies each of Histone H2A (Blue), H2B (Green), H3.2 (Purple), and H4 (Red). Azide-A-DSBSO intra-subunit (yellow) and inter-subunit (black) inter-linked peptides are represented by dashed lines.

FIG. 31B shows zoomed in views of identified intra-subunit inter-links between H2BLys35-Lys58 and H2BLys35-Lys86 (black=dimer; red=monomer).

FIG. 31C shows zoomed in views of identified inter-subunit inter-links between H4Lys78-H2BLys86, H4Lys92-H2ALys37, H2ALys37-H2BLys35, and H2ALys37-H2BLys86.

FIG. 31D shows zoomed in views of identified inter-subunit inter-links between H3.2Lys80-H4Lys78, H3.2Lys80-H2BLys109, H2BLys109-H4Lys60, and H2B109-H2ALys96.

FIG. 31E shows zoomed in views of identified inter-subunit inter-links between H2ALys119-H3.2Lys123.

FIG. 32A shows evaluation of HB-tag Based Tandem Affinity Purification of In Vivo Azide-ADSBSO Cross-linked Proteasome Complexes from $293^{HB-Rpn11}$ cells.

FIG. 32B shows evaluation of HB-tag Based Tandem Affinity Purification of In Vivo Azide-ADSBSO Cross-linked Proteasome Complexes from $293^{HB-Rpt6}$ cells.

DESCRIPTION OF THE TABLES

Figure 2:
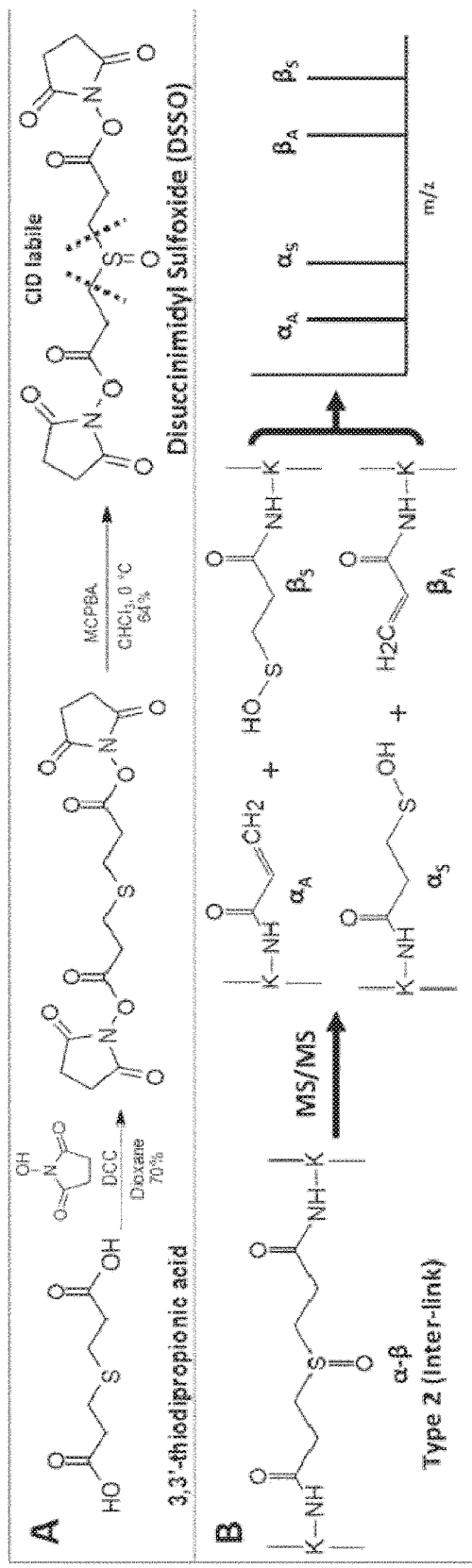
FIG. 2 shows proposed fragmentation schemes of DSSO-cross-linked peptides. A, DSSO synthesis and structure. B-D, MS/MS fragmentation patterns of the three types of DSSO-cross-linked peptides: interlinked (B), dead end (C), and intralinked (D). E, conversion of a sulfenic acid-modified fragment to an unsaturated thiol-modified fragment after a water loss. F, mass relationships between MS/MS fragment ions shown in B-D and their parent ions. DCC, N,N'-dicyclohexylcarbodiimide; MCPBA, m-chloroperbenzoic acid.
Figure 2:
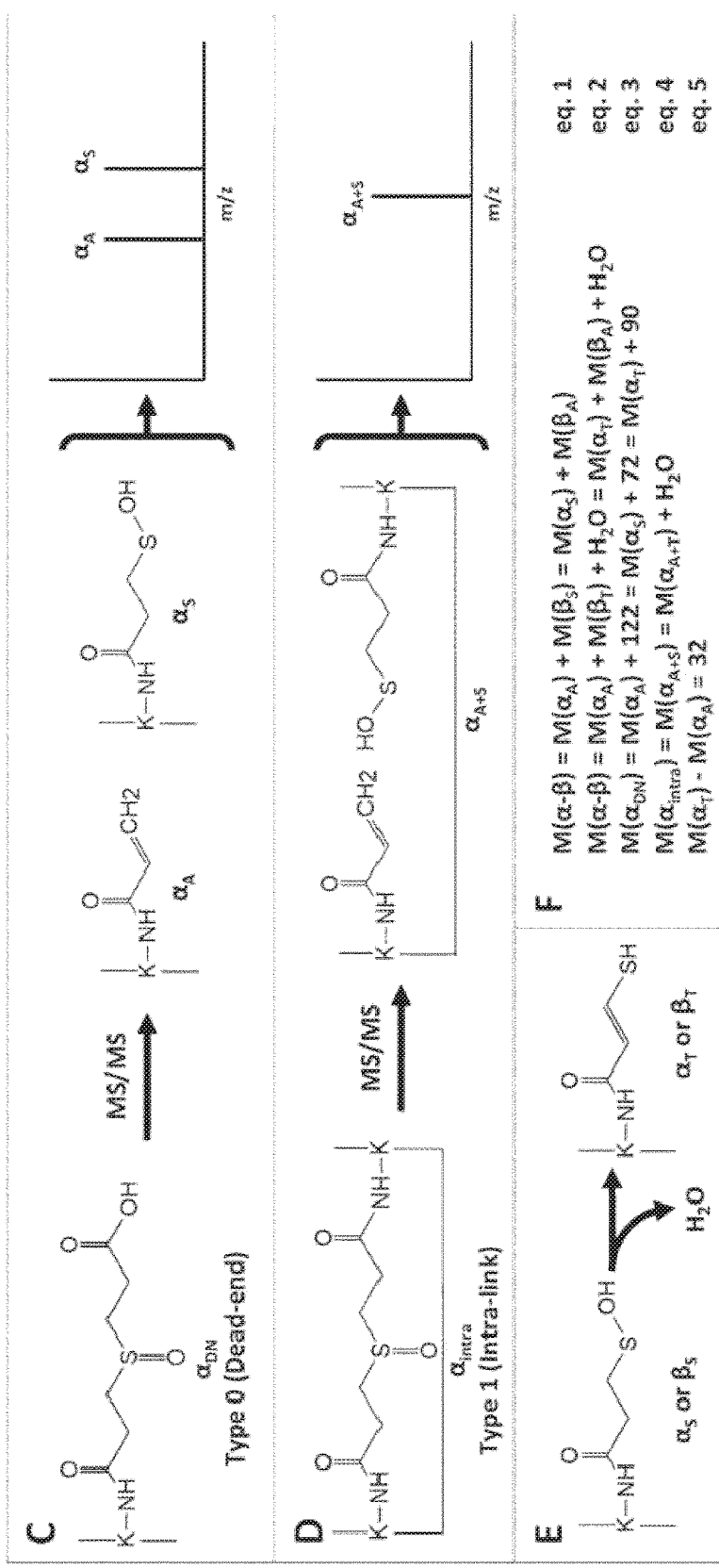

TABLE 1-Summary of DSSO-interlinked peptides of cytochrome c identified by LC MSn.

TABLE 2-Summary of DSSO-interlinked peptides of the yeast 20 S proteasome complex identified by LC MSn.

TABLE 3-Summary of DSSO cross-linked peptides—DSSO dead-end, intra-linked and multilinked peptides—of cytochrome c by LC MSn.

TABLE 4-Summary of DSSO cross-linked peptides of ubiquitin by LC MSn.

TABLE 5-Summary of DSSO inter-linked and dead-end peptides of the yeast 20S proteasome complex by LC MSn.

TABLE 6-Peptide sequences with their corresponding SEQ ID NOs.

TABLE 7-Summary of unique inter-linked peptides identified from azide-A-DSBSO cross-linked cytochrome C.

TABLE 8-Summary of proteins identified from in vivo cross-linked human 293 cells after enrichment.

TABLE 9-GO analysis of the identified azide-A-DSBSO cross-linked proteins.

TABLE 10
Detailed report of inter-linked peptides identified from in vivo cross-linked human 293 cells.

TABLE 11-Summary of identified inter-subunit inter-links of in vivo cross-linked proteasome complexes.

TABLE 12-Detailed summary of identified inter-subunit inter-linked peptides of in vivo cross-linked proteasome complexes.

TABLE 1

| Type | Peptide Sequence | AA Location | MS m/z (Observed) | z | Δ (PPM) | Mod Position | m/z sequenced in MS3 | z | Distance (Cα-Cα) | References |
|---|---|---|---|---|---|---|---|---|---|---|
| 2 | Ac-GDVEKGK (SEQ ID NO: 32) | G1-K7 | 565.30 | 3 | 1 | $K_T5$ | 860.38 | 1 | 5.3 Å | 19, 20, 21, 31 |
|   | KIFVQK (SEQ ID NO: 35) | K8-K13 |   |   |   | $K_A8$ | 408.75 | 2 |   |   |
| 2 | Ac-GDVEKGK (SEQ ID NO: 32) | G1-K7 | 603.81 | 2 | 0 | $K_A5$ | 828.41 | 1 | 13.0 Å | 21, 31, 43 |
|   | KK | K87-K88 |   |   |   | K87* |   |   |   |   |
| 2 | Ac-GDVEKGK (SEQ ID NO: 32) | G1-K7 | 516.93 | 3 | 0 | $K_T5$ | 860.38 | 1 | 13.0 Å | 21, 31 |
|   | KKGER (SEQ ID NO: 13) | K87-R91 |   |   |   | $K_A87$ | 336.20 | 2 |   |   |
| 2 | Ac-GDVEKGK (SEQ ID NO: 32) | G1-K7 | 474.23 | 3 | 2 | $K_A5$ | 414.71 | 2 | 13.0 Å | — |
|   | KGER (SEQ ID NO: 38) | K88-R91 |   |   |   | K88* |   |   |   |   |
| 2 | Ac-GDVEKGK (SEQ ID NO: 32) | G1-K7 | 675.35 | 3 | 4 | $K_T5$ | 860.38 | 1 | 13.2 Å | — |
|   | EDLIAYLKK (SEQ ID NO: 39) | E92-K100 |   |   |   | $K_A99$ | 573.83 | 2 |   |   |
| 2 | Ac-GDVEKGKK (SEQ ID NO: 11) | G1-K8 | 445.57 | 3 | 1 | $K_A7$ | 478.76 | 2 | 15.7 Å | 21, 31 |
|   | KK | K87-K88 |   |   |   | K87* |   |   |   |   |
| 2 | Ac-GDVEKGKK (SEQ ID NO: 11) | G1-K8 | 419.97 | 4 | 0 | $K_A7$ | 478.76 | 2 | 15.7 Å | 21, 31 |
|   | KKGER (SEQ ID NO: 13) | K87-K91 |   |   |   | $K_T87$ | 352.18 | 2 |   |   |
| 2 | GKK | G6-K8 | 641.67 | 3 | 0 | K7* | 760.39 | 2 | 18.7 Å | 14, 31, 43 |
|   | HKTGPNLHGLFGR (SEQ ID NO: 16) | H26-R38 |   |   |   | $K_T27$ |   |   |   |   |
| 2 | GKK | G6-K8 | 526.26 | 2 | 0 | K7* | 616.29 | 1 | 9.9 Å | 21, 43 |
|   | KATNE (SEQ ID NO: 42) | K100-E104 |   |   |   | K100* |   |   |   |   |
| 2 | KIFVQK (SEQ ID NO: 35) | K8-K13 | 398.90 | 3 | 2 | $K_T8$ | 424.74 | 2 | 14.8 Å | 31 |
|   | KK | K87-K88 |   |   |   | K87* |   |   |   |   |
| 2 | KIFVQK (SEQ ID NO: 35) | K8-K13 | 384.97 | 4 | 2 | $K_A8$ | 408.75 | 2 | 14.8 Å | 31 |
|   | KKGER (SEQ ID NO: 13) | K87-R91 |   |   |   | $K_T87$ | 352.18 | 2 |   |   |
| 2 | KIFVQK (SEQ ID NO: 35) | K8-K13 | 494.59 | 3 | 2 | $K_A8$ | 408.75 | 2 | 13.7 Å | 21, 31 |
|   | KATNE (SEQ ID NO: 42) | K100-E104 |   |   |   | K100* |   |   |   |   |
| 2 | GGKHK (SEQ ID NO: 44) | G23-K27 | 756.70 | 3 | 2 | $K_T25$ | 612.29 | 1 | 19.3 Å | — |
|   | KTGQAPGFSYTDANK (SEQ ID NO: 19) | K39-K53 |   |   |   | $K_A39$ | 819.89 | 2 |   |   |
| 2 | KTGQAPGFSYTDANK (SEQ ID NO: 19) | K39-K53 | 945.47 | 3 | 3 | $K_A39$ | 819.89 | 2 | 15.1 Å | 31 |
|   | EDLIAYLKK (SEQ ID NO: 39) | E92-K100 |   |   |   | $K_T99$ | 1178.62 | 1 |   |   |
| 2 | KTGQAPGFSYTDANK (SEQ ID NO: 19) | K39-K53 | 768.69 | 3 | 0 | $K_T39$ | 835.88 | 2 | 18.0 Å | 21, 31, 43 |
|   | KATNE (SEQ ID NO: 42) | K100-E104 |   |   |   | K100* |   |   |   |   |
| 2 | TGQAPGFSYTDANKNK (SEQ ID NO: 46) | T40-K55 | 1104.21 | 3 | 2 | $K_T53$ | 892.90 | 2 | 11.6 Å | 31 |
|   | YIPGTKMoxIFAGIK (SEQ ID NO: 49) | Y74-K86 |   |   |   | $K_A79$ | 1508.82 | 1 |   |   |
| 2 | KYIPGTK (SEQ ID NO: 51) | K73-K79 | 629.68 | 3 | 2 | $K_T73^‡$ | 892.46 | 1 | 13.2 Å | 31 |
|   | MoxIFAGIKK (SEQ ID NO: 54) | M80-K87 |   |   |   | $K_T68^‡$ | 1009.52 | 1 |   |   |

TABLE 1-continued

| Type | Peptide Sequence | AA Location | MS m/z (Observed) | z | Δ (PPM) | Mod Position | m/z sequenced in MS3 | z | Distance (Ca-Ca) | References |
|---|---|---|---|---|---|---|---|---|---|---|
| 2 | MIFAGIKK (SEQ ID NO: 53) | M80-K87 | 389.21 | 4 | 2 | $K_T86$ | 497.27 | 2 | 6.4 Å | 31 |
|   | KGER (SEQ ID NO: 38) | K88-R91 |   |   |   | K88* |   |   |   |   |
| 2 | MoxIFAGIKK (SEQ ID NO: 54) | M80-K87 | 393.21 | 4 | 2 | $K_T86$ | 505.27 | 2 | 6.4 Å | 31 |
|   | KGER (SEQ ID NO: 38) | K88-R91 |   |   |   | K88* |   |   |   |   |

*Peptide fragments containing these sites were not sequenced by MS³.
†They were identified from different fragment pair ions by MS³.

Note:
All of the inter-linked peptides displayed characteristic fragment pairs and were identified by Batch-tag, MS-Bridge and Link-Finder.

TABLE 2

| Type | Peptide Sequence | Subunit | AA Location | MS m/z (Observed) | z | Δ (PPM) | Mod. Position | m/z sequenced in MS3 | z | Distance (Ca-Ca) |
|---|---|---|---|---|---|---|---|---|---|---|
| 2 | ATATGPKQQEITTNLENHFK (SEQ ID NO: 66) | α1 (PRS2/SCL1) | A168-K187 | 595.10 | 5 | 2 | $K_A174$ | 571.29 | 4 | 14.8 Å |
|   | KVPDK (SEQ ID NO: 68) | α1 (PRS2/SCL1) | K58-K62 |   |   |   | $K_T58$ | 672.34 | 1 |   |
| 2 | KVAHTSYK (SEQ ID NO: 70) | α2 (PRE8) | K91-K98 | 477.51 | 4 | 2 | $K_T91$ | 510.25 | 2 | 5.1 Å |
|   | VLVDKSR (SEQ ID NO: 72) | α2 (PRE8) | V84-R90 |   |   |   | $K_A88$ | 435.76 | 2 |   |
| 2 | IFKPQEIK (SEQ ID NO: 74) | α3 (PRE9) | I229-K236 | 514.03 | 4 | 0 | $K_T231$ | 544.80 | 2 | 14.2 Å |
|   | LYKLNDK (SEQ ID NO: 76) | α3 (PRE9) | L66-K72 |   |   |   | $K_A68$ | 474.26 | 2 |   |
| 2 | IHAQNYLKTYNEDIPVEILVR (SEQ ID NO: 78) | α3 (PRE9) | I93-R113 | 904.47 | 4 | 1 | $K_T100$ | 1307.68 | 2 | 10.6 Å |
|   | YKTNLYK (SEQ ID NO: 80) | β3 (PUP3) | Y69-K75 |   |   |   | $K_A70$ | 492.27 | 2 |   |
| 2 | EFLEKNYDR (SEQ ID NO: 83) | α4 (PRE6) | E173-R181 | 692.33 | 3 | 2 | $K_A177$‡ | 634.30 | 2 | 13.1 Å |
|   | NSKTVR (SEQ ID NO: 85) | α4 (PRE6) | N167-R172 |   |   |   | $K_A169$‡ | 379.71 | 2 |   |
| 2 | ILKQVMEEK (SEQ ID NO: 87) | α5 (PUP2) | I203-K211 | 641.01 | 3 | 0 | $K_T205$ | 602.31 | 2 | 10.5 Å |
|   | ELKEK (SEQ ID NO: 89) | α5 (PUP2) | E242-K246 |   |   |   | K244* |   |   |   |
| 2 | SYKFPR (SEQ ID NO: 90)† | β2 (PUP1)† | S202-R207 | 539.26 | 3 | 1 | $K_A204$ | 426.23 | 2 | 12.1 Å |
|   | EEKQK (SEQ ID NO: 92)† | β2 (PUP1)† | E197-K201 |   |   |   | $K_T199$ | 747.34 | 1 |   |
| 2 | YKTNLYK (SEQ ID NO: 80) | β3 (PUP3) | Y69-K75 | 587.64 | 3 | 2 | $K_A70$‡ | 492.26 | 2 | 10.7 Å |
|   | LKEER (SEQ ID NO: 94) | β3 (PUP3) | L76-R80 |   |   |   | $K_A77$‡ | 364.70 | 2 |   |
| 2 | LGSQSLGVSNKFEK (SEQ ID NO: 29) | β3 (PUP3) | L29-K42 | 595.05 | 4 | 2 | $K_T39$ | 790.40 | 2 | 13.2 Å |
|   | YLKMoxR (SEQ ID NO: 97) | β3 (PUP3) | Y199-R203 |   |   |   | $K_A201$ | 390.71 | 2 |   |
| 2 | NKPELYQIDYLGTK (SEQ ID NO: 27) | β4 (PRE1) | N112-K125 | 833.92 | 4 | 0 | $K_A113$ | 868.45 | 2 | 19.1 Å |
|   | LGSQSLGVSNKFEK (SEQ ID NO: 29) | β3 (PUP3) | L29-K42 |   |   |   | $K_T39$ | 790.39 | 2 |   |

TABLE 2-continued

| Type | Peptide Sequence | Subunit | AA Location | MS m/z (Observed) | z | Δ (PPM) | Mod. Position | m/z sequenced in MS3 | z | Distance (Ca-Ca) |
|---|---|---|---|---|---|---|---|---|---|---|
| 2 | VQDSVILASSKAVTR (SEQ ID NO: 99) | β4 (PRE1) | V9-R23 | 633.74 | 5 | 1 | $K_A19$ | 543.30 | 3 | 7.8 Å |
|  | GISVLKDSDDKTR (SEQ ID NO: 101) | β4 (PRE1) | G24-R36 |  |  |  | $K_T29$ | 760.38 | 2 |  |
| 2 | FKNSVK (SEQ ID NO: 103) | β6 (PRE7) † | F59-K64 | 532.29 | 3 | 2 | $K_T60$ | 808.40 | 1 | 16.2 Å |
|  | KLAVER (SEQ ID NO: 105) | α6 (PRE5) | K102-R107 |  |  |  | $K_A102$ | 385.23 | 2 |  |
| 2 | NQYEPGTNGKVK (SEQ ID NO: 106) | β6 (PRE7) † | N149-K160 | 659.68 | 3 | 0 | $K_A158$ | 694.84 | 2 | 9.8 Å |
|  | KPLK (SEQ ID NO: 108) | β6 (PRE7) † | K161-K164 |  |  |  | K161* |  |  |  |

\* Peptide fragments containing these sites were not sequenced by MS³.
†They were identified from different fragment pair ions by MS³.
†Mature sequence from crystal data was used for data analysis.
Note:
All of the inter-linked peptides displayed characteristic fragment pairs and were identified by Batch-tag, MS-Bridge and Link-Finder.

TABLE 3

| Type | Peptide Sequence | AA Location | MS m/z (Observed) | z | Δ (PPM) | Mod. Position | m/z sequenced in MS3 | z | Peptide Score | Expectation Value | Identified in Other Refs |
|---|---|---|---|---|---|---|---|---|---|---|---|
| 0 | Ac-GDVEKGKK (SEQ ID NO: 11) | G1-K8 | 539.76 | 2 | 1 | $K_T5$ | 494.74 | 2 | 22.7 | 1.90E-05 | 21 |
| 0 | KIFVQK (SEQ ID NO: 35) | K8-K13 | 469.76 | 2 | 2 | $K_A8$ | 408.75 | 2 | 19.1 | 1.00E-04 | 19, 20, 21, 31 |
| 0 | KTGQAPGFSYTDANK (SEQ ID NO: 19) | K39-K53 | 880.90 | 2 | 2 | $K_T39$ | 835.88 | 2 | 41.5 | 2.10E-10 | 19, 20, 21, 41 |
| 0 | TGQAPGFSYTDANKNK (SEQ ID NO: 46) | T40-K55 | 937.92 | 2 | 0 | $K_T53$ | 892.90 | 2 | 28.8 | 4.60E-08 | 19, 31 |
| 0 | KYIPGTK (SEQ ID NO: 51) | K73-K79 | 491.75 | 2 | 2 | $K_A73$ | 430.75 | 2 | 23.9 | 1.40E-05 | 20, 21, 31 |
| 0 | YIPGTKMoxIFAGIK (SEQ ID NO: 49) | Y74-K86 | 815.92 | 2 | 2 | $K_T79$ | 770.90 | 2 | 18.3 | 5.00E-06 | 19, 31 |
| 0 | MoxIFAGIKK (SEQ ID NO: 54) | M80-K87 | 550.28 | 2 | 1 | $K_T86$ | 505.27 | 2 | 22.0 | 4.20E-06 | 31 |
| 0 | EDLIAYLKK (SEQ ID NO: 39) | E92-K100 | 634.83 | 2 | 1 | $K_A99$ | 573.83 | 2 | 32.9 | 2.70E-07 | 21, 31 |

| Type | Peptide Sequence | AA Location | MS m/z (Observed) | z | Δ (PPM) | Mod. Position | m/z sequenced in MS3 | z | Peptide Score | Expectation Value | Distance (Ca-Ca) | Identified in other Refs |
|---|---|---|---|---|---|---|---|---|---|---|---|---|
| 1 | Ac-GDVEKGKK (SEQ ID NO: 11) | G1-K8 | 530.75 | 2 | 2 | $K_A5$, $K_T7$ | 521.75 | 2 | 19.5 | 6.20E-05 | 5.4 Å | 21 |
| 1 | GGKHKTGPNLHGLFGR (SEQ ID NO: 23) | G23-R38 | 611.98 | 3 | 0 | $K_A25$, $K_T27$ | 605.98 | 3 | 37.7 | 2.80E-08 | 6.3 Å | 14, 19, 20, 21, 31, 42 |
| 1 | KYIPGTKMoxIFAGIK (SEQ ID NO: 114) | K73-K86 | 870.96 | 2 | 2 | K73, K79* | — | — | — | — | 12.1 Å | 31 |

TABLE 3-continued

| | Peptide Sequence | AA Location | MS m/z (Observed) | z | Δ (PPM) | Mod. Position | m/z sequenced in MS3 | z | Best Discovery Score | Best Expectation Value | Distance (Ca-Ca) | References |
|---|---|---|---|---|---|---|---|---|---|---|---|---|
| 1 | KYIPGTKMoxIFAGIKK (SEQ ID NO: 116) | K73-K87 | 623.67 | 3 | 2 | K73, K86* | — | | — | — | 13.2 Å | 31 |
| 1 | MoxIFAGIKKK (SEQ ID NO: 118) | M80-K88 | 605.32 | 2 | 2 | $K_A$86, $K_T$87 | 596.32 | 2 | 29.5 | 1.10E-08 | — | 14, 19, 20, 21, 31, 42 |
| 1 | KKGER (SEQ ID NO: 13) | K87-R91 | 388.19 | 2 | 1 | $K_A$87, $K_S$88* | — | | — | — | — | 20, 21 |
| 1 | EDLIAYLKKATNE (SEQ ID NO: 119) | E92-E104 | 833.41 | 2 | 3 | $K_A$99, $K_T$100 | 824.40 | 2 | 28.7 | 1.50E-06 | — | 21, 31 |

| Peptide Type | Peptide Sequence | AA Location | MS m/z (Observed) | z | Δ (PPM) | Mod. Position | m/z sequenced in MS3 | z | Best Discovery Score | Best Expectation Value | Distance (Ca-Ca) | References |
|---|---|---|---|---|---|---|---|---|---|---|---|---|
| 2 | Ac-GDVEKGK (SEQ ID NO: 32) | G1-K7 | 565.30 | 3 | 1 | $K_T$5 | 860.38 | 1 | 19.7 | 2.70E-05 | 5.3 Å | 19, 20, 21, 31 |
| | KIFVQK (SEQ ID NO: 35) | K8-K13 | | | | $K_A$8 | 408.75 | 2 | 20.3 | 1.90E-05 | | |
| 2 | Ac-GDVEKGK (SEQ ID NO: 32) | G1-K7 | 603.81 | 2 | 0 | $K_A$5 | 828.41 | 1 | 23.1 | 2.70E-06 | 13.0 Å | 21, 31, 43 |
| | KK | K87-K88 | | | | K87* | | | | | | |
| 2 | Ac-GDVEKGK (SEQ ID NO: 32) | G1-K7 | 516.93 | 3 | 0 | $K_T$5 | 860.38 | 1 | 19.7 | 2.70E-05 | 13.0 Å | 21, 31 |
| | KKGER (SEQ ID NO: 13) | K87-R91 | | | | $K_A$87 | 336.20 | 2 | 14.8 | 1.50E-04 | | |
| 2 | Ac-GDVEKGK (SEQ ID NO: 32) | G1-K7 | 474.23 | 3 | 2 | $K_A$5 | 414.71 | 2 | 25.5 | 8.60E-07 | 13.0 Å | — |
| | KGER (SEQ ID NO: 38) | K88-R91 | | | | K88* | | | | | | |
| 2 | Ac-GDVEKGK (SEQ ID NO: 32) | G1-K7 | 675.35 | 3 | 4 | $K_T$5 | 860.38 | 1 | 19.7 | 2.70E-05 | 13.2 Å | — |
| | EDLIAYLKK (SEQ ID NO: 39) | E92-K100 | | | | $K_A$99 | 573.83 | 2 | 32.9 | 2.10E-07 | | |
| 2 | Ac-GDVEKGKK (SEQ ID NO: 11) | G1-K8 | 445.57 | 3 | 1 | $K_A$7 | 478.76 | 2 | 23.1 | 7.50E-06 | 15.7 Å | 21, 31 |
| | KK | K87-K88 | | | | K87* | | | | | | |
| 2 | Ac-GDVEKGKK (SEQ ID NO: 11) | G1-K8 | 419.97 | 4 | 0 | $K_A$7 | 478.76 | 2 | 22.0 | 2.20E-05 | 15.7 Å | 21, 31 |
| | KKGER (SEQ ID NO: 13) | K87-K91 | | | | $K_T$87 | 352.18 | 2 | 15.5 | 1.40E-03 | | |
| 2 | GKK (SEQ ID NO: 16) | G6-K8 | 641.67 | 3 | 0 | K7* | | | | | 18.7 Å | 14, 31, 43 |
| | HKTGPNLHGLFGR | H26-R38 | | | | $K_T$27 | 760.39 | 2 | 35.0 | 7.10E-11 | | |

TABLE 3-continued

| | | | | | | | | | | | |
|---|---|---|---|---|---|---|---|---|---|---|---|
| 2 | GKK KATNE (SEQ ID NO: 42) | G6-K8 K100-E104 | 526.26 | 2 | 0 | K7* K$_A$100 | 616.29 | 1 | 14.2 | 2.40E-09 | 9.9 Å 21, 43 |
| 2 | KIFVQK (SEQ ID NO: 35) KK | K8-K13 K87-K88 | 398.90 | 3 | 2 | K$_T$8 K87* | 424.74 | 2 | 19.4 | 1.40E-04 | 14.8 Å 31 |
| 2 | KIFVQK (SEQ ID NO: 35) KKGER (SEQ ID NO: 13) | K8-K13 K87-R91 | 384.97 | 4 | 2 | K$_A$8 K$_T$87 | 408.75 352.18 | 2 2 | 20.3 15.0 | 1.90E-05 1.00E-04 | 14.8 Å 31 |
| 2 | KIFVQK (SEQ ID NO: 35) KATNE (SEQ ID NO: 42) | K8-K13 K100-E104 | 494.59 | 3 | 2 | K$_A$8 K100* | 408.75 | 2 | 20.6 | 3.20E-05 | 13.7 Å 21, 31 |
| 2 | GGKHK (SEQ ID NO: 44) KTGQAPG FSYTDANK (SEQ ID NO: 19) | G23-K27 K39-K53 | 756.70 | 3 | 2 | K$_T$25 K$_A$39 | 612.29 819.89 | 1 2 | 9.0# 44.7 | 8.00E-03 5.70E-11 | 19.3 Å — |
| 2 | KTGQAPG FSYTDANK (SEQ ID NO: 19) EDLIAYLKK (SEQ ID NO: 39) | K39-K53 E92-K100 | 945.47 | 3 | 3 | K$_A$39 K$_T$99 | 819.89 1178.62 | 2 1 | 42.5 22.9 | 2.50E-10 1.80E-05 | 15.1 Å 31 |
| 2 | KTGQAPG FSYTDANK (SEQ ID NO: 19) KATNE (SEQ ID NO: 42) | K39-K53 K100-E104 | 768.69 | 3 | 0 | K$_T$39 K100* | 835.88 | 2 | 39.9 | 1.20E-09 | 18.0 Å 21, 31, 43 |
| 2 | TGQAPGF SYTDANKN K (SEQ ID NO: 46) YIPGTKMo xIFAGIK (SEQ ID NO: 49) | T40-K55 Y74-K86 | 1104.21 | 3 | 2 | K$_T$53 K$_A$79 | 892.90 1508.82 | 2 1 | 28.8 9.3# | 4.60E-08 1.00E-03 | 11.6 Å 31 |
| 2 | KYIPGTK (SEQ ID NO: 51) MoxIFAGIK K (SEQ ID NO: 54) | K73-K79 M80-K87 | 629.68 | 3 | 2 | K$_T$73‡ K$_T$86‡ | 892.46 1009.52 | 1 1 | 17.6 15.0 | 2.00E-05 2.10E-05 | 13.2 Å 31 |
| 2 | MIFAGIKK (SEQ ID NO: 53) KGER (SEQ ID NO: 38) | M80-K87 K88-R91 | 389.21 | 4 | 2 | K$_T$86 K88* | 497.27 | 2 | 18.9 | 5.00E-05 | 6.4 Å 31 |
| 2 | MoxIFAGIK K (SEQ ID NO: 54) KGER (SEQ ID NO: 38) | M80-K87 K88-R91 | 393.21 | 4 | 2 | K$_T$86 K88* | 505.27 | 2 | 24.0 | 4.20E-07 | 6.4 Å 31 |

TABLE 3-continued

| Peptide Type | Peptide Sequence | AA Location | MS m/z (Observed) | z | Δ (PPM) | Mod. Position | m/z sequenced in MS3 | z | Peptide Score | Expectation Value | Distance (Ca-Ca) | Identified in Other Refs |
|---|---|---|---|---|---|---|---|---|---|---|---|---|
| 0.0 | GGKHKTGPNLHGLFGR (SEQ ID NO: 23) | G23-R38 | 507.74 | 4 | −2 | $K_A25$, $K_A27$ | 446.74 | 4 | 28.0 | 1.10E−06 | — | — |
| 0.1 | YIPGTKMoxIFAGIKKK (SEQ ID NO: 121) | Y74-K88 | 682.34 | 3 | 1 | $K_A79$, $K_A86$, $K_T87$ | 635.67 | 3 | 24.6 | 3.60E−05 | — | — |
| 0.1 | MoxIFAGIKKKGER (SEQ ID NO: 123) | M80-R91 | 576.61 | 3 | 2 | $K_A86$, $K_A87$, $K_T88$ | 529.94 | 3 | 31.8 | 1.20E−05 | — | — |
| 0.1 | MoxIFAGIKKKGER (SEQ ID NO: 123) | M80-R91 | 864.41 | 2 | 1 | $K_T86$, $K_A87$, $K_A88$ | 794.41 | 2 | 34.0 | 2.00E−08 | — | — |
| 0.2 | Ac-GDVEKGKK (SEQ ID NO: 11) | G1-K8 | 899.40 | 2 | 1 | K5, K7* | | | | | ~11.3 Å | — |
|  | KATNE (SEQ ID NO: 42) | K100-E104 | | | | $K_A100$ | 616.29 | 1 | 14.2 | 2.60E−08 | | |
| 0.2 | GKK | G6-K8 | 469.04 | 5 | 0 | K7* | | | | | ~18.7 Å | |
|  | GGKHKTGPNLHGLFGR (SEQ ID NO: 23) | G23-R38 | | | | $K_A25$, $K_A27$ | 446.74 | 4 | 22.3 | 4.20E−06 | | |
| 0.2 | GKKIFVQK (SEQ ID NO: 124) | G6-K13 | 519.28 | 3 | 2 | $K_T7$, $K_A8$ | 544.30 | 2 | 23.1 | 1.90E−05 | ~15.3 Å | |
|  | KK | K87-K88 | | | | K87* | | | | | | |
| 1.2 | Ac-GDVEKGK (SEQ ID NO: 32) | G1-K7 | 828.40 | 3 | 0 | $K_T5$ | 860.38 | 1 | 19.5 | 3.20E−05 | ~13.8 Å | — |
|  | MoxIFAGIKKKGER (SEQ ID NO: 123) | M80-R91 | | | | $K_A86$, $K_A87$, $K_T88$ | 794.41 | 2 | 36.3 | 2.00E−09 | | |
| 1.2 | Ac-GDVEKGKKIFVQK (SEQ ID NO: 126) | G1-K13 | 799.06 | 3 | 2 | $K_T5$, $K_T7$, $K_A8$ | 872.43 | 2 | 18.7 | 1.20E−04 | ~12.1 Å | — |
|  | KATNE (SEQ ID NO: 42) | K100-E104 | | | | $K_A100$ | 616.30 | 1 | 14.2 | 2.40E−09 | | |
| 1.2 | KYIPGTK (SEQ ID NO: 51) | K73-K79 | 839.10 | 3 | 1 | $K_T73$ | 892.46 | 1 | 17.6 | 2.00E−05 | ~15.3 Å | — |
|  | MoxIFAGIKKKGER (SEQ ID NO: 123) | M80-R91 | | | | $K_A86$ $K_T87$, $K_A88$ | 794.41 | 2 | 36.3 | 2.00E−09 | | |

TABLE 3-continued

| | | | | | | | | | | | |
|---|---|---|---|---|---|---|---|---|---|---|---|
| 2.2 | Ac-GDVEKGKK (SEQ ID NO: 11) | G1-K8 | 599.79 | 4 | 0 | K5, K7* | | | | ~14.38 Å, ~11.3 Å | — |
| | KKGER (SEQ ID NO: 13) | K87-R91 | | | | K$_A$87 | 336.20 | 2 | 14.8 | 1.50E-04 | |
| | KATNE (SEQ ID NO: 42) | K100-E104 | | | | K100* | | | | | |

*Peptide fragments containing these sites were not sequenced by MS3.
**These intra-linked were identified by MS/MS.
These MS3 data were considered due to the presence of other lines of evidence for identifying the cross-linked peptides.
†They were identified from different charged fragment pair ions by MS3

Note:
Type 0: dead-end
Type 1: intra-linked
Type0, 1; 0, 2; 1, 2, 2, 2: multi-linked
All of the peptides displayed characteristic fragment pairs.
All of the cross-linked peptides were identified by Link-Finder, Batch-tag and MS-Bridge.

TABLE 4

| Type | Peptide Sequence | AA Location | MS m/z (Observed) | z | Δ (PPM) | Mod. Position | m/z sequenced in MS3 | z | Peptide Score | Expectation Value | Identified in Other Refs |
|---|---|---|---|---|---|---|---|---|---|---|---|
| 0 | MQIFVKTLTGK (SEQ ID NO: 127) | M1-K11 | 721.38 | 2 | 9 | K$_T$6 | 676.36 | 2 | 30.1 | 5.40E-08 | 19, 38 |
| 0 | AKIQDK (SEQ ID NO: 128) | A28-K33 | 439.72 | 2 | 7 | K$_T$29 | 394.71 | 2 | 18.0 | 2.40E-04 | — |
| 0 | LIFAGKQLEDGR (SEQ ID NO: 60) | L43-R54 | 761.89 | 2 | 10 | K$_T$48 | 716.87 | 2 | 35.1 | 1.10E-07 | 19, 38 |
| 0 | LIFAGKQLEDGRTLSDYNIQK (SEQ ID NO: 129) | L43-K62 | 862.44 | 3 | 8 | K$_T$48 | 832.43 | 3 | 34.1 | 1.20E-07 | — |
| 0 | TLSDYNIQKESTLHLVLR (SEQ ID NO: 64) | T55-R72 | 769.40 | 3 | 10 | K$_A$63 | 728.73 | 3 | 36.1 | 1.40E-07 | 19, 38 |

| Type | Peptide Sequence | AA Location | MS m/z (Observed) | z | Δ (PPM) | Mod. Position | m/z sequenced in MS2 | z | Peptide Score | Expectation Value | Distance (Cα-Cα) | Identified in Other Refs |
|---|---|---|---|---|---|---|---|---|---|---|---|---|
| 1 | AKIQDKEGIPPDQQR (SEQ ID NO: 130) | A28-R42 | 940.97 | 2 | 5 | K29, K33 | 940.97 | | 28.5 | 4.40E-07 | 6.42 Å | 19 |
| 2 | TLTGKTITLEVEPSDTIENVK (SEQ ID NO: 57) | T7-K27 | 993.01 | 4 | 5 | K11* | | | | | 13.3 Å | 38 |
| | IQDKEGIPPDQQR (SEQ ID NO: 58) | I30-R42 | | | | K$_A$33 | 789.41 | 2 | 28.6 | 3.20E-08 | | |
| 2 | LIFAGKQLEDGR (SEQ ID NO: 319) | L43-R54 | 713.38 | 4 | 5 | K$_A$48 | 700.88 | 2 | 39.2 | 1.00E-08 | 15.3 Å | 19 |
| | LIFAGKQLEDGR (SEQ ID NO: 60) | L43-R54 | | | | K$_T$48 | 716.87 | 2 | 36.4 | 1.90E-08 | | |

TABLE 4-continued

| | | | | | | | | | | | |
|---|---|---|---|---|---|---|---|---|---|---|---|
| 2 | LIFAGKQLEDGR (SEQ ID NO: 319) | L43-R54 | 909.24 | 4 | 9 | $K_A$48 | 700.89 | 2 | 35.5 | 1.80E-08 | 18.4 Å | 19, 38 |
| | TLSDYNIQKESTLHLVLR (SEQ ID NO: 443) | T55-R72 | | | | $K_T$63 | 1108.58 | 2 | 31.3 | 1.20E-08 | | |

*Peptide fragments containing these sites were not sequenced by MS3.
Note:
Type 0: dead-end
Type 1: intra-linked
Type 2: inter-linked
All of the peptides displayed characteristic fragment pairs.
All of the cross-linked peptides were identified by Link-Finder, Batch-tag and MS-Bridge.

TABLE 5

| Type | Peptide Sequence | Subunit | AA Location | MS m/z (Observed) | z | Δ (PPM) | Mod. Position | m/z sequenced in MS3 | z | peptide Score | Expectation Value |
|---|---|---|---|---|---|---|---|---|---|---|---|
| 0 | AKAEAAEFR (SEQ ID NO: 131) | α1 (PRS2/SCL1) | A97-R105 | 584.77 | 2 | −1 | $K_T$98 | 539.75 | 2 | 35.0 | 1.50E-04 |
| 0 | VLVDKSR (SEQ ID NO: 72) | α2 (PRE8) | V84-R90 | 496.76 | 2 | 0 | $K_A$88 | 435.76 | 2 | 23.8 | 4.60E-04 |
| 0 | TFLEKR (SEQ ID NO: 132) | α2 (PRE8) | T173-R178 | 485.24 | 2 | 1 | $K_A$177 | 424.24 | 2 | 22.9 | 3.30E-04 |
| 0 | KVTSTLLEQDTSTEK (SEQ ID NO: 133) | α3 (PRE9) | K51-K65 | 928.45 | 2 | 0 | $K_A$51 | 867.45 | 2 | 47.2 | 3.50E-09 |
| 0 | STLKLQDTR (SEQ ID NO: 134) | α4 (PRE6) | S50-R58 | 619.31 | 2 | 1 | $K_A$53 | 558.31 | 2 | 36.3 | 3.90E-05 |
| 0 | ITPSKVSK (SEQ ID NO: 135) | α4 (PRE6) | I59-K66 | 518.27 | 2 | 1 | $K_T$63 | 473.26 | 2 | 21.3 | 2.30E-03 |
| 0 | ILIEKAR (SEQ ID NO: 136) | α4 (PRE6) | I84-R90 | 509.78 | 2 | −1 | $K_T$88 | 464.77 | 2 | 27.4 | 1.40E-03 |
| 0 | NSKTVR (SEQ ID NO: 85) | α4 (PRE6) | N167-R172 | 440.71 | 2 | 1 | $K_T$176 | 395.70 | 2 | 22.1 | 5.90E-03 |
| 0 | EFLEKNYDR (SEQ ID NO: 83) | α4 (PRE6) | E173-R181 | 695.30 | 2 | −1 | $K_T$177 | 650.29 | 2 | 30.9 | 1.40E-05 |
| 0 | TAELIKELK (SEQ ID NO: 137) | α5 (PUP2) | T236-K244 | 610.82 | 2 | −4 | $K_T$241 | 565.81 | 2 | 36.3 | 1.80E-04 |
| 0 | KLAVER (SEQ ID NO: 105) | α6 (PRE5) | K102-R107 | 446.23 | 2 | 2 | $K_A$102 | 385.23 | 2 | 18.1 | 3.00E-04 |
| 0 | LLVPQKNVK (SEQ ID NO: 138) | α7 (PRE10) | L58-K66 | 607.84 | 2 | 1 | $K_T$63 | 562.83 | 2 | 24.2 | 9.20E-05 |
| 0 | AELEKLVDHHPEGLSAR (SEQ ID NO: 109) | α7 (PRE10) | A174-R190 | 693.00 | 3 | −2 | $K_T$178 | 663.00 | 3 | 33.5 | 6.70E-06 |
| 0 | EAVKQAAK (SEQ ID NO: 139) | α7 (PRE10) | E191-K198 | 510.76 | 2 | 2 | $K_T$194 | 465.74 | 2 | 26.9 | 7.10E-04 |
| 0 | YKTNLYK (SEQ ID NO: 80) | β3 (PUP3) | Y69-K75 | 553.27 | 2 | 3 | $K_T$70 | 508.25 | 2 | 25.7 | 9.60E-05 |
| 0 | TNLYKLK (SEQ ID NO: 140) | β3 (PUP3) | T71-K77 | 528.27 | 2 | −5 | $K_A$75 | 467.27 | 2 | 25.9 | 2.50E-03 |
| 0 | QELAKSIR (SEQ ID NO: 141) | β4 (PRE1) | Q86-R93 | 560.79 | 2 | 2 | $K_A$90 | 499.79 | 2 | 22.5 | 4.00E-03 |
| 0 | IVDKDGIR (SEQ ID NO: 142) | β4 (PRE1) | I183-R190 | 546.27 | 2 | 1 | $K_T$186 | 501.26 | 2 | 30.6 | 1.40E-03 |
| 0 | FKNSVK (SEQ ID NO: 103) | β6 (PRE7)† | F59-K64 | 449.72 | 2 | 1 | $K_T$60 | 404.71 | 2 | 19.0 | 1.90E-02 |

TABLE 5-continued

| | | | | | | | | | | |
|---|---|---|---|---|---|---|---|---|---|---|
| 0 | KLSINSAAR (SEQ ID NO: 143) | β6 (PRE7)† | K74-R82 | 568.29 | 2 | 3 | $K_A74$ | 507.29 | 2 | 32.8 | 2.00E-04 |
| 0 | KEFYELK (SEQ ID NO: 144) | β6 (PRE7)† | K205-K211 | 566.77 | 2 | 2 | $K_A205$ | 505.77 | 2 | 24.7 | 5.40E-03 |

| Type | Peptide Sequence | Subunit | AA Location | MS m/z (Observed) | z | Δ (PPM) | Mod. Position | m/z sequenced in MS3 | z | Peptide Score | Expectation Value | Distance (Cα-Cα) |
|---|---|---|---|---|---|---|---|---|---|---|---|---|
| 2 | ATATGPKQQEITTNLENHFK (SEQ ID NO: 66) | α1 (PRS2/SCL1) | A168-K187 | 595.10 | 5 | 2 | $K_A174$ | 571.29 | 4 | 24.5 | 2.90E-04 | 14.8 Å |
| | KVPDK (SEQ ID NO: 68) | α1 (PRS2/SCL1) | K58-K62 | | | | $K_T58$ | 672.34 | 1 | 12.3 | 0.71** | |
| 2 | KVAHTSYK (SEQ ID NO: 70) | α2 (PRE8) | K91-K98 | 477.51 | 4 | 2 | $K_T91$ | 510.25 | 2 | 29.9 | 7.60E-05 | 5.1 Å |
| | VLVDKSR (SEQ ID NO: 72) | α2 (PRE8) | V84-R90 | | | | $K_A88$ | 435.76 | 2 | 27.6 | 2.50E-03 | |
| | KVAHTSYK (SEQ ID NO: 70) | α2 (PRE8) | K91-K98 | 382.21 | 5 | 1 | $K_A91$ | 329.85 | 3 | 19.3 | 1.90E-02 | |
| | VLVDKSR (SEQ ID NO: 72) | α2 (PRE8) | V84-R90 | | | | $K_T88$ | 451.74 | 2 | 25.4 | 2.50E-04 | |
| 2 | IFKPQEIK (SEQ ID NO: 74) | α3 (PRE9) | I229-K236 | 514.03 | 4 | 0 | $K_T231$ | 544.80 | 2 | 23.6 | 1.50E-02 | 14.2 Å |
| | LYKLNDK (SEQ ID NO: 76) | α3 (PRE9) | L66-K72 | | | | $K_A68$ | 474.26 | 2 | 25.5 | 5.50E-03 | |
| 2 | IHAQNYLKTYNEDIPVEILVR (SEQ ID NO: 78) | α3 (PRE9) | I93-R113 | 904.47 | 4 | 1 | $K_T100$ | 1307.68 | 2 | 26.6 | 7.90E-05 | 10.6 Å |
| | YKTNLYK (SEQ ID NO: 80) | β3 (PUP3) | Y69-K75 | | | | $K_A70$ | 492.27 | 2 | 23.9 | 3.00E-03 | |
| | IHAQNYLKTYNEDIPVEILVR (SEQ ID NO: 78) | α3 (PRE9) | I93-R113 | 723.78 | 5 | 5 | K100* | | | | | |
| | YKTNLYK (SEQ ID NO: 80) | β3 (PUP3) | Y69-K75 | | | | $K_A70$ | 492.27 | 2 | 24.2 | 2.90E-03 | |
| 2 | EFLEKNYDR (SEQ ID NO: 83) | α4 (PRE6) | E173-R181 | 692.33 | 3 | 2 | $K_A177$‡ | 634.30 | 2 | 23.6 | 2.60E-04 | 13.1 Å |
| | NSKTVR (SEQ ID NO: 85) | α4 (PRE6) | N167-R172 | | | | $K_A169$‡ | 379.71 | 2 | 22.6 | 2.80E-03 | |
| | EFLEKNYDR (SEQ ID NO: 83) | α4 (PRE6) | E173-R181 | 519.50 | 4 | 2 | $K_T177$ | 650.29 | 2 | 33.2 | 1.70E-05 | |
| | NSKTVR (SEQ ID NO: 85) | α4 (PRE6) | N167-R172 | | | | $K_A169$ | 379.71 | 2 | 22.6 | 2.80E-03 | |
| 2 | ILKQVMEEK (SEQ ID NO: 87) | α5 (PUP2) | I203-K211 | 641.01 | 3 | 0 | $K_T205$ | 602.31 | 2 | 29.2 | 3.50E-03 | 10.5 Å |
| | ELKEK (SEQ ID NO: 89) | α5 (PUP2) | E242-K246 | | | | K244* | | | | | |
| | ILKQVMEEK (SEQ ID NO: 87) | α5 (PUP2) | I203-K211 | 481.01 | 4 | 0 | $K_T205$ | 602.31 | 2 | 27.6 | 2.60E-04 | |
| | ELKEK (SEQ ID NO: 89) | α5 (PUP2) | E242-K246 | | | | K244* | | | | | |
| 2 | SYKFPR (SEQ ID NO: 90) | β2 (PUP1)† | S202-R207 | 539.26 | 3 | 1 | $K_A204$ | 426.23 | 2 | 23.1 | 6.40E-03 | 12.1 Å |

TABLE 5-continued

| Peptide | Subunit | Residues | m/z | z | Type | Site | Mass | z2 | Score | E-value | Distance |
|---|---|---|---|---|---|---|---|---|---|---|---|
| EEKQK (SEQ ID NO: 92) | β2 (PUP1)† | E197-K201 | | | | $K_T$199 | 747.34 | 1 | 10.4 | 0.33** | |
| SYKFPR (SEQ ID NO: 90) | β2 (PUP1)† | S202-R207 | 404.70 | 4 | 2 | $K_T$204 | 442.21 | 2 | 21.1 | 8.20E-04 | |
| EEKQK (SEQ ID NO: 92) | β2 (PUP1)† | E197-K201 | | | | K199* | | | | | |
| 2 YKTNLYK (SEQ ID NO: 80) | β3 (PUP3) | Y69-K75 | 587.64 | 3 | 2 | $K_A$70† | 492.26 | 2 | 23.8 | 4.60E-04 | 10.7 Å |
| LKEER (SEQ ID NO: 94) | β3 (PUP3) | L76-R80 | | | | $K_A$77† | 364.70 | 2 | 17.0 | 2.70E-02 | |
| YKTNLYK (SEQ ID NO: 80) | β3 (PUP3) | Y69-K75 | 440.98 | 4 | 2 | $K_T$70 | 508.25 | 2 | 25.7 | 1.10E-04 | |
| LKEER (SEQ ID NO: 94) | β3 (PUP3) | L76-R80 | | | | $K_A$77 | 364.70 | 2 | 16.5 | 8.40E-03 | |
| 2 LGSQSLGVSNKFEK (SEQ ID NO: 29) | β3 (PUP3) | L29-K42 | 793.07 | 3 | 2 | $K_A$39 | 774.41 | 2 | 42.0 | 5.30E-07 | 13.2 Å |
| YLKMoxR (SEQ ID NO: 97) | β3 (PUP3) | Y199-R203 | | | | $K_T$201 | 406.69 | 2 | 16.2 | 1.10E-03 | |
| LGSQSLGVSNKFEK (SEQ ID NO: 29) | β3 (PUP3) | L29-K42 | 595.05 | 4 | 2 | $K_T$39 | 790.40 | 2 | 40.7 | 8.40E-07 | |
| YLKMoxR (SEQ ID NO: 97) | β3 (PUP3) | Y199-R203 | | | | $K_A$201 | 390.71 | 2 | 18.1 | 6.10E-03 | |
| 2 NKPELYQIDYLGTK (SEQ ID NO: 27) | β4 (PRE1) | N112-K125 | 833.92 | 4 | 0 | $K_A$113 | 868.45 | 2 | 32.0 | 9.50E-08 | 19.1 Å |
| LGSQSLGVSNKFEK (SEQ ID NO: 29) | β3 (PUP3) | L29-K42 | | | | $K_T$39 | 790.39 | 2 | 26.5 | 3.90E-05 | |
| 2 VQDSVILASSKAVTR (SEQ ID NO: 99) | β4 (PRE1) | V9-R23 | 633.74 | 5 | 1 | $K_A$19 | 543.30 | 3 | 23.0 | 4.90E-03 | 7.8 Å |
| GISVLKDSDDKTR (SEQ ID NO: 101) | β4 (PRE1) | G24-R36 | | | | $K_T$29 | 760.38 | 2 | 35.4 | 2.40E-05 | |
| 2 FKNSVK (SEQ ID NO: 103) | β6 (PRE7)† | F59-K64 | 532.29 | 3 | 2 | $K_T$60 | 808.40 | 1 | 16.2 | 2.00E-02 | 16.2 Å |
| KLAVER (SEQ ID NO: 105) | α6 (PRE5) | K102-R107 | | | | $K_A$102 | 385.23 | 2 | 21.2 | 9.80E-04 | |
| FKNSVK (SEQ ID NO: 103) | β6 (PRE7)† | F59-K64 | 399.47 | 4 | 2 | $K_T$60 | 404.71 | 2 | 16.5 | 1.10E-02 | |
| KLAVER (SEQ ID NO: 105) | α6 (PRE5) | K102-R107 | | | | $K_A$102 | 385.23 | 2 | 18.3 | 1.60E-04 | |
| 2 NQYEPGTNGKVK (SEQ ID NO: 106) | β6 (PRE7)† | N149-K160 | 659.68 | 3 | 0 | $K_A$158 | 694.84 | 2 | 29.8 | 4.20E-05 | 9.8 Å |
| KPLK (SEQ ID NO: 108) | β6 (PRE7)† | K161-K164 | | | | K161* | | | | | |
| NQYEPGTNGKVK (SEQ ID NO: 106) | β6 (PRE7)† | N149-K160 | 495.01 | 4 | 2 | $K_T$158 | 710.83 | 2 | 26.3 | 3.00E-04 | |
| KPLK (SEQ ID NO: 108) | β6 (PRE7)† | K161-K164 | | | | K161* | | | | | |

*Peptide fragment containing these sites were not sequenced by MS3
**The peptide identification was above 1% false positive rate but MS3 was validated manually.
‡They were identified from different fragment pair ions by MS3
†Mature sequence from crystal data was used for data analysis.
Note:
Type 0: dead-end
All of the peptides displayed characteristic fragment pairs.
All of the cross-linked peptides were identified by Link-Finder, Batch-tag and MS-Bridge.

TABLE 6

| SEQ ID NO: | Sequence |
|---|---|
| SEQ ID NO: 1 | IEAEKGR |
| SEQ ID NO: 2 | Ac-IEAEKGR |
| SEQ ID NO: 3 | Ac-IEAEK$_A$GR |
| SEQ ID NO: 4 | Ac-IEAEK$_S$GR |
| SEQ ID NO: 5 | ASQKRPSQRHG |
| SEQ ID NO: 6 | Ac-ASQKRPSQRHG |
| SEQ ID NO: 7 | RPKPQQF |
| SEQ ID NO: 8 | RPK$_A$PQQF |
| SEQ ID NO: 9 | RPK$_{DN}$PQQF |
| SEQ ID NO: 10 | GDVEKGKK |
| SEQ ID NO: 11 | Ac-GDVEKGKK |
| SEQ ID NO: 12 | Ac-GDVEK$_A$GKK |
| SEQ ID NO: 13 | KKGER |
| SEQ ID NO: 14 | K$_T$KGER |
| SEQ ID NO: 15 | K$_A$KGER |
| SEQ ID NO: 16 | HKTGPNLHGLFGR |
| SEQ ID NO: 17 | HK$_A$TGPNLHGLFGR |
| SEQ ID NO: 18 | HK$_T$TGPNLHGLFGR |
| SEQ ID NO: 19 | KTGQAPGFSYTDANK |
| SEQ ID NO: 20 | K$_{DN}$TGQAPGFSYTDANK |
| SEQ ID NO: 21 | K$_A$TGQAPGFSYTDANK |
| SEQ ID NO: 22 | K$_T$TGQAPGFSYTDANK |
| SEQ ID NO: 23 | GGKHKTGPNLHGLFGR |
| SEQ ID NO: 24 | GGK*HK*TGPNLHGLFGR |
| SEQ ID NO: 25 | GGK$_A$HK$_T$TGPNLHGLFGR |
| SEQ ID NO: 26 | GGK$_T$HK$_A$TGPNLHGLFGR |
| SEQ ID NO: 27 | NKPELYQIDYLGTK |
| SEQ ID NO: 28 | NK$_A$PELYQIDYLGTK |
| SEQ ID NO: 29 | LGSQSLGVSNKFEK |
| SEQ ID NO: 30 | LGSQSLGVSNK$_T$FEK |
| SEQ ID NO: 31 | GDVEKGK |
| SEQ ID NO: 32 | Ac-GDVEKGK |
| SEQ ID NO: 33 | Ac-GDVEK$_T$GK |
| SEQ ID NO: 34 | Ac-GDVEK$_A$GK |
| SEQ ID NO: 35 | KIFVQK |
| SEQ ID NO: 36 | K$_A$IFVQK |
| SEQ ID NO: 37 | K$_T$IFVQK |
| SEQ ID NO: 38 | KGER |
| SEQ ID NO: 39 | EDLIAYLKK |
| SEQ ID NO: 40 | EDLIAYLK$_A$K |
| SEQ ID NO: 41 | EDLIAYLK$_T$K |
| SEQ ID NO: 42 | KATNE |
| SEQ ID NO: 43 | K$_A$ATNE |
| SEQ ID NO: 44 | GGKHK |
| SEQ ID NO: 45 | GGK$_T$HK |
| SEQ ID NO: 46 | TGQAPGFSYTDANKNK |
| SEQ ID NO: 47 | TGQAPGFSYTDANK$_T$NK |
| SEQ ID NO: 48 | YIPGTKMIFAGIK |
| SEQ ID NO: 49 | YIPGTKM$_{OX}$IFAGIK |
| SEQ ID NO: 50 | YIPGTK$_A$M$_{OX}$IFAGIK |
| SEQ ID NO: 51 | KYIPGTK |
| SEQ ID NO: 52 | K$_T$YIPGTK |
| SEQ ID NO: 53 | MIFAGIKK |
| SEQ ID NO: 54 | M$_{OX}$IFAGIKK |
| SEQ ID NO: 55 | M$_{OX}$IFAGIK$_T$K |
| SEQ ID NO: 56 | MIFAGIK$_T$K |
| SEQ ID NO: 57 | TLTGKTITLEVEPSDTIENVK |
| SEQ ID NO: 58 | IQDKEGIPPDQQR |
| SEQ ID NO: 59 | IQDK$_A$EGIPPDQQR |
| SEQ ID NO: 60 | LIFAGKQLEDGR |
| SEQ ID NO: 61 | LIFAGK$_A$QLEDGR |
| SEQ ID NO: 62 | LIFAGK$_T$QLEDGR |
| SEQ ID NO: 63 | LIFAGK$^{48}$QLEDGR |
| SEQ ID NO: 64 | TLSDYNIQKESTLHLVLR |
| SEQ ID NO: 65 | TLSDYNIQK$_T$ESTLHLVLR |
| SEQ ID NO: 66 | ATATGPKQQEITTNLENHFK |
| SEQ ID NO: 67 | ATATGPK$_A$QQEITTNLENHFK |
| SEQ ID NO: 68 | KVPDK |
| SEQ ID NO: 69 | K$_T$VPDK |
| SEQ ID NO: 70 | KVAHTSYK |
| SEQ ID NO: 71 | K$_T$VAHTSYK |
| SEQ ID NO: 72 | VLVDKSR |
| SEQ ID NO: 73 | VLVDK$_A$SR |
| SEQ ID NO: 74 | IFKPQEIK |
| SEQ ID NO: 75 | IFK$_T$PQEIK |
| SEQ ID NO: 76 | LYKLNDK |
| SEQ ID NO: 77 | LYK$_A$LNDK |
| SEQ ID NO: 78 | IHAQNYLKTYNEDIPVEILVR |

TABLE 6-continued

| SEQ ID NO: | Sequence |
|---|---|
| SEQ ID NO: 79 | IHAQNYLK$_T$TYNEDIPVEILVR |
| SEQ ID NO: 80 | YKTNLYK |
| SEQ ID NO: 81 | YK$_A$TNLYK |
| SEQ ID NO: 82 | YK$_T$TNLYK |
| SEQ ID NO: 83 | EFLEKNYDR |
| SEQ ID NO: 84 | EFLEK$_A$NYDR |
| SEQ ID NO: 85 | NSKTVR |
| SEQ ID NO: 86 | NSK$_{Ak}$TVR |
| SEQ ID NO: 87 | ILKQVMEEK |
| SEQ ID NO: 88 | ILK$_T$QVMEEK |
| SEQ ID NO: 89 | ELKEK |
| SEQ ID NO: 90 | SYKFPR |
| SEQ ID NO: 91 | SYK$_A$FPR |
| SEQ ID NO: 92 | EEKQK |
| SEQ ID NO: 93 | EEK$_T$QK |
| SEQ ID NO: 94 | LKEER |
| SEQ ID NO: 95 | LK$_A$EER |
| SEQ ID NO: 96 | YLKMR |
| SEQ ID NO: 97 | YLKM$_{OX}$R |
| SEQ ID NO: 98 | YLK$_A$M$_{OX}$R |
| SEQ ID NO: 99 | VQDSVILASSKAVTR |
| SEQ ID NO: 100 | VQDSVILASSK$_{Ak}$AVTR |
| SEQ ID NO: 101 | GISVLKDSDDKTR |
| SEQ ID NO: 102 | GISVLK$_T$DSDDKTR |
| SEQ ID NO: 103 | FKNSVK |
| SEQ ID NO: 104 | FK$_A$NSVK |
| SEQ ID NO: 105 | KLAVER |
| SEQ ID NO: 106 | NQYEPGTNGKVK |
| SEQ ID NO: 107 | NQYEPGTNGK$_A$VK |
| SEQ ID NO: 108 | KPLK |
| SEQ ID NO: 109 | AELEKLVDHHPEGLSAR |
| SEQ ID NO: 110 | AELEK$_{DN}$LVDHHPEGLSAR |
| SEQ ID NO: 111 | AELEK$_A$LVDHHPEGLSAR |
| SEQ ID NO: 112 | AELEK$_T$LVDHHPEGLSAR |
| SEQ ID NO: 113 | KYIPGTKMIFAGIK |
| SEQ ID NO: 114 | KYIPGTKMoxIFAGIK |
| SEQ ID NO: 115 | KYIPGTKMIFAGIKK |
| SEQ ID NO: 116 | KYIPGTKMoxIFAGIKK |
| SEQ ID NO: 117 | MIFAGIKKK |

TABLE 6-continued

| SEQ ID NO: | Sequence |
|---|---|
| SEQ ID NO: 118 | MoxIFAGIKKK |
| SEQ ID NO: 119 | EDLIAYLKKATNE |
| SEQ ID NO: 120 | YIPGTKMIFAGIKKK |
| SEQ ID NO: 121 | YIPGTKMoxIFAGIKKK |
| SEQ ID NO: 122 | MIFAGIKKKGER |
| SEQ ID NO: 123 | MoxIFAGIKKKGER |
| SEQ ID NO: 124 | GKKIFVQK |
| SEQ ID NO: 125 | GDVEKGKKIFVQK |
| SEQ ID NO: 126 | Ac-GDVEKGKKIFVQK |
| SEQ ID NO: 127 | MQIFVKTLTGK |
| SEQ ID NO: 128 | AKIQDK |
| SEQ ID NO: 129 | LIFAGKQLEDGRTLSDYNIQK |
| SEQ ID NO: 130 | AKIQDKEGIPPDQQR |
| SEQ ID NO: 131 | AKAEAAEFR |
| SEQ ID NO: 132 | TFLEKR |
| SEQ ID NO: 133 | KVTSTLLEQDTSTEK |
| SEQ ID NO: 134 | STLKLQDTR |
| SEQ ID NO: 135 | ITPSKVSK |
| SEQ ID NO: 136 | ILIEKAR |
| SEQ ID NO: 137 | TAELIKELK |
| SEQ ID NO: 138 | LLVPQKNVK |
| SEQ ID NO: 139 | EAVKQAAK |
| SEQ ID NO: 140 | TNLYKLK |
| SEQ ID NO: 141 | QELAKSIR |
| SEQ ID NO: 142 | IVDKDGIR |
| SEQ ID NO: 143 | KLSINSAAR |
| SEQ ID NO: 144 | KEFYELK |

Ac—Acetyl
Xaa$_A$—Alkene modification
Xaa$_{Ak}$—Alkane modification
Xaa$_{DN}$—Dead-end modification
Xaa$_T$—Thiol modification
Xaa$_S$—Sulfenic acid modification
Xaa$_{OX}$—Oxidation
*Intra-peptide linkage
Xaa$^{48}$—Inter-peptide linkage

TABLE 7

| K-K Linkage | MS" m/z | z | Sequence | Modification(s) |
|---|---|---|---|---|
| K6-K9 | MS2 615.3107 | | | 3 |
| | MS3 828.41 | 1 | MGDVEK$_A$GK (SEQ ID NO: 145) | Met-loss + Acetyl@1; Akene@6 |
| | MS3 408.75 | 2 | K$_A$IFVQK (SEQ ID NO: 36) | Alkene@9 |
| K6-K88 | MS2 457.4806 | | | 4 |
| | MS3 478.76 | 2 | MGDVEK$_A$GKK (SEQ ID NO: 146) | Met-loss + Acetyl@1, Alkene@6 |
| | MS3 336.20 | 2 | K$_A$KGER (SEQ ID NO: 15) | AlKene@88 |
| K6-K89 | MS2 555.2882 | | | 5 |
| | MS3 478.76 | 2 | MGDVEK$_A$GKK (SEQ ID NO: 146) | Met-loss + Acetyl@1, Alkene@6 |
| | MS3 539.64 | 3 | KK$_A$GEREDLIAYLK (SEQ ID NO: 147) | Alkene@89 |
| K8I9-K88* | MS2 482.2605 | | | 4 |
| | MS3 528.32 | 2 | GK$_A$K$_A$IEVQK (SEQ ID NO: 148) | Alkene@8, Alkene@9 |
| | MS3 336.20 | 2 | K$_A$KGER (SEQ ID NO: 15) | Alkene@88 |
| K9-K88 | MS2 422.4780 | | | 4 |
| | MS3 408.75 | 2 | K$_A$IFVQK (SEQ ID NO: 36) | Alkene@9 |
| | MS3 336.20 | 2 | K$_A$KGER (SEQ ID NO: 15) | Alkene@88 |
| K9-K88I89** | MS2 527.2882 | | | 5 |
| | MS3 408.75 | 2 | K$_A$IFVQK (SEQ ID NO: 36) | Alkene@9 |
| | MS3 600.31 | 3 | K$_T$KGEREDLIAYLK (SEQ ID NO: 149) Or KK$_T$GEREDLIAYLK (SEQ ID NO: 150) | ThiolB@88I89 |
| K87-K89 | MS2 530.6801 | | | 5 |
| | MS3 481.28 | | MIFAGIK$_A$K (SEQ ID NO: 151) | Alkene@87 |
| | MS3 496.94 | 3 | K$_A$GEREDLIAYLK (SEQ ID NO: 152) | Alkene@89 |

Note:
K$_A$: aikene modified lysine;
K$_T$: unsaturated thiol modified lysine.
*Either K8 or K9 was inter-linked with K88.
**Either K88 or K89 was inter-linked with K9. ThiolB is the thiol fragment β$_t$ shown in the workflow in FIG. 20.

TABLE 8

| | | 1) Click Reaction On Protein | | | | | | 2) Click Reaction On Peptide 2) Ultrafiltration | | | Alkene, Sulfenic or Thiol Modified peptide |
|---|---|---|---|---|---|---|---|---|---|---|---|
| | | 1A) Cell Lysate | | | 1B) Cell Fractionation | | | | | | |
| Acc# | Gene Name | Num Unique | % Cov | Best Expect Val | Num Unique | % Cov | Best Expect Val | Num Unique | % Cov | Best Expect Val | |
| O60814 | H2B1K | 38 | 79.4 | 2.00E−10 | 24 | 81 | 7.00E−10 | 19 | 70.6 | 2.50E−09 | Yes |
| P06733 | ENOA | 56 | 90.6 | 5.50E−09 | 3 | 6.2 | 8.80E−05 | 8 | 17.7 | 2.20E−05 | Yes |
| P06748 | NPM | 29 | 59.9 | 1.90E−09 | 23 | 38.8 | 7.20E−07 | 2 | 7.1 | 6.60E−05 | Yes |
| P06899 | H2B1J | 38 | 79.4 | 2.00E−10 | 23 | 79.4 | 7.00E−10 | 17 | 70.6 | 2.50E−09 | Yes |
| P07197 | NFM | 75 | 60.9 | 2.80E−08 | 90 | 51.6 | 8.10E−10 | 6 | 4.4 | 3.20E−04 | Yes |
| P07900 | HS90A | 38 | 49 | 5.50E−09 | 10 | 15 | 1.90E−07 | 5 | 5.3 | 5.60E−06 | Yes |
| P07910 | HNRPC | 19 | 43.8 | 4.80E−07 | 5 | 8.5 | 2.20E−04 | 8 | 19.9 | 3.60E−04 | Yes |
| P08107 | HSP71 | 69 | 71.8 | 2.80E−09 | 10 | 16.4 | 3.50E−09 | 17 | 31.4 | 1.00E−06 | Yes |
| P08238 | HS90B | 41 | 57.9 | 5.50E−09 | 7 | 9.1 | 3.30E−07 | 5 | 5.4 | 5.60E−06 | Yes |
| P08670 | VIME | 40 | 74.5 | 5.10E−08 | 24 | 34.3 | 9.40E−08 | 1 | 2.1 | 0.0022 | Yes |
| P0C0S5 | H2AZ | 6 | 33.6 | 3.80E−05 | 4 | 25.8 | 7.10E−06 | 3 | 23.4 | 3.20E−04 | Yes |
| P0C0S8 | H2A1 | 24 | 82.3 | 2.90E−09 | 11 | 48.5 | 1.20E−07 | 13 | 55.4 | 2.00E−07 | Yes |
| P10412 | H14 | 41 | 71.2 | 7.00E−09 | 15 | 39.7 | 1.20E−06 | 15 | 42 | 1.10E−05 | Yes |
| P10809 | CH60 | 39 | 66.1 | 1.40E−08 | 2 | 3.3 | 2.80E−04 | 5 | 9.9 | 4.50E−05 | Yes |

TABLE 8-continued

| | | 1) Click Reaction On Protein | | | | | | 2) Click Reaction | | | Alkene, |
| | | 1A) Cell Lysate | | | 1B) Cell Fractionation | | | On Peptide 2) Ultrafiltration | | | Sulfenic or |
| Acc# | Gene Name | Num Unique | % Cov | Best Expect Val | Num Unique | % Cov | Best Expect Val | Num Unique | % Cov | Best Expect Val | Thiol Modified peptide |
|---|---|---|---|---|---|---|---|---|---|---|---|
| P12277 | KCRB | 17 | 54.1 | 2.70E−07 | 3 | 5 | 2.30E−05 | 3 | 5 | 1.50E−04 | Yes |
| P13639 | EF2 | 55 | 55.4 | 1.50E−07 | 4 | 5.2 | 0.0014 | 6 | 7 | 0.0012 | Yes |
| P14314 | GLU2B | 5 | 10.2 | 7.10E−05 | | | | | | | Yes |
| P16403 | H12 | 37 | 70.4 | 7.00E−09 | 14 | 35.7 | 1.20E−06 | 18 | 50.2 | 7.50E−06 | Yes |
| P19338 | NUCL | 27 | 32.7 | 8.40E−08 | 14 | 18.2 | 1.70E−05 | | | | Yes |
| P20671 | H2A1D | 25 | 82.3 | 2.90E−09 | 11 | 48.5 | 1.20E−07 | 13 | 55.4 | 2.00E−07 | Yes |
| P20700 | LMNB1 | 11 | 18.1 | 1.70E−05 | 11 | 15.5 | 1.20E−05 | | | | Yes |
| P23527 | H2B1O | 38 | 79.4 | 2.00E−10 | 21 | 79.4 | 7.00E−10 | 17 | 70.6 | 2.50E−09 | Yes |
| P24534 | EF1B | 5 | 28.4 | 4.20E−08 | 1 | 3.1 | 8.10E−04 | | | | Yes |
| P27824 | CALX | 13 | 21.1 | 9.60E−07 | 1 | 2.7 | 2.00E−05 | 1 | 1.7 | 1.40E−04 | Yes |
| P30101 | PDIA3 | 11 | 24.8 | 8.70E−06 | | | | 2 | 2.2 | 1.80E−05 | Yes |
| P51572 | BAP31 | 3 | 11.8 | 1.70E−04 | | | | 2 | 8.1 | 9.80E−05 | Yes |
| P52272 | HNRPM | 25 | 41.2 | 2.50E−04 | 4 | 5.2 | 1.50E−06 | | | | Yes |
| P61353 | RL27 | 5 | 24.3 | 7.90E−07 | 2 | 29.4 | 6.80E−04 | | | | Yes |
| P61604 | CH10 | 8 | 65.7 | 1.60E−09 | 2 | 11.8 | 1.70E−07 | 2 | 11.8 | 2.30E−07 | Yes |
| P61978 | HNRPK | 29 | 52.9 | 2.00E−07 | 4 | 13.8 | 6.40E−10 | 2 | 6.3 | 7.90E−05 | Yes |
| P62805 | H4 | 29 | 82.5 | 2.00E−07 | 19 | 71.8 | 7.60E−08 | 18 | 75.7 | 1.60E−06 | Yes |
| P62807 | H2B1C | 38 | 79.4 | 2.00E−10 | 24 | 81 | 7.00E−10 | 20 | 70.6 | 2.50E−09 | Yes |
| P62826 | RAN | 10 | 37.5 | 2.90E−06 | 6 | 28.2 | 4.60E−07 | | | | Yes |
| P62841 | RS15 | 4 | 26.9 | 1.20E−07 | | | | 2 | 13.8 | 3.20E−04 | Yes |
| P62937 | PPIA | 24 | 92.7 | 1.20E−07 | 2 | 13.3 | 7.60E−06 | 3 | 29.7 | 5.00E−06 | Yes |
| Q00839 | HNRPU | 20 | 22.9 | 1.10E−05 | 12 | 10.1 | 3.30E−09 | 3 | 4.6 | 9.20E−06 | Yes |
| Q02878 | RL6 | 14 | 46.2 | 3.10E−07 | 4 | 16.7 | 1.60E−05 | | | | Yes |
| Q14103 | HNRPD | 9 | 18 | 5.00E−08 | 3 | 9.6 | 2.40E−07 | 2 | 5.1 | 5.10E−05 | Yes |
| Q15149 | PLEC | | | | 25 | 5.7 | 2.10E−07 | | | | Yes |
| Q15233 | NONO | 19 | 44.4 | 1.70E−07 | 12 | 17.4 | 3.10E−06 | 2 | 4 | 1.30E−04 | Yes |
| Q16778 | H2B2E | 38 | 79.4 | 2.00E−10 | 23 | 79.4 | 7.00E−10 | 18 | 70.6 | 2.50E−09 | Yes |
| Q6FI13 | H2A2A | 24 | 82.3 | 2.90E−09 | 11 | 48.5 | 1.20E−07 | 13 | 55.4 | 2.00E−07 | Yes |
| Q71DI3 | H32 | 24 | 60.3 | 2.20E−06 | 20 | 56.6 | 2.50E−05 | 15 | 58.1 | 6.90E−06 | Yes |
| Q93079 | H2B1H | 38 | 79.4 | 2.00E−10 | 22 | 81 | 7.00E−10 | 19 | 70.6 | 2.50E−09 | Yes |
| Q9NVA2 | SEPT11 | 3 | 7 | 0.0017 | | | | | | | Yes |
| A2RU54 | HMX2 | 2 | 2.9 | 3.30E−04 | | | | | | | Yes |
| O00148 | DX39A | 9 | 21.3 | 1.60E−06 | 1 | 3.5 | 1.40E−05 | | | | Yes |
| O00231 | PSD11 | 4 | 11.4 | 2.10E−04 | | | | | | | Yes |
| O00232 | PSD12 | 4 | 9 | 1.30E−04 | | | | 2 | 9.2 | 1.60E−05 | Yes |
| O00264 | PGRC1 | 2 | 11.8 | 1.30E−09 | | | | | | | Yes |
| O00410 | IPO5 | 6 | 5.7 | 3.00E−06 | | | | | | | Yes |
| O00425 | IF2B3 | 3 | 6.7 | 9.10E−06 | | | | | | | Yes |
| O00567 | NOP56 | 6 | 12.5 | 2.40E−04 | 1 | 1.9 | 4.40E−05 | | | | Yes |
| O00571 | DDX3X | 16 | 26.6 | 2.70E−07 | 1 | 2.4 | 1.60E−04 | | | | Yes |
| O14737 | PDCD5 | 2 | 19.2 | 3.90E−04 | | | | | | | Yes |
| O14979 | HNRDL | 7 | 17.9 | 6.20E−08 | | | | 1 | 2.4 | 5.10E−05 | Yes |
| O14980 | XPO1 | 11 | 12 | 6.80E−06 | | | | | | | Yes |
| O15042 | SR140 | 1 | 0.8 | 0.0014 | 1 | 1.4 | 3.10E−05 | | | | Yes |
| O15260 | SURF4 | 4 | 23 | 5.50E−06 | 1 | 8.9 | 2.10E−04 | | | | Yes |
| O15347 | HMGB3 | 3 | 19 | 1.00E−06 | | | | | | | Yes |
| O15371 | EIF3D | 3 | 5.3 | 6.00E−04 | | | | | | | Yes |
| O15372 | EIF3H | 2 | 8.2 | 7.00E−05 | | | | | | | Yes |
| O15397 | IPO8 | 3 | 3.2 | 3.10E−06 | | | | | | | Yes |
| O15511 | ARPC5 | 2 | 14.6 | 2.00E−05 | | | | | | | Yes |
| O15523 | DDX3Y | 11 | 17.9 | 9.10E−06 | 1 | 2.4 | 1.60E−04 | | | | Yes |
| O43169 | CYB5B | 2 | 17.1 | 1.60E−05 | | | | | | | Yes |
| O43175 | SERA | 10 | 22.7 | 1.20E−06 | | | | | | | Yes |
| O43390 | HNRPR | 10 | 17.5 | 5.00E−06 | | | | | | | Yes |
| O43707 | ACTN4 | 8 | 9.4 | 3.60E−04 | 1 | 1 | 0.0015 | | | | Yes |
| O43776 | SYNC | 4 | 8.4 | 2.30E−06 | | | | | | | Yes |
| O60264 | SMCA5 | 6 | 5.6 | 2.20E−05 | | | | | | | Yes |
| O60506 | HNRPQ | 10 | 17.5 | 5.00E−06 | | | | | | | Yes |
| O60841 | IF2P | 4 | 3.5 | 1.70E−04 | | | | | | | Yes |
| O75131 | CPNE3 | 3 | 5 | 1.50E−04 | | | | | | | Yes |
| O75347 | TBCA | 2 | 17.6 | 5.20E−04 | | | | | | | Yes |
| O75367 | H2AY | 5 | 20.7 | 1.00E−06 | 1 | 5.6 | 0.0037 | | | | Yes |
| O75369 | FLNB | 2 | 1.1 | 6.00E−05 | | | | | | | Yes |
| O75390 | CISY | 7 | 15 | 8.10E−06 | | | | | | | Yes |
| O75396 | SC22B | 3 | 16.3 | 8.30E−04 | | | | | | | Yes |
| O75436 | VP26A | 2 | 6.1 | 7.10E−06 | | | | | | | Yes |
| O75475 | PSIP1 | 3 | 7.9 | 7.10E−05 | | | | | | | Yes |
| O75533 | SF3B1 | 5 | 4.6 | 6.50E−07 | | | | | | | Yes |
| O75534 | CSDE1 | 3 | 4.4 | 1.80E−04 | | | | | | | Yes |
| O75643 | U520 | 15 | 8 | 6.60E−07 | | | | | | | Yes |
| O75821 | EIF3G | 3 | 12.2 | 1.10E−04 | | | | | | | Yes |

TABLE 8-continued

| | | 1) Click Reaction On Protein | | | | | | 2) Click Reaction | | | Alkene, |
| | | 1A) Cell Lysate | | | 1B) Cell Fractionation | | | On Peptide 2) Ultrafiltration | | | Sulfenic or |
| Acc# | Gene Name | Num Unique | % Cov | Best Expect Val | Num Unique | % Cov | Best Expect Val | Num Unique | % Cov | Best Expect Val | Thiol Modified peptide |
|---|---|---|---|---|---|---|---|---|---|---|---|
| O75844 | FACE1 | 3 | 8.4 | 1.00E−04 | | | | | | | Yes |
| O76021 | RL1D1 | 7 | 15.3 | 6.40E−06 | 4 | 5.9 | 1.30E−04 | | | | Yes |
| O94826 | TOM70 | 3 | 5.1 | 1.10E−04 | | | | | | | Yes |
| O95202 | LETM1 | 3 | 4.5 | 9.50E−06 | | | | | | | Yes |
| O95232 | LC7L3 | 2 | 6.9 | 1.60E−06 | | | | | | | Yes |
| O95373 | IPO7 | 4 | 5 | 6.30E−05 | | | | | | | Yes |
| O95433 | AHSA1 | 2 | 5.9 | 6.10E−04 | | | | | | | Yes |
| O95757 | H574L | 4 | 6.2 | 1.80E−06 | | | | | | | Yes |
| O95782 | AP2A1 | 4 | 5.1 | 1.60E−05 | | | | | | | Yes |
| O95831 | AIFM1 | 6 | 12.7 | 3.30E−04 | | | | | | | Yes |
| P00387 | NB5R3 | 4 | 16.9 | 1.60E−06 | | | | | | | Yes |
| P00441 | SODC | 3 | 25.3 | 3.50E−06 | | | | | | | Yes |
| P00491 | PNPH | 4 | 18.7 | 2.10E−05 | | | | | | | Yes |
| P00492 | HPRT | 6 | 34.9 | 1.10E−06 | | | | | | | Yes |
| P00558 | PGK1 | 16 | 38.8 | 1.30E−06 | | | | | | | Yes |
| P00918 | CAH2 | 9 | 43.8 | 2.20E−07 | | | | | | | Yes |
| P01893 | HLAH | 1 | 3.9 | 0.0038 | | | | 1 | 3 | 6.10E−04 | Yes |
| P02545 | LMNA | 4 | 6.5 | 1.50E−04 | 3 | 3 | 0.005 | | | | Yes |
| P04075 | ALDOA | 13 | 31.9 | 1.50E−08 | | | | | | | Yes |
| P04264 | K2C1 | 7 | 12.9 | 1.10E−04 | | | | 2 | 3.3 | 1.30E−05 | Yes |
| P04350 | TBB4A | 27 | 58.1 | 2.10E−07 | | | | 2 | 5.2 | 0.0037 | Yes |
| P04406 | G3P | 29 | 69.9 | 1.20E−09 | 4 | 16.7 | 6.30E−05 | 4 | 14.3 | 1.60E−05 | Yes |
| P04908 | H2A1B | 23 | 82.3 | 2.90E−09 | 11 | 48.5 | 1.20E−07 | 12 | 52.3 | 2.00E−07 | Yes |
| P05023 | AT1A1 | 13 | 15.4 | 9.00E−07 | | | | | | | Yes |
| P05091 | ALDH2 | 2 | 4.3 | 3.50E−04 | | | | | | | Yes |
| P05141 | ADT2 | 22 | 49.3 | 2.50E−08 | 7 | 32.6 | 1.30E−09 | 3 | 8.1 | 1.70E−05 | Yes |
| P05198 | IF2A | 5 | 16.8 | 2.00E−05 | | | | | | | Yes |
| P05204 | HMGN2 | 4 | 40 | 2.60E−06 | | | | | | | Yes |
| P05387 | RLA2 | 5 | 70.4 | 1.30E−06 | 1 | 14.8 | 3.10E−06 | 2 | 25.2 | 2.40E−04 | Yes |
| P05388 | RLA0 | 9 | 28.7 | 2.60E−07 | | | | | | | Yes |
| P05455 | LA | 8 | 22.8 | 4.50E−06 | | | | | | | Yes |
| P05783 | K1C18 | 3 | 6.3 | 4.60E−04 | | | | | | | Yes |
| P06454 | PTMA | 6 | 37.8 | 8.60E−07 | 2 | 29.7 | 8.20E−05 | | | | Yes |
| P06576 | ATPB | 18 | 41.4 | 1.40E−07 | 1 | 4.7 | 5.10E−04 | | | | Yes |
| P06732 | KCRM | 2 | 2.9 | 4.70E−06 | 1 | 3.7 | 4.70E−04 | | | | Yes |
| P07195 | LDHB | 13 | 45.8 | 2.50E−08 | | | | 3 | 12 | 1.10E−07 | Yes |
| P07196 | NFL | 29 | 48.3 | 3.60E−09 | 18 | 23.9 | 9.40E−08 | | | | Yes |
| P07237 | PDIA1 | 12 | 26 | 4.80E−06 | | | | | | | Yes |
| P07339 | CATD | 2 | 4.6 | 5.60E−06 | | | | | | | Yes |
| P07437 | TBB5 | 37 | 75.7 | 7.80E−08 | | | | 2 | 5.2 | 0.0037 | Yes |
| P07477 | TRY1 | 5 | 7.3 | 2.90E−04 | | | | 2 | 7.3 | 0.0019 | Yes |
| P07602 | SAP | 3 | 7.1 | 9.00E−05 | | | | | | | Yes |
| P07737 | PROF1 | 14 | 85 | 2.40E−08 | | | | 1 | 7.9 | 0.0015 | Yes |
| P07814 | SYEP | 6 | 4.1 | 2.70E−07 | | | | | | | Yes |
| P08133 | ANXA6 | 9 | 14.1 | 1.90E−04 | | | | | | | Yes |
| P08195 | 4F2 | 4 | 8.3 | 1.90E−05 | 2 | 5.2 | 0.0018 | | | | Yes |
| P08243 | ASNS | 3 | 6.1 | 2.00E−05 | | | | | | | Yes |
| P08559 | ODPA | 2 | 5.1 | 1.80E−04 | | | | | | | Yes |
| P08621 | RU17 | 5 | 9.8 | 9.10E−06 | | | | | | | Yes |
| P09429 | HMGB1 | 9 | 31.2 | 1.00E−06 | 2 | 13.5 | 7.00E−05 | 2 | 6.5 | 1.80E−05 | Yes |
| P09622 | DLDH | 4 | 8.8 | 2.20E−05 | | | | | | | Yes |
| P09651 | ROA1 | 14 | 38.2 | 2.10E−10 | 6 | 16.4 | 1.20E−07 | 5 | 13.7 | 2.70E−05 | Yes |
| P09874 | PARP1 | 24 | 27.9 | 4.00E−08 | 3 | 3.9 | 7.20E−06 | 2 | 3 | 4.40E−04 | Yes |
| P0C7M2 | RA1L3 | 11 | 33.8 | 1.30E−07 | 4 | 14.1 | 6.90E−07 | 3 | 10.9 | 9.60E−04 | Yes |
| P0CG48 | UBC | 19 | 9.6 | 8.20E−07 | 9 | 6 | 2.80E−08 | 9 | 8.3 | 4.20E−06 | Yes |
| P10599 | THIO | 7 | 41.9 | 8.20E−06 | | | | 1 | 12.4 | 0.0014 | Yes |
| P11021 | GRP78 | 23 | 42.2 | 3.90E−08 | | | | 1 | 1.7 | 8.30E−04 | Yes |
| P11142 | HSP7C | 33 | 37.8 | 2.90E−08 | 4 | 8.4 | 1.50E−04 | 3 | 5.9 | 3.20E−05 | Yes |
| P11387 | TOP1 | 3 | 3.5 | 7.30E−04 | | | | | | | Yes |
| P11388 | TOP2A | 7 | 5.8 | 8.40E−06 | | | | | | | Yes |
| P11586 | C1TC | 14 | 18.3 | 3.80E−07 | | | | | | | Yes |
| P11940 | PABP1 | 15 | 29.7 | 3.30E−09 | | | | | | | Yes |
| P12004 | PCNA | 10 | 31 | 8.50E−07 | | | | | | | Yes |
| P12081 | SYNC | 6 | 12.2 | 9.90E−05 | | | | | | | Yes |
| P12235 | ADT1 | 13 | 33.2 | 3.20E−07 | 2 | 12.8 | 1.50E−04 | 2 | 4 | 1.70E−05 | Yes |
| P12236 | ADT3 | 17 | 39.9 | 1.50E−05 | 5 | 32.6 | 1.50E−05 | 2 | 4 | 1.70E−05 | Yes |
| P12268 | IMDH2 | 6 | 14.8 | 1.20E−07 | | | | | | | Yes |
| P12270 | TPR | 1 | 0.4 | 0.0013 | 2 | 1.3 | 6.90E−05 | | | | Yes |
| P12814 | ACTN1 | 8 | 10 | 3.60E−04 | 1 | 1 | 0.0015 | | | | Yes |
| P12956 | XRCC6 | 14 | 29.6 | 8.80E−08 | 1 | 1.6 | 0.0026 | | | | Yes |
| P13010 | XRCC5 | 22 | 38.7 | 1.20E−06 | 2 | 3.8 | 1.40E−05 | | | | Yes |

TABLE 8-continued

| | | 1) Click Reaction On Protein | | | | | | 2) Click Reaction | | | Alkene, |
| | | 1A) Cell Lysate | | | 1B) Cell Fractionation | | | On Peptide 2) Ultrafiltration | | | Sulfenic or |
| Acc# | Gene Name | Num Unique | % Cov | Best Expect Val | Num Unique | % Cov | Best Expect Val | Num Unique | % Cov | Best Expect Val | Thiol Modified peptide |
|---|---|---|---|---|---|---|---|---|---|---|---|
| P13667 | PDIA4 | 18 | 34.3 | 3.90E−07 | | | | 1 | 1.6 | 5.90E−04 | Yes |
| P13796 | PLSL | 10 | 20.6 | 4.20E−05 | | | | | | | Yes |
| P13861 | KAP2 | 3 | 12.9 | 9.50E−06 | | | | | | | Yes |
| P14618 | KPYM | 23 | 51.2 | 1.50E−08 | 2 | 4.1 | 9.20E−05 | | | | Yes |
| P14625 | ENPL | 23 | 27.3 | 2.00E−07 | 1 | 1.7 | 1.50E−04 | 2 | 0.9 | 8.10E−04 | Yes |
| P14678 | RSMB | 6 | 17.5 | 1.90E−06 | 1 | 4.6 | 4.70E−05 | | | | Yes |
| P14866 | HNRPL | 18 | 35.8 | 2.20E−07 | 4 | 13.4 | 1.20E−05 | 1 | 1.9 | 6.30E−05 | Yes |
| P15170 | ERF3A | 4 | 5.2 | 7.00E−05 | | | | | | | Yes |
| P15311 | EZRI | 5 | 7.5 | 1.20E−05 | | | | | | | Yes |
| P15374 | UCHL3 | 2 | 8.7 | 0.0011 | | | | | | | Yes |
| P15880 | RS2 | 10 | 37.5 | 4.10E−06 | | | | 1 | 3.8 | 9.30E−05 | Yes |
| P16104 | H2AX | 12 | 67.8 | 1.40E−08 | 5 | 42.7 | 3.40E−07 | 4 | 21 | 3.00E−04 | Yes |
| P16152 | CBR1 | 6 | 25.6 | 1.20E−05 | | | | | | | Yes |
| P16402 | H13 | 27 | 48.4 | 7.00E−09 | 11 | 23.5 | 1.20E−06 | 12 | 28.5 | 1.10E−05 | Yes |
| P16949 | STMN1 | 2 | 12.1 | 2.60E−04 | | | | | | | Yes |
| P16989 | DBPA | 6 | 15.1 | 3.10E−06 | | | | | | | Yes |
| P17066 | HSP76 | 19 | 17.9 | 2.80E−09 | 3 | 3.1 | 2.30E−05 | 5 | 9.5 | 1.70E−06 | Yes |
| P17661 | DESM | 5 | 6.4 | 1.40E−04 | 4 | 4.7 | 5.70E−06 | | | | Yes |
| P17844 | DDX5 | 16 | 27.4 | 6.00E−07 | 1 | 1.6 | 1.60E−04 | | | | Yes |
| P18077 | RL35A | 3 | 27.3 | 7.80E−05 | 1 | 12.7 | 3.60E−06 | | | | Yes |
| P18124 | RL7 | 10 | 40.7 | 1.30E−05 | | | | | | | Yes |
| P18621 | RL17 | 4 | 20.7 | 1.00E−04 | | | | 2 | 14.1 | 6.90E−04 | Yes |
| P18669 | PGAM1 | 11 | 52 | 5.10E−08 | | | | | | | Yes |
| P18754 | RCC1 | 3 | 7.8 | 6.30E−06 | | | | | | | Yes |
| P19367 | HXK1 | 3 | 3.4 | 1.10E−06 | | | | | | | Yes |
| P21333 | FLNA | 5 | 2.3 | 6.00E−05 | 1 | 0.5 | 2.70E−05 | | | | Yes |
| P21796 | VDAC1 | 8 | 35 | 4.40E−07 | | | | | | | Yes |
| P21912 | DHSB | 2 | 7.5 | 2.40E−05 | | | | | | | Yes |
| P22234 | PUR6 | 10 | 23.3 | 5.00E−08 | | | | | | | Yes |
| P22307 | NLTP | 6 | 9.7 | 3.20E−04 | | | | | | | Yes |
| P22314 | UBA1 | 22 | 26.1 | 2.50E−07 | | | | | | | Yes |
| P22392 | NDKB | 6 | 48 | 4.90E−05 | | | | 1 | 7.9 | 7.80E−04 | Yes |
| P22626 | ROA2 | 23 | 61.5 | 4.80E−11 | 8 | 22.9 | 1.70E−08 | 5 | 11.6 | 1.50E−04 | Yes |
| P23246 | SFPQ | 12 | 21.4 | 4.80E−07 | 1 | 1.8 | 9.10E−04 | | | | Yes |
| P23284 | PPIB | 7 | 35.2 | 1.40E−05 | | | | 2 | 12.5 | 4.70E−06 | Yes |
| P23396 | RS3 | 14 | 60.1 | 8.60E−07 | 1 | 9.1 | 1.30E−04 | 1 | 3.7 | 4.20E−04 | Yes |
| P23526 | SAHH | 7 | 17.6 | 9.00E−08 | | | | 1 | 3 | 1.40E−04 | Yes |
| P23528 | COF1 | 9 | 51.8 | 1.30E−08 | | | | 1 | 7.8 | 0.0055 | Yes |
| P23588 | IF4B | 2 | 3.9 | 0.0016 | | | | | | | Yes |
| P24539 | AT5F1 | 6 | 28.9 | 9.70E−07 | | | | | | | Yes |
| P24941 | CDK2 | 3 | 10.4 | 1.30E−04 | | | | | | | Yes |
| P25398 | RS12 | 5 | 40.2 | 8.90E−08 | | | | 1 | 6.8 | 5.80E−04 | Yes |
| P25705 | ATPA | 19 | 45.8 | 1.90E−07 | 5 | 11.8 | 6.50E−07 | 1 | 1.8 | 3.60E−04 | Yes |
| P25789 | PSA4 | 5 | 20.7 | 4.60E−05 | | | | | | | Yes |
| P26038 | MOES | 5 | 6.1 | 1.20E−05 | | | | | | | Yes |
| P26358 | DNMT1 | 3 | 2.4 | 1.10E−04 | | | | | | | Yes |
| P26368 | U2AF2 | 6 | 13.3 | 8.10E−06 | 1 | 2.3 | 1.30E−04 | | | | Yes |
| P26583 | HMGB2 | 3 | 15.3 | 1.00E−06 | 2 | 13.9 | 1.90E−04 | 1 | 6.7 | 5.20E−05 | Yes |
| P26599 | PTBP1 | 13 | 27.3 | 6.90E−09 | 2 | 6 | 3.40E−07 | | | | Yes |
| P26639 | SYTC | 7 | 10.7 | 9.50E−05 | | | | | | | Yes |
| P26641 | EF1G | 14 | 32.5 | 1.60E−07 | 1 | 2.3 | 0.0027 | | | | Yes |
| P27348 | 1433T | 10 | 45.3 | 2.20E−08 | | | | | | | Yes |
| P27694 | RFA1 | 5 | 10.6 | 5.10E−05 | | | | | | | Yes |
| P27695 | APEX1 | 5 | 18.2 | 2.30E−06 | | | | | | | Yes |
| P27708 | PYR1 | 7 | 3.5 | 6.80E−05 | | | | | | | Yes |
| P27797 | CALR | 16 | 47.2 | 1.30E−08 | 1 | 3.1 | 1.90E−05 | 3 | 6.2 | 5.40E−04 | Yes |
| P28066 | PSA5 | 3 | 17 | 7.60E−05 | | | | | | | Yes |
| P28288 | ABCD3 | 2 | 4.7 | 3.40E−07 | | | | | | | Yes |
| P28838 | AMPL | 4 | 9.8 | 3.30E−05 | | | | | | | Yes |
| P29692 | EF1D | 9 | 35.2 | 5.30E−06 | 1 | 2.5 | 8.10E−04 | | | | Yes |
| P30040 | ERP29 | 3 | 12.3 | 7.20E−05 | | | | | | | Yes |
| P30041 | PRDX6 | 8 | 44.6 | 8.70E−10 | | | | | | | Yes |
| P30048 | PRDX3 | 6 | 25.4 | 2.50E−06 | 2 | 11.7 | 0.0034 | | | | Yes |
| P30050 | RL12 | 5 | 24.8 | 1.10E−06 | 1 | 10.9 | 4.70E−09 | | | | Yes |
| P30084 | ECHM | 5 | 24.8 | 7.70E−07 | | | | 1 | 4.1 | 0.0062 | Yes |
| P30153 | 2AAA | 6 | 16 | 5.00E−06 | | | | | | | Yes |
| P30520 | PURA2 | 4 | 10.5 | 4.00E−05 | | | | | | | Yes |
| P30626 | SORCN | 3 | 14.6 | 0.0013 | | | | | | | Yes |
| P31040 | DHSA | 3 | 8.9 | 2.00E−06 | | | | | | | Yes |
| P31930 | QCR1 | 2 | 3.8 | 5.00E−04 | | | | | | | Yes |
| P31939 | PUR9 | 8 | 19.3 | 4.30E−07 | | | | | | | Yes |

TABLE 8-continued

| | | 1) Click Reaction On Protein | | | | | | 2) Click Reaction | | | Alkene, |
| | | 1A) Cell Lysate | | | 1B) Cell Fractionation | | | On Peptide 2) Ultrafiltration | | | Sulfenic or |
| Acc# | Gene Name | Num Unique | % Cov | Best Expect Val | Num Unique | % Cov | Best Expect Val | Num Unique | % Cov | Best Expect Val | Thiol Modified peptide |
|---|---|---|---|---|---|---|---|---|---|---|---|
| P31943 | HNRH1 | 13 | 27.6 | 1.90E−07 | 2 | 4.7 | 2.50E−08 | | | | Yes |
| P31946 | 1433B | 9 | 42.3 | 9.00E−07 | | | | | | | Yes |
| P31947 | 1433S | 3 | 9.3 | 0.0021 | | | | | | | Yes |
| P31948 | STIP1 | 10 | 15.8 | 3.50E−06 | | | | | | | Yes |
| P32119 | PRDX2 | 7 | 27.8 | 9.40E−06 | | | | | | | Yes |
| P32969 | RL9 | 7 | 45.3 | 3.70E−07 | | | | 1 | 5.2 | 3.10E−05 | Yes |
| P33778 | H2B1B | 31 | 70.6 | 2.00E−10 | 16 | 68.3 | 7.00E−10 | 14 | 58.7 | 2.50E−09 | Yes |
| P33992 | MCM5 | 4 | 6.9 | 7.40E−07 | | | | | | | Yes |
| P34931 | HS71L | 30 | 32.6 | 4.90E−09 | 3 | 4.1 | 7.40E−04 | 5 | 8.6 | 3.20E−05 | Yes |
| P34932 | HSP74 | 12 | 18.1 | 5.50E−07 | | | | | | | Yes |
| P35232 | PHB | 10 | 42.6 | 3.30E−07 | 2 | 3.7 | 0.0049 | 1 | 4.4 | 2.50E−07 | Yes |
| P35241 | RADI | 5 | 6.3 | 1.20E−05 | | | | | | | Yes |
| P35268 | RL22 | 5 | 52.3 | 1.40E−06 | | | | 2 | 18.8 | 2.20E−05 | Yes |
| P35579 | MYH9 | 5 | 3.3 | 1.10E−06 | 3 | 1.5 | 1.00E−04 | | | | Yes |
| P35580 | MYH10 | 3 | 1.8 | 1.40E−05 | 2 | 1.1 | 2.70E−05 | | | | Yes |
| P35606 | COPB2 | 2 | 2.3 | 4.00E−04 | 1 | 1.2 | 1.00E−06 | | | | Yes |
| P35659 | DEK | 5 | 16.3 | 1.30E−04 | | | | | | | Yes |
| P36542 | ATPG | 4 | 21.5 | 3.60E−06 | | | | | | | Yes |
| P36578 | RL4 | 14 | 33.5 | 5.10E−06 | | | | | | | Yes |
| P36873 | PP1G | 7 | 19.5 | 6.20E−06 | 1 | 4.6 | 1.10E−09 | | | | Yes |
| P37802 | TAGL2 | 12 | 62.8 | 1.40E−07 | | | | 1 | 6 | 5.90E−04 | Yes |
| P37837 | TALDO | 5 | 16.9 | 4.50E−05 | | | | | | | Yes |
| P38117 | ETFB | 5 | 19.2 | 8.80E−06 | | | | | | | Yes |
| P38159 | RBMX | 13 | 30.9 | 9.40E−07 | | | | | | | Yes |
| P38646 | GRP75 | 27 | 41.8 | 5.00E−09 | | | | | | | Yes |
| P38919 | IF4A3 | 7 | 18.5 | 6.40E−07 | 3 | 5.8 | 4.00E−08 | | | | Yes |
| P39019 | RS19 | 11 | 57.9 | 1.40E−06 | | | | 1 | 7.6 | 6.20E−04 | Yes |
| P39023 | RL3 | 10 | 30.5 | 2.30E−05 | | | | 2 | 5.2 | 8.90E−04 | Yes |
| P39687 | AN32A | 4 | 19.7 | 2.20E−07 | | | | | | | Yes |
| P40227 | TCPZ | 11 | 26.9 | 8.70E−07 | | | | | | | Yes |
| P40429 | RL13A | 3 | 14.3 | 1.30E−04 | | | | | | | Yes |
| P40925 | MDHC | 5 | 18.3 | 4.10E−08 | | | | | | | Yes |
| P40926 | MDHM | 23 | 68.3 | 1.10E−09 | 1 | 2.7 | 2.00E−04 | 1 | 2.7 | 2.30E−05 | Yes |
| P40939 | ECHA | 7 | 12.7 | 1.80E−07 | | | | | | | Yes |
| P41091 | IF2G | 2 | 6.6 | 5.30E−06 | | | | | | | Yes |
| P41219 | PERI | 4 | 6.4 | 2.50E−06 | 2 | 4.5 | 4.40E−06 | | | | Yes |
| P41250 | SYG | 6 | 12.2 | 2.00E−07 | | | | | | | Yes |
| P41252 | SYIC | 10 | 9.5 | 2.80E−05 | | | | | | | Yes |
| P42166 | LAP2A | 7 | 11.1 | 6.60E−07 | | | | | | | Yes |
| P42167 | LAP2B | 8 | 19.4 | 6.60E−07 | 3 | 7 | 8.10E−04 | | | | Yes |
| P42285 | SK2L2 | 2 | 1.9 | 2.80E−05 | | | | | | | Yes |
| P42704 | LPPRC | 17 | 15.9 | 8.70E−07 | | | | | | | Yes |
| P42766 | RL35 | 1 | 8.1 | 1.30E−04 | | | | 1 | 8.1 | 6.60E−04 | Yes |
| P43243 | MATR3 | 13 | 17.9 | 2.00E−06 | 1 | 1.1 | 0.0017 | | | | Yes |
| P43246 | MSH2 | 3 | 3.7 | 4.00E−04 | | | | | | | Yes |
| P43487 | RANG | 3 | 15.4 | 7.30E−06 | | | | | | | Yes |
| P45880 | VDAC2 | 10 | 28.9 | 2.90E−07 | | | | | | | Yes |
| P45973 | CBX5 | 2 | 11.5 | 2.30E−04 | | | | | | | Yes |
| P46013 | K167 | 4 | 1.3 | 7.50E−05 | | | | | | | Yes |
| P46087 | NOP2 | 3 | 4.1 | 0.0037 | 1 | 1.2 | 1.80E−05 | | | | Yes |
| P46776 | RL27A | 2 | 14.2 | 1.00E−04 | 1 | 8.8 | 6.20E−07 | 1 | 7.4 | 1.70E−04 | Yes |
| P46777 | RL5 | 7 | 26.9 | 2.00E−07 | | | | | | | Yes |
| P46778 | RL21 | 3 | 25 | 1.20E−07 | | | | 1 | 9.4 | 4.40E−05 | Yes |
| P46779 | RL28 | 7 | 40.1 | 2.80E−06 | | | | | | | Yes |
| P46781 | RS9 | 12 | 43.8 | 7.00E−07 | | | | | | | Yes |
| P46782 | RS5 | 8 | 46.1 | 1.10E−06 | | | | | | | Yes |
| P46783 | RS10 | 2 | 14.5 | 1.60E−05 | | | | | | | Yes |
| P46940 | IQGA1 | 5 | 4 | 3.70E−05 | | | | | | | Yes |
| P47914 | RL29 | 3 | 16.4 | 6.20E−08 | | | | | | | Yes |
| P48643 | TCPE | 17 | 32.3 | 1.50E−07 | | | | | | | Yes |
| P49207 | RL34 | 5 | 30.8 | 3.20E−04 | | | | | | | Yes |
| P49327 | FAS | 31 | 7.70E−07 | 7.70E−07 | 1 | 0.4 | 0.0026 | | | | Yes |
| P49368 | TCPG | 19 | 42.9 | 8.70E−07 | | | | | | | Yes |
| P49411 | EFTU | 7 | 18.6 | 2.10E−07 | | | | | | | Yes |
| P49419 | AL7A1 | 2 | 4.6 | 1.10E−06 | | | | | | | Yes |
| P49458 | SRP09 | 2 | 26.7 | 4.00E−06 | | | | | | | Yes |
| P49915 | GUAA | 7 | 13.4 | 7.00E−05 | | | | | | | Yes |
| P50454 | SERPH | 4 | 12.4 | 6.60E−06 | | | | | | | Yes |
| P50502 | F10A1 | 4 | 12.2 | 1.30E−05 | | | | | | | Yes |
| P50914 | RL14 | 9 | 35.3 | 1.10E−06 | | | | 2 | 10.7 | 2.30E−06 | Yes |
| P50990 | TCPQ | 24 | 47.8 | 2.10E−08 | | | | | | | Yes |

TABLE 8-continued

| | | 1) Click Reaction On Protein | | | | | | 2) Click Reaction | | | Alkene, |
| | | 1A) Cell Lysate | | | 1B) Cell Fractionation | | | On Peptide 2) Ultrafiltration | | | Sulfenic or Thiol Modified peptide |
| Acc# | Gene Name | Num Unique | % Cov | Best Expect Val | Num Unique | % Cov | Best Expect Val | Num Unique | % Cov | Best Expect Val | |
| --- | --- | --- | --- | --- | --- | --- | --- | --- | --- | --- | --- |
| P50991 | TCPD | 20 | 38.4 | 7.50E−08 | | | | | | | Yes |
| P50995 | ANX11 | 2 | 4.6 | 9.00E−05 | | | | | | | Yes |
| P51148 | RAB5C | 4 | 22.2 | 7.60E−05 | | | | | | | Yes |
| P51659 | DHB4 | 4 | 5.7 | 4.50E−05 | 1 | 4.3 | 9.80E−05 | | | | Yes |
| P51665 | PSD7 | 2 | 11.7 | 0.0021 | | | | 1 | 7.4 | 0.0018 | Yes |
| P51991 | ROA3 | 7 | 21.4 | 3.70E−11 | 4 | 8.5 | 1.10E−07 | 1 | 3.7 | 0.0022 | Yes |
| P52209 | 6PGD | 10 | 31.9 | 2.50E−07 | | | | | | | Yes |
| P52597 | HNRPF | 9 | 28 | 1.90E−06 | 1 | 2.2 | 3.40E−04 | | | | Yes |
| P52701 | MSH6 | 4 | 3.6 | 9.80E−06 | | | | | | | Yes |
| P52815 | RM12 | 2 | 11.1 | 8.30E−06 | | | | | | | Yes |
| P52907 | CAZA1 | 4 | 18.5 | 4.70E−06 | | | | | | | Yes |
| P53396 | ACLY | 12 | 14.1 | 1.60E−06 | | | | | | | Yes |
| P53618 | COPB | 1 | 1.2 | 2.10E−04 | 1 | 1.2 | 6.20E−04 | | | | Yes |
| P53621 | COPA | 7 | 6.9 | 8.60E−07 | | | | | | | Yes |
| P53999 | TCP4 | 2 | 18.9 | 5.10E−04 | | | | | | | Yes |
| P54136 | SYRC | 6 | 9.8 | 1.40E−06 | | | | | | | Yes |
| P54652 | HSP72 | 14 | 15 | 3.90E−08 | | | | 2 | 3.8 | 3.20E−05 | Yes |
| P54709 | AT1B3 | 6 | 22.9 | 5.40E−06 | | | | | | | Yes |
| P55036 | PSMD4 | 4 | 12.5 | 4.20E−07 | | | | | | | Yes |
| P55060 | XPO2 | 16 | 23.4 | 4.60E−07 | | | | | | | Yes |
| P55072 | TERA | 19 | 31.4 | 6.70E−07 | | | | | | | Yes |
| P55084 | ECHB | 9 | 19.4 | 2.40E−04 | | | | | | | Yes |
| P55209 | NP1L1 | 4 | 12.5 | 2.00E−06 | | | | | | | Yes |
| P55263 | ADK | 2 | 9.9 | 2.00E−07 | | | | | | | Yes |
| P55786 | PSA | 6 | 7.8 | 4.90E−05 | | | | | | | Yes |
| P55795 | HNRH2 | 4 | 13.4 | 2.80E−07 | 2 | 4.7 | 2.50E−08 | | | | Yes |
| P57053 | H2BFS | 36 | 71.4 | 2.00E−10 | 22 | 72.2 | 7.00E−10 | 19 | 70.6 | 2.50E−09 | Yes |
| P58876 | H2B1D | 37 | 79.4 | 2.00E−10 | 22 | 81 | 7.00E−10 | 17 | 65.9 | 2.50E−09 | Yes |
| P60709 | ACTB | 37 | 74.7 | 3.80E−09 | 17 | 17.9 | 3.20E−09 | 18 | 31.7 | 3.80E−06 | Yes |
| P60842 | IF4A1 | 21 | 57.4 | 1.30E−07 | 1 | 3.9 | 2.50E−08 | | | | Yes |
| P60866 | RS20 | | | | 2 | 16 | 3.40E−07 | | | | Yes |
| P60900 | PSA6 | 3 | 13 | 3.50E−05 | | | | 1 | 7.3 | 3.70E−05 | Yes |
| P60981 | DEST | 2 | 16.4 | 1.50E−06 | | | | | | | Yes |
| P61077 | UB2D3 | 1 | 7.5 | 5.90E−04 | 2 | 6.8 | 1.30E−04 | | | | Yes |
| P61081 | UBC12 | 3 | 18.6 | 6.30E−05 | | | | | | | Yes |
| P61088 | UBE2N | 3 | 27 | 1.50E−05 | | | | | | | Yes |
| P61163 | ACTZ | 2 | 8.8 | 1.40E−06 | | | | | | | Yes |
| P61221 | ABCE1 | 5 | 11.4 | 8.80E−06 | | | | | | | Yes |
| P61224 | RAP1B | 4 | 22.3 | 1.70E−05 | | | | | | | Yes |
| P61247 | RS3A | 9 | 34.8 | 5.60E−05 | 1 | 4.5 | 0.0069 | 2 | 6.8 | 3.00E−04 | Yes |
| P61254 | RL26 | 5 | 26.2 | 0.0013 | 1 | 11 | 0.0014 | | | | Yes |
| P61289 | PSME3 | 5 | 21.3 | 1.10E−05 | | | | | | | Yes |
| P61313 | RL15 | 4 | 20.6 | 2.00E−07 | | | | | | | Yes |
| P61326 | MGN | 3 | 19.9 | 2.90E−04 | 1 | 5.5 | 8.50E−04 | | | | Yes |
| P61769 | B2MG | | | | 2 | 21.8 | 8.40E−05 | | | | Yes |
| P61956 | SUMO2 | 3 | 33.7 | 4.70E−06 | | | | | | | Yes |
| P61981 | 1433G | 8 | 40.9 | 1.60E−07 | | | | | | | Yes |
| P62081 | RS7 | 4 | 29.4 | 1.20E−06 | 3 | 13.9 | 1.40E−04 | 4 | 28.4 | 1.70E−05 | Yes |
| P62136 | PP1A | 9 | 27.3 | 6.20E−06 | 1 | 4.5 | 1.10E−09 | | | | Yes |
| P62158 | CALM | 6 | 25.5 | 3.00E−06 | | | | | | | Yes |
| P62191 | PRS4 | 4 | 11.4 | 1.00E−05 | | | | 1 | 3.6 | 2.90E−06 | Yes |
| P62244 | RS15A | 5 | 33.1 | 1.20E−04 | | | | | | | Yes |
| P62249 | RS16 | 5 | 28.8 | 1.60E−07 | | | | | | | Yes |
| P62266 | RS23 | 5 | 29.4 | 2.00E−06 | 1 | 8.4 | 1.90E−05 | 1 | 7.7 | 1.40E−06 | Yes |
| P62277 | RS13 | 8 | 37.7 | 9.10E−07 | | | | | | | Yes |
| P62280 | RS11 | 6 | 29.1 | 6.60E−04 | | | | | | | Yes |
| P62314 | SMD1 | 4 | 54.6 | 2.90E−08 | 1 | 18.5 | 1.40E−05 | | | | Yes |
| P62316 | SMD2 | 2 | 16.9 | 1.20E−06 | | | | | | | Yes |
| P62333 | PRS10 | 3 | 9.5 | 3.70E−05 | | | | | | | Yes |
| P62424 | RL7A | 9 | 35.7 | 3.10E−08 | 4 | 18.8 | 7.50E−06 | 4 | 12 | 1.00E−04 | Yes |
| P62495 | ERF1 | 8 | 20.4 | 4.10E−06 | 1 | 4.6 | 0.0049 | | | | Yes |
| P62701 | RS4X | 11 | 41.4 | 2.10E−07 | 1 | 8.7 | 0.0015 | 3 | 11.8 | 1.60E−04 | Yes |
| P62736 | ACTA | 24 | 30.8 | 3.70E−08 | 16 | 18 | 3.20E−09 | 14 | 18.6 | 3.80E−06 | Yes |
| P62750 | RL23A | 6 | 32.7 | 3.10E−06 | 1 | 6.4 | 0.0018 | | | | Yes |
| P62753 | RS6 | 4 | 16.1 | 2.40E−05 | | | | 1 | 4.8 | 7.50E−04 | Yes |
| P62829 | RL23 | 5 | 40 | 8.10E−08 | 3 | 7.1 | 3.40E−05 | | | | Yes |
| P62847 | RS24 | 4 | 28.6 | 7.20E−07 | | | | 2 | 19.5 | 8.90E−05 | Yes |
| P62851 | RS25 | 9 | 44.8 | 1.70E−05 | | | | 3 | 21.6 | 0.0011 | Yes |
| P62854 | RS26 | 3 | 33.9 | 3.30E−06 | | | | | | | Yes |
| P62857 | RS28 | 4 | 56.5 | 4.00E−04 | | | | | | | Yes |
| P62888 | RL30 | 5 | 48.7 | 1.40E−05 | | | | | | | Yes |

TABLE 8-continued

| | | 1) Click Reaction On Protein | | | | | | | | Alkene, |
| | | 1A) Cell Lysate | | | 1B) Cell Fractionation | | | 2) Click Reaction On Peptide 2) Ultrafiltration | | | Sulfenic or Thiol |
| Acc# | Gene Name | Num Unique | % Cov | Best Expect Val | Num Unique | % Cov | Best Expect Val | Num Unique | % Cov | Best Expect Val | Modified peptide |
|---|---|---|---|---|---|---|---|---|---|---|---|
| P62899 | RL31 | 3 | 26.4 | 4.50E−08 | | | | 1 | 11.2 | 9.90E−04 | Yes |
| P62906 | RL10A | 8 | 26.3 | 2.60E−06 | 2 | 8.8 | 4.50E−05 | | | | Yes |
| P62910 | RL32 | 4 | 29.6 | 4.20E−05 | | | | 2 | 13.3 | 9.70E−04 | Yes |
| P62913 | RL11 | 3 | 18.5 | 6.40E−07 | | | | | | | Yes |
| P62917 | RL8 | 2 | 10.5 | 5.80E−06 | | | | 1 | 4.3 | 1.00E−04 | Yes |
| P63010 | AP2B1 | 3 | 3.4 | 1.10E−04 | | | | | | | Yes |
| P63104 | 1433Z | 7 | 36.3 | 2.80E−08 | | | | | | | Yes |
| P63167 | DYL1 | 2 | 24.7 | 6.10E−06 | 1 | 13.5 | 4.60E−04 | | | | Yes |
| P63173 | RL38 | 3 | 45.7 | 1.30E−05 | | | | | | | Yes |
| P63208 | SKP1 | 3 | 25.2 | 3.60E−05 | | | | | | | Yes |
| P63241 | IF5A1 | 8 | 70.1 | 2.20E−07 | | | | 3 | 24 | 6.70E−04 | Yes |
| P63261 | ACTG | 37 | 74.7 | 5.30E−08 | 17 | 17.9 | 3.20E−09 | 18 | 31.7 | 3.80E−06 | Yes |
| P63267 | ACTH | 24 | 30.9 | 3.70E−08 | 16 | 18.1 | 3.20E−09 | 14 | 18.6 | 3.80E−06 | Yes |
| P67809 | YBOX1 | 9 | 32.1 | 3.10E−06 | | | | | | | Yes |
| P68032 | ACTC | 25 | 33.7 | 3.70E−08 | 17 | 21 | 3.20E−09 | 15 | 21.5 | 3.80E−06 | Yes |
| P68104 | EF1A1 | 30 | 39.8 | 1.40E−08 | 10 | 19.7 | 9.20E−09 | 2 | 4.8 | 2.30E−05 | Yes |
| P68133 | ACTS | 25 | 33.7 | 3.70E−08 | 17 | 21 | 3.20E−09 | 15 | 21.5 | 3.80E−06 | Yes |
| P68363 | TBA1B | 31 | 57 | 1.50E−09 | 6 | 18.2 | 3.40E−10 | 4 | 8.2 | 4.90E−06 | Yes |
| P68371 | TBB4B | 32 | 69.4 | 2.10E−07 | | | | 2 | 5.2 | 0.0037 | Yes |
| P78347 | GTF2I | 4 | 8.8 | 1.10E−06 | | | | | | | Yes |
| P78371 | TCPB | 17 | 42.6 | 3.10E−08 | 1 | 6.2 | 0.0024 | | | | Yes |
| P78417 | GSTO1 | 2 | 7.5 | 6.60E−06 | | | | | | | Yes |
| P78527 | PRKDC | 32 | 8.5 | 4.80E−06 | 2 | 0.6 | 8.90E−07 | | | | Yes |
| P82979 | SARNP | 4 | 18.1 | 2.10E−04 | | | | | | | Yes |
| P83731 | RL24 | 3 | 19.1 | 2.30E−06 | 1 | 8.9 | 2.00E−04 | 2 | 13.4 | 9.30E−06 | Yes |
| P84090 | ERH | 6 | 35.6 | 4.50E−08 | 3 | 25 | 1.00E−04 | | | | Yes |
| P84098 | RL19 | 2 | 13.3 | 8.60E−09 | 1 | 5.1 | 7.50E−04 | | | | Yes |
| P99999 | CYC | 4 | 25.7 | 1.60E−05 | | | | | | | Yes |
| Q00610 | CLH1 | 23 | 16.4 | 4.50E−08 | 4 | 3.1 | 6.80E−07 | | | | Yes |
| Q00688 | FKBP3 | 2 | 9.8 | 1.30E−05 | | | | | | | Yes |
| Q01082 | SPTB2 | 2 | 1.1 | 4.80E−05 | | | | | | | Yes |
| Q01105 | SET | 4 | 11.4 | 5.20E−06 | 1 | 3.1 | 0.0074 | 1 | 3.1 | 0.0038 | Yes |
| Q01518 | CAP1 | 2 | 6.1 | 1.40E−05 | | | | | | | Yes |
| Q01813 | K6PP | 4 | 5.4 | 8.20E−05 | | | | | | | Yes |
| Q02790 | FKBP4 | 9 | 20.5 | 4.60E−05 | | | | | | | Yes |
| Q02880 | TOP2B | 4 | 2.5 | 3.70E−05 | | | | | | | Yes |
| Q03252 | LMNB2 | 4 | 8 | 1.30E−06 | 3 | 3.5 | 8.60E−05 | | | | Yes |
| Q04637 | IF4G1 | 11 | 7.8 | 1.70E−06 | 1 | 0.9 | 0.0032 | 1 | 0.9 | 2.00E−05 | Yes |
| Q04760 | LGUL | 4 | 27.2 | 1.50E−06 | | | | | | | Yes |
| Q04917 | 1433F | 3 | 9.3 | 0.0021 | | | | | | | Yes |
| Q05639 | EF1A2 | 18 | 22 | 1.40E−10 | 5 | 9.7 | 9.20E−09 | 1 | 2.2 | 1.40E−04 | Yes |
| Q06830 | PRDX1 | 17 | 56.3 | 1.10E−06 | | | | | | | Yes |
| Q07021 | C1QBP | 9 | 51.4 | 4.40E−07 | | | | 1 | 3.9 | 6.80E−04 | Yes |
| Q07065 | CKAP4 | 5 | 9.5 | 1.10E−05 | | | | | | | Yes |
| Q07666 | KHDR1 | 5 | 9.7 | 1.40E−05 | | | | | | | Yes |
| Q07955 | SRSF1 | 5 | 25.8 | 6.30E−05 | | | | | | | Yes |
| Q08211 | DHX9 | 28 | 27.2 | 1.00E−07 | 2 | 2.2 | 2.10E−04 | | | | Yes |
| Q08945 | SSRP1 | 6 | 9.9 | 1.00E−05 | 2 | 3.9 | 1.70E−04 | 1 | 1.3 | 0.0016 | Yes |
| Q08J23 | NSUN2 | 2 | 3.9 | 2.90E−04 | | | | | | | Yes |
| Q12873 | CHD3 | 3 | 1.4 | 2.00E−04 | | | | | | | Yes |
| Q12905 | ILF2 | 9 | 33.6 | 5.50E−07 | 2 | 10 | 4.00E−04 | | | | Yes |
| Q12906 | ILF3 | 13 | 16.6 | 2.90E−07 | 3 | 2.8 | 5.30E−06 | | | | Yes |
| Q12931 | TRAP1 | 10 | 16.9 | 5.50E−07 | | | | 2 | 3.1 | 4.90E−05 | Yes |
| Q13148 | TADBP | 5 | 17.9 | 1.40E−08 | | | | | | | Yes |
| Q13151 | ROA0 | 5 | 23.6 | 2.10E−07 | | | | | | | Yes |
| Q13162 | PRDX4 | 6 | 25.5 | 2.40E−06 | | | | | | | Yes |
| Q13185 | CBX3 | 4 | 22.4 | 3.10E−06 | | | | | | | Yes |
| Q13200 | PSMD2 | 5 | 6.7 | 3.00E−06 | | | | 7 | 16.6 | 2.50E−06 | Yes |
| Q13263 | TIF1B | 13 | 22.3 | 2.10E−07 | 1 | 1 | 0.0015 | | | | Yes |
| Q13283 | G3BP1 | 7 | 21.5 | 1.60E−06 | 1 | 4.7 | 0.0072 | | | | Yes |
| Q13310 | PABP4 | 13 | 25.3 | 3.30E−09 | | | | | | | Yes |
| Q13428 | TCOF | 4 | 3 | 7.40E−05 | | | | | | | Yes |
| Q13619 | CUL4A | 5 | 10 | 0.0012 | | | | | | | Yes |
| Q13748 | TBA3C | 25 | 42 | 1.50E−09 | 5 | 14.7 | 3.40E−10 | 3 | 4.7 | 0.0041 | Yes |
| Q13765 | NACA | 5 | 32.6 | 8.40E−08 | 2 | 9.8 | 4.70E−04 | | | | Yes |
| Q13813 | SPTN1 | 3 | 1.2 | 7.40E−06 | 4 | 2.2 | 7.00E−09 | | | | Yes |
| Q13838 | DX39B | 10 | 23.8 | 5.00E−07 | 2 | 3.7 | 1.30E−05 | | | | Yes |
| Q13885 | TBB2A | 29 | 58.9 | 8.10E−08 | | | | 1 | 3.1 | 0.0037 | Yes |
| Q14151 | SAFB2 | 3 | 3.5 | 6.70E−06 | | | | | | | Yes |
| Q14152 | EIF3A | 12 | 9 | 2.40E−05 | | | | | | | Yes |
| Q14204 | DYNC1 | 11 | 2.3 | 2.90E−04 | | | | | | | Yes |

TABLE 8-continued

| | | 1) Click Reaction On Protein | | | | | | 2) Click Reaction | | | Alkene, |
|---|---|---|---|---|---|---|---|---|---|---|---|
| | | 1A) Cell Lysate | | | 1B) Cell Fractionation | | | On Peptide 2) Ultrafiltration | | | Sulfenic or |
| Acc# | Gene Name | Num Unique | % Cov | Best Expect Val | Num Unique | % Cov | Best Expect Val | Num Unique | % Cov | Best Expect Val | Thiol Modified peptide |
|---|---|---|---|---|---|---|---|---|---|---|---|
| Q14498 | RBM39 | 4 | 10 | 5.50E−05 | | | | | | | Yes |
| Q14568 | HS902 | 10 | 20.4 | 1.30E−05 | 5 | 14.9 | 3.30E−07 | 1 | 2.6 | 5.60E−06 | Yes |
| Q14651 | PLSI | 3 | 5.6 | 3.30E−05 | | | | | | | Yes |
| Q14677 | EPN4 | 1 | 2.1 | 1.40E−04 | 1 | 3.2 | 1.30E−05 | | | | Yes |
| Q14683 | SMC1A | 2 | 1.5 | 0.0012 | | | | | | | Yes |
| Q14684 | RRP1B | 1 | 1.5 | 0.0096 | 1 | 1.1 | 3.60E−04 | | | | Yes |
| Q14690 | RRP5 | 2 | 0.9 | 0.0018 | 2 | 1.1 | 9.10E−06 | | | | Yes |
| Q14739 | LBR | 3 | 5.7 | 1.10E−05 | 1 | 2.3 | 3.20E−04 | | | | Yes |
| Q14978 | NOLC1 | 4 | 5.9 | 1.80E−05 | | | | | | | Yes |
| Q14997 | PSME4 | 2 | 1.6 | 0.0017 | | | | | | | Yes |
| Q15029 | U5S1 | 11 | 14.6 | 3.60E−06 | 1 | 0.9 | 3.70E−04 | | | | Yes |
| Q15056 | IF4H | 4 | 22.2 | 4.70E−05 | | | | | | | Yes |
| Q15061 | WDR43 | 1 | 2.2 | 0.0024 | 1 | 2.2 | 7.60E−04 | | | | Yes |
| Q15084 | PDIA6 | 9 | 28.9 | 3.10E−08 | | | | | | | Yes |
| Q15181 | IPYR | 9 | 41.2 | 1.30E−09 | | | | | | | Yes |
| Q15185 | TEBP | 5 | 27.5 | 9.50E−08 | | | | 1 | 8.1 | 3.30E−04 | Yes |
| Q15293 | RCN1 | 3 | 12.1 | 4.00E−05 | | | | | | | Yes |
| Q15365 | PCBP1 | 7 | 24.4 | 1.50E−06 | | | | | | | Yes |
| Q15366 | PCBP2 | 7 | 23.8 | 1.50E−06 | | | | | | | Yes |
| Q15393 | SF3B3 | 13 | 12.3 | 1.50E−06 | | | | | | | Yes |
| Q15424 | SAFB1 | 3 | 3.6 | 3.20E−06 | | | | | | | Yes |
| Q15819 | UB2V2 | 2 | 13.8 | 6.00E−04 | | | | | | | Yes |
| Q15843 | NEDD8 | 2 | 8.6 | 4.10E−05 | | | | | | | Yes |
| Q16181 | SEPT7 | 2 | 5.3 | 2.90E−05 | | | | | | | Yes |
| Q16531 | DDB1 | 9 | 7.6 | 1.50E−04 | | | | | | | Yes |
| Q16777 | H2A2C | 19 | 75.2 | 2.90E−09 | 7 | 41.1 | 1.20E−07 | 10 | 48.1 | 2.00E−07 | Yes |
| Q16881 | TRXR1 | 2 | 4.2 | 1.40E−04 | | | | | | | Yes |
| Q16891 | IMMT | 2 | 2.4 | 9.60E−04 | | | | | | | Yes |
| Q1KMD3 | HNRL2 | 3 | 4 | 2.20E−05 | 1 | 1.2 | 0.0012 | | | | Yes |
| Q32P51 | RA1L2 | 10 | 26.6 | 1.30E−07 | 4 | 14.1 | 6.90E−07 | 3 | 10.9 | 9.60E−04 | Yes |
| Q4VCS5 | AMOT | 3 | 3.8 | 2.10E−04 | | | | | | | Yes |
| Q562R1 | ACTBL | 13 | 14.9 | 3.70E−08 | 4 | 6.1 | 5.30E−07 | 6 | 11.2 | 1.20E−05 | Yes |
| Q58FF3 | ENPLL | 4 | 7.3 | 4.00E−04 | | | | 2 | 1.8 | 8.10E−04 | Yes |
| Q58FG0 | HS905 | 4 | 13.2 | 1.90E−04 | | | | | | | Yes |
| Q5JQF8 | PAP1M | 2 | 10 | 9.00E−06 | | | | | | | Yes |
| Q5JTH9 | RRP12 | 1 | 0.8 | 0.0011 | 2 | 1.4 | 7.40E−04 | | | | Yes |
| Q5QNW6 | H2B2F | 36 | 77 | 2.00E−10 | 19 | 75.4 | 7.00E−10 | 18 | 63.5 | 2.50E−09 | Yes |
| Q5T9A4 | ATD3B | 4 | 6.3 | 1.90E−04 | | | | 1 | 1.4 | 0.0046 | Yes |
| Q6DN03 | H2B2C | 9 | 16.6 | 2.10E−05 | 8 | 16.6 | 3.40E−06 | 3 | 10.9 | 4.80E−05 | Yes |
| Q6DRA6 | H2B2D | 9 | 19.5 | 2.10E−05 | 8 | 19.5 | 3.40E−06 | 3 | 12.8 | 4.80E−05 | Yes |
| Q6NUK1 | SCMC1 | 2 | 5 | 1.60E−05 | 1 | 5.7 | 0.0022 | | | | Yes |
| Q6P2Q9 | PRP8 | 12 | 5.7 | 5.40E−06 | | | | | | | Yes |
| Q6PEY2 | TBA3E | 15 | 36.7 | 1.50E−09 | 3 | 12.7 | 3.10E−06 | 2 | 3.8 | 0.0041 | Yes |
| Q6UB35 | C1TM | 2 | 2.9 | 9.30E−06 | | | | | | | Yes |
| Q71U36 | TBA1A | 31 | 57 | 1.50E−09 | 6 | 18.2 | 3.40E−10 | 4 | 8.2 | 4.90E−06 | Yes |
| Q71UI9 | H2AV | 6 | 33.6 | 3.80E−05 | 4 | 25.8 | 7.10E−06 | 3 | 23.4 | 3.20E−04 | Yes |
| Q7KZF4 | SND1 | 5 | 6.4 | 5.80E−04 | | | | 1 | 1.2 | 0.0022 | Yes |
| Q7L1Q6 | BZW1 | 3 | 5.7 | 0.0012 | | | | | | | Yes |
| Q7L7L0 | H2A3 | 23 | 82.3 | 2.90E−09 | 11 | 48.5 | 1.20E−07 | 12 | 52.3 | 2.00E−07 | Yes |
| Q86SE5 | RALYL | 2 | 6.5 | 2.40E−04 | | | | 2 | 6.2 | 0.0023 | Yes |
| Q86U42 | PABP2 | 3 | 14.4 | 1.00E−05 | | | | | | | Yes |
| Q86VP6 | CAND1 | 11 | 12 | 1.10E−06 | | | | | | | Yes |
| Q8IUE6 | H2A2B | 11 | 74.6 | 1.40E−08 | 4 | 30 | 3.40E−07 | 7 | 29.2 | 2.30E−04 | Yes |
| Q8IWX8 | CHERP | 2 | 2.8 | 0.0028 | | | | | | | Yes |
| Q8N1F7 | NUP93 | 2 | 5.3 | 7.30E−06 | | | | | | | Yes |
| Q8N257 | H2B3B | 35 | 74.6 | 2.00E−10 | 20 | 74.6 | 7.00E−10 | 14 | 64.3 | 2.50E−09 | Yes |
| Q8NB90 | SPAT5 | 2 | 2.4 | 4.60E−04 | | | | | | | Yes |
| Q8NC51 | PAIRB | 5 | 17.9 | 4.30E−07 | | | | | | | Yes |
| Q8NE71 | ABCF1 | 4 | 5.1 | 1.10E−04 | | | | | | | Yes |
| Q8NEN0 | ARMC2 | | | | 2 | 1.6 | 0.004 | | | | Yes |
| Q8TDN6 | BRX1 | 1 | 3.1 | 2.30E−04 | 1 | 3.4 | 0.0011 | | | | Yes |
| Q92499 | DDX1 | 5 | 8.9 | 2.30E−08 | | | | | | | Yes |
| Q92598 | HS105 | 8 | 10.5 | 1.90E−05 | | | | | | | Yes |
| Q92616 | GCN1L | 3 | 1.4 | 7.50E−05 | | | | | | | Yes |
| Q92688 | AN32B | 5 | 24.7 | 2.20E−07 | | | | | | | Yes |
| Q92804 | RBP56 | 3 | 5.4 | 2.50E−06 | | | | | | | Yes |
| Q92841 | DDX17 | 15 | 24.1 | 5.70E−07 | 1 | 1.4 | 1.60E−04 | | | | Yes |
| Q92922 | SMRC1 | 3 | 3.9 | 4.80E−07 | | | | | | | Yes |
| Q92945 | FUBP2 | 13 | 15.3 | 1.20E−05 | | | | | | | Yes |
| Q93077 | H2A1C | 22 | 82.3 | 2.90E−09 | 11 | 48.5 | 1.20E−07 | 12 | 52.3 | 2.00E−07 | Yes |
| Q969X6 | CIR1A | 1 | 1.5 | 0.0023 | 1 | 1.7 | 2.00E−04 | | | | Yes |

TABLE 8-continued

| | | 1) Click Reaction On Protein | | | | | | 2) Click Reaction On Peptide | | | Alkene, Sulfenic or |
|---|---|---|---|---|---|---|---|---|---|---|---|
| | | 1A) Cell Lysate | | | 1B) Cell Fractionation | | | 2) Ultrafiltration | | | |
| Acc# | Gene Name | Num Unique | % Cov | Best Expect Val | Num Unique | % Cov | Best Expect Val | Num Unique | % Cov | Best Expect Val | Thiol Modified peptide |
| Q96A72 | MGN2 | 3 | 20.9 | 2.90E−04 | 1 | 5.4 | 8.50E−04 | | | | Yes |
| Q96AE4 | FUBP1 | 4 | 6.8 | 1.20E−05 | 1 | 1.9 | 0.0045 | | | | Yes |
| Q96AG4 | LRC59 | 5 | 20.8 | 7.10E−06 | | | | | | | Yes |
| Q96KK5 | H2A1H | 22 | 82 | 2.90E−09 | 10 | 47.7 | 1.20E−07 | 12 | 54.7 | 2.00E−07 | Yes |
| Q96PK6 | RBM14 | 8 | 13.8 | 6.80E−07 | | | | | | | Yes |
| Q96QK1 | VPS35 | 3 | 3 | 6.00E−04 | | | | | | | Yes |
| Q96QV6 | H2A1A | 11 | 47.3 | 2.00E−07 | 5 | 35.1 | 3.40E−07 | 7 | 29 | 2.30E−04 | Yes |
| Q99460 | PSMD1 | 4 | 6.4 | 3.40E−05 | | | | | | | Yes |
| Q99497 | PARK7 | 7 | 45.5 | 7.80E−05 | | | | | | | Yes |
| Q99615 | DNJC7 | 7 | 17 | 3.00E−04 | | | | | | | Yes |
| Q99623 | PHB2 | 11 | 43.5 | 7.70E−08 | 1 | 3 | 0.01 | | | | Yes |
| Q99729 | ROAA | 7 | 21.7 | 1.60E−08 | | | | 3 | 7.8 | 5.10E−05 | Yes |
| Q99798 | ACON | 2 | 2.7 | 0.0035 | | | | | | | Yes |
| Q99832 | TCPH | 17 | 35.5 | 6.00E−09 | | | | | | | Yes |
| Q99873 | ANM1 | 3 | 9.1 | 9.30E−05 | | | | | | | Yes |
| Q99880 | H2B1L | 37 | 79.4 | 2.00E−10 | 21 | 76.2 | 7.00E−10 | 17 | 65.9 | 2.50E−09 | Yes |
| Q9BPX3 | CND3 | 3 | 3.9 | 2.00E−04 | | | | | | | Yes |
| Q9BQ39 | DDX50 | 5 | 7.6 | 6.00E−05 | | | | | | | Yes |
| Q9BQE3 | TBA1C | 31 | 57.7 | 1.50E−09 | 6 | 18.3 | 3.40E−10 | 4 | 8.2 | 4.90E−06 | Yes |
| Q9BQG0 | MBB1A | 6 | 4.9 | 1.20E−05 | 3 | 2.4 | 1.40E−06 | | | | Yes |
| Q9BRA2 | TXD17 | 4 | 17.9 | 9.50E−05 | | | | | | | Yes |
| Q9BTM1 | H2AJ | 16 | 69 | 2.90E−09 | 6 | 34.9 | 1.20E−07 | 7 | 41.9 | 2.00E−07 | Yes |
| Q9BTT0 | AN32E | 3 | 17.2 | 3.70E−05 | | | | | | | Yes |
| Q9BUJ2 | HNRL1 | 2 | 1.9 | 0.0073 | 1 | 2.5 | 0.0049 | | | | Yes |
| Q9BVA1 | TBB2B | 29 | 58.9 | 8.10E−08 | | | | 1 | 3.1 | 0.0037 | Yes |
| Q9BXJ9 | NAA15 | 3 | 3.2 | 1.30E−04 | | | | | | | Yes |
| Q9BXP5 | SRRT | 2 | 1.9 | 8.80E−05 | | | | | | | Yes |
| Q9BY67 | CADM1 | 2 | 1.8 | 1.60E−04 | | | | | | | Yes |
| Q9BZE4 | NOG1 | 2 | 3.2 | 1.00E−03 | | | | | | | Yes |
| Q9BZZ5 | API5 | 6 | 14.1 | 3.10E−07 | | | | | | | Yes |
| Q9GZT3 | SLIRP | 3 | 33 | 1.60E−04 | | | | | | | Yes |
| Q9H2U2 | IPYR2 | 2 | 7.5 | 6.50E−07 | | | | | | | Yes |
| Q9H307 | PININ | 2 | 3.1 | 3.60E−05 | | | | | | | Yes |
| Q9H3K2 | GHITM | 2 | 6.1 | 6.50E−04 | | | | | | | Yes |
| Q9HAV4 | XPO5 | 3 | 3.9 | 2.00E−05 | | | | | | | Yes |
| Q9HB71 | CYBP | 8 | 31.6 | 6.40E−05 | | | | | | | Yes |
| Q9NQ88 | TIGAR | 2 | 6.7 | 1.20E−04 | | | | | | | Yes |
| Q9NQC3 | RTN4 | 2 | 2.2 | 1.80E−04 | | | | | | | Yes |
| Q9NR30 | DDX21 | 18 | 30.1 | 8.90E−07 | 3 | 3.4 | 4.40E−07 | | | | Yes |
| Q9NR31 | SAR1A | 2 | 11.6 | 1.30E−04 | 1 | 6.6 | 8.30E−04 | | | | Yes |
| Q9NTK5 | OLA1 | 3 | 9.8 | 2.30E−05 | | | | | | | Yes |
| Q9NV96 | CC50A | 1 | 3.3 | 1.50E−05 | | | | 1 | 3.3 | 6.70E−04 | Yes |
| Q9NVI7 | ATD3A | 7 | 11.8 | 4.90E−06 | | | | 1 | 1.4 | 0.0046 | Yes |
| Q9NVP1 | DDX18 | 5 | 10 | 1.40E−04 | 1 | 1.5 | 3.30E−04 | | | | Yes |
| Q9NX63 | CHCH3 | 2 | 11.5 | 1.20E−05 | | | | | | | Yes |
| Q9NY65 | TBA8 | 16 | 29.2 | 1.80E−08 | 4 | 9.4 | 3.40E−10 | 2 | 2.4 | 0.0041 | Yes |
| Q9NZ01 | TECR | 2 | 6.8 | 4.20E−04 | 1 | 4.5 | 1.10E−05 | | | | Yes |
| Q9NZI8 | IF2B1 | 9 | 21.1 | 8.60E−06 | | | | | | | Yes |
| Q9P258 | RCC2 | 5 | 7.3 | 9.60E−07 | | | | | | | Yes |
| Q9P2J5 | SYLC | 10 | 9.7 | 1.40E−05 | | | | | | | Yes |
| Q9UHB9 | SRP68 | 2 | 3.8 | 0.0025 | | | | | | | Yes |
| Q9UJS0 | CMC2 | 2 | 4.6 | 1.10E−04 | | | | | | | Yes |
| Q9ULV4 | COR1C | 3 | 5.9 | 1.40E−04 | | | | | | | Yes |
| Q9UMS4 | PRP19 | 4 | 11.1 | 1.60E−04 | 1 | 3.2 | 9.60E−06 | | | | Yes |
| Q9UQ35 | SRRM2 | 5 | 2.3 | 4.30E−05 | | | | | | | Yes |
| Q9UQ80 | PA2G4 | 17 | 44.9 | 9.50E−06 | | | | | | | Yes |
| Q9Y262 | EIF3L | 6 | 9.6 | 5.60E−05 | | | | | | | Yes |
| Q9Y265 | RUVB1 | 7 | 19.1 | 3.20E−06 | | | | | | | Yes |
| Q9Y266 | NUDC | 7 | 23 | 2.70E−04 | | | | | | | Yes |
| Q9Y277 | VDAC3 | 3 | 12 | 4.00E−05 | | | | | | | Yes |
| Q9Y2L1 | RRP44 | 3 | 3.5 | 3.00E−04 | | | | | | | Yes |
| Q9Y2W1 | TR150 | 3 | 3.3 | 3.30E−05 | | | | | | | Yes |
| Q9Y2X3 | NOP58 | 6 | 15.3 | 2.10E−06 | 1 | 2.8 | 3.60E−04 | | | | Yes |
| Q9Y383 | LC7L2 | 6 | 13.3 | 9.00E−06 | | | | | | | Yes |
| Q9Y3B4 | PM14 | 2 | 20.8 | 1.70E−06 | | | | | | | Yes |
| Q9Y3F4 | STRAP | 4 | 16.9 | 3.90E−08 | | | | | | | Yes |
| Q9Y3I0 | RTCB | 7 | 14.3 | 1.50E−05 | 2 | 4.4 | 0.0042 | | | | Yes |
| Q9Y3T9 | NOC2L | | | | 2 | 2.7 | 0.0045 | | | | Yes |
| Q9Y3U8 | RL36 | 5 | 41 | 7.00E−06 | | | | | | | Yes |
| Q9Y490 | TLN1 | 3 | 1.4 | 5.30E−06 | | | | | | | Yes |
| Q9Y4L1 | HYOU1 | 3 | 3.3 | 4.90E−05 | | | | | | | Yes |

TABLE 8-continued

| | | 1) Click Reaction On Protein | | | | | | 2) Click Reaction On Peptide 2) Ultrafiltration | | | Alkene, Sulfenic or |
| | | 1A) Cell Lysate | | | 1B) Cell Fractionation | | | | | | |
| Acc# | Gene Name | Num Unique | % Cov | Best Expect Val | Num Unique | % Cov | Best Expect Val | Num Unique | % Cov | Best Expect Val | Thiol Modified peptide |
|---|---|---|---|---|---|---|---|---|---|---|---|
| Q9Y5B9 | SP16H | 4 | 3.9 | 1.90E−06 | | | | | | | Yes |
| Q9Y617 | SERC | 3 | 8.1 | 1.20E−04 | | | | | | | Yes |
| O00151 | PDLI1 | 3 | 13.1 | 4.40E−05 | | | | | | | |
| O00303 | EIF3F | 6 | 20.4 | 3.80E−07 | | | | | | | |
| O00506 | STK25 | 2 | 5.2 | 0.0011 | | | | | | | |
| O14579 | COPE | 2 | 9.1 | 2.20E−04 | | | | | | | |
| O14654 | IRS4 | 5 | 3.9 | 9.10E−05 | | | | | | | |
| O14744 | ANM5 | 5 | 8 | 2.10E−05 | | | | | | | |
| O14818 | PSA7 | 3 | 16.1 | 5.10E−07 | | | | | | | |
| O14874 | BCKD | 2 | 6.8 | 1.80E−06 | | | | | | | |
| O15067 | PUR4 | 6 | 5.5 | 6.70E−05 | | | | | | | |
| O15131 | IMA5 | 3 | 8.6 | 9.30E−05 | | | | | | | |
| O15145 | ARPC3 | 2 | 13.5 | 3.10E−04 | | | | | | | |
| O15173 | PGRC2 | 2 | 10.3 | 1.90E−07 | | | | | | | |
| O15355 | PPM1G | 3 | 6.2 | 2.80E−07 | | | | | | | |
| O15382 | BCAT2 | 2 | 5.1 | 0.0013 | | | | | | | |
| O43143 | DHX15 | 6 | 8.7 | 9.90E−05 | | | | | | | |
| O43242 | PSMD3 | 4 | 9.2 | 4.00E−06 | | | | | | | |
| O43423 | AN32C | 2 | 8.5 | 0.0013 | | | | | | | |
| O43615 | TIM44 | 4 | 9.7 | 6.30E−04 | | | | | | | |
| O43684 | BUB3 | 3 | 10.7 | 2.70E−05 | | | | | | | |
| O43747 | AP1G1 | 2 | 2.2 | 0.0018 | | | | | | | |
| O43809 | CPSF5 | 4 | 27.8 | 4.40E−06 | | | | | | | |
| O43852 | CALU | 2 | 7.6 | 3.40E−06 | | | | | | | |
| O60701 | UGDH | 2 | 3.8 | 0.0013 | | | | | | | |
| O75083 | WDR1 | 2 | 2.8 | 0.0012 | | | | | | | |
| O75153 | CLU | 2 | 1.7 | 0.0018 | | | | | | | |
| O75400 | PR40A | 2 | 1.9 | 0.0075 | | | | | | | |
| O75489 | NDUS3 | 2 | 9.5 | 1.70E−05 | 1 | 6.8 | 0.0012 | | | | |
| O75494 | SRS10 | 2 | 10.7 | 1.20E−06 | | | | | | | |
| O75694 | NU155 | 2 | 1.2 | 6.10E−04 | | | | | | | |
| O75794 | CD123 | 2 | 6.5 | 1.00E−04 | | | | | | | |
| O75947 | ATP5H | 5 | 41 | 3.80E−08 | | | | | | | |
| O75964 | ATP5L | 2 | 19.4 | 1.20E−05 | | | | | | | |
| O76003 | GLRX3 | 5 | 17.6 | 4.00E−05 | | | | | | | |
| O94808 | GFPT2 | 2 | 4.4 | 0.0012 | | | | | | | |
| O95486 | SC24A | 2 | 1.8 | 2.60E−04 | | | | | | | |
| O95716 | RAB3D | 2 | 11.9 | 9.40E−05 | | | | | | | |
| O95747 | OXSR1 | 2 | 3 | 0.0023 | | | | | | | |
| O95861 | BPNT1 | 2 | 8.4 | 1.20E−05 | | | | | | | |
| P00338 | LDHA | 15 | 53.3 | 8.30E−09 | 1 | 4.2 | 2.20E−04 | | | | |
| P00367 | DHE3 | 6 | 11.5 | 2.80E−05 | | | | | | | |
| P00374 | DYR | 2 | 18.2 | 0.0012 | | | | | | | |
| P00403 | COX2 | 4 | 24.7 | 5.30E−06 | | | | | | | |
| P00505 | AATM | 9 | 21.4 | 4.60E−07 | | | | | | | |
| P00568 | KAD1 | 2 | 13.4 | 2.30E−04 | | | | | | | |
| P02768 | ALBU | 3 | 5.7 | 2.70E−07 | | | | | | | |
| P02786 | TFR1 | 2 | 3.4 | 6.00E−04 | | | | | | | |
| P04181 | OAT | 9 | 33 | 4.70E−06 | 1 | 3.6 | 0.0015 | | | | |
| P04843 | RPN1 | 9 | 19.1 | 2.20E−04 | | | | | | | |
| P04844 | RPN2 | 4 | 9.5 | 1.20E−07 | | | | | | | |
| P06280 | AGAL | 2 | 4.9 | 3.30E−05 | | | | | | | |
| P06493 | CDK1 | 4 | 18.5 | 7.50E−05 | | | | | | | |
| P06744 | G6PI | 10 | 23.3 | 2.50E−07 | | | | | | | |
| P07355 | ANXA2 | 7 | 24.8 | 5.70E−05 | 1 | 2.4 | 0.008 | | | | |
| P07741 | APT | 6 | 42.2 | 2.10E−05 | | | | | | | |
| P08134 | RHOC | 4 | 26.4 | 3.60E−05 | | | | | | | |
| P08579 | RU2B | 3 | 11.6 | 0.0021 | 1 | 8.9 | 8.50E−04 | | | | |
| P08708 | RS17 | 3 | 40 | 9.70E−09 | | | | | | | |
| P08758 | ANXA5 | 8 | 25.9 | 4.50E−06 | | | | | | | |
| P08865 | RSSA | 8 | 34.9 | 4.70E−08 | | | | | | | |
| P09012 | SNRPA | 3 | 8.9 | 8.60E−04 | | | | | | | |
| P09211 | GSTP1 | 8 | 41.9 | 3.40E−08 | | | | | | | |
| P09661 | RU2A | 3 | 12.5 | 1.30E−04 | | | | | | | |
| P09936 | UCHL1 | 3 | 11.7 | 6.90E−04 | | | | | | | |
| P09960 | LKHA4 | 7 | 16.2 | 1.10E−06 | 1 | 2.8 | 2.30E−04 | | | | |
| P10515 | ODP2 | 2 | 4.9 | 3.90E−06 | | | | | | | |
| P10768 | ESTD | 2 | 9.6 | 4.00E−06 | | | | | | | |
| P11166 | GTR1 | 2 | 3.7 | 5.90E−04 | | | | | | | |
| P11177 | ODPB | 6 | 22 | 2.60E−06 | | | | | | | |
| P11802 | CDK4 | 2 | 7.6 | 0.0037 | | | | | | | |

TABLE 8-continued

| | | 1) Click Reaction On Protein | | | | | | 2) Click Reaction On Peptide | | | Alkene, Sulfenic or Thiol Modified peptide |
|---|---|---|---|---|---|---|---|---|---|---|---|
| | | 1A) Cell Lysate | | | 1B) Cell Fractionation | | | 2) Ultrafiltration | | | |
| Acc# | Gene Name | Num Unique | % Cov | Best Expect Val | Num Unique | % Cov | Best Expect Val | Num Unique | % Cov | Best Expect Val | |
| P12955 | PEPD | 2 | 5.5 | 7.20E−06 | | | | | | | |
| P13073 | COX41 | 4 | 24.9 | 1.40E−05 | | | | | | | |
| P13489 | RINI | 2 | 4.6 | 1.50E−05 | | | | | | | |
| P13645 | K1C10 | | | | | | | 2 | 6 | 9.10E−06 | |
| P13797 | PLST | 16 | 29.2 | 1.80E−06 | | | | | | | |
| P13804 | ETFA | 7 | 30.3 | 3.20E−09 | | | | | | | |
| P14136 | GFAP | 1 | 1.9 | 4.30E−04 | | | | 1 | 2.5 | 1.30E−05 | |
| P14174 | MIF | 4 | 18.3 | 5.20E−06 | | | | 1 | 10.4 | 1.00E−04 | |
| P14406 | CX7A2 | 2 | 27.7 | 9.90E−05 | | | | | | | |
| P14868 | SYDC | 4 | 7.8 | 1.70E−04 | | | | | | | |
| P14927 | QCR7 | 2 | 20.7 | 1.40E−04 | | | | | | | |
| P15531 | NDKA | 5 | 38.2 | 5.50E−05 | | | | 1 | 7.9 | 7.80E−04 | |
| P16615 | AT2A2 | 6 | 6.1 | 1.00E−04 | | | | | | | |
| P17174 | AATC | 3 | 12.6 | 5.40E−06 | | | | | | | |
| P17812 | PYRG1 | 8 | 17.1 | 4.80E−08 | | | | | | | |
| P17858 | K6PL | 2 | 3.1 | 4.00E−04 | | | | | | | |
| P17980 | PRS6A | 8 | 22.1 | 5.60E−06 | | | | | | | |
| P17987 | TCPA | 17 | 36.9 | 2.90E−06 | | | | | | | |
| P18085 | ARF4 | 3 | 27.8 | 7.20E−06 | 1 | 11.1 | 0.0015 | | | | |
| P18206 | VINC | 9 | 9.2 | 2.70E−05 | | | | | | | |
| P19105 | ML12A | 3 | 22.8 | 1.80E−05 | | | | | | | |
| P19623 | SPEE | 3 | 11.3 | 1.40E−05 | | | | | | | |
| P20042 | IF2B | 5 | 16.8 | 2.30E−05 | | | | | | | |
| P20336 | RAB3A | 2 | 11.8 | 9.40E−05 | | | | | | | |
| P20337 | RAB3B | 2 | 11.9 | 9.40E−05 | | | | | | | |
| P20618 | PSB1 | 2 | 13.3 | 1.30E−07 | | | | | | | |
| P20674 | COX5A | 2 | 16 | 8.00E−04 | | | | | | | |
| P21266 | GSTM3 | 3 | 19.6 | 5.10E−05 | | | | | | | |
| P22061 | PIMT | 4 | 21.1 | 1.80E−07 | | | | | | | |
| P22102 | PUR2 | 8 | 9.2 | 2.20E−06 | | | | | | | |
| P22695 | QCR2 | 4 | 8.8 | 1.20E−05 | | | | | | | |
| P23368 | MAOM | 3 | 6.8 | 1.20E−04 | | | | | | | |
| P23921 | RIR1 | 3 | 5.9 | 0.0023 | | | | | | | |
| P24666 | PPAC | 2 | 15.2 | 4.10E−05 | | | | | | | |
| P24752 | THIL | 4 | 12.9 | 5.50E−06 | | | | | | | |
| P25205 | MCM3 | 11 | 15.3 | 1.60E−05 | | | | | | | |
| P25786 | PSA1 | 4 | 18.3 | 3.20E−06 | | | | | | | |
| P25787 | PSA2 | 2 | 12 | 4.10E−04 | | | | | | | |
| P25788 | PSA3 | 3 | 12.2 | 7.10E−05 | | | | | | | |
| P26373 | RL13 | 4 | 19.4 | 8.00E−05 | | | | 1 | 5.2 | 0.0012 | |
| P26640 | SYVC | 3 | 3.4 | 3.70E−05 | | | | | | | |
| P27635 | RL10 | 4 | 21.5 | 2.10E−05 | | | | | | | |
| P28070 | PSB4 | 2 | 12.9 | 1.10E−04 | | | | | | | |
| P28072 | PSB6 | 3 | 13 | 3.30E−05 | | | | | | | |
| P28074 | PSB5 | 5 | 16 | 3.00E−05 | | | | | | | |
| P28331 | NDUS1 | 2 | 2.9 | 1.20E−04 | | | | | | | |
| P29401 | TKT | 10 | 23.9 | 4.70E−07 | | | | | | | |
| P30046 | DOPD | 2 | 19.5 | 5.10E−05 | | | | | | | |
| P30085 | KCY | 2 | 13.8 | 2.90E−06 | | | | | | | |
| P30086 | PEBP1 | 3 | 19.3 | 3.20E−06 | | | | | | | |
| P30837 | AL1B1 | 3 | 7 | 1.40E−04 | | | | | | | |
| P31150 | GDIA | 6 | 17.9 | 6.10E−07 | | | | | | | |
| P31153 | METK2 | 3 | 8.9 | 6.60E−06 | | | | | | | |
| P31689 | DNJA1 | 4 | 18.9 | 3.10E−07 | | | | | | | |
| P31942 | HNRH3 | 4 | 15.3 | 2.10E−06 | | | | | | | |
| P33176 | KINH | 4 | 3.9 | 2.00E−04 | | | | | | | |
| P33240 | CSTF2 | 3 | 6.6 | 1.20E−05 | | | | | | | |
| P33316 | DUT | 3 | 14.7 | 1.60E−06 | | | | | | | |
| P33991 | MCM4 | 6 | 8.6 | 7.00E−06 | | | | | | | |
| P33993 | MCM7 | 8 | 13.4 | 4.80E−05 | | | | | | | |
| P34897 | GLYM | 11 | 24 | 1.70E−06 | | | | | | | |
| P35221 | CTNA1 | 3 | 5.7 | 7.60E−04 | | | | | | | |
| P35244 | RFA3 | 2 | 33.1 | 2.70E−05 | | | | | | | |
| P35527 | K1C9 | 1 | 2.2 | 6.80E−04 | | | | 1 | 2.6 | 1.10E−04 | |
| P35908 | K22E | 2 | 4.4 | 1.10E−04 | | | | 1 | 2.2 | 9.90E−06 | |
| P35998 | PRS7 | 2 | 6.5 | 9.80E−06 | | | | | | | |
| P36405 | ARL3 | 2 | 11.5 | 5.20E−04 | | | | | | | |
| P36551 | HEM6 | 3 | 7.7 | 8.00E−05 | | | | | | | |
| P36776 | LONM | 5 | 8.2 | 8.40E−05 | | | | | | | |
| P36957 | ODO2 | 2 | 3.8 | 3.60E−04 | | | | | | | |
| P37108 | SRP14 | 2 | 18.4 | 8.50E−05 | | | | | | | |

TABLE 8-continued

| | | 1) Click Reaction On Protein | | | | | | | | Alkene, |
| | | 1A) Cell Lysate | | | 1B) Cell Fractionation | | | 2) Click Reaction On Peptide 2) Ultrafiltration | | | Sulfenic or |
| Acc# | Gene Name | Num Unique | % Cov | Best Expect Val | Num Unique | % Cov | Best Expect Val | Num Unique | % Cov | Best Expect Val | Thiol Modified peptide |
|---|---|---|---|---|---|---|---|---|---|---|---|
| P38606 | VATA | 3 | 6 | 3.50E−04 | | | | | | | |
| P39656 | OST48 | 3 | 8.1 | 2.10E−05 | | | | | | | |
| P39748 | FEN1 | 2 | 5.8 | 0.002 | | | | | | | |
| P42765 | THIM | 2 | 8.3 | 6.80E−04 | | | | | | | |
| P45974 | UBP5 | 2 | 2.6 | 2.00E−05 | | | | | | | |
| P46060 | RAGP1 | 7 | 14.7 | 1.70E−06 | | | | | | | |
| P46459 | NSF | 2 | 2.7 | 0.0047 | | | | | | | |
| P46977 | STT3A | 2 | 4.3 | 3.20E−06 | | | | | | | |
| P47756 | CAPZB | 3 | 13.4 | 2.10E−06 | | | | | | | |
| P47897 | SYQ | 7 | 10.5 | 1.20E−04 | | | | | | | |
| P48047 | ATPO | 6 | 35.2 | 5.00E−06 | | | | | | | |
| P48444 | COPD | 2 | 4.3 | 7.00E−04 | | | | | | | |
| P48556 | PSMD8 | 2 | 6.6 | 0.0043 | | | | | | | |
| P48735 | IDHP | 5 | 11.7 | 0.0012 | | | | | | | |
| P48739 | PIPNB | 2 | 8.1 | 5.50E−04 | | | | | | | |
| P49321 | NASP | 10 | 17.3 | 1.40E−06 | | | | | | | |
| P49588 | SYAC | 7 | 9.7 | 1.60E−04 | | | | | | | |
| P49721 | PSB2 | 3 | 20.4 | 4.30E−05 | | | | | | | |
| P49736 | MCM2 | 8 | 10.4 | 2.20E−04 | | | | | | | |
| P49755 | TMEDA | 2 | 12.8 | 1.30E−04 | | | | | | | |
| P49916 | DNLI3 | 3 | 3.6 | 0.0062 | | | | | | | |
| P50213 | IDH3A | 4 | 12 | 2.30E−05 | | | | | | | |
| P50395 | GDIB | 11 | 30.1 | 6.10E−07 | | | | | | | |
| P50402 | EMD | 3 | 16.9 | 2.20E−05 | | | | | | | |
| P50570 | DYN2 | 4 | 3.9 | 4.20E−04 | | | | | | | |
| P51114 | FXR1 | 2 | 5 | 1.40E−07 | | | | | | | |
| P51149 | RAB7A | 8 | 50.2 | 1.00E−05 | | | | | | | |
| P51649 | SSDH | 2 | 3.7 | 0.0014 | | | | | | | |
| P52292 | IMA2 | 6 | 14.9 | 4.10E−06 | | | | | | | |
| P52565 | GDIR1 | 5 | 21.1 | 2.30E−07 | | | | | | | |
| P54105 | ICLN | 2 | 16 | 1.40E−04 | | | | | | | |
| P54577 | SYYC | 8 | 14.8 | 2.50E−04 | | | | | | | |
| P54727 | RD23B | 2 | 4.2 | 0.0044 | | | | | | | |
| P54819 | KAD2 | 8 | 34.3 | 5.60E−05 | | | | | | | |
| P54886 | P5CS | 7 | 10.8 | 2.00E−08 | | | | | | | |
| P55010 | IF5 | 2 | 4.4 | 0.0048 | | | | | | | |
| P55265 | DSRAD | 2 | 2.1 | 3.80E−04 | | | | | | | |
| P55884 | EIF3B | 11 | 15.4 | 6.60E−06 | | | | | | | |
| P56134 | ATPK | 2 | 25.5 | 1.70E−07 | | | | | | | |
| P56192 | SYMC | 3 | 4.1 | 2.40E−07 | | | | | | | |
| P60174 | TPIS | 13 | 57 | 1.20E−08 | | | | 5 | 22 | 5.00E−04 | |
| P60228 | EIF3E | 10 | 26.5 | 4.90E−06 | | | | | | | |
| P60660 | MYL6 | 5 | 38.4 | 5.20E−06 | | | | | | | |
| P61158 | ARP3 | 2 | 5.5 | 5.70E−06 | | | | | | | |
| P61160 | ARP2 | 3 | 9.6 | 9.90E−04 | | | | | | | |
| P61204 | ARF3 | 7 | 47.5 | 8.30E−07 | 1 | 11 | 0.0015 | | | | |
| P61513 | RL37A | 2 | 28.3 | 1.70E−07 | | | | | | | |
| P61619 | S61A1 | 2 | 4.6 | 3.50E−04 | | | | | | | |
| P61758 | PFD3 | 3 | 19.3 | 2.30E−04 | | | | | | | |
| P62195 | PRS8 | 4 | 14 | 3.60E−04 | | | | | | | |
| P62241 | RS8 | 8 | 47.1 | 4.60E−07 | | | | | | | |
| P62258 | 1433E | 16 | 63.5 | 1.30E−08 | | | | 1 | 11.4 | 0.0016 | |
| P62263 | RS14 | 4 | 24.5 | 1.90E−06 | | | | 1 | 7.3 | 1.20E−05 | |
| P62269 | RS18 | 9 | 38.8 | 9.80E−06 | | | | | | | |
| P62306 | RUXF | 2 | 24.4 | 1.10E−05 | | | | | | | |
| P62491 | RB11A | 4 | 22.2 | 3.70E−05 | | | | | | | |
| P62714 | PP2AB | 3 | 11 | 4.00E−06 | | | | | | | |
| P62873 | GBB1 | 3 | 9.7 | 1.90E−05 | | | | | | | |
| P62891 | RL39 | 2 | 19.6 | 3.60E−04 | | | | | | | |
| P63220 | RS21 | 4 | 42.2 | 3.90E−07 | | | | | | | |
| P63244 | GBLP | 9 | 36.9 | 1.20E−05 | | | | | | | |
| P78344 | IF4G2 | 3 | 3.1 | 8.20E−04 | | | | | | | |
| P84103 | SRSF3 | 6 | 31.7 | 5.40E−06 | | | | | | | |
| P84157 | MXRA7 | 2 | 14.2 | 1.20E−05 | | | | | | | |
| P98179 | RBM3 | 3 | 27.4 | 2.60E−04 | | | | | | | |
| Q00325 | MPCP | 5 | 10.8 | 2.90E−06 | | | | | | | |
| Q00526 | CDK3 | 3 | 10.2 | 1.30E−04 | | | | | | | |
| Q00535 | CDK5 | 2 | 6.5 | 0.0025 | | | | | | | |
| Q01081 | U2AF1 | 2 | 10.8 | 8.30E−04 | | | | | | | |
| Q01085 | TIAR | 3 | 9.1 | 1.20E−04 | | | | | | | |
| Q01130 | SRSF2 | 4 | 22.6 | 1.30E−07 | | | | | | | |

TABLE 8-continued

| | | 1) Click Reaction On Protein | | | | | | | | Alkene, |
|---|---|---|---|---|---|---|---|---|---|---|
| | | 1A) Cell Lysate | | | 1B) Cell Fractionation | | | 2) Click Reaction On Peptide 2) Ultrafiltration | | Sulfenic or |
| Acc# | Gene Name | Num Unique | % Cov | Best Expect Val | Num Unique | % Cov | Best Expect Val | Num Unique | % Cov | Best Expect Val | Thiol Modified peptide |
| Q01844 | EWS | 2 | 3.5 | 1.80E−04 | | | | | | | |
| Q02543 | RL18A | 4 | 18.2 | 3.40E−07 | | | | | | | |
| Q02809 | PLOD1 | 3 | 5.9 | 0.0024 | | | | | | | |
| Q02978 | M2OM | 6 | 22.6 | 9.30E−06 | | | | | | | |
| Q04837 | SSBP | 5 | 38.5 | 9.80E−07 | 2 | 15.5 | 1.00E−03 | | | | |
| Q06323 | PSME1 | 2 | 8.4 | 9.00E−04 | | | | | | | |
| Q07020 | RL18 | 6 | 31.4 | 3.90E−07 | | | | | | | |
| Q08752 | PPID | 2 | 4.9 | 0.0011 | | | | | | | |
| Q09028 | RBBP4 | 6 | 13.9 | 5.40E−07 | | | | | | | |
| Q10471 | GALT2 | 2 | 3.7 | 0.0014 | | | | | | | |
| Q10713 | MPPA | 2 | 5.3 | 0.0016 | | | | | | | |
| Q12874 | SF3A3 | 4 | 9.6 | 6.60E−05 | | | | | | | |
| Q12904 | AIMP1 | 2 | 7.7 | 0.0049 | | | | | | | |
| Q12907 | LMAN2 | 2 | 8.4 | 4.80E−05 | | | | | | | |
| Q13011 | ECH1 | 2 | 4.9 | 0.003 | | | | | | | |
| Q13242 | SRSF9 | 3 | 14 | 5.70E−05 | | | | | | | |
| Q13347 | EIF3I | 7 | 22.2 | 3.10E−07 | | | | | | | |
| Q13509 | TBB3 | 20 | 32.9 | 8.10E−08 | | | | | | | |
| Q13616 | CUL1 | 2 | 2.4 | 5.80E−04 | | | | | | | |
| Q13620 | CUL4B | 3 | 3.2 | 0.0012 | | | | | | | |
| Q13867 | BLMH | 3 | 7 | 6.30E−04 | | | | | | | |
| Q14008 | CKAP5 | 2 | 1.2 | 6.00E−04 | | | | | | | |
| Q14157 | UBP2L | 2 | 1.8 | 1.10E−04 | | | | | | | |
| Q14257 | RCN2 | 2 | 10.1 | 1.20E−05 | | | | | | | |
| Q14444 | CAPR1 | 8 | 12.3 | 1.80E−06 | | | | | | | |
| Q14566 | MCM6 | 5 | 7.6 | 2.90E−06 | | | | | | | |
| Q14669 | TRIPC | 2 | 0.9 | 9.40E−04 | | | | | | | |
| Q14692 | BMS1 | 2 | 1.4 | 1.50E−04 | | | | | | | |
| Q14697 | GANAB | 12 | 15.7 | 2.80E−04 | | | | | | | |
| Q14839 | CHD4 | 5 | 3.2 | 2.00E−04 | | | | | | | |
| Q14974 | IMB1 | 13 | 18.2 | 1.10E−07 | | | | | | | |
| Q15008 | PSMD6 | 5 | 15.2 | 4.00E−05 | | | | | | | |
| Q15021 | CND1 | 2 | 1.2 | 6.40E−04 | | | | | | | |
| Q15126 | PMVK | 2 | 10.9 | 5.80E−04 | | | | | | | |
| Q15269 | PWP2 | 2 | 2.7 | 0.0028 | | | | | | | |
| Q15363 | TMED2 | 2 | 10.9 | 3.00E−04 | | | | | | | |
| Q15427 | SF3B4 | 2 | 7.3 | 1.30E−05 | | | | | | | |
| Q15637 | SF01 | 2 | 5.8 | 5.30E−04 | | | | | | | |
| Q15691 | MARE1 | 3 | 14.2 | 3.00E−06 | | | | | | | |
| Q15717 | ELAV1 | 9 | 28.2 | 4.00E−07 | | | | | | | |
| Q15758 | AAAT | 2 | 4.4 | 1.30E−04 | | | | | | | |
| Q16555 | DPYL2 | 2 | 2.4 | 0.0024 | | | | | | | |
| Q16576 | RBBP7 | 6 | 13.6 | 5.40E−07 | | | | | | | |
| Q16629 | SRSF7 | 4 | 17.6 | 4.20E−05 | | | | | | | |
| Q16630 | CPSF6 | 3 | 8.7 | 2.20E−04 | | | | | | | |
| Q16658 | FSCN1 | 3 | 8.9 | 2.50E−06 | | | | | | | |
| Q16718 | NDUA5 | 3 | 29.3 | 4.00E−05 | | | | | | | |
| Q16836 | HCDH | 3 | 13.7 | 1.50E−05 | | | | | | | |
| Q16850 | CP51A | 2 | 4.8 | 6.70E−06 | | | | | | | |
| Q3ZCM7 | TBB8 | 13 | 25.7 | 2.10E−07 | | | | 1 | 3.2 | 0.0037 | |
| Q3ZCQ8 | TIM50 | 2 | 7.6 | 7.20E−05 | | | | | | | |
| Q49A53 | ARF1L | 2 | 33.3 | 0.0065 | | | | | | | |
| Q53EL6 | PDCD4 | 2 | 3.8 | 2.70E−04 | | | | | | | |
| Q58FF6 | H90B4 | 6 | 10.1 | 1.70E−05 | | | | | | | |
| Q66LE6 | 2ABD | 2 | 5.7 | 5.70E−04 | | | | | | | |
| Q6EEV6 | SUMO4 | 2 | 23.2 | 4.70E−06 | | | | | | | |
| Q6NVY1 | HIBCH | 2 | 5.7 | 0.0027 | | | | | | | |
| Q6PI48 | SYDM | 2 | 3.3 | 1.80E−04 | | | | | | | |
| Q71UM5 | RS27L | 3 | 26.2 | 3.60E−05 | | | | | | | |
| Q7KZ85 | SPT6H | 2 | 1 | 1.70E−04 | | | | | | | |
| Q7L014 | DDX46 | 2 | 2 | 2.10E−04 | | | | | | | |
| Q7L2H7 | EIF3M | 3 | 11 | 5.50E−04 | | | | | | | |
| Q86V81 | THOC4 | 3 | 22.2 | 8.20E−06 | | | | | | | |
| Q8N983 | RM43 | 2 | 10.2 | 0.0024 | | | | | | | |
| Q8NBS9 | TXND5 | 2 | 4.4 | 3.10E−04 | | | | | | | |
| Q8NCW5 | NNRE | 3 | 13.5 | 5.00E−06 | | | | | | | |
| Q8TCS8 | PNPT1 | 2 | 3.6 | 1.90E−04 | | | | | | | |
| Q8TEX9 | IPO4 | 2 | 1.9 | 8.50E−05 | | | | | | | |
| Q8WUA2 | PPIL4 | 2 | 5.5 | 3.50E−04 | | | | | | | |
| Q8WUM4 | PDC6I | 6 | 8.9 | 8.70E−05 | | | | | | | |
| Q8WXF1 | PSPC1 | 4 | 9.4 | 3.50E−05 | | | | | | | |

TABLE 8-continued

| | | 1) Click Reaction On Protein | | | | | | | | Alkene, |
| | | 1A) Cell Lysate | | | 1B) Cell Fractionation | | | 2) Click Reaction On Peptide 2) Ultrafiltration | | | Sulfenic or |
| Acc# | Gene Name | Num Unique | % Cov | Best Expect Val | Num Unique | % Cov | Best Expect Val | Num Unique | % Cov | Best Expect Val | Thiol Modified peptide |
|---|---|---|---|---|---|---|---|---|---|---|---|
| Q8WYA6 | CTBL1 | 2 | 3 | 1.50E−04 | | | | | | | |
| Q92769 | HDAC2 | 2 | 5.9 | 1.30E−07 | | | | | | | |
| Q92783 | STAM1 | 2 | 5.9 | 9.20E−05 | | | | | | | |
| Q92900 | RENT1 | 4 | 4.5 | 4.90E−06 | | | | | | | |
| Q92905 | CSN5 | 7 | 25.4 | 2.70E−06 | | | | | | | |
| Q92973 | TNPO1 | 3 | 3.6 | 2.20E−04 | | | | | | | |
| Q96AY3 | FKB10 | 2 | 4.1 | 6.40E−04 | 1 | 4.5 | 9.10E−04 | | | | |
| Q96CX2 | KCD12 | 4 | 14.2 | 4.80E−06 | | | | | | | |
| Q96DV4 | RM38 | 2 | 4.2 | 8.60E−04 | | | | | | | |
| Q96E17 | RAB3C | 2 | 11.5 | 9.40E−05 | | | | | | | |
| Q96EP5 | DAZP1 | 2 | 7.6 | 8.20E−07 | | | | | | | |
| Q96ER9 | CCD51 | 2 | 6.1 | 0.0014 | | | | | | | |
| Q96IX5 | USMG5 | 2 | 44.8 | 5.20E−05 | | | | | | | |
| Q96T88 | UHRF1 | 2 | 2.3 | 0.0016 | | | | | | | |
| Q99436 | PSB7 | 2 | 10.5 | 8.30E−04 | | | | | | | |
| Q99536 | VAT1 | 4 | 14.8 | 4.10E−05 | | | | | | | |
| Q99613 | EIF3C | 4 | 5 | 6.10E−06 | | | | | | | |
| Q99614 | TTC1 | 3 | 13.4 | 5.00E−05 | | | | | | | |
| Q99714 | HCD2 | 3 | 17.6 | 4.10E−05 | | | | | | | |
| Q99733 | NP1L4 | 4 | 13.1 | 8.90E−06 | | | | | | | |
| Q99867 | TBB4Q | 8 | 17.5 | 2.10E−07 | | | | | | | |
| Q99878 | H2A1J | 20 | 80.5 | 2.90E−09 | 8 | 46.1 | 1.20E−07 | 10 | 48.4 | 2.00E−07 | |
| Q9BQ67 | GRWD1 | 2 | 5.6 | 2.00E−05 | | | | | | | |
| Q9BSJ8 | ESYT1 | 3 | 3.3 | 3.90E−05 | | | | | | | |
| Q9BUF5 | TBB6 | 13 | 19.1 | 5.00E−07 | | | | 1 | 3.1 | 0.0037 | |
| Q9BV20 | MTNA | 2 | 13 | 1.90E−04 | | | | | | | |
| Q9BVP2 | GNL3 | 2 | 4.7 | 8.30E−04 | | | | | | | |
| Q9GZS3 | WDR61 | 2 | 11.8 | 3.60E−06 | | | | | | | |
| Q9GZZ1 | NAA50 | 2 | 11.2 | 5.20E−06 | | | | | | | |
| Q9H0D6 | XRN2 | 2 | 2.7 | 0.0044 | | | | | | | |
| Q9H0L4 | CSTFT | 3 | 6.2 | 4.60E−06 | | | | | | | |
| Q9H0S4 | DDX47 | 2 | 4.8 | 3.40E−04 | | | | | | | |
| Q9H0U4 | RAB1B | 4 | 23.9 | 9.40E−05 | | | | | | | |
| Q9H3N1 | TMX1 | 2 | 7.5 | 3.40E−04 | | | | | | | |
| Q9H3U1 | UN45A | 2 | 2.9 | 0.0017 | | | | | | | |
| Q9H857 | NT5D2 | 2 | 4 | 8.80E−05 | | | | | | | |
| Q9H9B4 | SFXN1 | 3 | 8.4 | 8.60E−05 | | | | | | | |
| Q9HAV7 | GRPE1 | 3 | 14.3 | 5.70E−04 | | | | | | | |
| Q9HC38 | GLOD4 | 3 | 11.2 | 1.20E−04 | | | | | | | |
| Q9NRG9 | AAAS | 3 | 7.7 | 7.60E−06 | | | | | | | |
| Q9NRX2 | RM17 | 2 | 9.7 | 0.0054 | | | | | | | |
| Q9NSD9 | SYFB | 6 | 10.9 | 2.00E−04 | | | | | | | |
| Q9NSE4 | SYIM | 2 | 2.1 | 5.10E−04 | | | | | | | |
| Q9NTJ5 | SAC1 | 3 | 5.8 | 3.50E−04 | | | | | | | |
| Q9NTZ6 | RBM12 | 2 | 1.7 | 9.10E−04 | | | | | | | |
| Q9NUU7 | DD19A | 2 | 4.6 | 4.40E−04 | | | | | | | |
| Q9NY12 | GAR1 | 2 | 10.1 | 5.60E−04 | | | | | | | |
| Q9NZL9 | MAT2B | 2 | 6.6 | 9.60E−07 | | | | | | | |
| Q9P0M6 | H2AW | 2 | 6.2 | 0.0026 | | | | | | | |
| Q9UBB4 | ATX10 | 2 | 5.7 | 3.50E−04 | | | | | | | |
| Q9UBT2 | SAE2 | 2 | 3.1 | 1.60E−04 | | | | | | | |
| Q9UBX3 | DIC | 2 | 6.6 | 5.00E−05 | | | | | | | |
| Q9UG63 | ABCF2 | 3 | 5.3 | 0.0029 | | | | | | | |
| Q9UHD8 | SEPT9 | 2 | 4.8 | 0.0025 | | | | | | | |
| Q9UHV9 | PFD2 | 3 | 22.7 | 1.90E−05 | | | | | | | |
| Q9UHX1 | PUF60 | 2 | 4.5 | 5.00E−04 | | | | | | | |
| Q9UIG0 | BAZ1B | 2 | 1.5 | 6.80E−04 | | | | | | | |
| Q9UJZ1 | STML2 | 3 | 11.8 | 2.40E−04 | | | | | | | |
| Q9UKD2 | MRT4 | 3 | 11.7 | 0.0058 | | | | | | | |
| Q9UKK9 | NUDT5 | 2 | 12.8 | 0.0011 | | | | | | | |
| Q9UKV3 | ACINU | 2 | 1.6 | 6.50E−04 | | | | | | | |
| Q9UN86 | G3BP2 | 2 | 5.4 | 1.90E−06 | | | | | | | |
| Q9Y224 | CN166 | 4 | 24.2 | 6.20E−06 | | | | | | | |
| Q9Y230 | RUVB2 | 13 | 32.6 | 9.50E−07 | | | | | | | |
| Q9Y295 | DRG1 | 3 | 9.5 | 9.90E−04 | | | | | | | |
| Q9Y2B0 | CNPY2 | 2 | 17.6 | 5.30E−04 | | | | | | | |
| Q9Y3D9 | RT23 | 3 | 15.8 | 2.00E−05 | | | | | | | |
| Q9Y5L4 | TIM13 | 2 | 25.3 | 8.60E−06 | | | | | | | |
| Q9Y5S9 | RBM8A | 2 | 10.9 | 4.80E−06 | | | | | | | |
| Q9Y678 | COPG1 | 2 | 3.3 | 1.30E−04 | | | | | | | |
| Q9Y6C9 | MTCH2 | 2 | 5.6 | 0.0019 | | | | | | | |

TABLE 8-continued

| | | 1) Click Reaction On Protein | | | | | | 2) Click Reaction On Peptide | | | Alkene, Sulfenic or Thiol Modified peptide |
| --- | --- | --- | --- | --- | --- | --- | --- | --- | --- | --- | --- |
| | | 1A) Cell Lysate | | | 1B) Cell Fractionation | | | 2) Ultrafiltration | | | |
| Acc# | Gene Name | Num Unique | % Cov | Best Expect Val | Num Unique | % Cov | Best Expect Val | Num Unique | % Cov | Best Expect Val | |
| Q9Y6M1 | IF2B2 | 2 | 4.5 | 9.10E−06 | | | | | | | |

TABLE 9

| Category | GO_ID | GO_Description | Count | % | PValue | Fold Enrichment | FDR |
| --- | --- | --- | --- | --- | --- | --- | --- |
| GOTERM_BP_FAT | GO: 0022402 | cell cycle process | 47 | 8.1174439 | 3.53E−06 | 2.0762695 | 0.0061068 |
| | GO: 0045454 | cell redox homeostasis | 15 | 2.5906736 | 1.39E−07 | 5.9427166 | 2.40E−04 |
| | GO: 0034622 | cellular macromolecular complex assembly | 69 | 11.917098 | 3.88E−31 | 5.4157209 | 6.71E−28 |
| | GO: 0034621 | cellular macromolecular complex subunit organization | 73 | 12.607945 | 3.17E−31 | 5.1037448 | 5.48E−28 |
| | GO: 0043623 | cellular protein complex assembly | 24 | 4.1450777 | 1.21E−07 | 3.6976903 | 2.09E−04 |
| | GO: 0031497 | chromatin assembly | 36 | 6.2176166 | 1.37E−26 | 10.328032 | 2.38E−23 |
| | GO: 0006333 | chromatin assembly or disassembly | 41 | 7.0811744 | 1.86E−25 | 8.0577622 | 3.22E−22 |
| | GO: 0006325 | chromatin organization | 49 | 8.462867 | 9.82E−13 | 3.235479 | 1.70E−09 |
| | GO: 0051276 | chromosome organization | 62 | 10.708117 | 9.68E−16 | 3.1906874 | 1.73E−12 |
| | GO: 0006259 | DNA metabolic process | 45 | 7.7720207 | 1.03E−06 | 2.2197103 | 0.0017757 |
| | GO: 0006323 | DNA packaging | 39 | 6.7357513 | 8.72E−25 | 8.3198032 | 1.51E−21 |
| | GO: 0051236 | establishment of RNA localization | 17 | 2.9360967 | 1.35E−06 | 4.3743295 | 0.0023393 |
| | GO: 0006091 | generation of precursor metabolites and energy | 32 | 5.5267703 | 3.10E−06 | 2.5517607 | 0.0053624 |
| | GO: 0006007 | glucose catabolic process | 14 | 2.417962 | 3.50E−07 | 6.0246851 | 6.06E−04 |
| | GO: 0006096 | glycolysis | 12 | 2.0725389 | 1.78E−06 | 6.3726152 | 0.0030752 |
| | GO: 0019320 | hexose catabolic process | 14 | 2.417962 | 2.86E−06 | 5.064228 | 0.0049557 |
| | GO: 0006886 | intracellular protein transport | 36 | 6.2176166 | 2.64E−06 | 2.40251 | 0.0045756 |
| | GO: 0046907 | intracellular transport | 60 | 10.362694 | 3.97E−09 | 2.2793981 | 6.86E−06 |
| | GO: 0065003 | macromolecular complex assembly | 81 | 13.989637 | 2.21E−19 | 3.0401687 | 3.82E−16 |
| | GO: 0043933 | macromolecular complex subunit organization | 85 | 14.680484 | 7.15E−20 | 2.9880983 | 1.24E−16 |
| | GO: 0046365 | monosaccharide catabolic process | 14 | 2.417962 | 4.00E−06 | 4.9215737 | 0.0069237 |
| | GO: 0016071 | mRNA metabolic process | 63 | 10.880829 | 1.90E−22 | 4.2498454 | 3.28E−19 |
| | GO: 0006397 | mRNA processing | 58 | 10.017271 | 5.78E−22 | 4.5097999 | 1.00E−18 |
| | GO: 0034660 | ncRNA metabolic process | 33 | 5.6994819 | 6.77E−10 | 3.5811327 | 1.17E−06 |
| | GO: 0034470 | ncRNA processing | 25 | 4.3177893 | 4.39E−07 | 3.3368195 | 7.60E−04 |
| | GO: 0032269 | negative regulation of cellular protein metabolic process | 23 | 3.9723661 | 3.02E−06 | 3.1892579 | 0.0052313 |
| | GO: 0051248 | negative regulation of protein metabolic process | 24 | 4.1450777 | 1.62E−06 | 3.2033467 | 0.0028 |
| | GO: 0000398 | nuclear mRNA splicing, via spliceosome | 39 | 6.7357513 | 3.40E−20 | 6.3622024 | 5.88E−17 |
| | GO: 0051169 | nuclear transport | 24 | 4.1450777 | 7.55E−08 | 3.7913027 | 1.31E−04 |
| | GO: 0050657 | nucleic acid transport | 17 | 2.9360967 | 1.35E−06 | 4.3743295 | 0.0023393 |
| | GO: 0015931 | nucleobase, nucleoside, nucleotide and nucleic acid transport | 19 | 3.2815199 | 5.08E−07 | 4.1967149 | 8.80E−04 |
| | GO: 0006913 | nucleocytoplasmic transport | 24 | 4.1450777 | 5.94E−08 | 3.8399092 | 1.03E−04 |
| | GO: 0006334 | nucleosome assembly | 36 | 6.2176166 | 3.21E−27 | 10.69689 | 5.56E−24 |
| | GO: 0034728 | nucleosome organization | 37 | 6.3903282 | 1.30E−26 | 9.9300877 | 2.24E−23 |
| | GO: 0051351 | positive regulation of ligase activity | 14 | 2.417962 | 5.52E−06 | 4.7867361 | 0.0095539 |
| | GO: 0051443 | positive regulation of ubiquitin-protein ligase activity | 14 | 2.417962 | 3.39E−06 | 4.9918819 | 0.005867 |
| | GO: 0010608 | posttranscriptional regulation of gene expression | 33 | 5.6994819 | 7.06E−11 | 3.9036043 | 1.22E−07 |
| | GO: 0006457 | protein folding | 31 | 5.3540587 | 1.63E−11 | 4.371422 | 2.83E−08 |
| | GO: 0051258 | protein polymerization | 12 | 2.0725389 | 2.76E−06 | 6.1125085 | 0.0047839 |
| | GO: 0065004 | protein-DNA complex assembly | 36 | 6.2176166 | 8.57E−26 | 9.8740521 | 1.48E−22 |
| | GO: 0006417 | regulation of translation | 20 | 3.4542314 | 2.17E−06 | 3.6437094 | 0.0037532 |
| | GO: 0006986 | response to unfolded protein | 14 | 2.417962 | 4.00E−06 | 4.9215737 | 0.0069237 |
| | GO: 0022613 | ribonucleoprotein complex biogenesis | 35 | 6.044905 | 2.65E−14 | 4.8532185 | 4.59E−11 |
| | GO: 0042273 | ribosomal large subunit biogenesis | 8 | 1.3816926 | 1.70E−08 | 19.967528 | 2.94E−05 |
| | GO: 0042274 | ribosomal small subunit biogenesis | 8 | 1.3816926 | 4.52E−08 | 18.152298 | 7.82E−05 |
| | GO: 0042254 | ribosome biogenesis | 28 | 4.835924 | 2.38E−13 | 5.7283891 | 4.12E−10 |
| | GO: 0006403 | RNA localization | 18 | 3.1088083 | 4.06E−07 | 4.4926937 | 7.03E−04 |
| | GO: 0006396 | RNA processing | 90 | 15.544041 | 4.13E−31 | 4.106667 | 7.15E−28 |
| | GO: 0008380 | RNA splicing | 58 | 10.017271 | 1.02E−24 | 5.0973442 | 1.76E−21 |
| | GO: 0000375 | RNA splicing, via transesterification reactions | 39 | 6.7357513 | 3.40E−20 | 6.3622024 | 5.88E−17 |
| | GO: 0000377 | RNA splicing, via transesterification reactions with bulged adenosine as nucleophile | 39 | 6.7357513 | 3.40E−20 | 6.3622024 | 5.88E−17 |
| | GO: 0050658 | RNA transport | 17 | 2.9360967 | 1.35E−06 | 4.3743295 | 0.0023393 |
| | GO: 0016072 | rRNA metabolic process | 22 | 3.7996546 | 1.42E−10 | 5.7198647 | 2.45E−07 |

TABLE 9-continued

| Category | GO_ID | GO_Description | Count | % | PValue | Fold Enrichment | FDR |
|---|---|---|---|---|---|---|---|
| | GO: 0006364 | rRNA processing | 22 | 3.7996546 | 6.03E−11 | 5.9685545 | 1.04E−07 |
| | GO: 0006412 | translation | 96 | 16.580311 | 7.62E−56 | 7.2389828 | 1.32E−52 |
| | GO: 0006414 | translational elongation | 66 | 11.398964 | 2.39E−66 | 16.310109 | 4.13E−63 |
| GOTERM_CC_FAT | GO: 0005832 | chaperonin-containing T-complex | 6 | 1.0362694 | 2.03E−06 | 21.273786 | 0.0028758 |
| | GO: 0000785 | chromatin | 42 | 7.253886 | 2.34E−18 | 5.2120777 | 3.32E−15 |
| | GO: 0044427 | chromosomal part | 56 | 9.671848 | 1.10E−16 | 3.6007445 | 1.55E−13 |
| | GO: 0005694 | chromosome | 66 | 11.398964 | 2.26E−19 | 3.5610469 | 3.20E−16 |
| | GO: 0005829 | cytosol | 188 | 32.469775 | 1.16E−58 | 3.5083086 | 1.65E−55 |
| | GO: 0022625 | cytosolic large ribosomal subunit | 27 | 4.6632124 | 4.73E−28 | 17.634849 | 6.71E−25 |
| | GO: 0044445 | cytosolic part | 61 | 10.535406 | 2.58E−44 | 9.9604241 | 3.66E−41 |
| | GO: 0022626 | cytosolic ribosome | 49 | 8.462867 | 1.82E−46 | 15.014216 | 2.58E−43 |
| | GO: 0022627 | cytosolic small ribosomal subunit | 22 | 3.7996546 | 2.05E−19 | 13.65068 | 2.91E−16 |
| | GO: 0031975 | envelope | 57 | 9.8445596 | 1.06E−08 | 2.2744482 | 1.51E−05 |
| | GO: 0030530 | heterogeneous nuclear ribonucleoprotein complex | 15 | 2.5906736 | 1.47E−17 | 21.899486 | 2.09E−14 |
| | GO: 0043232 | intracellular non-membrane-bounded organelle | 263 | 45.423143 | 1.84E−56 | 2.5144479 | 2.61E−53 |
| | GO: 0070013 | intracellular organelle lumen | 188 | 32.469775 | 3.06E−39 | 2.6228502 | 4.34E−36 |
| | GO: 0015934 | large ribosomal subunit | 31 | 5.3540587 | 1.41E−24 | 11.483611 | 2.00E−21 |
| | GO: 0042470 | melanosome | 30 | 5.1813472 | 3.38E−19 | 8.3660958 | 4.80E−16 |
| | GO: 0031974 | membrane-enclosed lumen | 189 | 32.642487 | 3.47E−37 | 2.5274084 | 4.93E−34 |
| | GO: 0031980 | mitochondrial lumen | 28 | 4.835924 | 4.33E−07 | 3.0614259 | 6.15E−04 |
| | GO: 0005759 | mitochondrial matrix | 28 | 4.835924 | 4.33E−07 | 3.0614259 | 6.15E−04 |
| | GO: 0042645 | mitochondrial nucleoid | 10 | 1.7271157 | 2.34E−06 | 8.0062637 | 0.0033233 |
| | GO: 0044429 | mitochondrial part | 49 | 8.462867 | 3.12E−06 | 2.043952 | 0.0044341 |
| | GO: 0005739 | mitochondrion | 76 | 13.126079 | 2.19E−06 | 1.7353043 | 0.0031087 |
| | GO: 0043228 | non-membrane-bounded organelle | 263 | 45.423143 | 1.84E−56 | 2.5144479 | 2.61E−53 |
| | GO: 0031981 | nuclear lumen | 145 | 25.043178 | 1.71E−26 | 2.4819417 | 2.42E−23 |
| | GO: 0009295 | nucleoid | 10 | 1.7271157 | 2.34E−06 | 8.0062637 | 0.0033233 |
| | GO: 0005730 | nucleolus | 87 | 15.025907 | 1.96E−21 | 3.0935377 | 2.79E−18 |
| | GO: 0005654 | nucleoplasm | 76 | 13.126079 | 3.57E−10 | 2.1386346 | 5.06E−07 |
| | GO: 0000786 | nucleosome | 31 | 5.3540587 | 1.41E−25 | 12.212729 | 2.01E−22 |
| | GO: 0031967 | organelle envelope | 57 | 9.8445596 | 9.57E−09 | 2.2817852 | 1.36E−05 |
| | GO: 0019866 | organelle inner membrane | 34 | 5.8721934 | 1.23E−06 | 2.5649246 | 0.0017425 |
| | GO: 0043233 | organelle lumen | 188 | 32.469775 | 7.95E−38 | 2.563764 | 1.13E−34 |
| | GO: 0048770 | pigment granule | 30 | 5.1813472 | 3.38E−19 | 8.3660958 | 4.80E−16 |
| | GO: 0000502 | proteasome complex | 13 | 2.2452504 | 4.53E−06 | 5.2893841 | 0.0064322 |
| | GO: 0032993 | protein-DNA complex | 34 | 5.8721934 | 2.71E−24 | 9.8123278 | 3.85E−21 |
| | GO: 0030529 | ribonucleoprotein complex | 136 | 23.488774 | 4.52E−75 | 6.5542539 | 6.41E−72 |
| | GO: 0033279 | ribosomal subunit | 53 | 9.1537133 | 3.11E−39 | 10.27679 | 4.41E−36 |
| | GO: 0005840 | ribosome | 66 | 11.398964 | 1.43E−39 | 7.618984 | 2.03E−36 |
| | GO: 0015935 | small ribosomal subunit | 23 | 3.9723661 | 1.45E−15 | 9.0610572 | 2.05E−12 |
| | GO: 0005681 | spliceosome | 35 | 6.044905 | 1.11E−18 | 6.5809061 | 1.58E−15 |

TABLE 10

| Exp | Intra-subunit Inter-subunit | MS1 m/z | MS1 z | P1 m/z | P1 z | P1 ppm | P1 score | P1 ev | P1 Accession | P1 Gene Name | P1 Protein Name | P1 Peptide | P1 Modification |
|---|---|---|---|---|---|---|---|---|---|---|---|---|---|
| Frac | O60814, P0C0S5 | 484.9986 | 4 | 511.778 | 2 | -2.9 | 18.8 | 2.00E-03 | O60814 | H2B1K | Histone H2B type 1-K | AVTKYTSAK (SEQ ID NO: 153) | [Alkene@121] |
| Fil, Frac | O60814, P0C0S8 | 603.2783 | 4 | 660.328 | 2 | -2.3 | 31.8 | 1.70E-05 | O60814 | H2B1K | Histone H2B type 1-K | KESYSVVYK (SEQ ID NO: 154) | [Alkene@35] |
| Fil, Frac | O60814, P0C0S8 | 512.2441 | 4 | 446.219 | 2 | -1.3 | 27.1 | 2.80E-03 | P0C0S8 | H2A1 | Histone H2A type 1 | KGNYAER (SEQ ID NO: 155) | [Alkene@37] |
| Fil | O60814, P0C0S8 | 512.2441 | 4 | 446.219 | 2 | -1.3 | 27.1 | 2.80E-03 | P0C0S8 | H2A1 | Histone H2A type 1 | KGNYAER (SEQ ID NO: 155) | [Alkene@37] |
| Frac, Lys | O60814, P0CG48 | 834.6972 | 4 | 909.011 | 2 | -1.1 | 38.8 | 7.50E-08 | O60814 | H2B1K | Histone H2B type 1-K | LLLPGELAKHAVSEGTK (SEQ ID NO: 156) | [Alkene@109] |
| Lys | O60814, P20671 | 434.2124 | 3 | 314.674 | 2 | -0.9 | 18.2 | 1.00E-01 | P20671 | H2A1D | Histone H2A type 1-D | GKQGGK (SEQ ID NO: 157) | [Alkene@6] |
| Lys | O60814, P20671 | 516.2424 | 4 | 454.216 | 2 | -2.3 | 23.9 | 1.20E-03 | P20671 | H2A1D | Histone H2A type 1-D | KGNYSER (SEQ ID NO: 158) | [Alkene@37] |
| Fil | O60814, P62805 | 538.0886 | 5 | 335.697 | 2 | -2.3 | 19.1 | 5.40E-02 | P62805 | H4 | Histone H4 | GGKGLGK (SEQ ID NO: 159) | [Alkene@9] |
| Frac | O60814, P62805 | 504.7589 | 4 | 335.697 | 2 | -2.3 | 19.3 | 2.20E-02 | P62805 | H4 | Histone H4 | GGKGLGK (SEQ ID NO: 159) | [Alkene@9] |
| Frac | O60814, P62805 | 648.7487 | 5 | 612.345 | 2 | 0.2 | 36.5 | 1.80E-05 | P62805 | H4 | Histone H4 | GGKGLGKGGAKR (SEQ ID NO: 160) | [Alkene@9 = 29, Acetyl@13 = 29, Acetyl@17 = 65] |
| Frac | O60814, P62805 | 694.1724 | 5 | 725.910 | 2 | -0.9 | 33.1 | 3.20E-05 | P62805 | H4 | Histone H4 | GKGGKGLGKGGAKR (SEQ ID NO: 161) | [Acetyl@6 = 8, Alkene@9 = 8, Acetyl@13 = 40, Acetyl@17 = 59] |
| Frac | O60814, P62805 | 522.5168 | 4 | 371.216 | 2 | -2.5 | 12.8 | 6.20E-02 | P62805 | H4 | Histone H4 | GLGKGGAK (SEQ ID NO: 162) | [Alkene@13] |
| Frac | O60814, P62805 | 739.6469 | 4 | 470.271 | 2 | -2.5 | 18.3 | 1.20E-01 | P62805 | H4 | Histone H4 | GLGKGGAKR (SEQ ID NO: 163|SEQ ID NO: 206) | [Acetyl@13&Alkene@17|Acetyl@13] |
| Frac | O60814, Q6FI13 | 494.2473 | 4 | 314.674 | 2 | -0.9 | 19.8 | 6.10E-02 | Q6FI13 | H2A2A | Histone H2A type 2-A | GKQGGK (SEQ ID NO: 157) | [Alkene@6] |

TABLE 10-continued

| | | | | | | | | | |
|---|---|---|---|---|---|---|---|---|---|
| Frac | O60814, Q6FI13 | 603.2783 | 4 | 660.328 | 2 | -2.3 | 31.8 | 1.70E-05 | O60814 H2B1K | Histone H2B type 1-K | KESYSVVYK (SEQ ID NO: 154) | [Alkene@35] |
| Frac | O60814, Q6FI13 | 512.2441 | 4 | 446.219 | 2 | -1.3 | 27.1 | 2.80E-03 | Q6FI13 H2A2A | Histone H2A type 2-A | KGNYAER (SEQ ID NO: 155) | [Alkene@37] |
| Frac | O60814, Q6FI13 | 836.4354 | 4 | 909.010 | 2 | -2.2 | 38.8 | 4.70E-08 | O60814 H2B1K | Histone H2B type 1-K | LLLPGELAKHAVSEGTK (SEQ ID NO: 156) | [Alkene@109] |
| Frac | O60814, Q71DI3 | 852.1877 | 4 | 695.353 | 2 | -1.5 | 33.9 | 8.20E-05 | Q71DI3 H32 | Histone H3.2 | EIAQDFKTDLR (SEQ ID NO: 164) | [Alkene@80] |
| Frac | O60814, Q71DI3 | 522.7735 | 4 | 371.725 | 2 | -4.1 | 21.8 | 2.40E-03 | Q71DI3 H32 | Histone H3.2 | KQLATK (SEQ ID NO: 165) | [Alkene@19] |
| Frac | O60814, Q71DI3 | 694.3665 | 4 | 909.008 | 2 | -4.4 | 32.2 | 2.00E-05 | O60814 H2B1K | Histone H2B type 1-K | LLLPGELAKHAVSEGTK (SEQ ID NO: 156) | [Alkene@109] |
| Fil | P06899, P0C0S8 | 512.2441 | 4 | 446.219 | 2 | -1.3 | 27.1 | 2.80E-03 | P0C0S8 H2A1 | Histone H2A type 1 | KGNYAER (SEQ ID NO: 155) | [Alkene@37] |
| Fil | P06899, P0CG48 | 834.6972 | 4 | 909.011 | 2 | -1.1 | 38.8 | 7.50E-08 | P06899 H2B1J | Histone H2B type 1-J | LLLPGELAKHAVSEGTK (SEQ ID NO: 156) | [Alkene@109] |
| Fil | P06899, P62805 | 538.0886 | 5 | 335.697 | 2 | -2.3 | 19.1 | 5.40E-02 | P62805 H4 | Histone H4 | GGKGLGK (SEQ ID NO: 159) | [Alkene@9] |
| Frac | P07197, P08670 | 525.5099 | 4 | 590.310 | 2 | -2.5 | 32.1 | 1.50E-04 | P08670 VIME | Vimentin | FANYIDKVR (SEQ ID NO: 166) | [Alkene@120] |
| Frac | P07197, P08670 | 869.1570 | 4 | 1047.995 | 2 | -0.6 | 48.9 | 1.60E-07 | P08670 VIME | Vimentin | FANYIDKVR (SEQ ID NO: 166) | [Alkene@120] |
| Frac | P07197, P08670 | 745.8425 | 4 | 434.685 | 2 | -2.8 | 12.7 | 1.60E-01 | P08670 VIME | Vimentin | GQGKSR (SEQ ID NO: 167) | [ThioIB@143] |
| Frac | P07197, P08670 | 639.5882 | 4 | 564.797 | 2 | -2.5 | 23.5 | 9.60E-04 | P07197 NFM | Neurofilament medium polypeptide | KLLEGEETR (SEQ ID NO: 168) | [Alkene@403] |
| Frac | P07197, P08670 | 880.8981 | 4 | 1047.992 | 2 | -3.4 | 52.6 | 6.80E-07 | P07197 NFM | Neurofilament medium polypeptide | QKQASHAQLGDAVDQEIR (SEQ ID NO: 169) | [Gln->pyro-Glu@138, ThioIB@139] |
| Frac | P07197, P08670 | 786.1388 | 4 | 650.858 | 2 | -1.5 | 37.9 | 4.60E-04 | P07197 NFM | Neurofilament medium polypeptide | TDISTALKEIR (SEQ ID NO: 170) | [Alkene@271] |
| Frac | P07197, P08670 | 712.3697 | 4 | 614.368 | 2 | -1.6 | 28.2 | 8.20E-04 | P08670 VIME | Vimentin | TLLIKTVETR (SEQ ID NO: 171) | [Alkene@445] |

TABLE 10-continued

| | | | | | | | | | | |
|---|---|---|---|---|---|---|---|---|---|---|
| Frac | P07900, | P14625 | 867.6945 | 4 | 835.457 | 2 | -3.1 | 41.1 | 7.60E-08 P07900 HS90A Heat shock protein HSP 90-alpha | ADLINNLGTIAKSGTK (SEQ ID NO: 172) | [ThiolB@112] |
| Frac | P08670, | P08670 | 785.8627 | 4 | 789.878 | 2 | 3.3 | 11.5 | 1.50E+00 P08670 VIME Vimentin | NLQEAEEWYKSK (SEQ ID NO: 173) | [Alkene@292] |
| Frac | P0C0S5, | Q71D13 | 620.3456 | 6 | 702.378 | 3 | -2.4 | 13.2 | 1.90E+00 P0C0S5 H2AZ Histone H2A.Z | ATIAGGVIPHIHKSLIGK (SEQ ID NO: 197) | [ThiolB@116] |
| Lys | P0C0S8, | P23527 | 606.7844 | 4 | 667.336 | 2 | -2.0 | 25.0 | 1.80E-04 P23527 H2B10 Histone H2B type 1-O | KESYSIVYK (SEQ ID NO: 175) | [Alkene@35] |
| Lys | P0C0S8, | P23527 | 512.2441 | 4 | 446.219 | 2 | -1.3 | 27.1 | 2.80E-03 P0C0S8 H2A1 Histone H2A type 1 | KGNYAER (SEQ ID NO: 155) | [Alkene@37] |
| Lys | P0C0S8, | P23527 | 836.4354 | 4 | 909.010 | 2 | -2.2 | 38.8 | 4.70E-08 P23527 H2B10 Histone H2B type 1-O | LLLPGELAKHAVSEGTK (SEQ ID NO: 156) | [Alkene@109] |
| Lys | P0C0S8, | P58876 | 603.2783 | 4 | 660.328 | 2 | -2.3 | 31.8 | 1.70E-05 P58876 H2B1D Histone H2B type 1-D | KESYSVVYK (SEQ ID NO: 154) | [Alkene@35] |
| Lys | P0C0S8, | P58876 | 512.2441 | 4 | 446.219 | 2 | -1.3 | 27.1 | 2.80E-03 P0C0S8 H2A1 Histone H2A type 1 | KGNYAER (SEQ ID NO: 155) | [Alkene@37] |
| Fil | P0C0S8, | P62807 | 1044.5538 | 4 | 1079.606 | 2 | 3.2 | 16.3 | 2.10E-02 P0C0S8 H2A1 Histone H2A type 1 | HLQLAIRNDEELNKLLGK (SEQ ID NO: 176) | [Alkene@35] |
| Frac | P0C0S8, | P62807 | 603.2783 | 4 | 660.328 | 2 | -2.3 | 31.8 | 1.70E-05 P62807 H2B1C Histone H2B type 1-C/E/F/G/I | KESYSVVYK (SEQ ID NO: 154) | [Alkene@35] |
| Fil, Frac | P0C0S8, | P62807 | 512.2441 | 4 | 446.219 | 2 | -1.3 | 27.1 | 2.80E-03 P0C0S8 H2A1 Histone H2A type 1 | KGNYAER (SEQ ID NO: 155) | [Alkene@37] |
| Fil | P0C0S8, | P62807 | 512.2441 | 4 | 446.219 | 2 | -1.3 | 27.1 | 2.80E-03 P0C0S8 H2A1 Histone H2A type 1 | KGNYAER (SEQ ID NO: 155) | [Alkene@37] |
| Frac | P0C0S8, | P62807 | 836.4354 | 4 | 909.010 | 2 | -2.2 | 38.8 | 4.70E-08 P62807 H2B1C Histone H2B type 1-C/E/F/G/I | LLLPGELAKHAVSEGTK (SEQ ID NO: 156) | [Alkene@109] |
| Fil | P0C0S8, | Q16778 | 1044.5538 | 4 | 1079.606 | 2 | 3.2 | 16.3 | 2.10E-02 P0C0S8 H2A1 Histone H2A type 1 | HLQLAIRNDEELNKLLGK (SEQ ID NO: 176) | [Alkene@35] |
| Fil | P0C0S8, | Q16778 | 606.7844 | 4 | 667.336 | 2 | -2.0 | 25.0 | 1.80E-04 Q16778 H2B2E Histone H2B type 2-E | KESYSIVYK (SEQ ID NO: 175) | [Alkene@35] |
| Fil, Frac | P0C0S8, | Q16778 | 512.2441 | 4 | 446.219 | 2 | -1.3 | 27.1 | 2.80E-03 P0C0S8 H2A1 Histone H2A type 1 | KGNYAER (SEQ ID NO: 155) | [Alkene@37] |
| Frac | P0C0S8, | Q16778 | 836.4354 | 4 | 909.010 | 2 | -2.2 | 38.8 | 4.70E-08 Q16778 H2B2E Histone H2B type 2-E | LLLPGELAKHAVSEGTK (SEQ ID NO: 156) | [Alkene@109] |
| Fil | P0C0S8, | Q71D13 | 645.8282 | 4 | 460.733 | 2 | 0.3 | 13.8 | 1.20E+00 P0C0S8 H2A1 Histone H2A type 1 | KTESHHK (SEQ ID NO: 177) | [Alkene@120] |

TABLE 10-continued

| | | | | | | | | | | | |
|---|---|---|---|---|---|---|---|---|---|---|---|
| Frac | P0C0S8 | Q71DI3 | 606.8022 | 4 | 551.735 | 2 | -2.6 | 10.0 | 5.50E-01 P0C0S8 | Histone H2A type 1 | KTESHHK (SEQ ID NO: 198) | [ThiolB@120] |
| Fil | P0C0S8 | Q71DI3 | 782.2435 | 5 | 532.307 | 3 | -2.1 | 23.1 | 1.40E-02 Q71DI3 H32 | Histone H3.2 | RVTIMPKDIQLAR (SEQ ID NO: 178) | [Alkene@123] |
| Frac | P0C0S8 | Q71DI3 | 938.5287 | 4 | 1057.139 | 2 | -1.7 | 34.8 | 1.40E-06 P0C0S8 H2A1 | Histone H2A type 1 | VTIAQGGVLPNIQAVLLPKK (SEQ ID NO: 179) | [Alkene@119] |
| Lys | P0C0S8 | Q8N257 | 512.2441 | 4 | 446.219 | 2 | -1.3 | 27.1 | 2.80E-03 P0C0S8 H2A1 | Histone H2A type 1 | KGNYAER (SEQ ID NO: 155) | [Alkene@37] |
| Lys | P0C0S8 | Q93079 | 603.2783 | 4 | 660.328 | 2 | -2.3 | 31.8 | 1.70E-05 Q93079 H2B1H | Histone H2B type 1-H | KESYSVVYK (SEQ ID NO: 154) | [Alkene@35] |
| Lys | P0C0S8 | Q93079 | 512.2441 | 4 | 446.219 | 2 | -1.3 | 27.1 | 2.80E-03 P0C0S8 H2A1 | Histone H2A type 1 | KGNYAER (SEQ ID NO: 155) | [Alkene@37] |
| Lys | P0C0S8 | Q93079 | 836.4354 | 4 | 909.010 | 2 | -2.2 | 38.8 | 4.70E-08 Q93079 H2B1H | Histone H2B type 1-H | LLLPGELAKHAVSEGTK (SEQ ID NO: 156) | [Alkene@109] |
| Fil | P0C0S8 | Q99877 | 512.2441 | 4 | 446.219 | 2 | -1.3 | 27.1 | 2.80E-03 P0C0S8 H2A1 | Histone H2A type 1 | KGNYAER (SEQ ID NO: 155) | [Alkene@37] |
| Fil | P0C0S8 | Q99879 | 603.2783 | 4 | 660.328 | 2 | -2.3 | 31.8 | 1.70E-05 Q99879 H2B1M | Histone H2B type 1-M | KESYSVVYK (SEQ ID NO: 154) | [Alkene@35] |
| Fil, Lys | P0C0S8 | Q99879 | 512.2441 | 4 | 446.219 | 2 | -1.3 | 27.1 | 2.80E-03 P0C0S8 H2A1 | Histone H2A type 1 | KGNYAER (SEQ ID NO: 155) | [Alkene@37] |
| Frac | P0C0S8 | P62805 | 523.0272 | 4 | 376.675 | 2 | -0.3 | 12.3 | 9.30E-01 P62805 H4 | Histone H4 | GGVKR (SEQ ID NO: 180) | [ThiolB@45] |
| Frac | P0CG48 | P62807 | 834.6972 | 4 | 909.011 | 2 | -1.1 | 38.8 | 7.50E-08 P62807 H2B1C | Histone H2B type 1-C/E/F/G/I | LLLPGELAKHAVSEGTK (SEQ ID NO: 156) | [Alkene@109] |
| Frac | P0CG48 | Q6FI13 | 557.7816 | 4 | 314.674 | 2 | -0.9 | 12.0 | 8.80E-02 Q6FI13 H2A2A | Histone H2A type 2-A | GKQGGK (SEQ ID NO: 157) | [Alkene@6] |
| Frac | P0CG48 | Q71DI3 | 570.0469 | 4 | 660.372 | 2 | -1.9 | 10.1 | 1.50E+00 P0CG48 UBC | Polyubiquitin-C | MQIFVKTLTGK (SEQ ID NO: 314) | [Alkene@6 = 26] |
| Frac | P0CG48 | Q71DI3 | 706.6240 | 4 | 660.372 | 2 | -1.9 | 28.2 | 4.50E-04 P0CG48 UBC | Polyubiquitin-C | MQIFVKTLTGK (SEQ ID NO: 315) | [Alkene@6 = 34] |
| Frac | P0CG48 | Q71DI3 | 711.3011 | 4 | 759.376 | 2 | 2.3 | 21.8 | 5.90E-02 P0CG48 UBC | Polyubiquitin-C | MQIFVKTLTGK (SEQ ID NO: 316) | [Oxidation@1, ThiolB@6 = 36] |
| Lys | P20671 | O60814 | 836.4354 | 4 | 909.010 | 2 | -2.2 | 38.8 | 4.70E-08 O60814 H2B1K | Histone H2B type 1-K | LLLPGELAKHAVSEGTK (SEQ ID NO: 156) | [Alkene@109] |
| Lys | P20671 | Q71DI3 | 938.5287 | 4 | 1057.139 | 2 | -1.7 | 34.8 | 1.40E-06 P20671 H2A1D | Histone H2A type 1-D | VTIAQGGVLPNIQAVLLPKK (SEQ ID NO: 179) | [Alkene@119] |

TABLE 10-continued

| | | | | | | | | | |
|---|---|---|---|---|---|---|---|---|---|
| Lys | P23527, Q71DI3 | 852.1877 | 4 | 695.353 | 2 | -1.5 | 33.9 | 8.20E-05 Q71DI3 H32 | Histone H3.2 | EIAQDFKTDLR (SEQ ID NO: 164) | [Alkene@80] |
| Lys | P23527, Q93077 | 606.7844 | 4 | 667.336 | 2 | -2.0 | 25.0 | 1.80E-04 P23527 H2B1O | Histone H2B type 1-O | KESYSIVYK (SEQ ID NO: 175) | [Alkene@35] |
| Lys | P23527, Q93077 | 512.2441 | 4 | 446.219 | 2 | -1.3 | 27.1 | 2.80E-03 Q93077 H2A1C | Histone H2A type 1-C | KGNYAER (SEQ ID NO: 155) | [Alkene@37] |
| Lys | P23527, Q93077 | 512.2441 | 4 | 446.219 | 2 | -1.3 | 27.1 | 2.80E-03 Q93077 H2A1C | Histone H2A type 1-C | KGNYAER (SEQ ID NO: 155) | [Alkene@37] |
| Frac | P62805 | 538.0886 | 5 | 335.697 | 2 | -2.3 | 19.1 | 5.40E-02 P62805 H4 | Histone H4 | GGKGLGK (SEQ ID NO: 159) | [Alkene@9] |
| Frac | P62805 | 536.0743 | 5 | 478.260 | 2 | 2.0 | 19.5 | 2.90E-02 P62807 H2B1C | Histone H2B type 1-C/E/F/G/I | LAHYNKR (SEQ ID NO: 181) | [Alkene@86] |
| Frac | P62805, Q6FI13 | 657.5676 | 4 | 446.218 | 2 | -3.6 | 24.6 | 6.20E-04 Q6FI13 H2A2A | Histone H2A type 2-A | KGNYAER (SEQ ID NO: 155) | [ThiolB@37] |
| Fil, Frac, Lys | P62805, Q71DI3 | 734.0969 | 4 | 672.829 | 2 | -2.6 | 32.4 | 6.20E-05 P62805 H4 | Histone H4 | DAVTYTEHAKR (SEQ ID NO: 182) | [Alkene@78] |
| Fil | P62805, Q71DI3 | 766.1234 | 4 | 736.878 | 2 | -0.3 | 21.7 | 1.10E-03 P62805 H4 | Histone H4 | DAVTYTEHAKRK (SEQ ID NO: 183) | [Alkene@78] |
| Frac | P62805, Q71DI3 | 703.8565 | 4 | 695.353 | 2 | -1.5 | 24.6 | 1.10E-02 Q71DI3 H32 | Histone H3.2 | EIAQDFKTDLR (SEQ ID NO: 164) | [Alkene@80] |
| Frac | P62805, Q71DI3 | 760.6363 | 4 | 695.352 | 2 | -3.0 | 30.8 | 3.90E-04 Q71DI3 H32 | Histone H3.2 | EIAQDFKTDLR (SEQ ID NO: 164) | [Alkene@80] |
| Lys | P62805, Q93079 | 864.9775 | 4 | 720.931 | 2 | -1.8 | 23.5 | 1.30E-03 P62805 H4 | Histone H4 | GVLKVFLENVIR (SEQ ID NO: 184) | [Alkene@60] |
| Frac | P62807, Q6FI13 | 494.2473 | 4 | 314.674 | 2 | -0.9 | 19.8 | 6.10E-02 Q6FI13 H2A2A | Histone H2A type 2-A | GKQGGK (SEQ ID NO: 157) | [Alkene@6] |
| Fil, Frac | P62807, Q6FI13 | 603.2783 | 4 | 660.328 | 2 | -2.3 | 31.8 | 1.70E-05 P62807 H2B1C | Histone H2B type 1-C/E/F/G/I | KESYSVVYK (SEQ ID NO: 154) | [Alkene@35] |
| Fil, Frac | P62807, Q6FI13 | 512.2441 | 4 | 446.219 | 2 | -1.3 | 27.1 | 2.80E-03 Q6FI13 H2A2A | Histone H2A type 2-A | KGNYAER (SEQ ID NO: 155) | [Alkene@37] |
| Fil, Frac | P62807, Q6FI13 | 836.4354 | 4 | 909.010 | 2 | -2.2 | 38.8 | 4.70E-08 P62807 H2B1C | Histone H2B type 1-C/E/F/G/I | LLLPGELAKHAVSEGTK (SEQ ID NO: 156) | [Alkene@109] |
| Fil, Frac | P62807, Q71DI3 | 852.1877 | 4 | 695.353 | 2 | -1.5 | 33.9 | 8.20E-05 Q71DI3 H32 | Histone H3.2 | EIAQDFKTDLR (SEQ ID NO: 164) | [Alkene@80] |

TABLE 10-continued

| | | | | | | | | | | |
|---|---|---|---|---|---|---|---|---|---|---|
| Frac | P62807, Q71DI3 | 694.3665 | 4 | 909.008 | 2 | -4.4 | 32.2 | 2.00E-05 | P62807 H2B1C | Histone H2B type 1-C/E/F/G/I | LLLPGELAKHAVSEGTK (SEQ ID NO: 156) | [Alkene@109] |
| Frac | P62807, Q96KK5 | 603.2783 | 4 | 660.328 | 2 | -2.3 | 31.8 | 1.70E-05 | P62807 H2B1C | Histone H2B type 1-C/E/F/G/I | KESYSVVYK (SEQ ID NO: 154) | [Alkene@35] |
| Frac | P62807, Q96KK5 | 512.2441 | 4 | 446.219 | 2 | -1.3 | 27.1 | 2.80E-03 | Q96KK5 H2A1H | Histone H2A type 1-H | KGNYAER (SEQ ID NO: 155) | [Alkene@37] |
| Frac | P62807, Q96KK5 | 836.4354 | 4 | 909.010 | 2 | -2.2 | 38.8 | 4.70E-08 | P62807 H2B1C | Histone H2B type 1-C/E/F/G/I | LLLPGELAKHAVSEGTK (SEQ ID NO: 156) | [Alkene@109] |
| Frac | Q13765, Q15149 | 526.2927 | 4 | 455.788 | 2 | -16.0 | 20.4 | 1.70E-03 | Q13765 NACA | Nascent polypeptide associated complex subunit alpha | AKAVRALK (SEQ ID NO: 185) | [Alkene@194] |
| Frac | Q13765, Q15149 | 526.2927 | 4 | 455.788 | 2 | -16.0 | 20.4 | 1.70E-03 | Q15149 PLEC | Plectin | AKAVRALK (SEQ ID NO: 185) | [Alkene@194] |
| Frac | Q6DN03, Q6FI13 | 606.7844 | 4 | 667.336 | 2 | -2.0 | 25.0 | 1.80E-04 | Q6DN03 H2B2C | Putative histone H2B type 2-C | KESYSIVYK (SEQ ID NO: 175) | [Alkene@35] |
| Frac | Q6FI13, Q71DI3 | 543.6813 | 5 | 460.732 | 2 | -1.9 | 17.5 | 2.00E-02 | Q6FI13 H2A2A | Histone H2A type 2-A | KTESHHK (SEQ ID NO: 177) | [Alkene@120] |
| Frac | Q6FI13, Q71DI3 | 512.4611 | 5 | 460.732 | 2 | -1.9 | 15.4 | 1.10E-01 | Q6FI13 H2A2A | Histone H2A type 2-A | KTESHHK (SEQ ID NO: 177) | [Alkene@120] |
| Frac | Q6FI13, Q71DI3 | 606.8022 | 4 | 551.735 | 2 | -2.6 | 10.0 | 5.50E-01 | Q6FI13 H2A2A | Histone H2A type 2-A | KTESHHK (SEQ ID NO: 198) | [ThiolB@120] |
| Frac | Q6FI13, Q71DI3 | 782.2435 | 4 | 532.307 | 3 | -2.1 | 23.1 | 1.40E-02 | Q71DI3 H32 | Histone H3.2 | RVTIMPKDIQLAR (SEQ ID NO: 178) | [Alkene@123] |
| Frac | Q6FI13, Q71DI3 | 785.4438 | 5 | 537.638 | 3 | -3.2 | 22.7 | 2.10E-02 | Q71DI3 H32 | Histone H3.2 | RVTIMPKDIQLAR (SEQ ID NO: 200) | [Oxidation@121, Alkene@123] |
| Frac | Q6FI13, Q71DI3 | 942.5272 | 4 | 1057.139 | 2 | -1.7 | 35.5 | 1.20E-07 | Q6FI13 H2A2A | Histone H2A type 2-A | VTIAQGGVLPNIQAVLLPKK (SEQ ID NO: 179) | [Alkene@119] |
| Frac | Q6FI13, Q99877 | 619.2982 | 4 | 660.328 | 2 | -2.3 | 30.2 | 3.90E-05 | Q99877 H2B1N | Histone H2B type 1-N | KESYSVVYK (SEQ ID NO: 154) | [Alkene@35] |
| Frac | Q6FI13, Q99880 | 603.2783 | 4 | 660.328 | 2 | -2.3 | 31.8 | 1.70E-05 | Q99880 H2B1L | Histone H2B type 1-L | KESYSVVYK (SEQ ID NO: 154) | [Alkene@35] |
| Frac | Q6FI13, Q99880 | 512.2441 | 4 | 446.219 | 2 | -1.3 | 27.1 | 2.80E-03 | Q6FI13 H2A2A | Histone H2A type 2-A | KGNYAER (SEQ ID NO: 155) | [Alkene@37] |
| Frac | Q6FI13, Q99880 | 836.4354 | 4 | 909.010 | 2 | -2.2 | 38.8 | 4.70E-08 | Q99880 H2B1L | Histone H2B type 1-L | LLLPGELAKHAVSEGTK (SEQ ID NO: 156) | [Alkene@109] |

TABLE 10-continued

| | | | | | | | | | | | | | | |
|---|---|---|---|---|---|---|---|---|---|---|---|---|---|---|
| Lys | Q71DI3, Q93077 | 938.5287 | 4 | 1057.139 | 2 | -1.7 | 34.8 | 1.40E-06 | Q93077 | H2A1C | Histone H2A type 1-C | VTIAQGGVLPNIQAVLLPKK (SEQ ID NO: 179) | [Alkene@119] |
| Lys | Q71DI3, Q93079 | 852.1877 | 4 | 695.353 | 2 | -1.5 | 33.9 | 8.20E-05 | Q71DI3 | H32 | Histone H3.2 | EIAQDFKTDLR (SEQ ID NO: 164) | [Alkene@80] |
| Frac | Q71DI3, Q96KK5 | 938.5287 | 4 | 1057.139 | 2 | -1.7 | 34.8 | 1.40E-06 | Q96KK5 | H2A1H | Histone H2A type 1-H | VTIAQGGVLPNIQAVLLPKK (SEQ ID NO: 179) | [Alkene@119] |
| Frac | Q71DI3, Q99880 | 852.1877 | 4 | 695.353 | 2 | -1.5 | 33.9 | 8.20E-05 | Q71DI3 | H32 | Histone H3.2 | EIAQDFKTDLR (SEQ ID NO: 164) | [Alkene@80] |
| Frac | | 537.0284 | 4 | 400.236 | 2 | -3.1 | 25.1 | 2.80E-02 | O60814 | H2B1K | Histone H2B type 1-K | AVTKAQK (SEQ ID NO: 186) | [Alkene@21] |
| Frac | | 649.3370 | 3 | 600.369 | 1 | -4.2 | 12.7 | 2.00E-01 | O60814 | H2B1K | Histone H2B type 1-K | KAVTK (SEQ ID NO: 187) | [Alkene@17] |
| Fil, Lys | | 517.9415 | 3 | 391.692 | 2 | -2.5 | 15.4 | 5.90E-01 | O60814 | H2B1K | Histone H2B type 1-K | KAVTK (SEQ ID NO: 201) | [ThiolB@17] |
| Frac, Lys | | 619.2982 | 4 | 660.328 | 2 | -2.3 | 30.2 | 3.90E-05 | O60814 | H2B1K | Histone H2B type 1-K | KESYSVVVYK (SEQ ID NO: 154) | [Alkene@35] |
| Fil, Frac, Lys | | 598.3129 | 4 | 579.305 | 2 | -1.8 | 32.8 | 3.20E-04 | P06733 | ENOA | Alpha-enolase | IEEELGSKAK (SEQ ID NO: 188) | [Alkene@420] |
| Lys | | 663.6019 | 4 | 685.860 | 2 | -2.5 | 33.3 | 5.50E-03 | P06733 | ENOA | Alpha-enolase | LNVTEQEKIDK (SEQ ID NO: 189) | [Alkene@89] |
| Fil, Lys | | 541.2728 | 4 | 392.730 | 2 | -4.6 | 11.1 | 9.00E-02 | P06733 | ENOA | Alpha-enolase | NVIKEK (SEQ ID NO: 190) | [Alkene@197] |
| Frac | | 643.3171 | 4 | 530.278 | 2 | -1.5 | 29.4 | 6.80E-05 | P06748 | NPM | Nucleophosmin | AKMQASIEK (SEQ ID NO: 191) | [ThiolB@250] |
| Frac | | 731.3334 | 3 | 514.754 | 2 | 0.0 | 11.7 | 9.20E-01 | P06748 | NPM | Nucleophosmin | DSKPSSTPR (SEQ ID NO: 192) | [Alkene@215] |
| Frac | | 574.0543 | 4 | 464.287 | 2 | 4.9 | 20.9 | 5.10E-03 | P06748 | NPM | Nucleophosmin | LLSISGKR (SEQ ID NO: 193) | [Alkene@141] |
| Frac | | 760.0324 | 3 | 656.341 | 2 | -3.3 | 38.5 | 2.20E-05 | P06748 | NPM | Nucleophosmin | QEKTPK (SEQ ID NO: 194) | [Gln->pyro-Glu@231, Alkene@233] |
| Frac | | 574.5322 | 4 | 392.710 | 2 | -9.2 | 11.5 | 4.90E-02 | P06748 | NPM | Nucleophosmin | QEKTPK (SEQ ID NO: 202) | [Alkene@233] |
| Frac | | 619.5454 | 4 | 482.740 | 2 | -0.7 | 15.3 | 4.90E-02 | P06748 | NPM | Nucleophosmin | SKGQESFK (SEQ ID NO: 195) | [Alkene@223] |

TABLE 10-continued

| | | | | | | | | | |
|---|---|---|---|---|---|---|---|---|---|
| Frac | P06748 | 472.9812 | 4 | 573.741 | 2 | −5.1 | 10.3 | 1.30E−01 P06748 NPM | Nucleophosmin | SKGQESFK (SEQ ID NO: 203) | [ThiolB@223] |
| Fil | P06899 | 517.9415 | 3 | 391.692 | 2 | −2.5 | 15.4 | 5.90E−01 P06899 H2B1J | Histone H2B type 1-J | KAVTK (SEQ ID NO: 201) | [ThiolB@17] |
| Fil | P06899 | 622.8040 | 4 | 667.338 | 2 | 1.0 | 26.8 | 1.90E−04 P06899 H2B1J | Histone H2B type 1-J | KESYSIYVYK (SEQ ID NO: 175) | [Alkene@35] |
| Frac | P07197 | 557.5172 | 4 | 500.258 | 2 | −1.8 | 31.6 | 7.60E−04 P07197 NFM | Neurofilament medium polypeptide | AEVGKGKGQK (SEQ ID NO: 208) | [Alkene@698] |
| Frac | P07197 | 477.4917 | 4 | 390.734 | 2 | −0.9 | 22.1 | 6.40E−03 P07197 NFM | Neurofilament medium polypeptide | AKSPVPK (SEQ ID NO: 209) | [Alkene@614] |
| Frac | P07197 | 555.2757 | 4 | 390.733 | 2 | −3.4 | 18.1 | 2.30E−02 P07197 NFM | Neurofilament medium polypeptide | AKSPVPK (SEQ ID NO: 209) | [Alkene@614] |
| Frac | P07197 | 441.4798 | 4 | 390.734 | 2 | −0.9 | 15.0 | 6.90E−02 P07197 NFM | Neurofilament medium polypeptide | AKSPVPK (SEQ ID NO: 209) | [Alkene@614] |
| Frac | P07197 | 594.2940 | 3 | 769.407 | 1 | −2.7 | 6.5 | 8.70E+00 P07197 NFM | Neurofilament medium polypeptide | DVPEKK (SEQ ID NO: 210) | [Alkene@731] |
| Frac | P07197 | 788.3696 | 4 | 976.902 | 2 | −1.0 | 15.7 | 1.80E−02 P07197 NFM | Neurofilament medium polypeptide | EEEPEAEEEVAAKK (SEQ ID NO: 211) | [ThiolB@509] |
| Frac | P07197 | 765.3303 | 4 | 620.313 | 2 | −2.3 | 22.2 | 1.80E−03 P07197 NFM | Neurofilament medium polypeptide | EEGKPLQQEK (SEQ ID NO: 212) | [Alkene@766] |
| Frac | P07197 | 757.3589 | 3 | 629.336 | 1 | −0.9 | 3.6 | 1.10E−01 P07197 NFM | Neurofilament medium polypeptide | GAKGSR (SEQ ID NO: 213) | [Alkene@793] |
| Frac | P07197 | 757.6872 | 3 | 629.334 | 1 | −4.1 | 7.9 | 2.60E−02 P07197 NFM | Neurofilament medium polypeptide | GAKGSR (SEQ ID NO: 213) | [Alkene@793] |
| Frac | P07197 | 533.4902 | 4 | 671.261 | 2 | −2.8 | 26.8 | 1.20E−03 P07197 NFM | Neurofilament medium polypeptide | GEQKEEEEK (SEQ ID NO: 214) | [ThiolB@702] |
| Frac | P07197 | 700.8235 | 4 | 452.205 | 2 | −3.0 | 28.8 | 5.30E−03 P07197 NFM | Neurofilament medium polypeptide | GGDKSEEK (SEQ ID NO: 215) | [Alkene@847] |

TABLE 10-continued

| | | | | | | | | | |
|---|---|---|---|---|---|---|---|---|---|
| Frac | P07197 | 540.5170 | 4 | 452.208 | 2 | 3.7 | 20.5 | 3.20E-02 | P07197 NFM | Neurofilament medium polypeptide | GGDKSEEK (SEQ ID NO: 215) | [Alkene@847] |
| Frac | P07197 | 473.9890 | 4 | 383.726 | 2 | -1.4 | 22.0 | 3.50E-03 | P07197 NFM | Neurofilament medium polypeptide | GKSPVPK (SEQ ID NO: 216) | [Alkene@627] |
| Frac | P07197 | 552.2787 | 4 | 378.716 | 2 | -0.4 | 22.4 | 4.70E-03 | P07197 NFM | Neurofilament medium polypeptide | GKSPVPK (SEQ ID NO: 216) | [Alkene@627] |
| Frac | P07197 | 554.7847 | 4 | 383.726 | 2 | -1.4 | 13.3 | 5.00E-03 | P07197 NFM | Neurofilament medium polypeptide | GKSPVSK (SEQ ID NO: 217) | [Alkene@666] |
| Frac | P07197 | 774.6290 | 4 | 655.320 | 2 | -4.2 | 10.1 | 5.30E-01 | P07197 NFM | Neurofilament medium polypeptide | GSPSTVSSSYKR (SEQ ID NO: 218) | [Alkene@53] |
| Frac | P07197 | 743.1202 | 4 | 940.426 | 2 | -12.0 | 15.1 | 1.80E-01 | P07197 NFM | Neurofilament medium polypeptide | GWTNGLDLSPADEKK (SEQ ID NO: 219) | [Deamidated@832, ThiolB@842] |
| Frac | P07197 | 585.5341 | 4 | 720.391 | 1 | -2.3 | 13.6 | 2.90E-01 | P07197 NFM | Neurofilament medium polypeptide | KDYLK (SEQ ID NO: 220) | [Alkene@259] |
| Frac | P07197 | 856.4033 | 4 | 564.797 | 2 | -2.5 | 33.7 | 2.10E-05 | P07197 NFM | Neurofilament medium polypeptide | KLLEGEETR (SEQ ID NO: 204) | [ThiolB@403] |
| Frac | P07197 | 744.6050 | 4 | 763.893 | 2 | -1.4 | 43.6 | 3.00E-05 | P07197 NFM | Neurofilament medium polypeptide | LTEAAEQNKEAIR (SEQ ID NO: 221) | [Alkene@307] |
| Frac | P07197 | 627.1050 | 5 | 854.894 | 2 | -4.3 | 12.4 | 2.60E-01 | P07197 NFM | Neurofilament medium polypeptide | LTEAAEQNKEAIR (SEQ ID NO: 222) | [ThiolB@307] |
| Frac | P07197 | 439.4437 | 5 | 456.232 | 2 | -1.0 | 10.6 | 2.10E+00 | P07197 NFM | Neurofilament medium polypeptide | LVSTKK (SEQ ID NO: 223) | [ThiolB@898] |
| Frac | P07197 | 705.3453 | 4 | 536.797 | 2 | -1.6 | 28.1 | 1.50E-03 | P07197 NFM | Neurofilament medium polypeptide | SEEKVVTK (SEQ ID NO: 224) | [Alkene@851] |
| Frac | P07197 | 664.5715 | 4 | 927.916 | 2 | -5.4 | 21.6 | 7.40E-03 | P07197 NFM | Neurofilament medium polypeptide | SEEVATKELVADAK (SEQ ID NO: 225) | [ThiolB@598] |

TABLE 10-continued

| | | | | | | | | | |
|---|---|---|---|---|---|---|---|---|---|
| Frac | P07197 | 574.0381 | 4 | 386.713 | 2 | -1.6 | 21.0 | 6.70E-02 | P07197 NFM | Neurofilament medium polypeptide | SKAEVGK (SEQ ID NO: 226) | [Alkene@693] |
| Frac | P07197 | 616.3067 | 4 | 471.249 | 2 | -3.3 | 29.9 | 1.90E-03 | P07197 NFM | Neurofilament medium polypeptide | SPVEEKAK (SEQ ID NO: 227) | [Alkene@677] |
| Frac | P07197 | 595.0430 | 4 | 464.242 | 2 | -1.6 | 30.9 | 4.70E-03 | P07197 NFM | Neurofilament medium polypeptide | SPVEEKGK (SEQ ID NO: 228) | [Alkene@625] |
| Frac | P07197 | 789.7181 | 3 | 927.477 | 1 | -1.3 | 17.1 | 2.50E-02 | P07197 NFM | Neurofilament medium polypeptide | SPVEEKGK (SEQ ID NO: 228) | [Alkene@625] |
| Frac | P07197 | 673.3341 | 4 | 625.834 | 2 | -1.6 | 23.0 | 2.50E-03 | P07197 NFM | Neurofilament medium polypeptide | SPVPKSPVEEK (SEQ ID NO: 230) | [Alkene@619] |
| Frac | P07197 | 767.6319 | 4 | 864.888 | 2 | 1.2 | 21.5 | 4.20E-03 | P07197 NFM | Neurofilament medium polypeptide | TVEKITSEGGDGATK (SEQ ID NO: 232) | [ThiolB@860] |
| Frac | P07197 | 705.8660 | 4 | 419.754 | 2 | -3.0 | 14.6 | 8.00E-02 | P07197 NFM | Neurofilament medium polypeptide | VEAPKLK (SEQ ID NO: 233) | [ThiolB@445] |
| Frac | P07197 | 645.0975 | 4 | 528.818 | 2 | -1.1 | 28.2 | 3.00E-05 | P07197 NFM | Neurofilament medium polypeptide | VVVTKTVEK (SEQ ID NO: 234) | [Alkene@856] |
| Frac | P07900 | 871.6938 | 4 | 835.459 | 2 | -0.7 | 33.9 | 1.60E-06 | P07900 HS90A | Heat shock protein HSP 90-alpha | ADLINNLGTIAKSGTK (SEQ ID NO: 205) | [Alkene@112] |
| Frac | P07910 | 515.2593 | 4 | 352.682 | 2 | -0.9 | 17.8 | 2.40E-02 | P07910 HNRPC | Heterogeneous nuclear ribonucleoproteins C1/C2 | GSSKSGK (SEQ ID NO: 236) | [Alkene@184] |
| Frac | P07910 | 855.7723 | 3 | 457.270 | 2 | -2.8 | 29.7 | 9.90E-03 | P07910 HNRPC | Heterogeneous nuclear ribonucleoproteins C1/C2 | KELTQIK (SEQ ID NO: 237) | [Alkene@198] |
| Frac | P07910 | 646.3376 | 4 | 457.270 | 2 | -2.8 | 28.5 | 8.30E-03 | P07910 HNRPC | Heterogeneous nuclear ribonucleoproteins C1/C2 | KELTQIK (SEQ ID NO: 237) | [Alkene@198] |

TABLE 10-continued

| | | | | | | | | | | |
|---|---|---|---|---|---|---|---|---|---|---|
| Frac | P07910 | 559.2748 | 4 | 457.271 | 2 | −0.6 | 19.7 | 2.10E−02 | P07910 HNRPC | Heterogeneous nuclear ribonucleoproteins C1/C2 | KELTQIK (SEQ ID NO: 237) | [Alkene@198] |
| Frac | P08107 | 747.0454 | 3 | 743.392 | 1 | −1.9 | 14.1 | 6.00E−01 | P08107 HSP71 | Heat shock 70 kDa protein 1A/1B | DAKLDK (SEQ ID NO: 238) | [Alkene@325] |
| Fil, Frac, Lys | P08107 | 582.7902 | 4 | 536.292 | 2 | −2.4 | 16.5 | 1.20E−01 | P08107 HSP71 | Heat shock 70 kDa protein 1A/1B | ITITNDKGR (SEQ ID NO: 239) | [Alkene@507] |
| Frac | P08107 | 490.2351 | 4 | 529.279 | 2 | −1.6 | 13.2 | 1.20E−01 | P08107 HSP71 | Heat shock 70 kDa protein 1A/1B | LSKEEIER (SEQ ID NO: 240) | [Alkene@512] |
| Frac | P08238 | 867.6945 | 4 | 835.457 | 2 | −3.1 | 41.1 | 7.60E−08 | P08238 HS90B | Heat shock protein HSP 90-beta | ADLINNLGTIAKSGTK (SEQ ID NO: 172) | [ThiolB@107] |
| Frac | P08670 | 873.2054 | 4 | 590.310 | 2 | −2.5 | 28.8 | 8.30E−05 | P08670 VIME | Vimentin | FANYIDKVR (SEQ ID NO: 166) | [Alkene@120] |
| Frac | P08670 | 675.1106 | 4 | 557.789 | 2 | −2.8 | 31.2 | 1.60E−03 | P08670 VIME | Vimentin | KLLEGEESR (SEQ ID NO: 241) | [Alkene@402] |
| Frac | P08670 | 636.0847 | 4 | 557.790 | 2 | −1.0 | 22.4 | 2.00E−03 | P08670 VIME | Vimentin | KLLEGEESR (SEQ ID NO: 241) | [Alkene@402] |
| Frac | P08670 | 844.4402 | 4 | 794.433 | 2 | −2.6 | 34.2 | 8.50E−06 | P08670 VIME | Vimentin | KVESLQEEIAFLK (SEQ ID NO: 242) | [Alkene@223] |
| Frac | P08670 | 1098.7781 | 4 | 1276.136 | 2 | −1.1 | 36.4 | 3.50E−06 | P08670 VIME | Vimentin | LLQDSVDFSLADAINTEFK NTR (SEQ ID NO: 243) | [Alkene@97] |
| Frac | P0C0S5 | 709.8815 | 4 | 641.710 | 3 | −1.0 | 25.2 | 1.90E−04 | P0C0S5 H2AZ | Histone H2A.Z | ATIAGGGVIPHIHKSLIGK (SEQ ID NO: 174) | [Alkene@116] |
| Frac | P0C0S5 | 709.8815 | 4 | 641.710 | 3 | −1.0 | 25.2 | 8.90E−04 | P0C0S5 H2AZ | Histone H2A.Z | ATIAGGGVIPHIHKSLIGK (SEQ ID NO: 174) | [Alkene@116] |
| Frac | P10412 | 607.3190 | 4 | 456.742 | 2 | −2.0 | 21.4 | 1.10E−02 | P10412 H14 | Histone H1.4 | AASGEAKPK (SEQ ID NO: 244) | [Alkene@117] |
| Fil | P10412 | 392.2068 | 4 | 335.699 | 2 | 3.7 | 24.0 | 3.10E−02 | P10412 H14 | Histone H1.4 | AGAAKAK (SEQ ID NO: 245) | [Alkene@127] |
| Fil | P10412 | 560.0715 | 4 | 656.883 | 2 | 0.3 | 22.8 | 3.00E−03 | P10412 H14 | Histone H1.4 | ERSGVSLAALKK (SEQ ID NO: 246) | [Alkene@63] |
| Frac | P10412 | 630.0876 | 4 | 796.916 | 2 | −2.0 | 32.6 | 1.90E−05 | P10412 H14 | Histone H1.4 | GTLVQTKGTGASGSFK (SEQ ID NO: 247) | [Alkene@97] |

TABLE 10-continued

| | | | | | | | | | | | |
|---|---|---|---|---|---|---|---|---|---|---|---|
| Frac | P10412 | 698.3719 | 4 | 796.915 | 2 | -3.2 | 27.4 | 4.70E-05 P10412 H14 | Histone H1.4 | GTLVQTKGTGASGSFK (SEQ ID NO: 247) | [Alkene@97] |
| Frac | P10412 | 724.3936 | 4 | 690.891 | 2 | 1.0 | 17.7 | 1.10E-02 P10412 H14 | Histone H1.4 | KASGPPVSELITK (SEQ ID NO: 248) | [Alkene@34] |
| Lys | P10412 | 504.5979 | 3 | 343.695 | 2 | -0.6 | 14.6 | 2.00E-01 P10412 H14 | Histone H1.4 | KSAGAAK (SEQ ID NO: 249) | [Alkene@26] |
| Fil | P10809 | 691.8912 | 4 | 399.758 | 2 | 0.5 | 21.3 | 1.30E-03 P10809 CH60 | 60 kDa heat shock protein, mitochondrial | KGVITVK (SEQ ID NO: 250) | [Alkene@196] |
| Fil | P10809 | 480.4926 | 4 | 436.741 | 2 | 2.7 | 17.9 | 1.00E-01 P10809 CH60 | 60 kDa heat shock protein, mitochondrial | SIDLKDK (SEQ ID NO: 251) | [Alkene@87] |
| Frac, Lys | P12277 | 433.2298 | 4 | 557.766 | 2 | -2.2 | 20.1 | 3.40E-03 P12277 KCRB | Creatine kinase B-type | FSEVLKR (SEQ ID NO: 252) | [ThioIB@313] |
| Lys | P13639 | 678.1007 | 4 | 742.878 | 2 | -0.3 | 37.9 | 1.10E-04 P13639 EF2 | Elongation factor 2 | FAAKGEQLGPAER (SEQ ID NO: 253) | [Alkene@239] |
| Fil | P14314 | 549.5410 | 4 | 471.755 | 2 | 2.0 | 18.9 | 2.60E-01 P14314 GLU2B | Glucosidase 2 subunit beta | AREEKQK (SEQ ID NO: 254) | [Alkene@155] |
| Fil | P16403 | 560.0715 | 4 | 656.883 | 2 | 0.3 | 22.8 | 3.00E-03 P16403 H12 | Histone H1.2 | ERSGVSLAALKK (SEQ ID NO: 246) | [Alkene@63] |
| Frac | P19338 | 965.2560 | 4 | 843.477 | 2 | -0.3 | 31.6 | 1.70E-05 P19338 NUCL | Nucleolin | ALELTGLKVFGNEIK (SEQ ID NO: 255) | [Alkene@370] |
| Frac | P19338 | 677.0848 | 4 | 646.299 | 2 | -0.5 | 19.3 | 5.70E-04 P19338 NUCL | Nucleolin | GGKNSTWSGESK (SEQ ID NO: 256) | [ThioIB@477] |
| Frac, Lys | P19338 | 491.5202 | 4 | 504.247 | 2 | -3.3 | 17.1 | 6.00E-03 P19338 NUCL | Nucleolin | KAAVTPGK (SEQ ID NO: 257) | [ThioIB@80] |
| Lys | P19338 | 656.6004 | 4 | 605.328 | 2 | -2.2 | 26.1 | 2.50E-04 P19338 NUCL | Nucleolin | SKGIAYIEFK (SEQ ID NO: 258) | [Alkene@429] |
| Frac | P20700 | 617.0859 | 4 | 527.317 | 2 | -3.4 | 23.0 | 3.10E-04 P20700 LMNB1 | Lamin-B1 | AKLQIELGK (SEQ ID NO: 259) | [Alkene@102] |
| Frac | P20700 | 621.8014 | 4 | 401.687 | 2 | -2.8 | 10.3 | 4.90E-02 P20700 LMNB1 | Lamin-B1 | EKDNSR (SEQ ID NO: 260) | [Alkene@332] |
| Frac | P20700 | 744.6227 | 4 | 576.299 | 2 | -3.1 | 29.5 | 6.40E-05 P20700 LMNB1 | Lamin-B1 | KIGDTSVSYK (SEQ ID NO: 261) | [Alkene@474] |
| Lys | P23527 | 622.8040 | 4 | 667.338 | 2 | 1.0 | 26.8 | 1.90E-04 P23527 H2B1O | Histone H2B type 1-O | KESYSIVYK (SEQ ID NO: 175) | [Alkene@35] |

TABLE 10-continued

| | | | | | | | | | |
|---|---|---|---|---|---|---|---|---|---|
| Lys | P23527 | 1116.5245 | 4 | 667.339 | 2 | 2.5 | 21.3 | 3.60E-03 P23527 H2B10 Histone H2B type 1-O | KESYSIYVYK (SEQ ID NO: 175) | [Alkene@35] |
| Frac | P24534 | 500.7666 | 4 | 390.752 | 2 | -1.4 | 25.1 | 1.20E-03 P24534 EF1B Elongation factor 1-beta | KPALVAK (SEQ ID NO: 262) | [Alkene@133] |
| Lys | P27824 | 566.4846 | 5 | 339.190 | 2 | -0.3 | 12.2 | 3.40E+00 P27824 CALX Calnexin | HKNPK (SEQ ID NO: 263) | [Alkene@207] |
| Fil | P30101 | 554.0370 | 4 | 396.220 | 2 | 3.7 | 20.7 | 2.40E-01 P30101 PDIA3 Protein disulfide-isomerase A3 | KFISDK (SEQ ID NO: 264) | [Alkene@147] |
| Fil | P51572 | 650.5767 | 4 | 472.757 | 2 | 2.1 | 17.1 | 4.90E-03 P51572 BAP31 B-cell receptor-associated protein 31 | KQSEGLIK (SEQ ID NO: 265) | [Alkene@214] |
| Frac | P52272 | 869.1990 | 4 | 1066.508 | 2 | -1.1 | 10.0 | 1.20E+00 P52272 HNRPM Heterogeneous nuclear ribonucleoprotein M | GEIIAKQGGGGGGSVPGIER (SEQ ID NO: 266) | [ThiolB@388] |
| Frac | P61353 | 652.0794 | 4 | 381.204 | 2 | -1.0 | 10.4 | 1.90E-01 P61353 RL27 60S ribosomal protein L27 | FMKPGK (SEQ ID NO: 267) | [Alkene@6] |
| Frac | P61353 | 656.0769 | 4 | 389.201 | 2 | -2.1 | 9.0 | 9.30E-01 P61353 RL27 60S ribosomal protein L27 | FMKPGK (SEQ ID NO: 268) | [Oxidation@5, Alkene@6] |
| Fil | P61604 | 676.8530 | 4 | 717.854 | 2 | 2.8 | 28.1 | 5.70E-05 P61604 CH10 10 kDa heat shock protein, mitochondrial | GKGGEIQPVSVK (SEQ ID NO: 269) | [ThiolB@56] |
| Frac, Lys | P61978 | 746.0631 | 3 | 663.360 | 2 | -3.4 | 27.8 | 2.40E-04 P61978 HNRPK Heterogeneous nuclear ribonucleoprotein K | DLAGSIIGKGGQR (SEQ ID NO: 271) | [Alkene@405] |
| Frac | P61978 | 759.1172 | 4 | 1061.997 | 2 | -1.0 | 27.8 | 7.20E-05 P61978 HNRPK Heterogeneous nuclear ribonucleoprotein K | HESGASIKIDEPLEGSEDR (SEQ ID NO: 272) | [Alkene@422] |
| Fil, Frac, Lys | P62805 | 471.2395 | 3 | 362.659 | 2 | -1.3 | 11.0 | 1.20E+00 P62805 H4 Histone H4 | GGAKR (SEQ ID NO: 273) | [ThiolB@17] |
| Frac, Lys | P62805 | 480.9111 | 3 | 341.650 | 2 | 4.2 | 10.4 | 4.50E-01 P62805 H4 Histone H4 | GKGGK (SEQ ID NO: 274) | [ThiolB@6] |
| Frac | P62805 | 645.6061 | 4 | 470.271 | 2 | -2.5 | 26.6 | 6.20E-03 P62805 H4 Histone H4 | GLGKGGAKR (SEQ ID NO: 207) | [Alkene@13 = 25, Acetyl@17 = 25] |
| Frac | P62807 | 537.0284 | 4 | 400.236 | 2 | -3.1 | 25.1 | 2.80E-02 P62807 H2B1C Histone H2B type 1-C/E/F/G/I | AVTKAQK (SEQ ID NO: 186) | [Alkene@21] |

TABLE 10-continued

| Category | Accession | m/z | z | Mass | # | Score | p-value | Accession | Gene | Protein | Peptide | Modification |
|---|---|---|---|---|---|---|---|---|---|---|---|---|
| Frac | P62807 | 649.3370 | 3 | 600.369 | 1 | -4.2 | 12.7 | 2.00E-01 | P62807 H2B1C | Histone H2B type 1-C/E/F/G/I | KAVTK (SEQ ID NO: 187) | [Alkene@17] |
| Frac | P62807 | 517.9415 | 3 | 391.692 | 2 | -2.5 | 15.4 | 5.90E-01 | P62807 H2B1C | Histone H2B type 1-C/E/F/G/I | KAVTK (SEQ ID NO: 201) | [ThiolB@17] |
| Frac | P62807 | 607.2775 | 4 | 660.329 | 2 | -0.8 | 28.6 | 1.10E-04 | P62807 H2B1C | Histone H2B type 1-C/E/F/G/I | KESYSVVYK (SEQ ID NO: 154) | [Alkene@35] |
| Fil, Frac | P62807 | 619.2982 | 4 | 660.328 | 2 | -2.3 | 30.2 | 3.90E-05 | P62807 H2B1C | Histone H2B type 1-C/E/F/G/I | KESYSVVYK (SEQ ID NO: 154) | [Alkene@35] |
| Frac | P62807 | 1113.2683 | 4 | 660.327 | 2 | -3.8 | 18.7 | 5.80E-03 | P62807 H2B1C | Histone H2B type 1-C/E/F/G/I | KESYSVVYK (SEQ ID NO: 154) | [Alkene@35] |
| Fil | P62807 | 680.0826 | 4 | 478.260 | 2 | 2.0 | 17.5 | 1.00E-01 | P62807 H2B1C | Histone H2B type 1-C/E/F/G/I | LAHYNKR (SEQ ID NO: 181) | [Alkene@86] |
| Lys | P62826 | 697.0198 | 6 | 872.439 | 2 | 0.4 | 32.0 | 3.40E-06 | P62826 RAN | GTP-binding nuclear protein Ran | GPIKFNVWDTAGQEK (SEQ ID NO: 275) | [Alkene@60] |
| Fil, Lys | P62841 | 531.4732 | 5 | 512.609 | 3 | -0.9 | 28.4 | 3.30E-04 | P62841 RS15 | 40S ribosomal protein S15 | KEAPPMEKPEWK (SEQ ID NO: 276) | [Alkene@65 = 48] |
| Lys | P62937 | 657.3184 | 4 | 747.335 | 2 | -1.6 | 27.2 | 1.20E-04 | P62937 PPIA | Peptidyl-prolyl cis-trans isomerase A | ALSTGEKGFGYK (SEQ ID NO: 278) | [ThiolB@44] |
| Frac | Q00839 | 536.2779 | 4 | 407.736 | 2 | -2.7 | 23.5 | 1.30E-01 | Q00839 HNRPU | Heterogeneous nuclear ribonucleoprotein U | LSDKGLK (SEQ ID NO: 279) | [Alkene@28] |
| Fil, Frac | Q00839 | 524.4593 | 5 | 413.232 | 2 | -1.2 | 13.4 | 3.10E-01 | Q00839 HNRPU | Heterogeneous nuclear ribonucleoprotein U | QRTQKK (SEQ ID NO: 280) | [Gln->pyro-Glu@615, Alkene@619] |
| Frac | Q02878 | 791.1782 | 4 | 754.916 | 2 | -4.7 | 31.8 | 9.10E-04 | Q02878 RL6 | 60S ribosomal protein L6 | IDQKAVDSQILPK (SEQ ID NO: 281) | [Alkene@251] |
| Frac | Q14103 | 679.0915 | 4 | 906.478 | 2 | -2.8 | 31.0 | 1.70E-04 | Q14103 HNRPD | Heterogeneous nuclear ribonucleoprotein D0 | IFVGGLSPDTPEEKIR (SEQ ID NO: 282) | [Alkene@197] |
| Frac | Q15149 | 704.1021 | 4 | 609.311 | 2 | -1.1 | 22.4 | 2.70E-03 | Q15149 PLEC | Plectin | AQFEQLKDGK (SEQ ID NO: 283) | [Alkene@3469] |
| Frac | Q15149 | 694.8314 | 4 | 702.857 | 2 | -3.6 | 33.9 | 5.30E-04 | Q15149 PLEC | Plectin | ASFAEKTAQLER (SEQ ID NO: 284) | [ThiolB@1725] |
| Frac | Q15149 | 729.1006 | 4 | 528.277 | 2 | -1.2 | 19.0 | 6.40E-02 | Q15149 PLEC | Plectin | EAKELQQR (SEQ ID NO: 285) | [Alkene@1528] |

TABLE 10-continued

| | | | | | | | | | |
|---|---|---|---|---|---|---|---|---|---|
| Frac | Q15149 | 689.3405 | 4 | 549.792 | 2 | -2.0 | 30.2 | 3.40E-05 Q15149 PLEC | Plectin | KAALEEVER (SEQ ID NO: 266) | [Alkene@2142] |
| Frac | Q15233 | 462.7337 | 4 | 588.264 | 2 | -1.4 | 9.6 | 2.00E-01 Q15233 NONO | Non-POU domain-containing octamer-binding protein | DKGFGFIR (SEQ ID NO: 287) | [ThiolB@109] |
| Frac | Q16778 | 537.0284 | 4 | 400.236 | 2 | -3.1 | 25.1 | 2.80E-02 Q16778 H2B2E | Histone H2B type 2-E | AVTKAQK (SEQ ID NO: 186) | [Alkene@21] |
| Fil, Frac | Q16778 | 622.8040 | 4 | 667.338 | 2 | 1.0 | 26.8 | 1.90E-04 Q16778 H2B2E | Histone H2B type 2-E | KESYSIVYYK (SEQ ID NO: 175) | [Alkene@35] |
| Frac | Q6FI13 | 467.7418 | 4 | 349.718 | 2 | -3.0 | 16.0 | 3.20E-01 Q6FI13 H2A2A | Histone H2A type 2-A | ARAKAK (SEQ ID NO: 288) | [Alkene@14] |
| Frac | Q71DI3 | 485.5123 | 4 | 371.726 | 2 | -1.4 | 21.5 | 3.70E-02 Q71DI3 H32 | Histone H3.2 | KQLATK (SEQ ID NO: 165) | [Alkene@19] |
| Lys | Q71DI3 | 482.0097 | 4 | 371.726 | 2 | -1.4 | 22.6 | 3.70E-02 Q71DI3 H32 | Histone H3.2 | KQLATK (SEQ ID NO: 165) | [Alkene@19] |
| Fil, Frac, Lys | Q71DI3 | 425.7235 | 4 | 371.726 | 2 | -1.4 | 20.9 | 2.30E-02 Q71DI3 H32 | Histone H3.2 | KQLATK (SEQ ID NO: 165) | [Alkene@19] |
| Frac | Q71DI3 | 562.2980 | 4 | 371.726 | 2 | -1.4 | 22.0 | 4.90E-04 Q71DI3 H32 | Histone H3.2 | KQLATK (SEQ ID NO: 165) | [Alkene@19] |
| Frac | Q71DI3 | 567.0562 | 4 | 541.818 | 2 | -2.7 | 27.4 | 1.50E-04 Q71DI3 H32 | Histone H3.2 | KQLATKAAR (SEQ ID NO: 289) | [Alkene@19 = 48, Acetyl@24 = 48] |
| Frac | Q71DI3 | 570.5511 | 4 | 541.819 | 2 | -0.9 | 29.7 | 6.50E-04 Q71DI3 H32 | Histone H3.2 | KQLATKAAR (SEQ ID NO: 290) | [Alkene@19 = 36, Acetyl@24 = 36] |
| Frac, Lys | Q71DI3 | 510.7692 | 4 | 541.819 | 2 | -0.9 | 30.1 | 1.90E-04 Q71DI3 H32 | Histone H3.2 | KQLATKAAR (SEQ ID NO: 291) | [Alkene@19 = 57, Acetyl@24 = 57] |
| Fil | Q71DI3 | 689.0198 | 3 | 485.272 | 2 | 0.4 | 18.1 | 9.10E-04 Q71DI3 H32 | Histone H3.2 | KSAPATGGVK (SEQ ID NO: 292) | [Alkene@28] |
| Frac | Q71DI3 | 397.9483 | 4 | 316.175 | 2 | 2.8 | 15.4 | 1.00E-01 Q71DI3 H32 | Histone H3.2 | KSTGGK (SEQ ID NO: 293) | [Alkene@10] |
| Frac | Q71DI3 | 599.8130 | 4 | 379.710 | 2 | -3.7 | 17.5 | 9.00E-02 Q71DI3 H32 | Histone H3.2 | TKQTAR (SEQ ID NO: 294) | [Alkene@5] |
| Frac | Q71DI3 | 566.7612 | 4 | 379.711 | 2 | -1.1 | 18.6 | 1.90E-02 Q71DI3 H32 | Histone H3.2 | TKQTAR (SEQ ID NO: 294) | [Alkene@5] |
| Lys | Q93079 | 517.9415 | 3 | 391.692 | 2 | -2.5 | 15.4 | 5.90E-01 Q93079 H2B1H | Histone H2B type 1-H | KAVTK (SEQ ID NO: 201) | [ThiolB@17] |

TABLE 10-continued

| Exp | | | | | | | P2 m/z | P2 z | P2 ppm | P2 score | P2 ev | P2 Gene Accession | Name | P2 Protein Name | P2 Peptide | P2 Modification |
|---|---|---|---|---|---|---|---|---|---|---|---|---|---|---|---|---|
| Fil | | | | | | Q99877 | 517.9415 | 3 | 391.692 | 2 | 15.4 | 5.90E-01 | Q99877 | H2B1N | Histone H2B type 1-N | KAVTK (SEQ ID NO: 201) | [ThiolB@17] |
| Fil | | | | | | Q99877 | 680.0826 | 4 | 478.260 | 2 | 17.5 | 1.00E-01 | Q99877 | H2B1N | Histone H2B type 1-N | LAHYNKR (SEQ ID NO: 181) | [Alkene@86] |
| Frac | | | | | | Q9NVA2 | 500.2460 | 4 | 423.247 | 2 | 21.6 | 2.80E-03 | Q9NVA2 | SEPT11 | Septin-11 | FDLLKR (SEQ ID NO: 441) | [Alkene@371] |

| Exp | P2 m/z | P2 z | P2 ppm | P2 score | P2 ev | P2 Gene Accession | P2 Name | P2 Protein Name | P2 Peptide | P2 Modification |
|---|---|---|---|---|---|---|---|---|---|---|
| Frac | 358.208 | 2 | −1.4 | 13.1 | 5.70E-02 | P0C0S5 | H2AZ | Histone H2A.Z | TKAVSR (SEQ ID NO: 296) | [Alkene@16] |
| Fil, Frac | 446.218 | 2 | −3.6 | 27.5 | 1.10E-03 | P0C0S8 | H2A1 | Histone H2A type 1 | KGNYAER (SEQ ID NO: 155) | [Alkene@37] |
| Fil, Frac | 478.258 | 2 | −2.2 | 27.0 | 8.60E-03 | O60814 | H2B1K | Histone H2B type 1-K | LAHYNKR (SEQ ID NO: 181) | [Alkene@86] |
| Fil | 478.258 | 2 | −2.2 | 27.0 | 8.60E-03 | O60814 | H2B1K | Histone H2B type 1-K | SRKESYSVYVYK (SEQ ID NO: 297) | [Alkene@35] |
| Frac, Lys | 660.373 | 2 | −0.3 | 34.4 | 5.40E-05 | P0CG48 | UBC | Polyubiquitin-C | MQIFVKTLTGK (SEQ ID NO: 317) | [Alkene@6] |
| Lys | 328.143 | 2 | −0.4 | 4.7 | 1.00E+00 | O60814 | H2B1K | Histone H2B type 1-K | KGSK (SEQ ID NO: 298) | [ThiolB@13] |
| Lys | 478.258 | 2 | −2.2 | 21.5 | 1.90E-01 | O60814 | H2B1K | Histone H2B type 1-K | LAHYNKR (SEQ ID NO: 181) | [Alkene@86] |
| Fil | 667.011 | 3 | −2.7 | 12.8 | 3.10E-01 | O60814 | H2B1K | Histone H2B type 1-K | LLLPGELAKHAVSEGTK (SEQ ID NO: 299) | [ThiolB@109] |
| Frac | 664.815 | 2 | 0.2 | 14.7 | 1.60E-02 | O60814 | H2B1K | Histone H2B type 1-K | MPEPAKSAPAPK (SEQ ID NO: 300) | [Met-loss@1, ThiolB@6] |
| Frac | 606.342 | 3 | −2.9 | 16.4 | 2.50E-01 | O60814 | H2B1K | Histone H2B type 1-K | LLLPGELAKHAVSEGTK (SEQ ID NO: 156) | [Alkene@109] |
| Frac | 909.010 | 2 | −2.2 | 26.4 | 2.70E-03 | O60814 | H2B1K | Histone H2B type 1-K | LLLPGELAKHAVSEGTK (SEQ ID NO: 156) | [Alkene@109] |
| Frac | 573.811 | 2 | −0.6 | 19.5 | 2.60E-03 | O60814 | H2B1K | Histone H2B type 1-K | MPEPAKSAPAPK (SEQ ID NO: 301) | [Met-loss@1, Alkene@6] |
| Frac | 909.011 | 2 | −1.1 | 34.0 | 7.40E-07 | O60814 | H2B1K | Histone H2B type 1-K | LLLPGELAKHAVSEGTK (SEQ ID NO: 156) | [Alkene@109] |

TABLE 10-continued

| | | | | | | | | | |
|---|---|---|---|---|---|---|---|---|---|
| Frac | 573.809 | 2 | -4.0 | 28.6 | 9.10E-05 | O60814 | H2B1K | Histone H2B type 1-K | MPEPAKSAPAPK (SEQ ID NO: 301) [Met-loss@1, Alkene@6] |
| Frac | 446.218 | 2 | -3.6 | 27.5 | 1.10E-03 | Q6FI13 | H2A2A | Histone H2A type 2-A | KGNYAER (SEQ ID NO: 155) [Alkene@37] |
| Frac | 478.258 | 2 | -2.2 | 27.0 | 8.60E-03 | O60814 | H2B1K | Histone H2B type 1-K | LAHYNKR (SEQ ID NO: 181) [Alkene@86] |
| Fil | 663.847 | 2 | -2.4 | 40.0 | 3.00E-05 | Q6FI13 | H2A2A | Histone H2A type 2-A | NDELNKLLGK (SEQ ID NO. 302) [Alkene@96] |
| Fil | 909.011 | 2 | -1.1 | 31.3 | 4.90E-06 | O60814 | H2B1K | Histone H2B type 1-K | LLLPGELAKHAVSEGTK (SEQ ID NO: 156) [Alkene@109] |
| Fil | 664.814 | 2 | -1.3 | 10.9 | 3.40E-01 | O60814 | H2B1K | Histone H2B type 1-K | MPEPAKSAPAPK (SEQ ID NO: 300) [Met-loss@1, ThiolB@6] |
| Frac | 379.711 | 2 | -1.1 | 19.5 | 3.90E-03 | Q71DI3 | H32 | Histone H3.2 | TKQTAR (SEQ ID NO: 294) [Alkene@5] |
| Fil | 478.258 | 2 | -2.2 | 27.0 | 8.60E-03 | P06899 | H2B1J | Histone H2B type 1-J | LAHYNKR (SEQ ID NO: 181) [Alkene@86] |
| Frac | 660.373 | 2 | -0.3 | 34.4 | 5.40E-05 | P0CG48 | UBC | Polyubiquitin-C | MQIFVKTLTGK (SEQ ID NO: 317) [Alkene@6] |
| Fil | 667.011 | 3 | -2.7 | 12.8 | 3.10E-01 | P06899 | H2B1J | Histone H2B type 1-J | LLLPGELAKHAVSEGTK (SEQ ID NO: 299) [ThiolB@109] |
| Frac | 360.699 | 2 | -2.7 | 16.5 | 1.60E-01 | P07197 | NFM | Neurofilament medium polypeptide | KDYLK (SEQ ID NO: 220) [Alkene@259] |
| Frac | 590.310 | 2 | -2.5 | 31.2 | 2.60E-04 | P07197 | NFM | Neurofilament medium polypeptide | KQASHAQLGDAYDQEIR (SEQ ID NO: 169) [Gln->pyro-Glu@138, Alkene@139] |
| Frac | 1047.993 | 2 | -2.5 | 57.2 | 3.10E-08 | P07197 | NFM | Neurofilament medium polypeptide | QKQASHAQLGDAYDQEIR (SEQ ID NO: 169) [Gln->pyro-Glu@138, Alkene@139] |
| Frac | 614.368 | 2 | -1.6 | 21.4 | 2.80E-03 | P08670 | VIME | Vimentin | TLLIKTVETR (SEQ ID NO: 171) [Alkene@445] |
| Frac | 614.367 | 2 | -3.3 | 32.9 | 2.90E-04 | P08670 | VIME | Vimentin | TLLIKTVETR (SEQ ID NO: 171) [Alkene@445] |
| Frac | 821.406 | 2 | -1.9 | 27.9 | 1.20E-04 | P08670 | VIME | Vimentin | TNEKVELQELNDR (SEQ ID NO: 303) [Alkene@104] |
| Frac | 801.360 | 2 | -3.7 | 17.8 | 1.10E-02 | P07197 | NFM | Neurofilament medium polypeptide | YAKLTEAAEQNK (SEQ ID NO: 304) [ThiolB@298] |
| Frac | 799.920 | 2 | -3.6 | 31.5 | 1.40E-04 | P14625 | ENPL | Endoplasmin | ELISNASDALDKIR (SEQ ID NO: 306) [Alkene@114] |

TABLE 10-continued

| | | | | | | | | | |
|---|---|---|---|---|---|---|---|---|---|
| Frac | 681.834 | 2 | −3.0 | 31.4 | 1.20E−04 | P08670 | VIME | Vimentin | SKFADLSEAANR (SEQ ID NO: 308) [Alkene@294] |
| Frac | 532.307 | 3 | −2.1 | 17.4 | 4.40E−02 | Q71DI3 | H32 | Histone H3.2 | RVTIMPKDIQLAR (SEQ ID NO: 178) [Alkene@123] |
| Lys | 446.221 | 2 | 3.2 | 22.7 | 2.80E−03 | P0C0S8 | H2A1 | Histone H2A type 1 | KGNYAER (SEQ ID NO: 155) [Alkene@37] |
| Lys | 478.258 | 2 | −2.2 | 27.0 | 8.60E−03 | P23527 | H2B10 | Histone H2B type 1-O | LAHYNKR (SEQ ID NO: 181) [Alkene@86] |
| Lys | 663.847 | 2 | −2.4 | 40.0 | 3.00E−05 | P0C0S8 | H2A1 | Histone H2A type 1 | NDEELNKLLGK (SEQ ID NO: 302) [Alkene@96] |
| Lys | 446.218 | 2 | −3.6 | 27.5 | 1.10E−03 | P0C0S8 | H2A1 | Histone H2A type 1 | KGNYAER (SEQ ID NO: 155) [Alkene@37] |
| Lys | 478.258 | 2 | −2.2 | 27.0 | 8.60E−03 | P58876 | H2B1D | Histone H2B type 1-D | LAHYNKR (SEQ ID NO: 181) [Alkene@86] |
| Fil | 909.015 | 2 | 3.3 | 17.7 | 5.50E−03 | P62807 | H2B1C | Histone H2B type 1-C/E/F/G/I | LLLPGELAKHAVSEGTK (SEQ ID NO: 156) [Alkene@109] |
| Frac | 446.218 | 2 | −3.6 | 27.5 | 1.10E−03 | P0C0S8 | H2A1 | Histone H2A type 1 | KGNYAER (SEQ ID NO: 155) [Alkene@37] |
| Fil, Frac | 478.258 | 2 | −2.2 | 27.0 | 8.60E−03 | P62807 | H2B1C | Histone H2B type 1-C/E/F/G/I | LAHYNKR (SEQ ID NO: 181) [Alkene@86] |
| Fil | 478.258 | 2 | −2.2 | 27.0 | 8.60E−03 | P62807 | H2B1C | Histone H2B type 1-C/E/F/G/I | SRKESYSVYVYK (SEQ ID NO: 297) [Alkene@35] |
| Frac | 663.847 | 2 | −2.4 | 40.0 | 3.00E−05 | P0C0S8 | H2A1 | Histone H2A type 1 | NDEELNKLLGK (SEQ ID NO: 302) [Alkene@96] |
| Fil | 909.015 | 2 | 3.3 | 17.7 | 5.50E−03 | Q16778 | H2B2E | Histone H2B type 2-E | LLLPGELAKHAVSEGTK (SEQ ID NO: 156) [Alkene@109] |
| Fil | 446.221 | 2 | 3.2 | 22.7 | 2.80E−03 | P0C0S8 | H2A1 | Histone H2A type 1 | KGNYAER (SEQ ID NO: 155) [Alkene@37] |
| Fil, Frac | 478.258 | 2 | −2.2 | 27.0 | 8.60E−03 | Q16778 | H2B2E | Histone H2B type 2-E | LAHYNKR (SEQ ID NO: 181) [Alkene@86] |
| Frac | 663.847 | 2 | −2.4 | 40.0 | 3.00E−05 | P0C0S8 | H2A1 | Histone H2A type 1 | NDEELNKLLGK (SEQ ID NO: 302) [Alkene@96] |
| Fil | 730.917 | 2 | 3.2 | 16.6 | 2.40E−01 | Q71DI3 | H32 | Histone H3.2 | RYQKSTELLIR (SEQ ID NO: 309) [Alkene@57] |

TABLE 10-continued

| | | | | | | | | | | |
|---|---|---|---|---|---|---|---|---|---|---|
| Frac | 652.863 | 2 | -1.7 | 22.4 | 9.30E-03 | Q71DI3 | H32 | Histone H3.2 | YQKSTELLIR (SEQ ID NO: 310) | [Alkene@57] |
| Fil | 1057.134 | 2 | -6.4 | 38.1 | 7.20E-07 | P0C0S8 | H2A1 | Histone H2A type 1 | VTIAQGGVLPNIQAVLLPKK (SEQ ID NO: 179) | [Alkene@119] |
| Frac | 719.907 | 2 | -1.3 | 33.1 | 1.10E-03 | Q71DI3 | H32 | Histone H3.2 | VTIMPKDIQLAR (SEQ ID NO: 312) | [Alkene@123] |
| Lys | 478.258 | 2 | -2.2 | 27.0 | 8.60E-03 | Q8N257 | H2636 | Histone H2B type 3-B | LAHYNKR (SEQ ID NO: 181) | [Alkene@86] |
| Lys | 446.218 | 2 | -3.6 | 27.5 | 1.10E-03 | P0C0S8 | H2A1 | Histone H2A type 1 | KGNYAER (SEQ ID NO: 155) | [Alkene@37] |
| Lys | 478.258 | 2 | -2.2 | 27.0 | 8.60E-03 | Q93079 | H2B1H | Histone H2B type 1-H | LAHYNKR (SEQ ID NO: 181) | [Alkene@86] |
| Lys | 663.847 | 2 | -2.4 | 40.0 | 3.00E-05 | P0C0S8 | H2A1 | Histone H2A type 1 | NDEELNKLLGK (SEQ ID NO: 302) | [Alkene@96] |
| Fil | 478.258 | 2 | -2.2 | 27.0 | 8.60E-03 | Q99877 | H2B1N | Histone H2B type 1-N | LAHYNKR (SEQ ID NO: 181) | [Alkene@86] |
| Fil | 446.218 | 2 | -3.6 | 27.5 | 1.10E-03 | P0C0S8 | H2A1 | Histone H2A type 1 | KGNYAER (SEQ ID NO: 155) | [Alkene@37] |
| Fil, Lys | 478.258 | 2 | -2.2 | 27.0 | 8.60E-03 | Q99879 | H2B1M | Histone H2B type 1-M | LAHYNKR (SEQ ID NO: 181) | [Alkene@86] |
| Frac | 751.375 | 2 | -2.4 | 21.2 | 7.90E-02 | P0CG48 | UBC | Polyubiquitin-C | MQIFVKTLTGK (SEQ ID NO: 318) | [ThiolB@6 = 22] |
| Frac | 660.373 | 2 | -0.3 | 34.4 | 5.40E-05 | P0CG48 | UBC | Polyubiquitin-C | MQIFVKTLTGK (SEQ ID NO: 317) | [Alkene@6] |
| Frac | 700.882 | 2 | 2.5 | 22.0 | 8.80E-03 | P0CG48 | UBC | Polyubiquitin-C | LIFAGKQLEDGR (SEQ ID NO: 319) | [Alkene@48] |
| Frac | 379.711 | 2 | -1.1 | 15.0 | 1.10E-02 | Q71DI3 | H32 | Histone H3.2 | TKQTAR (SEQ ID NO: 294) | [Alkene@5] |
| Frac | 652.863 | 2 | -1.7 | 26.8 | 6.00E-03 | Q71DI3 | H32 | Histone H3.2 | YQKSTELLIR (SEQ ID NO: 310) | [Alkene@57] |
| Frac | 652.863 | 2 | -1.7 | 26.0 | 4.00E-04 | Q71DI3 | H32 | Histone H3.2 | YQKSTELLIR (SEQ ID NO: 310) | [Alkene@57] |
| Lys | 663.847 | 2 | -2.4 | 40.0 | 3.00E-05 | P20671 | H2A1D | Histone H2A type 1-D | NDEELNKLLGK (SEQ ID NO: 302) | [Alkene@96] |
| Lys | 719.907 | 2 | -1.3 | 33.1 | 1.10E-03 | Q71DI3 | H32 | Histone H3.2 | VTIMPKDIQLAR (SEQ ID NO: 312) | [Alkene@123] |

TABLE 10-continued

| | | | | | | | | | |
|---|---|---|---|---|---|---|---|---|---|
| Lys | 909.011 | 2 | -1.1 | 4.90E-06 | P23527 | H2B10 | Histone H2B type 1-O | LLLPGELAKHAVSEGTK (SEQ ID NO: 156) | [Alkene@109] |
| Lys | 446.221 | 2 | 3.2 | 2.80E-03 | Q93077 | H2A1C | Histone H2A type 1-C | KGNYAER (SEQ ID NO: 155) | [Alkene@37] |
| Lys | 478.258 | 2 | -2.2 | 8.60E-03 | P23527 | H2B10 | Histone H2B type 1-O | LAHYNKR (SEQ ID NO: 181) | [Alkene@86] |
| Lys | 478.258 | 2 | -2.2 | 8.60E-03 | P23527 | H2B10 | Histone H2B type 1-O | LAHYNKR (SEQ ID NO: 181) | [Alkene@86] |
| Frac | 667.011 | 3 | -2.7 | 3.10E-01 | P62807 | H2B1C | Histone H2B type 1-C/E/F/G/I | LLLPGELAKHAVSEGTK (SEQ ID NO: 299) | [ThiolB@109] |
| Frac | 507.611 | 3 | 2.8 | 6.40E-03 | P62805 | H4 | Histone H4 | TVTAMDVVYALKR (SEQ ID) | [Alkene@92 NO: 320] |
| Frac | 768.905 | 2 | -4.1 | 9.20E-04 | P62805 | H4 | Histone H4 | TVTAMDVVYALKR (SEQ ID NO: 321) | [Oxidation@85, Alkene@92] |
| Fil, Lys | 695.352 | 2 | -3.0 | 2.10E-04 | Q71DI3 | H32 | Histone H3.2 | EIAQDFKTDLR (SEQ ID NO: 164) | [Alkene@80] |
| Fil | 695.355 | 2 | 1.3 | 6.40E-03 | Q71DI3 | H32 | Histone H3.2 | EIAQDFKTDLR (SEQ ID NO: 164) | [Alkene@80] |
| Frac | 612.344 | 2 | 3.9 | 1.30E-04 | P62805 | H4 | Histone H4 | GGKGLGKGGAKR (SEQ ID NO: 160) | [Alkene@9 = 18, Acetyl@13 = 18, Acetyl@17 = 45] |
| Frac | 725.907 | 2 | -4.0 | 5.80E-04 | P62805 | H4 | Histone H4 | GKGGKGLGKGGAKR (SEQ ID NO: 322) | [Acetyl@13 = 27, Acetyl@17 = 55, Acetyl@6&Alkene@9|Acetyl @9&Alkene @6] |
| Lys | 909.011 | 2 | -1.1 | 1.90E-04 | Q93079 | H2B1H | Histone H2B type 1-H | LLLPGELAKHAVSEGTK (SEQ ID NO: 156) | [Alkene@109] |
| Frac | 573.809 | 2 | -4.0 | 9.10E-05 | P62807 | H2B1C | Histone H2B type 1-C/E/F/G/I | MPEPAKSAPARK (SEQ ID NO: 301) | [Met-loss@1, Alkene@6] |
| Fil, Frac | 446.218 | 2 | -3.6 | 1.10E-03 | Q6FI13 | H2A2A | Histone H2A type 2-A | KGNYAER (SEQ ID NO: 155) | [Alkene@37] |
| Fil, Frac | 478.258 | 2 | -2.2 | 8.60E-03 | P62807 | H2B1C | Histone H2B type 1-C/E/F/G/I | LAHYNKR (SEQ ID NO: 181) | [Alkene@86] |
| Frac | 663.847 | 2 | -2.4 | 3.00E-05 | Q6FI13 | H2A2A | Histone H2A type 2-A | NDEELNKLLGK (SEQ ID NO: 302) | [Alkene@96] |
| Fil, Frac | 909.011 | 2 | -1.1 | 4.90E-06 | P62807 | H2B1C | Histone H2B type 1-C/E/F/G/I | LLLPGELAKHAVSEGTK (SEQ ID NO: 156) | [Alkene@109] |

TABLE 10-continued

| | | | | | | | | |
|---|---|---|---|---|---|---|---|---|
| Frac | 379.711 | 2 | -1.1 | 19.5 | 3.90E-03 | Q71DI3 | H32 | Histone H3.2 | TKQTAR (SEQ ID NO: 294) [Alkene@5] |
| Frac | 446.218 | 2 | -3.6 | 27.5 | 1.10E-03 | Q96KK5 | H2A1H | Histone H2A type 1-H | KGNYAER (SEQ ID NO: 155) [Alkene@37] |
| Frac | 478.258 | 2 | -2.2 | 27.0 | 8.60E-03 | P62807 | H2B1C | Histone H2B type 1-C/E/F/G/I | LAHYNKR (SEQ ID NO: 181) [Alkene@86] |
| Frac | 663.847 | 2 | -2.4 | 40.0 | 3.00E-05 | Q96KK5 | H2A1H | Histone H2A type 1-H | NDEELNKLLGK (SEQ ID NO: 302) [Alkene@96] |
| Frac | 496.784 | 2 | -2.9 | 26.5 | 6.50E-05 | Q15149 | PLEC | Plectin | GHLSGLAKR (SEQ ID NO: 323) [Alkene@923] |
| Frac | 496.784 | 2 | -2.9 | 26.5 | 6.50E-05 | Q13765 | NACA | Nascent polypeptide-associated complex subunit alpha | GHLSGLAKR (SEQ ID NO: 323) [Alkene@923] |
| Frac | 446.221 | 2 | 3.2 | 22.7 | 2.80E-03 | Q6FI13 | H2A2A | Histone H2A type 2-A | KGNYAER (SEQ ID NO: 155) [Alkene@37] |
| Frac | 532.308 | 3 | -0.2 | 21.2 | 5.70E-03 | Q71DI3 | H32 | Histone H3.2 | RVTIMPKDIQLAR (SEQ ID NO: 178) [Alkene@123] |
| Frac | 480.274 | 3 | -0.8 | 16.2 | 1.80E-01 | Q71DI3 | H32 | Histone H3.2 | VTIMPKDIQLAR (SEQ ID NO: 312) [Alkene@123] |
| Frac | 652.863 | 2 | -1.7 | 22.4 | 9.30E-03 | Q71DI3 | H32 | Histone H3.2 | YQKSTELLIR (SEQ ID NO: 310) [Alkene@57] |
| Frac | 1057.134 | 2 | -6.4 | 38.1 | 7.20E-07 | Q6FI13 | H2A2A | Histone H2A type 2-A | VTIAQGGVLPNIQAVLLPKK (SEQ ID NO: 179) [Alkene@119] |
| Frac | 1148.143 | 2 | -1.2 | 20.3 | 1.70E-03 | Q6FI13 | H2A2A | Histone H2A type 2-A | VTIAQGGVLPNIQAVLLPKK (SEQ ID NO: 324) [ThioIB@119] |
| Frac | 727.903 | 2 | -3.3 | 27.4 | 1.10E-03 | Q71DI3 | H32 | Histone H3.2 | VTIMPKDIQLAR (SEQ ID NO: 313) [Oxidation@121, Alkene@123] |
| Frac | 478.258 | 2 | -2.2 | 26.6 | 1.30E-02 | Q6FI13 | H2A2A | Histone H2A type 2-A | KGNYAER (SEQ ID NO: 155) [Alkene@37] |
| Frac | 446.218 | 2 | -3.6 | 27.5 | 1.10E-03 | Q6FI13 | H2A2A | Histone H2A type 2-A | KGNYAER (SEQ ID NO: 155) [Alkene@37] |
| Frac | 478.258 | 2 | -2.2 | 27.0 | 8.60E-03 | Q99880 | H2B1L | Histone H2B type 1-L | LAHYNKR (SEQ ID NO: 181) [Alkene@86] |
| Frac | 663.847 | 2 | -2.4 | 40.0 | 3.00E-05 | Q6FI13 | H2A2A | Histone H2A type 2-A | NDEELNKLLGK (SEQ ID NO: 302) [Alkene@96] |

TABLE 10-continued

| | | | | | | | | | | |
|---|---|---|---|---|---|---|---|---|---|---|
| Lys | 719.907 | 2 | -1.3 | 33.1 | 1.10E-03 | Q71DI3 | H32 | Histone H3.2 | VTIMPKDIQLAR (SEQ ID NO: 312) | [Alkene@123] |
| Lys | 909.011 | 2 | -1.1 | 31.3 | 4.90E-06 | Q93079 | H2B1H | Histone H2B type 1-H | LLLPGELAKHAVSEGTK (SEQ ID NO: 156) | [Alkene@109] |
| Frac | 719.907 | 2 | -1.3 | 33.1 | 1.10E-03 | Q71DI3 | H32 | Histone H3.2 | VTIMPKDIQLAR (SEQ ID NO: 312) | [Alkene@123] |
| Frac | 909.011 | 2 | -1.1 | 31.3 | 4.90E-06 | Q99880 | H2B1L | Histone H2B type 1-L | LLLPGELAKHAVSEGTK (SEQ ID NO: 299) | [ThiolB@109] |
| Frac | 573.809 | 2 | -4.0 | 24.8 | 5.40E-05 | O60814 | H2B1K | Histone H2B type 1-K | MPEPAKSAPAPK (SEQ ID NO: 301) | [Met-loss@1, Alkene@6] |
| Frac | 573.808 | 2 | -5.8 | 21.4 | 1.20E-03 | O60814 | H2B1K | Histone H2B type 1-K | MPEPAKSAPAPK (SEQ ID NO: 301) | [Met-loss@1, Alkene@6] |
| Fil, Lys | 467.721 | 2 | -2.7 | 10.0 | 8.30E-01 | O60814 | H2B1K | Histone H2B type 1-K | SAPAPKK (SEQ ID NO: 325) | [ThiolB@12] |
| Frac, Lys | 478.258 | 2 | -2.2 | 26.6 | 1.30E-02 | O60814 | H2B1K | Histone H2B type 1-K | LAHYNKR (SEQ ID NO: 181) | [Alkene@86] |
| Fil, Frac, Lys | 517.310 | 2 | -2.5 | 31.5 | 1.20E-03 | P06733 | ENOA | Alpha-enolase | MSILKIHAR (SEQ ID NO: 326) | [Met-loss + Acetyl@1, Alkene@5] |
| Lys | 632.337 | 2 | -1.6 | 13.6 | 9.30E-01 | P06733 | ENOA | Alpha-enolase | TIAPALVSKK (SEQ ID NO: 327) | [ThiolB@80] |
| Fil, Lys | 589.806 | 2 | -0.4 | 16.5 | 3.50E-03 | P06733 | ENOA | Alpha-enolase | TAIGKAGYTDK (SEQ ID NO: 328) | [Alkene@233] |
| Frac | 656.340 | 2 | -4.8 | 21.9 | 6.10E-03 | P06748 | NPM | Nucleophosmin | TPKGPSSVEDIK (SEQ ID NO: 329) | [Alkene@239] |
| Frac | 573.743 | 2 | -1.6 | 11.5 | 1.40E-02 | P06748 | NPM | Nucleophosmin | SKGQESFK (SEQ ID NO: 203) | [ThiolB@223] |
| Frac | 674.817 | 2 | 2.4 | 10.5 | 6.70E-01 | P06748 | NPM | Nucleophosmin | SAPGGGSKVPQK (SEQ ID NO: 442) | [ThiolB@150] |
| Frac | 767.391 | 1 | -3.1 | 13.3 | 3.70E-01 | P06748 | NPM | Nucleophosmin | TPKGPSSVEDIK (SEQ ID NO: 329) | [Alkene@239] |
| Frac | 747.345 | 2 | -2.3 | 14.1 | 2.60E-01 | P06748 | NPM | Nucleophosmin | TPKGPSSVEDIK (SEQ ID NO: 330) | [Thiol@239] |
| Frac | 656.342 | 2 | -1.8 | 24.9 | 2.70E-05 | P06748 | NPM | Nucleophosmin | TPKGPSSVEDIK (SEQ ID NO: 330) | [ThiolB@239] |
| Frac | 363.213 | 2 | -0.7 | 22.0 | 7.80E-03 | P06748 | NPM | Nucleophosmin | TPKTPK (SEQ ID NO: 331) | [Alkene@236] |

TABLE 10-continued

| | | | | | | | | | | |
|---|---|---|---|---|---|---|---|---|---|---|
| Fil | 467.721 | 2 | -2.7 | 10.0 | 8.30E-01 | P06899 | H2B1J | Histone H2B type 1-J | SAPAPKK (SEQ ID NO: 325) | [ThiolB@12] |
| Fil | 478.261 | 2 | 4.1 | 14.1 | 8.60E-01 | P06899 | H2B1J | Histone H2B type 1-J | LAHYNKR (SEQ ID NO: 181) | [Alkene@86] |
| Frac | 514.765 | 2 | -3.1 | 27.5 | 4.20E-04 | P07197 | NFM | Neurofilament medium polypeptide | SPVEEAKSK (SEQ ID NO: 332) | [Alkene@691] |
| Frac | 555.246 | 2 | -0.5 | 15.6 | 3.10E-02 | P07197 | NFM | Neurofilament medium polypeptide | SPVEEKGK (SEQ ID NO: 229) | [ThiolB@625] |
| Frac | 620.821 | 2 | -5.8 | 23.4 | 8.20E-04 | P07197 | NFM | Neurofilament medium polypeptide | SPVSKSPVEEK (SEQ ID NO: 333) | [Alkene@671] |
| Frac | 392.215 | 2 | -2.5 | 16.3 | 4.10E-01 | P07197 | NFM | Neurofilament medium polypeptide | VEKPEK (SEQ ID NO: 334) | [Alkene@609] |
| Frac | 406.728 | 2 | -3.1 | 23.7 | 2.90E-03 | P07197 | NFM | Neurofilament medium polypeptide | KAESPVK (SEQ ID NO: 336) | [ThiolB@733] |
| Frac | 590.831 | 2 | -2.1 | 24.1 | 2.70E-04 | P07197 | NFM | Neurofilament medium polypeptide | SPVKATAPEVK (SEQ ID NO: 337) | [Alkene@514] |
| Frac | 901.338 | 2 | -2.9 | 26.0 | 1.40E-05 | P07197 | NFM | Neurofilament medium polypeptide | EKAGGEGGSEEEGSDK (SEQ ID NO: 338) | [ThiolB@776] |
| Frac | 721.361 | 2 | -1.5 | 12.7 | 1.20E-01 | P07197 | NFM | Neurofilament medium polypeptide | KEDIAVNGEVEGK (SEQ ID NO: 339) | [Alkene@797] |
| Frac | 721.852 | 2 | -2.9 | 42.7 | 1.10E-06 | P07197 | NFM | Neurofilament medium polypeptide | KEDIAVNGEVEGK (SEQ ID NO: 340) | [Alkene@797, Deamidated@803] |
| Frac | 386.713 | 2 | -1.6 | 28.4 | 2.00E-02 | P07197 | NFM | Neurofilament medium polypeptide | SKAEVGK (SEQ ID NO: 226) | [Alkene@693] |
| Frac | 940.433 | 2 | -4.1 | 21.9 | 4.30E-03 | P07197 | NFM | Neurofilament medium polypeptide | GVVTNGLDLSPADEKK (SEQ ID NO: 219) | [Deamidated@832, ThiolB@842] |
| Frac | 619.825 | 2 | 4.6 | 15.6 | 2.60E-02 | P07197 | NFM | Neurofilament medium polypeptide | VVVTKTVEK (SEQ ID NO: 235) | [ThiolB@856] |
| Frac | 464.242 | 2 | -1.6 | 23.7 | 2.70E-03 | P07197 | NFM | Neurofilament medium polypeptide | SPVEEKGK (SEQ ID NO: 229) | [ThiolB@625] |
| Frac | 716.837 | 2 | -2.2 | 14.0 | 9.20E-02 | P07197 | NFM | Neurofilament medium polypeptide | SPVPKSPVEEK (SEQ ID NO: 231) | [ThiolB@619] |
| Frac | 625.833 | 2 | -3.2 | 9.0 | 2.30E+00 | P07197 | NFM | Neurofilament medium polypeptide | SPVPKSPVEEK (SEQ ID NO: 231) | [ThiolB@619] |
| Frac | 884.931 | 2 | -3.4 | 22.7 | 1.70E-03 | P07197 | NFM | Neurofilament medium polypeptide | KVQSLQDEVAFLR (SEQ ID NO: 341) | [ThiolB@223] |

| | | | | | | | | |
|---|---|---|---|---|---|---|---|---|
| Frac | 536.797 | 2 | -1.6 | 25.6 | 8.70E-03 | P07197 | NFM | Neurofilament medium polypeptide | SEEKVVVTK (SEQ ID NO: 224) | [Alkene@851] |
| Frac | 710.358 | 2 | -1.9 | 36.1 | 1.70E-04 | P07197 | NFM | Neurofilament medium polypeptide | YAKLTEAAEQNK (SEQ ID NO: 305) | [Alkene@298] |
| Frac | 1047.990 | 2 | -5.3 | 52.5 | 1.00E-06 | P07197 | NFM | Neurofilament medium polypeptide | QKQASHAQLGDAYDQEIR (SEQ ID NO: 169) | [Gln->pyro-Glu@138, Alkene@139] |
| Frac | 625.305 | 2 | -2.5 | 31.8 | 1.90E-04 | P07197 | NFM | Neurofilament medium polypeptide | SAKEIAEYR (SEQ ID NO: 342) | [Alkene@314] |
| Frac | 469.239 | 3 | -3.3 | 15.1 | 1.40E-01 | P07197 | NFM | Neurofilament medium polypeptide | SAKEIAEYRR (SEQ ID NO: 343) | [Alkene@314] |
| Frac | 422.246 | 3 | -2.0 | 28.1 | 1.00E-03 | P07197 | NFM | Neurofilament medium polypeptide | VEKVTSHAIVK (SEQ ID NO: 344) | [Alkene@902] |
| Frac | 864.886 | 2 | -1.1 | 22.7 | 4.90E-04 | P07197 | NFM | Neurofilament medium polypeptide | TVEKITSEGGDGATK (SEQ ID NO: 232) | [ThiolB@860] |
| Frac | 483.217 | 2 | -5.3 | 15.9 | 5.80E-02 | P07197 | NFM | Neurofilament medium polypeptide | VEKPEK (SEQ ID NO: 335) | [ThiolB@609] |
| Frac | 661.353 | 2 | -0.8 | 23.4 | 9.80E-04 | P07197 | NFM | Neurofilament medium polypeptide | SPVPKSPVEEAK (SEQ ID NO: 345) | [Alkene@684] |
| Frac | 661.351 | 2 | -3.8 | 24.4 | 2.90E-04 | P07197 | NFM | Neurofilament medium polypeptide | SPVPKSPVEEAK (SEQ ID NO: 345) | [Alkene@684] |
| Frac | 625.834 | 2 | -1.6 | 26A | 3 40E-03 | P07197 | NFM | Neurofilament medium polypeptide | SPVPKSPVEEK (SEQ ID NO: 230) | [Alkene@619] |
| Frac | 620.824 | 2 | -1.0 | 39.3 | 9.30E-05 | P07197 | NFM | Neurofilament medium polypeptide | SPVSKSPVEEK (SEQ ID NO: 333) | [Alkene@671] |
| Frac | 620.824 | 2 | -1.0 | 26.3 | 1.60E-04 | P07197 | NFM | Neurofilament medium polypeptide | SPVSKSPVEEK (SEQ ID NO: 333) | [Alkene@671] |
| Frac | 661.370 | 2 | -2.6 | 30.5 | 4.30E-05 | P07197 | NFM | Neurofilament medium polypeptide | YITKSVTVTQK (SEQ ID NO: 346) | [Alkene@875] |
| Frac | 891.966 | 2 | -1.4 | 35.8 | 2.00E-05 | P07197 | NFM | Neurofilament medium polypeptide | VQHKFVEEIIEETK (SEQ ID NO: 348) | [Alkene@451] |
| Frac | 752.376 | 2 | 0.9 | 12.3 | 6.90E-01 | P07197 | NFM | Neurofilament medium polypeptide | YITKSVTVTQK (SEQ ID NO: 347) | [ThiolB@875] |
| Frac | 807.919 | 2 | -1.6 | 33.9 | 1.60E-06 | P07900 | HS90A | Heat shock protein HSP 90-alpha | ELISNSSDALDKIR (SEQ ID NO: 349) | [Alkene@58] |

TABLE 10-continued

| | | | | | | | | | |
|---|---|---|---|---|---|---|---|---|---|
| Frac | 668.826 | 2 | −3.0 | 14.0 | 1.50E−01 | P07910 | HNRPC | Heterogeneous nuclear ribonucleoproteins C1/C2 | LKGDDLQAIK (SEQ ID NO: 350) | [ThiolB@189] |
| Frac | 1452.754 | 1 | −2.8 | 25.9 | 9.40E−03 | P07910 | HNRPC | Heterogeneous nuclear ribonucleoproteins C1/C2 | QKVDSLLENLEK (SEQ ID NO: 351) | [Gln->pyro-Glu@205, Alkene@206] |
| Frac | 735.395 | 2 | −1.3 | 31.9 | 6.00E−05 | P07910 | HNRPC | Heterogeneous nuclear ribonucleoproteins C1/C2 | QKVDSLLENLEK (SEQ ID NO: 352) | [Alkene@206] |
| Frac | 652.272 | 2 | −2.9 | 10.0 | 2.50E−02 | P07910 | HNRPC | Heterogeneous nuclear ribonucleoproteins C1/C2 | SGFNSKSGQR (SEQ ID NO: 353) | [ThiolB@176] |
| Frac | 648.860 | 2 | −2.4 | 32.7 | 6.80E−04 | P08107 | HSP71 | Heat shock 70 kDa protein 1A/1B | STLEPVEKALR (SEQ ID NO: 354) | [Alkene@319] |
| Fil, Frac, Lys | 529.278 | 2 | −3.5 | 32.3 | 6.30E−03 | P08107 | HSP71 | Heat shock 70 kDa protein 1A/1B | LSKEEIER (SEQ ID NO: 240) | [Alkene@512] |
| Frac | 351.182 | 2 | −1.4 | 18.0 | 5.30E−02 | P08107 | HSP71 | Heat shock 70 kDa protein 1A/1B | TGKGER (SEQ ID NO: 355) | [Alkene@190] |
| Frac | 799.920 | 2 | −3.6 | 31.5 | 1.40E−04 | P08238 | HS90B | Heat shock protein HSP 90-beta | ELISNASDALDKIR (SEQ ID NO: 307) | [Alkene@53] |
| Frac | 1147.091 | 2 | −3.1 | 22.0 | 3.40E−03 | P08670 | VIME | Vimentin | FLEQQNKILLAELEQLK (SEQ ID NO: 356) | [ThiolB@129] |
| Frac | 692.419 | 2 | −0.8 | 18.5 | 2.10E−02 | P08670 | VIME | Vimentin | RTLLIKTVETR (SEQ ID NO: 357) | [Alkene@445] |
| Frac | 614.369 | 2 | 0.0 | 20.7 | 1.10E−02 | P08670 | VIME | Vimentin | TLLIKTVETR (SEQ ID NO: 171) | [Alkene@445] |
| Frac | 885.437 | 2 | −1.8 | 29.0 | 4.70E−05 | P08670 | VIME | Vimentin | VESLQEEIAFLKK (SEQ ID NO: 358) | [ThiolB@235] |
| Frac | 821.405 | 2 | −3.1 | 45.2 | 3.30E−05 | P08670 | VIME | Vimentin | TNEKVELQELNDR (SEQ ID NO: 303) | [Alkene@104] |
| Frac | 714.377 | 1 | −1.5 | 7.8 | 1.60E−01 | P0C0S5 | H2AZ | Histone H2A.Z | GQQKTV (SEQ ID NO: 359) | [Alkene@126] |
| Frac | 714.377 | 2 | −1.5 | 7.8 | 1.00E−01 | P0C0S5 | H2AZ | Histone H2A.Z | KGQQK (SEQ ID NO: 360) | [Alkene@122] |
| Frac | 657.886 | 2 | 1.5 | 16.9 | 8.50E−03 | P10412 | H14 | Histone H1.4 | SLVSKGTLVQTK (SEQ ID NO: 361) | [Alkene@90] |
| Fil | 348.706 | 2 | 1.2 | 18.5 | 1.80E−02 | P10412 | H14 | Histone H1.4 | KPAGAAK (SEQ ID NO: 362) | [Alkene@130] |
| Fil | 363.250 | 2 | 1.0 | 19.9 | 1.30E−02 | P10412 | H14 | Histone H1.4 | IKLGLK (SEQ ID NO: 363) | [Alkene@81] |

TABLE 10-continued

| | | | | | | | | | |
|---|---|---|---|---|---|---|---|---|---|
| Frac | 363.249 | 2 | -1.7 | 16.5 | 3.10E-02 | P10412 | H14 | Histone H1.4 | IKLGLK (SEQ ID NO: 363) | [Alkene@81] |
| Frac | 499.814 | 2 | -3.7 | 32.5 | 2.10E-04 | P10412 | H14 | Histone H1.4 | LGLKSLVSK (SEQ ID NO: 364) | [Alkene@85] |
| Frac | 657.883 | 2 | -3.1 | 9.0 | 7.40E-01 | P10412 | H14 | Histone H1.4 | SLVSKGTLVQTK (SEQ ID NO: 361) | [Alkene@90] |
| Lys | 404.701 | 2 | 0.5 | 8.9 | 9.20E-01 | P10412 | H14 | Histone H1.4 | TPVKK (SEQ ID NO: 365) | [ThiolB@21] |
| Fil | 884.018 | 2 | 5.1 | 24.9 | 2.10E-03 | P10809 | CH60 | 60 kDa heat shock protein, mitochondrial | RGVMLAVDAVIAELKK (SEQ ID NO: 366) | [Alkene@156] |
| Fil | 424.237 | 2 | -0.6 | 22.9 | 1.10E-01 | P10809 | CH60 | 60 kDa heat shock protein, mitochondrial | YKNIGAK (SEQ ID NO: 367) | [Alkene@91] |
| Frac, Lys | 390.690 | 2 | -2.0 | 8.4 | 5.30E+00 | P12277 | KCRB | Creatine kinase B-type | LQKR (SEQ ID NO: 368) | [ThiolB@319] |
| Lys | 513.315 | 2 | -1.4 | 30.7 | 7.90E-03 | P13639 | EF2 | Elongation factor 2 | LIEKLDIK (SEQ ID NO: 369) | [Alkene@318] |
| Fil | 527.320 | 2 | 2.3 | 18.9 | 2.80E-03 | P14314 | GLU2B | Glucosidase 2 subunit beta | KLIELQAGK (SEQ ID NO: 370) | [Alkene@158] |
| Fil | 363.250 | 2 | 1.0 | 19.9 | 1.30E-02 | P16403 | H12 | Histone H1.2 | IKLGLK (SEQ ID NO: 363) | [Alkene@81] |
| Frac | 1078.015 | 2 | -8.5 | 29.9 | 1.30E-04 | P19338 | NUCL | Nucleolin | TGISDVFAKNDLAVVDVR (SEQ ID NO: 371) | [ThiolB@333] |
| Frac | 607.859 | 2 | -3.0 | 34.9 | 1.50E-04 | P19338 | NUCL | Nucleolin | TLLAKNLPYK (SEQ ID NO: 372) | [Alkene@398] |
| Frac | 469.786 | 2 | -2.4 | 25.9 | 1.00E-04 | P19338 | NUCL | Nucleolin | KVAVATPAK (SEQ ID NO: 373) | [Alkene@71] |
| Frac, Lys | 607.860 | 2 | -1.3 | 23.0 | 4.60E-04 | P19338 | NUCL | Nucleolin | TLLAKNLPYK (SEQ ID NO: 372) | [Alkene@398] |
| Frac | 606.844 | 2 | -2.2 | 19.6 | 9.60E-04 | P20700 | LMNB1 | Lamin-B1 | KQLADETLLK (SEQ ID NO: 374) | [Alkene@182] |
| Frac | 832.906 | 2 | -4.5 | 19.6 | 1.80E-02 | P20700 | LMNB1 | Lamin-B1 | IQELEDLLAKEK (SEQ ID NO: 375) | [ThiolB@330] |
| Frac | 812.935 | 2 | -1.6 | 37.7 | 1.30E-05 | P20700 | LMNB1 | Lamin-B1 | VILKNSQGEEVAQR (SEQ ID NO: 376) | [Alkene@532] |
| Lys | 478.261 | 2 | 4.1 | 14.1 | 8.60E-01 | P23527 | H2B10 | Histone H2B type 1-O | LAHYNKR (SEQ ID NO: 181) | [Alkene@86] |

TABLE 10-continued

| | | | | | | | | | | |
|---|---|---|---|---|---|---|---|---|---|---|
| Lys | 1465.693 | 2 | -0.8 | 15.4 | 8.60E-02 | P23527 | H2B10 | Histone H2B type 1-O | QVHPDTGISSKAMGIMNSFVNDIFER (SEQ ID NO: 377) | [Gln->pyro-Glu@48, Alkene@58] |
| Frac | 510.770 | 2 | -3.2 | 22.0 | 1.70E-02 | P24534 | EF1B | Elongation factor 1-beta | LAQYESKK (SEQ ID NO: 378) | [ThiolB@129] |
| Lys | 651.342 | 3 | -0.5 | 22.9 | 1.80E-02 | P27824 | CALX | Calnexin | LLSKTPELNLDQFHDK (SEQ ID NO: 379) | [Alkene@170] |
| Fil | 611.845 | 2 | 3.0 | 25.5 | 1.60E-03 | P30101 | PDIA3 | Protein disulfide-isomerase A3 | TADGIVSHLKK (SEQ ID NO: 380) | [Alkene@129] |
| Fil | 728.387 | 2 | 3.0 | 30.7 | 1.70E-04 | P51572 | BAP31 | B-cell receptor-associated protein 31 | LEKAENQVLAMR (SEQ ID NO: 381) | [Alkene@204] |
| Frac | 662.881 | 2 | -2.7 | 12.8 | 6.80E-01 | P52272 | HNRPM | Heterogeneous nuclear ribonucleoprotein M | INEILSNALKR (SEQ ID NO: 382) | [Alkene@381] |
| Frac | 913.948 | 2 | -1.5 | 14.5 | 2.50E-01 | P61353 | RL27 | 60S ribosomal protein L27 | YSVDIPLDKTVVNK (SEQ ID NO: 383) | [ThiolB@93] |
| Frac | 822.945 | 2 | -1.0 | 18.7 | 1.90E-03 | P61353 | RL27 | 60S ribosomal protein L27 | YSVDIPLDKTVVNK (SEQ ID NO: 384) | [Alkene@93] |
| Fil | 626.848 | 2 | -0.7 | 27.6 | 2.30E-05 | P61604 | CH10 | 10 kDa heat shock protein, mitochondrial | GKGGEIQPVSVK (SEQ ID NO: 270) | [Alkene@56] |
| Frac, Lys | 356.228 | 2 | -3.5 | 11.6 | 8.40E-01 | P61978 | HNRPK | Heterogeneous nuclear ribonucleoprotein K | IKQIR (SEQ ID NO: 385) | [Alkene@411] |
| Frac | 356.228 | 2 | -3.5 | 16.8 | 2.90E-01 | P61978 | HNRPK | Heterogeneous nuclear ribonucleoprotein K | IKQIR (SEQ ID NO: 385) | [Alkene@411] |
| Fil, Frac, Lys | 335.697 | 2 | -2.3 | 21.5 | 5.30E-02 | P62805 | H4 | Histone H4 | GGKGLGK (SEQ ID NO: 159) | [Alkene@9] |
| Frac, Lys | 371.217 | 2 | 1.8 | 21.9 | 1.90E-02 | P62805 | H4 | Histone H4 | GLGKGGAK (SEQ ID NO: 162) | [Alkene@13] |
| Frac | 811.933 | 2 | -3.5 | 22.5 | 1.00E-01 | P62805 | H4 | Histone H4 | GVLKVFLENVIR (SEQ ID NO: 386) | [Alkene@60] |
| Frac | 573.809 | 2 | -4.0 | 24.8 | 5.40E-05 | P62807 | H2B1C | Histone H2B type 1-C/E/F/G/I | MPEPAKSAPAPK (SEQ ID NO: 301) | [Met-loss@1, Alkene@6] |
| Frac | 573.808 | 2 | -5.8 | 21.4 | 1.20E-03 | P62807 | H2B1C | Histone H2B type 1-C/E/F/G/I | MPEPAKSAPAPK (SEQ ID NO: 301) | [Met-loss@1, Alkene@6] |
| Frac | 467.721 | 2 | -2.7 | 10.0 | 8.30E-01 | P62807 | H2B1C | Histone H2B type 1-C/E/F/G/I | SAPAPKK (SEQ ID NO: 325) | [ThiolB@12] |

TABLE 10-continued

| | | | | | | | | | |
|---|---|---|---|---|---|---|---|---|---|
| Frac | 454.216 | 2 | -2.3 | 26.2 | 6.80E-03 | P20671 | H2A1D | Histone H2A type 1-D | KGNYSER (SEQ ID NO: 158) | [Alkene@37] |
| Fil, Frac | 478.258 | 2 | -2.2 | 26.6 | 1.30E-02 | P62807 | H2B1C | Histone H2B type 1-C/E/F/G/I | LAHYNKR (SEQ ID NO: 181) | [Alkene@86] |
| Frac | 1465.693 | 2 | -0.8 | 28.1 | 2.90E-04 | P62807 | H2B1C | Histone H2B type 1-C/E/F/G/I | QVHPDTGISSKAMGIMNSFVNDIFER (SEQ ID NO: 377) | [Gln->pyro-Glu@48, Alkene@58] |
| Fil | 781.896 | 2 | -0.1 | 17.3 | 1.90E-01 | P62807 | H2B1C | Histone H2B type 1-C/E/F/G/I | SRKESYSVYVYK (SEQ ID NO: 297) | [Alkene@35] |
| Lys | 559.308 | 4 | 1.0 | 33.5 | 2.40E-03 | P62826 | RAN | GTP-binding nuclear protein Ran | KYVATLGVEVHPLVFHTNR (SEQ ID NO: 387) | [Alkene@38] |
| Fil, Lys | 550.764 | 2 | -1.8 | 23.7 | 3.20E-04 | P62841 | RS15 | 40S ribosomal protein S15 | QHSLLKR (SEQ ID NO: 388) | [Gln->pyro-Glu@53, ThiolB@58] |
| Lys | 558.295 | 2 | -1.5 | 30.9 | 6.90E-05 | P62937 | PPIA | Peptidyl-prolyl cis-trans isomerase A | VPKTAENFR (SEQ ID NO: 390) | [Alkene@31] |
| Frac | 564.810 | 2 | -1.7 | 36.8 | 6.30E-04 | Q00839 | HNRPU | Heterogeneous nuclear ribonucleoprotein U | VSELKEELK (SEQ ID NO: 391) | [Alkene@17] |
| Fil, Frac | 531.938 | 3 | -1.6 | 22.6 | 3.00E-03 | Q00839 | HNRPU | Heterogeneous nuclear ribonucleoprotein U | TTWVTKHAAENPGK (SEQ ID NO: 392) | [Alkene@516] |
| Frac | 727.428 | 2 | -2.6 | 28.6 | 2.70E-04 | Q02878 | RL6 | 60S ribosomal protein L6 | IKAIPQLQGYLR (SEQ ID NO: 393) | [Alkene@262] |
| Frac | 442.699 | 2 | -2.1 | 9.3 | 3.30E-01 | Q14103 | HNRPD | Heterogeneous nuclear ribonucleoprotein D0 | IMEKK (SEQ ID NO: 394) | [ThiolB@242] |
| Frac | 789.885 | 2 | -1.7 | 18.2 | 8.80E-04 | Q15149 | PLEC | Plectin | TPVEVPVGGFKGR (SEQ ID NO: 395) | [Alkene@3384] |
| Frac | 586.798 | 2 | -1.6 | 26.6 | 2.00E-02 | Q15149 | PLEC | Plectin | SAEAELQSKR (SEQ ID NO: 396) | [Alkene@1718] |
| Frac | 920.918 | 2 | -1.6 | 25.5 | 9.90E-04 | Q15149 | PLEC | Plectin | QLAEAHAQAKAQAER (SEQ ID NO: 397) | [Gln->pyro-Glu@1511, ThiolB@1520] |
| Frac | 819.380 | 2 | 1.1 | 14.6 | 2.20E-01 | Q15149 | PLEC | Plectin | VQKSLAAEEEAAR (SEQ ID NO: 398) | [ThiolB@2129] |
| Frac | 328.197 | 2 | -2.8 | 13.8 | 3.90E-01 | Q15233 | NONO | Non-POU domain-containing octamer-binding protein | GKQLR (SEQ ID NO: 399) | [Alkene@137] |
| Frac | 573.809 | 2 | -4.0 | 24.8 | 5.40E-05 | Q16778 | H2B2E | Histone H2B type 2-E | MPEPAKSAPAPK (SEQ ID NO: 301) | [Met-loss@1, Alkene@6] |

TABLE 10-continued

| Category | Mass | Charge | Val1 | Val2 | E-val | Accession | Gene | Protein | Peptide (SEQ ID NO) | Modifications |
|---|---|---|---|---|---|---|---|---|---|---|
| Fil, Frac | 478.261 | 2 | 4.1 | 14.1 | 8.60E-01 | Q16778 | H2B2E | Histone H2B type 2-E | LAHYNKR (SEQ ID NO: 400) | [ThioIB@86] |
| Frac | 485.756 | 2 | -1.8 | 21.3 | 3.00E-01 | Q6FI13 | H2A2A | Histone H2A type 2-A | MSGRGKQGGK (SEQ ID NO: 401) | [Met-loss + Acetyl@1, Alkene@6] |
| Frac | 499.292 | 2 | -2.2 | 19.3 | 1.40E-01 | Q71DI3 | H32 | Histone H3.2 | KSTGKAPR (SEQ ID NO: 402) | [TriMethyl@10 = 27, Alkene@15 = 27] |
| Lys | 492.284 | 2 | -2.6 | 20.9 | 5.40E-02 | Q71DI3 | H32 | Histone H3.2 | KSTGKAPR (SEQ ID NO: 403) | [Dimethyl@10 = 35, Alkene@15 = 35] |
| Fil, Frac, Lys | 379.711 | 2 |  | 22.3 | 2.70E-02 | Q71DI3 | H32 | Histone H3.2 | TKQTAR (SEQ ID NO: 294) | [Alkene@5] |
| Frac | 743.867 | 2 | -0.9 | 16.1 | 1.20E-01 | Q71DI3 | H32 | Histone H3.2 | YQKSTELLIR (SEQ ID NO: 311) | [ThioIB@57] |
| Frac | 492.285 | 2 | -0.5 | 19.6 | 1.20E-01 | Q71DI3 | H32 | Histone H3.2 | KSTGKAPR (SEQ ID NO: 404) | [Dimethyl@10 = 24, Alkene@15 = 24] |
| Frac | 499.274 | 2 | -1.8 | 25.7 | 1.00E-03 | Q71DI3 | H32 | Histone H3.2 | KSTGKAPR (SEQ ID NO: 405) | [Acetyl@10&Alkene@15 Acetyl@15&Alkene@10] |
| Frac, Lys | 379.711 | 1 | -1.1 | 22.4 | 3.70E-01 | Q71DI3 | H32 | Histone H3.2 | TKQTAR (SEQ ID NO: 294) | [Alkene@5] |
| Fil | 895.502 | 2 | 2.7 | 12.7 | 8.10E-02 | Q71DI3 | H32 | Histone H3.2 | QLATKAAR (SEQ ID NO: 406) | [Gln->pyro-Glu@20, Alkene@24] |
| Frac | 470.718 | 2 | 6.4 | 11.7 | 2.60E-01 | Q71DI3 | H32 | Histone H3.2 | TKQTAR (SEQ ID NO: 295) | [ThioIB@5] |
| Frac | 719.905 | 2 | -4.1 | 12.8 | 2.50E-01 | Q71DI3 | H32 | Histone H3.2 | VTIMPKDIQLAR (SEQ ID NO: 312) | [Alkene@123] |
| Frac | 652.861 | 2 | -4.7 | 25.7 | 2.30E-03 | Q71DI3 | H32 | Histone H3.2 | YQKSTELLIR (SEQ ID NO: 310) | [Alkene@57] |
| Lys | 467.721 | 2 | -2.7 | 10.0 | 8.30E-01 | Q93079 | H2B1H | Histone H2B type 1-H | SAPAPKK (SEQ ID NO: 325) | [ThioIB@12] |
| Fil | 467.721 | 2 | -2.7 | 10.0 | 8.30E-01 | Q99877 | H2B1N | Histone H2B type 1-N | SAPAPKK (SEQ ID NO: 325) | [ThioIB@12] |
| Fil | 781.896 | 2 | -0.1 | 17.3 | 1.90E-01 | Q99877 | H2B1N | Histone H2B type 1-N | SRKESYSVVYK (SEQ ID NO: 297) | [Alkene@35] |
| Frac | 568.240 | 2 | -2.7 | 14.0 | 4.20E-03 | Q9NVA2 | SEPT11 | Septin-11 | THQEKK (SEQ ID NO: 407) | [ThioIB@378] |

TABLE 11

| Subunit ACC# | Protein Name | K-K linkage Sites | Bait |
|---|---|---|---|
| P25789-P62195 | alpha3:Rpt6 | alpha-3:K210-Rpt6:K402 | Rpt6 |
| P25789-P62195 | alpha3-Rpt6 | alpha3:K205-Rpt6:K330 | Rpt6 |
| P25789-P62195 | alpha3-Rpt6 | alpha3:K210-Rpt6:K393 | Rpt6 |
| O00487-P62195 | Rpn11-Rpt6 | Rpn11:K277-Rpt6:K55 | Rpn11 |
| P62195-Q99460 | Rpn2-Rpt6 | Rpn2:K720-Rpt6:K82 | Rpt6 |
| O00231-O00232 | Rpn5-Rpn6 | Rpn5:K207-Rpn6:K295 | Rpn11 |
| O00232-Q9UNM6 | Rpn5-Rpn9 | Rpn5:K368-Rpn9:K321 | Rpn11 |
| P62191-P62195 | Rpt2-Rpt6 | Rpt2:K258-Rpt6:K222 | Rpt6 |
| P43686-P62195 | Rpt3-Rpt6 | Rpt3:K238-Rpt6:K222 | Rpt6 |
| P43686-P62195 | Rpt3-Rpt6 | Rpt3:K80-Rpt6:K55 | Rpt6 |
| P62195-P62333 | Rpt4-Rpt6 | Rpt4:K72-Rpt6:K222 | Rpt6 |
| P08107-P11142 | HSPA1A-HSPA8 | HSPA1A:K512-HSPA8:K507 | Rpn11 |
| [P25789] | alpha-3 | K231-K239 | Rpt6 |
| [O00487] | Rpn11 | K257-K273 | Rpn11 |
| [O00487] | Rpn11 | K257-K277 | Rpn11 |
| [P17980] | Rpt5 | K70-K74 | Rpt6 |
| [P62195] | Rpt6 | K330-K335 | Rpt6 |
| [P62195] | Rpt6 | K393-K402 | Rpt6 |
| [P62195] | Rpt6 | K55-K82 | Rpt6 |
| [P62195] | Rpt6 | K82-K84 | Rpt6 |
| [P62195] | Rpt6 | K84-K94 | Rpt6 |
| [P62195] | Rpt6 | K88-K222 | Rpt6 |
| [P62195] | Rpt6 | K94-K222 | Rpt6 |
| [P13639] | EEF2 | K239-K318 | Rpt6 |
| [P13639] | EEF2 | K252-K259 | Rpt6 |
| [P08107] | HSPA1A | K507-K512 | Rpt6 |
| [P62841] | RPS15 | K58-K65 | Rpn11 |

TABLE 12

| MS1 m/z | MS1 z | ppm | P1 m/z | P1 z | P1 ppm | P1 score | P1 ev | P1 ACC | P1 protein | P1 peptide | P1 mod |
|---|---|---|---|---|---|---|---|---|---|---|---|
| 571.7661 | 4 | 0.059 | 719.858 | 2 | 0.5 | 15.4 | 2.10E-02 | Q99460 | Rpn2 | VINDKHDDVMAK (SEQ ID NO: 408) | XL:B-Alkene@720 |
| 540.2740 | 4 | 1.989 | 436.266 | 2 | 0.0 | 15.9 | 1.60E-01 | O00232 | Rpn5 | TQIISKK (SEQ ID NO: 409) | XL:B-Alkene@207 |
| 746.3817 | 4 | 0.305 | 550.286 | 2 | 3.9 | 24.7 | 9.10E-04 | O00232 | Rpn5 | IMAKYYTR (SEQ ID NO: 410) | XL:B-Alkene@368 |
| 534.7686 | 4 | 1.794 | 470.249 | 2 | 1.4 | 19 | 1.10E-02 | O00487 | Rpn11 | NVGKQDPK (SEQ ID NO: 411) | XL:B-Alkene@277 |
| 922.4770 | 4 | 9.846 | 878.969 | 2 | -9.8 | 23.3 | 3.60E-03 | P62191 | Rpt2 | WGSELIQKYLGDGPK (SEQ ID NO: 412) | XL:B-Alkene@258 |
| 659.8259 | 4 | 2.235 | 720.366 | 2 | -0.7 | 26 | 1.60E-04 | P43686 | Rpt3 | EFLHAQEVKR (SEQ ID NO: 413) | XL:B-Alkene@80 |
| 937.9707 | 4 | 0.243 | 909.974 | 2 | 1.2 | 27.4 | 1.70E-03 | P43686 | Rpt3 | WGSEFVQKYLGEGPR (SEQ ID NO: 414) | XL:B-Alkene@238 |
| 772.3973 | 4 | 1.131 | 578.828 | 2 | -0.5 | 31.7 | 7.30E-05 | P62333 | Rpt4 | FTVKATNGPR (SEQ ID NO: 415) | XL:B-Alkene@72 |
| 653.3353 | 4 | 0.571 | 574.845 | 2 | 0.1 | 21 | 6.40E-03 | P62195 | Rpt6 | LDILKIHSR (SEQ ID NO: 416) | XL:B-Alkene@330 |
| 676.3400 | 4 | 0.211 | 509.748 | 2 | 1.3 | 26.2 | 3.10E-03 | P62195 | Rpt6 | VMQKDSEK (SEQ ID NO: 417) | XL:B-Alkene@393 |
| 615.3207 | 4 | 0.094 | 478.715 | 2 | -2.4 | 13.3 | 5.70E-01 | P62195 | Rpt6 | NMSIKK (SEQ ID NO: 418) | XL:B-Thiol@402 |
| 820.0922 | 4 | 0.769 | 774.417 | 1 | -1.1 | 14.4 | 8.60E-01 | P62195 | Rpt6 | NMSIKK (SEQ ID NO: 419) | XL:B-Alkene@402 |
| 582.7930 | 3 | 1.964 | 529.282 | 2 | 0.0 | 24.5 | 3.60E-03 | P08107 | HSP1A/B | LSKEEIER (SEQ ID NO: 240) | XL:B-Alkene@512 |
| 769.3677 | 4 | 0.260 | 696.824 | 2 | 5.0 | 25.8 | 1.30E-03 | O00487 | Rpn11 | NYNKAVEEEDK (SEQ ID NO: 420) | XL:B-Alkene@257 |
| 633.5399 | 4 | 0.383 | 696.819 | 2 | 2.1 | 25.2 | 1.30E-03 | O00487 | Rpn11 | NYNKAVEEEDK (SEQ ID NO: 420) | XL:B-Alkene@257 |
| 614.2955 | 4 | 0.583 | 677.346 | 2 | 0.0 | 31 | 2.20E-05 | P17980 | Rpt5 | VTHELQAMKDK (SEQ ID NO: 421) | XL:B-Alkene@70 |
| 461.4756 | 4 | 0.470 | 499.276 | 2 | 0.0 | 21.4 | 9.00E-03 | P62195 | Rpt6 | NELNAKVR (SEQ ID NO: 422) | XL:B-Alkene@55 |
| 495.9291 | 3 | 0.855 | 414.669 | 2 | 0.0 | 8.5 | 5.20E-01 | P62195 | Rpt6 | AMDKK (SEQ ID NO: 423) | XL:B-Thiol@82 |
| 591.3166 | 3 | 2.046 | 640.440 | 1 | 0.0 | 8.1 | 7.10E-01 | P62195 | Rpt6 | KVLVK (SEQ ID NO: 425) | XL:B-Alkene@84 |
| 773.1585 | 4 | 2.684 | 580.346 | 2 | 1.7 | 29.8 | 3.20E-05 | P62195 | Rpt6 | VLVKVHPEGK (SEQ ID NO: 426) | XL:B-Alkene@88 |
| 863.9333 | 4 | 1.921 | 761.901 | 2 | 1.8 | 24.4 | 3.10E-04 | P62195 | Rpt6 | VHPEGKFVVDVDK (SEQ ID NO: 427) | XL:B-Alkene@94 |
| 541.7886 | 4 | 0.846 | 574.843 | 2 | 0.0 | 32.2 | 6.70E-05 | P62195 | Rpt6 | LDILKIHSR (SEQ ID NO: 416) | XL:B-Alkene@330 |
| 664.6444 | 3 | 0.819 | 509.748 | 2 | 0.0 | 24.1 | 8.40E-03 | P62195 | Rpt6 | VMQKDSEK (SEQ ID NO: 417) | XL:B-Alkene@393 |
| 601.7863 | 4 | 3.899 | 527.246 | 2 | 0.0 | 22.6 | 2.40E-03 | P25789 | α3 | KHEEEAK (SEQ ID NO: 428) | XL:B-Alkene@239 |
| 678.1033 | 4 | 6.140 | 742.878 | 2 | 0.0 | 22.9 | 2.60E-02 | P13639 | EEF2 | FAAKGEGQLGPAER (SEQ ID NO: 253) | XL:B-Alkene@239 |

TABLE 12-continued

| P2 m/z | P2 z | P2 ppm | P2 score | P2 ev | P2 ACC | P2 protein | P2 peptide | P2 mod | linkage | lysine-lysine linkage | Bait |
|---|---|---|---|---|---|---|---|---|---|---|---|
| 491.2270 | 4 | 1.168 | | | | | KVEDMMK (SEQ ID NO: 429) | XL:B-Thiol@252 | | | |
| 582.7930 | 4 | 1.964 | | | | | ITITNDKGR (SEQ ID NO: 239) | XL:B-Alkene@507 | | | |
| 531.6768 | 5 | -2.563 | | | | | QHSLLKR (SEQ ID NO: 389) | XL:B-Alkene@58 | | | |
| 646.323 | 1 | 0.2 | 7.4 | 5.70E-01 | P62195 | Rpt6 | AMDKK (SEQ ID NO: 424) | XL:B-Alkene@82 | Rpn2:Rpt6 | Rpn2-K720:Rpt6-K82 | Rpt6 |
| 544.271 | 2 | 3.1 | 20.9 | 7.70E-03 | O00231 | Rpn6 | CVAQASKNR (SEQ ID NO: 430) | XL:B-Alkene@295 | Rpn5:Rpn6 | Rpn5-K207:Rpn6-K295 | Rpn11 |
| 842.469 | 2 | 8.5 | 14.8 | 2.80E-02 | Q9UNM6 | Rpn9 | ALSVGLVKGSIDEVDK (SEQ ID NO: 431) | XL:B-Alkene@321 | Rpn5:Rpn9 | Rpn5-K368:Rpn9-K321 | Rpn11 |
| 499.276 | 2 | 2.2 | 27.7 | 3.40E-03 | P62195 | Rpt6 | NELNAKVR (SEQ ID NO: 422) | XL:B-Alkene@55 | Rpn11:Rpt6 | Rpn11-K277:Rpt6-K55 | Rpn11 |
| 865.958 | 2 | 0.9 | 31.3 | 5.60E-04 | P62195 | Rpt6 | VSGSELVQKFIGEGAR (SEQ ID NO: 432) | XL:B-Alkene@222 | Rpt2:Rpt6 | Rpt2-K258:Rpt6-K222 | Rpt6 |
| 499.274 | 2 | 0.2 | 27.6 | 3.20E-03 | P62195 | Rpt6 | NELNAKVR (SEQ ID NO: 422) | XL:B-Alkene@55 | Rpt3:Rpt6 | Rpt3-K80:Rpt6-K55 | Rpt6 |
| 865.959 | 2 | 0.9 | 29.5 | 1.10E-03 | P62195 | Rpt6 | VSGSELVQKFIGEGAR (SEQ ID NO: 432) | XL:B-Alkene@222 | Rpt3:Rpt6 | Rpt3-K238:Rpt6-K222 | Rpt6 |
| 865.956 | 2 | 0.9 | 31.5 | 4.00E-04 | P62195 | Rpt6 | VSGSELVQKFIGEGAR (SEQ ID NO: 432) | XL:B-Alkene@222 | Rpt4:Rpt6 | Rpt4-K72:Rpt6-K222 | Rpt6 |
| 631.816 | 2 | -3.9 | 22.4 | 2.50E-03 | P25789 | α3 | TMDVSKLSAEK (SEQ ID NO: 434) | XL:B-Alkene@205 | Rpt6:α3 | Rpt6-K330:α3-K205 | Rpt6 |
| 742.922 | 2 | 0.6 | 23.7 | 1.10E-03 | P25789 | α3 | LSAEKVEIATLTR (SEQ ID NO: 435) | XL:B-Alkene@210 | Rpt6:α3 | Rpt6-K393:α3-K210 | Rpt6 |
| 742.921 | 2 | 0.6 | 29.4 | 1.40E-04 | P25789 | α3 | LSAEKVEIATLTR (SEQ ID NO: 435) | XL:B-Alkene@210 | Rpt6:α3 | Rpt6-K402:α3-K210 | Rpt6 |
| 742.920 | 2 | 0.6 | 37.3 | 5.50E-05 | P25789 | α3 | LSAEKVEIATLTR (SEQ ID NO: 435) | XL:B-Alkene@210 | Rpt6:α3 | Rpt6-K402:α3-K210 | Rpt6 |
| 536.29 | 2 | 0.0 | 20.6 | 2.10E-02 | P11142 | HSPA8 | ITITNDKGR (SEQ ID NO: 239) | XL:B-Alkene@507 | HSPA1A/B:HSPA8* | HSPA1A/B-K512:HSPA8-K507 | Rpn11 |
| 741.910 | 2 | 0.2 | 20 | 7.90E-03 | O00487 | Rpn11 | MTPEQLAIKNVGK (SEQ ID NO: 436) | XL:B-Alkene@273 | Rpn11 | Rpn11-K257:Rpn11-K273 | Rpn11 |
| 470.250 | 2 | 3.5 | 16.6 | 4.20E-02 | O00487 | Rpn11 | NVGKQDPK (SEQ ID NO: 411) | XL:B-Alkene@277 | Rpn11 | Rpn11-K257:Rpn11-K277 | Rpn11 |
| 451.235 | 2 | 0.0 | 20.8 | 6.70E-03 | P17980 | Rpt5 | IKENSEK (SEQ ID NO: 437) | XL:B-Alkene@74 | Rpt5 | Rpt5-K70:Rpt5-K74 | Rpt6 |
| 646.324 | 1 | 0.0 | 8.9 | 4.80E-01 | P62195 | Rpt6 | AMDKK (SEQ ID NO: 424) | XL:B-Alkene@82 | Rpt6 | Rpt6-K55:Rpt6-K82 | Rpt6 |
| 640.440 | 1 | 0.0 | 12.6 | 1.60E-01 | P62195 | Rpt6 | KVLVK (SEQ ID NO: 425) | XL:B-Alkene@84 | Rpt6 | Rpt6-K82:Rpt6-K84 | Rpt6 |
| 568.937 | 3 | 0.0 | 26.6 | 1.00E-04 | P62195 | Rpt6 | VHPEGKFVDVDK (SEQ ID NO: 427) | XL:B-Alkene@94 | Rpt6 | Rpt6-K84:Rpt6-K94 | Rpt6 |
| 865.958 | 2 | 0.9 | 16.6 | 6.30E-02 | P62195 | Rpt6 | VSGSELVQKFIGEGAR (SEQ ID NO: 432) | XL:B-Alkene@222 | Rpt6 | Rpt6-K88:Rpt6-K222 | Rpt6 |
| 956.957 | 2 | -4.0 | 22.8 | 1.10E-02 | P62195 | Rpt6 | VSGSELVQKFIGEGAR (SEQ ID NO: 433) | XL:B-Thiol@222 | Rpt6 | Rpt6-K94:Rpt6-K222 | Rpt6 |

TABLE 12-continued

| | | | | | | | | |
|---|---|---|---|---|---|---|---|---|
| 408.724 | 2 | 0.0 | 21.6 | 1.40E-01 | P62195 | Rpt6 | KMNLTR (SEQ ID NO: 438) | XL:B-Alkene@335 | Rpt6 | Rpt6-K330:Rpt6-K335 | Rpt6 |
| 774.419 | 1 | 0.0 | 13.1 | 1.60E-01 | P62195 | Rpt6 | NMSIKK (SEQ ID NO: 419) | XL:B-Alkene@402 | Rpt6 | Rpt6-K393:Rpt6-K402 | Rpt6 |
| 576.323 | 2 | 0.0 | 18.3 | 3.30E-02 | P25789 | α3 | QKEVEQLIK (SEQ ID NO: 439) | XL:B-Alkene@231 | α3 | α3-K239:α3-K231 | Rpt6 |
| 513.315 | 2 | 0.0 | 20.6 | 1.60E-02 | P13639 | EEF2 | LIEKLDIK (SEQ ID NO: 369) | XL:B-Alkene@318 | EEF2 | EEF2-K239:EEF2-K318 | Rpt6 |
| 414.723 | 2 | 0.0 | 19.9 | 6.10E-03 | P13639 | EEF2 | KLWGDR (SEQ ID NO: 440) | XL:B-Alkene@259 | EEF2 | EEF2-K252:EEF2-K259 | Rpt6 |
| 529.282 | 2 | 0.0 | 26 | 1.10E-02 | P08107 | HSP1A/B | LSKEEIER (SEQ ID NO: 240) | XL:B-Alkene@512 | HSPA1A/1B | HSP1A/B-K507:HSP1A/B-K512 | Rpt6 |
| 512.611 | 3 | 0.0 | 18.7 | 8.10E-03 | P62841 | RPS15 | KEAPPMEKPEWK (SEQ ID NO: 277) | XL:B-Alkene@65 | RPS15 | RPS15-K58:RPS15-K65 | Rpn11 |

Note:
*since the identical sequence (ITINDKGR) present in both HSP1A and HSP8A, this identification could also present the inter-linked peptide within HSP1A protein.

DETAILED DESCRIPTION

Mass Spectrometry-Cleavable Cross-Linking Agents to Facilitate Structural Analysis of Proteins and Protein Complexes, and Method of Using Same Proteins form stable and dynamic multi-subunit complexes under different physiological conditions to maintain cell viability and normal cell homeostasis. Detailed knowledge of protein interactions and protein complex structures is fundamental to understanding how individual proteins function within a complex and how the complex functions as a whole. However, structural elucidation of large multi-subunit protein complexes has been difficult due to lack of technologies which can effectively handle their dynamic and heterogeneous nature. Traditional methods such as nuclear magnetic resonance (NMR) analysis and X-ray crystallography can yield detailed information on protein structures. However, NMR spectroscopy requires large quantities of pure protein in a specific solvent while X-ray crystallography is often limited by the crystallization process.

In recent years, chemical cross-linking coupled with mass spectrometry (MS) has become a powerful method for studying protein interactions. See for example the disclosures of Sinz, A. (2003) Chemical Cross-Linking and Mass Spectrometry for Mapping Three-Dimensional Structures of Proteins and Protein Complexes. *J Mass Spectrom.* 38, 1225-1237; Sinz, A. (2006) Chemical Cross-Linking and Mass Spectrometry to Map Three-Dimensional Protein Structures and Protein-Protein Interactions. *Mass Spectrom Rev* 25, 663-682; and Leitner, A., Walzthoeni, T., Kahraman, A., Herzog, F., Rinner, O., Beck, M., and Aebersold, R. (2010) Probing Native Protein Structures by Chemical Cross-Linking, Mass Spectrometry and Bioinformatics. *Molecular & Cellular Proteomics* 9, 1634-1649.

Chemical cross-linking stabilizes protein interactions through the formation of covalent bonds and allows the detection of stable, weak and/or transient protein-protein interactions in native cells or tissues See for example the disclosures of Sinz, A. (2010) Investigation of Protein-Protein Interactions in Living Cells by Chemical Cros slinking and Mass Spectrometry. *Anal Bioanal Chem* 397, 3433-3440; Vasilescu, J., Guo, X., and Kast, J. (2004) Identification of Protein-Protein Interactions Using in Vivo Cross-Linking and Mass Spectrometry. *Proteomics* 4, 3845-3854; Guerrero, C., Tagwerker, C., Kaiser, P., and Huang, L. (2006) An Integrated Mass Spectrometry-Based Proteomic Approach: Quantitative Analysis of Tandem Affinity-Purified in Vivo Cross-Linked Protein Complexes (Qtax) to Decipher the 26 S Proteasome-Interacting Network. *Mol Cell Proteomics* 5, 366-378; Tagwerker, C., Flick, K., Cui, M., Guerrero, C., Dou, Y., Auer, B., Baldi, P., Huang, L., and Kaiser, P. (2006) A Tandem Affinity Tag for Two-Step Purification under Fully Denaturing Conditions: Application in Ubiquitin Profiling and Protein Complex Identification Combined with in Vivocross-Linking. *Mol Cell Proteomics* 5, 737-748; Guerrero, C., Milenkovic, T., Przulj, N., Kaiser, P., and Huang, L. (2008) Characterization of the Proteasome Interaction Network Using a Qtax-Based Tag-Team Strategy and Protein Interaction Network Analysis. *Proc Natl Acad Sci USA* 105, 13333-13338; and Kaake, R. M., Milenkovic, T., Przulj, N., Kaiser, P., and Huang, L. (2010) Characterization of Cell Cycle Specific Protein Interaction Networks of the Yeast 26s Proteasome Complex by the Qtax Strategy. *J Proteome Res* 9, 2016-2019.

In addition to capturing protein interacting partners, many studies have shown that chemical cross-linking can yield low-resolution structural information about the constraints within a molecule. See for example the disclosures of Sinz, A. (2006) Chemical Cross-Linking and Mass Spectrometry to Map Three-Dimensional Protein Structures and Protein-Protein Interactions. *Mass Spectrom Rev* 25, 663-682; Leitner, A., Walzthoeni, T., Kahraman, A., Herzog, F., Rinner, O., Beck, M., and Aebersold, R. (2010) Probing Native Protein Structures by Chemical Cross-Linking, Mass Spectrometry and Bioinformatics. *Molecular & Cellular Proteomics* 9, 1634-1649; and Back, J. W., de Jong, L., Muijsers, A. O., and de Koster, C. G. (2003) Chemical Cross-Linking and Mass Spectrometry for Protein Structural Modeling. *J Mol Biol.* 331, 303-313, or protein complex, as disclosed in Rappsilber, J., Siniossoglou, S., Hurt, E. C., and Mann, M. (2000) A Generic Strategy to Analyze the Spatial Organization of Multi-Protein Complexes by Cross-Linking and Mass Spectrometry. *Anal Chem.* 72, 267-275; Maiolica, A., Cittaro, D., Borsotti, D., Sennels, L., Ciferri, C., Tarricone, C., Musacchio, A., and Rappsilber, J. (2007) Structural Analysis of Multiprotein Complexes by Cross-Linking, Mass Spectrometry, and Database Searching. *Mol Cell Proteomics* 6, 2200-2211; and Chen, Z. A., Jawhari, A., Fischer, L., Buchen, C., Tahir, S., Kamenski, T., Rasmussen, M., Lariviere, L., Bukowski-Wills, J. C., Nilges, M., Cramer, P., and Rappsilber, J. (2010) Architecture of the Rna Polymerase Ii-Tfiif Complex Revealed by Cross-Linking and Mass Spectrometry. *Embo J* 29, 717-726.

The application of chemical cross-linking, enzymatic digestion, and subsequent mass spectrometric and computational analysis for the elucidation of three dimensional protein structures offers distinct advantages over traditional methods due to its speed, sensitivity, and versatility. Identification of cross-linked peptides provides distance constraints that aid in constructing the structural topology of proteins and/or protein complexes.

Although this approach has been successful, effective detection and accurate identification of cross-linked peptides as well as unambiguous assignment of cross-linked sites remain extremely challenging due to their low abundance and complicated fragmentation behavior in MS analysis. See for the example the disclosures of Sinz, A. (2006) Chemical Cross-Linking and Mass Spectrometry to Map Three-Dimensional Protein Structures and Protein-Protein Interactions. *Mass Spectrom Rev* 25, 663-682; Leitner, A., Walzthoeni, T., Kahraman, A., Herzog, F., Rinner, O., Beck, M., and Aebersold, R. (2010) Probing Native Protein Structures by Chemical Cross-Linking, Mass Spectrometry and Bioinformatics. *Molecular & Cellular Proteomics* 9, 1634-1649; Back, J. W., de Jong, L., Muijsers, A. O., and de Koster, C. G. (2003) Chemical Cross-Linking and Mass Spectrometry for Protein Structural Modeling. *J Mol Biol.* 331, 303-313; and Schilling, B., Row, R. H., Gibson, B. W., Guo, X., and Young, M. M. (2003) Ms2assign, Automated Assignment and Nomenclature of Tandem Mass Spectra of Chemically Crosslinked Peptides. *J Am Soc Mass Spectrom.* 14, 834-850.

Therefore, new reagents and methods are urgently needed to allow unambiguous identification of cross-linked products and to improve the speed and accuracy of data analysis to facilitate its application in structural elucidation of large protein complexes.

A number of approaches have been developed to facilitate MS detection of low abundance cross-linked peptides from complex mixtures. These include selective enrichment using affinity purification with biotinylated cross-linkers, for example, as described in Trester-Zedlitz, M., Kamada, K., Burley, S. K., Fenyo, D., Chait, B. T., and Muir, T. W. (2003) A Modular Cross-Linking Approach for Exploring Protein Interactions. *J Am Chem Soc.* 125, 2416-2425; Tang, X., Munske, G. R., Siems, W. F., and Bruce, J. E. (2005) Mass Spectrometry Identifiable Cross-Linking Strategy for Studying Protein-Protein Interactions. *Anal Chem* 77, 311-318; and Chu, F., Mahrus, S., Craik, C. S., and Burlingame, A. L. (2006) Isotope-Coded and Affinity-Tagged Cross-Linking (Icatxl): An Efficient Strategy to Probe Protein Interaction Surfaces. *J Am Chem Soc* 128, 10362-10363, and click chemistry with alkyne-tagged (Chowdhury, S. M., Du, X., Tolic, N., Wu, S., Moore, R. J., Mayer, M. U., Smith, R. D., and Adkins, J. N. (2009) Identification of Cross-Linked Peptides after Click-Based Enrichment Using Sequential Collision-Induced Dissociation and Electron Transfer Dissociation Tandem Mass Spectrometry. *Anal Chem* 81, 5524-5532) or azide tagged cross-linkers, see for example Kasper, P. T., Back, J. W., Vitale, M., Hartog, A. F., Roseboom, W., de Koning, L. J., van Maarseveen, J. H., Muijsers, A. O., de Koster, C. G., and de Jong, L. (2007) An Aptly Positioned Azido Group in the Spacer of a Protein Cross-Linker for Facile Mapping of Lysines in Close Proximity. *Chembiochem* 8, 1281-1292; and Nessen, M. A., Kramer, G., Back, J., Baskin, J. M., Smeenk, L. E., de Koning, L. J., van Maarseveen, J. H., de Jong, L., Bertozzi, C. R., Hiemstra, H., and de Koster, C. G. (2009) Selective Enrichment of Azide-Containing Peptides from Complex Mixtures. *J Proteome Res* 8, 3702-3711.

In addition, Staudinger ligation has recently been shown to be effective for selective enrichment of azide-tagged cross-linked peptides (Vellucci, D., Kao, A., Kaake, R. M., Rychnovsky, S. D., and Huang, L. (2010) Selective Enrichment and Identification of Azide-Tagged Cross-Linked Peptides Using Chemical Ligation and Mass Spectrometry. *J Am Soc Mass Spectrom* 21, 1432-1445).

Apart from enrichment, detection of cross-linked peptides can be achieved by isotope-labeled, as described in Collins, C. J., Schilling, B., Young, M., Dollinger, G., and Guy, R. K. (2003) Isotopically Labeled Crosslinking Reagents: Resolution of Mass Degeneracy in the Identification of Cross-linked Peptides. *Bioorg Med Chem Lett.* 13, 4023-4026; Petrotchenko, E. V., Olkhovik, V. K., and Borchers, C. H. (2005) Isotopically Coded Cleavable Cross-Linker for Studying Protein-Protein Interaction and Protein Complexes. *Mol Cell Proteomics* 4, 1167-1179; and Petrotchenko, E., and Borchers, C. (2010) Icc-Class: Isotopically-Coded Cleavable Crosslinking Analysis Software Suite. *BMC bioinformatics* 11, 64, fluorescently labeled (Sinz, A., and Wang, K. (2004) Mapping Spatial Proximities of Sulfhydryl Groups in Proteins Using a Fluorogenic Cross-Linker and Mass Spectrometry. *Anal Biochem.* 331, 27-32), and mass-tag labeled cross-linking reagents, for example as described in Tang, X., Munske, G. R., Siems, W. F., and Bruce, J. E. (2005) Mass Spectrometry Identifiable Cross-Linking Strategy for Studying Protein-Protein Interactions. *Anal Chem* 77, 311-318; and Back, J. W., Hartog, A. F., Dekker, H. L., Muijsers, A. O., de Koning, L. J., and de Jong, L. (2001) A New Crosslinker for Mass Spectrometric Analysis of the Quaternary Structure of Protein Complexes. *J. Am. Soc. Mass Spectrom.* 12, 222-227.

These methods can identify cross-linked peptides with MS analysis, but interpretation of the data generated from inter-linked peptides (two peptides connected with the cross-link) by automated database searching remains difficult. Several bioinformatics tools have thus been developed to interpret MS/MS data and determine inter-linked peptide sequences from complex mixtures, as described in Maiolica, A. et al.; Schilling, B. et al.; Chu, F., Baker, P. R., *Burlingame, A. L., and Chalkley, R. J.* (2009) Finding Chimeras: A Bioinformatic Strategy for Identification of Cross-Linked Peptides. *Mol Cell Proteomics* 9, 25-31; Gao, Q., Xue, S., Shaffer, S. A., Doneanu, C. E., Goodlett, D. R., and Nelson, S. D. (2008) Minimize the Detection of False Positives by the Software Program Detectshift for 18o-Labeled Cross-Linked Peptide Analysis. *Eur J Mass Spectrom* (Chichester, Eng) 14, 275-280; Singh, P., Shaffer, S. A., Scherl, A., Holman, C., Pfuetzner, R. A., Larson Freeman, T. J., Miller, S. I., Hernandez, P., Appel, R. D., and Goodlett, D. R. (2008) Characterization of Protein Cross-Links Via Mass Spectrometry and an Open-Modification Search Strategy. *Anal Chem* 80, 8799-8806; Rinner, O., Seebacher, J., Walzthoeni, T., Mueller, L. N., Beck, M., Schmidt, A., Mueller, M., and Aebersold, R. (2008) Identification of Cross-Linked Peptides from Large Sequence Databases. *Nat Methods* 5, 315-318; Lee, Y. J., Lackner, L. L., Nunnari, J. M., and Phinney, B. S. (2007) Shotgun Cross-Linking Analysis for Studying Quaternary and Tertiary Protein Structures. *J Proteome Res* 6, 3908-3917; and Nadeau, O. W., Wyckoff, G. J., Paschall, J. E., Artigues, A., Sage, J., Villar, M. T., and Carlson, G. M. (2008) Crosssearch, a User-Friendly Search Engine for Detecting Chemically Cross-Linked Peptides in Conjugated Proteins. *Mol Cell Proteomics* 7, 739-749.

Although promising, further developments are still needed to make such data analyses as robust and reliable as analyzing MS/MS data of single peptide sequences using existing database searching tools (e.g. Protein Prospector, Mascot or SEQUEST).

Various types of cleavable cross-linkers with distinct chemical properties have been developed to facilitate MS identification and characterization of cross-linked peptides. These include UV photocleavable (Nadeau, O. W., Wyckoff, G. J., Paschall, J. E., Artigues, A., Sage, J., Villar, M. T., and Carlson, G. M. (2008) Crosssearch, a User-Friendly Search Engine for Detecting Chemically Cross-Linked Peptides in Conjugated Proteins. *Mol Cell Proteomics* 7, 739-749), chemical cleavable (Kasper, P. T., et al.), isotopically-coded cleavable (Petrotchenko, E. V., et al.), and MS-cleavable reagents, as described in Tang, X, et. al.; Back, J. W., et. al.; Zhang, H., Tang, X., Munske, G. R., Tolic, N., Anderson, G. A., and Bruce, J. E. (2009) Identification of Protein-Protein Interactions and Topologies in Living Cells with Chemical Cross-Linking and Mass Spectrometry. *Mol Cell Proteomics* 8, 409-420; Soderblom, E. J., and Goshe, M. B. (2006) Collision-Induced Dissociative Chemical Cross-Linking Reagents and Methodology: Applications to Protein Structural Characterization Using Tandem Mass Spectrometry Analysis. *Anal Chem* 78, 8059-8068; Soderblom, E. J., Bobay, B. G., Cavanagh, J., and Goshe, M. B. (2007) Tandem Mass Spectrometry Acquisition Approaches to Enhance Identification of Protein-Protein Interactions Using Low-Energy Collision-Induced Dissociative Chemical Crosslinking Reagents. *Rapid Commun Mass Spectrom* 21, 3395-3408; Lu, Y., Tanasova, M., Borhan, B., and Reid, G. E. (2008) Ionic Reagent for Controlling the Gas-Phase Fragmentation Reactions of Cross-Linked Peptides. *Anal Chem* 80, 9279-9287; and Gardner, M. W., Vasicek, L. A., Shabbir, S., Anslyn, E. V., and Brodbelt, J. S. (2008) Chromogenic Cross-Linker for the Characterization of Protein Structure by Infrared Multiphoton Dissociation Mass Spectrometry. *Anal Chem* 80, 4807-4819.

MS-cleavable cross-linkers have received considerable attention since the resulting cross-linked products can be identified based on their characteristic fragmentation behavior observed during MS analysis. Gas-phase cleavage sites result in the detection of a "reporter" ion (Back, J. W., et al.), single peptide chain fragment ions (Soderblom, E. J., and Goshe; Soderblom, E. J., Bobay, B. G., et al.; Lu, Y., et al. and Gardner, M. W. et al.), or both reporter and fragment ions (Tang, X., et al.; and Zhang, H. et. al.).

In each case, further structural characterization of the peptide product ions generated during the cleavage reaction can be accomplished by subsequent $MS^{n1}$ analysis. Among these linkers, the "fixed charge" sulfonium ion containing cross-linker developed by Lu. et. al appears to be the most attractive as it allows specific and selective fragmentation of cross-linked peptides regardless of their charge and amino acid composition based on their studies with model peptides.

Thus, in some embodiments, a novel cross-linking strategy for structural analysis of model proteins and the yeast 20 S proteasome complex by combining a newly designed MS-cleavable cross-linker bis(2,5-dioxopyrrolidin-1-yl) 3,3'-sulfinyldipropanoate ("DSSO") with an integrated data analysis workflow is provided. As noted herein, while this discussion has centered around DSSO (shown as Compound 1 in FIG. 1), other compounds having the General Structure 2, such as Compounds 3-6 can also be used.

In some embodiments, an effective approach that facilitates fast and accurate identification of DSSO cross-linked peptides by LC $MS^n$ is provided. In some embodiments, the new MS-cleavable cross-linker DSSO is attractive for cross-linking studies of protein complexes for a number of reasons: 1) it can be easily synthesized and can cross-link protein complexes effectively at sub-micromolar concentrations (~1 µM); 2) it has two symmetric CID labile C—S bonds that preferentially fragment prior to peptide backbone breakage; 3) the CID-induced cleavage of inter-linked peptides is specific and independent of peptide charges and sequences; 4) DSSO cross-linked peptides can generate characteristic fragmentation patterns in MS/MS spectra that are unique to different types of cross-linked peptides for easy identification; 5) there are unique mass and charge relationships between MS/MS peptide fragment ions and their parent ions, permitting automated data processing.

In comparison to existing MS-cleavable cross-linkers (Tang, X., et al.; Zhang, H., et al.; Soderblom, E. J., and Goshe, M. B. et al.; Soderblom, E. J., Bobay, B. G., et al.; and Gardner, M. W., et al.), in some embodiments, the DSSO cross-linker can provide a specific and selective fragmentation of cross-linked peptides for identification. The fragmentation patterns of DSSO cross-linked peptides are similar to those of "fixed charge" sulfonium ion containing cross-linked model peptides developed by Lu, Y. et al.

Although DSSO does not carry a fixed charge, in some embodiments, the preferential cleavage of C—S bond adjacent to the sulfoxide in DSSO is as effective as cleavage of the C—S bond in the sulfonium ion containing cross-linker (i.e. S-methyl 5,5'-thiodipentanoylhydroxysuccinimide) (Lu, Y. et al.).

Fragmentation of the sulfonium ion containing cross-linked peptide requires the formation of a five-membered ring with the sulfonium ion and the amide of the linker such that it is not feasible to change spacer lengths in these cross-linkers. In contrast, in some embodiments, the simple fragmentation mechanism gives DSSO the flexibility of changing its spacer lengths to accommodate cross-linking lysines at different distances while maintaining the symmetry of the linker with easily interpretable fragmentation patterns.

In addition, in some embodiments, DSSO has better potential for studying protein interactions by in vivo cross-linking. It is well known that cross-linking study of protein complexes is extremely challenging due to the inherent limitations of current cross-linkers. With the improvement on database searching of non-cleavable inter-linked peptides, it is possible to identify cross-linked peptides of protein complexes using non-cleavable cross-linkers (Maiolica, A., et al.; and Chen, Z. A. et al.). However, this requires a special program for data interpretation and the false positive rate of identifying inter-linked sequences is higher than that of identifying single sequences.

Thus, in some embodiments, the feasibility of using novel DSSO cross-linking strategy to study the structure of the yeast 20S proteasome complex is provided, which is a significant advancement in structural elucidation of multi-subunit protein complexes with improved data analysis and accuracy as such application of MS-cleavable cross-linkers has not been reported before.

In addition to the design of this novel MS-cleavable linker, in some embodiments, an integrated data analysis workflow to achieve fast, easy and accurate identification of cross-linked peptides and the cross-linking sites is provided. Identification of DSSO cross-linked peptides from complex mixtures has been accomplished with high confidence by integrating data analyses of three different datasets, MS, MS/MS and $MS^3$ data. Due to the difficulty in interpreting MS/MS spectra of unseparated inter-linked peptides, many of previously reported inter-linked products were determined only based on parent masses.

In contrast, in some embodiments, all of the inter-linked peptides of cytochrome c, ubiquitin and the yeast 20 S proteasome complex have been identified in this work with three lines of evidence including characteristic fragmentation pairs (Link-Finder), peptide sequence determination by $MS^3$ sequencing (Batch-Tag), and mass mapping (MS-Bridge). In some embodiments, this procedure permits the identification of cross-linked peptides with high accuracy, reliability and speed. It is important to note that existing database search programs can be easily adapted for analyzing DSSO cross-linked peptides, thus a broad application of the DSSO-based cross-linking strategy is foreseeable. Furthermore, in some embodiments, cross-linked peptides of cytochrome c with two links can be identified, suggesting the capability of the new cross-linking strategy for identifying more complex cross-linked products.

Cross-linking/mass spectrometry has been previously attempted to study the yeast 20S proteasome complex using $Ru(II)(bpy)_3^{2+/3}$ tris(2,2'-ipyridyl)ruthenium (II) dication)/ammonium persulfate/light-mediated cross-linking (Denison, C., and Kodadek, T. (2004) Toward a General Chemical Method for Rapidly Mapping Multi-Protein Complexes. *J Proteome Res* 3, 417-425), in which multiple subunit inter-connectivity has been determined based on MS identification of co-migrated subunits by SDS-PAGE after cross-linking. No cross-linked peptides were identified due to complicated chemistry of the radical based cross-linking reaction.

Therefore, in some embodiments, a successful use of a cross-linking/mass spectrometry strategy to determine inter-subunit and intra-subunit interaction interfaces of the yeast 20 S proteasome complex. In some embodiments, although only 13 inter-linked peptides of the yeast 20 S proteasome have been identified and reported here, this disclosure presents the first step toward full characterization of proteasome structures using cross-linking/mass spectrometry in the future. The feasibility of using the DSSO-based cross-linking strategy to identify cross-linked peptides of a large protein complex at 1 µM or less concentration is very significant and of great promise to structural studies of protein complexes since purifying protein complexes at high concentrations is technically challenging.

During LC MS" analysis using LTQ-Orbitrap XL MS, collision energy cannot be adjusted on the fly to account for differences in peptide charge states, therefore compromised collision energy is set during the entire LC MS" run. Thus, it is contemplated that there exists a possibility that the collision energy may be too high for the highly charged ions while too low for peptides with lower charges. It is contemplated that future improvement on charge selection and energy adjustment during LC MS" data acquisition may be needed to further enhance the quality of the results. Additionally, it is contemplated that optimized peptide separation prior to LC MS" analysis will be necessary to improve the dynamic range of peptide analysis and allow the detection of low abundance cross-linked peptides. Moreover, it is contemplated that refinement of the Link-Finder program is needed to improve the identification of intra-linked peptides. Lastly, it is contemplated that the addition of an affinity tag to the sulfoxide containing cross-linker will improve detection of cross-linked peptides, which will be the subject of future study.

Thus, in some embodiments, a new MS-cleavable cross-linker family of compounds, including DSSO that are applicable for model peptides, proteins and a multi-subunit protein complex is provided. The unique MS features of DSSO cross-linked peptides together with the integrated data analysis workflow for analyzing LC MS" data provided herein greatly reduce the time spent identifying cross-linked peptides. Given its simplicity, speed and accuracy, in some embodiments, this cross-linking strategy will have a broad application in elucidating structures of proteins and protein complexes in the future.

In some embodiments, a new crosslinking compound is provided and has the structure:

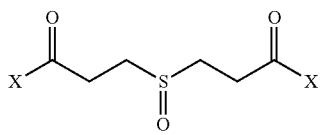

where x is selected from the group consisting of

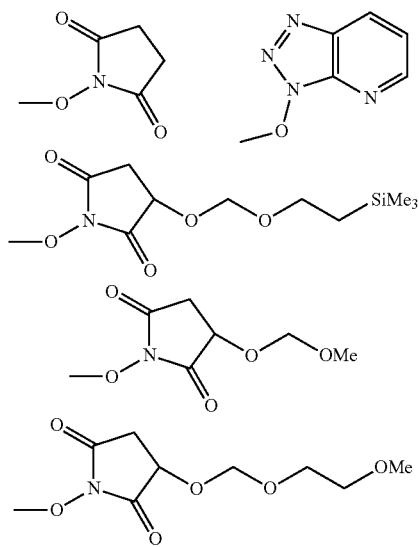

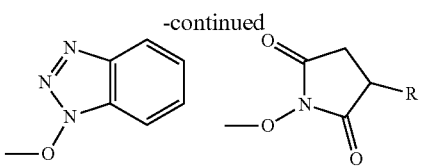

wherein R is methyl or ethyl, and

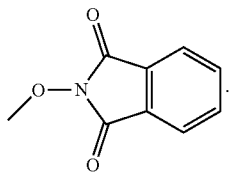

In some embodiments, the cross-linking agent is DSSO:

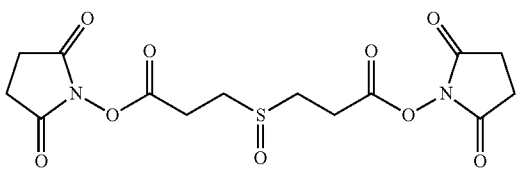 [SMILES: O=C(CCS(=O)CCC(=O)ON1C(=O)CCC1=O)ON1C(=O)CCC1=O]

In some embodiments, the new cross-linking agents are used to facilitate mapping of protein-protein interactions of protein complexes. In some embodiments, the method comprises the steps of providing a MS-cleavable cross-linker having the structure described above; forming a cross-linked protein complex by cross-linking proteins with the MS-cleavable cross-linker; forming cross-linked peptide fragments that are chemically bound to the MS-cleavable cross-linker by digesting the cross-linked protein complex with an enzyme such as trypsin; and using mass spectrometry (MS) and MS" analysis to identify the protein and/or peptide fragments. For convenience, in the discussion that follows, reference is sometimes made to the particular crosslinker, DSSO. It will be understood, however, that any of the other MS-cleavable crosslinkers that fit the general structure may also be used. Thus, DSSO fragments, DSSO remnants, DSSO cross-linked peptides, and like language applies equally to other crosslinkers as described herein.

The CID-induced separation of inter-linked peptides in MS/MS permits MS³ analysis of single peptide chain fragment ions with defined modifications (due to diamide remnants) for easy interpretation and unambiguous identification using existing database searching tools. Integration of data analyses from three generated datasets (MS, MS/MS and MS³) allows high confidence identification of DSSO cross-linked peptides. The efficacy of the newly developed DSSO-based cross-linking strategy has been demonstrated using model peptides and proteins. In addition, this method has been successfully employed for structural characterization of the yeast 20 S proteasome complex. In total, 13 non-redundant inter-linked peptides of the 20 S proteasome have been identified, representing the first application of an MS-cleavable cross-linker for the characterization of a multi-subunit protein complex. Given its effectiveness and simplicity, this cross-linking strategy can find a broad range of applications in elucidating structural topology of proteins and protein complexes.

In some embodiments, in combination with new software developed for data integration, DSSO cross-linked peptides were identified from complex peptide mixtures with speed and accuracy. Given its effectiveness and simplicity, in some embodiments, a broader application of this MS-cleavable cross-linker in the study of structural topology of other protein complexes using cross-linking and mass spectrometry is contemplated.

In order to develop a robust MS-cleavable cross-linking reagent, the incorporated MS-labile bond must have the ability to selectively and preferentially fragment prior to peptide backbone breakage independent of peptide charges and sequences. It is well documented that methionine sulfoxide containing peptides have preferential fragmentation at the C—S bond adjacent to the sulfoxide during collision induced dissociation (CID) analysis (see Reid, G. E., Roberts, K. D., Kapp, E. A., and Simpson, R. I. (2004) Statistical and Mechanistic Approaches to Understanding the Gas-Phase Fragmentation Behavior of Methionine Sulfoxide Containing Peptides. *J Proteome Res* 3, 751-759), and this fragmentation is dominant and much more labile than peptide bonds.

Such labile fragmentation has often been observed as the loss of 64 Da (—SOCH$_4$) from oxidized methionine containing peptides in routine peptide analysis. Therefore, in some embodiments, it is contemplated that if a sulfoxide is incorporated in the spacer region of a NHS ester, the C—S bond adjacent to the sulfoxide will be MS-labile and prone to preferential fragmentation.

In some embodiments, the synthesis of a CID cleavable cross-linker having a general structure of 3,3'-sulfinylbispropanoic acid, also known as 3,3-'sulfonyldipropanoic acid is provided. The molecular structure is $C_6H_{10}O_5S$, and it has a general structure as shown in General Structure 2 of FIG. 1 where X=—OH. In some embodiments, more specific cleaving agents are as shown in FIG. 1 including Compound 1, namely Disuccinimidyl Sulfoxide (sometimes hereinafter referred to as "DSSO"), which is one exemplary compound of the invention.

In some embodiments, other compounds where the X in the General Structure 2 are substituted are shown as Compounds 3-6 in FIG. 1. Hereinafter, while reference is made to DSSO, other MS-cleavable cross-linker having the general structure as shown in General Structure 2 of FIG. 1 are included as MS-cleavable cross-linkers of invention. Disuccinimidyl sulfoxide (DSSO) contains two NHS ester functional groups and two symmetric MS-labile C—S bonds adjacent to the sulfoxide (FIG. 2A). DSSO has a spacer length of 10.1 Å, making it well suited for detecting protein interaction interfaces of protein complexes and generating highly informative distance constraints. In comparison to existing MS-cleavable cross-linkers, DSSO can be easily synthesized in a two-step process as shown in FIG. 2A.

General chemicals were purchased from Fisher Scientific (Hampton, N.H.) or VWR International (West Chester, Pa.). Bovine heart cytochrome c (98% purity) and bovine erythrocyte ubiquitin (98% purity) were purchased from Sigma Aldrich (St. Louis, Mo.). Synthetic peptide Ac-IR7 (Ac-IEAEKGR (SEQ ID NO: 2), 98.1% purity) was synthesized by GL Biochem (Shanghai, China). Sequencing grade modified trypsin was purchased from Promega (Fitchburg, Wis.). The 20 S proteasome core particle was affinity purified using Pre1-TAP expressing yeast strain as previously described in Leggett, D. S., Hanna, J., Borodovsky, A., Crosas, B., Schmidt, M., Baker, R. T., Walz, T., Ploegh, H., and Finley, D. (20032) Multiple Associated Proteins Regulate Proteasome Structure and Function. *Mol Cell.* 10, 495-507.

FIG. 2A displays a two-step synthesis scheme of DSSO with an extended spacer length of 10.1 Å. Sulfide S-1 was first synthesized by mixing 3,3'-thiodipropionic acid (2.50 g, 14.0 mmol) with N-hydroxysuccinimide (3.30 g, 28.6 mmol) in dioxane (60 ml). The reaction mixture was stirred under an atmosphere of argon, and a solution of DCC (5.79 g, 28.1 mmol) in dioxane (20 ml) was added drop-wise. After 12 h, the insoluble urea was filtered from the reaction. The filtrate was concentrated to form a white solid. The solid residue was washed with cold diethyl ether followed by cold hexanes. After drying under reduced pressure, 5.20 g (70%) of sulfide S-1 was recovered and used without further purification: 1H (500 MHz, DMSO-d6) δ 3.02 (t, J=7.0 Hz, 4H), 2.86 (t, J=7.0 Hz, 4H), 2.81 (s, 8H); $^{13}$C (125 MHz, DMSO-d6) δ 170.1, 167.8, 31.4, 25.6, 25.4; IR (KBr pellet) 1801, 1732 cm$^{-1}$; HRMS (ES/MeOH) m/z calcd for $C_{14}H_{16}N_2O_8SNa$ [M+Na]$^+$ 395.0525, found 395.0531.

In some embodiments, to synthesize DSSO, a solution of sulfide S-1 (0.600 g, 1.61 mmol) in CHCl$_3$ (30 ml) at 0° C. was mixed with a solution of m-chloroperbenzoic acid (MCPBA) (0.371 g, 1.61 mmol) in CHCl$_3$ (10 ml). The reaction product was filtered and washed with cold CHCl$_3$ (10 ml) and cold MeOH (10 ml). The filtrate was cooled to −10° C. for 1 h, washed again with CHCl$_3$ and MeOH, and dried under reduced pressure to yield 0.400 g (64%) of DSSO: 1H (600 MHz, DMSO-d6) δ 3.28-3.21 (m, 2H), 3.17-3.13 (m, 4H), 3.08-2.99 (m, 2H), 2.88-2.75 (s, 8H); $^{13}$C (125 MHz, DMSO-d6) δ 170.08, 167.74, 44.62, 25.46, 23.41; IR (KBr pellet) 2943, 1786, 1720 cm$^{-1}$; HRMS (ES/MeOH) m/z calculated for $C_{14}H_{16}N_2O_9Na$ [M+Na]$^+$ 411.0474, found 411.0471.

In some embodiments, a similar synthetic approach is used to make the other symmetric diesters identified above and having the general structure 2, where X is as defined above. Thus, the symmetric sulfide is prepared by reacting 3,3'-thiodipropionic acid with the appropriate N-hydroxyamine (e.g., a functionalized analogue of N-hydroxysucinimide (compounds 4-7), or other N-hydroxy-functionalized heterocycle (compounds 3, 8, and 9), and then the sulfinyl group is made by treating the symmetric sulfide with MCPBA in CHCl$_3$ or another appropriate solvent.

CID Fragmentation Pattern of DSSO Cross-Linked Peptides

Three types of cross-linked peptides can be formed during the cross-linking reaction: inter-linked (type 2), intra-linked (type 1) and dead-end (type 0) modified peptides (Schilling, B., et al.), among which inter-linked peptides are the most informative for generating distance constraints. FIGS. 2B-D shows the proposed fragmentation schemes of DSSO cross-linked peptides. As shown in FIG. 2B, during CID analysis of a DSSO inter-linked peptide α-β, the cleavage of one C—S bond next to the sulfoxide separates the inter-linked peptide into a pair of peptide fragments, i.e. $α_A/β_S$, in which the α peptide fragment is modified with the alkene (A) moiety (+54 Da) and the β peptide fragment is modified with the sulfenic acid (S) moiety (+104 Da).

If peptides α and β have different sequences, two possible pairs of fragments (i.e. $α_A/β_S$ and $α_S/β_A$) will be observed due to the breakage of either of the two symmetric C—S bonds next to the sulfoxide in the spacer region of DSSO (FIG. 2B), thus resulting in four individual peaks in the MS/MS spectrum. But if peptides α and β have the same sequences, only one fragment pair, i.e. two peaks, will be detected in the MS/MS spectrum. To determine sequences of inter-linked peptides and assign the cross-linking site, the resulting peptide fragments (i.e. $α_A$, $β_S$, $α_S$, or $β_A$) generated in MS/MS can be further subjected to LTQ-Orbitrap XL MS for MS$^3$ analysis. Because these fragments represent single peptide sequences, the interpretation of the MS³ spectra by Batch-Tag program in Protein Prospector is identical to the identification of a single peptide with a defined modification (remnant of the cross-linker). This will dramatically simplify data interpretation and improve the identification accuracy of cross-linked products.

DSSO dead-end modified peptides have a defined mass modification (+176 Da) due to the half-hydrolyzed DSSO (FIG. 2C). MS/MS analysis of a dead-end modified peptide $\alpha_{DN}$ would result in two possible fragment ions, i.e. $\alpha_A$ and $\alpha_S$, due to the cleavage of the C—S bond on either side of the sulfoxide. The $\alpha_A$ and $\alpha_S$ fragments are called dead end fragment pair and the mass difference between these fragments correlates to the difference between the remnants of DSSO attached to the fragments. Similarly, intra-linked peptides (e.g. $\alpha_{intra}$) also have a defined mass modification (+158 Da) due to DSSO cross-linking of two distinct lysines in the same peptide sequence (FIG. 2D). The cleavage of the C—S bond will result in only one fragment peak in MS/MS with the same mass as the parent ion observed in MS. MS³ analysis of fragment ions detected in MS/MS will lead to the detection of y or b ions containing either alkene (A) or sulfenic acid (S) modifications.

As shown in FIG. 2E, the sulfenic acid containing fragment (e.g. $\alpha_S$, $\beta_S$, or $\alpha_{A+S}$) may undergo further fragmentation and lose a water molecule (−18 Da) to generate a new fragment containing an unsaturated thiol (T) moiety (+86 Da) (e.g. $\alpha_T$, $\beta_T$, or $\alpha_{A+T}$). Complications with data analysis are not expected as the thiol-containing fragment ion will become the dominant ion instead of the sulfenic acid modified fragment ion in the MS/MS spectrum. Thus, it is contemplated that the total number of pairs and peaks will remain similar as shown in FIGS. 2B-D. Due to specific and unique MS/MS fragmentation patterns for different types of DSSO cross-linked peptides, there are fixed mass relationships between parent ions and their fragment ions as listed in FIG. 2F.

For DSSO inter-linked peptides ($\alpha$-$\beta$), the mass sum of each fragment pair ($\alpha A/\beta_S$ or $\alpha_S/\beta_A$) is equivalent to the mass of the parent ion (FIG. 2F, Eq. 1). If $\alpha_S$ or $\beta_S$ loses a water and becomes $\alpha_T$ or $\beta_T$ respectively, the fragment pairs will be $\alpha_A/\beta_T$ and $\alpha_T/\beta_A$ and the mass sum of each fragment pair plus a water will be the same as the parent mass (FIG. 2F, Eq. 2).

As for the dead-end (DN) modified peptide $\alpha_{DN}$, each fragment (i.e. $\alpha_A$, $\alpha_S$ or $\alpha_T$) has a distinct mass difference from the parent ion (FIG. 2F, Eq. 3). For the intra-link peptide αintra, the fragment mass could be either the same as the parent mass (i.e. $\alpha_{A+S}$), or 18 Da less than the parent mass (i.e. $\alpha_{A+T}$) (FIG. 2F, Eq. 4). Moreover, there is a definite mass difference (Δ 32 Da) between the thiol (T) and alkene (A) modified forms of the same sequence (FIG. 2F, Eq. 5). These characteristic mass relationships have been incorporated into the Link-Finder program to identify DSSO cross-linked peptides.

LC MS″ analysis of DSSO cross-linked peptides was performed using a LTQ-Orbitrap XL MS (Thermo Scientific, San Jose, Calif.) with an on-line Eksigent NanoLC system (Eksigent, Dublin, Calif.). The LC separation was the same as previously described by Vellucci, D., et al. The MS″ method was set specifically for analyzing DSSO cross-linked peptides. Each acquisition cycle of a MS″ experiment includes one MS scan in FT mode (350-1800 m/z, resolution of 60,000 at m/z 400) followed by two data-dependent MS/MS scans with normalized collision energy at 10 or 15% on the top two peaks from the MS scan, and then three MS³ scans operated in LTQ with normalized collision energy at 29% on the top three peaks from each of the MS/MS scans. For initial analyses, MS/MS spectra were acquired in LTQ in LC MS″ experiments. For automated data analysis, MS/MS spectra were obtained in FT mode (resolution of 7500).

Characterization of DSSO Cross-Linked Model Peptides by MS″ Analysis

Figure 3:
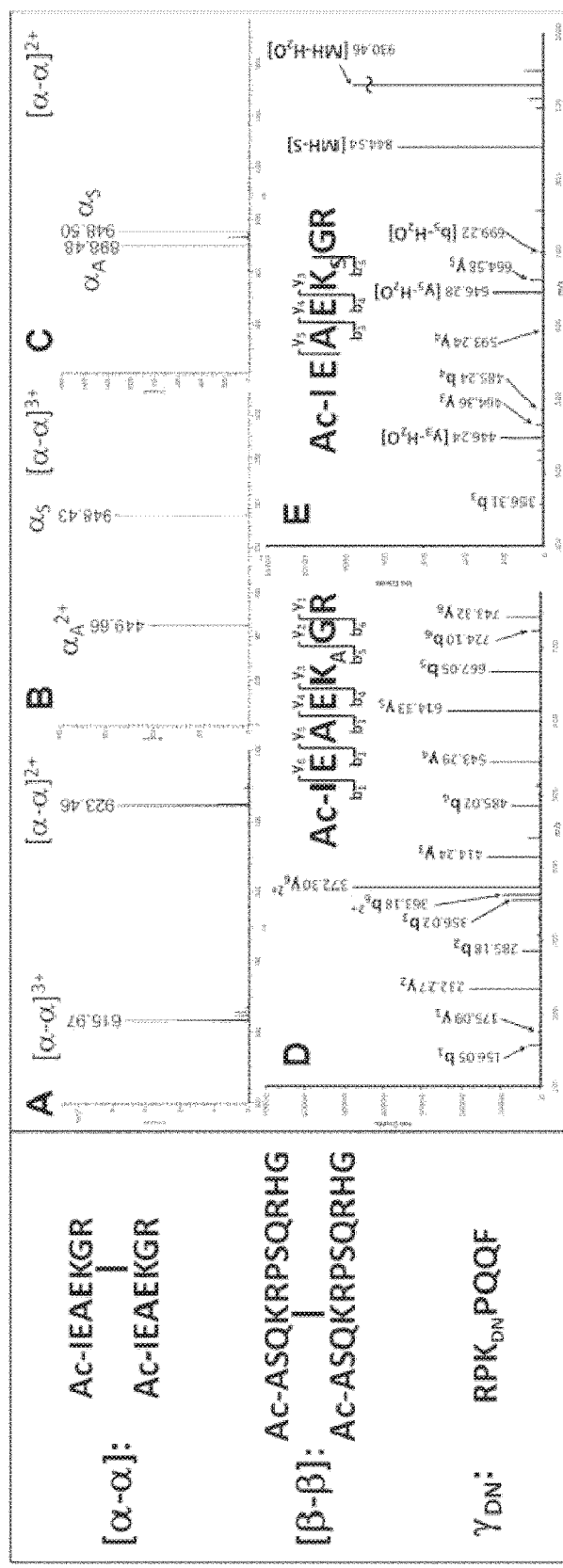
FIG. 3 is an exemplary MS$^n$ analysis of DSSO-cross-linked model peptides. A-E, MS$^n$ analysis of the DSSO-interlinked Ac-IR7 ($\alpha$-$\alpha$). A, MS spectrum of $\alpha$-$\alpha$: $[\alpha$-$\alpha]^{3+}$ (m/z 615.97$^{3+}$) and $[\alpha$-$\alpha]^{2+}$ (m/z 923.46$^{2+}$). B and C, MS/MS spectra of $[\alpha$-$\alpha]^{3+}$ (B) and $[\alpha$-$\alpha]^{2+}$ (C) in which alkene ($\alpha_A$) and sulfenic acid ($\alpha_S$) fragments were detected. D and E, MS$^3$ spectra of $\alpha_A$ (m/z 449.66$^{2+}$) (D) and $\alpha_S$ (m/z 948.43) (E). F-I, MS$^n$ analysis of DSSO-interlinked Ac-myelin ($\beta$-$\beta$). F, MS spectrum of $\beta$-$\beta$: $[\beta$-$\beta$3]$^{6+}$ (m/z 458.23$^{6+}$), $[\beta$-$\beta]^{5+}$ (m/z 549.68$^{5+}$), and $[\beta$-$\beta]^{4+}$ (m/z 686.84$^{4+}$). G-I, MS/MS spectra of $[\beta$-$\beta]^{6+}$ in which $\beta_A/\beta_T$ pair was observed (G), $[\beta$-$\beta]^{5+}$ in which the $\beta_A/\beta_S$ pair was observed (H), and $[\beta$-$\beta]^{4+}$ in which $\beta_A/\beta_S$ pair was observed (I). J-L, MS$^n$ analysis of DSSO dead end-modified substance P peptide $\gamma_{DN}$. J, MS spectrum of $\gamma_{DN}$ (m/z 538.76$^{2+}$). K, MS/MS spectrum of $\gamma_{DN}$ in which two fragments, $\gamma_A$ (m/z 478.03$^{2+}$) and $\gamma_S$ (m/z 502.95$^{2+}$), were detected. L, MS$^3$ spectrum of $\gamma_A$ (m/z 478.03$^{2+}$). Sequences of Ac-IR7, Ac-myelin, and substance P are Ac-IEAEKGR (SEQ ID NO: 2), Ac-ASQKRPSQRHG (SEQ ID NO: 6), and RPKPQQF (SEQ ID NO: 7), respectively.
Figure 3:
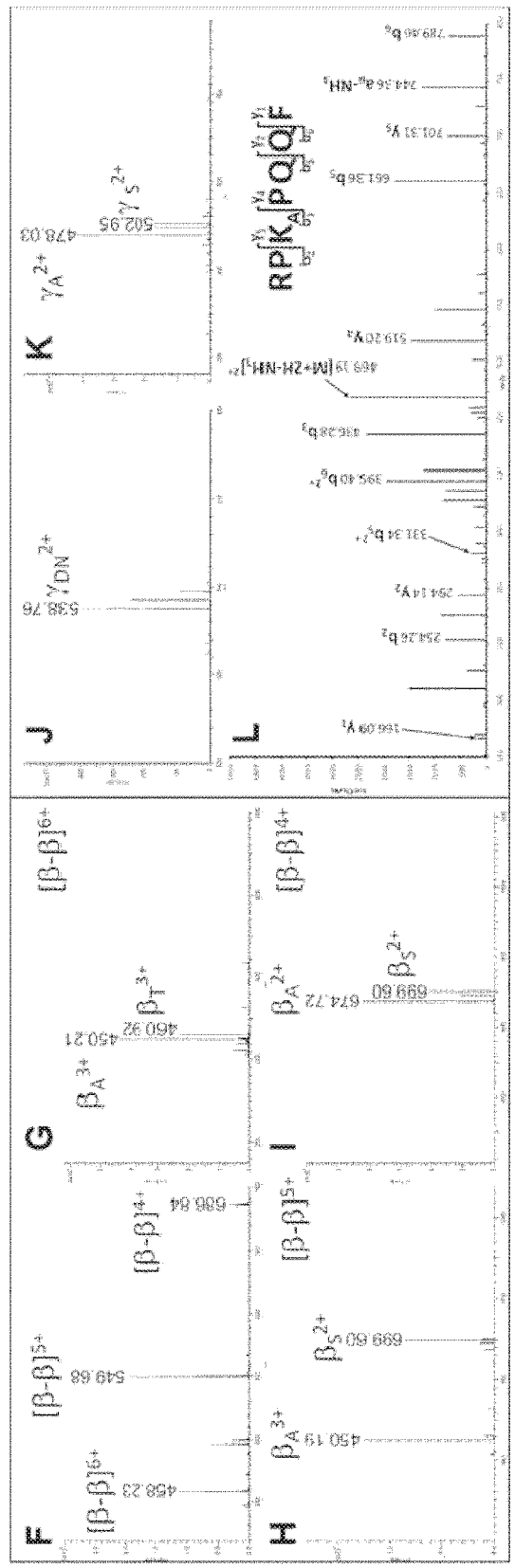

In some embodiments, in order to characterize the new DSSO linker, several model peptides were cross-linked including Ac-IR7, Ac-myelin, and substance P. Under the experimental conditions, the major cross-linked products for Ac-IR7 and Ac-myelin are inter-linked, whereas substance P mostly formed dead-end modified peptides. All of the cross-linked model peptides were subjected to LC MS″ analysis. The inter-linked Ac-IR7 peptide ($\alpha$-$\alpha$) was detected as doubly charged (m/z 923.46$^{2+}$) and triply charged (m/z 615.97$^{3+}$) ions (FIG. 3A). MS/MS analyses of the two differently charged parent ions resulted in two dominant fragment ions respectively (FIGS. 3B-C).

Cross-linking of synthetic peptides with DSSO was performed by dissolving synthetic peptides Ac-IR7, Ac-myelin and substance P in DMSO to 1 mM and cross-linked with DSSO dissolved in DMSO in a ratio of 1:1 in the presence of 1 equivalent diisopropylethylamine similarly as described Vellucci, D, et al. The cross-linked peptide solution was then diluted to 1 pmol/μl in 4% ACN, 0.1% formic acid for liquid chromatography multi-stage tandem mass spectrometry (LC MS') analysis.

Since the two inter-linked sequences are identical, only one fragment pair (i.e. $\alpha_A/\alpha_S$) was observed as expected. The results suggest that MS/MS fragmentation of inter-linked peptides is independent of peptide charges. It should be noted that besides unique mass relationships, the fragment ions in each pair have a defined charge relationship associated to the charge of the parent ion. In other words, the sum of the observed charges for each fragment in a pair equals the charge of the parent ion. For example, the triply charged parent ion (m/z 615.97$^{3+}$) generated the fragment pair with one doubly charged ($\alpha_A^{2+}$) and one singly charged ($\alpha_S^{1+}$) ion, whereas the doubly charge parent ion (m/z 923.46$^{2+}$) only produced a fragment pair with two singly charged ($\alpha_A^{1+}$ and $\alpha_S^+$) ions.

This information can be used to validate the fragment pairs identified by masses. The respective MS³ analysis of $\alpha_A$ and $\alpha_S$ ions (FIGS. 3D-E) allowed unambiguous identification of the peptide sequence and cross-linked site based on a series of y and b ions. Similar analysis was carried out for inter-linked Ac-myelin ($\beta$-$\beta$), and a characteristic fragment pair was observed in MS/MS spectra of the parent ion ($\beta$-$\beta$) at three different charge states (m/z 458.23$^{6+}$, 549.68$^{5+}$, 686.84$^{4+}$) respectively (FIGS. 3F-I), which represent the expected fragmentation of two identical inter-linked peptides.

While the fragment pair $\beta_A/\beta_S$ was detected in MS/MS spectra of quintuply and quadruply charged inter-linked Ac-myelin ($\beta$-$\beta$) (m/z 549.68$^{5+}$, 686.84$^{4+}$) (FIGS. 2H-I), the fragment pair $\beta_A/\beta_T$ was observed in the MS/MS spectrum of sextuply charged inter-linked Ac-myelin ($\beta$-$\beta$) (458.23$^{6+}$) (FIG. 3G). The $\beta_T$ fragment, namely the $\beta$ peptide fragment containing an unsaturated thiol (T) moiety (+86 Da), was generated due to the loss of H₂O from the sulfenic acid moiety on the $\beta_S$ fragment (FIG. 2E). This is likely due to excess collision energy deposited on the highest charged species as the collision energy chosen for CID analysis in LTQ-Orbitrap XL MS does not change with peptide charges during LC MS″ runs.

In addition to inter-linked peptides, dead-end modified peptides were analyzed. FIG. 2J displays the MS spectrum of the dead-end (DN) modified substance P ($\gamma_{DN}$, m/z 538.76$^{2+}$). As predicted in FIG. 2D, MS/MS analysis of $\gamma_{DN}$ led to two major fragments, the alkene ($\gamma$A, m/z 478.03$^{2+}$) and sulfenic acid ($\gamma_S$, m/z 502.95$^{2+}$) containing peptide fragments, representing the characteristic feature of dead-end modified peptides. The fragment ions carry the same charge state as the parent ion, and MS$^3$ analysis of the $\gamma_A$ fragment confirmed its sequence unambiguously (FIG. 3L). Taken together, the results clearly demonstrate that the new MS-cleavable bonds in DSSO are labile and can be preferentially fragmented prior to peptide bond breakage, and the desired fragmentation is independent of peptide charge states and sequences.

Characterization of DSSO Cross-Linked Peptides of Model Proteins by MS$^n$ Analysis In some embodiments, the applicability of DSSO for protein cross-linking under physiological conditions was evaluated. Model proteins cytochrome c (see for previously described Sinz, A. (2003); Kasper, P. T., et al.; Nessen, M. A., et al.; Vellucci, D., et al.; Lee, Y. J., et al.; Pearson, K. M., Pannell, L. K., and Fales, H. M. (2002) Intramolecular Cross-Linking Experiments on Cytochrome C and Ribonuclease a Using an Isotope Multiplet Method. *Rapid Commun. Mass Spectrom.* 16, 149-159; Dihazi, G. H., and Sinz, A. (2003) Mapping Low-Resolution Three-Dimensional Protein Structures Using Chemical Cross-Linking and Fourier Transform Ion-Cyclotron Resonance Mass Spectrometry. 17, 2005-2014; and Guo, X., Bandyopadhyay, P., Schilling, B., Young, M. M., Fujii, N., Aynechi, T., Guy, R. K., Kuntz, I. D., and Gibson, B. W. (2008) Partial Acetylation of Lysine Residues Improves Intraprotein Cross-Linking. *Anal Chem* 80, 951-960) and ubiquitin (Chowdhury, S. M., et al.; and Gardner, M. W., et al.) have been extensively utilized to test various new cross-linking strategies since they have a relatively large number of lysine residues accessible for cross-linking.

Cross-linking of Cytochrome C and Ubiquitin with DSSO was performed using lyophilized bovine cytochrome c or ubiquitin reconstituted in 1×PBS (pH 7.5) to 200 µM, 20 µl of which was mixed with 2 µl 20 mM DSSO (in DMSO) in a molar ratio of 1:10 (protein: cross-linker) for the cross-linking reaction as described in Vellucci, D., et al. The cross-linked protein was digested with trypsin (1% w/w) overnight at 37° C. The cross-linked peptide digest was then diluted to 1 pmol/µl in 4% ACN, 0.1% formic acid for LC MS$^n$ analysis.

Figure 4:
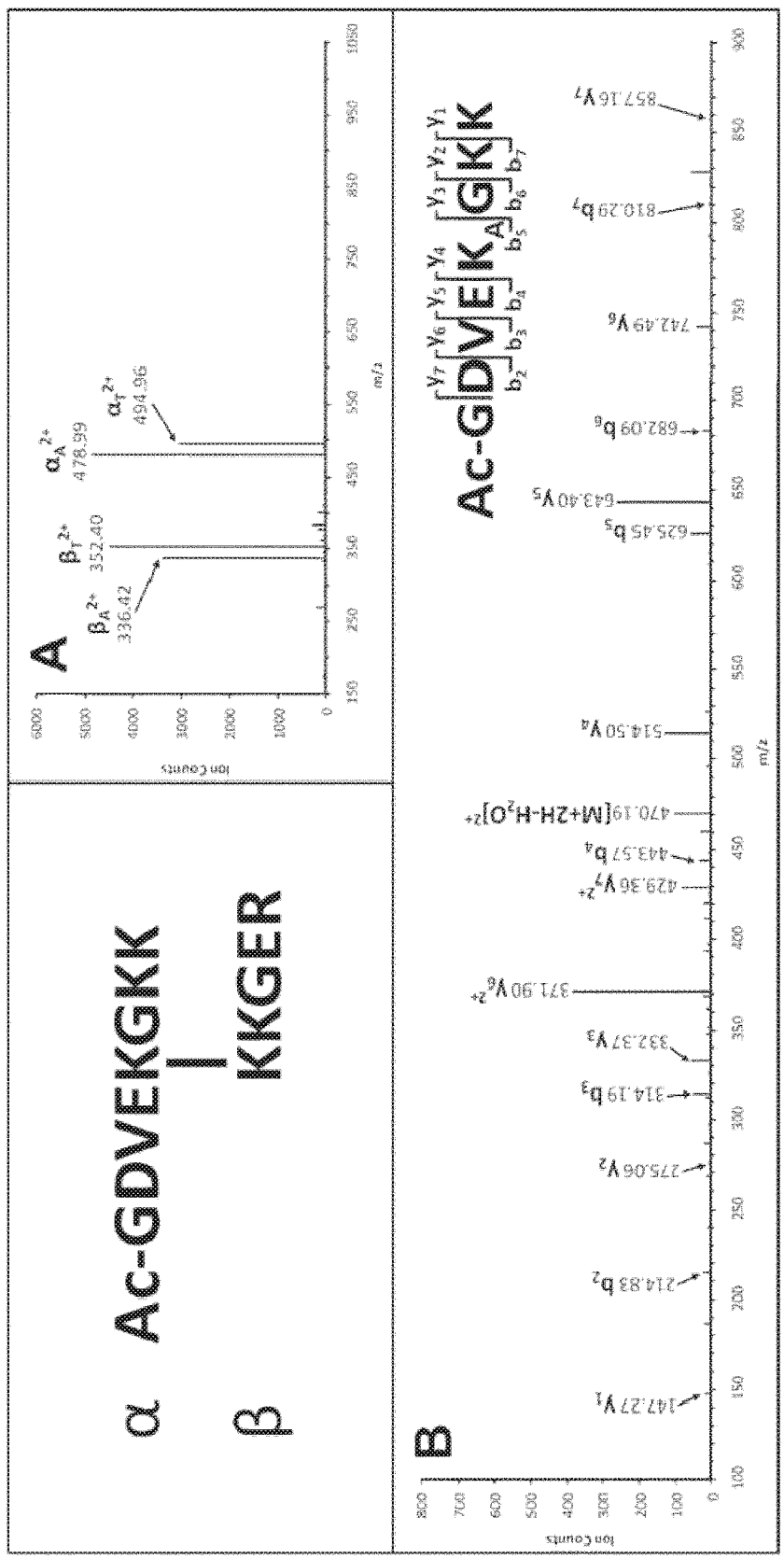
FIG. 4 is an exemplary MS$^n$ analysis of DSSO heterodimeric interlinked peptide of cytochrome c ($\alpha$-$\beta$: Ac-GD-VEKGKK (SEQ ID NO: 11) interlinked to KKGER (SEQ ID NO: 13)). A, MS/MS spectrum of $[\alpha$-$\beta]^{4+}$ (m/z 419.9716$^{4+}$) in which two fragment pairs were observed: $\alpha_A$ (m/z 478.99$^{2+}$)/$\beta_T$ (m/z 352.40$^{2+}$) and $\alpha_T$ (m/z 494.96$^{2+}$)/$\beta_A$ (m/z 336.42$^{2+}$). B, MS$^3$ spectrum of $\alpha_A$ (m/z 478.99$^{2+}$) in which detection of $y_1$-$y_7$ and $b_2$-$b_7$ determined the sequence unambiguously as Ac-GDVEK$_A$GKK (SEQ ID NO: 12). C, MS$^3$ spectrum of $\beta_T$ (m/z 352.40$^{2+}$) in which detection of $y_1$-$y_4$, $\alpha_1$, and $b_2$-$b_7$ ions determined the sequence unambiguously as K$_T$KGER (SEQ ID NO: 14). K$_A$ is modified with the alkene moiety, and K$_T$ is modified with the unsaturated thiol moiety.
Figure 4:
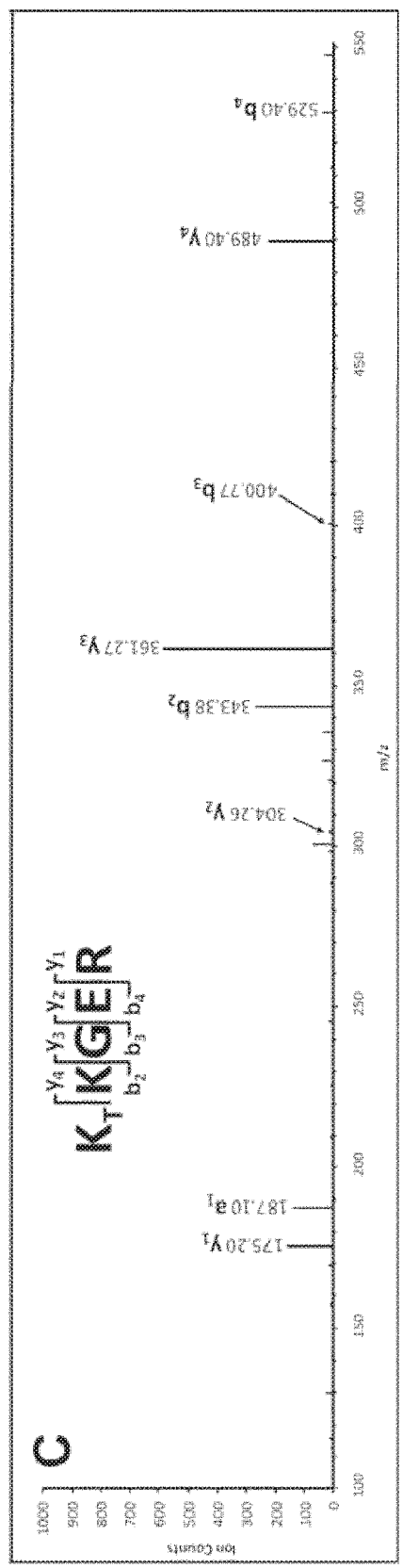

Based on previous work (see Vellucci, D., et al.), cytochrome c was cross-linked with a 10-fold excess of DSSO. The cytochrome c cross-linking efficiency using DSSO was comparable to the efficiency using DSG or previously developed Azide-DSG cross-linkers (see Vellucci, D., et al.), indicating that DSSO is as effective for protein cross-linking reactions. The DSSO cross-linked cytochrome c was then digested with trypsin and analyzed by LC MS$^n$. Three types of cross-linked peptides of cytochrome c (i.e. inter-link, intra-link and dead-end) have been observed. FIG. 4A displays the MS/MS spectrum of a tryptic peptide of cytochrome c with m/z 419.9716$^{4+}$, in which only four abundant fragment ions (m/z 336.42$^{2+}$, 352.40$^{2+}$, 478.99$^{2+}$, 494.96$^{2+}$) were detected, suggesting this peptide as a potential heterodimeric inter-linked peptide ($\alpha$-$\beta$).

Two possible fragment pairs, $\alpha_A/\beta_{S/T}$ and $\alpha_{S/T}/\beta_A$ are thus expected, in which S/T means either S (sulfenic) or T (unsaturated thiol) containing fragment ions will be observed. Using the mass relationship between the pairs and the parent ion of inter-linked peptides (Eqs. 1, 2, 5 in FIG. 2F), two fragment pairs as $\alpha_A/\beta_T$ (478.99$^{2+}$/352.40$^{2+}$) and $\alpha_1/\beta_A$ (494.96$^{2+}$/336.42$^{2+}$) were identified, confirming that this peptide is a heterodimeric inter-linked peptide ($\alpha$-$\beta$).

Mass mapping of the parent ion (m/z 419.9716$^{4+}$) by MS-Bridge revealed that it matches to an inter-linked peptide [Ac-GDVEKGKK (SEQ ID NO: 11) inter-linked to KKGER (SEQ ID NO: 13)] with an error of 0.48 ppm. The fragment ions $\alpha_A$ (m/z 478.99$^{2+}$) and $\beta_T$ (m/z 352.40$^{2+}$) were further subjected to MS$^3$ sequencing and their MS$^3$ spectra are illustrated in FIGS. 4B-C. Based on the series of y (i.e. $\gamma_{1-7}$) and b (i.e. b$_{2-7}$) ions, the sequence of the MS/MS fragment ion $\alpha_A$ (m/z 478.99$^{2+}$) was unambiguously identified as Ac-GDVEK$_A$GKK (SEQ ID NO: 12), in which K (Lys) at 5th position from N-terminus was determined to be modified with the alkene moiety. MS$^3$ analysis of the corresponding fragment pair ion $\beta_T$ (m/z 352.40$^{2+}$) determined its sequence as K$_T$KGER (SEQ ID NO: 14). Although there are two lysine residues in the sequence, occurrence of $\gamma_4$ and $\alpha_1$ ions indicates that the first N-terminal K is modified with an unsaturated thiol moiety. Taken together, the identity and cross-linking site of the inter-link peptide [Ac-GDVEKGKK (SEQ ID NO: 11) inter-linked to KKGER (SEQ ID NO: 13)] was determined unambiguously.

Figure 5:
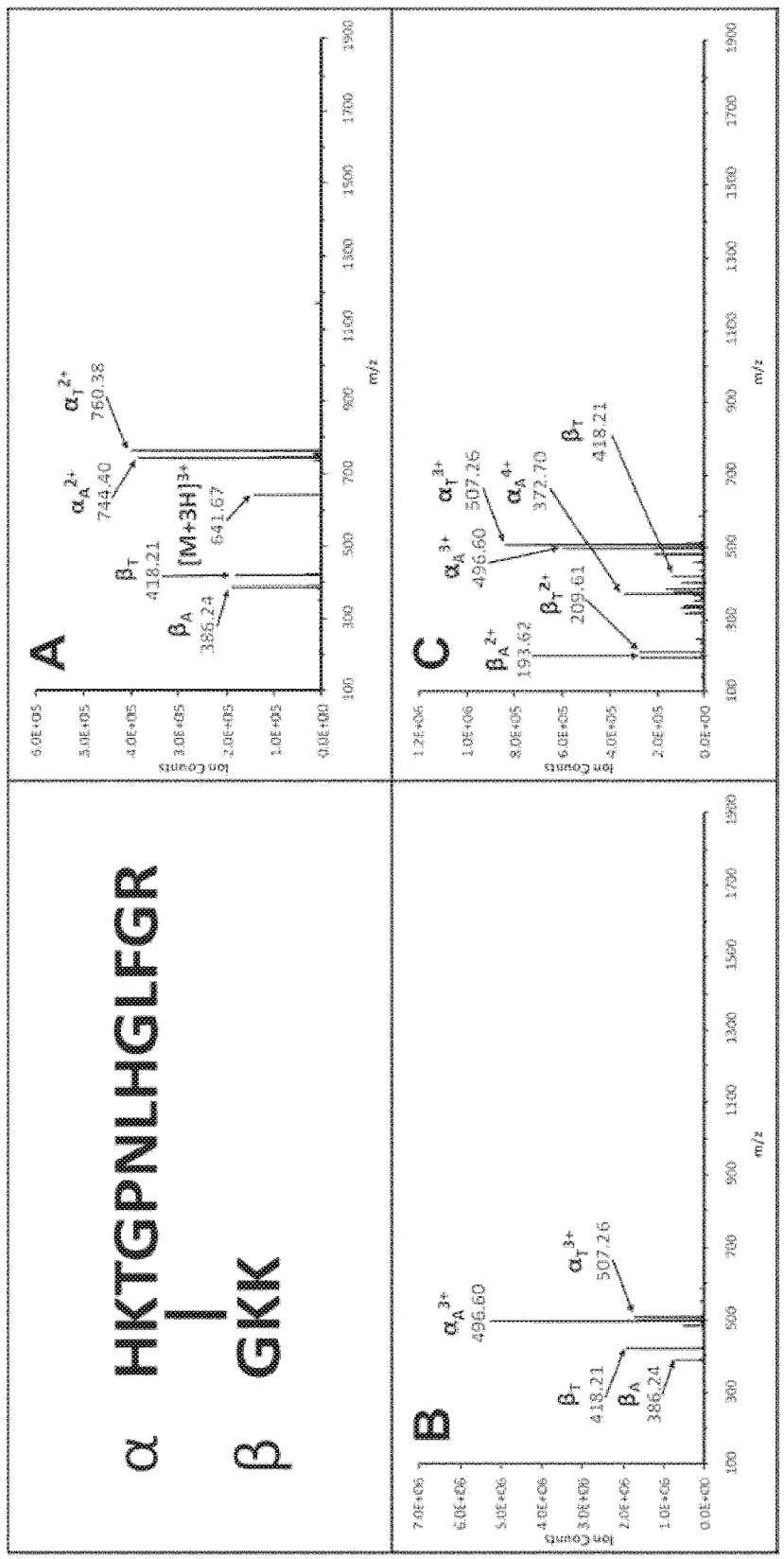
FIG. 5 is an exemplary MS$^n$ analysis of DSSO heterodimeric interlinked peptide of cytochrome c ($\alpha$-$\beta$: HKTGPN-LHGLFGR (SEQ ID NO: 16) interlinked to GKK). This peptide was detected in MS as triply charged $[\alpha$-$\beta]^{3+}$ (m/z 641.6730$^{3+}$), quadruply charged $[\alpha$-$\beta]^{4+}$ (m/z 481.5069$^{4+}$), and quintuply charged $[\alpha$-$\beta]^{5+}$ (m/z 385.4070$^{5+}$) ions. A, MS/MS spectrum of $[\alpha$-$\beta]^{3+}$ (m/z 641.6730$^{3+}$) in which two fragment pairs were observed: $\alpha_A$ (m/z 744.40$^{2+}$)/$\beta_T$ (m/z 418.21) and $\alpha_T$ (m/z 760.38$^{2+}$)/$\beta_A$ (m/z 386.24). B, MS/MS spectrum of $[\alpha$-$\beta]^{4+}$ (m/z 481.5069$^{4+}$) in which two fragment pairs were observed: $\alpha_A$ (m/z 496.60$^{3+}$)/$\beta_T$ (m/z 418.21) and $\alpha_T$ (m/z 507.26$^{3+}$)/$\beta_A$ (m/z 386.24). C, MS/MS spectrum of $[\alpha$-$\beta]^{5+}$ (m/z 385.4070$^{5+}$) in which two fragment pairs were observed: $\alpha_A/\beta_T$ (m/z 496.60$^{3+}$/209.61$^{2+}$ and 372.70$^{4+}$/418.21) and $\alpha_T$ (m/z 507.26$^{3+}$)/$\beta_A$ (m/z 193.62$^{2+}$). D, MS$^3$ spectrum of $\alpha_A$ fragment (m/z 496.6$^{3+}$) in which detection of a series of y and b ions determined its sequence unambiguously as HK$_A$TGPNLHGLFGR (SEQ ID NO: 17). K$_A$ is modified with the alkene moiety.
Figure 5:
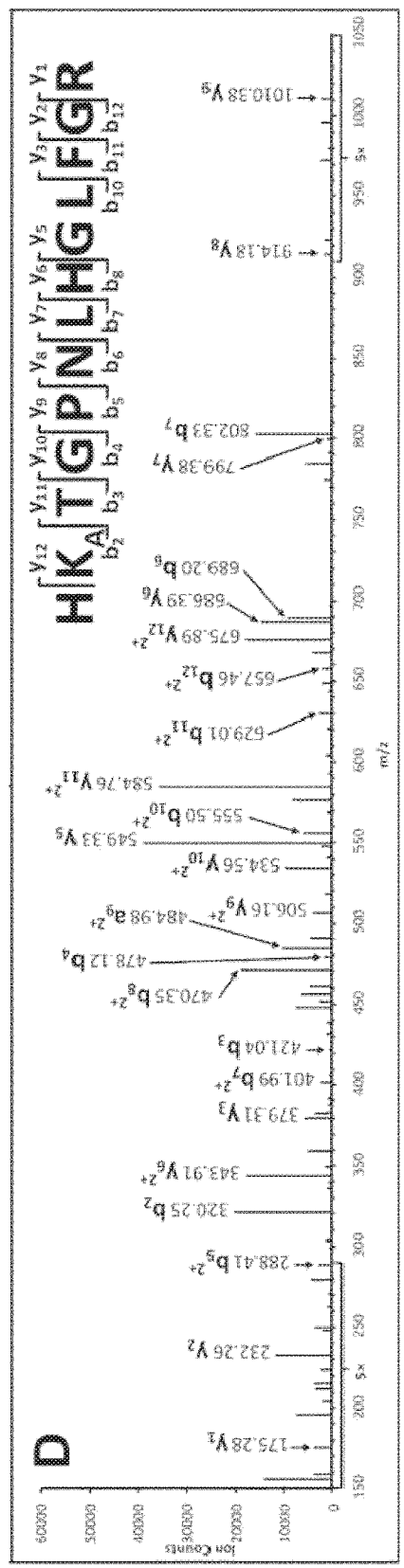

FIGS. 5A-C display MS/MS spectra of triply (m/z 641.6730$^{3+}$), quadruply (m/z 481.5069$^{4+}$), and quintuply (m/z 385.4070$^{5+}$) charged ions of a cytochrome c cross-linked peptide. The MS/MS spectrum of the triply charged ion (m/z 641.6730$^{3+}$) resulted in four dominant fragment ions (m/z 386.24, 418.21, 744.40$^{2+}$, 760.38$^{2+}$), which have been determined as the two fragment pairs $\alpha_A/\beta_T$ (744.40$^{2+}$/418.21) and $\alpha_1/\beta_A$ (760.38$^{2+}$/386.24), indicating this peptide is a heterodimeric inter-linked peptide. The same characteristic fragment pairs, i.e. $\alpha_A/\beta_T$ and $\alpha_1/\beta_A$ have also been identified but with different charges in the MS/MS spectra of the quadruply (m/z 481.5069$^{4+}$) and quintuply (m/z 385.4070$^{5+}$) charged parent ions respectively (FIGS. 5B-C).

It is noted that some charge distribution of fragment ions was observed in the pairs (FIG. 5C) due to the high charge state of the parent ion. Nevertheless, the dominant ions are the characteristic fragment ions of the inter-linked peptide. MS$^3$ analysis of the $\alpha_A$ (m/z 496.6e) fragment has revealed its sequence identity unambiguously as HK$_A$TGPNLHGLFGR (SEQ ID NO: 17), in which the K (Lys) at position 2 from N-terminus was modified with the alkene moiety (FIG. 5D). In combination with the MS-Bridge result, the inter-linked peptide is identified as [HKTGPNLHGLFGR (SEQ ID NO: 16) inter-linked to GKK]. These results demonstrate that preferred fragmentation of the C—S bonds in DSSO inter-linked peptides of cytochrome c occurs as expected and is independent of peptide charge states and sequences.

Figure 6:
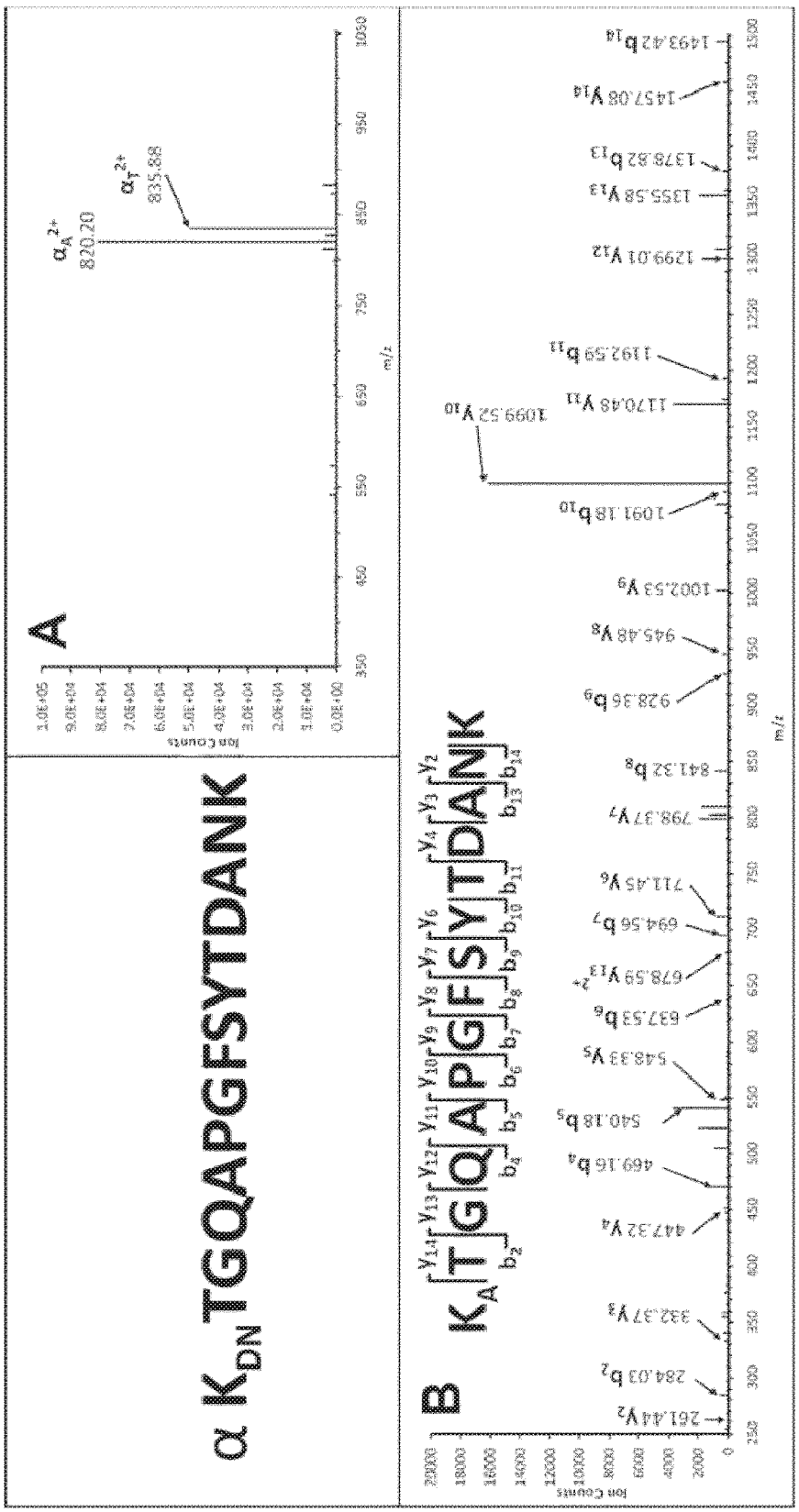
FIG. 6 is an exemplary MS$^n$ analysis of DSSO dead end-modified peptide (A and B) and intralinked peptide of cytochrome c (C and D). A, MS/MS spectrum of a dead end-modified peptide ($\alpha_{DN}$; m/z 880.8975$^{2+}$, K$_{DN}$T-GQAPGFSYTDANK (SEQ ID NO: 20)) in which two fragment ions were determined as $\alpha_A$ (m/z 820.20$^{2+}$) and $\alpha_T$ (m/z 835.88$^{2+}$). B, MS$^3$ spectrum of $\alpha_A$ (m/z 820.20$^{2+}$) in which detection of a series of y and b ions determined its sequence unambiguously as K$_A$TGQAPGFSYTDANK (SEQ ID NO: 21). C, MS/MS spectrum of an intralinked peptide ($\alpha_{intra}$; m/z 611.9802$^{3+}$, GGK*HK*TGPNLHGLFGR (SEQ ID NO: 24)) in which one fragment ion was observed and determined as $\alpha_{A+T}$ (m/z 606.24$^{3+}$). D, MS$^3$ spectrum of $\alpha_{A+T}$ (m/z 606.24$^{3+}$) in which detection of a series of y and b ions determined the presence of a mixture of GGK$_A$HK$_T$TGPNLHGLFGR (SEQ ID NO: 25) and GGK$_T$HK$_A$TGPNLHGLFGR (SEQ JD NO: 26). K$_A$ is modified with the alkene moiety, and K$_T$ is modified with the unsaturated thiol moiety.
Figure 6:
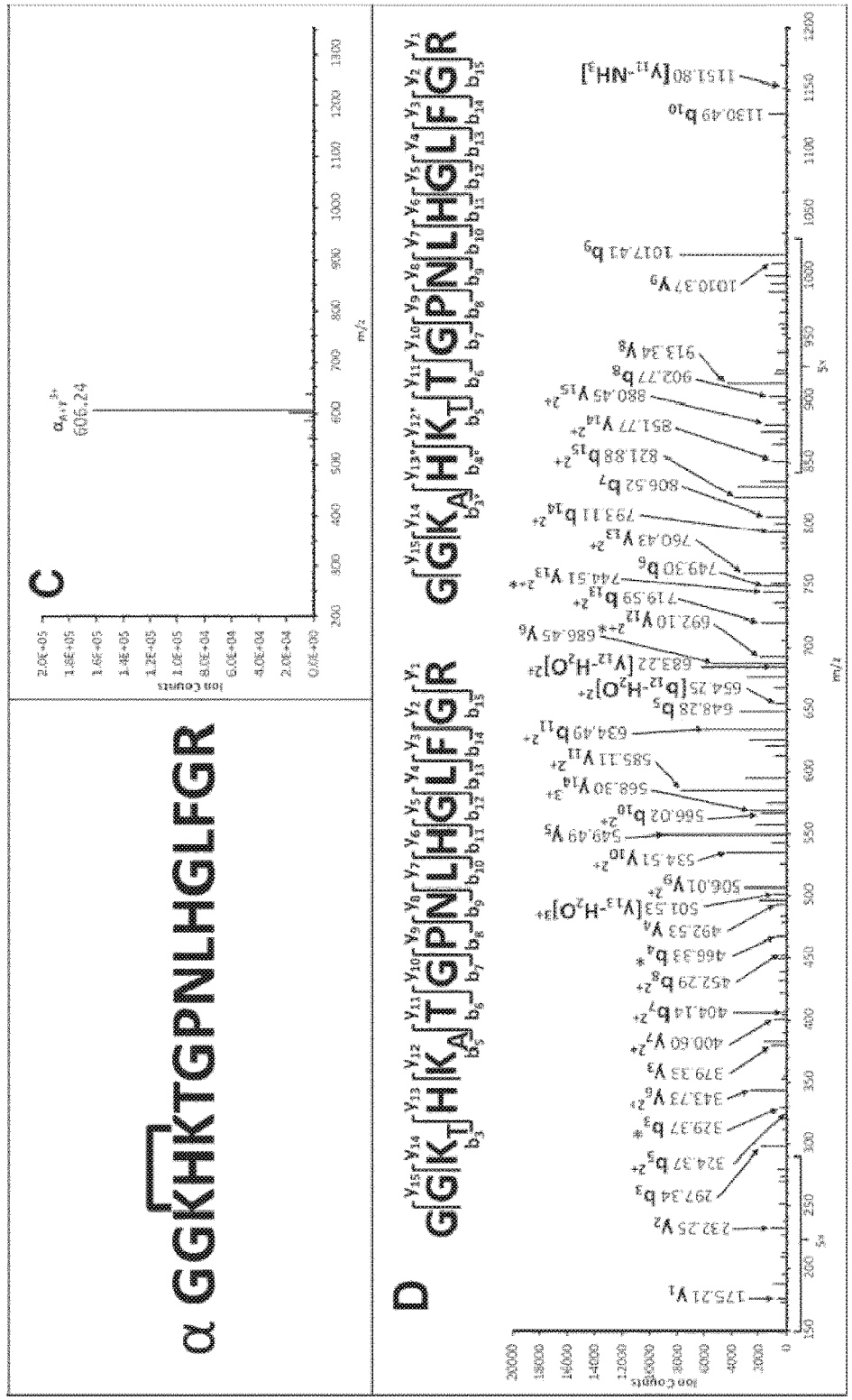

To understand how dead-end modified peptides of cytochrome c behave in MS$^n$ analysis, FIG. 6A illustrates the MS/MS spectrum of a selected dead-end modified peptide (m/z 880.8975$^{2+}$). As shown, two major fragment ions (m/z 820.20$^{2+}$ and 835.88$^{2+}$) were detected and they are 122 and 90 Da less than the parent ion respectively. Such mass differences between the parent ion and its fragment ions fit well with those predicted for DSSO dead-end modified peptides (eq. 3 in FIG. 2F), identifying the ion m/z 820.20$^{2+}$ as $\alpha_A$ and 835.88$^{2+}$ as $\alpha_T$ fragment. MS$^3$ analysis of the $\alpha_A$ fragment (m/z 820.20$^{2+}$) (FIG. 6B) as well as the MS-Bridge result of the parent ion (m/z 880.8975$^{2+}$) identified its sequence as K$_{DN}$TGQAPGFSYTDANK (SEQ ID NO: 20).

As discussed above (FIG. 2D), in some embodiments, it is contemplated that MS/MS analysis of the intra-linked peptide ($\alpha_{intra}$) will lead to either a fragment ion ($\alpha_{A+S}$) containing one $K_A$ ($Lys_A$) and one $K_S$ ($Lys_S$) with the same mass as the parent ion or a fragment ion ($\alpha_{A+T}$) containing one $K_A$ ($Lys_A$) and one $K_S$ ($Lys_T$) with a mass 18 Da less than the original parent ion. FIG. 6C displays the MS/MS spectrum of a cytochrome c tryptic peptide with m/z $611.9802^{3+}$ in which only one major fragment ion (m/z $606.24^{2+}$) was detected with a mass 18 Da less than the parent ion.

This suggests that the peptide is potentially an intra-linked peptide of cytochrome c and its MS/MS fragment ion (m/z $606.24^{2+}$) can be labeled as $\alpha_{A+T}$. Mass mapping of the parent ion m/z $611.9802^{3+}$ using MS-Bridge matched to an intra-linked peptide, GGK*HK*TGPNLHGLFGR (SEQ ID NO: 24), where the two N-terminal K* (Lys*) are linked. Since the CID-induced C—S bond breakage can occur at either side of the sulfoxide, a mixture of two fragments with identical masses but with alkene (A) or thiol (T) moieties at either K can be generated.

FIG. 6D illustrates the $MS^3$ spectrum of the MS/MS fragment ion (m/z $606.24^{3+}$), with a series of y and b ions confirming its identity as $GGK_THK_ATGPNLHGLFGR$ (SEQ ID NO: 26) and/or $GGK_AHK_TTGPNLHGLFGR$ (SEQ ID NO: 25). The detection of $y_{13}$ ($760.43^{2+}$), and $b_3$ (297.34) ions indicates the presence of the peptide fragments from the sequence of $GGK_THK_ATGPNLHGLFGR$ (SEQ ID NO: 26), and the detection of $b_3^*$ (329.37), $b_4^*$ (466.33), $y_{12}^*$ ($692.10^{2+}$), and $y_{13}^*$($744.51^{2+}$) identified the peptide fragments from the $GGK_AHK_TTGPNLHGLFGR$ (SEQ ID NO: 25) sequence.

Figure 7:
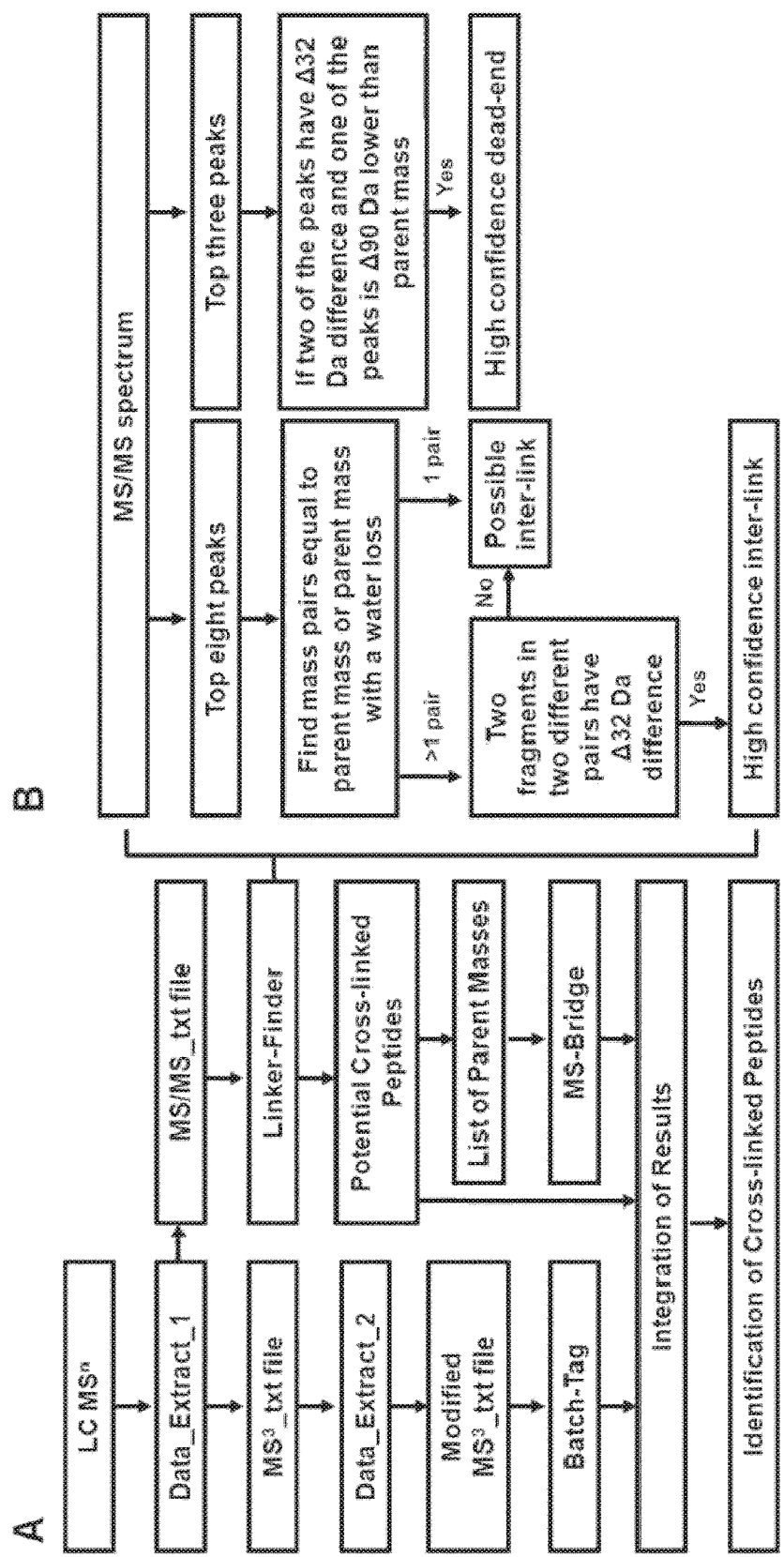
FIG. 7 shows A, the integrated data analysis work flow for identifying DSSO-crosslinked peptides by LC MS$^n$ and B, the work flow for the Link-Finder program.

Development of an Integrated Workflow for Fast and Accurate Identification of DSSO Cross-Linked Peptides by LC $MS^n$ In order to facilitate data analysis for the identification of DSSO cross-linked peptides from complex mixtures, an integrated workflow for processing LC $MS^n$ data acquired by LTQ-Orbitrap XL MS was developed (FIG. 7A). During LC $MS^n$ analysis, three types of data are collected, i.e. MS, MS/MS and $MS^3$ spectra, in which MS and MS/MS are acquired in FT mode to allow accurate mass measurement and charge determination of both parent ions in MS and their fragment ions in MS/MS spectra. $MS^3$ is obtained in LTQ to achieve the highest sensitivity. As shown, the first data extraction step is to generate the text files containing peak lists of MS/MS and $MS^3$ data respectively.

Based on the unique MS/MS fragmentation profiles of DSSO cross-linked peptides and the defined mass relationships between parent ions and their fragment ions (FIG. 2), Link-Finder program was developed to automatically search MS/MS data to identify putative DSSO cross-linked peptides (FIG. 7B). As discussed above, the inter-linked products produce distinct MS/MS spectra with two pairs of dominant peptide fragments ($\alpha_A/\beta_{T/S}$ and $\alpha_{T/S}/\beta_A$) For each MS/MS scan, among the top eight most abundant peaks, if there is a fragment pair with a mass sum equal to their parent mass with or without a water loss (~18 Da), the parent ion will be categorized as a possible inter-linked peptide.

If two of those pairs can be found, and the mass difference between any two fragments from the two distinct pairs is 32 Da, i.e., the mass difference between the thiol and alkene moieties, then it is almost certain that the parent ion is a true inter-linked product. The dead-end product typically has two major fragment ions representing the parent peptide attached with either a thiol or an alkene moiety. Among the top three peaks, if there are two peaks with mass difference of 32 Da, and one of them is 90 Da less than the parent mass, then it is categorized as a possible dead-end peptide. Using the Link-Finder program, a list of parent ions are identified as putative inter-linked or dead-end modified peptides. The generated list of parent ion masses is then subjected to MS-Bridge to identify putative cross-linked peptides of all types by mass matching with high mass accuracy (<10 ppm).

For $MS^3$ data, only the original parent ion observed in MS scan is listed as the precursor ion during database searching. In order to extract the $MS^3$ parent ion (fragment ions in MS/MS), for Batch-Tag search, the second data extraction step is carried out using in-house scripts to generate a modified $MS^3$-txt file. The Batch-Tag search result provides high confidence identification of single peptide fragments generated in MS/MS that are initially cross-linked. Finally, the results from three different types of searches, i.e. Batch-Tag ($MS^3$ data), Link-Finder (MS/MS data), and MS-Bridge (MS data) are integrated using in-house scripts within Link-Finder program to obtain accurate and reliable identification of cross-linked peptides. Among them, $MS^3$ sequencing with Batch-Tag searching is essential for unambiguous identification of cross-linking sites.

Identification of DSSO Cross-Linked Peptides of Model Proteins by Automated Database Searching The newly developed integrated workflow was first employed to identify DSSO cross-linked peptides of cytochrome c. In total, 19 inter-linked peptides have been unambiguously identified and summarized in TABLE 1 (for details see TABLE 3). Each peptide has characteristic fragment pairs in MS/MS spectra and was identified by Link-Finder program. In addition, one or two MS/MS fragment pair ions have been sequenced by $MS^3$ to provide unambiguous identification. Moreover, all of the parent masses fit well with identified cross-linked peptides by MS-Bridge program with high mass accuracy. In comparison to reported cross-linking studies of cytochrome c (Schilling, B., et al.; Kasper, P. T. et al.; Nessen, M. A. et al.; Vellucci, D. et al.; Lee, Y. J., et al.; Pearson, K. M., et al.; Dihazi, G. H.; and Guo, X., et al.), three novel inter-links have been identified in this work. Besides the inter-linked peptides, 7 intra-linked and 8 dead-end peptides have also been identified (See TABLE 3). For the dead-end modified peptides, each has a dead-end fragment pair and at least one of the fragment ions has been sequenced, which correlates very well with MS-Bridge and Batch-Tag results. The intra-linked peptides were mainly identified by Batch-Tag and MS-Bridge results.

In addition to products with one cross-link (i.e. type 0, 1 and 2), peptides containing two cross-links have also been identified using this integrated workflow. In this work, 11 non-redundant DSSO cross-linked peptides with two links (e.g. one inter-link with one dead-end, one inter-link with one intra-link, or one intra-link with one dead-end) have been identified and summarized in TABLE 3. This type of information is not commonly reported since peptide sequencing of multi-linked peptides is highly complicated. This demonstrates the ability of the new cross-linking strategy provided herein for identifying such complex products.

Based on the crystal structure of bovine heart cytochrome c (PDB ID; 2B4Z) (44), the distances between alpha carbons of the identified cross-linked lysine residues were calculated (TABLE 1 and TABLE 3). Among the 26 non-redundant inter-linked lysines in cytochrome c identified in this work (excluding linkages between two adjacent lysines), all of the linkages have the distances between their alpha carbons within the range of 5.3 Å to 19.3 Å. This is consistent not only with the length of a fully expanded DSSO (10.1 Å spacer length) and two lysine side chains, but also with the previous results using similar lengths of NHS ester crosslinkers (see Vellucci, D., et al.; Lee, Y. J., et al.; Guo, X., et al.; and Kruppa, G. H., Schoeniger, J., and Young, M. M. (2003) A Top Down Approach to Protein Structural Studies Using Chemical Cross-Linking and Fourier Transform Mass Spectrometry. *Rapid Commun Mass Spectrom* 17, 155-162). The results suggest that the cross-linking conditions herein did not induce significant disturbance to cytochrome c structural conformations.

In addition to cytochrome c, the same strategy has been successfully applied to identify DSSO cross-linked peptides of ubiquitin. Using the same analysis strategy, 3 inter-linked, 1 intra-linked, and 5 dead-end peptides have been identified as summarized in TABLE 4. Based on the crystal structure of bovine ubiquitin (PDB ID; 1AAR), all of the identified inter-/intra-linked lysines in ubiquitin have the distances between their alpha carbons within the range of 6 to 18 Å. The identified cross-linked lysines are consistent with the known structure of ubiquitin and previous reports (Chowdhury, S. M., et al.; and Gardner, M. W., et al.)

It is interesting to note that one of the identified inter-linked peptides is [LIFAGK$^{48}$QLEDGR (SEQ ID NO: 63) inter-linked to LIFAGK$^{48}$QLEDGR (SEQ ID NO: 63)], which is a cross-link formed between the ubiquitin dimer. Residue K$^{48}$ is located at a hydrophobic patch important for protein interactions and K$^{48}$ is also an in vivo chain linkage site for polyubiquitination required for ubiquitin/ATP dependent proteasomal degradation (Pickart, C. M., and Cohen, R. E. (2004) Proteasomes and Their Kin: Proteases in the Machine Age. *Nat Rev Mol Cell Biol.* 5, 177-187). The same K$^{48}$-K$^{48}$ (Lys$^{48}$-Lys$^{48}$) cross-link was identified previously using an alkyne-tagged NHS ester, but only after selective enrichment coupled with CID and ETD analyses (Chowdhury, S. M., et al.). In comparison, in some embodiment, the K$^{48}$ inter-linked peptide without any enrichment was identified, thus further demonstrating the effectiveness of the approach disclosed herein to identify DSSO cross-linked peptides from complex mixtures.

Structural Elucidation of the Yeast 20 S Proteasome Complex Using DSSO Cross-Linking The ubiquitin-proteasome degradation pathway plays an important role in regulating many biological processes (Pickart, C. M., et al.) The 26 S proteasome complex is the macromolecular machine responsible for ubiquitin/ATP dependent protein degradation, and it is composed of two subcomplexes: the 20S core particle and the 19 S regulatory complex. To date, only the crystal structure of the 20 S proteasome complex has been resolved. However, structures of the 19 S and 26 S remain elusive, thus hindering the understanding of the structure and functional relationship of the 26 S proteasome complex. To develop an effective cross-linking strategy to elucidate structures of the 19 S and 26 S proteasome complexes, the structure of the yeast 20 S proteasome complex using the DSSO cross-linking approach was investigated.

In some embodiments, cross-linking of the Yeast 20 S Proteasome with DSSO was performed. Affinity purified yeast 20S proteasome complex was concentrated by Microcon (Billerica, Mass.) to ~1.2 µM in 1×PBS buffer (pH 7.5). Typically 50 µl of the 20S proteasome was cross-linked with 3 µl DSSO (20 mM) dissolved in DMSO (final concentration ~1 mM) at a molar ratio of 1:1000 (protein:cross-linker). Cross-linking was performed for a half hour or overnight and quenched with excess ammonium bicarbonate buffer. Cysteine residues were reduced with 5 mM DTT at 56° C. for 30 mins, and alkylated with 10 mM choloroacetamide for 30 min at room temperature. The cross-linked protein complex was digested with trypsin (2% w/w) overnight at 37° C. Digested peptides were desalted by C18 OMIX ZipTip (Varian, Palo Alto, Calif.) prior to LC MS$^n$ analysis.

For some analyses, 2-dimensional LC MS$^n$ analysis was carried out. Off-line strong cation exchange (SCX) chromatography was performed as the first dimension of separation using an ÄKTA HPLC system (GE Healthcare Life Sciences, Uppsala, Sweden) as described in Kaake, R. M., et al. Each fraction was desalted by ZipTip prior to LC MS$^n$ analysis.

Figure 11:
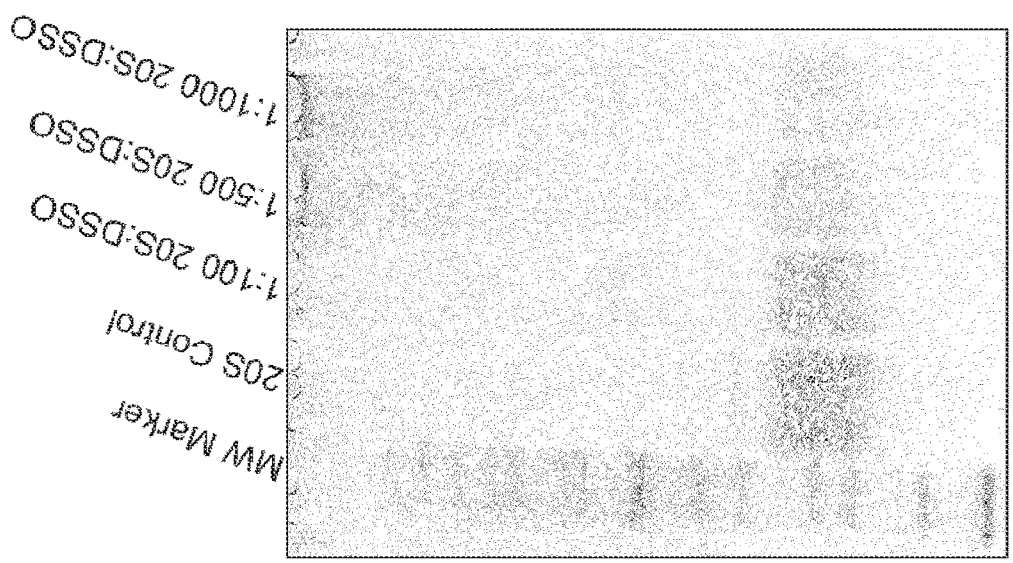
FIG. 11 is an exemplary SDS-PAGE gel picture of the 20S proteasome cross-linked with various molar ratios of cross-linker DSSO, i.e. 1:100, 1:500 and 1:1000. The 20S proteasome without cross-linking served as a control. The cross-linked proteasome complex was separated using 4-20% gradient gel.

The cross-linking of the 20 S proteasome complex was carried out in PBS buffer under conditions allowing efficient cross-linking of all subunits as based on 1-D SDS-PAGE (FIG. 11). The tryptic digest of the cross-linked proteasome complex was subjected to LC MS$^n$ analysis and the data were analyzed using the integrated work flow described above (FIG. 7). In total, 13 unique inter-linked peptides were identified including 10 intra-subunit and 3 inter-subunit heterodimeric inter-links as summarized in TABLE 2 (for details see TABLE 5), which were determined unambiguously by integration of Link-Finder, Batch-Tag (MS$^3$ sequencing), and MS-Bridge (mass mapping of the cross-linked peptides) results.

Figure 8:
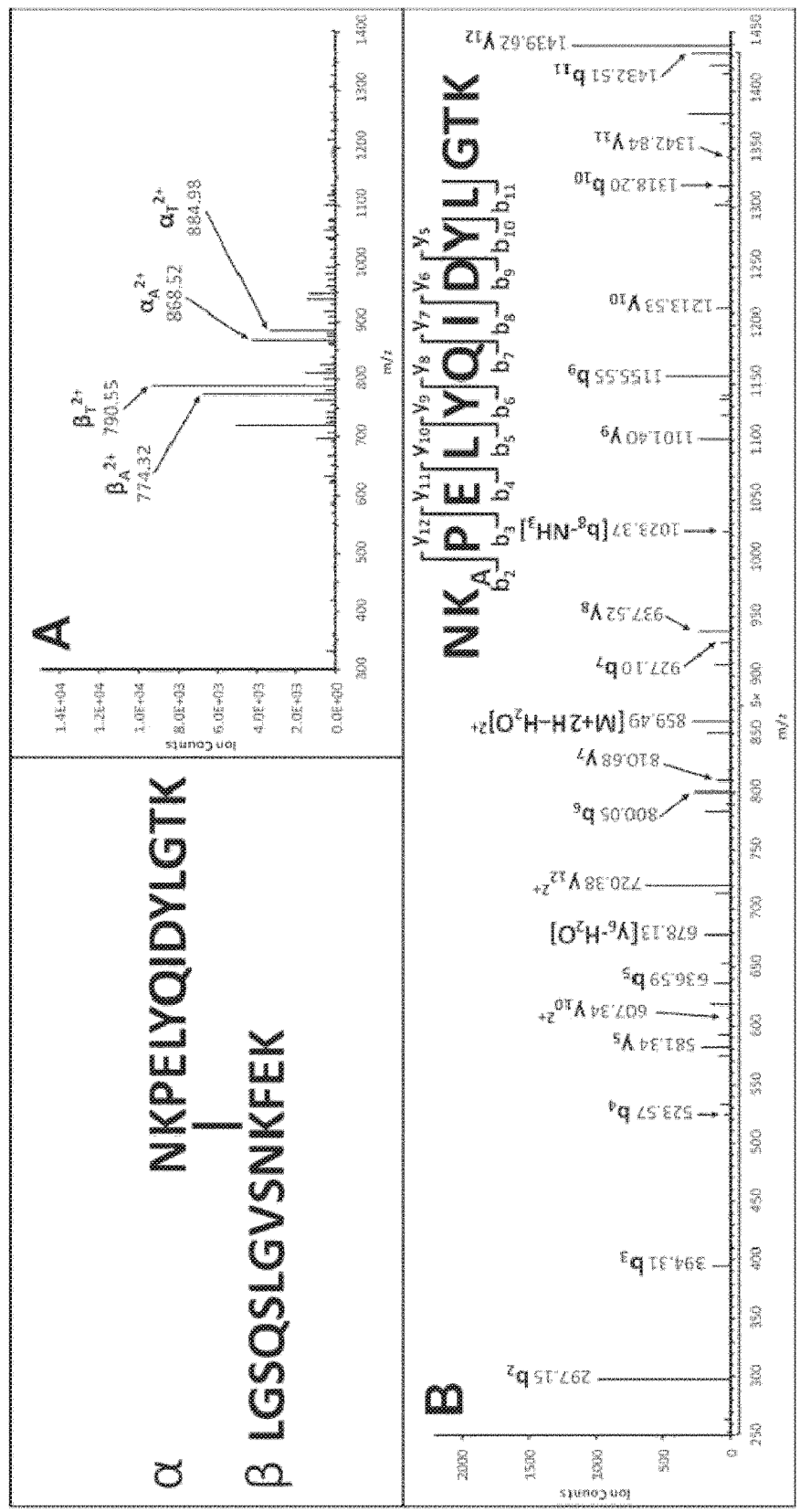
FIG. 8 is an exemplary MS$^n$ analysis of DSSO heterodimeric interlinked peptide of the yeast 20 S proteasome complex ($\alpha$-$\beta$: NKPELYQIDYLGTK (SEQ ID NO: 27) interlinked to LGSQSLGVSNKFEK (SEQ ID NO: 29)) with intersubunit link between 20 S subunit $\beta$4 and $\beta$3. A, MS/MS spectrum of $[\alpha$-$\beta]^{4+}$ (m/z 833.9231$^{4+}$) in which two fragment pairs were detected and determined as $\alpha_A$ (m/z 868.52$^{2+}$)/$\beta_T$ (m/z 790.55$^{2+}$) and $\alpha_T$ (m/z 884.98$^{2+}$)/$\beta_A$ (m/z 774.32$^{2+}$). B, MS$^3$ spectrum of $\alpha_A$ (m/z 868.52$^{2+}$) in which detection of a series of y and b ions determined its sequence unambiguously as NK$_A$PELYQIDYLGTK (SEQ ID NO: 28). C, MS$^3$ spectrum of $\beta_T$ (m/z 790.55$^{2+}$) in which detection of a series of y and b ions determined its sequence unambiguously as LGSQSLGVSNK$_T$FEK (SEQ ID NO: 30). K$_A$ is modified with the alkene moiety, and K$_T$ is modified with the unsaturated thiol moiety.
Figure 8:
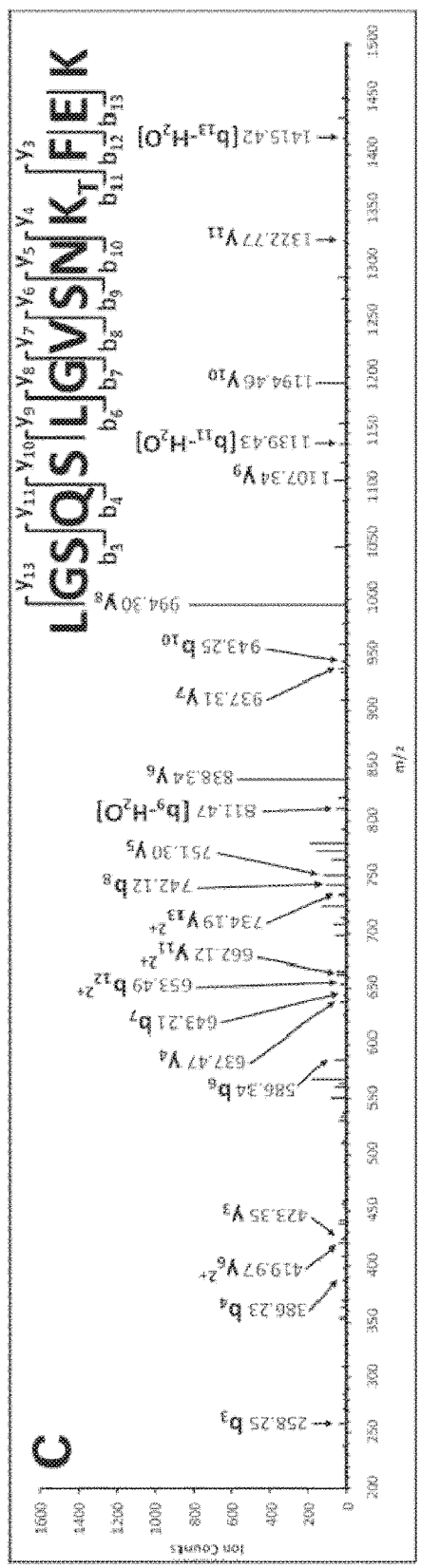

As an example, FIG. 8A displays the MS/MS spectrum of a DSSO heterodimeric inter-linked peptide α-β (m/z 833.9231$^{4+}$) of the yeast 20 S proteasome complex, in which two fragment pairs were detected and determined as $α_A/β_T$ (868.45$^{2+}$/790.39$^{2+}$) and $α_T/β_T$ (884.44$^{2+}$/774.41$^{2+}$). MS$^3$ analysis of the $α_A$ fragment (m/z 868.45$^{2+}$) identified the a chain unambiguously as NK$_A$PELYQIDYLGTK (SEQ ID NO: 28), which matched to 20 S subunit β4. In this sequence, $K_A$ is modified with the alkene moiety. In addition, MS$^3$ analysis of the $β_T$ fragment (m/z 790.39$^{2+}$) identified the β chain unambiguously as LGSQSLGVSNK$_T$FEK (SEQ ID NO: 30), which matched to 20 S subunit $β_3$. Here, $K_T$ is modified with an unsaturated thiol moiety. Mass mapping by MS-Bridge further confirmed this inter-subunit (β4-β3) inter-linked peptide as [NKPELYQIDYLGTK (SEQ ID NO: 27) inter-linked to LGSQSLGVSNKFEK (SEQ ID NO: 29)].

Figure 12:
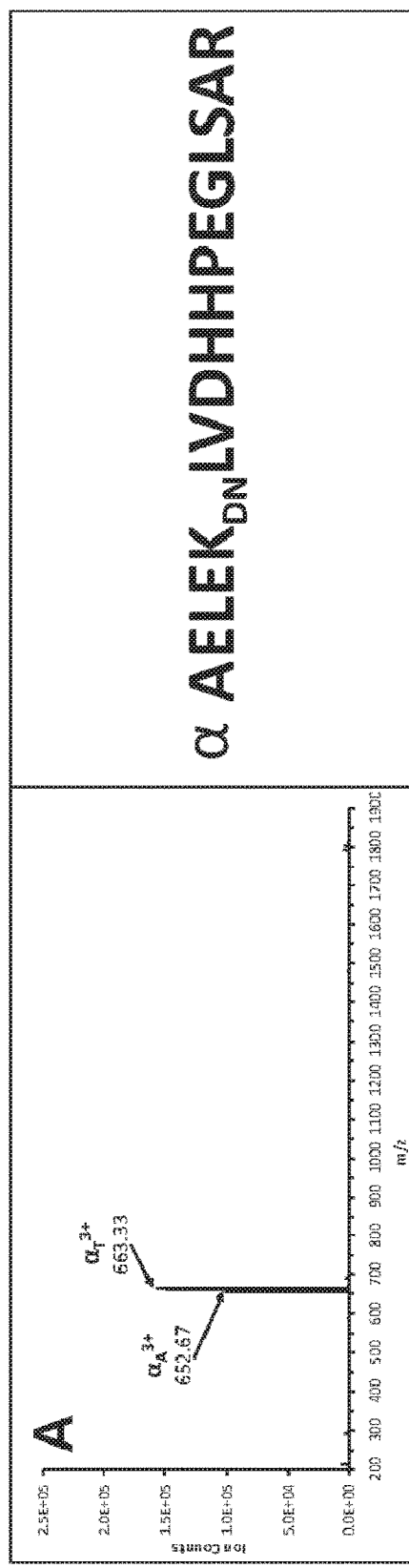
FIG. 12 is an exemplary MS$^n$ analysis of a DSSO dead-end peptide of the yeast 20S proteasome complex. A) MS/MS spectrum of a dead-end (DN) peptide ($\alpha_{DN}$, m/z 693.0078$^{3+}$, AELEK$_{DN}$LVDHHPEGLSAR (SEQ ID NO: 110)), in which two fragment ions were determined as αA (m/z 652.67$^{3+}$) and $\alpha_T$ (m/z 663.33$^{3+}$); B) MS$^3$ spectrum of $\alpha_A$ (m/z 652.67$^{3+}$), detection of a series of y and b ions determined its sequence unambiguously as AELEK$_A$LVDHHPEGLSAR (SEQ ID NO: 111), in which K$_A$ is modified with the alkene moiety. The sequence matched to subunit α7; C) MS3 spectrum of αT (m/z 663.33$^{3+}$), detection of a series of y and b ions determined its sequence unambiguously as AELEK$_T$LVDHHPEGLSAR (SEQ ID NO: 112), in which K$_T$ is modified with the unsaturated thiol moiety.
Figure 12:
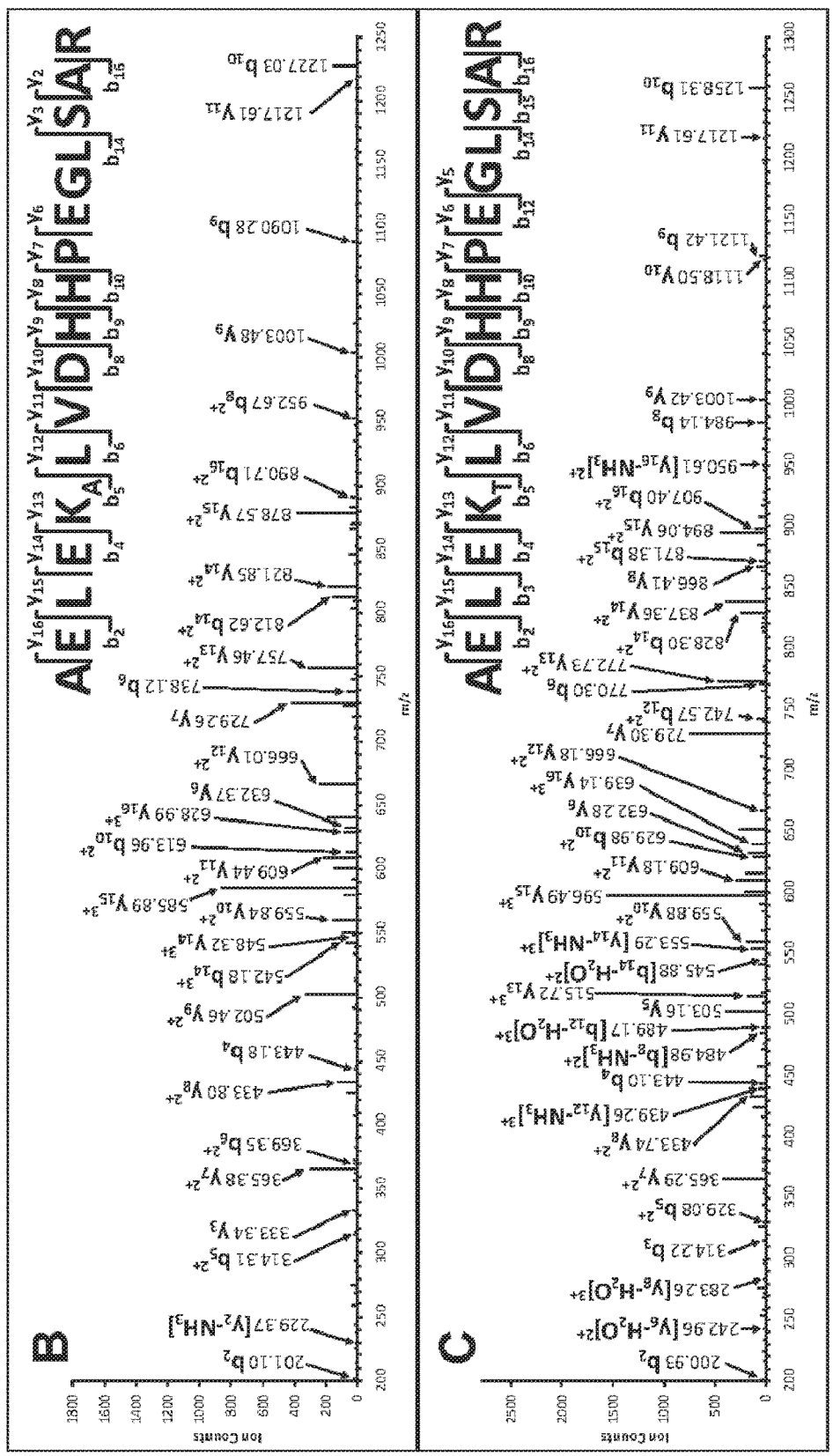

In addition, 21 dead-end modified peptides were identified by multiple lines of evidence as illustrated in TABLE 5. The fragmentation behavior for the dead-end modified peptides of the 20 S subunits is the same as that of cytochrome c showing two distinct dead-end pairs in MS/MS spectra. This is illustrated with an example shown in FIG. 12.

Figure 9:
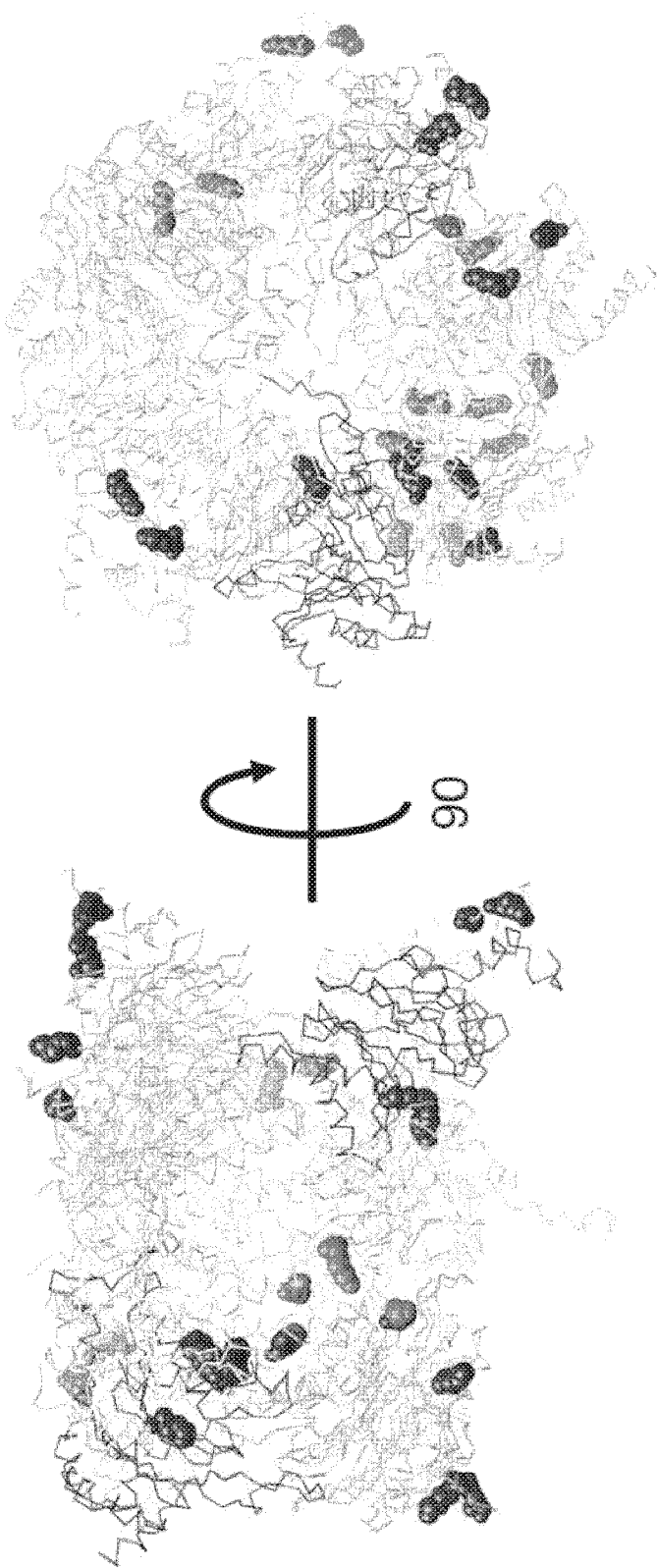
FIG. 9 shows a mapping identified DSSO-interlinked lysines onto crystal structure of yeast 20 S proteasome. The lysines forming intrasubunit cross-links appear space-filled in blue, and those forming intersubunit cross-links appear space-filled in red.
Figure 10:
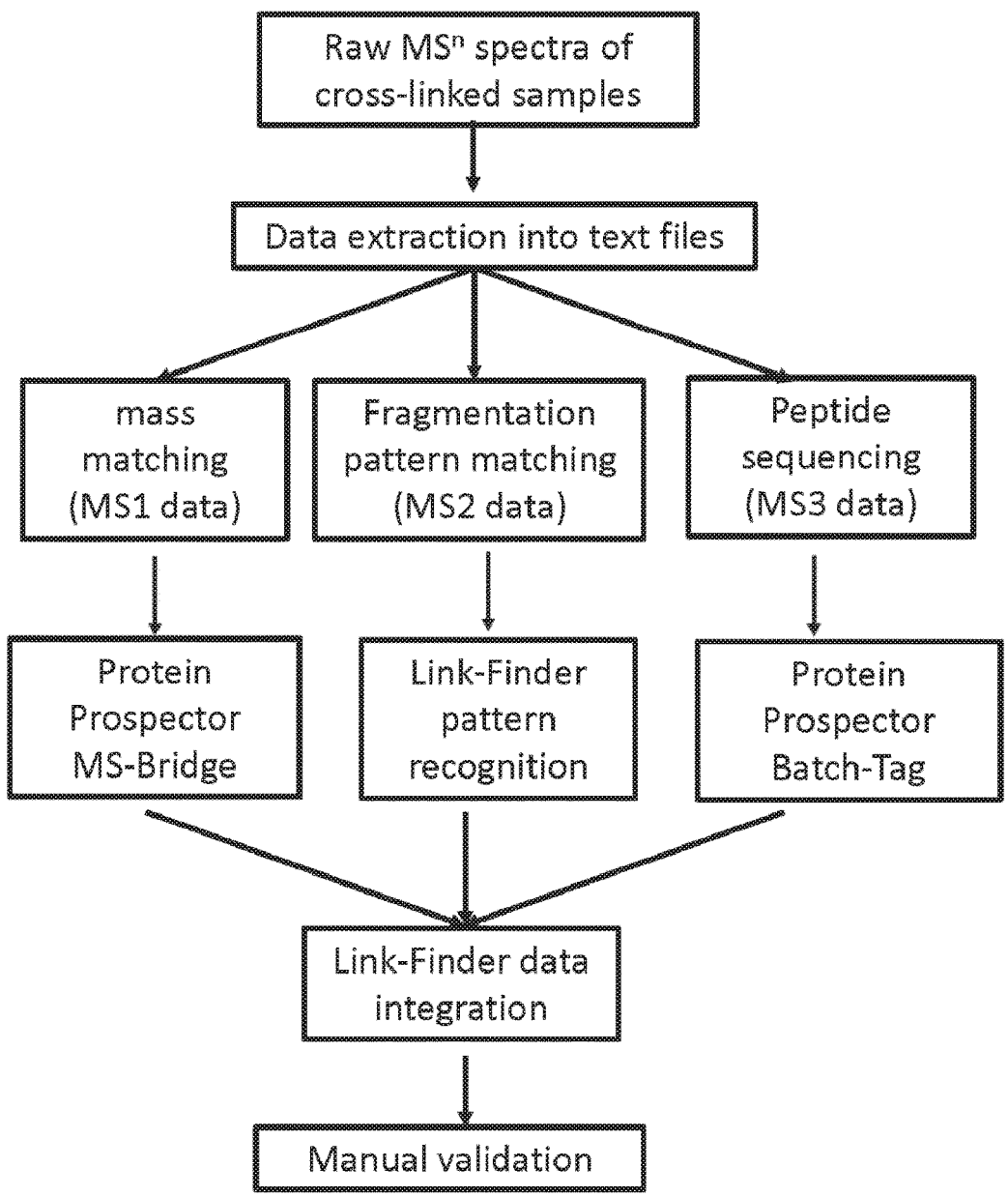
FIG. 10 is a flowchart showing a general technique for identifying crosslinked peptides according to one embodiment of the invention.

The experimentally determined structure of the yeast 20 S proteasome holocomplex was utilized (Protein Data Bank code 1RYP) to assess the cross-linked lysine pairs identified in this study. For each identified cross-link the distance between the alpha carbons was calculated and the results are summarized in TABLE 2. Considering the spacer length of DSSO and lysine side chains, the theoretical upper limit for the distance between the alpha carbon atoms of paired lysines is approximately 26 Å. In some embodiments, the distances are within this upper limit, providing some evidence that the proteasome cross-links are formed in the native state. The quaternary proteasome structure is formed by four stacked seven-member rings in the order αββα. The side view and basal view of the arrangement among one set of the symmetric αβ rings and their subunits are shown in FIG. 9. The alpha carbon trace is shown for all subunits and the cross-linked lysines are shown in space fill representation. Lysines forming intra-subunit cross-links appear in blue and those forming inter-subunit cross-links appear in red. The images in FIG. 9 were generated using UCSF Chimera visualization software (Pettersen, E., Goddard, T., Huang, C., Couch, G., Greenblatt, D., Meng, E., and Ferrin, T. (2004) Ucsf Chimera—a Visualization System for Exploratory Research and Analysis. *Journal of computational chemistry* 25, 1605-1612).

Data Analysis of DSSO Cross-linked Peptides as follows. Monoisotopic masses of parent ions and corresponding fragment ions, parent ion charge states and ion intensities from LC MS/MS and LC MS$^3$ spectra were extracted using in-house software based on Raw_Extract script from Xcalibur v2.4 (Thermo Scientific, San Jose, Calif.). Database searching was performed with a developmental version of Protein Prospector (v. 5.5.0, University of California, San Francisco) (http://prospector.ucsf.edu/prospector/mshome.htm) using its software suite, i.e. Batch-Tag and MS-Bridge as described in Chu, F., et al. Using in-house scripts, extracted MS$^3$ data were reformatted such that MS$^3$ fragment ions were directly linked to their MS/MS parent ions.

For cytochrome c (P62894) and ubiquitin (P62990) analyses, database searching of MS$^3$ spectra was performed using Batch-Tag against their accession numbers in SwisProt.2009.09.01 database. For the 20S proteasome, Batch-Tag search of MS$^3$ data was performed against a decoy database consisting of a normal SGD yeast database concatenated with its reversed version (total 13490 protein entries). The mass tolerances for parent ions and fragment ions were set as ±20 ppm and 0.6 Da, respectively. Trypsin was set as the enzyme and a maximum of two missed cleavages were allowed. Protein N-terminal acetylation, methionine oxidation, and N-terminal conversion of glutamine to pyroglutamic acid were selected as variable modifications. In addition, three defined modifications on uncleaved lysines were chosen, including alkene ($C_3H_2O$, +54 Da), sulfenic acid ($C_3H_4O_2S$, +104 Da), and thiol ($C_3H_2SO$, +86 Da) modifications due to remnants of the cross-linker (FIG. 1). Initial acceptance criteria for peptide identification required a reported expectation value<0.05. For the 20S proteasome analysis, the false positive rate for peptide identification is less than 1%.

The Link-Finder program (http://www.ics.uci.edu/~baldig/Link-Finder/) was developed to search MS/MS data and identify the list of putative DSSO inter-linked and dead-end products based on their unique MS fragmentation patterns as illustrated in FIG. 2 (details see results section). For example, one embodiment of the invention includes identifying the MS/MS data that display characteristic fragmentation profiles of DSSO cross-linked peptides based on the unique mass relationships between parent ions of cross-linked peptides and their fragment ions to obtain an MS/MS result including a list of parent ions corresponding to cross-linked peptide candidates (e.g., the putative or potential identities of the cross-linked peptides being analyzed).

In some embodiments, analysis of the MS/MS data is carried out using the Link-Finder program. Monoisotopic masses and charges of parent ions measured in MS scans for those putative cross-linked peptides identified by the Link-Finder program were subsequently submitted to MS-Bridge to determine cross-linked peptide sequences by mass mapping with a given cross-linker (i.e. DSSO) and protein sequences (see Chu, F., et al.). For example, one embodiment of the invention further includes mass mapping the MS data using the list of parent ions corresponding to the cross-linked peptide candidates and the MS-cleavable cross-linker againt known protein sequences to obtain an MS result comprising possible cross-linked peptide sequences.

In some embodiments, the mass mapping is carried out using MS-Bridge. The parent mass error for MS-Bridge search was set as ±10 ppm and only one cross-link was allowed in the cross-linked peptides for general search. All of the three types of the cross-linked peptides (Schilling, B., et al.), i.e. inter-linked (type 2), intra-linked (type 1) and dead-end modified (type 0), can be computed and matched in MS-Bridge (see Chu, F., et al.).

The search results from Link-Finder, Batch-Tag and MS-Bridge programs are integrated together using in-house scripts to compile a list of cross-linked peptides identified with high confidence. The final results were validated manually by examining MS/MS spectra and MS$^3$ spectra respectively.

Synthesis of Two New Enrichable and MS-Cleavable Cross-Linkers to Define Protein-Protein Interactions by Mass Spectrometry The cross-linking Mass Spectrometry (XL-MS) technique extracts structural information from protein complexes without requiring highly purified samples, crystallinity, or large amounts of material. However, there are challenges to applying the technique to protein complexes in vitro, and those challenges become more daunting with in vivo experiments. Issues include effective detection and identification of cross-linked peptides from complex mixtures. While MS-cleavable cross-linkers facilitate the sequencing and identification of cross-linked peptides, enrichable cross-linkers increase their detectability by allowing their separation from non-cross-linked peptides prior to MS analysis. Although a number of cross-linkers with single functionality have been developed in recent years, an ideal reagent would incorporate both capabilities for XL-MS studies.

Therefore, two new cross-linkers have been designed and prepared that incorporate an azide (azide-A-DSBSO) or alkyne (alkyne-A-DSBSO) to enable affinity purification strategies based on click chemistry. The integration of an acid cleavage site next to the enrichment handle allows easy recovery of cross-linked products during affinity purification. In addition, these sulfoxide containing cross-linking reagents possess robust MS-cleavable bonds to facilitate fast and easy identification of cross-linked peptides using MS analysis. Optimized, gram-scale syntheses of these cross-linkers have been developed and the azide-A-DSBSO cross-linker has been evaluated with peptides and proteins to demonstrate its utility in XL-MS analysis.

In some embodiments, the preparation of two-CID-cleavable lysine cross-linkers, an azide (azide-A-DSBSO) and an alkyne (alkyne-A-DSBSO) are provided.

In some embodiments, initial characterization of azide (azide-A-DSBSO) and an alkyne (alkyne-A-DSBSO) using a model peptide and a model protein are provided.

In some embodiments, while not trivial, the syntheses procedures provided herein have been optimized to make these useful compounds available on multigram scale.

In some embodiments, the azide and alkyne functional groups are suitable for click enrichment strategies.

In some embodiments, the cross-linkers described herein have been utilized in mammalian HEK-293 cells[6].

In some embodiments, the cross-linkers described herein facilitate the study of the interaction of subunits in the proteasome complex, which is responsible for degradation of ubiquitin tagged proteins.[6]

In some embodiments, the importance of developing XL-MS reagents that are applicable for in vivo studies is significant because protein-protein interactions are involved in most cell function and are not well understood.

Most proteins act in association with other proteins to form protein complexes stably or transiently in cells, and mapping these interactions is essential to understand their cellular functions. Protein complexes represent functional entities that are often difficult to analyze using conventional structural tools clue to their heterogeneous and dynamic nature. Recently, cross-linking Mass Spectrometry (XL-MS) has been recognized as a valuable tool for the structural analysis of protein assemblies,—which can be used alone and in combination with other techniques.[1,2] In addition to in vitro studies, XL-MS approaches have been extended to capture protein interactions in living cells.[3]

Identification of cross-linked peptides by MS analysis can provide distance constraints to assist computational modeling and yield structural information at amino acid resolution.[4] The advantages of cross-linking studies include small sample size, robust tolerance for size and environment of the protein complex, instrument accessibility, and the speed of handling and data collection. Although successful, inherent limitations in current XL-MS strategies require further developments to enable MS detection and identification of cross-linked peptides with better efficiency, accuracy, sensitivity and speed. Among various approaches to improve existing XL-MS workflow,[5] developing new cross-linking reagents holds the greatest promise towards the ultimate goal of mapping protein-protein interactions in living cells at the systems level.

In some embodiments, the chemical synthesis of two new cross-linking agents is provided whose effectiveness has recently been demonstrated for in vivo protein-protein analysis.[6]

Figure 13:
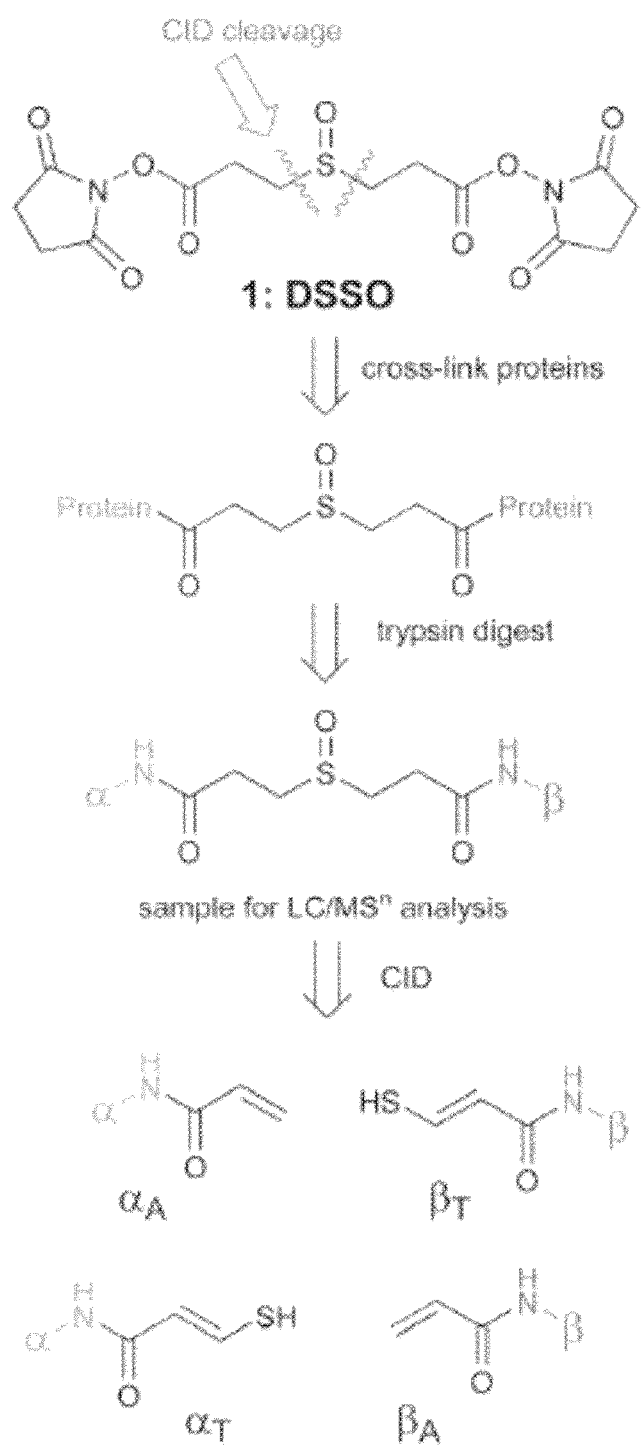
FIG. 13 shows CID cleavable cross-linker DSSO is based on the sulfoxide functional group. The arrow points to the bond that is broken during the CID process. A workflow for cross-linking proteins is shown. After protein cross-linking, trypsin digest generates the cross-linked peptide for LC/MS$^n$ analysis. CID leads to selective cleavage of the bonds adjacent to the sulfoxide functional group.

Unambiguous identification of cross-linked peptides can be greatly facilitated by the introduction of a MS cleavable bond in a cross-linking reagent, which can fragment during collision induced dissociation (CID) prior to peptide backbone breakage.[7] In some embodiments, successful development of a new class of robust MS-cleavable reagents that contain labile C—S sulfoxide bonds (e.g. DSSO (disuccinimidylsulfoxide), FIG. 13) is provided, which enables fast and accurate identification of cross-linked peptides using liquid chromatography-multistage tandem mass spectrometry analysis (LC/MS$^n$).[8,9]

In some embodiments, with DSSO as an example, the new XL-MS workflow provided herein involves protein DSSO cross-linking, trypsin digestion of cross-linked proteins, and LC/MS$^n$ analysis of resulting peptide mixtures. During MS$^n$ analysis, the cross-linked peptides are first detected in MS$^1$ and selected for subsequent MS$^2$ analysis. The CID-fragmentation site, i.e. one of the C—S sulfoxide bonds, is selectively fragmented in MS$^2$, allowing the physical separation of the two DSSO cross-linked peptide constituents for subsequent sequencing. The resulting peptide fragments in MS$^2$ are then analyzed in MS for unambiguous identification. The integration of these three types of MS data (MS$^1$, MS$^2$, MS$^3$) enables simplified analysis of DSSO cross-linked peptides with improved speed and accuracy. This strategy has been demonstrated to be effective in the structural analysis of purified protein complexes in vitro.[4]

The analytical problem with effectively detecting and identifying cross-linked peptides becomes much more daunting with large, complex protein assemblies and especially when studying protein-protein interactions in living cells. A strategy to improve the sensitivity and efficiency of XL-MS analysis is to incorporate an affinity purification handle into the cross-linker itself.

To this end, in some embodiments, an azide-tagged cross-linking reagent is provided that allows the incorporation of an affinity purification handle based on click chemistry for enriching cross-linked peptides prior to MS analysis, thus improving their detection and identification.[18] In comparison to other enrichment handles incorporated in cross-linking reagents,[10] the azide group is advantageous as it is small, bioorthogonal, and click chemistry has been proven effective in enriching biological samples for various proteomic analyses including cross-linking studies.[11]

In some embodiments, in order to combine these unique features in a multifunctional cross-linking reagent that can advance current XL-MS workflow for studying protein-protein interactions in vivo as well as in vitro, a new class of low molecular weight, membrane permeable, enrichable and MS-cleavable cross-linkers is provided.

In some embodiments, in order to explore the flexibility of using azide-alkyne click chemistry in the XL-MS workflow, two new cross-linkers, i.e., azide-tagged and an alkyne-tagged reagents were designed and synthesized as presented in FIG. 14. The structure of azide-A-DSBSO (azide-tagged, acid-cleavable disuccinimidyl-bissulfoxide) 3 incorporates a number of important design elements (FIG. 14).

The N-hydroxysuccinimidyl (NHS) esters are designed to react with lysine side chains thus cross-linking the proteins in the complex. The sulfoxide groups provide MS-cleavable bonds, and because only one side of each sulfoxide has β-hydrogen atoms, the elimination must take place regioselectively at the outer c-s bond. The design incorporates an

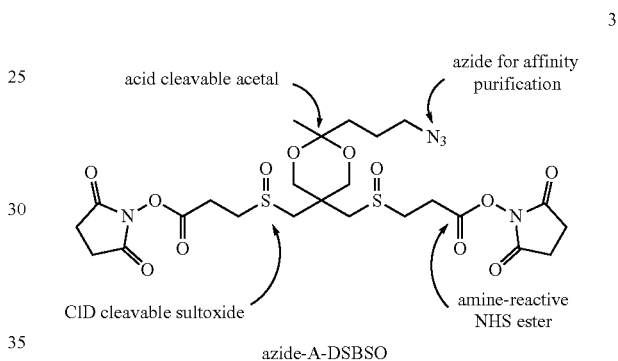

azide-A-DSBSO azide functional group to be used in click reactions with strained alkynes or in a coppe(r)-catalyzed azide-alkyne cycloaddition (CuAAC).[12]

The click and CuAAC reactions enable several strategies for affinity purification, including direct coupling with alkyne or azide-functionalized beads or by linking with common affinity ligands such as biotin.[11] Finally, the azide portion of the molecule is joined to the cross-linker with an acid labile acetal bond, which can be cleaved under aqueous acidic conditions to facilitate selective elution from an affinity column.

The same elements are incorporated into the alkyne-A-DSBSO (alkyne-tagged, acid-cleavable disuccinimidyl-bissulfoxide) 4, except that the azide functional group

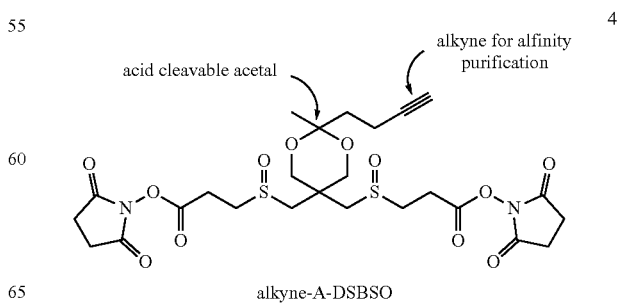

alkyne-A-DSBSO has been exchanged for the complementary alkyne. One other design feature is that both of these cross-linkers, prior to the introduction of the sulfoxides, are achiral and exist as single stereoisomers (FIG. 14).

This feature offers considerable simplification in the preparation and analysis of the synthetic intermediates, and decreases the chance of any stereoselective behavior in the crosslinking environment. These reagents have been under investigation for several years in our program and their applications in mapping protein-protein interactions at the systems level in living cells were recently described.[6] In this report, the syntheses of these reagents are described in full along with foundational studies on the cross-linking effectiveness and LC/MS[n] sequencing.

Synthesis of the Cross-Linkers 3 and 4

Figure 15:
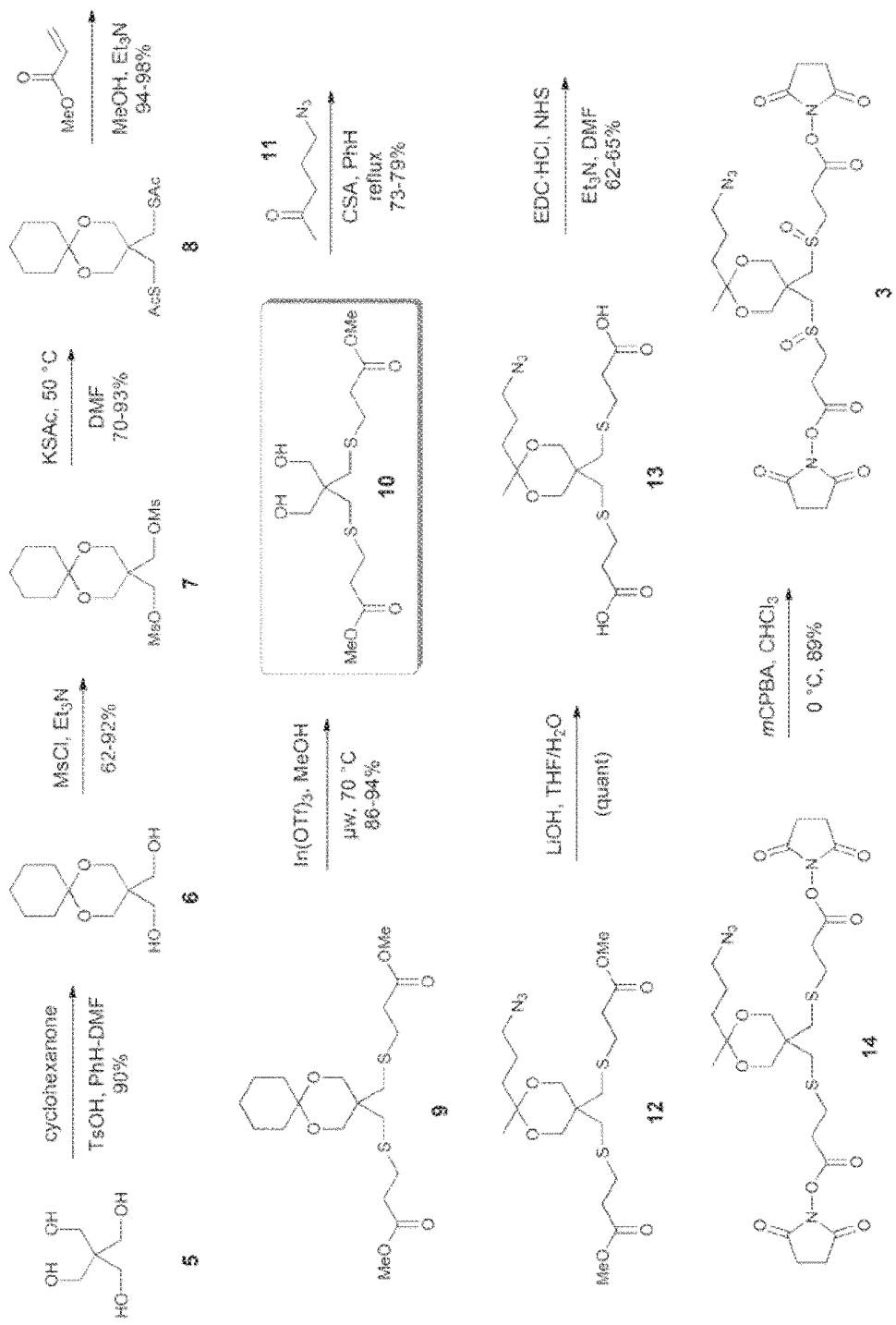
FIG. 15 shows an embodiment of a scheme for the synthesis of azide-A-DSBSO.

The original synthesis of azide-A-DSBSO 3 began with pentaerythritol (5) and is presented in FIG. 15. Selective protection of 5 (2,2-bis(hydroxymethyl)propane-1,3-diol) as cyclohexanone acetal 6 ((1,5-dioxaspiro[5.5]undecane-3,3-diyl)dimethanol) represented an improvement of the literature procedure.[13] Mesylation followed by displacement with potassium thioacetate produced the bis-thioacetate 8 (S,S'-((1,5-dioxaspiro[5.5]undecane-3,3-diyl)bis(methylene)) diethanethioate) in good overall yield. All three intermediates, 6, 7 ((1,5-dioxaspiro[5.5]undecane-3,3-diyl)bis(methylene) dimethanesulfonate) and 8, were crystalline solids that were isolated and purified on multi-gram scale without chromatography. Thioacetate methanalysis and Michael addition of 8 into methyl acrylate was accomplished in a single step in the presence of triethylamine and methanol. The key intermediate 9 (dimethyl 3,3'-(((1,5-dioxaspiro[5.5] undecane-3,3-diyl)bis(methylene))bis(sulfanediyl))dipropionate) was isolated in nearly quantitative yield and used without further purification. Careful hydrolysis of the cyclohexanone acetal using In(OTf)$_3$ catalysis produced 86% of the diol 10 (dimethyl 3,3'-((2,2-bis(hydroxymethyl)propane-1,3-diyl)bis(sulfanediyl))dipropionate) and 8% recovered starting material, which were separated by chromatography. Incomplete hydrolysis of the acetal was a recurring problem in this step when using Brønsted or Lewis acids in refluxing solvent, which required isolation and recycling of a small amount of the recovered acetal 9. By carefully optimizing the catalyst quantity, time, and temperature in microwave reaction conditions the conversion to diol 10 could be pushed to completion with isolated yields of ~94%. Diol 10 is a key intermediate in the synthesis, and it is the branch point for the preparation of the azide cross-linker 3 and the alkyne cross-linker 4. It was prepared in five steps following this route in 64% overall yield with only one chromatographic purification.[14]

The remainder of the synthesis of azide cross-linker 3 is outlined in FIG. 15. The diol 10 was reacted with 5-azidopentan-2-one (11)[15] with acid catalysis using a Dean-Stark trap to remove water. The acetal 12 (dimethyl 3,3'-(((2-(3-azidopropyl)-2-methyl-1,3-dioxane-5,5-diyl)bis (methylene))bis(sulfanediyl))dipropionate) was isolated in 77% yield by chromatography. The NHS esters were introduced in two steps: hydrolysis of the methyl ester and coupling with N-hydroxysuccinimide using EDC-HCl in dimethylformamide (DMF). In FIG. 15, 13 is 3,3'-(((2-(3-azidopropyl)-2-methyl-1,3-dioxane-5,5-diyl)bis(methylene))bis(sulfanediyl))dipropionic acid. The overall yield was typically around 60% and the bis-NHS ester 14 (bis(2,5-dioxopyrrolidin-1-yl) 3,3'-(((2-(3-azidopropyl)-2-methyl-1,3-dioxane-5,5-diyl)bis(methylene))bis(sulfanediyl))dipropionate) was isolated with chromatography. The final oxidation was carried out with meta-chloroperoxybenzoic acid (m-CPBA); the oxidant was added in aliquots and conversion was monitored by ESI-MS until the starting material and monosulfoxide were no longer present. Azide cross-linker 3 was isolated by extraction. This route produced several grams of the cross-linker 3 in ca. 18% overall yield for the sequence.[14]

Figure 16:
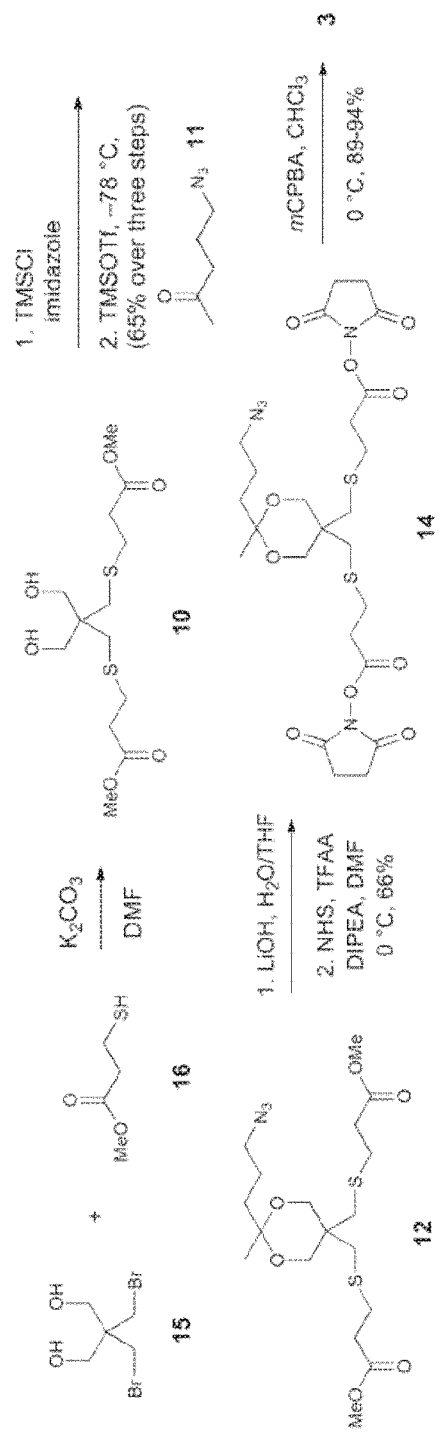
FIG. 16 shows an embodiment of a scheme for the synthesis of azide-A-DSBSO.

In the course of in vivo studies,[6] it was found that the azide 3 cross the membrane and produced cross-links in targeted protein complexes.[6] The studies require a large excess of cross-linker, and led to an ongoing demand for more material. Although the original optimized synthesis in FIG. 15 was effective, it did require nine steps. A shorter route was developed that incorporated several improvements in the individual transformations and avoided the use of protecting groups. The new route is presented in FIG. 16.

The new route (FIG. 16) begins with the commercially available and inexpensive dibromide 15 (2,2-bis(bromomethyl)propane-1,3-diol) and thiol 16 (methyl 3-mercaptopropanoate). Direct alkylation with K$_2$CO$_3$ in DMF generate the key intermediate 10 in a single step. Diol 10 could be purified by chromatography on silica gel to produce 75% of pure 10, but the crude product was carried on in the sequence. By comparison to the original route (FIG. 15), this synthesis was carried out using the Noyori protocol,[16] which was found to be more reliable than the original acid-catalyzed method. Diol 10 was silylated and then combined with ketone 11 in the present of TMSOTf to give acetal 12 in 65% overall yield. Hydrolysis of the dimethyl ester 12 used LiOH as before. The bis-NHS ester 14 was prepared using in situ generated TFA-NHS,[17] which lead to similar overall yields but shorter reaction times, fewer side products, and a more reliable purification. Finally, oxidation to the bis-sulfoxide as previously described gave azide 3. The new route requires only six steps, three chromatographic purifications, and led to an overall yield of 38%.[14] It is more convenient and reliable than the prior route and has been used to produce multiple grams of azide-A-DSBSO 3.

Figure 17:
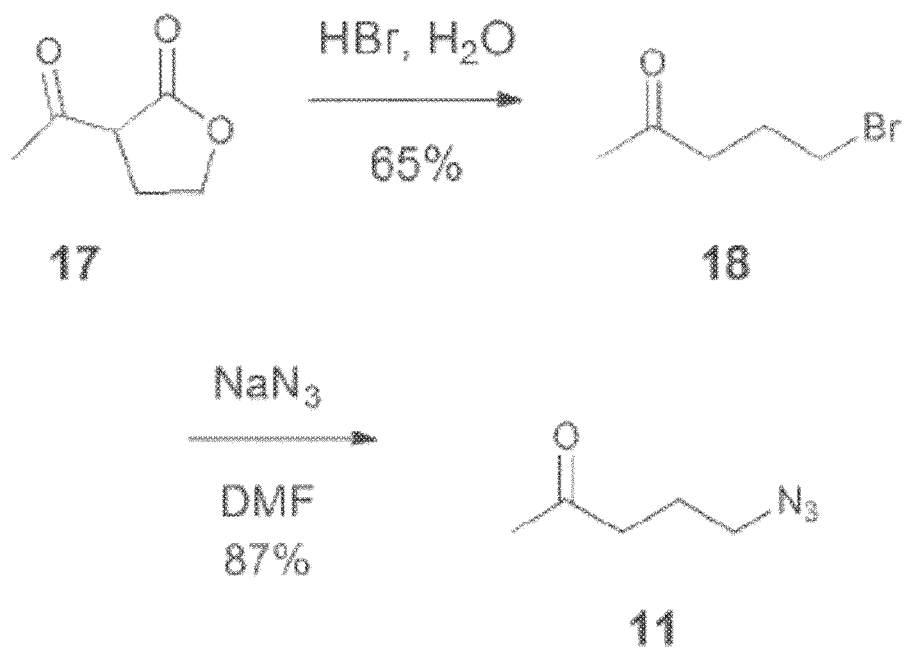
FIG. 17 shows an embodiment of a scheme for the synthesis of 5-azidopentan-2-one.

The 5-azidopentan-2-one was initially prepared by the alkylation of commercially available bromide 18 with NaN$_3$.[15] The very high cost of bromide 18 led us to develop a more economical approach starting with lactone 17 (3-acetyldihydrofuran-2(3H)-one) (FIG. 17). The lactone 17 was treated with HBr to generate the required 5-bromopentan-2-one (18). The standard displacement with sodium azide gave the designed ketone 11 in good overall yield. Scaling up the synthesis of azide-A-DSBSO 3 required a significant quantity of the volatile azide 11, and the starting with lactone 17 was both effective and economical.

Figure 18:
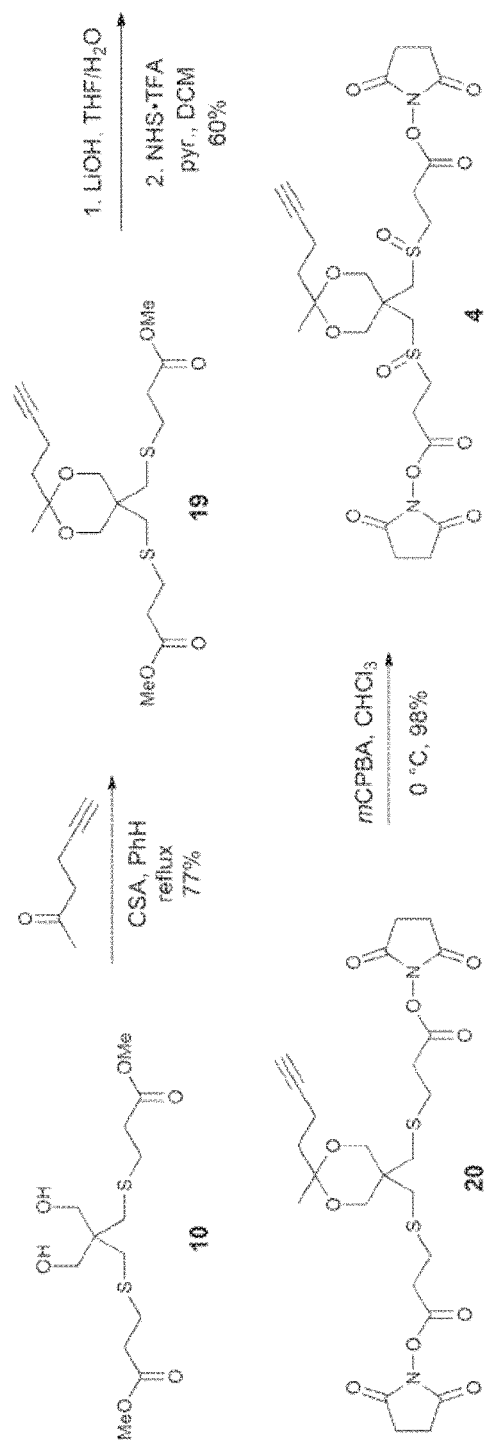
FIG. 18 shows an embodiment of a scheme for the synthesis of alkyne-A-DSBSO.

The alkyne 4 was prepared from diol 10 using a very similar route (FIG. 18). The acetal 19 (dimethyl 3,3'-(((2-(but-3-yn-1-yl)-2-methyl-1,3-dioxane-5,5-diyl)bis(methylene))bis(sulfanediyl))dipropionate) was formed from 5-hexyn-2-one and the diol under Dean-Stark conditions. The dimethyl ester was hydrolyzed to a diacid using LiOH, and the di-NHS ester was prepared using TFA-NHS reagent.[17] Di=NHS ester 20 (bis(2,5-dioxopyrrolidin-1-yl) 3,3'-(((2-(but-3-yn-1-yl)-2-methyl-1,3-dioxane-5,5-diyl)bis (methylene))bis(sulfanediyl))dipropionate) was isolated in 60% yield using this method. The same compound was also prepared using an EDCI coupling, but the yield was lower and the purification was more difficult. The m-CPBA oxidation was conducted as described for the azide substrate to give the Alkyne-A-DSBSO 4. The route required only four steps from diol 10 and made cross-linker 4 available on gram scale.

MSn Analysis of Azide-A-DSBSO Cross-Linked Ac-Myelin Peptide

Given the similarity of cleavable C—S bonds in azide-A-DSBSO and DSSO, it was anticipated that azide-A-DSBSO cross-linked peptides would display comparable fragmentation characteristics to DSSO cross-linked peptides (FIG. 19A).[4] In such experiments, $MS^2$ produces peptide fragments that are modified with remnant portions of the cross-linking reagents. These remnants are not identical thus producing two products with a separation of 254 Da, the $\alpha_A$ and the $\alpha_T$ fragments. The $\alpha_A$ fragment has an alkene group, while the other half of the cleaved linker results in a terminal thiol group (after hydrolysis of the sulfenic acid intermediate). Although azide•A•DSBSO contains four C—S bonds due to the presence of two sulfoxide groups, the two central C—S bonds cannot undergo fragmentation due to the lack of β-hydrogens. Therefore, only the two C—S bonds closer to cross-linked residues are expected to fragment during $MS^2$.

Figure 19:
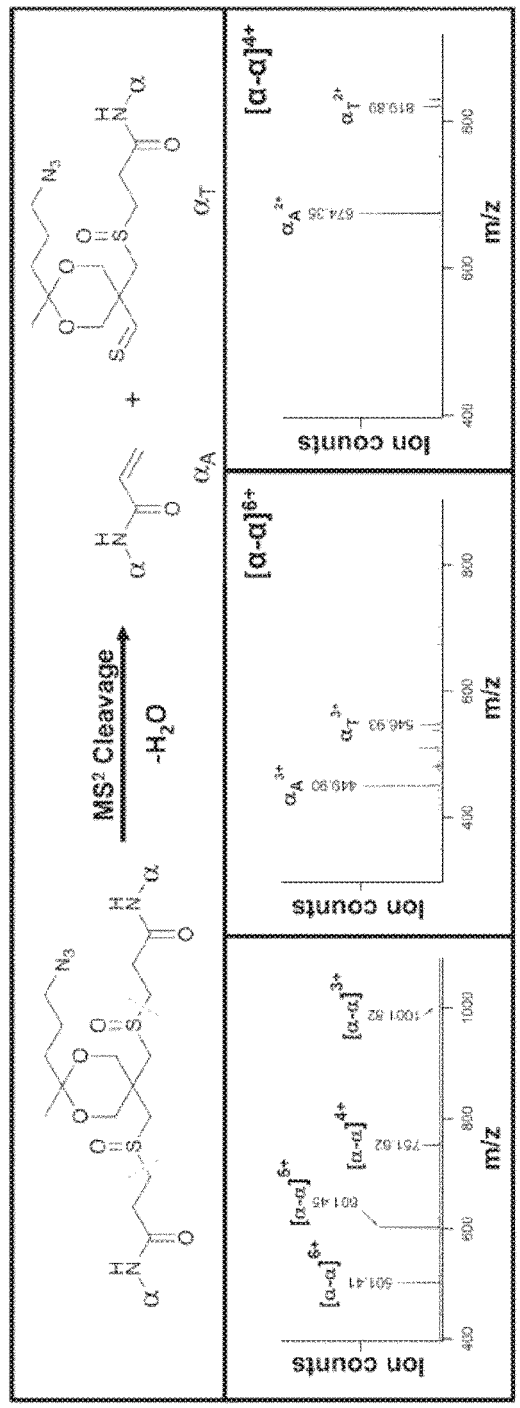
FIG. 19A-FIG. 19D show data for MS$^n$ analysis of azide•A•DSBSO cross-linked Ac-myelin synthetic peptide.

To examine $MS^2$ fragmentation patterns of azide-A-DSBSO cross-linked peptides during MS″ analysis, the model peptide Ac-myelin was first cross-linked and analyzed. $MS^1$ analysis detected azide-A-DSBSO cross-linked Ac-myelin (α-α) homodimer at four different charge states (m/z $501.41^{6+}$, $601.4^{5+}$, $751.62^{4+}$, $1001.82^{3+}$) (FIG. 19B). $MS^2$ analyses of inter-linked Ac-myelin homodimer at different charge states yielded the expected fragmentation of two identical inter-linked pep-tides, i.e. a characteristic fragment pair ($\alpha_A/\alpha_T$). As an example, the fragment pair $\alpha_A/\alpha_T$ detected in MS/MS spectra of the quadruply (m/z $751.62^{4+}$) and sextuply (m/z $501.411^{6+}$) charged interlinked Ac-myelin (α-α) was displayed in FIG. 19C and FIG. 19D, respectively. The results demonstrate that the MS-cleavable C—S bonds in azide-A-DSBSO cross-linked peptides are preferentially fragmented during $MS^2$ analysis prior to the breakage of peptide backbones. Similar results were observed with alkyne-A-DSBSO cross-linked Ac-myelin peptide (data not shown) as azide-A-DSBSO and alkene-A-DSBSO are almost identical in structures.

LC/MSn Analysis of DSBSO Cross-Linked Peptides of Cytochrome C after Enrichment

In some embodiments, to demonstrate the applicability of azide-A-DSBSO for XL-MS studies, the model protein cytochrome C was cross-linked with with azide-A-DSBSO. Cytochrome C has been used extensively by us and other groups for evaluating cross-linking reagents because it is a small protein with a high number of lysine residues. Given its success in the past for cross-linking studies,[4,18] it was decided to use it as the model protein for characterizing our new cross-linking reagent. The resulting cross-linked cytochrome C products were conjugated with BARAC-biotin,[19] affinity purified by binding to Streptavidin beads, and digested with trypsin.

Figure 20:
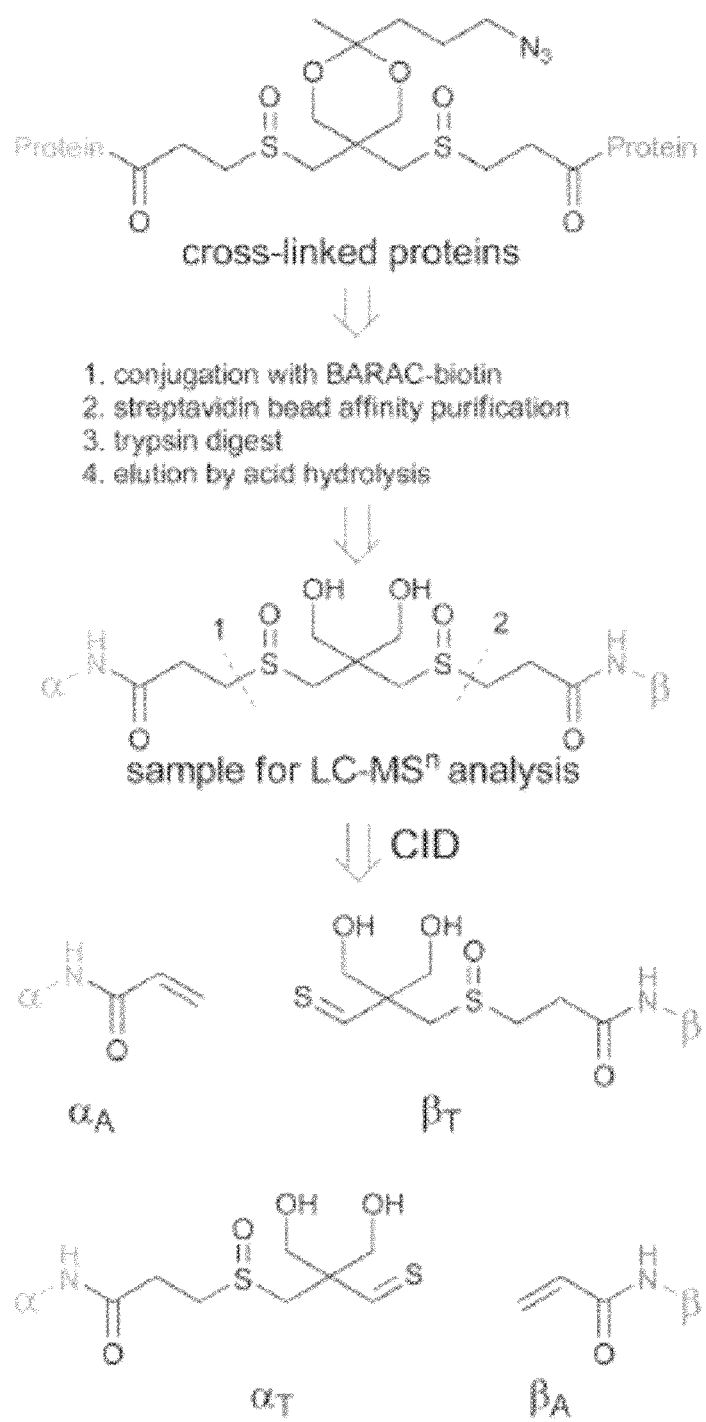
FIG. 20 shows an embodiment of a workflow for affinity purification of cross-linked cytochrome C proteins. The MS$^2$ fragments resulting from CID cleavage sites are shown.
Figure 21:
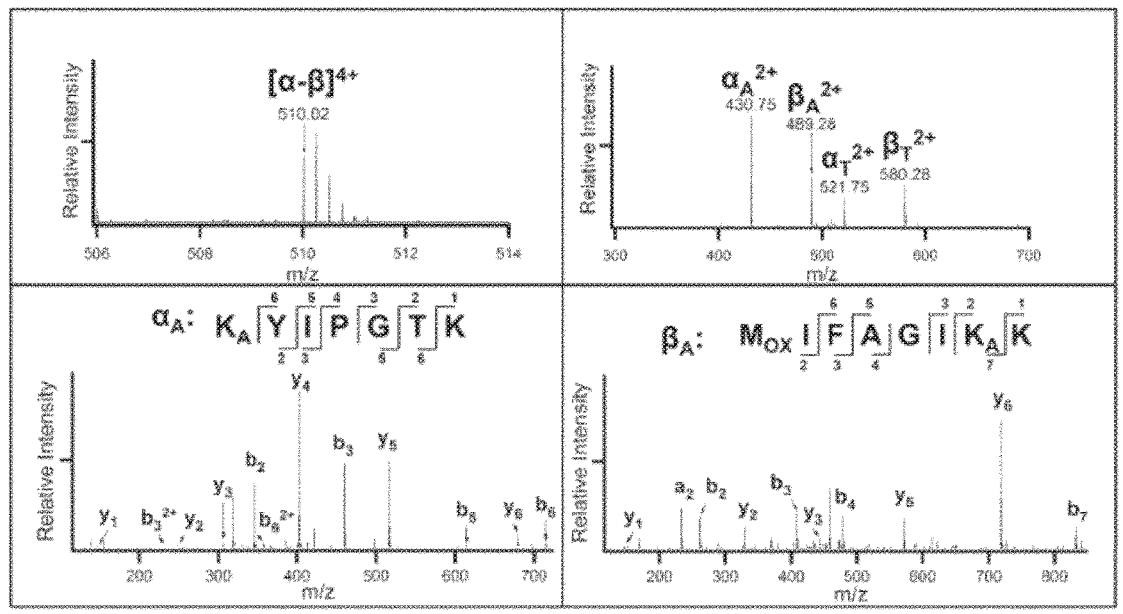
FIG. 21A-FIG. 21D show MS$^n$ analysis of a representative DSBSO 3 inter-linked peptide (α-β) of cytochrome C (m/z 510.02$^{4+}$).

The cross-linked peptides were eluted from the beads with acid, and thus became acid-cleaved products of azide-A-DSBSO cross-linked peptides, i.e., DSBSO cross-linked peptides, which were then subjected to LC/MS″ analysis. The general workflow and the structure of the cross-linked peptides leading up to LC/MS″ analysis are illustrated in FIG. 20. As illustrated, the acid-cleaved products are the final analytes for LC/MS″ analysis. It is noted that the acid-cleaved products of azide-A-DSBSO and alkyne-A-DSBSO cross-linked peptides are the same, because the differentiated group is lost during the acid elution of cross-linked peptides form affinity matrix during enrichment.

Since the cleavable C—S bonds in SDBSO are similar to those in DSSO, the general data analysis work flow for the identification of SDBSO cross-linked peptides by LC/MS″ is similar to the analysis of DSSO cross-linked peptides.[4] There are three types of cross-linked peptides, i.e., dead-end, intra-linked, and inter-linked peptides. Among them, inter-linked peptides provide the most informative structure details for defining protein-protein interaction interfaces. Therefore, in some embodiments, the goal that is most interested is to identify inter-linked peptides between the same and/or different proteins.

As an example, FIG. 21A-FIG. 21D describe a representative MS″ analysis of a DSBSO inter-linked cytochrome C peptide (α-β) that was detected as a quadruply charged ion (m/z, $510.0166^{4+}$). As shown $MS^2$ analysis resulted in two pairs of peptide fragments (i.e., $\alpha_A/\beta_T$ or $\alpha_T/\beta_A$), characteristic fragmentation of inter-linked heterodimeric peptide. Subsequent $MS^3$ analysis of $MS^2$ fragment $\alpha_A$ (m/z $430.75^{2+}$) and PA (m/z $489.28^{2+}$) determined their sequences as $K_A$YPIGTK and $M_{(ox)}$IFAGIK$_A$K respectively, in which $K_A$ is modified with the alkene moiety. Integration of $MS^1$, $MS^2$, $MS^3$ results has unambiguously determined this DSBSO cross-linked cytochrome C peptide as [$^{74}$KY-IPGTK$^{80}$ inter-linked to $^{81}$M$_{(ox)}$IFAGIKK$^{88}$], in which a cross-link was formed between K74 and K87 in cytochrome C.

In total, LC/MS″ analysis of enriched cross-linked cytochrome C identified 7 unique inter-linked peptides. TABLE 7 provides summary of Unique Inter-linked Peptides Identified from Azide-A-DSBSO Cross-linked CytC. In addition, 11 unique dead-end and 5 unique intralinked cytochrome C peptides were identified since all types of cross-linked peptides can be selectively enriched (data not shown). The results are comparable to those obtained using DSSO cross-linking,[4] demonstrating the effectiveness of azide-A-DSBSO based XL-MS strategy. Although it is not necessary to enrich cross-linked peptides for simple proteins like cytochrome C, it is evident that such a process is essential for mapping protein interaction interfaces at the systems level.[6]

References—1

1 (a) F. Herzog. A. Kahraman, D. Boehringer, R. Mak, A. Bracher, T. Walztboeni, A. Leitner, M. Beck, F. U. Hartl, N. Ban, L. Malmstrom and R. Aebersolcl, *Science*, 2012, 337, 1348-1352; (b) A. Policis, F. Stengel, z. Hall, H. Hernandez, A. Leitner, T. Walzlhoeni, C. V. Robinson and R. Aebersold, *Nat. Methods*, 2014, 11, 40.3-406.

2 (a) C. V. Robinson, A. Sali and W. Baumeister, *Nature*, 2007, 450, 973-982; (b) J. P. Erzberger, F. Stengel, R. Pellarin, S. Zhang, T. Schaefer, C. H. S. Aylett, P. CimermanCic, D. Boehringer, A. Sali, R. Aebersolel and N. Ban, *Cell*, 2014, 158, 1123-1135; (c) A. Kao, A. Randall, Y. Yang, V. R. Patel, W. Kandur, S. Guan, S. D. Rychnovsky, P. Baldi and L. Huang, *Mol. Cell. Proteomics*, 2012, 11, 1566-1577.

3 (a) C. Guerrero, C. Tagwerker, P. Kaiser and L. Huang, *Mol. Cell. Proteomics*, 2006, 5, 366-378; (b). J. D. Chavez, C. R. Weisbrod, C. Zheng, J. K. Eng and J. E. Bruce, *Mol. Cell. Proteomics*, 2013, 12, 1451-1467.

4 A. Kao, C.-L. Chiu, D. Vellucci, Y. Yang, V. 1.1. Patel, S. Guan, A. Randall, P. Baldi, S. D. Rychnovsky and L. Huang, *Mol. Cell. Proteomics*, 2011, 10, M110.002212.

5 A. Leitner, T. Walzthoeni, A. Kahraman, F. Herzog, O. Rinner, M. Beck and R. Aebersold, *Mol. Cell. Proteomics*, 2010, 9, 1634-1649.

6 R. M. Kaake, X. Wang, A. Burke, C. Yu, W. Kandur, Y. Yang, E. J. Novitsky, T. Second, J. Duan, A. Kao, S. Guan, D. Vellucci, S. D. Rychnovsky and L. Huang, *Mol. Cell. Proteomics,* 2014, 13, 3533-3543, DOI: 10.1074/mcp.M114.042630.

7 D. Paramelle, G. Miralles, G. Subra and J. Martinez, *J. Proteomics,* 2013, 13, 438-456.

8 (a) E. v. Petrotchenko, J. J. Serpa and c. H. Borchers, *Mol. Cell. Proteomics,* 2011, 10, DOI: 10.1074/mcp.M110.001420; (b) M. Q. Muller, F. Dreiocker, C. H. Ihling, M. Schafer and A. Sinz, *J. Mass. Spectrom.,* 2010, 45, 880-891; (c) F. Dreiocker, M. Q. Muller, A. Sinz and M. Schafer, *J. Mass. Spectrom.,* 2010, 45, 178-189.

9 Y. Lu, M. Tanasova, B. Borhan and G. E. Reid, *Anal. Chem.,* 2008, 80, 9279-9287.

10 J. Luo, J. Fishburn, S. Hahn and J. Ranish, *Mo!. Celf. Proteomics,* 2012, 11, DOI: 10.1074/mcp.M111.008318.

11 (a) J. Szychowski, A. Mandavi, J. J. L. Hodas, J. D. Bagert, J. T. Ngo, P. Landgraf, D. C. Dieterich, E. M. Schuman and D. A. Tirrell,]. *Am. Chem. Soc.,* 2010, 132, 18351-18360; (b) M. A. Nessen, G. Kramer, J. Back, J. M. Baskin, L. E. J. Smeenk, L. J. de Koning, J. H. van Maarseveen, L. de Jong, C. R. Bertozzi, H. Hiemstra and C. G. de Koster, *J. Proteome Res.,* 2009, 8, 3702-3711; (c) S. M. Chowdhury, X. Du, N. Tolic, S. Wu, R. J. Moore, M. u. Mayer, R. D. Smith and J. N. Adkins, *Anal. Chem.,* 2009, 81, 5524-5532.

12 Lead reference: M. G. Finn and V. V. Fokin, *Chem. Soc. Rev.,* 2010, 39, 1231-1232.

13 M. C. Murguia, S. E. Vaillard and R. J. Grau, *Synthesis,* 2001, 7, 1093-1097.

14 Although yield ranges were reported for many transformations to reflect our experience with the sequence, the overall yields were calculated based on the specific examples written up in the experimental section.

15 Y. Ma, *Heteroat. Chem.,* 2002, 13, 307-309.

16 T. Tsunoda, M. Suzuki and R. Noyori, *Tetrahedron Lett.,* 1980, 21, 1357-1358.

17 N. M. Leonard and J. Brnnckova, *J. Org. Chem.,* 2011, 76, 9169-9174.

18 D. Vellucci, A. Kao, R. M. Kaake, S. D. Rychnovsky and L. Huang, *J. Am Soc. Mass Spectrom.,* 2010, 21, 1432-1445.

19 J. C. Jewett, E. M. Sletten and C. R. Bettozzi, *J. Am. Chem. Soc.,* 2010, 132, 3688-3690.

General Experimental Details

All chemicals were purchased from Sigma-Aldrich, Acros Organics, Alfa Aesar, TCI, Advanced ChemTech, or Fisher and used without further purification unless otherwise noted. 1,5-Dioxaspiro [5.5]undecane-3,3-diyldimethanol (diol$_6$)[1], N-hydroxysuccinimidyl trifluoroacetate[2], and 5-azido pentanone (azide 11)[3] were synthesized according to literature procedure. Ethanol was purchased from Gold Shield. Solvents were of reagent grade and used as without further purification except as follows: N,N-dimethylformamide (DMF), dichloromethane (DCM), and tetrahydrofuran (THF) were degassed and then passed through anhydrous neutral alumina A-2 before use, according to the procedure described by Grubbs.[4] Methanol was dried over activated 3 Å molecular sieves prior to use. Triethylamine was distilled over calcium hydride and stored over activated 3 Å molecular sieves prior to use. Diisopropylethylamine (DIPEA) was distilled over calcium hydride prior to use. Trifluoroacetic anhydride (TFAA) and trimethylsilyl triflate (TMSOTf) were distilled prior to use. Reported reaction temperatures refer to the temperature of the heating medium. Reactions were performed in flame- or oven-dried glassware under an atmosphere of dry argon using standard Schlenk techniques unless otherwise noted. Room temperature (rt) refers to 25±3° C. Reactions were monitored by thin-layer chromatography (TLC) using EMD Chemicals Inc. silica gel 60 F256 plates. Flash chromatography was performed using Ultra Pure SiliaFlash P60, 230-400 mesh (40-63 μm) silica gel (SiO$_2$) following the general procedure by Still and co-workers.[5]

Instrumentation

Proton NMR spectra measurements were acquired at 500 MHz and 600 MHz. Carbon NMR spectra were obtained at 125 MHz. Proton NMR chemical shifts (δ) are reported in parts per million (ppm) and referenced to the residual solvent peak at 7.27 ppm for deuterated chloroform (CDCl$_3$) and 2.50 for deuterated dimethyl sulfoxide (DMSO-d$_6$). Carbon NMR chemical shifts (δ) are reported in ppm and referenced to the residual solvent peak at 77.23 ppm for deuterated chloroform and 39.52 for deuterated dimethylsulfoxide.[6] NMR data are reported in the following manner: chemical shift, multiplicity, (s=singlet, d=doublet, t=triplet, q=quartet, quin=quintet, m=multiplet, br=broad, app=apparent), coupling constants (J) in hertz (Hz), and integration. High Resolution Mass Spectrometry (HRMS) accurate mass experiments were performed by the University of California, Irvine mass spectrometry laboratory.

Experimental Procedures

Bis(2,5-dioxopyrrolidin-1-yl)-3,3'4(2-(3-azidopropyl)-2-methyl-1,3-dioxane-5,5-diyl)bis(methylenesulfinyl))dipropanoate (azide-A-DSBSO) (3)

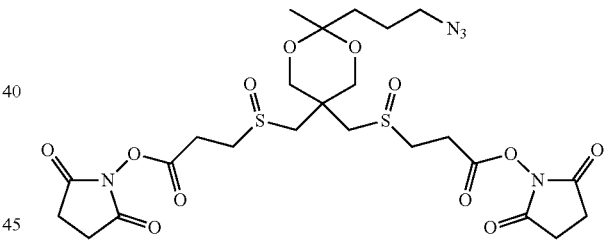

NHS ester 14 (1.21 g, 2.00 mmol) was dissolved in CHCl3 (40 mL), and the reaction mixture was cooled to 0° C. A solution of m-CPBA (0.905 g, 77% mixture with the remainder water, 4.03 mmol) in CHCl$_3$ (40 mL) was added drop-wise and the reaction mixture was stirred for 10 min. The reaction mixture was diluted with CHCl$_3$ (100 mL), and then washed with saturated aqueous NaHCO$_3$ (3×125 mL). The CHCl$_3$ layer was dried over MgSO$_4$, filtered, and concentrated to afford bis-sulfoxide 3 as a white solid and mixture of diastereomers (1.13 g, 89%): 1H NMR (500 MHz, DMSO-d6) δ 3.98-3.79 (m, 4H), 3.35 (appar. t, 2H, J=6.8 Hz), 3.29-2.98 (m, 12H), 2.82 (s, 8H), 1.76-1.56 (m, 4H), 1.36 (s, 3H); $^{13}$C NMR (125 MHz, DMSO-d$_6$) δ 170.10, 170.08, 167.78, 167.76, 99.18, 99.06, 79.19 (residual CHCl$_3$), 65.82, 65.4, 65.0, 64.68, 55.03, 54.75, 54.62, 50.82, 46.11, 46.02, 45.73, 45.67, 40.02, 36.43, 36.31, 34.66, 34.60, 25.48, 25.25, 23.21, 23.18, 23.08, 23.04, 22.66, 20.12, 20.06; IR (KBr) 2931, 2850, 2098, 1782, 1739, 1624 cm$^{-1}$; HRMS (ESI) m/z calcd for C$_{24}$H$_{33}$N$_5$O$_{12}$S$_2$Na [M+Na]$^+$ 670.1465, found 670.1450.

Bis(2,5-dioxopyrrolidin-1-yl) 3,3'4(2-(but-3-yn-1-yl)-2-methyl-1,3-dioxane-5,5-diyl)bis-(methylenesulfinyl))dipropanoate (alkyne-A-DSBSO) (4)

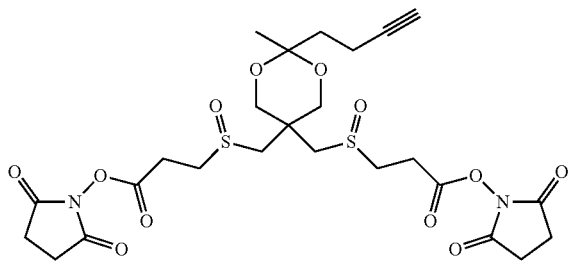 [SMILES: C#CCCC1(C)OCC(CS(=O)CCC(=O)ON2C(=O)CCC2=O)(CS(=O)CCC(=O)ON2C(=O)CCC2=O)CO1]

NHS ester 21 (1.82 g, 3.11 mmol) was dissolved in CHCl$_3$ (105 mL), and the solution was cooled to 0° C. Next m-CPBA (1.40 g, 77% mixture with the remainder water, 6.24 mmol) was dissolved in CHCl$_3$ (56.5 mL), then was added drop-wise, and the reaction mixture was stirred for 10 min. The reaction mixture was diluted with CHCl$_3$ (175 mL), and then washed with saturated aqueous NaHCO$_3$ (5×40 mL). The CHCl$_3$ layer was collected, dried over MgSO4, filtered, and concentrated to afford 4 as a white solid and mixture of diastereomers (1.88 g, 98%): 1H NMR (500 MHz, DMSO-d6) δ 4.01-3.79 (m, 4H), 3.32, (s, 1H), 3.29-2.97 (m, 10H), 2.82 (s, 8H), 2.75 (s, 1H), 2.26-2.19 (m, 2H), 1.94-1.85 (m, 3H), 1.37 (s, 3H); $^{13}$C NMR (125 MHz, DMSO-d$_6$) δ 170.1, 167.8, 98.46, 98.36, 84.40, 79.19 (residual CHCl$_3$), 71.03, 65.8, 65.3, 65.0, 64.59, 55.1, 54.7, 54.5, 46.00, 45.69, 45.63, 40.12, 40.02, 36.7, 36.37, 36.27, 25.46, 23.20, 23.15, 23.07, 23.01, 19.81, 12.28; IR (thin film) 3294, 2989, 2934, 2877, 2117, 1813, 1782, 1736, 1427, 1365, 1207, 1134, 1088, 1068. 1034 cm$^{-1}$; HRMS (ESI) m/z calcd for $C_{25}H_{32}N_2O_{12}S_2$ [M+Na]$^+$ 639.1295, found 639.1295.

1,5-Dioxaspiro[5.5]undecane-3,3-diylbis(methylene) dimethanesulfonate (7)

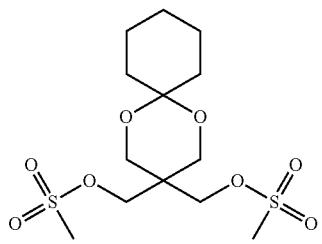 [SMILES: CS(=O)(=O)OCC1(COS(C)(=O)=O)COC2(CCCCC2)OC1]

Diol 6 (30.18 g, 139.5 mmol)[1] was dissolved in DMF (420 mL), and triethylamine (78 mL, 560 mmol) was added via syringe. At 0° C., methanesulfonyl chloride (30.0 mL, 388 mmol) was added drop-wise via addition funnel. The solution was gradually warmed to rt, and stirred for 24 h. More DMF (240 mL), triethylamine (38 mL, 270 mmol) and methanesulfonyl chloride (11 mL, 140 mmol) were added at rt and the mixture was stirred another 24 h. The reaction mixture was filtered and the filter cake was rinsed with EtOAc (3×100 mL). Additional EtOAc (500 mL) was added, and the solution was washed with saturated aqueous NaHCO$_3$ (150 mL). The aqueous layer was back extracted with EtOAc (150 mL), and the combined organic layers were washed with saturated aqueous NaHCO$_3$ (2×150 mL), water (3×100 mL), and brine (150 mL). The EtOAc layer was dried over MgSO$_4$, filtered, and concentrated. The crude brown oil was dissolved in CH2Cl2 and concentrated repeatedly until a red solid formed. The red solid was scraped out of the flask and chopped into a fine powder at which point the appearance changed to a light yellow solid. The yellow solid was stirred in 900 mL boiling ether, 125 mL CH$_2$Cl$_2$ was slowly added while maintaining a boil and then filtered hot. The clear yellow filtrate was boiled down to 600 mL and then hexanes (100 mL) were added slowly while maintaining a boil. The solution was further boiled down to 600 mL, allowed to cool to room temperature then placed in a freezer overnight. The resulting crystals were filtered, washed 3 times with cold hexanes and dried under high vacuum to afford 7 as off-white long needle shaped crystals (32.17 g, 62%). The mother liquors and hot-filtration materials were purified by column chromatography (step-gradient from 6:4 hexanes:EtOAc to 1:2 hexanes:EtOAc) to afford additional 7 as off-white crystals (15.57 g, 30%): 1H NMR (500 MHz, CDCl$_3$) δ 4.28 (s, 4H), 3.79 (s, 4H), 3.07 (s, 6H), 1.76-1.66 (m, 4H), 1.51-1.44 (m, 4H), 1.45-1.41 (m, 2H); 13C NMR (125 MHz, CDCl$_3$) δ 99.4, 68.0, 60.8, 38.4, 37.4, 32.5, 25.6, 22.6; IR (KBr pellet) 2943, 2862, 1354 cm$^{-1}$; HRMS (ESI) m/z calcd for $C_{13}H_{24}O_8S_2Na$ [M+Na]+ 395.0810, found 395.0801.

S,S'-(1,5-Dioxaspiro[5.5]undecane-3,3-diylbis(methylene)) diethanethioate (8)

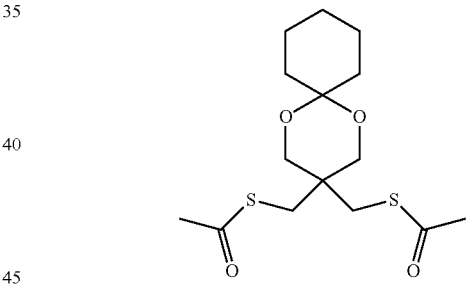

Mesylate 7 (6.38 g, 17.1 mmol) was dissolved in DMF (90 mL). Potassium thioacetate (7.85 g, 68.7 mmol) was added at room temp and the solution was heated to 55° C. for 48 h. The precipitates were filtered off, washed with excess EtOAc, and the filtrate was concentrated to dryness. The red crystalline solid was recrystallized from hexanes (9.82 g in 500 mL) after hot filtration the solution was brought back to a boil (total volume 375 mL). The solution was cooled, placed in the freezer overnight, filtered, and washed with cold hexanes affording 8 as off-white small crystals (3.95 g, 69%). The mother liquors and hot-filtration materials were purified by column chromatography (9:1 hexanes:EtOAc) to afford additional 8 as an off-white solid (1.14 g, 20%): 1H NMR (500 MHz, CDCl3) δ 3.65 (s, 4H), 3.09 (s, 4H), 2.37 (s, 6H), 1.75-1.67 (m, 4H), 1.58 (H2O), 1.52-1.44 (m, 4H), 1.40 (app d, J=4.2 Hz, 2H); 13C NMR (125 MHz, CDCl3) δ 195.1, 98.7, 65.3, 37.3, 32.6, 31.8, 30.9, 25.80, 22.70; IR (KBr pellet) 2927, 2866, 1693, 1446 cm$^{-1}$; HRMS (ESI) m/z calcd for $C_{15}H_{24}O_4S_2Na$ [M+Na]$^+$ 355.1014, found 355.1020.

Dimethyl 3,3'-((1,5-dioxaspiro[5.5]undecane-3,3-diylbis(methylene))bis(sulfanediyl))-dipropanoate (9)

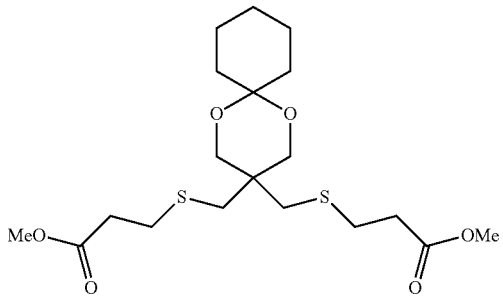 [SMILES: COC(=O)CCSCC1(CSCCC(=O)OC)COC2(CCCCC2)OC1]

Thioacetate 8 (3.95 g, 11.9 mmol) was dissolved in MeOH (300 mL), and triethylamine (8.5 mL, 61 mmol) was added. Methyl acrylate (3.20 mL, 36 mmol) was added dropwise via syringe and the solution was stirred at room temp for 6 h. The solution was concentrated, dissolved in CH2C12, and concentrated to dryness to afford 9 as a clear light brown oil (4.90 g, 98%): $^1$H NMR (500 MHz, CDCl$_3$) δ 3.73 (s, 4H), 3.71 (s, 6H), 2.82 (t, J=7.4 Hz, 4H), 2.74 (s, 4H), 2.64 (t, J=7.3 Hz, 4H), 1.74 (br s, 4H), 1.51 (t, J=5.4 Hz, 4H), 1.41 (app d, J=4.2 Hz, 2H); $^{13}$C NMR (125 MHz, CDCl$_3$) δ 172.5, 98.6, 65.5, 52.0, 38.4, 36.0, 34.9, 32.8, 29.1, 25.8, 22.7; IR (neat) 2947, 2862, 1739, 1439 cm$^{-1}$; HRMS (ESI) m/z calcd for C$_{19}$H$_{32}$O$_6$S$_2$Na [M+Na]' 443.1538, found 443.1522.

Dimethyl 3,3'-((2,2-bis(hydroxymethyl)propane-1,3-diyl)bis(sulfanediyl))dipropanoate (10)

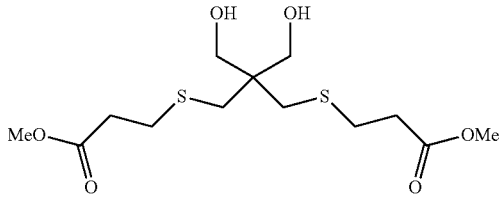 [SMILES: COC(=O)CCSCC(CO)(CO)CSCCC(=O)OC]

In(OTf)3 Procedure: Ketal 9 (0.202 g, 0.482 mmol) was placed in a microwave tube followed by In(OTf)$_3$ (0.0079 g, 0.014 mmol), MeOH (1.9 mL), and H$_2$O (433 mL, 24.0 mmol). The solution was placed in a microwave reactor and heated to 70° C. at 50 psi for 30 min. The solution was concentrated and purified by column chromatography: The solution was concentrated, redissolved in a minimal amount of CDCl$_3$ and loaded onto a silica gel column of 1.8 cm O.D. packed 12 cm high with a slurry of 20 mL silica in 3:1 Hexanes:EtOAc, and eluted with 100 mL 3:1, 50 mL 2:1, 50 mL 1:1, 100 mL 1:2, 100 mL 1:3 hexanes:EtOAc. After collecting 10 mL fractions; fractions 4-8 were concentrated to afford to afford starting material 9 (0.0175 g, 8.6%) and fractions 24-38 were concentrated to afford 10 as a clear yellow oil (0.140 g, 86%). Characterization data were identical to that of the products using the DOWEX procedure below.

DOWEX Procedure: Ketal 9 (5.07 g, 12.05 mmol) was dissolved in MeOH (150 mL), and DOWEX 50WX8-100 resin (35 g) was added to the solution. After stirring vigorously for 18 h, the reaction mixture was filtered, and the filtrate was concentrated under reduced pressure. The crude oil was purified by column chromatography: A column of 5 cm O.D. packed 16 cm high with a slurry of 200 mL silica was loaded with the crude oil and eluted using 600 mL 3:1, 250 mL 7:3, 250 mL 6:4, 250 mL 1:1, 500 mL 1:2, 250 mL 7:3, 250 mL 8:2 hexanes:EtOAc to afford starting material 9 (0.720 g, 14%) and 10 as a clear yellow oil (2.76 g, 67%): $^1$H NMR (500 MHz, CDCl$_3$) δ 3.72 (s, 6H), 3.67 (d, J=5.7 Hz, 4H), 2.83 (t, J=7.2 Hz, 4H), 2.69 (s, 4H) 2.65 (t, J=7.2 Hz, 4H), 2.39 (br s, 2H); $^{13}$C NMR (125 MHz, CDCl$_3$) δ 172.7, 66.1, 52.1, 44.9, 35.1, 34.8, 28.8; IR (neat) 3483, 2924, 1732, 1435 cm-1; HRMS (ESI) m/z calcd for C$_{13}$H$_{24}$O$_6$S$_2$Na [M+Na]+ 363.0192, found 363.0904.

Alkylation Procedure from Diol 15: To a three-necked round bottom flask equipped with an overhead stirrer, a water-cooled condenser, and an argon inlet was added diol 15 (22.0 mL, 197.7 mmol), thiol 16 (17.3 g, 65.9 mmol), potassium carbonate (18.2 g, 131.8 mmol), and DMF (330 mL). The mixture was heated to 40° C. for 24 h, after which the DMF was removed directly from the vessel by vacuum distillation affording diol 10 as a clear colorless oil (22.4 g). Purification of a small sample by column chromatography produced diol 10 in a 75% yield. Characterization data were identical to that of the product using the DOWEX procedure above.

Dimethyl 3,3'-(((2-(3-azidopropyl)-2-methyl-1,3-dioxane-5,5-diyl)bis(methylene))-bis(sulfanediyl)) dipropanoate (12)

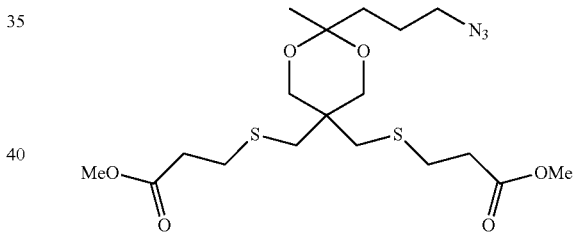

Dean-Stark Procedure: Diol 10 (4.58 g, 13.5 mmol) was dissolved in benzene (120 mL). 5-Azido pentanone$^3$ (11) (1.77 g, 13.9 mmol) and CSA (0.314 g, 1.35 mmol) were added to the solution, a Dean-Stark apparatus was attached, and the reaction mixture was heated to 115° C. After 21 h, the reaction mixture was cooled, diluted with EtOAc and partitioned between EtOAc (250 mL) and NaHCO$_3$ (125 mL). The EtOAc layer was separated, washed with brine (75 mL), dried over MgSO$_4$, filtered, and concentrated. The crude brown oil was purified by column chromatography: A 6 cm O.D. column packed 15 cm high with 325 mL silica slurry was loaded with the crude product in minimal CH$_2$Cl$_2$, eluting 750 mL 4:1, 1000 mL 3:1, 500 mL 7:3 hexanes:ethyl acetate and collecting 125-200 mL fractions. Fractions 8-15 were concentrated affording 12 as a clear light yellow oil (4.78 g, 79%): 1H NMR (500 MHz, CDCl$_3$) δ 3.78 (d, J=11.9 Hz, 2H), 3.74-3.70 (m, 8H), 3.32 (app t, J=3.4 Hz, 2H), 2.84 (t, J=7.3 Hz, 4H), 2.80 (J=7.3 Hz, 2H), 2.67-2.57 (m, 6H), 1.76-1.73 (m, 4H), 1.39 (s, 3H); $^{13}$C NMR (125 MHz, CDCl$_3$) δ 172.4, 99.4, 66.02, 52.0, 51.74, 38.1, 36.0, 35.8, 35.0, 34.9, 29.1, 29.0, 23.1, 20.1; IR (neat) 2954, 2870, 2098, 1739, 1435; cm$^{-1}$; HRMS (ESI) m/z calcd for C$_{18}$H$_{31}$N$_3$O$_6$S$_2$Na [M+Na]$^+$ 472.1552, found 472.1556.

Dimethyl 3,3'-(((2-(3-azidopropyl)-2-methyl-1,3-dioxane-5,5-diyl)bis(methylene))-bis(sulfanediyl))dipropanoate (12)

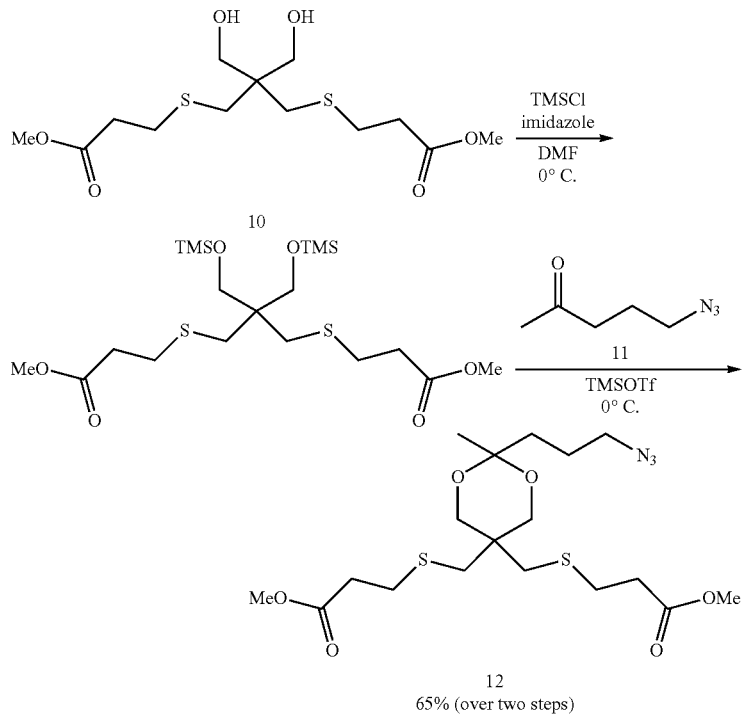

12
65% (over two steps)

Noyori Procedure:[7] To a stirred solution of crude diol 10 from the alkylation procedure (0.756 g, 2.23 mmol) and imidazole (1.04 g, 15.3 mmol) in DMF (28 mL) was added TMSCl (1 M solution in THF, 12.6 mL) resulting in the formation of a yellow solution. After stirring for 12 h, the reaction mixture was quenched with water (150 mL) and extracted with ethyl acetate (3×150 mL). The combined organic portions were washed with water (3×150 mL), dried over anhydrous sodium sulfate, filtered, and concentrated in vacuo to afford the crude TMS ether as an orange oil which was used immediately without further purification: 1H NMR (600 MHz, CDCl3): δ 3.71-3.67 (m, 10H), 2.78 (t, J=7.5 Hz, 4H), 2.61 (t, J=7.5 Hz, 4H), 2.57 (s, 4H), 0.08 (s, 18H).

To a cooled (−78° C.) solution of the crude TMS ether (1.00 g, 2.06 mmol) and azide 113 (0.262 g, 2.06 mmol) was added TMS-OTf (50 µL, 0.1 mmol). The solution was stirred for 12 h, over which the time gradually warmed to room temperature. The reaction was quenched with two drops of pyridine (ca. 100 µL), and the mixture was diluted in ethyl acetate (100 mL). The organic layer was washed with water (2×100 mL) and brine (100 mL), dried over anhydrous sodium sulfate, filtered, and concentrated in vacuo to give crude 12 as a black oil. The crude product was purified by column chromatography (1:3 ethyl acetate:hexanes) to afford 12 as an orange oil (0.651 g, 65% over three steps). 1H and 13C NMR spectra were consistent with those previously reported above.

3,3'-(((2-(3-Azidopropyl)-2-methyl-1,3-dioxane-5,5-diyl)bis(methylene))bis(sulfanediyl))-dipropanoic acid (13)

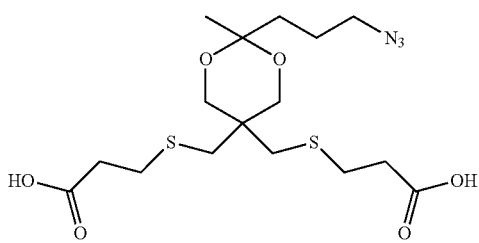 [SMILES: CC1(CCCN=[N+]=[N-])OCC(CSCCC(=O)O)(CSCCC(=O)O)CO1]

Azide 12 (4.65 g, 10.3 mmol) was dissolved in 4:1 THF:H2O (67 mL), and LiOH.H2O (0.913 g, 21.8 mmol) was added to the reaction mixture. After 1 h, additional LiOH.H2O (0.913 g, 21.8 mmol) was added. The reaction mixture was stirred for an additional 2 h and partitioned between H2O (50 mL) and hexanes (50 mL). The aqueous layer was acidified to pH 1 with 6 M HCl and extracted with EtOAc (5×25 mL). The combined EtOAc extracts were dried over MgSO4, filtered, and concentrated to afford 13 as a clear, light yellow oil (4.58 g, quant.): 1H NMR (500 MHz, CDCl3) δ 11.12 (br s, 2H), 3.78-3.69 (m, 4H), 3.29 (t, J=6.0 Hz, 2H), 2.83-2.76 (m, 6H), 2.67 (dt, J=12.0, 7.1 Hz, 4H), 2.60 (s, 2H), 1.73 (s, 4H), 1.33 (s, 3H); 13C NMR (125 MHz, CDCl3) δ 178.0, 177.9, 99.5, 65.9, 51.6, 38.1, 35.8, 35.6, 34.9, 34.8, 28.6, 28.57, 23.0, 20.0; IR (neat) 3097, 2989, 2098, 1712, 1412 cm-1; HRMS (ES/MeOH) m/z calcd for C₁₆H₂₇N₃O₆S₂Na [M+Na]⁺ 444.1239, found 444.1244.

Bis(2,5-dioxopyrrolidin-1-yl) 3,3'-(((2-(3-azidopropyl)-2-methyl-1,3-dioxane-5,5-diyl)bis(methylene))bis(sulfanediyl))dipropanoate (14)

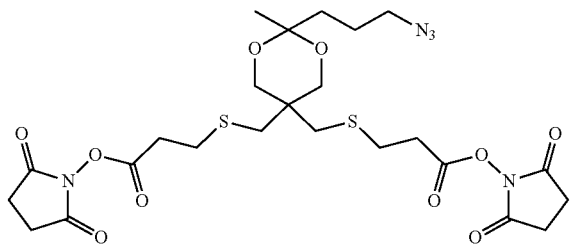 [SMILES: CC1(CCCN=[N+]=[N-])OCC(CSCCC(=O)ON2C(=O)CCC2=O)(CSCCC(=O)ON2C(=O)CCC2=O)CO1]

EDC Method: Diacid 13 (2.16 g, 5.12 mmol) was dissolved in DMF (52 mL), and N-hydroxysuccinimide was added (1.413 g, 12.3 mmol). 1-Ethyl-3(3-dimethylaminopropyl)carbodiimide hydrochloride (EDCI-HCl) (2.360 g, 12.3 mmol) was added followed by triethylamine (0.10 mL, 0.71 mmol) and the reaction mixture was stirred for 13 h. The reaction solution was concentrated by half, diluted with EtOAc (50 mL) then washed with sat. ammonium chloride (2×25 mL), sat. NaHCO₃ (2×25 mL), water (2×25 mL), and brine (25 mL). The organic layer was dried over Na₂SO₄, filtered, and concentrated. The crude oil was purified by column chromatography by loading onto a column 3.5 cm O.D packed 13 cm high with 100 mL silica slurry in 1:1 hexanes:EtOAc, eluting with 325 mL 1:1, 600 mL 1:2, 200 mL 1:3 hexanes:EtOAc and collecting 175 mL followed by 27 mL fractions. Fractions 9-29 were concentrated affording 14 as a white solid (1.97 g, 62%): ¹H NMR (500 MHz, CDCl₃) δ 3.79 (d, J=11.9 Hz, 2H), 3.73 (d, J=11.9 Hz, 2H) 3.32 (t, J=6.0 Hz, 2H), 3.00-2.78 (m, 18H), 2.66 (s, 2H), 2.05 (acetone), 1.71 (br s, 4H), 1.40 (s, 3H); ¹³C NMR (125 MHz, CDCl₃) δ 169.23, 169.20, 167.3, 99.57, 66.0, 51.76, 38.17, 36.05, 35.89, 35.70, 32.34, 32.25, 28.31, 25.80, 25.56, 23.18, 20.01; IR (KBr) 2931, 2850, 2098, 1782, 1739, 1624 cm⁻¹; LRMS (ES/MeOH) m/z calcd for C₂₄H₃₃N₅O₁₀S₂Na [M+Na]⁺ 638.2, found 638.3.

TFAA Method: To a cooled (0° C.) solution of diacid 13, (2.45 g, 5.81 mmol), N-hydroxysuccinimide (2.68 g, 23.3 mmol), and DIPEA (8.10 mL, 46.4 mmol) in DMF (30 mL) was added TFAA (3.28 mL, 23.3 mmol) dropwise, slowly. The light orange solution was stirred at 0° C. for 3 h, after which the reaction was determined complete by TLC. The reaction mixture was partitioned between ethyl acetate (125 mL) and hydrochloric acid (1 M, 100 mL). The layers were separated, after which the acidic aqueous layer was extracted with ethyl acetate (2×125 mL), and the combined organic layers were washed with sodium bicarbonate solution (1 M, 3×100 mL), water (100 mL), and brine (100 mL). The organic layer was dried over anhydrous sodium sulfate, filtered, and concentrated to a dark oil which was purified by column chromatography (step-gradient from 1:1 hexanes:EtOAc to 1:3 hexanes:EtOAc) affording 14 as a white solid (2.34 g, 66%). ¹H and ¹³C NMR spectra were consistent with those previously reported above.

Dimethyl 3,3'-(((2-(but-3-yn-1-yl)-2-methyl-1,3-dioxane-5,5-diyl)bis(methylene))-bis(sulfanediyl))dipropanoate (19)

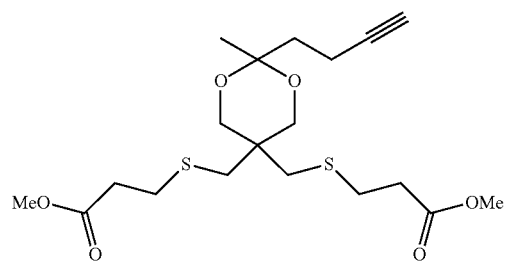 [SMILES: C#CCCC1(C)OCC(CSCCC(=O)OC)(CSCCC(=O)OC)CO1]

Diol 10 (2.21 g, 6.48 mmol) was dissolved in benzene (45 mL). 1-Hexyne-5-one (1.33 g, 13.8 mmol) and CSA (0.152 g, 0.654 mmol) were added to the solution, a Dean-Stark apparatus was attached, and the reaction mixture was heated to 115° C. After 27 h, the reaction mixture was cooled, diluted with EtOAc and partitioned between EtOAc (25 mL) and NaHCO₃ (125 mL). The EtOAc layer was separated, washed with brine (25 mL), dried over MgSO₄, filtered, and concentrated. The crude brown oil was purified by column chromatography using a column 6 cm O.D. packed 15 cm high with 300 mL silica slurried in 4:1 Hexanes:EtOAc. The crude was loaded after dissolution in minimal CH₂Cl₂ and the column was eluted with 250 mL 4:1, 1000 mL 3:1, 500 mL 7:3, 100 mL 65:35 hexanes:EtOAc. After collecting 2×200 mL fractions and 25×100 mL fractions, fractions 8-15 were concentrated affording 19 as a clear light yellow oil (2.08 g, 77%): ¹H NMR (500 MHz, CDCl₃) δ 3.76 (d, J=12.0, 2H), 3.71 (s, 6H), 3.70 (d, J=10.1 Hz, 2H), 2.86-2.77 (m, 6H), 2.66-2.59 (m, 6H), 2.33 (ddd, J=8.2, 6.7, 2.7 Hz, 2H), 1.98-1.93 (m, 3H), 1.39 (s, 3H); ¹³C NMR (125 MHz, CDCl₃) δ 172.40, 172.37, 98.8, 84.5, 68.3, 66.0, 52.0, 38.1, 37.7, 35.9, 35.8, 35.0, 34.9, 29.10, 29.08, 20.1, 12.9; IR (thin film) 3286, 2993, 2951, 2870, 2117, 1739, 1439, 1362, 1250, 1200, 1173, 1134, 1057, 1034; HRMS (ESI) m/z calcd for C₁₉H₃₀O₆S₂ [M+Na]⁺ 441.1382, found 441.1374.

Bis(2,5-dioxopyrrolidin-1-yl) 3,3'-(((2-(but-3-yn-1-yl)-2-methyl-1,3-dioxane-5,5-diyl)bis(methylene))bis(sulfanediyl))dipropanoate (20)

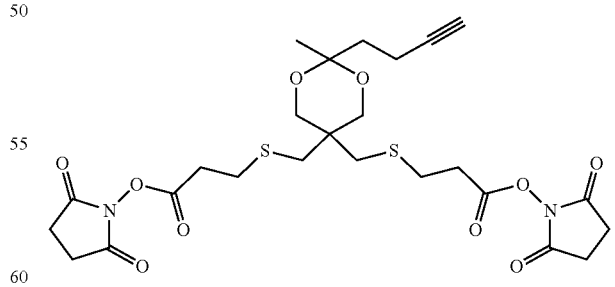

Dimethyl ester 19 (0.362 g, 0.864 mmol) was dissolved in 4:1 THF:H₂O (8.0 mL), and LiOH.H₂O (0.125 g, 2.98 mmol) was added to the reaction mixture. After 1 h, additional LiOH.H2O (0.058 g, 1.38 mmol) was added. The reaction mixture was stirred for an additional 2 h and partitioned between H₂O (50 mL) and hexanes (50 mL). The aqueous layer was acidified to pH 1 with 6 M HCl and extracted with EtOAc (5×5 mL). The combined EtOAc extracts were dried over MgSO$_4$, filtered, and concentrated, dissolved in CH$_2$Cl$_2$ and concentrated repeatedly to afford 0.380 g of a light yellow oil, which was used immediately without any further purification: $^1$H NMR (500 MHz, CDCl$_3$) δ 11.20 (br s, 2H), 3.72 (q, 4H, J=9.1 Hz), 2.88-2.76 (m, 6H), 2.73-2.60 (m, 6H), 2.32 (dt, 2H, J=7.9, 2.8 Hz), 1.99-1.90 (m, 3H), 1.39 (s, 3H).

To a portion of the crude diacid intermediate (0.180 g, 0.461 mmol) in CH$_2$Cl$_2$ (1.6 mL) and pyridine (0.30 mL, 3.7 mmol) was added N-hydroxysuccinimidyl trifluoroacetate (0.620 g, 2.94 mmol) and the solution was stirred at room temperature for 3 h. The solution was diluted with CH2C12, poured into a separatory funnel, washed with sat. NH$_4$Cl (5 mL), sat. NaHCO$_3$ (5 mL), water (5 mL), and brine (5 mL), dried over Na$_2$SO$_4$, filtered, and concentrated. The crude product was chromatographed using a column 1.8 cm O.D. packed 12 cm high with a slurry of 20 mL silica and eluting 380 mL 1:2 hexanes:ethyl acetate. After collecting 70 mL followed by 10 mL fractions, fractions 1-13 were concentrated to afford 20 as a white solid (0.162 g, 60%): $^1$H NMR (500 MHz, CDCl$_3$) δ 5.30 (CH$_2$Cl$_2$), 3.78 (d, J=12.0 Hz, 2H), 3.71 (d, J=12.5 Hz, 2H), 3.01-2.79 (m, 18H), 2.68 (s, 2H), 2.31 (ddd, J=9.7, 7.6, 2.6 Hz, 2H), 2.00-1.93 (m, 3H), 1.39 (s, 3H); $^{13}$C NMR (125 MHz, CDCl$_3$) δ 169.2, 167.3, 98.9, 84.6, 68.3, 66.0, 38.1, 37.4, 35.8, 35.7, 32.3, 32.2, 28.32, 28.26, 25.8, 20.2, 12.9; IR (thin film) 3282, 2947, 2870, 2252, 2114, 1813, 1786, 1739, 1431, 1369, 1250, 1207, 1134, 1068 cm-1; HRMS (ESI) m/z calcd for C$_{25}$H$_{32}$N$_2$O$_{10}$S$_2$ [M+Na]$^+$ 607.1396, found 607.1388.

Cross-Linking Experiments
In Vitro Cross-Linking of Synthetic Peptide Ac-Myelin

Synthetic peptide Ac-myelin was cross-linked with Azide-A-DSBSO in DMSO in a 1:1 molar ratio of peptide to cross-linker at 1 mM in the presence of 1 eq of diisopropylethylamine. Cross-linked peptide solutions were then diluted to 5 pmol/μL in a 3% CAN and 2% formic acid aqueous solution for liquid chromatography multistage tandem mass spectrometry (LC-MS$^n$) analysis.

Cytochrome C

Bovine cytochrome C was solubilized in 50 mM pH 8.0 phosphate buffer at 200 μM and reacted with 20 mM Azide-A-DSBSO dissolved in DMSO at a 1:10 molar ratio of protein to cross-linker for 1 hr at RT. The reaction was quenched with 500 mM NH$_4$HCO$_3$ and ultracentrifuged on a 10 kDa NMWL Amicon Ultra centrifugal filters to remove excess cross-linker. To establish the most efficient conditions for biotin conjugation, cross-linked products were washed and concentrated to 450 μM on filter in either 50 mM phosphate buffer or 8 M urea lysis buffer. Various amounts of BARAC were then reacted with the cross-linked cytochrome C in either phosphate or lysis buffer with agitation overnight. The reaction efficiency for each condition was evaluated by immunoblotting, with subsequent experiments carried out in optimal conditions: urea lysis buffer with 100 μM BARAC and agitation overnight. Following conjugation, excess BARAC was removed by ultracentrifugation and washed with 25 mM NH$_4$HCO$_3$. Biotin-conjugated cytochrome C was incubated with high-capacity Streptavidin beads and then digested on-bead with 1% trypsin (w/w) or 5% chymotrypsin (w/w) following reduction and alkylation of cysteine residues in 5 mM DTT at 56° C. and 10 mM chloroacetamide at RT, respectively. After digestion, non-cross-linked peptides were extracted and analyzed by LC-MS"; cross-linked peptides bound to streptavidin beads were eluted from beads by acid cleavage in 20% FA, 10% ACN solution prior to LC-MSn analysis.

Analysis of Cross-Linked Peptides by LC-MSn

Most of the enriched cross-linked peptides were analyzed by LC-MS$^n$ using an LTQ-Orbitrap XL mass spectrometer (Thermo Scientific, San Jose, Calif.) coupled on-line with either an Eksigent NanoLC system (Dublin, Calif.), or EASY-nLC-1000 (Thermo Scientific, San Jose, Calif.). A few of cross-linked samples from intact cells were analyzed using an Orbitrap Elite mass spectrometer (courtesy of Thermo Scientific Demo Lab, San Jose, Calif.) coupled on-line with an EASY-nLC 1000 (Thermo Scientific). LC/MS$^n$ data acquisition and analysis were as described.[8] Only ions with 3+ or higher in the MS1 scan were selected for MS2 analysis.

Identification of Cross-Linked Peptides by Database Searching

Due to the similarity between DSBSO and DSSO, the general data analysis workflow for the identification of DSBSO inter-linked peptides by LC/MS$^n$ is the same as the analysis of DSSO cross-linked peptides.[8,9] Using the Batch-Tag software within a developmental version of Protein Prospector (v5.10.10, University of California San Francisco), MS2 and MS3 spectra were searched against a decoy database consisting of a normal Swissprot database concatenated with its randomized version (SwissProt.2013.3.1.random.concat with a total of 454,402 protein entries). The mass tolerances for parent ions and fragment ions were set as ±20 ppm and 0.6 Da respectively. Trypsin was set as the enzyme with three maximum missed cleavages allowed. Cysteine carbamidomethylation was set as a constant modification. Protein N-terminal acetylation, asparagine deamidation, N-terminal conversion of glutamine to pyroglutamic acid, and methionine oxidation were selected as variable modifications. Similar to DSSO cross-linked peptides, DSBSO cross-linked peptides display unique and characteristic MS2 fragmentation patterns corresponding to their cross-linking types. Therefore, three additional defined modifications on uncleaved lysines and free protein N-terminus were chosen: alkene (C$_3$H$_2$O, +54 Da), sulfenic acid (C$_3$H$_4$O$_2$S, +254 Da), and unsaturated thiol (C$_3$H$_2$SO, +236 Da). These are modifications resulting from CID-induced cleavage of the DSBSO cross-linked peptides. The in-house program Link-Hunter is a revised version of the previously written Link-Finder program, designed to automatically validate and summarize cross-linked peptides based MSn data and database searching results as previously described.[8,9] In addition to checking MS2 spectra for predicted patterns, Link-Hunter automatically correlates sequence data from MS3 to MS2 and MS1 parent masses, reports identified inter-linked peptides with two associated sequences.

References—2

1. M
   C. Murguía, S. E. Vaillard, and R. J. Grau, SYNTHESIS-S, 2001, 7, 1093-1097.
2. N
   M. Leonard, J. Brunckova, *J. Org. Chem.* 2011, 76, 9169-9174.
3. 
   Ma, *Heteroatom Chem.,* 2002, 13, 307-309.
4. 
   Pangborn, M. A. Giardello, R. H. Grubbs, R. K. Rosen, and F. J. Timmers, *Organometallics,* 1996, 15, 1518-1520.

5.
C. Still, M. Kahn, and A. Mitra, *J. Org. Chem.*, 1978, 43, 2923-2925.

6.
R. Fulmer, A. J. M. Miller, N. H. Sherden, H. E. Gottlieb, A. Nudelman, B. M. Stoltz, J. E. Bercaw, and K. I. Goldberg, *Organometallics*, 2010, 29, 2176-2179.

7.
Tsunoda, M. Suzuki, and R. Noyori, *Tetrahedron Lett.*, 1980, 21, 1357-1358.

8.
ao, A. Randall, Y. Yang, V. R. Patel, W. Kandur, S. Guan, S. D. Rychnovsky, P. Baldi, and L. Huang, *Mol. Cell. Proteomics* MCP, 2012, 11, 1566-1577.

9.
ao, C. Chiu, D. Vellucci, Y. Yang, V. R. Patel, S. Guan, A. Randall, P. Baldi, S. D. Rychnovsky, and L. Huang, *Mol. Cell. Proteomics* MCP, 2011, 10, M110.002212.

A New In Vivo Cross-Linking Mass Spectrometry Platform to Define Protein-Protein Interactions in Living Cells Protein-protein interactions (PPIs) are fundamental to the structure and function of protein complexes. Resolving the physical contacts between proteins as they occur in cells is critical to uncovering the molecular details underlying various cellular activities. To advance the study of PPIs in living cells, in some embodiments, a new in vivo cross-linking mass spectrometry platform that couples a novel membrane-permeable, enrichable, and MS-cleavable cross-linker with multistage tandem mass spectrometry is provided. In some embodiments, this strategy permits the effective capture, enrichment, and identification of in vivo cross-linked products from mammalian cells and thus enables the determination of protein interaction interfaces. In some embodiments, the utility of the developed method has been demonstrated by profiling PPIs in mammalian cells at the proteome scale and the targeted protein complex level. In some embodiments, a general approach for studying in vivo PPIs is disclosed. Also provided is a solid foundation for future studies toward the complete mapping of PPI networks in living systems.

In some embodiments, a new and general XL-MS workflow based on Azide-A-DSBSO for studying PPIs in living cells is provided. This new XL-MS workflow differs from existing approaches by its collective abilities allowing (i) effective protein cross-linking in vivo to capture authentic protein interactions, (ii) selective enrichment of cross-linked proteins and peptides to improve their detection, (iii) simplified and unambiguous identification of cross-linked peptides by MSn, and (iv) direct coupling with affinity purification of in vivo cross-linked protein complexes to study their interactions.

In comparison to existing reagents for in vivo studies (24), the integration of several unique features (i.e. small size, proper spacer length, bio-orthogonal affinity handle, robust MS-cleavable bonds, and acid cleavage site) makes Azide-A-DSBSO a much more attractive reagent for defining protein-protein interactions in cells.

Apart from mapping PPIs at the proteome level, successful coupling was achieved of Azide-A-DSBSO-based XL-MS strategy with HB-tag-based affinity purification to delineate the in vivo subunit connectivity of human proteasome complexes for the first time. In some embodiments, this work expands the utility of previously developed cross-linking methodologies such as the QTAX (quantitative analysis of tandem affinity purified in vivo cross-linked (x) protein complexes) strategy in studying in vivo interaction networks of protein complexes beyond the identification of interacting partners (12, 13).

Interestingly, seven out of eight identified pair-wise interactions corroborated well with previous in vitro XL-MS studies of yeast proteasome complexes (19, 20, 36), suggesting that interaction similarity exists between orthologs as well as between in vivo and in vitro proteasome structures.

In this work, the close association between Rpt3 and Rpt6 through the identification of two interlinked peptides at their N-terminal (Rpt3:K80-Rpt6:K55) and central (Rpt3:K238-Rpt6:K222) regions was further confirmed. In addition, the identified contacts between the N termini of Rpt6 and Rpn11, as well as Rpn2, correlate with the electron microscopy structures of yeast proteasomes in which the N-terminal sequences of Rpt3 and Rpt6 form a coil structure for Rpn2 and the lid subcomplex to attach to the base (50, 51).

Moreover, a novel interaction between α3 and Rpt6 identified here implies the intimate relationship of Rpt6 and the 20S a ring. It is worth noting that the identification of these in vivo proteasome subunit contacts was possible only when HB-based affinity purification was incorporated into the workflow, indicating the necessity of targeted analysis for profiling PPIs of protein complexes in cells.

Importantly, our results have proven the feasibility of the Azide-A-DSBSO based XL-MS strategy for such targeted analysis, demonstrating a unique capability that current strategies do not possess. Although other proteasome components were captured and identified from affinity purified Azide-A-DSBSO cross-linked Rpn11-HB or HB-Rpt6 containing proteasome complexes (data not shown), it appears that direct interactions of protein baits are enriched, as eight of the interactions identified were directly with Rpt6.

Although additional baits would be needed to generate a more comprehensive in vivo subunit topology map of the proteasome complex, this would be advantageous when only the direct binding partner needs to be identified. Collectively, this work represents a significant step toward a full understanding of the in vivo PPIs of protein complexes.

Thus, in some embodiments, successful development was achieved of a new, versatile, and general XL-MS workflow for mapping PPIs at both the proteome scale and the targeted protein complex level, representing a technological advancement in defining protein interactions in living systems.

In comparison to previous AP-MS and quantitative tandem affinity purification studies relying on multiple reciprocal purifications and/or existing PPI databases for interaction validation and the construction of in silico interaction network maps (2, 13, 14, 52), our new in vivo XL-MS strategy allows the identification of direct protein interaction contacts for generating interaction networks experimentally.

In addition, this information can be used for determining protein structural topologies in future studies. In combination with stable isotope labeling (53) and cross-linking chemistry targeting other residues such as acidic residues (54), new reagents can be further developed to describe PPI dynamics in cells. The potential of this technology is enormous, and with improvements in instrumentation and sample preparation, a vast variety of unexplored biological applications can be envisioned.

Protein-protein interactions (PPIs)1 play a key role in defining protein functions in biological systems. Aberrant PPIs can have drastic effects on biochemical activities essential to cell homeostasis, growth, and proliferation, and thereby lead to various human diseases (1). Consequently, PPI interfaces have been recognized as a new paradigm for drug development. Therefore, mapping PPIs and their interaction interfaces in living cells is critical not only for a comprehensive understanding of protein function and regulation, but also for describing the molecular mechanisms underlying human pathologies and identifying potential targets for better therapeutics.

Several strategies exist for identifying and mapping PPIs, including yeast two-hybrid, protein microarray, and affinity purification mass spectrometry (AP-MS) (2-5). Thanks to new developments in sample preparation strategies, mass spectrometry technologies, and bioinformatics tools, AP-MS has become a powerful and preferred method for studying PPIs at the systems level (6-9). Unlike other approaches, AP-MS experiments allow the capture of protein interactions directly from their natural cellular environment, thus better retaining native protein structures and biologically relevant interactions. In addition, a broader scope of PPI networks can be obtained with greater sensitivity, accuracy, versatility, and speed. Despite the success of this very promising technique, AP-MS experiments can lead to the loss of weak/transient interactions and/or the reorganization of protein interactions during biochemical manipulation under native purification conditions. To circumvent these problems, in vivo chemical cross-linking has been successfully employed to stabilize protein interactions in native cells or tissues prior to cell lysis (10-16).

The resulting covalent bonds formed between interacting partners allow affinity purification under stringent and fully denaturing conditions, consequently reducing nonspecific background while preserving stable and weak/transient interactions (12-16). Subsequent mass spectrometric analysis can reveal not only the identities of interacting proteins, but also cross-linked amino acid residues. The latter provides direct molecular evidence describing the physical contacts between and within proteins (17).

This information can be used for computational modeling to establish structural topologies of proteins and protein complexes (17-22), as well as for generating experimentally derived protein interaction network topology maps (23, 24). Thus, cross-linking mass spectrometry (XL-MS) strategies represent a powerful and emergent technology that possesses unparalleled capabilities for studying PPIs.

Despite their great potential, current XL-MS studies that have aimed to identify cross-linked peptides have been mostly limited to in vitro cross-linking experiments, with few successfully identifying protein interaction interfaces in living cells (24, 25). This is largely because XL-MS studies remain challenging due to the inherent difficulty in the effective MS detection and accurate identification of cross-linked peptides, as well as in unambiguous assignment of cross-linked residues. In general, cross-linked products are heterogeneous and low in abundance relative to non-cross-linked products. In addition, their MS fragmentation is too complex to be interpreted using conventional database searching tools (17, 26). It is noted that almost all of the current in vivo PPI studies utilize formaldehyde cross-linking because of its membrane permeability and fast kinetics (10-16). However, in comparison to the most commonly used amine reactive NHS ester cross-linkers, identification of formaldehyde cross-linked peptides is even more challenging because of its promiscuous nonspecific reactivity and extremely short spacer length (27). Therefore, further developments in reagents and methods are urgently needed to enable simple MS detection and effective identification of in vivo cross-linked products, and thus allow the mapping of authentic protein contact sites as established in cells, especially for protein complexes.

Various efforts have been made to address the limitations of XL-MS studies, resulting in new developments in bioinformatics tools for improved data interpretation (28-32) and new designs of cross-linking reagents for enhanced MS analysis of cross-linked peptides (24, 33-39). Among these approaches, the development of new cross-linking reagents holds great promise for mapping PPIs on the systems level. One class of cross-linking reagents containing an enrichment handle have been shown to allow selective isolation of cross-linked products from complex mixtures, boosting their detectability by MS (33-35, 40-42). A second class of cross-linkers containing MS-cleavable bonds have proven to be effective in facilitating the unambiguous identification of cross-linked peptides (36-39, 43, 44), as the resulting cross-linked products can be identified based on their characteristic and simplified fragmentation behavior during MS analysis. Therefore, an ideal cross-linking reagent would possess the combined features of both classes of cross-linkers. To advance the study of in vivo PPIs, a new XL-MS platform based on a novel membrane-permeable, enrichable, and MS-cleavable cross-linker, Azide-A-DSBSO (azide-tagged, acid-cleavable disuccinimidyl bis-sulfoxide), and multistage tandem mass spectrometry (MS') was developed. This new XL-MS strategy has been successfully employed to map in vivo PPIs from mammalian cells at both the proteome scale and the targeted protein complex level.

Developing a New In Vivo XL-MS Platform for Mapping PPIs in Living Cells

Figure 22:
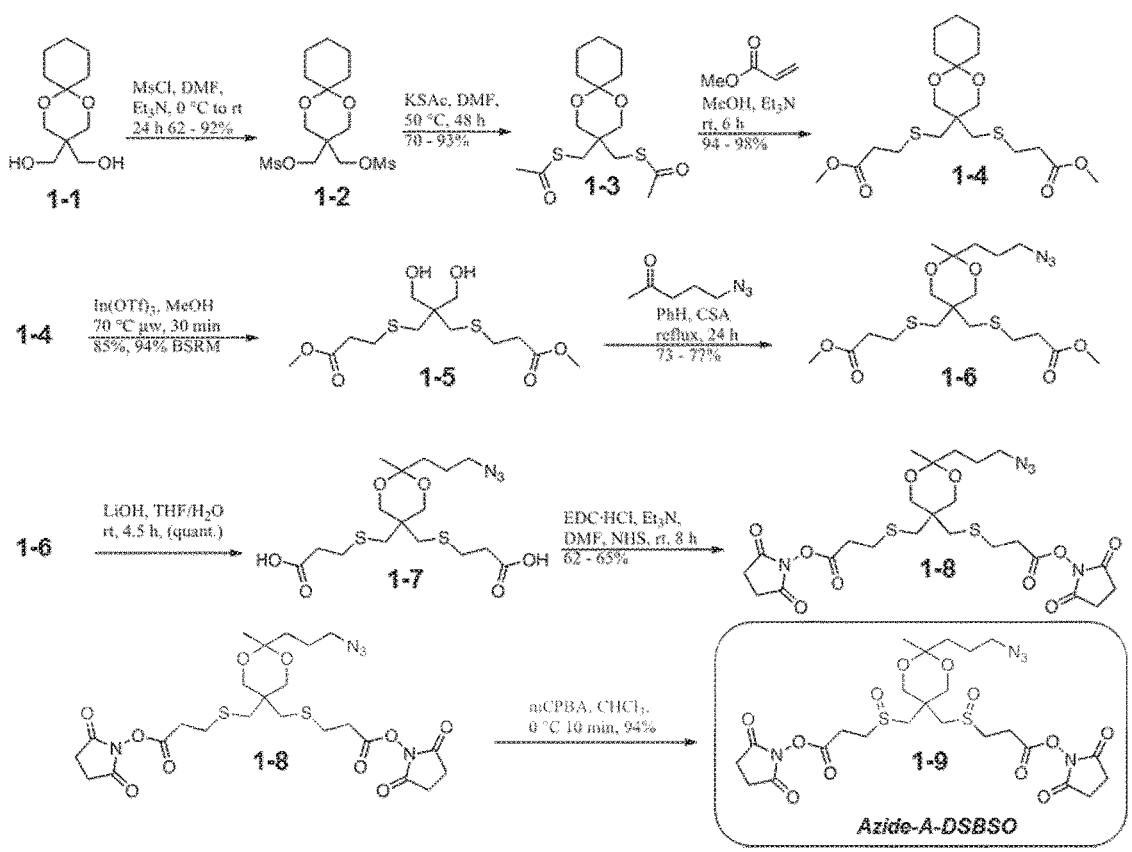
FIG. 22 shows an embodiment of a synthesis scheme of a novel cross-linking reagent, Azide-A-DSBSO.

In order to establish a robust in vivo XL-MS workflow, in some embodiments, the design and synthesis of a novel cross-linking reagent, Azide-A-DSBSO is provided (FIG. 22). The scheme shown in FIG. 22 is similar to the scheme shown in FIG. 15. This multifunctional cross-linker combines the unique features of both enrichable (i.e. azide disuccinimidyl glutarate) (35) and MS-cleavable (i.e. DSSO) cross-linkers previously developed in our lab (36). Azide-A-DSBSO is membrane permeable and has a spacer length of ~14 Å. In addition, it carries a bio-orthogonal azide tag that functions as an enrichment handle permitting selective isolation of cross-linked proteins and peptides through azide-based conjugation chemistry and subsequent affinity purification (35). The incorporation of an acid-cleavable site adjacent to the azide tag facilitates the purification and recovery of cross-linked peptides. Moreover, the integration of two symmetric sulfoxide groups in the spacer region of Azide-A-DSBSO results in robust MS-cleavable bonds that enable fast and unambiguous identification of cross-linked peptides via MSn analysis (20, 36). Together, these features make Azide-A-DSBSO an ideal reagent for studying PPIs, especially from living cells.

Bovine cytochrome C (>95% purity) was purchased from Sigma Aldrich (St. Louis, Mo.). Amicon Ultra 100-kDa, 30-kDa, and 10-kDa NMWL centrifugal filters were purchased from EMD Millipore (Billerica, Mass.). LaminA/C antibody was purchased from Cell Signaling Technology, Inc. (Danvers, Mass.). Calnexin and GAPDH antibodies were purchased from Santa Cruz Biotechnology (Dallas, Tex.). Streptavidin agarose resin, high-capacity streptavidin agarose resin, HRP-conjugated streptavidin, and Super Signal West Pico chemiluminescent substrate were purchased from Thermo Scientific (Rockford, Ill.). Sequencing-grade trypsin was purchased from Promega Corp. (Madison, Wis.). Endoproteinase Lys-C was purchased from WAKO Chemicals (Osaka, Japan). TPCK-treated trypsin was purchased from Worthington Biochemical Corp (Lakewood, N.J.). All other general chemicals for buffers and culture media were purchased from Fisher Scientific or VWR International (Radnor, Pa.).

The synthesis and characterization of the Azide-A-DSBSO cross-linker are described in Ref. 55. The simplified scheme is depicted in FIG. 22. BARAC reagent was synthesized as described elsewhere (45).

Figure 23:
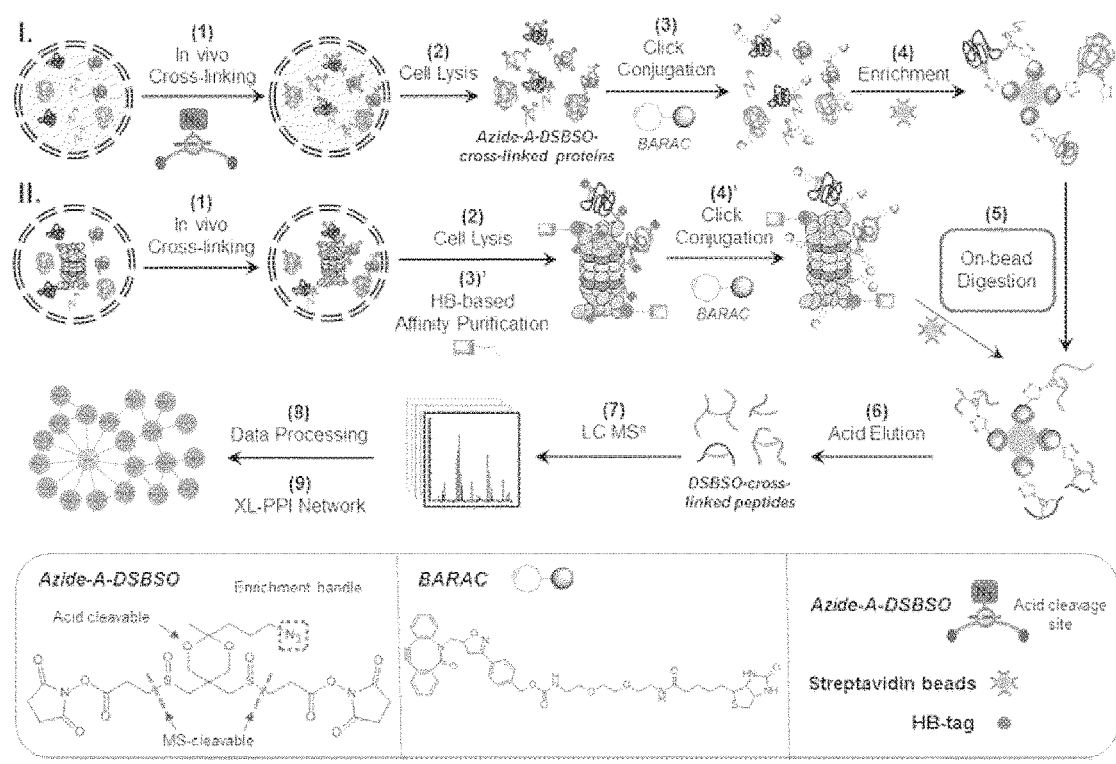
FIG. 23 shows an embodiment of azide-A-DSBSO-based in vivo XL-MS platform for mapping PPIs in living cells. Path I: at the proteome scale. Path II: at the targeted protein complex level. The inset displays structures of Azide-A-DSBSO and BARAC.

In some embodiments, there are nine steps in the general Azide-A-DSBSO-based XL-MS workflow for mapping in vivo PPIs in mammalian cells illustrated in FIG. 23. As shown, in vivo Azide-A-DSBSO cross-linking is first carried out in intact human cells (e.g. HEK 293) (step 1), which are then lysed under fully denaturing conditions (e.g. 8 m urea) to effectively solubilize cross-linked proteins (step 2). To map PPIs on the global scale (path I), the Azide-A-DSBSO cross-linked proteins in cell lysates are conjugated with a biotin-tagged strained alkyne (i.e. BARAC) through copper-free click chemistry (step 3) (47). The resulting biotinylated cross-linked proteins are then enriched via binding to streptavidin resin (step 4). After removal of the non-cross-linked proteins, bound proteins are directly digested on beads (step 5). The biotin-tagged cross-linked peptides are separated from non-cross-linked peptides, as only cross-linked peptides remain bound to streptavidin beads while other peptides are released to the supernatant during digestion. The bound cross-linked peptides are eluted from streptavidin beads by acid cleavage and become the acid-cleaved products of Azide-A-DSBSO peptides, that is, DSBSO cross-linked peptides (step 6) for subsequent LC-MSn analysis (step 7). The presence of an acid cleavage site in Azide-A-DSBSO not only improves enrichment selectivity, but also facilitates subsequent MS analysis by serving to remove the conjugated enrichment handle to yield a smaller mass tag (~308 Da) on cross-linked peptides. The analysis of LC-MSn data to identify cross-linked peptides (step 8) is similar to that described elsewhere (20, 36). Finally, the identified interlinked peptides can be used to generate an experimentally derived in vivo cross-linked protein-protein interaction network (step 9).

In addition to mapping PPIs in cells at the proteome scale, in some embodiments, the same strategy can be modified to study in vivo PPIs of protein complexes (FIG. 23, path II). In this workflow, HB-tag-based tandem affinity purification under fully denaturing conditions is implemented to enable the effective purification of in vivo cross-linked protein complexes as previously reported (12-15, 48). This step is crucial for enhancing the sensitivity and selectivity of subsequent analyses of the selected protein complexes. As shown in FIG. 23, after in vivo cross-linking of 293 cells stably expressing an HB-tagged proteasome subunit (e.g. Rpn11-HB), affinity purification of cross-linked HB-tagged protein complexes is carried out through binding first to Ni2+-Sepharose resins, and then to streptavidin beads (step 3'). In some embodiments, the proteins bound to streptavidin beads are directly conjugated with BARAC (step 4'), on-bead digested, and eluted and analyzed via LC-MSn similar to the corresponding steps in path I (steps 5-9).

Selective Enrichment of Azide-A-DSBSO Cross-Linked Peptides

SDS-PAGE and Immunoblotting Analysis was performed by separating protein samples via SDS-PAGE and either stained using Coomassie Blue or transferred to a PVDF membrane and analyzed via immunoblotting. Biotin-conjugated proteins and HB-tagged proteins were detected by streptavidin-HRP conjugate. Cross-linked and non-cross-linked Rpn11-HB and HB-Rpt6 were also detected with streptavidin-HRP conjugate. Lamin A/C, calnexin, and GAPDH were detected using specific primary antibodies and either rabbit or mouse secondary HRP-conjugated antibody. Biotin-conjugated peptides were blotted onto nitrocellulose membrane and detected with streptavidin-HRP conjugate.

Figure 27A:
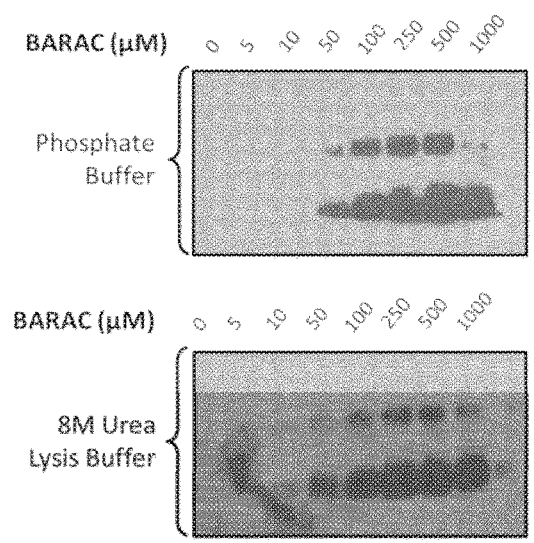
FIG. 27A & FIG. 27B show optimization of biotin-conjugation and subsequent affinity purification using Azide-A-DSBSO cross-linked cytochrome C.
Figure 27B:
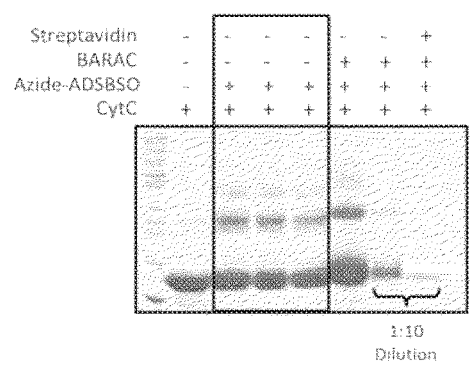

One of the key steps in the Azide-A-DSBSO cross-linking strategy is the selective enrichment of cross-linked products. This is achieved by incorporating an affinity tag (e.g. biotin tag) to Azide-A-DSBSO cross-linked products through azide-based conjugation chemistry. Although both copper-catalyzed click chemistry and Staudinger ligation were effective, they have proven to be technically challenging (35). In order to develop a more robust methodology, a copper-free click chemistry reaction using a biotin-tagged strained alkyne BARAC was adopted (47). The tests using Azide-A-DSBSO cross-linked standard protein cytochrome C showed that copper-free conjugation was efficient in both phosphate buffer and buffers containing 8 m urea (FIG. 27A & FIG. 27B), well suited to our goal of capturing protein interactions in living cells using denaturing buffer. Our results suggest that relative to other azide-based conjugation chemistry methods (35), copper-free chemical conjugation is simpler, more efficient, easier in terms of sample handling, and less labor intensive.

Identification of Azide-A-DSBSO Cross-Linked Peptides Via LC-MSn

In vitro cross-linking, biotin conjugation, and enrichment of azide-A-DSBSO cross-linked cytochrome C was performed by azide-A-DSBSO cross-linking of bovine cytochrome C was similar to that described elsewhere (35). The reaction was quenched with 500 mm NH4HCO3, and samples were ultracentrifuged on 10-kDa NMWL Amicon Ultra centrifugal filters to remove excess cross-linker. Various amounts of BARAC were then reacted with the cross-linked cytochrome C in either phosphate or 8 m urea lysis buffer with agitation overnight. The reaction efficiency for each condition was evaluated via immunoblotting. Following conjugation, excess BARAC was removed by ultracentrifugation and washed with 25 mm $NH_4HCO_3$. Biotin-conjugated cytochrome C was purified through binding to streptavidin beads (15).

Figure 24:
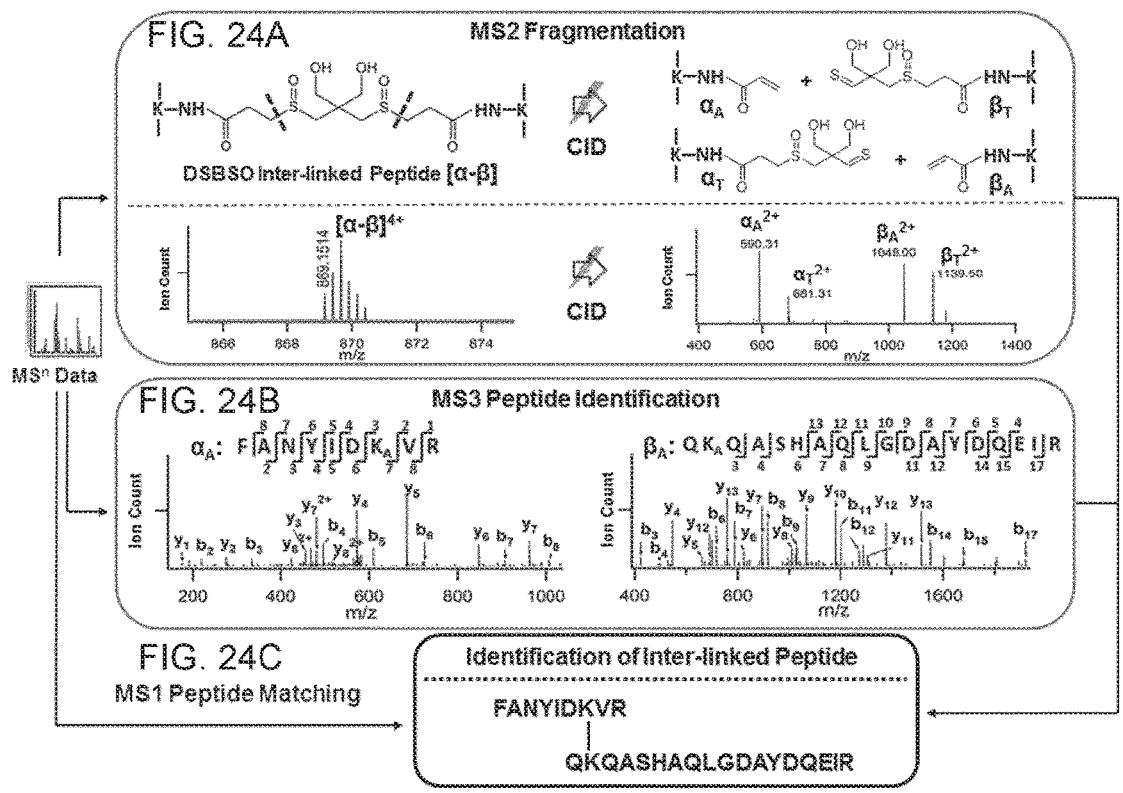
FIG. 24A-FIG. 24C show MS$^n$ analysis of a representative DSBSO interlinked peptide (α-β) from in vivo cross-linked human 293 cells.

As described above, LC-MS$^n$ analysis was performed on the acid-cleaved products of Azide-A-DSBSO cross-linked peptides (i.e. DSBSO cross-linked peptides) (FIG. 24A-FIG. 24C). DSBSO is symmetric and contains two sulfoxide groups that result in four C—S bonds. However, only the two outer C—S bonds proximal to the cross-linked lysines can be cleaved during collision-induced dissociation; the two inner C—S bonds cannot undergo fragmentation because of the lack of β hydrogens (FIG. 24A-FIG. 24C). Given that the same types of MS-cleavable C—S bonds are present in both DSBSO and DSSO, the identification of DSBSO cross-linked peptides by MSn should be as robust as that of DSSO cross-linked peptides (36). This is exemplified by a representative MSn analysis of a DSBSO interlinked peptide (α-β) from in vivo cross-linked 293 cells (FIG. 24A-FIG. 24C).

As shown, the cleavage of either of the two MS-cleavable C—S bonds during MS2 analysis leads to the physical separation of the two DSBSO cross-linked peptide constituents, α and β, yielding two characteristic fragment ion pairs (i.e. αA/βT and αT/βA) (FIG. 24A). These MS2 fragment ions are composed of single peptide chains with defined mass modifications (alkene (A) and thiol (T) remnants of DSBSO), which are then subjected to MS3 sequencing for easy identification by conventional database searching tools (FIG. 24B) (36).

In addition to MS2 and MS3 data, the MS1 parent ion information is used to further confirm the identities of cross-linked peptides by matching their measured peptide masses to the theoretical masses of predicted cross-linked peptides (FIG. 24C). In this representative example, integration of the MSn data identified the peptide unambiguously as FANYIDK$^{120}$VR cross-linked to QK$^{139}$QASHAQLGDAYDQEIR, describing a new interprotein interaction between vimentin and neurofilament medium polypeptide protein in human 293 cells.

Profiling PPIs from Intact HEK 293 Cells

In Vivo Azide-A-DSBSO Cross-linking of HEK 293 Cells was performed by growing HEK 293 cells on DMEM supplemented with 10% fetal bovine serum and 1% penicillin/streptomycin. Cells were grown to 80% confluence, trypsinized, washed with PBS, and cross-linked with 2 mm Azide-A-DSBSO in PBS for 1 h with rotation at 37° C. Following quenching of cross-linking reactions by the addition of 125 mm glycine, cells were pelleted and stored at −80° C. after removal of the supernatant. Frozen cell pellets were lysed in 8 m urea lysis buffer and clarified via centrifugation (15).

Figure 25:
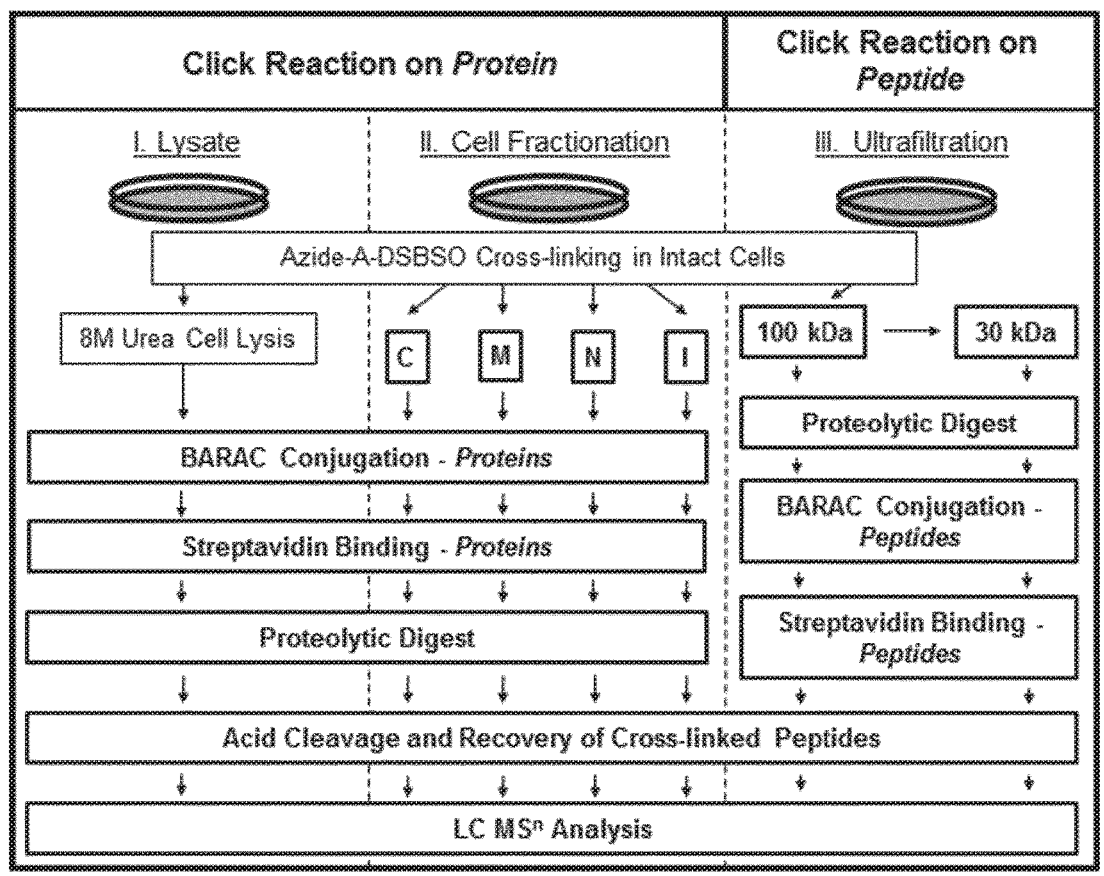
FIG. 25 shows three sample preparation strategies for analyzing in vivo Azide-A-DSBSO cross-linked human 293 cells. Biotin conjugation with BARAC on the protein level (Paths I and II) and on the peptide level (Path III) for subsequent enrichment. Path I, BARAC conjugation after cell lysis; Path II, BARAC conjugation after cell fractionation (C=cytosolic; M=membrane; N=nuclear; I=insoluble fractions); Path III, BARAC conjugation and enrichment of cross-linked peptides after 100-kDa and 30-kDa ultrafiltration and digestion
Figures 26A, 26B, 26C, 26D:
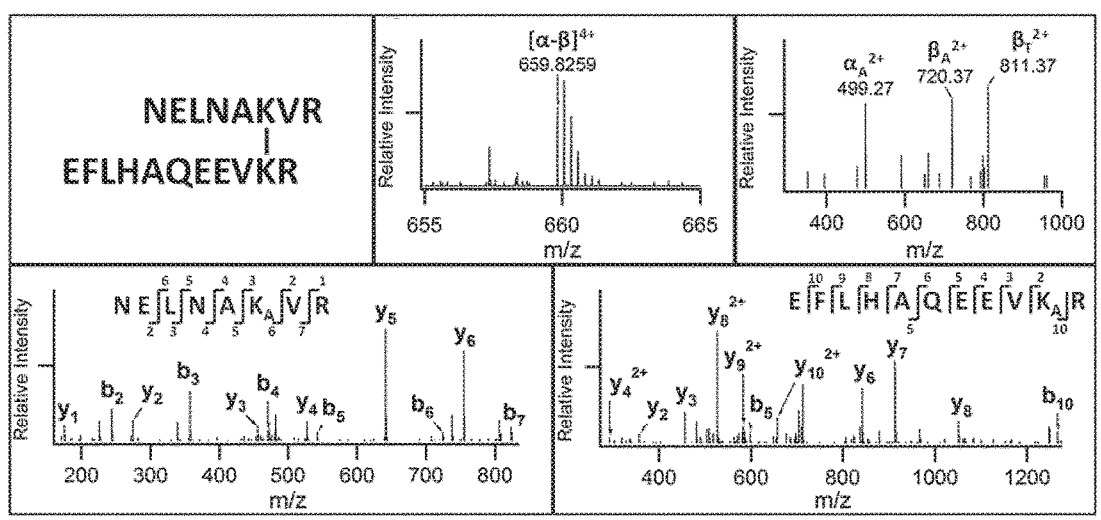
FIG. 26A-FIG. 26D show MS$^n$ analysis of a representative DSBSO interlinked peptide of in vivo cross-linked proteasome subunits. Integration of MS$^n$ data identified this peptide as an intersubunit interlink between Rpt3 and Rpt6. KA, alkene modified lysine; KT, unsaturated thiol modified lysine.

In order to maximize the information acquired on protein interaction interfaces from in vivo cross-linked HEK 293 cells, three different sample preparation strategies, paths I, II, and III was explored (FIG. 25). Path I describes the direct analysis of cross-linked cells as illustrated in FIG. 23. As shown in FIG. 28A-FIG. 28C, protein cross-linking, BARAC conjugation, and purification of cross-linked products were as effective for in vivo cross-linked cells as for standard proteins. Path II incorporates a subcellular fractionation step before BARAC conjugation, thus dividing cell lysates into four fractions: cytosolic, membrane, nuclear, and insoluble fractions. Immunoblotting analysis revealed that such subcellular fractionation was still possible under our experimental conditions, although there was a marked decrease in the amount of proteins in the cytosolic fraction (FIG. 29A-FIG. 29E).

Nonetheless, BARAC reactions and subsequent purification were also effective for each subcellular fraction (FIG. 29A-FIG. 29E). The third sample preparation strategy (path III) involved sequential filtration of in vivo cross-linked cell lysates through 100-kDa and then 30-kDa cutoff centrifugal filters to remove small and non-cross-linked components (FIG. 25). The two-step filtration was used to recover a wider range of cross-linked proteins larger than 30 kDa and to improve the dynamic range of subsequent MS' analysis. Proteins remaining on the two different membranes were digested, and the resulting peptides were collected for BARAC conjugation and streptavidin enrichment of cross-linked peptides. As shown in FIG. 29E, biotin-conjugation and subsequent enrichment were efficient for peptide digests as well, further suggesting the robustness of copper-free click chemistry using BARAC.

From all of the samples prepared, a total of 938 proteins in our analyses (TABLE 8) were identified, 584 of which were identified with at least one cross-linker modified peptide, amounting to 4812 redundant Azide-A-DSBSO labeled peptides, including dead-end, intralinked, and interlinked peptides. Functional annotation of the 584 proteins revealed that they are localized in various cellular compartments and involved in diverse biological processes (TABLE 9), demonstrating that Azide-A-DSBSO is well suited for capturing PPIs in cells.

Protein-Protein Interaction Network Mapping

In some embodiments, mapping Cross-links to 2.5-Å Nucleosome Crystal Structure was performed by downloading the 2.5-Å nucleosome crystal structure (PDB 3AV1) from the Protein Data Bank, and cross-linked residues were mapped and visualized using PyMOL. Distances were measured from the amino group of lysine side chains, also using PyMOL.

Figure 30:
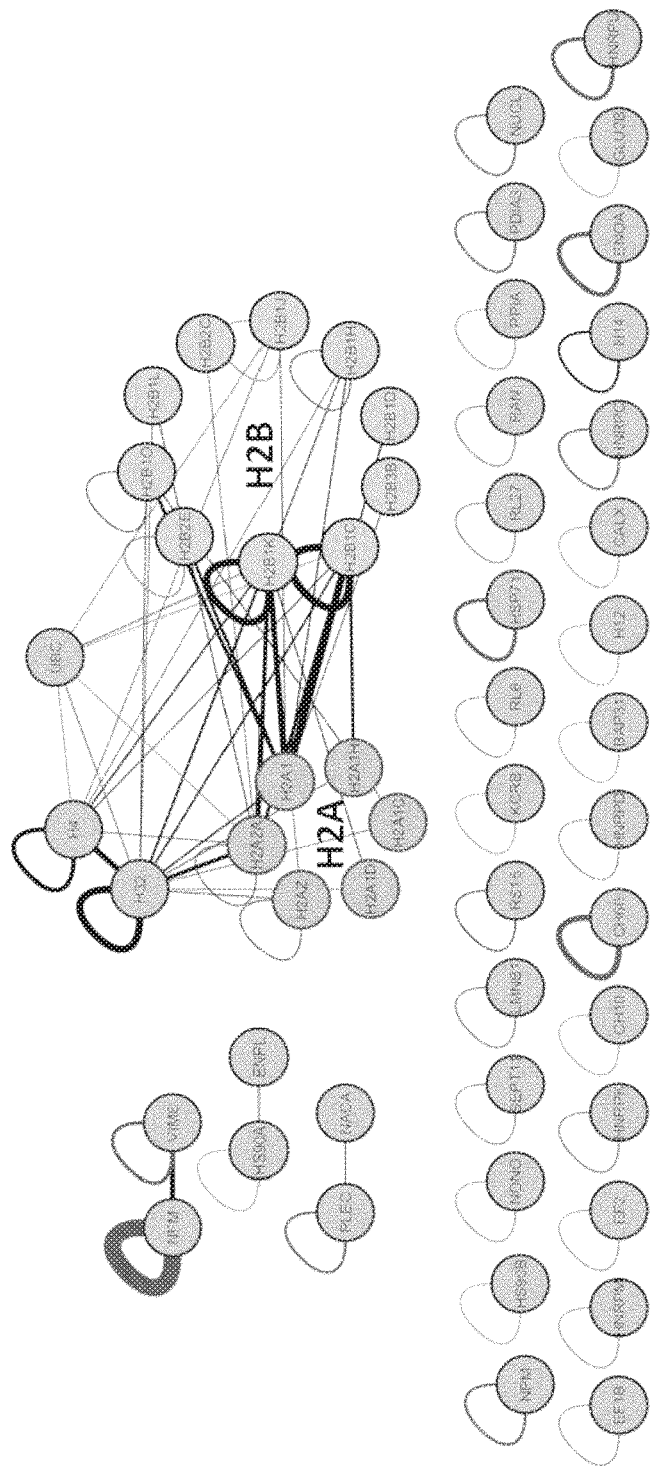
FIG. 30 shows azide-A-DSBSO Cross-link Derived Protein-Protein Interaction Network from 293 Cells. Proteins are represented by a single node and interactions between proteins as a single edge. Edge thickness represents the number of inter-links (redundant and unique) captured and identified for a given interactions. Purple edges represent interactions also found in the IDB (Interaction Database) network. Nodes with shared/homologous peptides are grouped (H2A and H2B).

Because of their unique capability for describing PPI interfaces, only interlinked peptides are provided in TABLE 10. In this work, 240 unique interlinked peptides were identified, including 136 intrasubunit and 104 intersubunit interlinks. Using this data, an in vivo PPI network map with 85 protein-protein interactions between 54 proteins was established (FIG. 30). In comparison to existing PPI databases, 50 novel intra- and intersubunit interactions were identified with direct physical evidence at specific amino acid residues. Among them, an interesting one is between two intermediate filament proteins, NFM and VIME, an interaction confirmed by seven unique interlinked peptides representing seven unique K-K linkages (TABLE 10). The identification of interlinked peptides between various domains of NFM and VIME suggests that extensive interaction interfaces exist between these two proteins and potentially implicate VIME involvement in the polymerization or regulation of neurofilament proteins in HEK 293 cells.

It has been reported that VIME co-localizes with neurofilament proteins dynamically during neuronal differentiation, and its co-purification with NFH and NFL has been observed (49). Given the close relationship among the three neurofilament subunits NFL, NFM, and NFH, our findings corroborate well with the known function of vimentin in the development of neurofilaments. In general, identifying intermediate filament protein interactions from the native cellular environment is a major challenge, and therefore the ability to capture and directly identify not only which intermediate filament proteins interact, but at which residues, represents a major step forward in this area of research.

It is noted that the most abundant interactions identified in this work resulted from histones and structural proteins (TABLE 10), most likely attributed to their abundance as previously reported (24). In total, 118 unique cross-linked peptides among the four (H2A, H2B, H3.2, and H4) core histones were identified, with 47 from H2A-H2B, 13 from H2A-H3.2, 10 from H2B-H4, 8 from H2B-H3.2, 4 from H3.2-H4, and 1 from H2A-H4 pairs. Additionally, 35 unique intraprotein interlinked peptides were identified, with 20 from H2B, 11 from H3.2, 3 from H4, and 1 from H2A (TABLE 10). Based on the known nucleosome crystal structures (PDB 3AV1) (FIG. 31A-FIG. 31E), the distances between the identified cross-linked lysines are <26 Å, which is consistent with other cross-linking studies (23, 36), suggesting that Azide-A-DSBSO has an ideal spacer length for studying protein structures. Collectively, these results have demonstrated the feasibility of the Azide-A-DSBSO-based XL-MS strategy for mapping PPI network topologies from intact cells.

Mapping In Vivo Subunit Interactions of Proteasome Complexes

Figures 32A, 32B:
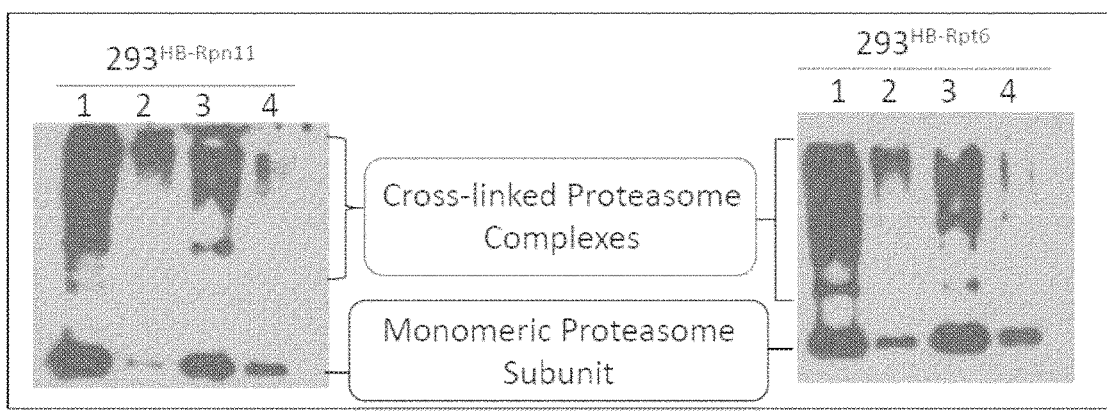
FIG. 32A & FIG. 32B show evaluation of HB-tag Based Tandem Affinity Purification of In Vivo Azide-ADSBSO Cross-linked Proteasome Complexes. Lanes: 1-cell lysate; 2-Flow through after the first step purification by binding to Ni-sepharose beads; 3-Elution from Ni-sepharose resins; 4-Flow through after second step purification by binding to streptavidin beads. Streptavidin-HRP was used to probe HB tagged proteasome subunits.

In order to establish an in vivo XL-MS workflow for protein complexes (FIG. 23), the Azide-A-DSBSO cross-linking strategy to study interactions of proteasome complexes was employed. To capture and isolate proteasome interacting proteins, 293 cell lines stably expressing an HB-tagged proteasome subunit (i.e. Rpn11-HB or HB-Rpt6) was used. In some embodiments, in vivo cross-linking of HB-tagged proteasome complexes was optimized. As shown in FIG. 32A and FIG. 32B, in vivo Azide-A-DSBSO crosslinking of human proteasome complexes and their subsequent HB-tag-based purification were effective. The BARAC conjugation and enrichment of cross-linked peptides was carried out after purification of in vivo cross-linked proteasome complexes as illustrated in FIG. 23 (path II).

FIG. 26A-FIG. 26D illustrate a representative MSn analysis of an in vivo intersubunit interlinked peptide (m/z 659.82594+) from human proteasome complexes. MS2 analysis of this peptide yielded three detectable fragments, $\alpha_A$ (m/z 499.272+), $\beta_A$ (m/z 720.372+), and PT (m/z 811.372+), displaying characteristic fragmentation of DSBSO interlinked peptides. Together with MS3 sequencing of αA (m/z 499.272+) and βT (m/z 811.372+) fragments, MSn analysis identified this cross-linked peptide as NELNAK55VR interlinked to EFLHAQEEVK80R unambiguously, which represents an intersubunit interaction between proteasome subunits Rpt6:K55 and Rpt3:K80.

In total, MS3 sequencing identified 119 non-redundant cross-linker modified peptides, 54 of which represent 27 unique interlinked peptides (TABLE 11 and TABLE 12). Among them, 22 unique interlinked peptides resulted from inter- or intrasubunit cross-links between known subunits of the proteasome complex, including 8 unique intersubunit (i.e. α3-Rpt6, Rpt2-Rpt6, Rpt3-Rpt6, Rpt4-Rpt6, Rpn5-Rpn6, Rpn11-Rpt6, Rpn5-Rpn9, Rpn2-Rpt6) and 11 unique intrasubunit interactions (TABLE 11 and TABLE 12). In addition to interactions between proteasome subunits, one interprotein interlink between HSPA1A and HSP8A and three intraprotein interlinked peptides from three known proteasome interacting proteins, HSPA1A, EEF2, and RPS15 were identified. In some embodiments, these results demonstrate that the new XL-MS workflow disclosed herein can be generalized to determine protein interaction interfaces of protein complexes in cells.

Biotin Conjugation and Enrichment Strategy for Azide-A-DSBSO Cross Linked Proteins Azide-A-DSBSO cross-linked 293 cell lysate was reacted with varying concentrations of BARAC with agitation overnight. The resulting biotin-conjugated lysates were analyzed via SDS-PAGE and immunoblot analysis to determine the conjugation efficiency. Bound proteins were reduced with 2 mm tris(2-carboxyethyl)phosphine for 30 min at room temperature and alkylated using 50 mm chloroacetamide in the dark at room temperature for 30 min prior to overnight digestion with 2% Lys-C (w/w) at 37° C. and subsequent overnight digestion with 2% trypsin TPCK (w/w) at 37° C. The Lys-C/trypsin combination is preferred for proteins purified under fully denaturing conditions to achieve optimal digestion efficiency. Non-cross-linked peptides were extracted and analyzed directly via LC-MS/MS, whereas streptavidin-bound peptides were first acid-cleaved from beads with 20% formic acid, 20% acetonitrile overnight before LC-MSn analysis.

Biotin Conjugation and Enrichment Strategy for Azide-A-DSBSO Cross-Linked Peptides In vivo cross-linked proteins in 293 cell lysates were concentrated using 100-kDa NMWL Amicon Ultra centrifugal filters, and the resulting filtrates were then passed through 30-kDa NMWL Amicon Ultra centrifugal filters. Proteins remaining on both membranes were reduced with 2 mm tris(2-carboxyethyl)phosphine for 30 min at room temperature and then alkylated with 50 mm chloroacetamide at room temperature in the dark for 30 min prior to a 3% Lys-C (w/w) overnight digestion at 37° C. and subsequent 3% trypsin TPCK (w/w) overnight digestion at 37° C. Digests were collected via centrifugation and reacted with 100 μm BARAC at room temperature with agitation overnight. The biotin-conjugated peptides were then enriched using high-capacity streptavidin agarose resin. Bound peptides were acid-cleaved and then submitted for LC-MSn analysis.

Affinity Purification of In Vivo Azide-A-DSBSO Cross-Linked Proteasome Complexes and Subsequent Enrichment of Cross-Linked Peptides Stable 293 cell lines expressing an HB tagged proteasome subunit (Rpn11 or Rpt6) were grown to confluence in DMEM containing 10% FBS and 1% Pen/strep. The cells were washed with PBS and cross-linked and quenched as described above. The cells were lysed in 8 m urea denaturing lysis buffer (15). The cleared lysates were subjected to HB-tag-based tandem affinity purification, which involved binding to Ni2+-Sepharose beads followed by binding to streptavidin resins (15). Proteins bound on beads were reduced, alkylated, and then incubated in 250 μm BARAC with rotation at room temperature overnight in 8 m urea buffer. After extensive washing, bound proteins were digested by Lys-C and trypsin (15). The peptides freed into solution during digestion were subjected to further enrichment through binding to Neutravidin resin for 1 h at room temperature, and cross-linked peptides were acid-eluted as described. The enriched cross-linked peptides were then subjected to LC-MSn analysis.

Analysis of Cross-Linked Peptides by LC-MSn

Most of the enriched cross-linked peptides were analyzed via LC-MSn using an LTQ-Orbitrap XL mass spectrometer (Thermo Scientific, San Jose, Calif.) coupled on-line with either an Eksigent NanoLC system (Dublin, Calif.) or an EASY-nLC-1000 (Thermo Scientific, San Jose, Calif.). A few cross-linked samples from intact cells were analyzed using an Orbitrap Elite mass spectrometer (courtesy of Thermo Scientific Demo Lab, San Jose, Calif.) coupled on-line with an EASY-nLC 1000 (Thermo Scientific). LC-MSn data acquisition and analysis were as described (20). Only ions with charge of 3+ or more in the MS1 scan were selected for MS2 analysis.

Identification of Cross-Linked Peptides Via Database Searching

Because of the similarity between DSBSO and DSSO, the general data analysis workflow for the identification of DSBSO interlinked peptides via LC-MSn is the same as the analysis of DSSO cross-linked peptides (20, 36). Using the Batch-Tag software within a developmental version of Protein Prospector (v5.10.10, University of California San Francisco), MS2 and MS3 spectra were searched against a decoy database consisting of a normal Swiss-Prot database concatenated with its randomized version (SwissProt.2013.3.1.random.concat with a total of 454,402 protein entries). *Homo sapiens* was set as the species (20, 501 entries) for analyzing data from human cells. The mass tolerances for parent ions and fragment ions were set as ±20 ppm and 0.6 Da, respectively. For Lys-C/trypsin digests, trypsin was set as the enzyme with a maximum of three missed cleavages allowed. Cysteine carbamidomethylation was set as a constant modification. Protein N-terminal acetylation, asparagine deamidation, N-terminal conversion of glutamine to pyroglutamic acid, and methionine oxidation were selected as variable modifications. Similar to DSSO cross-linked peptides, DSBSO cross-linked peptides display unique and characteristic MS2 fragmentation patterns corresponding to their cross-linking types. Therefore, three additional defined modifications on uncleaved lysines and free protein N termini were chosen: alkene (C3H2O, +54 Da), sulfenic acid (C3H4O2S, +254 Da), and unsaturated thiol (C3H2SO, +236 Da). These are modifications resulting from collision-induced dissociation cleavage of the DSBSO cross-linked peptides. Proteins were identified with expectation values ≤0.01 and a minimum of two unique peptides (15).

The in-house program Link-Hunter is a revised version of the previously written Link-Finder program, designed to automatically validate and summarize cross-linked peptide sequences based on MSn data and database searching results as previously described (20, 36). In addition to checking MS2 spectra for predicted patterns, Link-Hunter automatically correlates sequence data from MS3 to MS2 and MS1 parent masses and reports identified interlinked peptides with two associated sequences.

Interaction Network Mapping and Functional Enrichment Analysis

PPI network graphs resulting from cross-links identified in this work were generated manually in Excel from the final list of identified cross-linked proteins. For comparison with known interactions, the final list of cross-linked interacting proteins was fed into an analysis pipeline that automatically extracts physical (but not genetic) interactions from BioGRID, MINT, and IntAct using their Web services (15). Both PPI networks were imported into and visualized by Cytoscape v2.8.3. Functional enrichment was performed using the DAVID Bioinformatics Resources (v.6.7) Functional Annotation Tool (46). Gene I.D.s were submitted, and the Functional Enrichment Chart with enriched Gene Ontology annotations (cellular compartment and biological processes) was downloaded. Only high-confidence functional annotations (false discovery rate <0.01) were reported.

References—3

1. Ryan D. P., Matthews J. M. (2005) Protein-protein interactions in human disease. Curr. Opin. Struct. Biol. 15, 441-446 CrossRefMedlineGoogle Scholar
2. Gingras A. C., Gstaiger M., Raught B., Aebersold R. (2007) Analysis of protein complexes using mass spectrometry. Nat. Rev. Mol. Cell Biol. 8, 645-654 CrossRefMedlineGoogle Scholar
3. Kocher T., Superti-Furga G. (2007) Mass spectrometry-based functional proteomics: from molecular machines to protein networks. Nat. Methods 4, 807-815 CrossRefMedlineGoogle Scholar
4. Guan H., Kiss-Toth E. (2008) Advanced technologies for studies on protein interactomes. Adv. Biochem. Eng. Biotechnol. 110, 1-24 MedlineGoogle Scholar
5. Ryan C. J., Cimermancic P., Szpiech Z. A., Sali A., Hernandez R. D., Krogan N. J. (2013) High-resolution network biology: connecting sequence with function. Nat. Rev. Genet. 14, 865-879 CrossRefMedlineGoogle Scholar
6. Zheng Y., Zhang C., Croucher D. R., Soliman M. A., St-Denis N., Pasculescu A., Taylor L., Tate S. A., Hardy W. R., Colwill K., Dai A. Y., Bagshaw R., Dennis J. W., Gingras A. C., Daly R. J., Pawson T. (2013) Temporal regulation of EGF signalling networks by the scaffold protein Shc1. Nature 499, 166-171 CrossRefMedlineGoogle Scholar
7. Lambert J. P., Ivosev G., Couzens A. L., Larsen B., Taipale M., Lin Z. Y., Zhong Q., Lindquist S., Vidal M., Aebersold R., Pawson T., Bonner R., Tate S., Gingras A. C. (2013) Mapping differential interactomes by affinity purification coupled with data-independent mass spectrometry acquisition. Nat. Methods 10, 1239-1245 CrossRefMedlineGoogle Scholar
8. Collins B. C., Gillet L. C., Rosenberger G., Rost H. L., Vichalkovski A., Gstaiger M., Aebersold R. (2013) Quantifying protein interaction dynamics by SWATH mass spectrometry: application to the 14-3-3 system. Nat. Methods 10, 1246-1253 CrossRefMedlineGoogle Scholar
9. Sowa M. E., Bennett E. J., Gygi S. P., Harper J. W. (2009) Defining the human deubiquitinating enzyme interaction landscape. Cell 138, 389-403 CrossRefMedlineGoogle Scholar
10. Vasilescu J., Guo X., Kast J. (2004) Identification of protein-protein interactions using in vivo cross-linking and mass spectrometry. Proteomics 4, 3845-3854 CrossRefMedlineGoogle Scholar
11. Schmitt-Ulms G., Hansen K., Liu J., Cowdrey C., Yang J., DeArmond S. J., Cohen F. E., Prusiner S. B., Baldwin M. A. (2004) Time-controlled transcardiac perfusion cross-linking for the study of protein interactions in complex tissues. Nat. Biotechnol. 22, 724-731 CrossRefMedlineGoogle Scholar
12. Guerrero C., Tagwerker C., Kaiser P., Huang L. (2006) An integrated mass spectrometry-based proteomic approach: quantitative analysis of tandem affinity-purified in vivo cross-linked protein complexes (QTAX) to decipher the 26 S proteasome-interacting network. Mol. Cell. Proteomics 5, 366-378 Abstract/FREE Full Text
13. Guerrero C., Milenkovic T., Przulj N., Kaiser P., Huang L. (2008) Characterization of the proteasome interaction network using a QTAX-based tag-team strategy and protein interaction network analysis. Proc. Natl. Acad. Sci. U.S.A. 105, 13333-13338 Abstract/FREE Full Text
14. Kaake R. M., Milenkovic T., Przulj N., Kaiser P., Huang L. (2010) Characterization of cell cycle specific protein interaction networks of the yeast 26S proteasome complex by the QTAX strategy. J. Proteome Res. 9, 2016-2029 CrossRefMedlineGoogle Scholar
15. Fang L., Kaake R. M., Patel V. R., Yang Y., Baldi P., Huang L. (2012) Mapping the protein interaction network of the human COP9 signalosome complex using a label-free QTAX strategy. Mol. Cell. Proteomics 11, 138-147 Abstract/FREE Full Text
16. Tardiff D. F., Abruzzi K. C., Rosbash M. (2007) Protein characterization of Saccharomyces cerevisiae RNA polymerase II after in vivo cross-linking. Proc. Natl. Acad. Sci. U.S.A. 104, 19948-19953 Abstract/FREE Full Text
17. Leitner A., Walzthoeni T., Kahraman A., Herzog F., Rinner O., Beck M., Aebersold R. (2010) Probing native protein structures by chemical cross-linking, mass spectrometry, and bioinformatics. Mol. Cell. Proteomics 9, 1634-1649 Abstract/FREE Full Text
18. Greber B. J., Boehringer D., Leitner A., Bieri P., Voigts-Hoffmann F., Erzberger J. P., Leibundgut M., Aebersold R., Ban N. (2014) Architecture of the large subunit of the mammalian mitochondrial ribosome. Nature 505, 515-519 CrossRefMedlineGoogle Scholar
19. Lasker K., Forster F., Bohn S., Walzthoeni T., Villa E., Unverdorben P., Beck F., Aebersold R., Sali A., Baumeister W. (2012) Molecular architecture of the 26S proteasome holocomplex determined by an integrative approach. Proc. Natl. Acad. Sci. U.S.A. 109, 1380-1387 Abstract/FREE Full Text
20. Kao A., Randall A., Yang Y., Patel V. R., Kandur W., Guan S., Rychnovsky S. D., Baldi P., Huang L. (2012) Mapping the structural topology of the yeast 19S proteasomal regulatory particle using chemical cross-linking and probabilistic modeling. Mol. Cell. Proteomics 11, 1566-1577 Abstract/FREE Full Text 21. Chen Z. A., Jawhari A., Fischer L., Buchen C., Tahir S., Kamenski T., Rasmussen M., Lariviere L., Bukowski-Wills J. C., Nilges M., Cramer P., Rappsilber J. (2010) Architecture of the RNA polymerase II-TFIIF complex revealed by cross-linking and mass spectrometry. EMBO J. 29, 717-726 Abstract/FREE Full Text
22. Leitner A., Joachimiak L. A., Bracher A., Monkemeyer L., Walzthoeni T., Chen B., Pechmann S., Holmes S., Cong Y., Ma B., Ludtke S., Chiu W., Hartl F. U.,
Aebersold R., Frydman J. (2012) The molecular architecture of the eukaryotic chaperonin TRiC/CCT. Structure 20, 814-825 CrossRefMedlineGoogle Scholar
23. Herzog F., Kahraman A., Boehringer D., Mak R., Bracher A., Walzthoeni T., Leitner A., Beck M., Hartl F. U., Ban N., Malmstrom L., Aebersold R. (2012) Structural probing of a protein phosphatase 2A network by chemical cross-linking and mass spectrometry. Science 337, 1348-1352 Abstract/FREE Full Text
24. Chavez J. D., Weisbrod C. R., Zheng C., Eng J. K., Bruce J. E. (2013) Protein interactions, post-translational modifications and topologies in human cells. Mol. Cell. Proteomics 12, 1451-1467 Abstract/FREE Full Text
25. Zhang H., Tang X., Munske G. R., Zakharova N., Yang L., Zheng C., Wolff M. A., Tolic N., Anderson G. A., Shi L., Marshall M. J., Fredrickson J. K., Bruce J. E. (2008) In vivo identification of the outer membrane protein OmcA-MtrC interaction network in Shewanella oneidensis MR-1 cells using novel hydrophobic chemical cross-linkers. J. Proteome Res. 7, 1712-1720 CrossRefMedlineGoogle Scholar
26. Sinz A. (2006) Chemical cross-linking and mass spectrometry to map three-dimensional protein structures and protein-protein interactions. Mass Spectrom. Rev. 25, 663-682 CrossRefMedlineGoogle Scholar
27. Sutherland B. W., Toews J., Kast J. (2008) Utility of formaldehyde cross-linking and mass spectrometry in the study of protein-protein interactions. J. Mass Spectrom. 43, 699-715 CrossRefMedlineGoogle Scholar
28. Rinner O., Seebacher J., Walzthoeni T., Mueller L. N., Beck M., Schmidt A., Mueller M., Aebersold R. (2008) Identification of cross-linked peptides from large sequence databases. Nat. Methods 5, 315-318 CrossRefMedlineGoogle Scholar
29. Panchaud A., Singh P., Shaffer S. A., Goodlett D. R. (2010) xComb: a cross-linked peptide database approach to protein-protein interaction analysis. J. Proteome Res. 9, 2508-2515 CrossRefMedlineGoogle Scholar
30. Walzthoeni T., Claassen M., Leitner A., Herzog F., Bohn S., Forster F., Beck M., Aebersold R. (2012) False discovery rate estimation for cross-linked peptides identified by mass spectrometry. Nat. Methods 9, 901-903 CrossRefMedlineGoogle Scholar
31. Yang B., Wu Y. J., Zhu M., Fan S. B., Lin J., Zhang K., Li S., Chi H., Li Y. X., Chen H. F., Luo S. K., Ding Y. H., Wang L. H., Hao Z., Xiu L. Y., Chen S., Ye K., He S. M., Dong M. Q. (2012) Identification of cross-linked peptides from complex samples. Nat. Methods 9, 904-906 CrossRefMedlineGoogle Scholar
32. Trnka M. J., Baker P. R., Robinson P. J., Burlingame A. L., Chalkley R. J. (2014) Matching cross-linked peptide spectra: only as good as the worse identification. Mol. Cell. Proteomics 13, 420-434 Abstract/FREE Full Text
33. Chu F., Mahrus S., Craik C. S., Burlingame A. L. (2006) Isotope-coded and affinity-tagged cross-linking (ICATXL): an efficient strategy to probe protein interaction surfaces. J. Am. Chem. Soc. 128, 10362-10363 CrossRefMedlineGoogle Scholar
34. Chowdhury S. M., Du X., Tolic N., Wu S., Moore R. J., Mayer M. U., Smith R. D., Adkins J. N. (2009) Identification of cross-linked peptides after click-based enrichment using sequential collision-induced dissociation and electron transfer dissociation tandem mass spectrometry. Anal. Chem. 81, 5524-5532 CrossRefMedlineGoogle Scholar
35. Vellucci D., Kao A., Kaake R. M., Rychnovsky S. D., Huang L. (2010) Selective enrichment and identification of azide-tagged cross-linked peptides using chemical ligation and mass spectrometry. J. Am. Soc. Mass Spectrom. 21, 1432-1445 CrossRefMedlineGoogle Scholar
36. Kao A., Chiu C. L., Vellucci D., Yang Y., Patel V. R., Guan S., Randall A., Baldi P., Rychnovsky S. D., Huang L. (2011) Development of a novel cross-linking strategy for fast and accurate identification of cross-linked peptides of protein complexes. Mol. Cell. Proteomics 10, M110.002212 Abstract/FREE Full Text
37. Lu Y., Tanasova M., Borhan B., Reid G. E. (2008) Ionic reagent for controlling the gas-phase fragmentation reactions of cross-linked peptides. Anal. Chem. 80, 9279-9287 CrossRefMedlineGoogle Scholar
38. Petrotchenko E., Borchers C. (2010) ICC-CLASS: isotopically-coded cleavable crosslinking analysis software suite. BMC Bioinformatics 11, 64 CrossRefMedlineGoogle Scholar
39. Muller M. Q., Dreiocker F., Ihling C. H., Schafer M., Sinz A. (2010) Cleavable cross-linker for protein structure analysis: reliable identification of cross-linking products by tandem MS. Anal. Chem. 82, 6958-6968 CrossRefMedlineGoogle Scholar
40. Tang X., Munske G. R., Siems W. F., Bruce J. E. (2005) Mass spectrometry identifiable cross-linking strategy for studying protein-protein interactions. Anal. Chem. 77, 311-318 CrossRefMedlineGoogle Scholar
41. Kasper P. T., Back J. W., Vitale M., Hartog A. F., Roseboom W., de Koning L. J., van Maarseveen J. H., Muijsers A. O., de Koster C. G., de Jong L. (2007) An aptly positioned azido group in the spacer of a protein cross-linker for facile mapping of lysines in close proximity. Chembiochem 8, 1281-1292 CrossRefMedlineGoogle Scholar
42. Nessen M. A., Kramer G., Back J., Baskin J. M., Smeenk L. E., de Koning L. J., van Maarseveen J. H., de Jong L., Bertozzi C. R., Hiemstra H., de Koster C. G. (2009) Selective enrichment of azide-containing peptides from complex mixtures. J. Proteome Res. 8, 3702-3711 CrossRefMedlineGoogle Scholar
43. Petrotchenko E. V., Xiao K., Cable J., Chen Y., Dokholyan N. V., Borchers C. H. (2009) BiPS, a photocleavable, isotopically coded, fluorescent cross-linker for structural proteomics. Mol. Cell. Proteomics 8, 273-286 Abstract/FREE Full Text
44. Luo J., Fishburn J., Hahn S., Ranish J. (2012) An integrated chemical cross-linking and mass spectrometry approach to study protein complex architecture and function. Mol. Cell. Proteomics 11, M111.008318 Abstract/FREE Full Text
45. Jewett J. C., Sletten E. M., Bertozzi C. R. (2010) Rapid Cu-free click chemistry with readily synthesized biarylazacyclooctynones. J. Am. Chem. Soc. 132, 3688-3690 CrossRefMedlineGoogle Scholar
46. Huang da W., Sherman B. T., Lempicki R. A. (2009) Systematic and integrative analysis of large gene lists using DAVID bioinformatics resources. Nat. Protoc. 4, 44-57 CrossRefMedlineGoogle Scholar 47. Gordon C. G., Mackey J. L., Jewett J. C., Sletten E. M., Houk K. N., Bertozzi C. R. (2012) Reactivity of biarylazacyclooctynones in copper-free click chemistry. J. Am. Chem. Soc. 134, 9199-9208 CrossRefMedlineGoogle Scholar
48. Tagwerker C., Flick K., Cui M., Guerrero C., Dou Y., Auer B., Baldi P., Huang L., Kaiser P. (2006) A tandem affinity tag for two-step purification under fully denaturing conditions: application in ubiquitin profiling and protein complex identification combined with in vivo-cross-linking. Mol. Cell. Proteomics 5, 737-748 Abstract/FREE Full Text
49. Yabe J. T., Chan W. K., Wang F. S., Pimenta A., Ortiz D. D., Shea T. B. (2003) Regulation of the transition from vimentin to neurofilaments during neuronal differentiation. Cell Motil. Cytoskeleton 56, 193-205 CrossRefMedlineGoogle Scholar
50. Lander G. C., Estrin E., Matyskiela M. E., B ashore C., Nogales E., Martin A. (2012) Complete subunit architecture of the proteasome regulatory particle. Nature 482, 186-191 CrossRefMedlineGoogle Scholar
51. Beck F., Unverdorben P., Bohn S., Schweitzer A., Pfeifer G., Sakata E., Nickell S., Plitzko J. M., Villa E., Baumeister W., Forster F. (2012) Near-atomic resolution structural model of the yeast 26S proteasome. Proc. Natl. Acad. Sci. U.S.A. 109, 14870-14875 Abstract/FREE Full Text
52. Gavin A. C., Maeda K., Kuhner S. (2011) Recent advances in charting protein-protein interaction: mass spectrometry-based approaches. Curr. Opin. Biotechnol. 22, 42-49 CrossRefMedlineGoogle Scholar
53. Yu C., Kandur W., Kao A., Rychnovsky S., Huang L. (2014) Developing new isotope-coded mass spectrometry-cleavable cross-linkers for elucidating protein structures. Anal. Chem. 86, 2099-2106 CrossRefGoogle Scholar
54. Leitner A., Joachimiak L. A., Unverdorben P., Walzthoeni T., Frydman J., Forster F., Aebersold R. (2014) Chemical cross-linking/mass spectrometry targeting acidic residues in proteins and protein complexes. *Proc. Natl. Acad. Sci. U.S.A.* 111, 9455-9460 Abstract/FREE Full Text
55. Burke A. M. (2011) Ph.D. thesis, Reagents for in vivo Protein Cross-Linking and Automated Analysis of Protein-Protein Interactions with Tandem Mass Spectrometry University of California, Irvine

Definitions

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure.

It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

It should be understood, however, that this detailed description, while indicating preferred embodiments of the invention, is given by way of illustration only, since various changes and modifications within the spirit and scope of the invention will become apparent to those skilled in the art.

The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

Abbreviations

Ac Acetate
AlkyneA-DSBSO Alkyne-tagged, acid-cleavable disuccinimiclyl-bissulfoxide
AzideA-DSBSO Azide-tagged, acid-cleavable disuccinimidyl-bissulfoxide
BARAC Biarylazacycloocrynone
CID Collision-induced dissociation
CSA Camphorsulfonic acid
CuAAC Copper(1) catalyzed azide-alkyne cycloaddition
DIPEA N, N-Diisopropylethylamine
DMF Dimethylformamide
DSSO Disuccinimidylsulfoxide
EDC.HCl. N-(3-Dimethylaminopropyl)-N'-ethylcarbodiimide hydrochloride
$Et_3N$ Triethylamine
HB His-bio
ESI-MS Electrospray ionization-mass spectrometry
$In(OTf)_3$ Indium(111) trifluoromethanesulfonate
$K_A$YIPGTK Lysine(alkene modified)-tyrosine-isoleucineproline-glycine-threonine-lysine peptide
LC/MS Liquid chromatography-mass spectrometry
MeOH Methanol
M(ox) Methionine(oxidized)-isoleucine-phenyl
IFAGIK$_A$K alaninealanine-glycine-isoleucine-lysine(alkene modified)-lysine
m-CPBA meta-Chloroperoxybenzoic acid
MsCl Methanesulfonyl chloride
NHS N-Hydroxysuccinimiclyl
Ph-H Benzene
Pyr. Pyridine
QTAX Quantitative analysis of tandem affinity purified in vivo cross-linked (X) protein complexes
TFAA Trifluoroacetic anhydride
TFA-NHS N-Trifluoroacetoxy succinimide
THF Tetrahydrofuran TMSCI Trimethylsilyl chloride
TMSOTf Trimethylsilyl trifluoromethanesulfonate
TsOH para-Toluenesulfonic acid
XL-MS Cross-linking mass spectrometry
μw Microwave
MS Mass Spectrometry
MS/MS Tandem Mass Spectrometry
MS" Multi-Stage Tandem Mass Spectrometry (n=2, 3, ...)
LC MS" Liquid Chromatography Multi-Stage Tandem Mass Spectrometry
CID Collision Induced Dissociation
DSSO bis(2,5-dioxopyrrolidin-1-yl) 3,3'-sulfinyldipropanoate
NMR Nuclear Magnetic Resonance

What is claimed is:

1. An MS-cleavable cross-linker for mapping intra-protein interactions in a protein, inter-protein interactions in a protein complex or a combination thereof, the MS-cleavable cross-linker comprising:
   two amine-reactive N-hydroxysuccinimdyl (NHS) ester groups;
   a spacer arm with at least one central sulfoxide group, wherein the at least one central sulfoxide group is linked to each of the two amine-reactive N-hydroxysuccinimdyl (NHS) ester groups through at least two methylene groups; and
   two symmetric collision-induced dissociation (CID) cleavable bonds on the spacer arm,
   wherein each of the two CID cleavable bond is a C—S bond adjacent to the at least one central sulfoxide.

2. The MS-cleavable cross-linker of claim 1, wherein each amine-reactive NHS ester group is designed to react with a lysine side chain in a peptide or a protein.

3. The MS-cleavable cross-linker of claim 1, wherein the MS-cleavable cross-linker is DSSO, consisting of the structure:

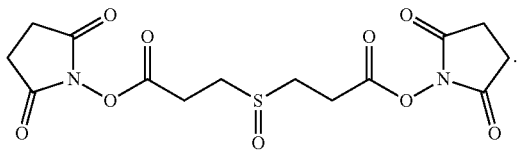 [SMILES: O=C(CCS(=O)CCC(=O)ON1C(=O)CCC1=O)ON1C(=O)CCC1=O]

4. The MS-cleavable cross-linker of claim 1, comprising:
   two central sulfoxide groups, and
   a moiety comprising:
      at least one enrichment handle; and
      at least one acid cleavage site,
   wherein the moiety links the two central sulfoxide groups, and
   wherein the MS-cleavable cross-linker is membrane permeable.

5. The MS-cleavable cross-linker of claim 4, wherein the at least one enrichment handle comprises a functional group, wherein the functional group is an azide functional group or an alkyne functional group, and wherein the functional group is designed for a click reaction with strained alkynes or a CuAAC reaction.

6. The MS-cleavable cross-linker of claim 4, wherein the at least one acid cleavage site is an acid labile acetal bond, wherein the acid labile acetal bond is designed to be cleaved under aqueous acidic conditions.

7. The MS-cleavable cross-linker of claim 4, wherein the MS-cleavable cross-linker is azide-A-DSBSO, consisting of the structure:

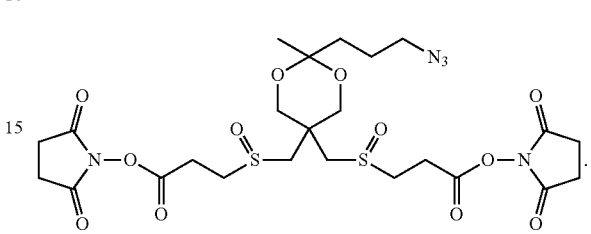

8. The MS-cleavable cross-linker of claim 4, wherein the MS-cleavable cross-linker is alkyne-A-DSBSO, consisting of the structure:

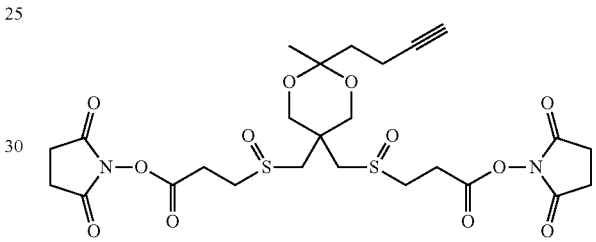

9. A method for synthesis of the MS-cleavable cross-linker of claim 3 for mapping intra-protein interactions in a protein, inter-protein interactions in a protein complex or a combination thereof, the method comprising the steps of:
   (i) providing 3,3'-thiodipropionic acid;
   (ii) deriving bis(2,5-dioxopyrrolidin-1-yl) 3,3'-thiodipropionate from the compound of step (i); and
   (iii) deriving DSSO from the compound of step (ii).

10. A method for synthesis of the MS-cleavable cross-linker of claim 7 for mapping intra-protein interactions in a protein, inter-protein interactions in a protein complex or a combination thereof, the method comprising the steps of:
   (i) providing 2,2-bis(hydroxymethyl)propane-1,3-diol;
   (ii) deriving (1,5-dioxaspiro[5.5]undecane-3,3-diyl)dimethanol from the compound of step (i);
   (iii) deriving (1,5-dioxaspiro[5.5]undecane-3,3-diyl)bis(methylene) dimethanesulfonate from the compound of step (ii);
   (iv) deriving S,S'-((1,5-dioxaspiro[5.5]undecane-3,3-diyl)bis(methylene)) diethanethioate from the compound of step (iii);
   (v) deriving dimethyl 3,3'-(((1,5-dioxaspiro[5.5]undecane-3,3-diyl)bis(methylene))bis(sulfanediyl))dipropionate from the compound of step (iv);
   (vi) deriving dimethyl 3,3'-((2,2-bis(hydroxymethyl)propane-1,3-diyl)bis(sulfanediyl))dipropionate from the compound of step (v);
   (vii) deriving dimethyl 3,3'-(((2-(3-azidopropyl)-2-methyl-1,3-dioxane-5,5-diyl)bis(methylene))bis(sulfanediyl))dipropionate from the compound of step (vi);
   (viii) deriving 3,3'-(((2-(3-azidopropyl)-2-methyl-1,3-dioxane-5,5-diyl)bis(methylene))bis(sulfanediyl))dipropionic acid from the compound of step (vii);

(ix) deriving bis(2,5-dioxopyrrolidin-1-yl) 3,3'-(((2-(3-azidopropyl)-2-methyl-1,3-dioxane-5,5-diyl)bis(methylene))bis(sulfanediyl))dipropionate from the compound of step (viii);

(x) deriving azide-A-DSBSO from the compound of step (ix).

11. A method for synthesis of the MS-cleavable cross-linker of claim 7 for mapping intra-protein interactions in a protein, inter-protein interactions in a protein complex or a combination thereof, the method comprising the steps of:

(i) providing 2,2-bis(bromomethyl)propane-1,3-diol and methyl 3-mercaptopropanoate;

(ii) deriving dimethyl 3,3'-((2,2-bis(hydroxymethyl)propane-1,3-diyl)bis(sulfanediyl))dipropionate from the compounds of step (i);

(iii) dimethyl 3,3'-(((2-(3-azidopropyl)-2-methyl-1,3-dioxane-5,5-diyl)bis(methylene))bis(sulfanediyl))dipropionate from the compound of step (ii);

(iv) deriving bis(2,5-dioxopyrrolidin-1-yl) 3,3'-(((2-(3-azidopropyl)-2-methyl-1,3-dioxane-5,5-diyl)bis(methylene))bis(sulfanediyl))dipropionate from the compound of step (iii); and (v) deriving azide-A-DSBSO from the compound of step (iv).

12. A method for synthesis of the MS-cleavable cross-linker of claim 8 for mapping intra-protein interactions in a protein, inter-protein interactions in a protein complex or a combination thereof, the method comprising the steps of:

(i) providing dimethyl 3,3'-((2,2-bis(hydroxymethyl)propane-1,3-diyl)bis(sulfanediyl))dipropionate;

(ii) deriving dimethyl 3,3'-(((2-(but-3-yn-1-yl)-2-methyl-1,3-dioxane-5,5-diyl)bis(methylene))bis(sulfanediyl)) dipropionate from the compound of step (i);

(iii) deriving bis(2,5-dioxopyrrolidin-1-yl) 3,3'-(((2-(but-3-yn-1-yl)-2-methyl-1,3-dioxane-5,5-diyl)bis(methylene))bis(sulfanediyl))dipropionatefrom the compound of step (ii); and (iv) deriving alkyne-A-DSBSO from the compound of step (iii).

13. A method for mapping intra-protein interactions in a protein, inter-protein interactions in a protein complex or a combination thereof, the method comprising:

providing the MS-cleavable cross-linker of claim 1;

forming a cross-linked protein or protein complex by cross-linking the protein or the protein complex with the MS-cleavable cross-linker;

forming one or more peptide fragments that are chemically bound to the MS-cleavable cross-linker by digesting the cross-linked protein or protein complex with an enzyme; and identifying the one or more peptide fragments using tandem mass spectrometry (MSn), thereby mapping intra-protein interactions in a protein and inter-protein interactions in a protein complex.

14. The method of claim 13, wherein the MS-cleavable cross-linking agent is a compound of structure:

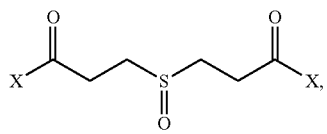

wherein X is selected from the group consisting of:

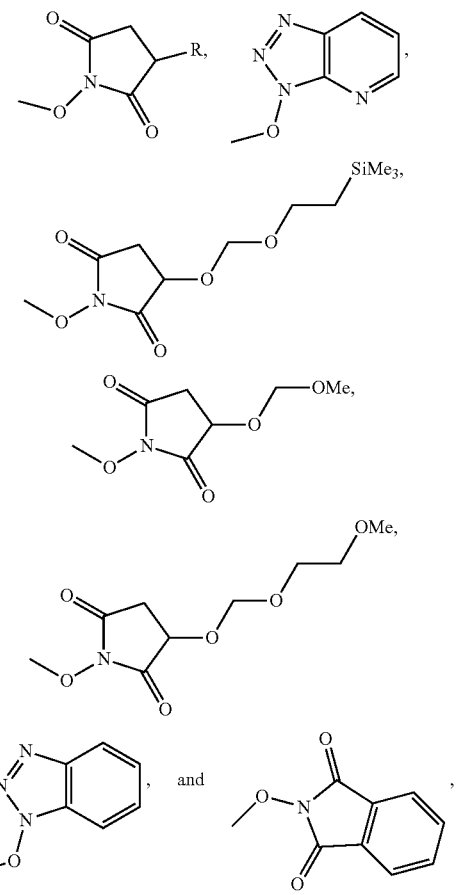

wherein R is H, methyl or ethyl.

15. The method of claim 13, wherein the MS-cleavable cross-linking agent is DSSO, consisting of the structure:

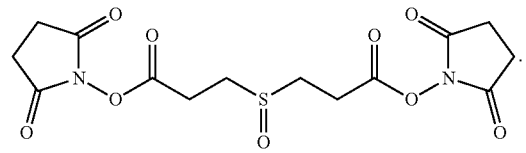

16. The method of claim 13, wherein the MS-cleavable cross-linking agent comprises:

two central sulfoxide groups, and a moiety comprising:

at least one enrichment handle; and at least one acid cleavage site, wherein the moiety links the two central sulfoxide groups, and wherein the MS-cleavable cross-linker is membrane permeable.

17. The method of claim 16, wherein the MS-cleavable cross-linking agent is azide-A-DSBSO, consisting of the structure:

18. The method of claim 16, wherein the MS-cleavable cross-linking agent is alkyne-A-DSBSO, consisting of the structure:

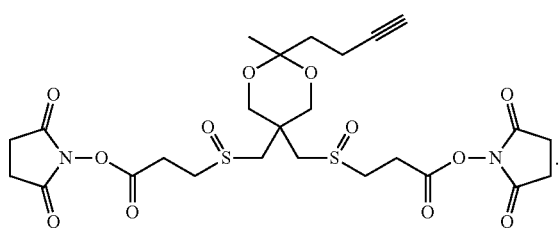 [SMILES: C#CCCC1(C)OCC(CS(=O)CCC(=O)ON2C(=O)CCC2=O)(CS(=O)CCC(=O)ON2C(=O)CCC2=O)CO1]

19. The method of claim 16, wherein the at least one enrichment handle comprises a functional group for an enrichment strategy, wherein the functional group is an azide functional group or an alkyne functional group, and wherein the functional group is designed for a click reaction with strained alkynes or a CuAAC reaction.

20. The method of claim 19, wherein the enrichment strategy is an affinity purification wherein the affinity purification comprises direct coupling with alkyne or azide functionalized beads or linking with one or more common affinity ligands such as biotin.

21. The method of claim 16, wherein the acid cleavable site is an acid labile acetal bond, wherein the acid labile acetal bond is designed to be cleaved under aqueous acidic conditions for selective elution from an affinity column.

22. A method for cross-linking mass spectrometry (XL-MS) for identifying one or more cross-linked peptides, the method comprising:
performing cross-linking with the MS-cleavable cross-linker of claim 1 to obtain one or more cross-linked proteins;
digesting the one or more cross-linked proteins with trypsin to obtain one or more cross-linked peptides;
performing a liquid chromatography-tandem mass spectrometry (LC-MS$^n$) analysis on the one or more cross-linked peptides, wherein the LC-MS analysis comprises:
detecting the one or more cross-linked peptides by MS1 analysis;
selecting the one or more cross-linked peptides detected by MS1 for MS2 analysis;
selectively fragmenting the at least one CID cleavable bond and separating the one or more cross-linked peptides during MS2 analysis;
sequencing the one or more cross-linked peptides separated during MS2 analysis by MS3 analysis; and
integrating data obtained during MS1, MS2 and MS3 analyses to identify the one or more cross-linked peptides.

23. The method of claim 22, wherein the MS-cleavable cross-linking agent is DSSO, consisting of the structure:

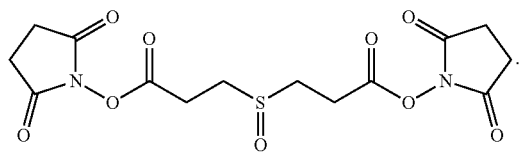 [SMILES: O=C(CCS(=O)CCC(=O)ON1C(=O)CCC1=O)ON1C(=O)CCC1=O]

24. The method of claim 22, wherein the MS-cleavable cross-linking agent comprises:
two central sulfoxide groups, and
a moiety comprising:
at least one enrichment handle; and
at least one acid cleavage site,
wherein the moiety links the two central sulfoxide groups, and
wherein the MS-cleavable cross-linker is membrane permeable.

25. The method of claim 24, wherein the MS-cleavable cross-linking agent is azide-A-DSBSO, consisting of the structure:

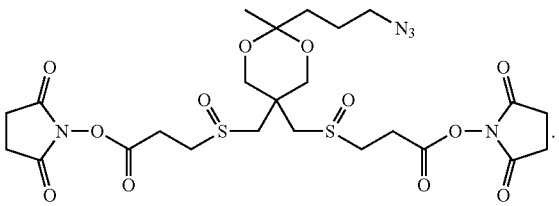 [SMILES: CC1(CCCN=[N+]=[N-])OCC(CS(=O)CCC(=O)ON2C(=O)CCC2=O)(CS(=O)CCC(=O)ON2C(=O)CCC2=O)CO1]

26. The method of claim 24, wherein the MS-cleavable cross-linking agent is alkyne-A-DSBSO, consisting of the structure:

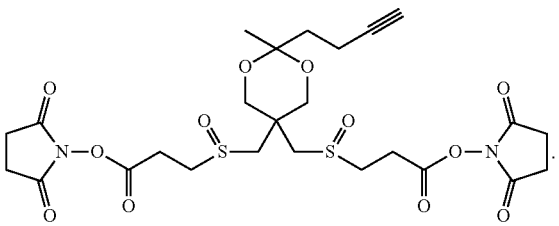 [SMILES: C#CCCC1(C)OCC(CS(=O)CCC(=O)ON2C(=O)CCC2=O)(CS(=O)CCC(=O)ON2C(=O)CCC2=O)CO1]

* * * * *

UNITED STATES PATENT AND TRADEMARK OFFICE
CERTIFICATE OF CORRECTION

| | |
|---|---|
| PATENT NO. | : 10,393,752 B2 |
| APPLICATION NO. | : 15/275001 |
| DATED | : August 27, 2019 |
| INVENTOR(S) | : Scott D. Rychnovsky et al. |

It is certified that error appears in the above-identified patent and that said Letters Patent is hereby corrected as shown below:

On the Title Page

Column 2, Item (56), Line 35, under Other Publications, delete "Chemisty," and insert --Chemistry,--.

In the Specification

In Column 2, Lines 21-22, delete "N-hydroxysuccinimdyl" and insert --N-hydroxysuccinimidyl--.

In Column 4, Line 25, delete "dipropionatefrom" and insert --dipropionate from--.

In Column 4, Line 36, delete "N-hydroxysuccinimdyl" and insert --N-hydroxysuccinimidyl--.

In Column 6, Line 32, delete "N-hydroxysuccinimdyl" and insert --N-hydroxysuccinimidyl--.

In Column 7, Line 48, delete "[β-f3]$^{6+}$" and insert --[β-β]$^{6+}$--.

In Column 7, Line 66, delete "(m/z 494.96$^{2+}$/β$_A$" and insert --(m/z 494.96$^{2+}$/β$_A$)--.

In Column 8, Line 24, delete "(m/z 496.6$^{3+}$)" and insert --(m/z 496.60$^{3+}$)--.

In Column 8, Line 44, delete "(SEQ JD" and insert --(SEQ_ID--.

In Column 9, Line 17, delete "αA" and insert --α$_A$--.

In Column 9, Line 35, delete "groups." and insert --groups--.

In Column 9, Line 53, delete "α$_A$," and insert --α$_A$--.

In Column 9, Line 55, delete "(m/z 1001.82$^{3+}$," and insert --m/z 1001.82$^{3+}$,--.

Signed and Sealed this
Second Day of June, 2020

Andrei Iancu
*Director of the United States Patent and Trademark Office*

CERTIFICATE OF CORRECTION (continued)
U.S. Pat. No. 10,393,752 B2

In Column 10, Line 13 Approx., delete "Mox1FAGIKAK." and insert --MoxlFAGIKAK.--.

In Column 10, Line 31 Approx., delete "αA/βT" and insert --$α_A/β_T$--.

In Column 10, Line 32 Approx., delete "αT/βA" and insert --$α_T/β_A$--.

In Column 10, Line 34 Approx., delete "αA, βA," and insert --$α_A$, $β_A$--.

In Column 10, Line 34 Approx., delete "KA" and insert --$K_A$--.

In Column 10, Line 35 Approx., delete "αT and βT" and insert --$α_T$ and $β_T$--.

In Column 10, Line 37 Approx., delete "αA" and insert --$α_A$--.

In Column 10, Line 38, delete "PA" and insert --$β_A$--.

In Columns 11, Line 1, delete "αA" and insert --$α_A$--.

In Columns 11, Line 62, delete "200. 500," and insert --200, 500,--.

In Columns 13-14, Table 1, Line 30, delete "K100*" and insert --$K_A$100--.

In Columns 23-24, Table 3, Line 9, delete "Kr87" and insert --$K_T$87--.

In Columns 37-38, Table 7, Line 3, delete "Akene@6" and insert --Alkene@6--.

In Columns 37-38, Table 7, Line 10, delete "AlKene@88" and insert --Alkene@88--.

In Columns 37-38, Table 7, Line 18, delete "$GK_AK_A$IEVQK" and insert --$GK_AK_A$IFVQK--.

In Columns 37-38, Table 7, Line 30, before "3 $K_T$KGEREDLIAYLK" delete "MS3 600.31".

In Columns 37-38, Table 7, Line 33, before "KK$_T$KGEREDLIAYLK" insert --MS3 600.31--.

In Columns 37-38, Table 7, Line 41, delete "aikene" and insert --alkene--.

In Columns 69-70, Table 10, Line 33, delete "163" and insert --163 & 196--.

In Columns 69-70, Table 10, Line 34, delete "206)" and insert --206 & 444)--.

In Columns 71-72, Table 10, Line 6, delete "Histone 2B" and insert --Histone H2B--.

In Columns 97-98, Table 10, Line 10, delete "NO: 266)" and insert --NO: 286)--.

In Columns 101-102, Table 10, Line 23, delete "KQASHAQLGDAYDQEIR" and insert --QKQASHAQLGDAYDQEIR--.

CERTIFICATE OF CORRECTION (continued)
U.S. Pat. No. 10,393,752 B2

In Columns 103-104, Table 10, Line 15, delete "H26" and insert --H2B--.

In Columns 103-104, Table 10, Line 19, delete "H26" and insert --H2B--.

In Columns 103-104, Table 10, Line 21, delete "H26" and insert --H2B--.

In Columns 103-104, Table 10, Line 23, delete "H26" and insert --H2B--.

In Columns 103-104, Table 10, Line 27, delete "H26" and insert --H2B--.

In Columns 105-106, Table 10, Line 7, delete "H26" and insert --H2B--.

In Columns 105-106, Table 10, Line 11, delete "H26" and insert --H2B--.

In Columns 105-106, Table 10, Line 15, delete "H26" and insert --H2B--.

In Columns 105-106, Table 10, Line 19, delete "H26" and insert --H2B--.

In Columns 107-108, Table 10, Line 12, delete "ID" and insert --ID NO: 320--.

In Columns 107-108, Table 10, Line 12, below "[Alkene@92]" delete "NO: 320)".

In Columns 107-108, Table 10, Line 22, below "(SEQ ID NO: 322)" insert --(SEQ ID NO: 445)--.

In Columns 115-116, Table 10, Line 21, delete "26A" and insert --26.4--.

In Column 135, Lines 40-41, delete "Cros slinking" and insert --Crosslinking--.

In Column 135, Line 55, delete "Vivocross-Linking." and insert --Vivo cross-Linking.--.

In Column 140, Line 44, delete "dication)/" and insert --dication/--.

In Column 144, Line 37, delete "(e.g.," and insert --e.g.,--.

In Column 144, Lines 37-38, delete "N-hydroxysucinimide" and insert --N-hydroxysuccinimide--.

In Column 145, Line 39, delete "($\alpha A/\beta s$" and insert --($\alpha_A/\beta_S$--.

In Column 145, Line 48, delete "$\alpha$intra," and insert --$\alpha_{intra}$,--.

In Column 146, Line 29, delete "MS')" and insert --$MS^n$)--.

In Column 146, Line 43, delete "$\alpha_S^+$)" and insert --$\alpha_S^{1+}$)--.

In Column 147, Line 47, delete "pmol/$\beta$l" and insert --pmol/µl--.

CERTIFICATE OF CORRECTION (continued)
U.S. Pat. No. 10,393,752 B2

In Column 148, Line 4, delete "$\alpha_1/\beta_A$" and insert --$\alpha_T/\beta_A$--.

In Column 148, Line 13 Approx., delete "$\gamma_{1-7}$)" and insert --$y_{1-7}$)--.

In Column 148, Line 21-22, delete "$\gamma_4$ and $\alpha_1$" and insert --$y_4$ and $a_1$--.

In Column 148, Line 34, delete "$\alpha_1/\beta_A$" and insert --$\alpha_T/\beta_A$--.

In Column 148, Line 36, delete "$\alpha_1/\beta_A$" and insert --$\alpha_T/\beta_A$--.

In Column 148, Line 44, delete "496.6e)" and insert --496.60$^{3+}$)--.

In Column 149, Line 54, delete "($\alpha_A/\beta_{T/S}$ and $\alpha_{T/S}\beta_A$)" and insert --($\alpha_A/\beta_{S/T}$ and $\alpha_{T/S}\beta_A$).--.

In Column 149, Line 57, delete "(~18 Da)," and insert --(-18 Da),--.

In Column 151, Line 58, delete "-1.2 μM" and insert --~1.2 μM--.

In Column 151, Line 65, delete "choloroacetamide" and insert --chloroacetamide--.

In Column 152, Line 28, delete "the a" and insert --the α--.

In Column 152, Line 34, delete "$\beta_3$." and insert --β3.--.

In Column 153, Line 36, delete "value<0.05." and insert --value ≤ 0.05.--.

In Column 153, Line 63, delete "againt" and insert --against--.

In Column 154, Line 59, delete "proteins.$^6$" and insert --proteins$^6$.--.

In Column 155, Line 8, delete "cells.$^3$" and insert --cells$^3$.--.

In Column 155, Lines 11-12, delete "resolution.$^4$" and insert --resolution$^4$.--.

In Column 155, Line 19, delete "workflow,$^5$" and insert --workflow$^5$,--.

In Column 155, Line 26, delete "analysis.$^6$" and insert --analysis$^6$.--.

In Column 155, Line 31, delete "breakage.$^7$" and insert --breakage$^7$.--.

In Column 155, Line 37 Approx., delete "(LC/MS$^{/2}$).$^{8,9}$" and insert --(LC/MS$^n$)$^{8,9}$.--.

In Column 155, Line 51 Approx., delete "vitro.$^4$" and insert --vitro$^4$.--.

In Column 155, Line 63 Approx., delete "identification.$^{18}$" and insert --identification$^{18}$.--.

In Column 155, Line 64 Approx., delete "reagents,[10]" and insert --reagents[10],--.

In Column 155, Line 67 Approx., delete "studies.[11]" and insert --studies[11].--.

In Column 156, Line 34 Approx., delete "sultoxide" and insert --sulfoxide--.

In Column 156, Line 39, delete "coppe(r)-catalyzed" and insert --copper-catalyzed--.

In Column 156, Line 40 Approx., delete "(CuAAC).[12]" and insert --(CuAAC)[12].--.

In Column 156, Line 44 Approx., delete "biotin.[11]" and insert --biotin[11].--.

In Column 157, Line 11 Approx., delete "described.[6]" and insert --described[6].--.

In Column 157, Line 21, delete "procedure.[13]" and insert --procedure[13].--.

In Column 157, Line 40, delete "using" and insert --using.--.

In Column 157, Line 51, delete "purification.[14]" and insert --purification[14].--.

In Column 158, Line 7, delete "sequence.[14]" and insert --sequence[14].--.

In Column 158, Line 8, delete "studies,[6]" and insert --studies[6],--.

In Column 158, Line 10, delete "complexes.[6]" and insert --complexes[6].--.

In Column 158, Line 26, delete "protocol,[16]" and insert --protocol[16],--.

In Column 158, Line 32, delete "TFA-NHS,[17]" and insert --TFA-NHS[17],--.

In Column 158, Line 37, delete "38%.[14]" and insert --38%[14].--.

In Column 158, Line 42, delete "NaN$_3$.[15]" and insert --NaN$_3$[15].--.

In Column 158, Line 58, delete "reagent.[17]" and insert --reagent[17].--.

In Column 159, Line 7, delete "(FIG. 19A).[4]" and insert --(FIG. 19A)[4].--.

In Column 159, Line 43, delete "with with" and insert --with--.

In Column 159, Line 47, delete "studies,[4,18]" and insert --studies[4,18],--.

In Column 159, Line 51, delete "biotin,[19]" and insert --biotin[19],--.

In Column 159, Line 67, delete "LC/MS"" and insert --LC/MS$^n$--.

CERTIFICATE OF CORRECTION (continued)
U.S. Pat. No. 10,393,752 B2

In Column 160, Line 1, delete "peptides.⁴" and insert --peptides[4].--, therefor.

In Column 160, Line 22, delete "⁸¹MC(ₒₓ)" and insert --$^{81}MC_{(ox)}$--.

In Column 160, Line 33, delete "cross-linking,⁴" and insert --cross-linking[4],--.

In Column 160, Line 38, delete "level.⁶" and insert --level[6].--.

In Column 160, Line 40, delete "References—1" and insert --References – 1--.

In Column 161, Line 50, delete "(diol₆)¹," and insert --(diol 6)[1],--.

In Column 161, Line 59, delete "Grubbs.⁴" and insert --Grubbs[4].--.

In Column 162, Line 8, delete "co-workers.⁵" and insert --co-workers[5].--.

In Column 162, Line 13, delete "(6)" and insert --(δ)--.

In Column 162, Line 17, delete "(6)" and insert --(δ)--.

In Column 162, Lines 19-20, delete "dimethylsulfoxide.⁶" and insert --dimethylsulfoxide[6].--.

In Column 162, Line 31 Approx., delete "-3,3'4" and insert -- -3,3'- --, therefor.

In Column 162, Line 32-33 Approx., delete "(methylenesulfinyl))" and insert --(methylenesulfinyl)--.

In Column 162, Line 49, delete "CHCl3" and insert --$CHCl_3$--.

In Column 163, Line 1, delete "3,3'4" and insert -- -3,3'- --, therefor.

In Column 163, Lines 2-3, delete "(methylenesulfinyl))" and insert --(methylenesulfinyl)--.

In Column 164, Line 5, delete "CH2Cl2" and insert --$CH_2Cl_2$--.

In Column 164, Line 61, delete "CDCl3)" and insert --$CDCl_3$)--.

In Column 164, Line 64, delete "CDCl3)" and insert --$CDCl_3$)--.

In Column 165, Line 25, delete "CH2Cl2," and insert --$CH_2Cl_2$,--.

In Column 165, Line 32, delete "[M+Na]'" and insert --$[M+Na]^+$--.

In Column 165, Line 49, delete "In(OTf)3" and insert --$In(OTf)_3$--.

In Column 166, Line 15, delete "[M+Na]+" and insert --$[M+Na]^+$--.

CERTIFICATE OF CORRECTION (continued)
U.S. Pat. No. 10,393,752 B2

In Column 167, Line 36, delete "Procedure:[7]" and insert --Procedure[7]:--.

In Column 167, Line 50 Approx., delete "CDCl3):" and insert --CDCl$_3$):--.

In Column 168, Line 61, delete "MgSO4," and insert --MgSO$_4$,--.

In Column 169, Line 24, delete "(EDCI-HC1)" and insert --(EDCI-HCl)--.

In Column 170, Line 65, delete "LiOH.H2O" and insert --LiOH.H$_2$O--.

In Column 171, Line 15 Approx., delete "CH2Cl2," and insert --CH$_2$Cl$_2$,--.

In Column 171, Line 67, delete "LC-MS'';" and insert --LC-MS[n];--.

In Column 172, Line 13, delete "described.[8]" and insert --described[8].--.

In Column 172, Line 21, delete "peptides.[8,9]" and insert --peptides[8,9].--.

In Column 172, Line 48, delete "described.[8,9]" and insert --described[8,9].--.

In Column 172, Line 62, delete "3." and insert --3. Y--.

In Column 172, Line 64, delete "4." and insert --4. B--.

In Column 173, Line 1, delete "5." and insert --5. W--.

In Column 173, Line 4, delete "6." and insert --6. G--.

In Column 173, Line 8, delete "7." and insert --7. T--.

In Column 173, Line 11, delete "8." and insert --8. K--.

In Column 173, Line 12, delete "ao," and insert --Ao,--.

In Column 173, Line 15, delete "9." and insert --9. K--.

In Column 173, Line 16, delete "ao," and insert --Ao,--.

In Column 176, Line 26, delete "(MS')" and insert --(MS[n])--.

In Column 178, Line 33, delete "NH4HCO3," and insert --NH$_4$HCO$_3$,--.

In Column 179, Line 50, delete "MS'" and insert --MS[n]--.

In Column 181, Lines 9-10, delete "(m/z 659.82594+)" and insert --(m/z 659.82594[+])--.

In Column 181, Line 12, delete "(m/z 499.272+), β_A (m/z 720.372+)," and insert --(m/z 499.272$^+$), β_A (m/z 720.372$^+$),--.

In Column 181, Line 12, delete "PT" and insert --β_T--.

In Column 181, Lines 12-13, delete "(m/z 811.3 72+ )," and insert --(m/z 811.3 72$^+$),--.

In Column 181, Line 15, delete "αA (m/z 499.272+) and βT (m/z 811.372+)" and insert --α_A (m/z 499.272$^+$) and β_T (m/z 811.372$^+$)--.

In Column 182, Line 66, delete "(C3H2O," and insert --($C_3H_2O$,--.

In Column 182, Line 67, delete "(C3H4O2S," and insert --($C_3H_4O_2S$,--.

In Column 183, Line 1, delete "(C3H2SO," and insert --($C_3H_2SO$,--.

In Column 187, Lines 10-11, delete "vivocross-linking." and insert --vivo cross-linking.--.

In Column 187, Line 60, delete "etc" and insert --etc.--.

In Column 188, Lines 34-35, delete "disuccinimiclyl-bissulfoxide" and insert --disuccinimidyl-bissulfoxide--.

In Column 188, Line 60, delete "N-Hydroxysuccinimiclyl" and insert --N-Hydroxysuccinimidyl--.

In the Claims

In Column 381, Line 16, Claim 1, delete "N-hydroxysuccinimdyl" and insert --N-hydroxysuccinimidyl--.

In Column 381, Lines 21-22, Claim 1, delete "N-hydroxysuccinimdyl" and insert --N-hydroxysuccinimidyl--.

In Column 383, Line 38, Claim 12, delete "dipropionatefrom" and insert --dipropionate from--.

In Column 383, Line 54, Claim 13, delete "(MSn)," and insert --($MS^n$),--.

In Column 385, Line 50, Claim 22, delete "LC-MS" and insert --LC-MSn--.